United States Patent
Ohmoto et al.

Patent Number: 6,136,834
Date of Patent: Oct. 24, 2000

[54] TETRAZOLE COMPOUNDS AND PHARMACEUTICAL AGENTS CONTAINING SUCH DERIVATIVE

[75] Inventors: Kazuyuki Ohmoto; Makoto Tanaka; Tohru Miyazaki; Hiroyuki Ohno, all of Osaka, Japan

[73] Assignee: Ono Pharmaceutical Co., Ltd., Osaka, Japan

[21] Appl. No.: 09/101,004

[22] PCT Filed: Dec. 26, 1996

[86] PCT No.: PCT/JP96/03801

§ 371 Date: Jun. 29, 1998

§ 102(e) Date: Jun. 29, 1998

[87] PCT Pub. No.: WO97/24339

PCT Pub. Date: Oct. 7, 1997

[30] Foreign Application Priority Data

Dec. 27, 1995 [JP] Japan ................................. 7-351241

[51] Int. Cl.<sup>7</sup> .......................... A61K 31/41; A61K 47/22; C07D 257/04; C07C 229/28; C07C 229/34

[52] U.S. Cl. .......................... 514/381; 514/532; 514/534; 514/542; 514/620; 514/784; 548/250; 548/251; 548/252; 548/253; 548/254; 560/19; 560/37; 560/38; 562/433; 562/442; 562/443; 562/450

[58] Field of Search .............................. 514/381; 548/250, 548/251, 252, 253, 254

[56] References Cited

FOREIGN PATENT DOCUMENTS

| | | |
|---|---|---|
| 0 339 549 A3 | 11/1989 | European Pat. Off. . |
| 0 519 748 A2 | 12/1992 | European Pat. Off. . |
| A20618223 | 10/1994 | European Pat. Off. . |
| A10644198 | 3/1995 | European Pat. Off. . |
| 0 761 680 A2 | 3/1997 | European Pat. Off. . |
| WO9309135 | 5/1993 | WIPO . |
| WO9526958 | 10/1995 | WIPO . |

*Primary Examiner*—Joseph McKane
*Assistant Examiner*—Jane C. Oswecki
*Attorney, Agent, or Firm*—Sughrue, Mion, Zinn, Macpeak & Seas, PLLC

[57] ABSTRACT

A tetrazole derivative of formula (I)

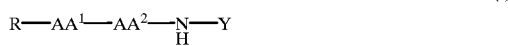

(I)

wherein R is H, alkyl, alkoxy, carbocyclic ring, alkyl or alkoxy substituted by carbocyclic ring;
$AA^1$ and $AA^2$ is a bond or

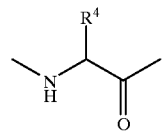

and

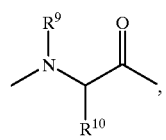

respectively, or
$AA^1$ and $AA^2$, together, may have the formula (a);

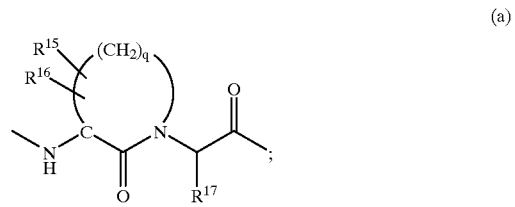

(a)

and
Y is formula (b)

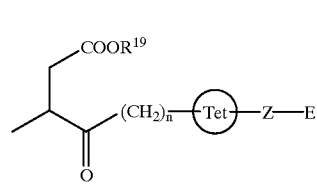

(b)

wherein the Tet ring is tetrazole; Z is alkylene, alkenylene, O, S, SO, $SO_2$, $NR^{26}$, methylene in alkylene replaced by O, S, —SO—, —$SO_2$— or —$NR^{26}$—; and E is H, alkyl, or $COOR^{27}$.

14 Claims, No Drawings

TETRAZOLE COMPOUNDS AND PHARMACEUTICAL AGENTS CONTAINING SUCH DERIVATIVE

This application is a 371 of PCT/JP96/03801 filed Dec. 26, 1996.

FIELD OF THE INVENTION

This invention relates to tetrazole compounds. More particularly, this invention relates to:

(1) tetrazole compounds having interleukin-1β converting enzyme inhibitory activity of the following formula (I):

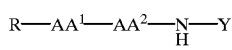

(I)

wherein all of the symbols have the same meanings as described hereinafter, or a non-toxic salt thereof, an acid addition salt thereof or a hydrate thereof;

(2) processes for the preparation thereof; and (3) pharmaceutical agents containing such devivative as an active ingredient.

BACKGROUND OF THE INVENTION

Interleukin 1 (IL-1) is a key cytokine that directly or indirectly participates in the regulation of, for example, the immune system, hemopoietic system and neuroendocrine system, and thus, has a crucial physiological role. There are two types of IL-1, which have different isoelectric points (IL-1α:pI=5, IL-1β:pI=7). Both of these are produced as a precursor having molecular weight of 31 Kd. The IL-1β precursor does not bind to the IL receptor nor exerts a biological function. The IL-1β converting enzyme (ICE) cleaves the precursor protein between Asp 116 and Ala 117 and converts into an active IL-1β mature form having a molecular weight of 17 Kd. Following the cleavage, IL-1β is secreted, binds to the receptor and triggers various biological activities (Ref. The New England Journal of Medicine, 328, 106 (1993)).

The inhibition of ICE enzymatic activity leads to prevention of conversion of the IL-1β precursor into the mature form and hence results in blockage of IL-1 biological activity. There are many possible target diseases for ICE inhibitors, for example, prevention and/or treatment of insulin dependent diabetes (type I), autoimmune diseases, including multiple sclerosis, immune diseases, such as acute or delayed type hypersensitivity, infectious diseases, infection complications, septic shock, acute or chronic inflammatory diseases, such as arthritis, colitis, glomelular nephritis, hepatitis, pancreatitis, reperfusion injury, cholangeitis, encephalitis, endocarditis, myocarditis and vasculitis, neural diseases, such as Alzheimer's disease and Parkinson's disease, bone or cartilage-resorption diseases, Crohn's disease, osteo arthritis etc.

It is believed that ICE and/or ICE-like cystein proteases play important roles in cell death by apoptosis. Therefore it is possible that an ICE inhibitor may be used in the prevention and/or treatment of diseases resulting from apoptosis disorders, such as infection, reduction or enhancement of immune or central nervous system function, neoplasm etc. Diseases associated with apoptosis disorders are as follows; AIDS, ARC (AIDS related complex), adult T cell leukemia, hairy cell (pilocytic) leukemia, myelosis, respiratory dysfunction, arthropathy, HIV or HTLV-I related diseases, such as uveitis, virus related diseases, such as hepatitis C, neoplasm, diffuse collagen diseases, such as systemic lupus erythematosis or rheumatoid arthritis, autoimmune diseases, such as ulcerative colitis, Sjogren's syndrome, primary biliary cirrhosis, idiopathic thrombocytopnic purpura, autoimmonohaemolytic anemia, severe myasthenia, insulin dependent (type I) diabetes, osteodysplasia syndrome, periodic thrombocytopenia, aplastic anemia, idiopathic thrombocytopenia, various diseases which accompany thrombocytopenia, such as disseminated intravascular coagulation, hepatic diseases, including hepatitis (type C, A, B, or F virus borne or drug mediated) and hepatic cirrhosis, Alzheimer's disease, dementia, such as Alzheimer type senile dementia, cerebral vascular disturbance, neurodegenerative diseases, adult dyspnea syndrome, infection, hyperplasia of the prostate, myoma of the uterus, asthma bronchiole, arteriosclerosis, various kinds of congenital teratoma, nephritis, senile cataract, chronic fatigue syndrome, myodystrophy, peripheral nervous disturbance, and so on (Ref. The New England Journal of Medicine, 328, 106–113 (1993), Arthritis & Rheumatism, 39, 1092 (1996)).

RELATED ARTS

Compounds having an inhibitory activity on IL-1β converting enzyme (ICE) are known. The sequence of the ICE cleavage site of pre-IL-1β (Tyr-Val-His-Asp) has high affinity with ICE. Substrate analog inhibitors which are chemically modified and based on the above substrate sequence, for example, a compound of formula (X):

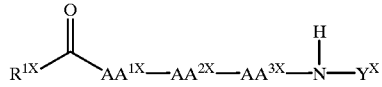

(X)

wherein $Y^X$ is

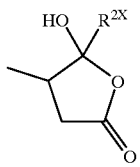

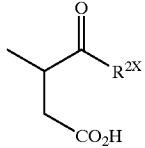

or

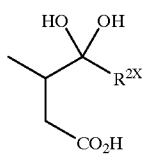

$R^{1X}$ is
(a) a substituted C1–12 alkyl (in which a substituent is hydrogen, hydroxy etc.) or
(b) an aryl C1–6 alkyl (in which aryl is phenyl, naphthyl, pyridyl, furyl, thienyl, thiazolyl, isothiazolyl, imidazolyl, benzoimidazolyl, pyrazinyl, pyrimidyl, quinolyl, isoquinolyl, benzofuryl, benzothienyl, pyrazolyl, indolyl, purinyl or isooxazolyl), wherein the aryl can be mono-substituted or di-substituted (in which a substituent is a C1–6 alkyl, halogen, hydroxyl, C1–6 alkylcarbonyl etc.);

$R^{2X}$ is (a) hydrogen,

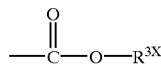

(b)

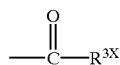

(c)

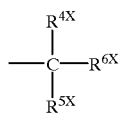

(d)

(in which $R^{3X}$ is
(1) a substituted C1–12 alkyl (in which a substituent is hydrogen, hydroxy etc.), or
(2) an aryl C1–6 alkyl or substituted aryl C1–6 alkyl as hereinbefore defined (in which an aryl may be mono-substituted or di-substituted by C1–6 alkyl, halogen, hydroxyl, C1–6 alkylcarbonyl etc.);

$R^{4X}$ and $R^{5X}$ are each hydrogen, hydroxyl etc.; and $R^{6X}$ is
(1) hydrogen,
(2) a substituted C1–6 alkyl (in which a substituent is hydrogen, hydroxyl etc.),
(3) an aryl C1–6 alkyl (in which alkyl is substituted by hydrogen, oxo, C1–3 alkyl etc., aryl has the same meaning as hereinbefore defined, said aryl is mono-substituted or di-substituted, said substituent is C1–6 alkyl, halogen, hydroxyl, C1–6 alkylcarbonyl etc.),
(4) a C1–6 alkylaminocarbonylC1–6 alkyl or C1–6 alkylcarbonylaminoC1–6 alkyl,
(5) an arylaminocarbonylC1–6 alkyl or arylcarbonylaminoC1–6 alkyl (in which aryl has the same meaning as hereinbefore defined, said aryl is mono-substituted or di-substituted, said substituent is C1–6 alkyl, halogen, hydroxyl, C1–6 alkylcarbonyl etc.) or
(6) an aryl C1–6 alkylaminocarbonyl C1–6 alkyl or aryl C1–6 alkylcarbonylamino C1–6 alkyl (in which aryl has the same meaning as hereinbefore defined, said aryl is mono-substituted or di-substituted, said substituent is C1–6 alkyl, halogen, hydroxyl, C1–6 alkylcarbonyl etc.) etc.;

$AA^{1X}$ is a bond etc.;

$AA^{2X}$ is a bond or

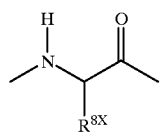

and $AA^{3X}$ is a bond or

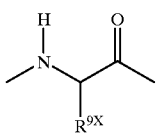

(wherein $R^{8X}$ and $R^{9X}$ is
(a) hydrogen,
(b) a substituted C1–6 alkyl (in which a substituent is hydrogen, hydroxyl etc.) or
(c) an aryl C1–6 alkyl (in which aryl has the same meaning as hereinbefore defined, said aryl is mono-substituted or di-substituted, said substituent is C1–6 alkyl, halogen, hydroxyl, C1–6 alkylcarbonyl, etc.))

(with the proviso that, definitions not related are omitted)

are disclosed as having an inhibitory activity on ICE (see EP 519748).

The compounds of formula (Y):

$$R^Y-[A^{1Y}-A^{2Y}]_{nY}-A^{3Y}-A^{4Y}-X^Y-A^{5Y} \qquad (Y)$$

wherein $R^Y$ is hydrogen, an amino protecting group or benzyloxy, which may be optionally substituted by a ring;

nY is 0 or 1;

$A^{1Y}$ is Val, Leu, Ala, Ile or trimethylsilyl-Ala;

$A^{2Y}$ is Phe or Tyr;

$A^{3Y}$ is Val, Leu, Ala, Ile, trimethylsilyl-Ala or a divalent radical group:

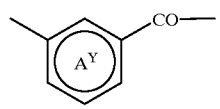

(in which ring $A^Y$ may be optionally substituted by hydroxy or C1–4 alkoxy);

$A^{4Y}$ is a bond or

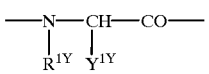

(in which $R^{1Y}$ is hydrogen or C1–4 alkyl, and $Y^{1Y}$ is a residue bonded to the α-carbon atom of an optionally protected α-amino acid);

wherein $A^{3Y}$ and $A^{4Y}$ together may form:

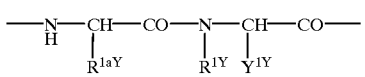

(wherein $Y^{1Y}$ has the same meaning as hereinbefore defined, and $R^{1Y}$ and $R^{1aY}$ are combined to form —$(CH_2)_{mY}$— (in which mY is 2, 3, 4 or 5));

$X^Y$ is a divalent radical group:

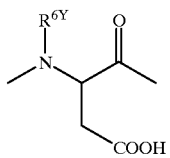

(wherein $R^{6Y}$ is hydrogen or C1–4 alkyl); and $A^{5Y}$ is hydrogen, $CF_3$, —$Z^{1Y}$—$Z^{2Y}$—$Y^{2Y}$ (in which $Z^{1Y}$ and $Z^{2Y}$ is each, independently, a bond or an α-amino acid residue and $Y^{2Y}$ is $NH_2$, C1–4 alkylamino, di-(C1–4 alkyl)amino or hetero ring bonded to the $Z^{2Y}$ nitrogen), —$CH_2$—$X^{1Y}$—$Y^{3Y}$ (in which $X^{1Y}$ is O or S and $Y^{3Y}$ is heteroaryl) or —$CH_2$—$Y^{3Y}$ wherein $Y^{3Y}$ is as previously defined)

(with the proviso that, definitions not related are omitted)

have an inhibitory activity on IL-1β release (see WO 93/09135).

Further, it is disclosed that compounds of formula (Z):

(Z)

wherein $R^Z$ is hydrogen, an amino or hydroxy protecting group or benzyloxy which may be optionally substituted by a ring;

$A^{1Z}$ is an α-hydroxy acid, amino acid residue or thiocarbonyl analogue, each with an optionally protected side chain, or

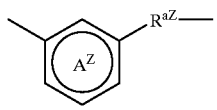

(in which ring $A^Z$ may be optionally substituted by hydroxy or C1–4 alkoxy and $R^{aZ}$ is CO or CS);

$A^{2Z}$ is an α-hydroxy acid, —NH—$CHR^{3Z}$—CO— (in which $R^{3Z}$ is an optionally protected side chain of an α-amino acid);

$X^Z$ is

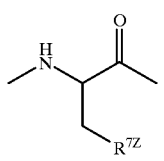

or

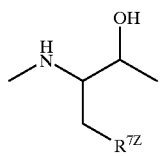

(in which $R^{7Z}$ is —$CO_2H$, —CONHOH or a bioisosteric group); and $A^{3Z}$ is —$CH_2$—$X^{1Z}$—CO—$Y^{1Z}$, —$CH_2$—O—$Y^{2Z}$ or —$CH_2$—S—$Y^{3Z}$ (in which $X^{1Z}$ is O or S, $Y^{1Z}$ is an aliphatic ring, optionally substituted with aryl, diphenylmethyl, optionally substituted by a ring, piperidino or optionally substituted mono, di or tricyclic heteroaryl, $Y^{2Z}$ is an aliphatic ring, diphenylmethyl, optionally substituted by a ring, or optionally substituted di or tricyclic heteroaryl etc. and $Y^{3Z}$ is an aliphatic ring, tri-(C1–4 alkyl)methylcarbonyl, di-(C1–4 alkyl) aminothiocarbonyl, 4-nitrophenyl, 2,6-dichloro-benzoyl, 2,3,6-trichloro-4-pyridyl, 5-membered heterocyclic ring containing a nitrogen atom or optionally substituted di or tricyclic heteroaryl, etc.) etc.; and $A^{1Z}$ and $A^{2Z}$ may form

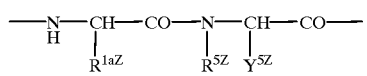

(in which $R^{1aZ}$ and $R^{5Z}$ together make form C2–5 alkylene or C2–5 alkenylene and $Y^{5Z}$ is an optionally protected side chain of an α-amino acid, etc.)

(with the proviso that, definitions not related are omitted)

have an inhibitory activity on IL-1β release (see EP 618223).

Furthermore, it is disclosed that compounds of formula (W):

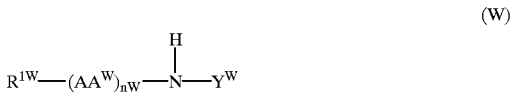
(W)

wherein nW is 0–4;

$Y^W$ is

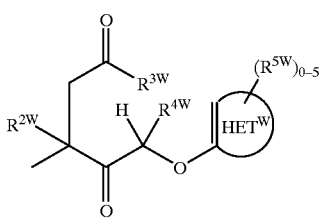

wherein when $R^{3W}$ is O, $Y^W$ is

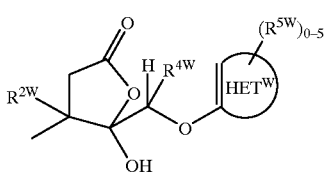

(in which $R^{2W}$ is hydrogen or deuterium;

$R^{3W}$ is O, OH, $OR^{6W}$, $NR^{6W}OR^{7W}$ or $NR^{6W}R^{7W}$;

$R^{6W}$ and $R^{7W}$ each, independently, is hydrogen, alkyl, aralkyl, heteroaralkyl, aryl or heteroaryl;

$R^{4W}$ is hydrogen or alkyl;

$R^{5W}$ is hydrogen, alkyl, alkenyl, aryl, heteroaryl, aralkyl, heteroaralkyl, halogen, haloalkyl, nitro or cyano, $HET^W$ is heteroaryl);

AA$^W$ is

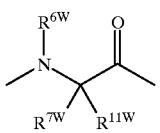

(in which R$^{6W}$ and R$^{7W}$ have the same meaning as hereinbefore defined and R$^{11W}$ is (CR$^{6W}$R$^{7W}$)$_{0-6}$—R$^{12W}$ (wherein R$^{12W}$ is aryl, heteroaryl or optionally selected from hereinbefore described R$^{5W}$)) or an amino acid; and R$^{1W}$ is R$^{12W}$—CO— or R$^{12W}$SO$_2$— (wherein R$^{12W}$ has the same meaning as hereinbefore defined)

(with the proviso that, definitions not related are omitted)

have an inhibitory activity on IL-1β converting enzyme (see CA 2125021).

PURPOSE OF THE INVENTION

Energetic investigations have been carried out to discover new compounds having inhibitory activity on IL-1β converting enzyme. As a result, the present inventors have achieved that goal by a tetrazole compound of formula (I).

COMPARISON OF THE INVENTION AND RELATED ARTS

The tetrazole compounds of the present invention are newly synthesized and therefore, are quite novel.

To summarize, in the compound of formula (X) known in the art (EP 519748), R$^{6X}$ of Y$^X$ can represent aryl C1–6 alkyl. But, the aryl group does not include a tetrazole. On the other hand, in the compound of the present invention, Y essentially is the tetrazole group. Therefore, it can be said that the compounds of the present invention have a chemical structure quite different from the compounds of formula (X). A representative example of formula (X) is compound (X-1).

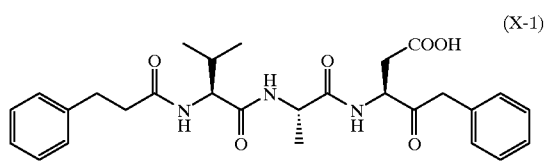

(X-1)

In the compound of formula (Y) of WO93/09135, Y$^{3Y}$ of A$^{5Y}$ can be a heteroaryl group. Further, exemplification of the heteroaryl group includes a tetrazole group. But, no substituents of the heteroaryl group are disclosed in detail in WO93/09135. On the other hand, a compound of the present invention has a ring essentially as substituents of the tetrazole of Y. It can be said that the compounds of the present invention have a chemical structure quite different from the compounds of formula (Y). Representative examples of formula (Y) are compounds (Y-1) and (Y-2).

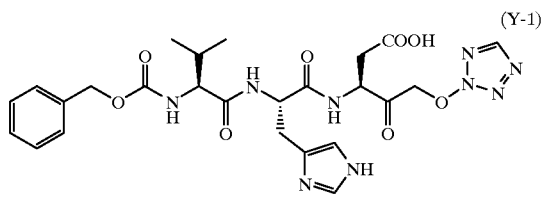

(Y-1)

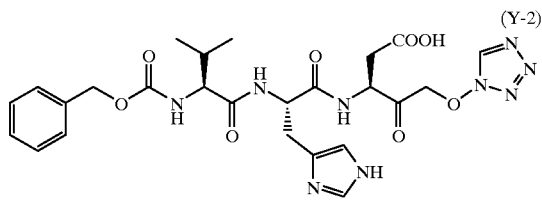

(Y-2)

Further, in a compound of formula (Z), EP 618223, Y$^{3Z}$ of A$^{3Z}$ can represent a heteroaryl group. Further, exemplification of the heteroaryl group includes a tetrazole. But, only C1–4 alkyl is disclosed as substituents of the heteroaryl group. On the other hand, a compound of the present invention has a ring as a substituent of the tetrazole of Y. Therefore, it can be said that the compounds of the present invention have a chemical structure quite different from the compounds of formula (Z). Furthermore, in the compounds of formula (Z), Y$^{3Z}$ as a heteroaryl group is essentially bonded to a hetero atom (oxygen or sulfur atom). On the other hand, in the present invention, the tetrazole group of Y is bonded to a carbon atom. Thus, for another reason, compounds of formula (I) of the present invention have a chemical structure quite different from a compound of formula (Z). A representative example of a compound of formula (Z) is compound (Z-1).

(Z-1)

Furthermore, in the compounds of formula (W) of CA 2125021, HET$^W$ of Y$^W$ can be a heteroaryl group. Further, exemplification of the heteroaryl group includes a tetrazole group. But, there are no preparative examples of compounds in which a heteroaryl group is a tetrazole. Additionally, in the compound of formula (W), HET$^W$ as a heteroaryl is bonded to a hetero atom (oxygen atom). On the other hand, in the present invention, the tetrazole group Y is bonded to a carbon atom. Thus, compounds of formula (I) of the present invention have a chemical structure quite different from compound of formula (W). A representative compound of formula (W) is compound (W-1).

(W-1)

Therefore, the compounds of the present invention have a chemical structure quite different from the compounds of formulae (X), (Y), (Z) and (W) known in the art. The instant compounds are novel and not previously described.

Therefore, the present inventors have found that tetrazole compounds of formula (I) have an inhibitory activity on IL-1β converting enzyme even if a hetero atom dose not exist between a ketone group and a ring. That observation is quite unexpected from what is known in the art, and has been confirmed from experiments by the present inventors for the first time.

SUMMARY OF THE INVENTION

The present invention is related to:
1) A tetrazole derivatives of the formula (I)

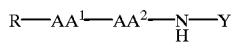
(I)

wherein R is a hydrogen atom,

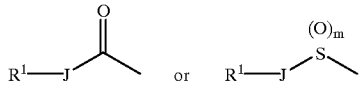

(in which J is bond, C1–6 alkylene, C1–6 oxyalkylene, C1–6 aminoalkylene, C1–6 thioalkylene, C2–6 alkenylene, carbocyclic ring, or hetero ring, carbocyclic ring and hetero ring may be substituted by C1–4 alkyl, with the proviso that, when J contains oxygen, nitrogen or sulfur atom, it is bond to C=O or $S(O)_m$ group in R), $R^1$ is
1) C1–8 alkyl,
2) C1–8 alkoxy,
3) C2–8 alkenyl,
4) C2–8 alkenyloxy,
5) C1–8 alkylamino,
6) di(C1–8 alkyl)amino,
7) C1–8 alkylthio,
8) $Cyc^1$ (in which $Cyc^1$ is a carbocyclic ring or hetero ring, and $Cyc^1$ may be substituted by 1 to 5 substituents selected from a hydrogen atom, C1–8 alkyl, phenyl, phenyloxy, C1–8 alkyl substituted by phenyl, a halogen atom, nitro, trifluoromethyl, nitrile, keto, $-OR^2$, $-NR^2R^3$, $-S(O)R^2$, $-SO_2R^2$, $-COOR^2$ or $-COR^2$, wherein $R^2$ is a hydrogen atom, C1–8 alkyl, phenyl or C1–4 alkyl substituted by phenyl, $R^3$ is a hydrogen atom, C1–8 alkyl, phenyl or C1–4 alkyl substituted by phenyl, C2–5 acyl, or R2 and R3, taken together bonded to nitrogen atom, represent hetero ring),
9) $Cyc^1-O-$,
10) $Cyc^1-S-$,
11) $Cyc^1-CO-$,
12) C1–8 alkyl, C1–8 alkoxy, C1–8 alkylamino, di(C1–8 alkyl)amino or C1–8 alkylthio mono or di-substituted by $Cyc^1$, $Cyc^1-O-$, $Cyc^1-S-$, or $Cyc^1-CO-$,
13) trifluoromethyl,
14) $Cyc^1-CO-NH-CH_2-$,
15) amino,
16) benzyloxycarbonyl,
17) C2–5 acylamino, or
18) C1–8 alkoxy substituted by C1–8 alkoxy, m is 0 or 1–2,
with the proviso that,
(1) when m is 0, then $-S(O)_m-$ is not directly bonded to nitrogen or sulfur atom, and
(2) when m is 1, then $-S(O)_m-$ is not directly bonded to sulfur atom, $AA^1$ is
1) a bond or
2)

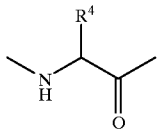

(in which $R^4$ is
(1) a hydrogen atom,
(2) C1–8 alkyl,
(3) $Cyc^2$ (in which $Cyc^2$ is a carbocyclic ring or hetero ring, and $Cyc^2$ may be substituted by 1 to 5 substituents selected from a hydrogen atom, C1–8 alkyl, phenyl, C1–4 alkyl substituted by phenyl, a halogen atom, nitro, trifluoromethyl, nitrile, tetrazole, $-OR^5$, $-NR^5R^6$, $-SR^5$, $-COOR^5$ or $-COR^5$, wherein $R^5$ and $R^6$ each, independently, is a hydrogen atom, C1–4 alkyl, phenyl or C1–4 alkyl substituted by phenyl) or
(4) C1–8 alkyl substituted by a substituent selected from $-OR^7$, $-NR^7R^8$, $-SR^7$, $-COOR^7$, $-COR^7$, $-CONH_2$, $-NR^7-CO-NR^7R^8$, guanidino or $Cyc^2$ (in which $R^7$ and $R^8$ each, independently, is a hydrogen atom, C1–4 alkyl, phenyl or C1–4 alkyl substituted by phenyl), $AA^2$ is
1) a bond or
2)

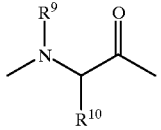

(in which $R^9$ and $R^{10}$ each, independently, is
(1) a hydrogen atom,
(2) C1–8 alkyl,
(3) $Cyc^3$ (in which $Cyc^3$ is a carbocyclic ring or hetero ring, and $Cyc^3$ may be substituted by 1 to 5 substituents selected from a hydrogen atom, C1–8 alkyl, phenyl, C1–4 alkyl substituted by phenyl, a halogen atom, nitro, trifluoromethyl, nitrile, tetrazole, $-OR^{11}$, $-NR^{11}R^{12}$, $-SR^{11}$, $-COOR^{11}$ or $-COR^{11}$, wherein $R^{11}$ and $R^{12}$ each, independently, is a hydrogen atom, C1–4 alkyl, phenyl or C1–4 alkyl substituted by phenyl),
(4) C1–8 alkyl substituted by a substituent selected from $-OR^{13}$, $-NR^{13}R^{14}$, $-SR^{13}$, $-COOR^{13}$, $-COR^{13}$, $-CONH_2$, $-NR^{13}-CO-NR^{13}R^{14}$, guanidino or $Cyc^3$ (in which $R^{13}$ is a hydrogen atom, C1–4 alkyl, phenyl or C1–4 alkyl substituted by phenyl, $R^{14}$ is a hydrogen atom, C1–4 alkyl, phenyl, C1–4 alkyl substituted by phenyl, t-butyloxycarbonyl or benzyloxycarbonyl) or (5) $R^9$ and $R^{10}$, together, is a C1–6 alkylene or C2–6 alkenylene), $AA^1$ and $AA^2$, together, may have the formula

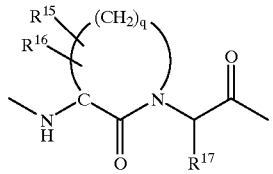

in which $R^{15}$ and $R^{16}$ each, independently, is a hydrogen atom, C1–4 alkyl, phenyl or C1–4 alkyl substituted by phenyl (with the proviso that, C1–4 alkyl or phenyl may be substituted by C1–4 alkyl, C1–4 alkoxy, a halogen atom, trifluoromethyl or phenyl), $R^{17}$ is (1) a hydrogen atom,
(2) C1–8 alkyl,
(3) $Cyc^3$ (in which $Cyc^3$ has the same meaning as hereinbefore defined) or
(4) C1–8 alkyl substituted by a substituent selected from —$OR^{13}$, —$NR^{13}R^{14}$, —$SR^{13}$, —$COOR^{13}$, —$COR^{13}$, —$CONH_2$, —$NR^{13}$—CO—$NR^{13}R^{14}$, guanidino or $Cyc^3$ (in which $R^{13}$ and $R^{14}$ have the same meaning as hereinbefore defined), q is 2–12, with the proviso that, a carbon atom in —$(CH_2)_q$— may be replaced by an oxygen atom, sulfur atom, —SO—, —$SO_2$— or —$NR^{18}$— (in which $R^{18}$ is a hydrogen atom, C1–4 alkyl, phenyl or C1–4 alkyl substituted by phenyl), or two hydrogen atom at ortho positions are replaced by a double bond and Y is

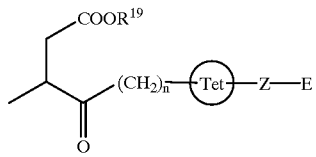

in which $R^{19}$ is a hydrogen atom, C1–8 alkyl, phenyl or C1–4 alkyl substituted by phenyl, n is 1–4,

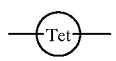

is

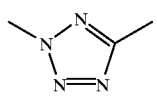

or

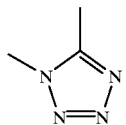

Z is
1) C1–6 alkylene,
2) C2–6 alkenylene,
3) oxygen atom,
4) sulfur atom,
5) —CO—,
6) —SO—,
7) —$SO_2$—,
8) —$NR^{26}$— (in which $R^{26}$ is a hydrogen atom, C1–4 alkyl, phenyl, C1–4 alkyl substituted by phenyl), or
9) a carbon atom in C1–6 alkylene replaced by an oxygen atom, sulfur atom, —CO—, —SO—, —$SO_2$— or —$NR^{26}$— (in which $R^{26}$ is the same meaning as hereinbefore defined), with the proviso that, Z is bonded directly to the carbon atom on a tetrazole ring, E is a hydrogen atom, a halogen atom, C1–4 alkyl, —$COOR^{27}$ (in which $R^{27}$ is a hydrogen atom, C1–4 alkyl, phenyl, C1–4 substituted by phenyl), —$CONR^{28}R^{29}$ (in which $R^{28}$ and $R^{29}$ each, independently, is a hydrogen atom, C1–4 alkyl, phenyl, C1–4 substituted by phenyl or $R^{28}$ and $R^{29}$, taken together, boned to nitrogen atom represent hetero ring), —$NR^{28}R^{29}$ (in which $R^{28}$ and $R^{29}$ are the same meaning as hereinbefore defined), or

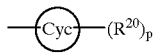

(in which

is carbocyclic ring or hetero ring, $R^{20}$ is
1) a hydrogen atom,
2) C1–8 alkyl,
3) a halogen atom,
4) nitro,
5) trifluoromethyl,
6) nitrile,
7) —$OR^{22}$,
8) —$NR^{22}R^{23}$,
9) —$SR^{22}$,
10) —$COOR^{22}$,
11) —$COR^{22}$,
12) —$CONR^{28}R^{29}$ (in which $R^{28}$ and $R^{29}$ are the same meaning as hereinbefore defined),
13) $Cyc^4$ (in which $Cyc^4$ is a carbocyclic ring or hetero ring, and $Cyc^4$ may be substituted by 1 to 5 substituents selected from a hydrogen atom, C1–8 alkyl, phenyl, C1–4 alkyl substituted by phenyl, a halogen atom, nitro, trifluoromethyl, nitrile, tetrazole, —$OR^{24}$, —$NR^{24}R^{25}$, —$SR^{24}$, —$COOR^{24}$ or —$COR^{24}$ (in which $R^{24}$ and $R^{25}$ each, independently, is a hydrogen atom, C1–4 alkyl, phenyl or C1–4 alkyl substituted by phenyl)), or 14) C1–8 alkyl substituted by $Cyc^4$ (in which $Cyc^4$ is the same meaning as hereinbefore defined), $R^{22}$ is a hydrogen atom, C1–4 alkyl, phenyl or C1–4 alkyl substituted by phenyl, $R^{23}$ is a hydrogen atom, C1–4 alkyl, phenyl, C1–4 alkyl substituted by phenyl, C2–5 acyl or trifluoromethylcarbonyl, p is 1–5), or —Z—E is a halogen atom, trifluoromethyl, C1–4 alkyl di-substituted by phenyl or tri(C1–4 alkyl)silyl, with the proviso that,
(1) when Z is C1–6 alkylene or C2–6 alkenylene, then E is not a hydrogen atom or C1–4 alkyl, or
(2) when Z is —SO—, then E is not a hydrogen atom, or a non-toxic salt thereof, an acid addition salt thereof or a hydrate thereof, 2) processes for the preparation thereof and
3) pharmaceutical agents containing such a derivative as an active ingredient.

Throughout the specification, including claims, it may be easily understood by those skilled in the art, that all isomers are included in the present invention. For example, the alkyl, alkoxy and alkylene groups include straight-chain and also branched-chain ones. Accordingly, all isomers produced by the existence of asymmetric carbon atoms are included in the present invention when branched-chain alkyl, alkoxy, alkylene, etc. exist.

In formula (I), C1–8 alkyl represented by substituent of $Cyc^1$, substituent of $Cyc^2$, substituent of $Cyc^3$, $R^1$, $R^2$, $R^3$, $R^4$, $R^9$, $R^{10}$, $R^{17}$, $R^{19}$ and $R^{20}$, C1–8 alkyl mono or di-substituted by $Cyc^1$, $Cyc^1$—O—, $Cyc^1$—S— or $Cyc^1$—CO—, C1–8 alkyl substituted by $Cyc^4$, C1–8 alkyl substituted by a group selected from —$OR^7$, —$NR^7R^8$, —$SR^7$, —$COOR^7$, —$COR^7$, —$CONH_2$, —$NR^7$—CO—$NR^8$, guanidino and $Cyc^2$ and C1–8 alkyl substituted by a group selected from —$OR^{13}$, —$NR^{13}R^{14}$, —$SR^{13}$, —$COOR^{13}$, —$COR^{13}$, —$CONH_2$, —$NR^{13}$—CO—$NR^{14}$, guanidino and $Cyc^3$ each means methyl, ethyl, propyl, butyl, pentyl, hexyl, heptyl, octyl and an isomer thereof.

In formula (I), C1–8 alkylamino represented by $R^1$ and C1–8 alkylamino mono or di-substituted by $Cyc^1$, $Cyc^1$—O—, $Cyc^1$—S— or $Cyc^1$—CO— each means methyl, ethyl, propyl, butyl, pentyl, hexyl, heptyl, octyl and an isomer thereof, which are substituted by an amino group.

In formula (I), di(C1–8 alkyl)amino represented by $R^1$ and di(C1–8 alkyl)amino mono or di-substituted by $Cyc^1$, $Cyc^1$—O—, $Cyc^1$—S— or $Cyc^1$—CO— each means methyl, ethyl, propyl, butyl, pentyl, hexyl, heptyl, octyl and an isomer thereof, which are each independently di-substituted by an amino group on nitrogen atom.

In formula (I), C1–8 alkylthio represented by $R^1$ and C1–8 alkylthio mono or di-substituted by $Cyc^1$, $Cyc^1$—O—, $Cyc^1$—S— or $Cyc^1$—CO— each means thiomethyl, thioethyl, thiopropyl, thiobutyl, thiopentyl, thiohexyl, thioheptyl, thiooctyl and an isomer thereof.

In formula (I), C1–8 alkoxy represented by $R^1$ and C1–8 alkoxy mono or di-substituted by $Cyc^1$, $Cyc^1$—O—, $Cyc^1$—S— or $Cyc^1$—CO— each means methoxy, ethoxy, propoxy, butoxy, pentyloxy, hexyloxy, heptyloxy, octyloxy and an isomer thereof.

In formula (I), C1–8 alkoxy substituted by C1–8 alkoxy represented by $R^1$ means methoxy, ethoxy, propoxy, butoxy, pentyloxy, hexyloxy, heptyloxy, octyloxy and the isomer thereof, which are substituted by a methoxy, ethoxy, propoxy, butoxy, pentyloxy, hexyloxy, heptyloxy, octyloxy and the isomer thereof.

In formula (I), C1–4 alkyl represented by a substituent of carbocyclic ring, substituent of hetero ring, substituent of $R^{15}$, substituent of $R^{16}$, $R^5$, $R^6$, $R^7$, $R^8$, $R^{11}$, $R^{12}$, $R^{13}$, $R^{14}$, $R^{15}$, $R^{16}$, $R^{18}$, $R^{22}$, $R^{23}$, $R^{24}$, $R^{25}$, $R^{26}$, $R^{27}$, $R^{28}$, $R^{29}$ and E means methyl, ethyl, propyl, butyl and an isomer thereof.

In formula (I), C1–4 alkoxy represented by $R^{15}$ and $R^{16}$ mean methoxy, ethoxy, propoxy, butoxy and an isomer thereof.

In formula (I), C1–4 alkyl substituted by phenyl represented by substituent of $Cyc^2$, substituent of $Cyc^3$, substituent of $Cyc^4$, $R^2$, $R^3$, $R^5$, $R^6$, $R^7$, $R^8$, $R^{11}$, $R^{12}$, $R^{13}$, $R^{14}$, $R^{15}$, $R^{16}$, $R^{18}$, $R^{19}$, $R^{22}$, $R^{23}$, $R^{24}$, $R^{25}$, $R^{26}$, $R^{27}$, $R^{28}$ and $R^{29}$ means methyl, ethyl, propyl, butyl and the isomer thereof, which are substituted by a phenyl group.

In formula (I), C1–8 alkyl substituted by phenyl represented by substituent of $Cyc^1$ means methyl, ethyl, propyl, butyl, pentyl, hexyl, heptyl, octyl and the isomer thereof, which are substituted by a phenyl group.

In formula (I), a halogen atom represented by a substituent of $R^{15}$ and $R^{16}$, substituent of $Cyc^1$, substituent of $Cyc^2$, substituent of $Cyc^3$, substituent of $Cyc^4$, $R^{20}$, E and —Z—E means fluorine, chlorine, bromine and iodine.

In formula (I), C1–6 alkylene represented by J, Z, and $R^9$ and $R^{10}$, taken together, means methylene, ethylene, trimethylene, tetramethylene, pentamethylene, hexamethylene and an isomer thereof.

In formula (I), C1–6 oxyalkylene represented by J means oxymethylene, oxyethylene, oxytrimethylene, oxytetramethylene, oxypentamethylene, oxyhexamethylene and an isomer thereof.

In formula (I), C1–6 aminoalkylene represented by J means aminomethylene, aminoethylene, aminotrimethylene, aminotetramethylene, aminopentamethylene, aminohexamethylene and an isomer thereof.

In formula (I), C1–6 thioalkylene represented by J means thiomethylene, thioethylene, thiotrimethylene, thiotetramethylene, thiopentamethylene, thiohexamethylene and an isomer thereof.

In formula (I), C2–6 alkenylene represented by J, Z, and $R^9$ and $R^{10}$, taken together, means vinylene, propenylene, butenylene, pentenylene, hexenylene, butadienylene, pentadienylene, hexadienylene, hexatrienylene and an isomer thereof.

In formula (I), C2–8 alkenyl represented by $R^1$ means vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and an isomer thereof.

In formula (I), C2–8 alkenyloxy represented by $R^1$ means vinyloxy, propenyloxy, butenyloxy, pentenyloxy, hexenyloxy, heptenyloxy, octenyloxy, butadienyloxy, pentadienyloxy, hexadienyloxy, heptadienyloxy, octadienyloxy, hexatrienyloxy, heptatrienyloxy, octatrienyloxy and an isomer thereof.

In formula (I), C2–5 acyl represented by $R^3$ and $R^{23}$ means acetyl, propionyl, butyryl, valeryl and an isomer thereof.

In formula (I), C2–5 acylamino represented by $R^1$ means acetylamino, propionylamino, butyrylamino, valerylamino and an isomer thereof.

In formula (I), tri(C1–4 alkyl)silyl represented by —Z—E means each independent tri-substituted by methyl, ethyl, propyl, butyl and the isomer thereof, on silicon atom.

In formula (I), a carbocyclic ring represented by J $Cyc^1$, $Cyc^2$, $Cyc^3$, $Cyc^4$ and

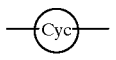

means a 3–10 membered mono-cyclic or bi-cyclic carbocyclic ring. For example, a 3–10 membered mono-cyclic or bi-cyclic carbocyclic ring include cyclopropyl, cyclobutyl, cyclopentyl, cyclohexyl, cycloheptyl, cyclopentadiene, benzene, pentalene, indene, naphthalene, azulene ring etc.

In formula (I), a hetero ring represented by J, $Cyc^1$, $Cyc^2$, $Cyc^3$, $Cyc^4$ and

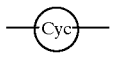

means a 5–18 membered mono-cyclic, bi-cyclic or tri-cyclic hetero ring containing 1–2 nitrogen atoms, one oxygen atom or one sulfur atom. For example, a 5–18 membered mono-cyclic, bi-cyclic or tri-cyclic hetero ring containing 1–3 nitrogen atoms, one oxygen atom or one sulfur atom includes pyrrole, imidazole, triazole, pyrazole, pyridine, pyrazine, pyrimidine, pyridazine, azepine, diazepine, furan, pyran, oxepine, oxazepine, thiophene, thiaine (thiopyran), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, pyrroline, pyrrolidine, imidazoline, imidazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, benzooxazepine, benzooxadiazepine, benzothiazepine, benzodithiazepine, benzoazepine, benzodiazepine, indolooxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphere, imidazothiazole ring etc.

In formula (I), hetero ring represented by $R^2$ and $R^3$, taken together bonded to nitrogen atom, and $R^{28}$ and $R^{29}$, taken together bonded to nitrogen atom, means a 5–7 membered mono-cyclic hetero ring containing 1–2 nitrogen atoms, one oxygen atom or one sulfur atom. For example, a 5–7 membered mono-cyclic hetero ring containing 1–2 nitrogen atoms, one oxygen atom or one sulfur atom includes pyrroline pyrrolidine, imidazoline, imidazolidine, pyrazoline, pyrazolidine, piperidine, piperazine, piperidine, piperazine, morpholine, thiomorpholine, tetrahydropyrimidine, tetrahydropyridazine ring etc.

In formula (I),

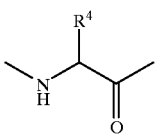

represented by $AA^1$ may be an α-amino acid residue. For example, glycine, alanine, serine, threonine, cystine, valine, methionine, leucine, isoleucine, phenylalanine, tyrosine, tryptophan, aspartic acid, glutamic acid, arginine, glutamine, lysine, histidine etc.

In formula (I),

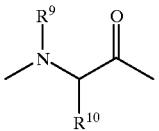

represented by $AA^2$ may be an α-amino acid residue. For example, glycine, alanine, serine, threonine, cystine, valine, methionine, leucine, isoleucine, phenylalanine, tyrosine, tryptophan, aspartic acid, glutamic acid, arginine, glutamine, lysine, histidine, proline etc.

In formula (I), C1–4 alkyl di-substituted by phenyl represented by —Z—E means methyl, ethyl, propyl, butyl and the isomer thereof, which are di-substituted by phenyl group.

In formula (I), keto group represented by substituent of $Cyc^1$ may be substituted at one carbon atom, one nitrogen atom, or one or two sulfar atom.

In the present invention, non-toxic salts includes all such salts. For example, the following salt, acid addition salt or hydrate, etc.

Salt

The compounds of formula (I) of the present invention in the case of free carboxylic acid or tetrazole may be converted into a corresponding non-toxic salt by methods known per se. Non toxic and water-soluble salts are preferable. Suitable salts, for example, are salts of an alkaline metal (potassium, sodium etc.), salts of an alkaline earth metal (calcium, magnesium etc.), ammonium salts and salts of pharmaceutically-acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

Acid Additional Salt

The compounds of formula (I) of the present invention may be converted into a corresponding acid addition salt by methods known per se. Non toxic and water-soluble salts are preferable. Suitable acid addition salts include salts of inorganic acids such as hydrochloric acid, hydrobromic acid, sulfuric acid, phosphoric acid and nitric acid, and salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

Hydrate

The compounds of formula (I) or salts thereof of the present invention may be converted into a corresponding hydrate by methods known per se.

Preferred compounds of the present invention are as follows:

tetrazole derivative of formula I (1)

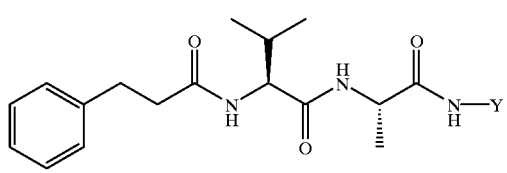

(wherein Y has the same meaning as hereinbefore defined), the compound of formula I (2)

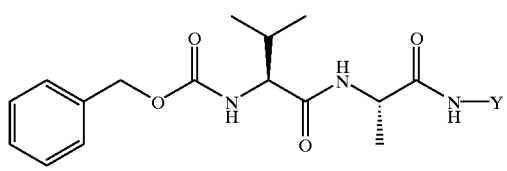

(wherein Y has the same meaning as hereinbefore defined), the compound of formula I (3)

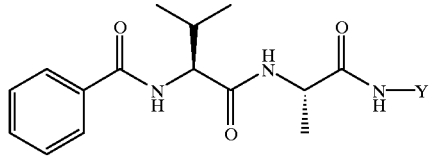

(wherein Y has the same meaning as hereinbefore defined), the compound of formula I (4)

(wherein Y has the same meaning as hereinbefore defined), the compound of formula I (5)

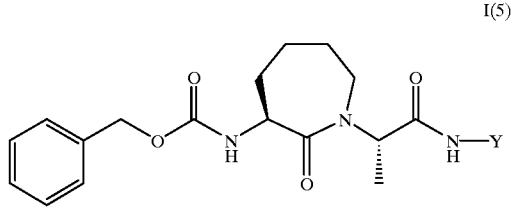

(wherein Y has the same meaning as hereinbefore defined), the compound of formula I (6)

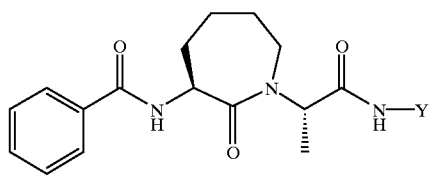

(wherein Y has the same meaning as hereinbefore defined), the compound of formula I (7)

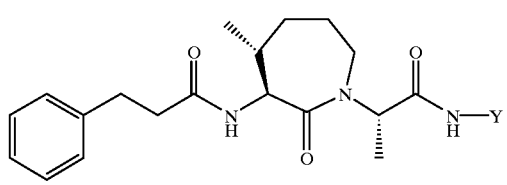

(wherein Y has the same meaning as hereinbefore defined), the compound of formula I (8)

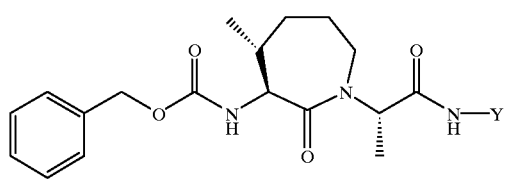

(wherein Y has the same meaning as hereinbefore defined), the compound of formula I (9)

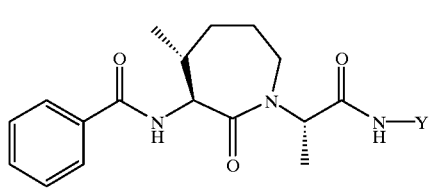

(wherein Y has the same meaning as hereinbefore defined), the compound of formula I (10)

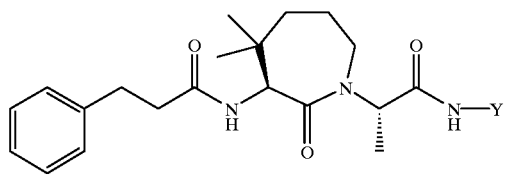

(wherein Y has the same meaning as hereinbefore defined), the compound of formula I (11)

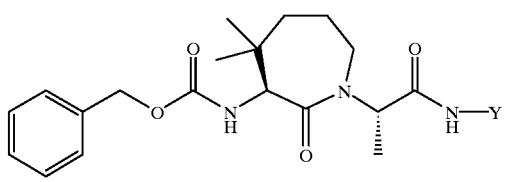

(wherein Y has the same meaning as hereinbefore defined), the compound of formula I (12)

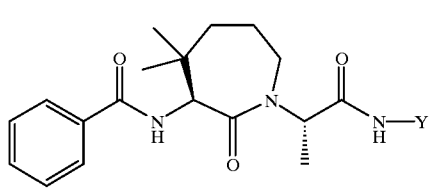

(wherein Y has the same meaning as hereinbefore defined), the compound of formula I (13)

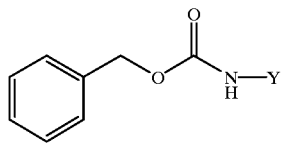

(wherein Y has the same meaning as hereinbefore defined), the compound of formula I (14)

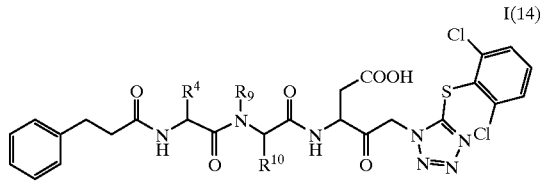

(wherein $R^4$, $R^9$ and $R^{10}$ have the same meaning as hereinbefore defined), the compound of formula I (15)

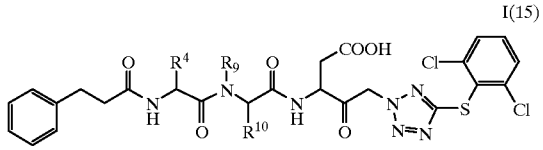

(wherein $R^4$, $R^9$ and $R^{10}$ have the same meaning as hereinbefore defined), the compound of formula I (16)

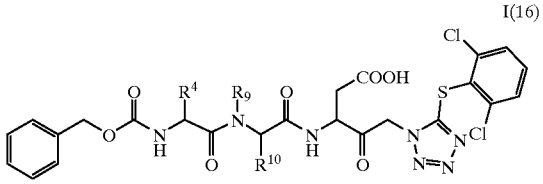

(wherein $R^4$, $R^9$ and $R^{10}$ have the same meaning as hereinbefore defined), the compound of formula I (17)

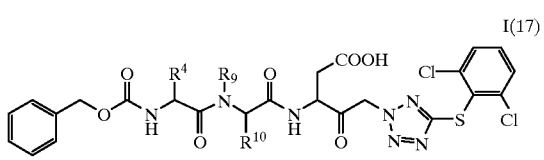

(wherein $R^4$, $R^9$ and $R^{10}$ have the same meaning as hereinbefore defined), the compound of formula I (18)

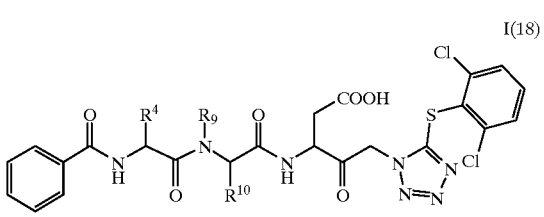

(wherein $R^4$, $R^9$ and $R^{10}$ have the same meaning as hereinbefore defined), the compound of formula I (19)

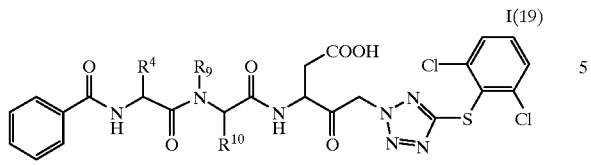

(wherein $R^4$, $R^9$ and $R^{10}$ have the same meaning as hereinbefore defined), the compound of formula I (20)

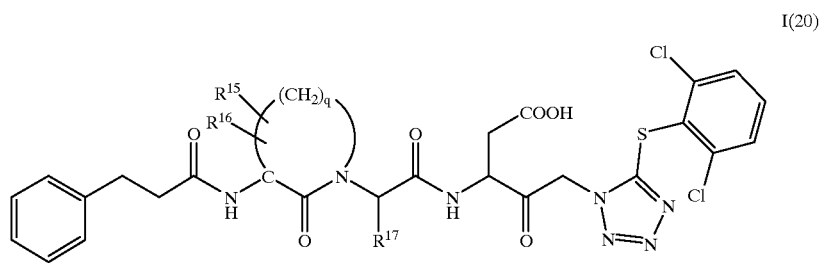

(wherein $R^{15}$, $R^{16}$, $R^{17}$ and —$(CH_2)_q$— have the same meaning as hereinbefore defined), the compound of formula I (21)

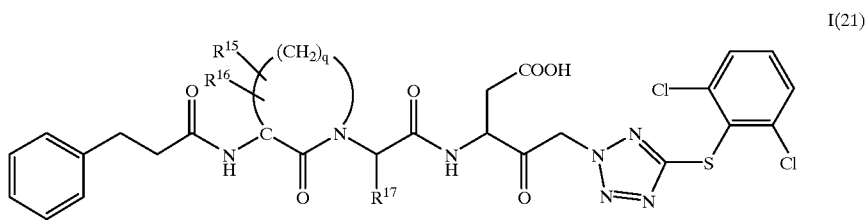

(wherein $R^{15}$, $R^{16}$, $R^{17}$ and —$(CH_2)_q$— have the same meaning as hereinbefore defined), the compound of formula I (22)

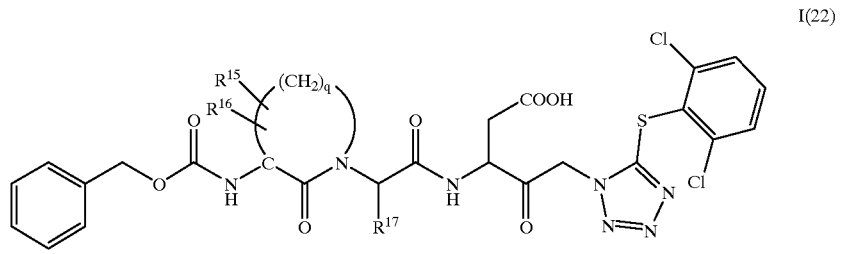

(wherein $R^{15}$, $R^{16}$, $R^{17}$ and —$(CH_2)_q$— have the same meaning as hereinbefore defined), the compound of formula I (23)

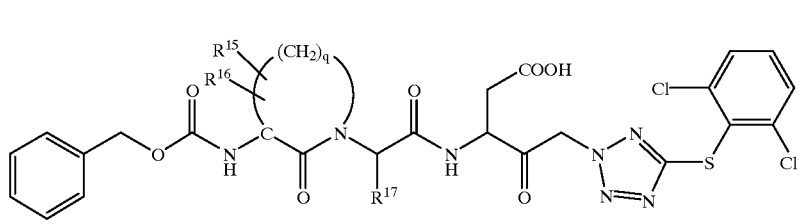

(wherein $R^{15}$, $R^{16}$, $R^{17}$ and —$(CH_2)_q$— have the same meaning as hereinbefore defined), the compound of formula I (24)

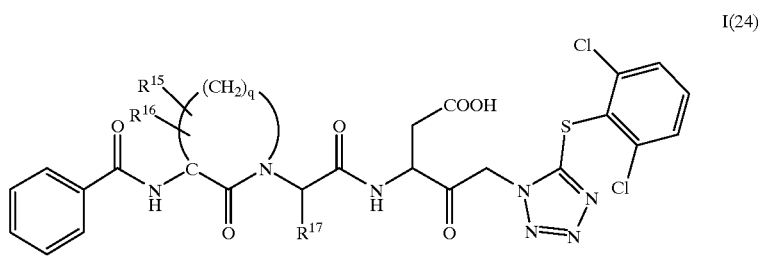

(wherein $R^{15}$, $R^{16}$, $R^{17}$ and —$(CH_2)_q$— have the same meaning as hereinbefore defined), the compound of formula I (25)

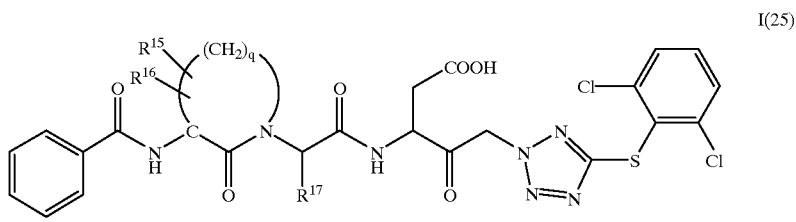

(wherein $R^{15}$, $R^{16}$, $R^{17}$ and —$(CH_2)_q$— have the same meaning as hereinbefore defined), the compound of formula I (26)

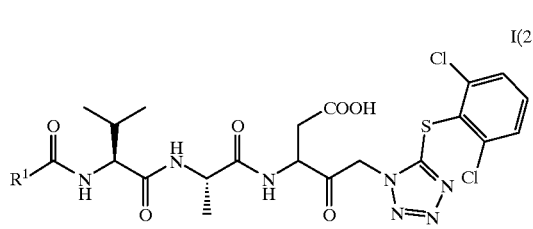

(wherein $R^1$ has the same meaning as hereinbefore defined), the compound of formula I (27)

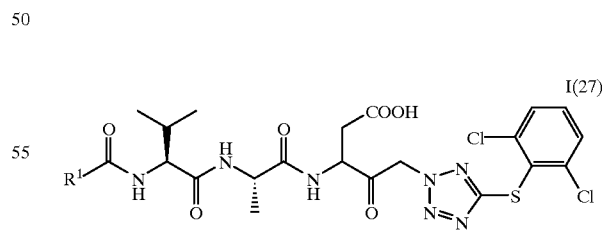

(wherein $R^1$ has the same meaning as hereinbefore defined), the compound of formula I (28)

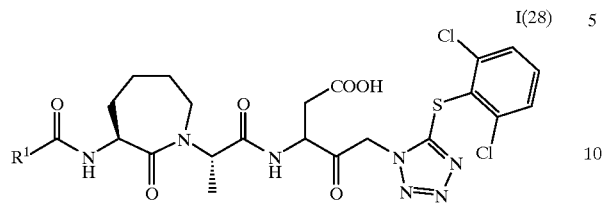

(wherein R¹ has the same meaning as hereinbefore defined), the compound of formula I (29)

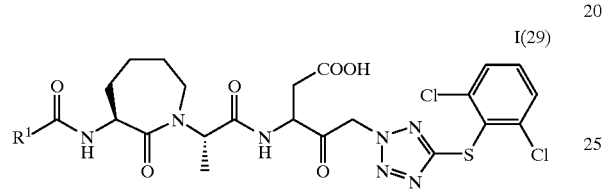

(wherein R¹ has the same meaning as hereinbefore defined), the compound of formula I (30)

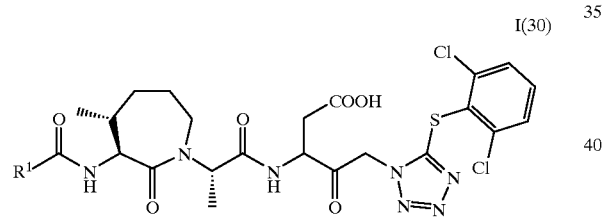

(wherein R¹ has the same meaning as hereinbefore defined), the compound of formula I (31)

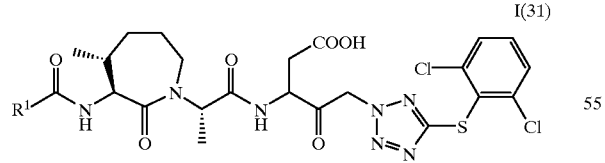

(wherein R¹ has the same meaning as hereinbefore defined), the compound of formula I (32)

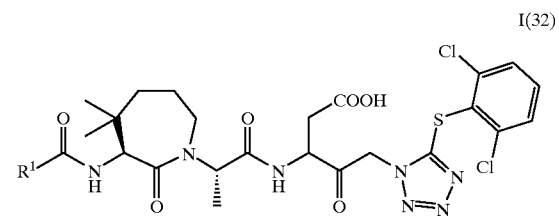

(wherein R¹ has the same meaning as hereinbefore defined), the compound of formula I (33)

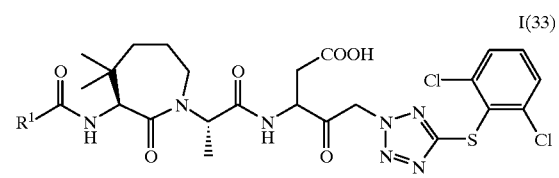

(wherein R¹ has the same meaning as hereinbefore defined), the compound of formula I (34)

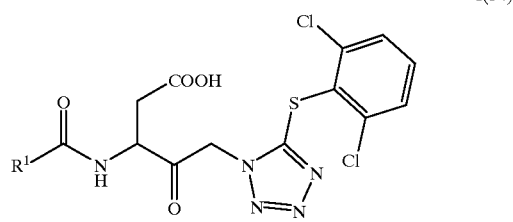

(wherein R¹ has the same meaning as hereinbefore defined), the compound of formula I (35)

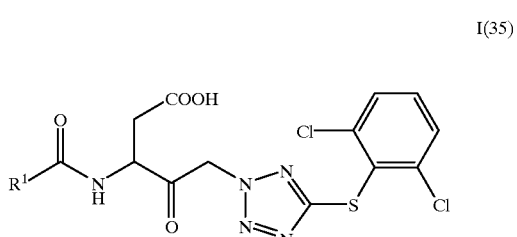

(wherein R¹ has the same meaning as hereinbefore defined), the compound of formula I (36)

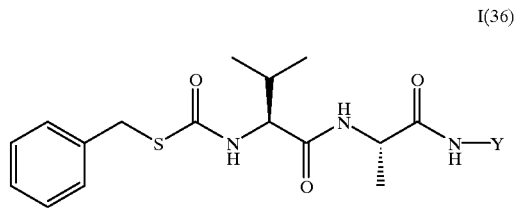

(wherein Y has the same meaning as hereinbefore defined),
the compound of formula I (37)

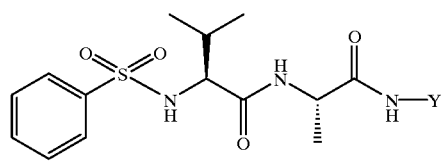

(wherein Y has the same meaning as hereinbefore defined),
the compound of formula I (38)

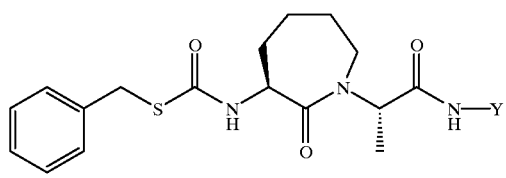

(wherein Y has the same meaning as hereinbefore defined),
the compound of formula I (39)

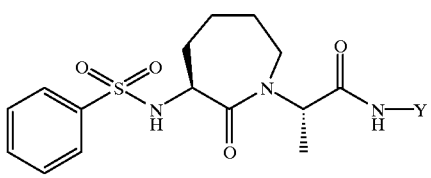

(wherein Y has the same meaning as hereinbefore defined),
the compound of formula I (40)

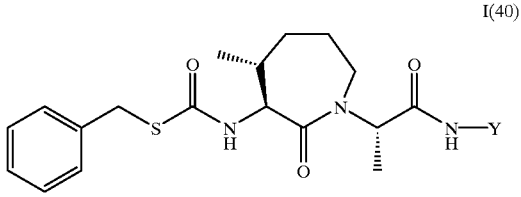

(wherein Y has the same meaning as hereinbefore defined), the compound of formula I (41)

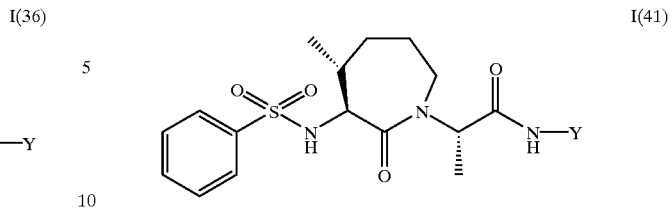

(wherein Y has the same meaning as hereinbefore defined),
the compound of formula I (42)

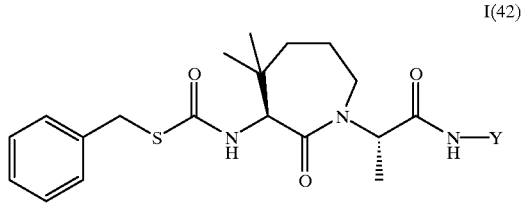

(wherein Y has the same meaning as hereinbefore defined),
the compound of formula I (43)

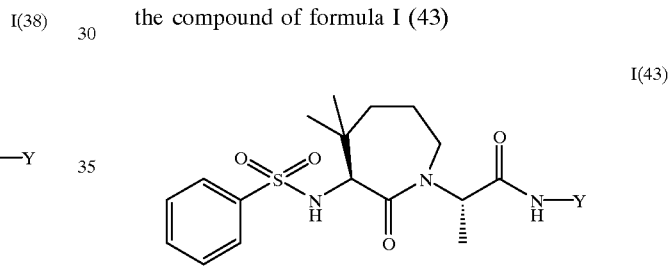

(wherein Y has the same meaning as hereinbefore defined),
the compound of formula I (44)

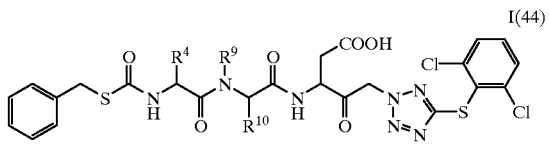

(wherein $R^4$, $R^9$ and $R^{10}$ have the same meaning as hereinbefore defined),
the compound of formula I (45)

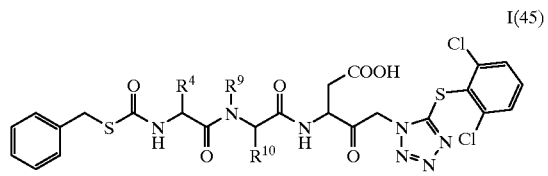

(wherein $R^4$, $R^9$ and $R^{10}$ have the same meaning as hereinbefore defined), the compound of formula I (46)

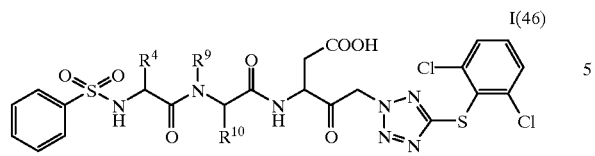

I(46)

(wherein $R^4$, $R^9$ and $R^{10}$ have the same meaning as hereinbefore defined), the compound of formula I (47)

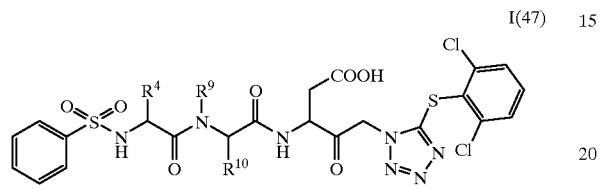

I(47)

(wherein $R^4$, $R^9$ and $R^{10}$ have the same meaning as hereinbefore defined), the compound of formula I (48)

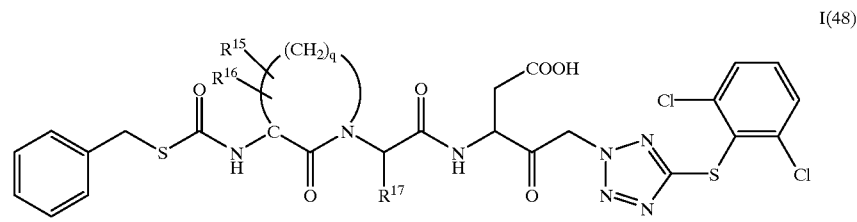

I(48)

(wherein $R^{15}$, $R^{16}$, $R^{17}$ and —$(CH_2)_q$— have the same meaning as hereinbefore defined), the compound of formula I (49)

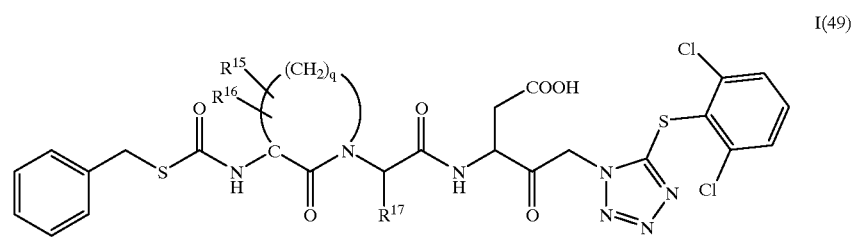

I(49)

(wherein $R^{15}$, $R^{16}$, $R^{17}$ and —$(CH_2)_q$— have the same meaning as hereinbefore defined), the compound of formula I (50)

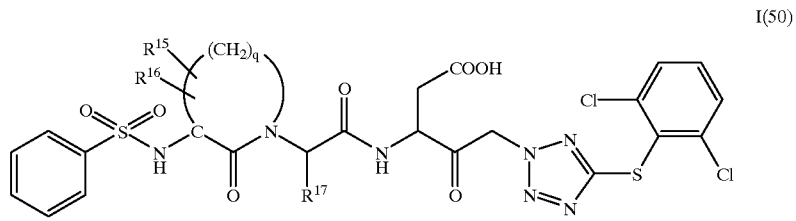

(wherein $R^{15}$, $R^{16}$, $R^{17}$ and —$(CH_2)_q$— have the same meaning as hereinbefore defined), the compound of formula I (51)

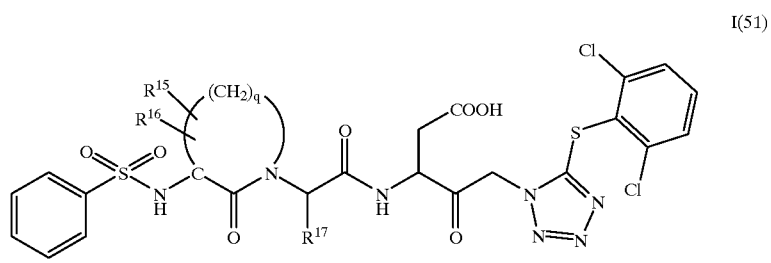

(wherein $R^{15}$, $R^{16}$, $R^{17}$ and —$(CH_2)_q$— have the same meaning as hereinbefore defined), the compound of formula I (52)

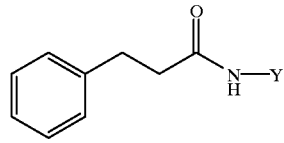

(wherein Y has the same meaning as hereinbefore defined), the compound of formula I (53)

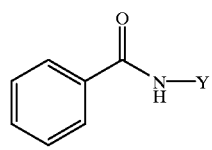

(wherein Y has the same meaning as hereinbefore defined), the compound of formula I (54)

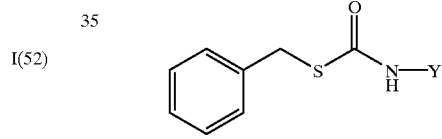

(wherein Y has the same meaning as hereinbefore defined), the compound of formula I (55)

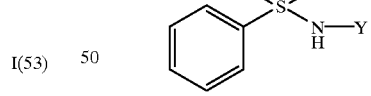

(wherein Y has the same meaning as hereinbefore defined), the compound of formula I (56)

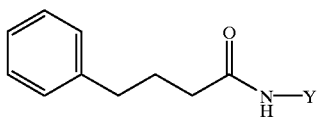

(wherein Y has the same meaning as hereinbefore defined), the compound of formula I (57)

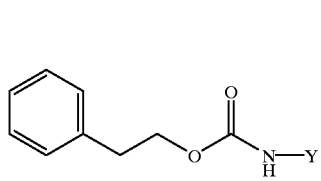
I(57)

(wherein Y has the same meaning as hereinbefore defined), the compound of formula I (58)

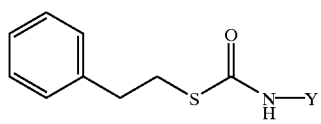
I(58)

(wherein Y has the same meaning as hereinbefore defined), the compound of formula I (59)

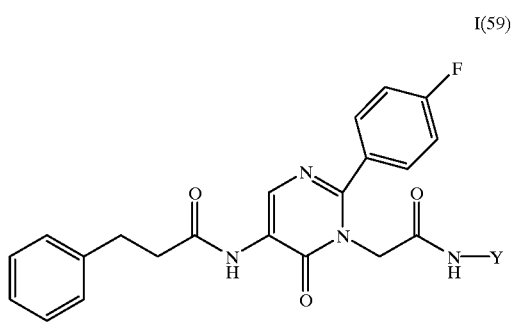
I(59)

(wherein Y has the same meaning as hereinbefore defined), the compound of formula I (60)

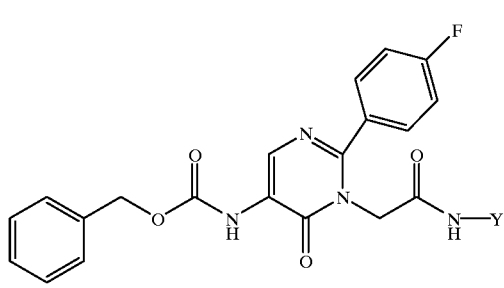
I(60)

(wherein Y has the same meaning as hereinbefore defined), the compound of formula I (61)

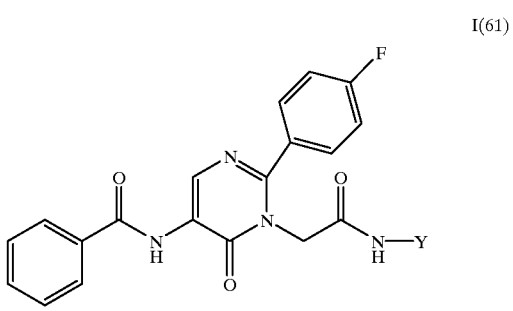
I(61)

(wherein Y has the same meaning as hereinbefore defined), the compound of formula I (62)

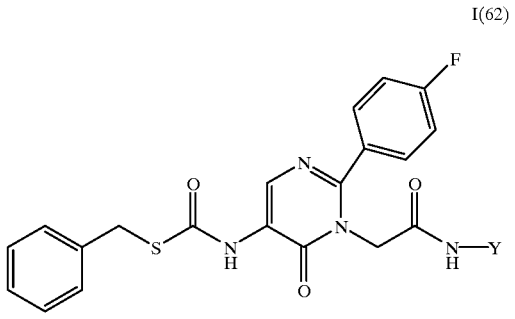
I(62)

(wherein Y has the same meaning as hereinbefore defined), the compound of formula I (63)

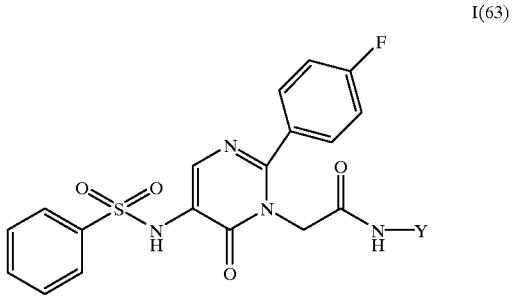
I(63)

(wherein Y has the same meaning as hereinbefore defined), the compound of formula I (64)

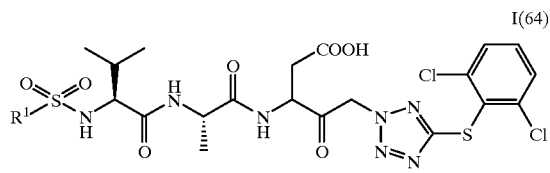
I(64)

(wherein R¹ has the same meaning as hereinbefore defined), the compound of formula I (65)

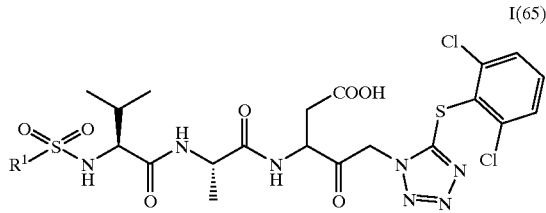

(wherein R¹ has the same meaning as hereinbefore defined), the compound of formula I (66)

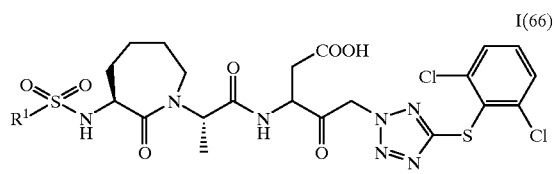

(wherein R¹ has the same meaning as hereinbefore defined), the compound of formula I (67)

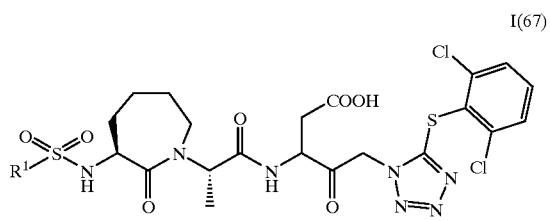

(wherein R¹ has the same meaning as hereinbefore defined), the compound of formula I (68)

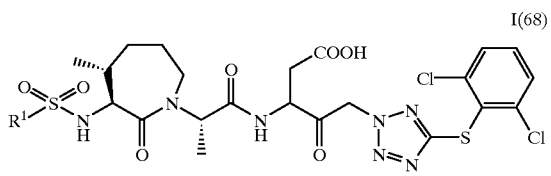

(wherein R¹ has the same meaning as hereinbefore defined), the compound of formula I (69)

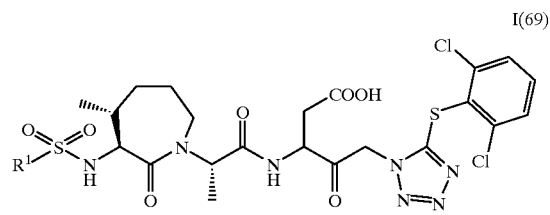

(wherein R¹ has the same meaning as hereinbefore defined), the compound of formula I (70)

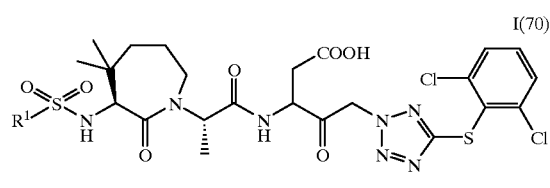

(wherein R¹ has the same meaning as hereinbefore defined), the compound of formula I (71)

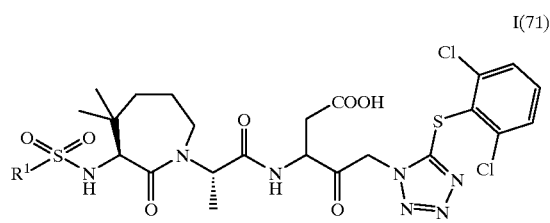

(wherein R¹ has the same meaning as hereinbefore defined), the compound of formula I (72)

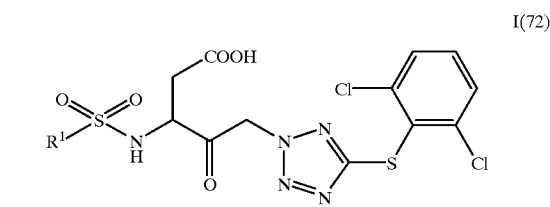

(wherein R¹ has the same meaning as hereinbefore defined), the compound of formula I (73)

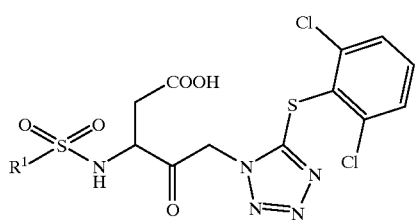

(wherein R¹ has the same meaning as hereinbefore defined), the compound of formula I (74)

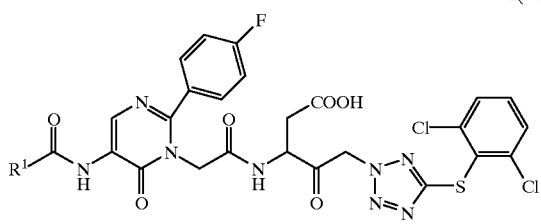

(wherein R¹ has the same meaning as hereinbefore defined), the compound of formula I (75)

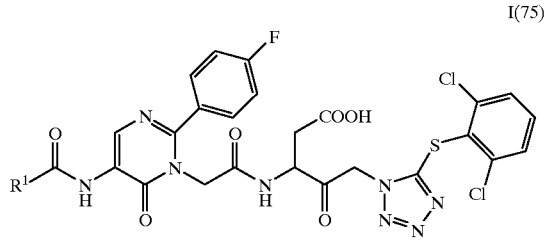

(wherein R¹ has the same meaning as hereinbefore defined), the compound of formula I (76)

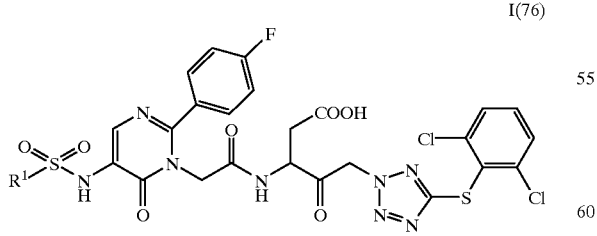

(wherein R¹ has the same meaning as hereinbefore defined), the compound of formula I (77)

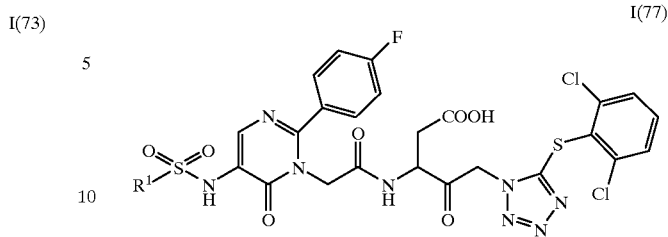

(wherein R¹ has the same meaning as hereinbefore defined)

or a non-toxic salt thereof, an acid addition salt thereof or a hydrate thereof.

Examples of representative compounds of formula (I) of the present invention are listed in Table 1–77 or a non-toxic salt thereof, an acid addition salt thereof or a hydrate thereof and described in example.

TABLE 1

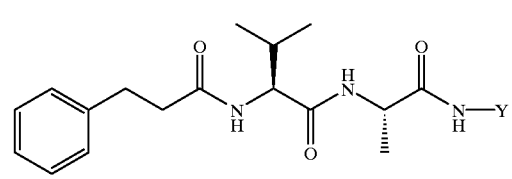

| No. | Y |
|---|---|
| 1 | 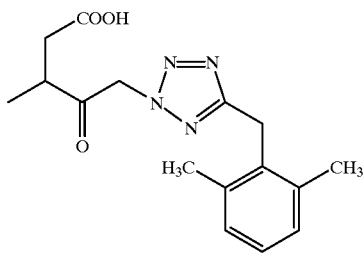 |
| 2 | 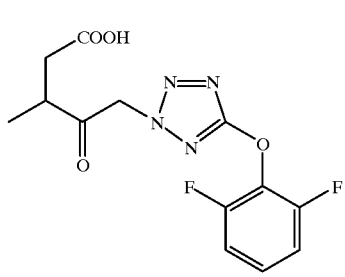 |
| 3 | 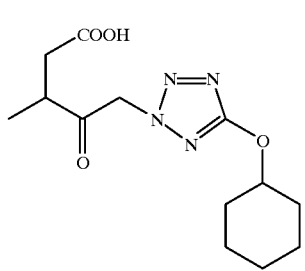 |

TABLE 1-continued
I (1)
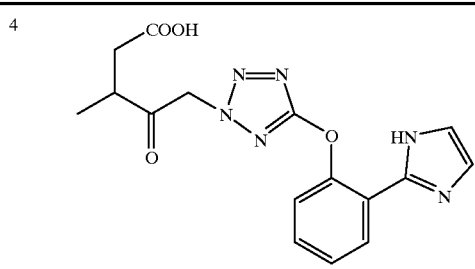
| No. | Y |
|---|---|
| 4 | 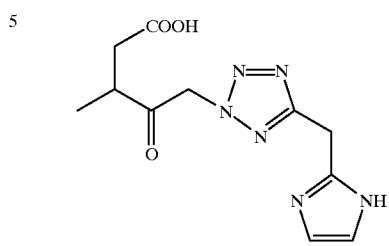 |
| 5 | 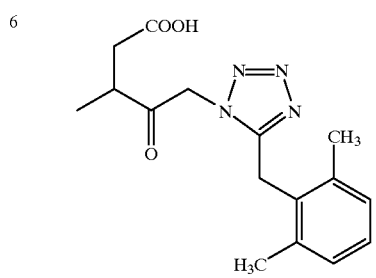 |
| 6 | 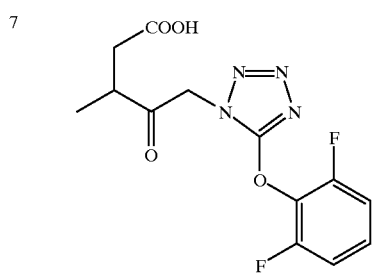 |
| 7 | 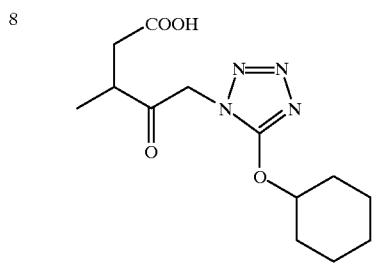 |
| 8 | |
TABLE 1-continued
I (1)
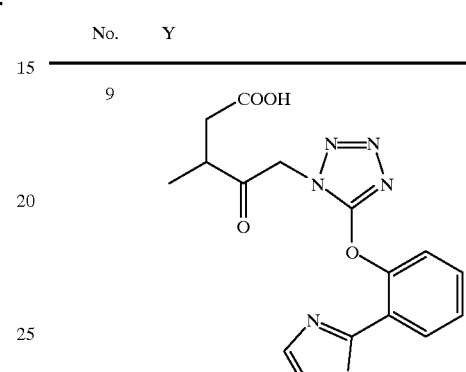
| No. | Y |
|---|---|
| 9 | 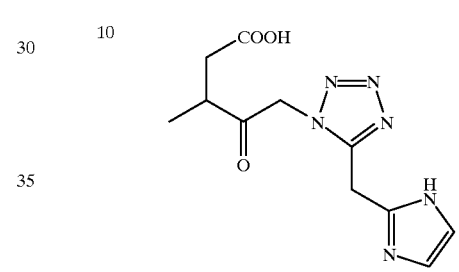 |
| 10 | |
TABLE 2
I (2)
| No. | Y |
|---|---|
| 1 | 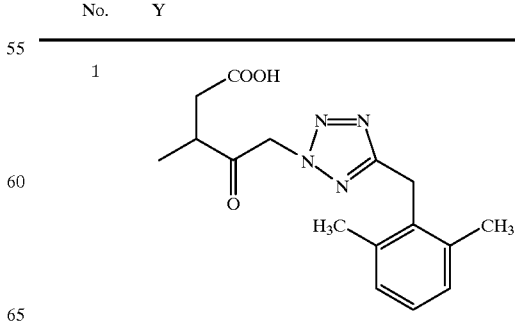 |

TABLE 2-continued
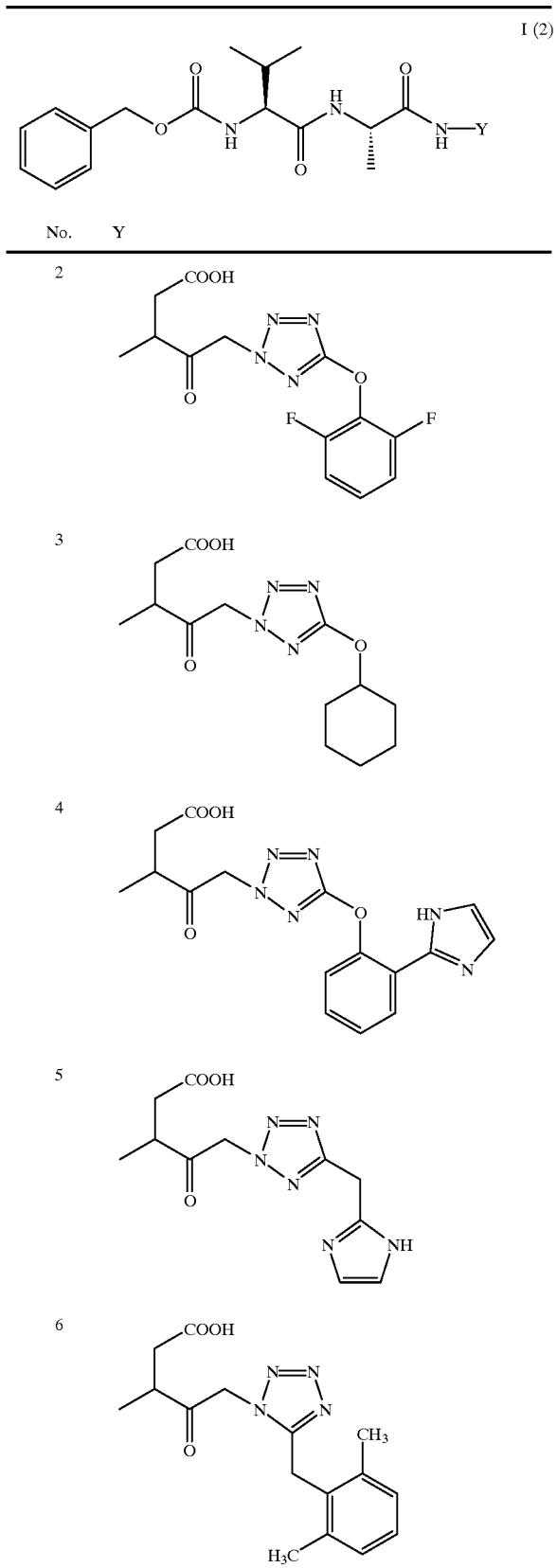
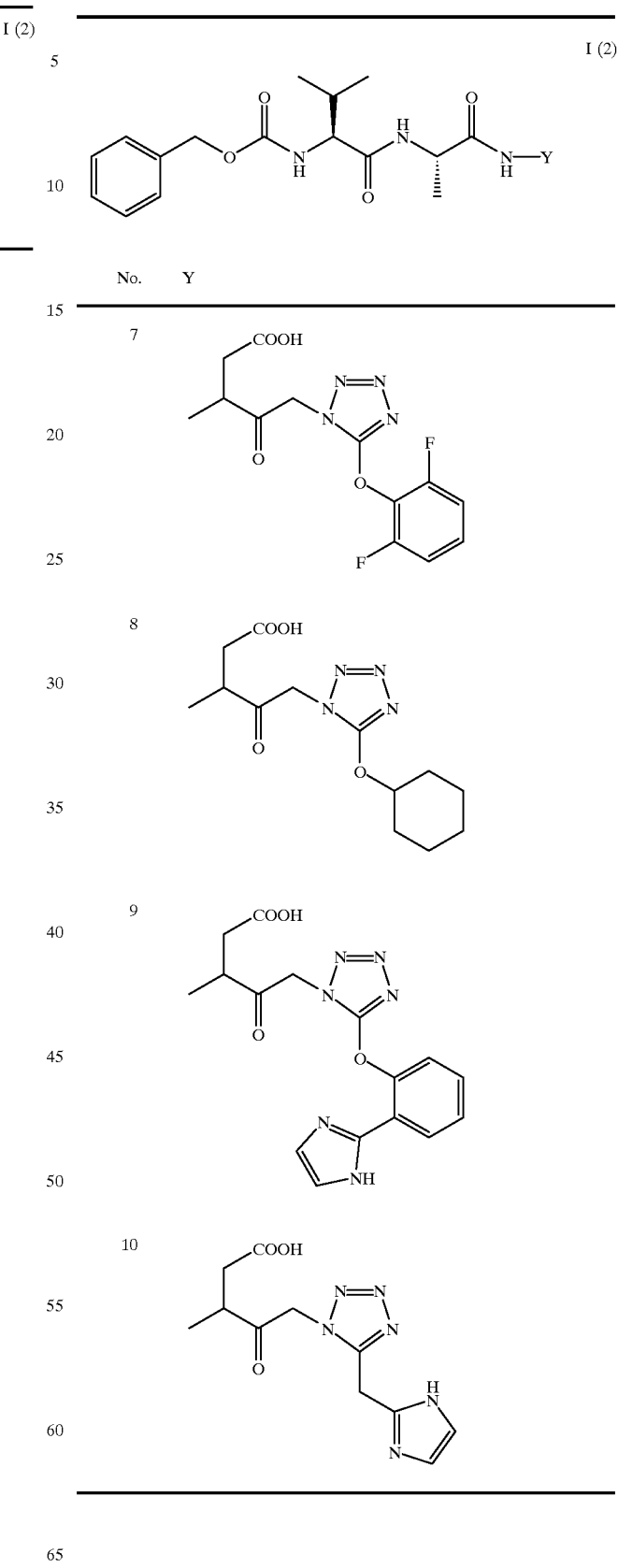

TABLE 3
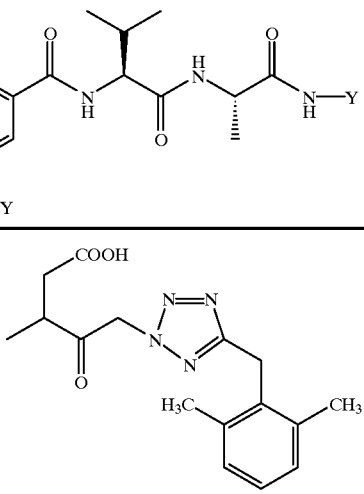
I (3)
| No. | Y |
|---|---|
| 1 | 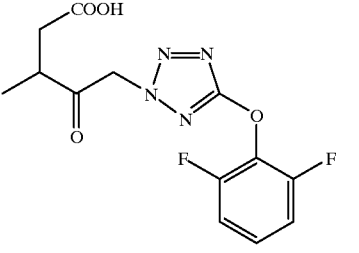 |
| 2 | 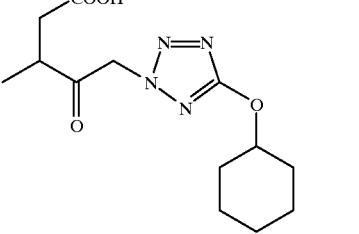 |
| 3 | 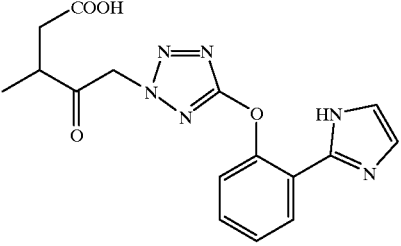 |
| 4 | 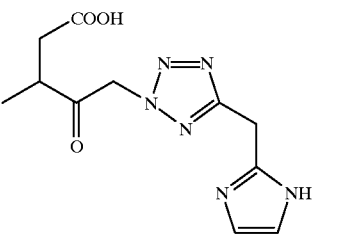 |
| 5 | 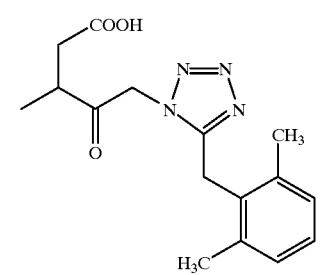 |
TABLE 3-continued
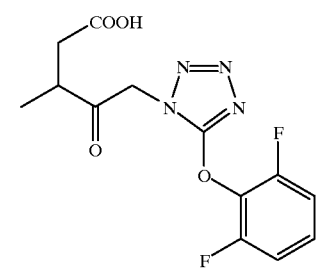
I (3)
| No. | Y |
|---|---|
| 6 | 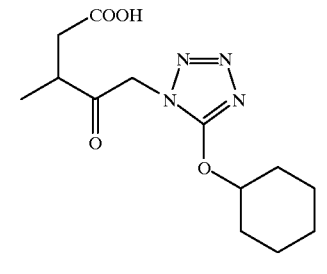 |
| 7 | 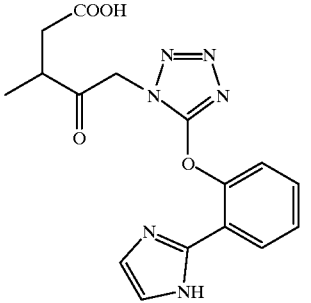 |
| 8 | |
| 9 | |

TABLE 3-continued

I (3)

| No. | Y |
|---|---|
| 10 | (structure: CH(CH3)-C(=O)-CH2-tetrazole-CH2-imidazole with COOH) |

TABLE 4

I (4)

| No. | Y |
|---|---|
| 1 | (structure with tetrazole-CH2-2,6-dimethylphenyl) |
| 2 | (structure with tetrazole-O-2,6-difluorophenyl) |

TABLE 4-continued

I (4)

| No. | Y |
|---|---|
| 3 | (structure with tetrazole-O-cyclohexyl) |
| 4 | (structure with tetrazole-O-phenyl-imidazole) |
| 5 | (structure with tetrazole-CH2-imidazole) |
| 6 | (structure with tetrazole-CH2-2,6-dimethylphenyl) |

TABLE 4-continued

I (4)

| No. | Y |
|-----|---|
| 7 | 3-methyl-4-oxo-5-[5-(2,6-difluorophenoxy)tetrazol-1-yl]pentanoic acid substituent |
| 8 | 3-methyl-4-oxo-5-[5-cyclohexyloxytetrazol-1-yl]pentanoic acid substituent |
| 9 | 3-methyl-4-oxo-5-[5-(2-(imidazol-2-yl)phenoxy)tetrazol-1-yl]pentanoic acid substituent |
| 10 | 3-methyl-4-oxo-5-[5-((imidazol-2-yl)methyl)tetrazol-1-yl]pentanoic acid substituent |

TABLE 5

I (5)

| No. | Y |
|-----|---|
| 1 | 3-methyl-4-oxo-5-[5-(2,6-dimethylbenzyl)tetrazol-2-yl]pentanoic acid substituent |
| 2 | 3-methyl-4-oxo-5-[5-(2,6-difluorophenoxy)tetrazol-2-yl]pentanoic acid substituent |
| 3 | 3-methyl-4-oxo-5-[5-cyclohexyloxytetrazol-2-yl]pentanoic acid substituent |
| 4 | 3-methyl-4-oxo-5-[5-(2-(imidazol-2-yl)phenoxy)tetrazol-2-yl]pentanoic acid substituent |
| 5 | 3-methyl-4-oxo-5-[5-((imidazol-2-yl)methyl)tetrazol-2-yl]pentanoic acid substituent |

TABLE 5-continued
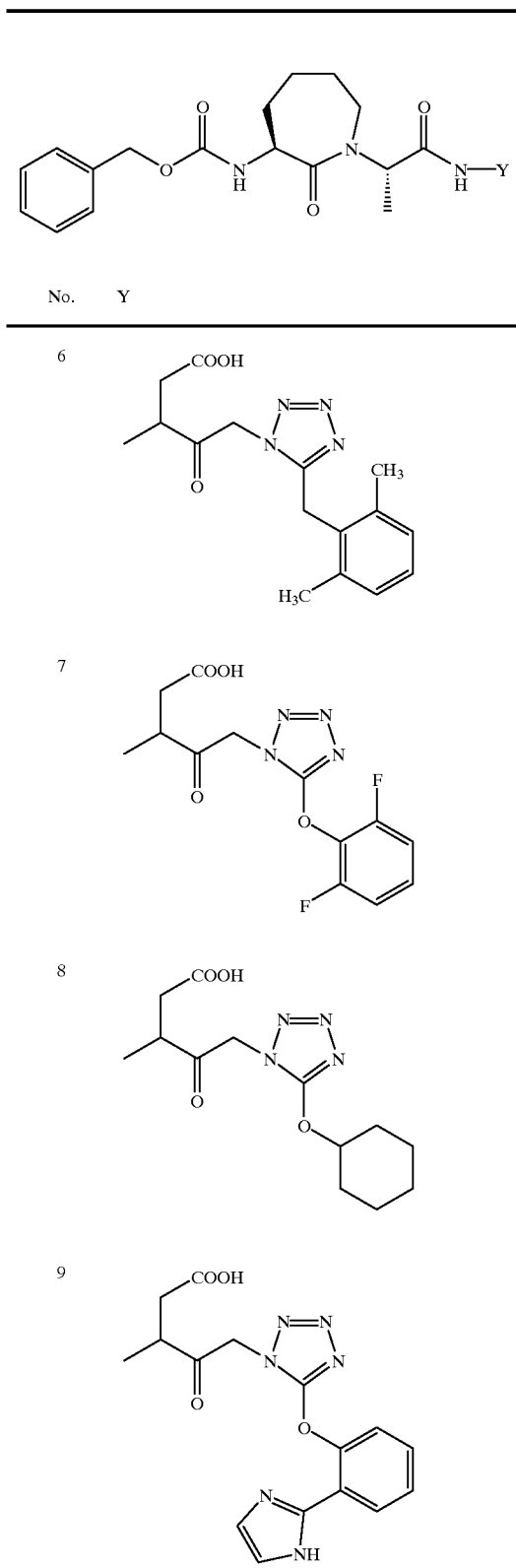
TABLE 5-continued
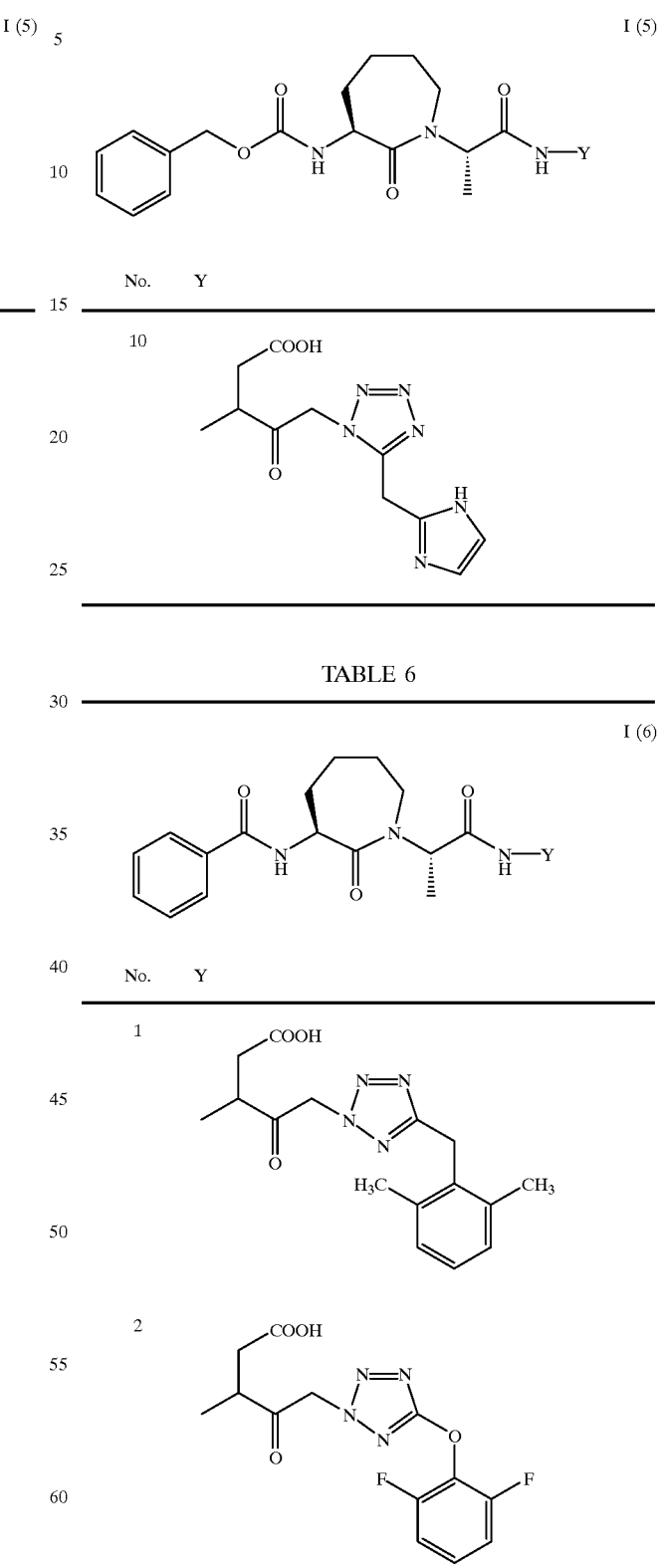

TABLE 6-continued

I (6)

| No. | Y |
|-----|---|
| 3 | (3-methyl-4-oxo-pentanoic acid with tetrazole-O-cyclohexyl) |
| 4 | (3-methyl-4-oxo-pentanoic acid with tetrazole-O-phenyl-imidazole) |
| 5 | (3-methyl-4-oxo-pentanoic acid with tetrazole-CH2-imidazole) |
| 6 | (3-methyl-4-oxo-pentanoic acid with tetrazole-CH2-2,6-dimethylphenyl) |
| 7 | (3-methyl-4-oxo-pentanoic acid with tetrazole-O-2,6-difluorophenyl) |
| 8 | (3-methyl-4-oxo-pentanoic acid with tetrazole-O-cyclohexyl) |
| 9 | (3-methyl-4-oxo-pentanoic acid with tetrazole-O-phenyl-imidazole) |
| 10 | (3-methyl-4-oxo-pentanoic acid with tetrazole-CH2-imidazole) |

TABLE 7
I (7)
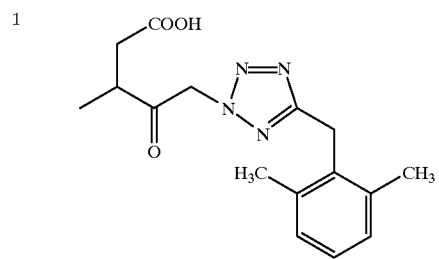
| No. | Y |
|-----|---|
| 1 | 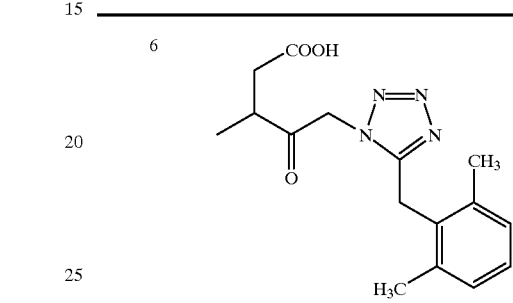 |
| 2 | |
| 3 | |
| 4 | |
| 5 | |
TABLE 7-continued
I (7)
| No. | Y |
|-----|---|
| 6 | 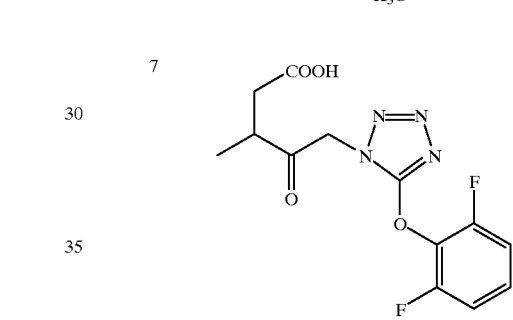 |
| 7 | |
| 8 | 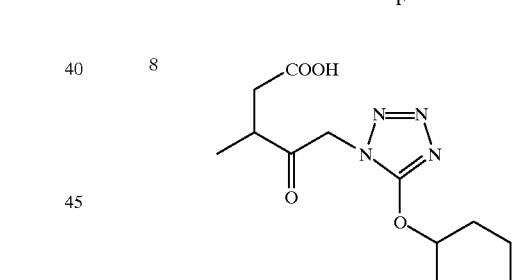 |
| 9 | 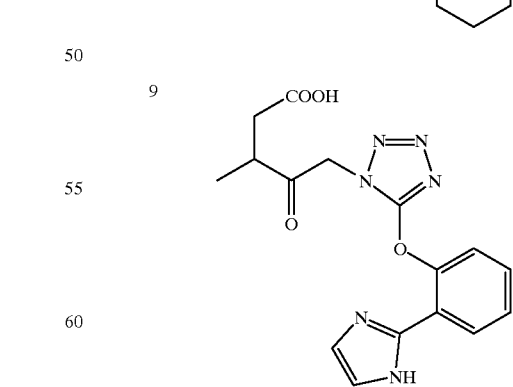 |

TABLE 7-continued

I (7)

| No. | Y |
|---|---|
| 10 | (structure: methyl-branched chain with COOH, ketone, tetrazole, and imidazole-CH₂) |

TABLE 8

I (8)

| No. | Y |
|---|---|
| 1 | (structure: COOH, methyl, ketone, tetrazole, CH₂-2,6-dimethylphenyl) |
| 2 | (structure: COOH, methyl, ketone, tetrazole-O-2,6-difluorophenyl) |
| 3 | (structure: COOH, methyl, ketone, tetrazole-O-cyclohexyl) |
| 4 | (structure: COOH, methyl, ketone, tetrazole-O-(2-(1H-imidazol-2-yl)phenyl)) |
| 5 | (structure: COOH, methyl, ketone, tetrazole-CH₂-1H-imidazol-2-yl) |
| 6 | (structure: COOH, methyl, ketone, tetrazole-CH₂-2,6-dimethylphenyl) |

TABLE 8-continued

TABLE 9

TABLE 9-continued
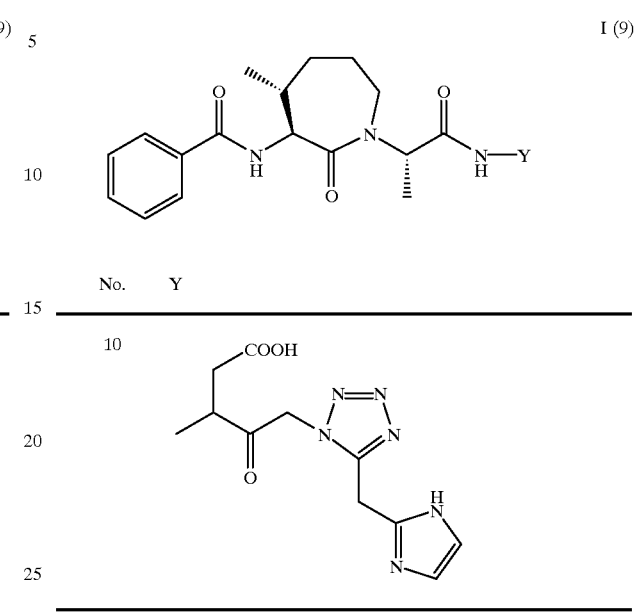
I (9)
| No. | Y |
|---|---|
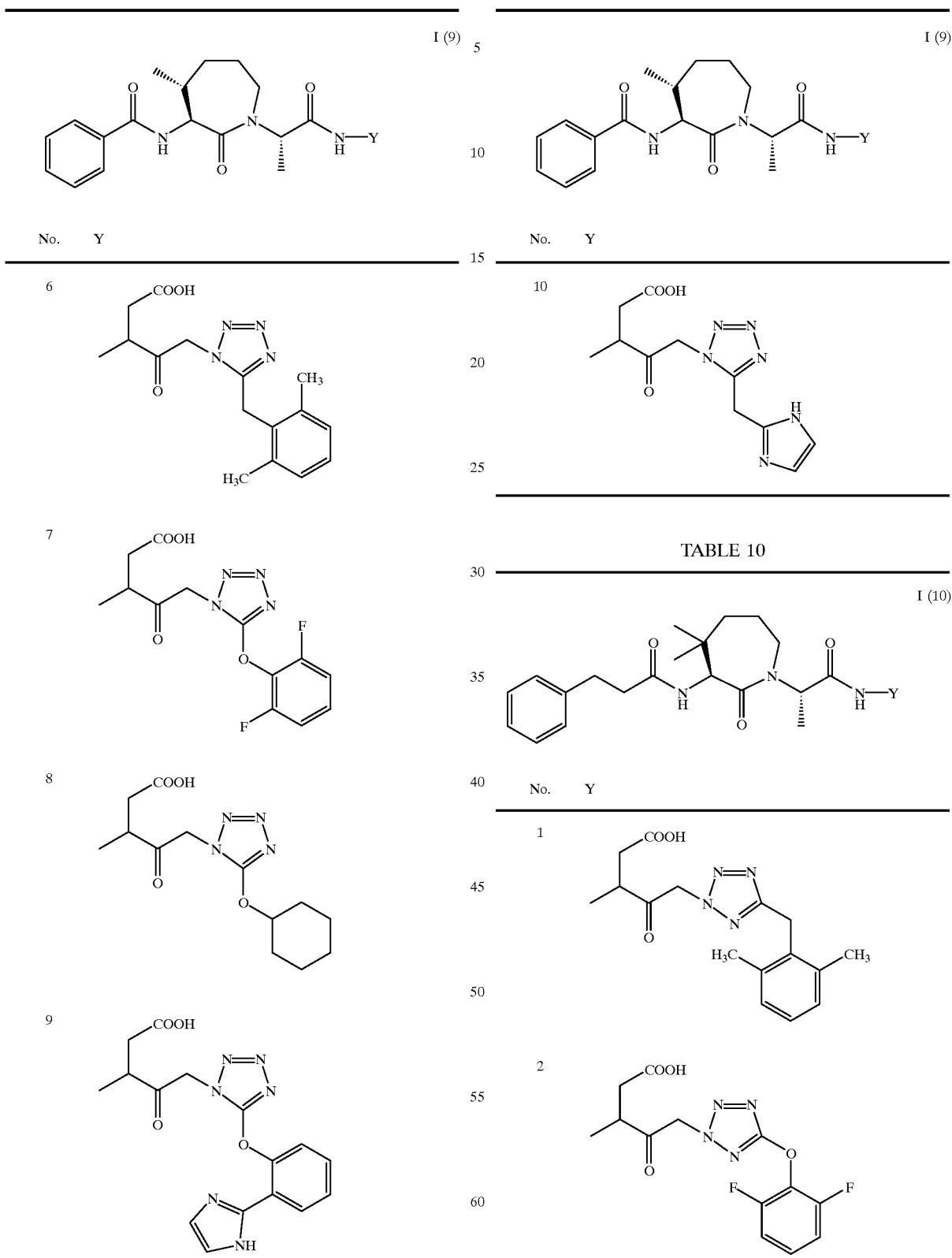
TABLE 10
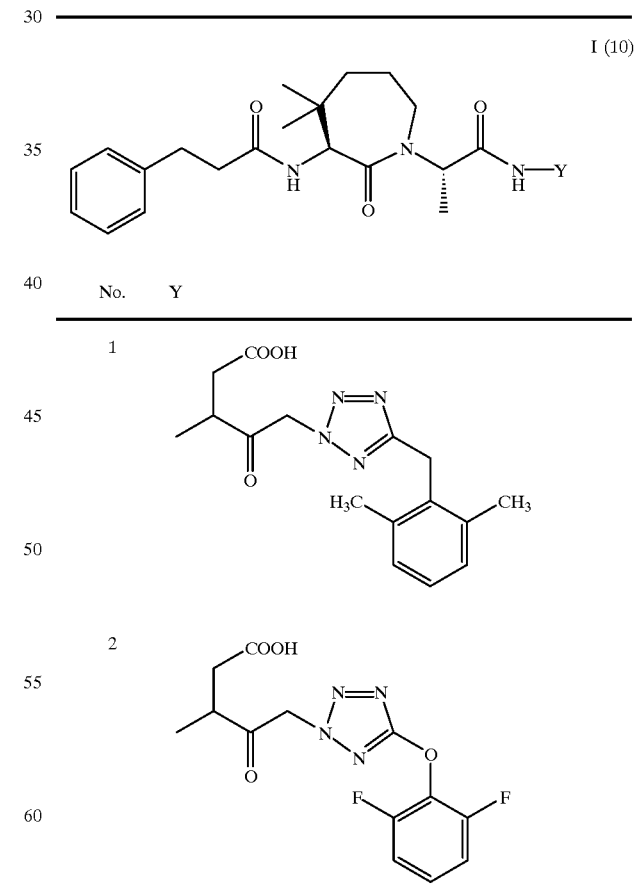
I (10)
| No. | Y |
|---|---|

TABLE 10-continued

I (10)

| No. | Y |
|---|---|
| 3 | (3-methyl-4-oxo-pentanoic acid with tetrazole-O-cyclohexyl) |
| 4 | (3-methyl-4-oxo-pentanoic acid with tetrazole-O-phenyl-imidazole) |
| 5 | (3-methyl-4-oxo-pentanoic acid with tetrazole-CH₂-imidazole) |
| 6 | (3-methyl-4-oxo-pentanoic acid with tetrazole-CH₂-2,6-dimethylphenyl) |
| 7 | (3-methyl-4-oxo-pentanoic acid with tetrazole-O-2,6-difluorophenyl) |
| 8 | (3-methyl-4-oxo-pentanoic acid with tetrazole-O-cyclohexyl) |
| 9 | (3-methyl-4-oxo-pentanoic acid with tetrazole-O-phenyl-imidazole) |
| 10 | (3-methyl-4-oxo-pentanoic acid with tetrazole-CH₂-imidazole) |

TABLE 11
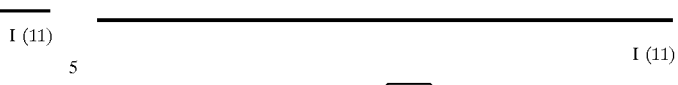
I (11)
| No. | Y |
|---|---|
| 1 | 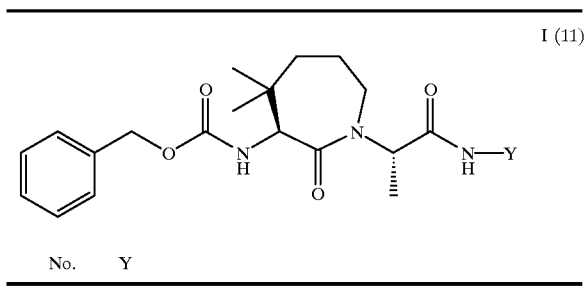 |
| 2 | 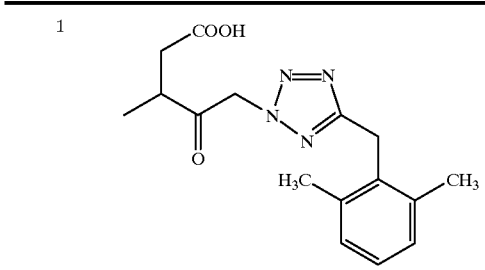 |
| 3 | 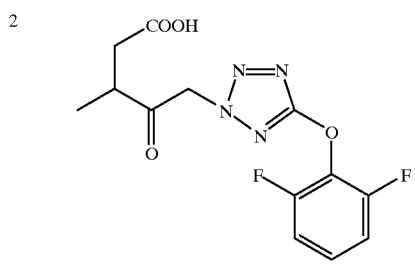 |
| 4 | 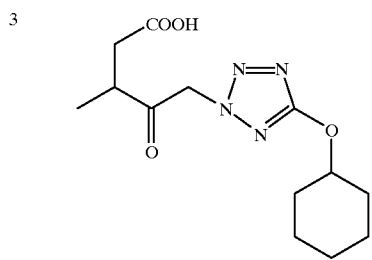 |
| 5 | 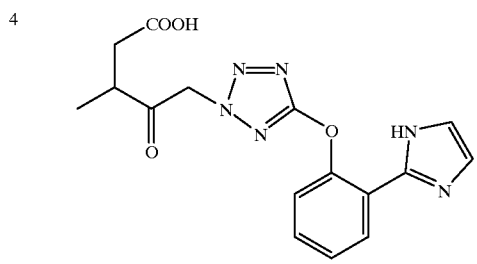 |
TABLE 11-continued
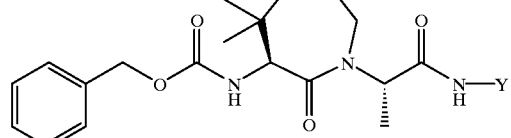
I (11)
| No. | Y |
|---|---|
| 6 |  |
| 7 | 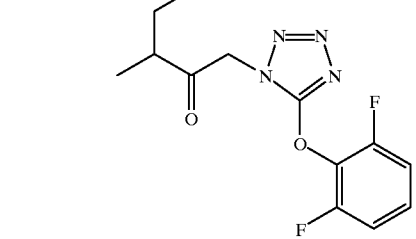 |
| 8 | 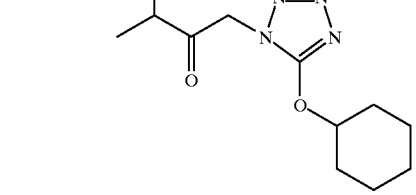 |
| 9 | 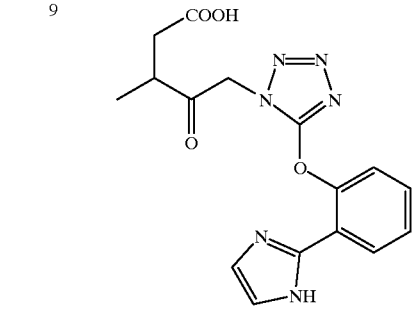 |

TABLE 11-continued
I (11)
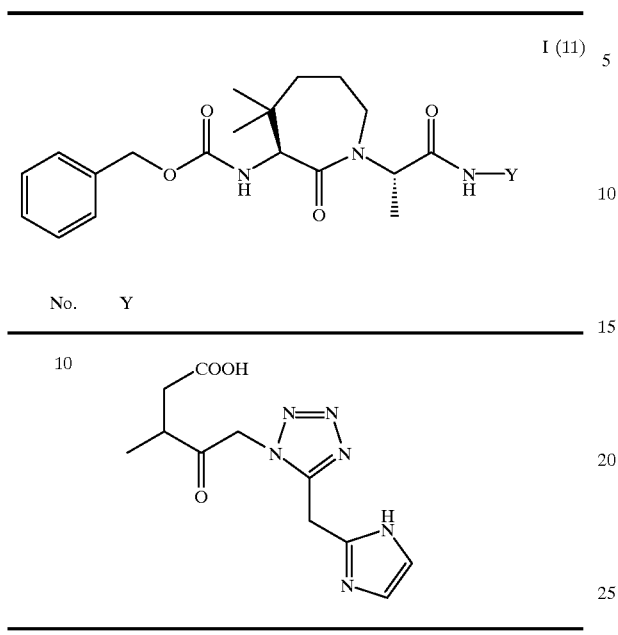
| No. | Y |
|---|---|
| 10 | 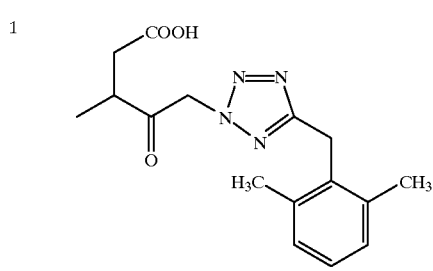 |
TABLE 12
I (12)
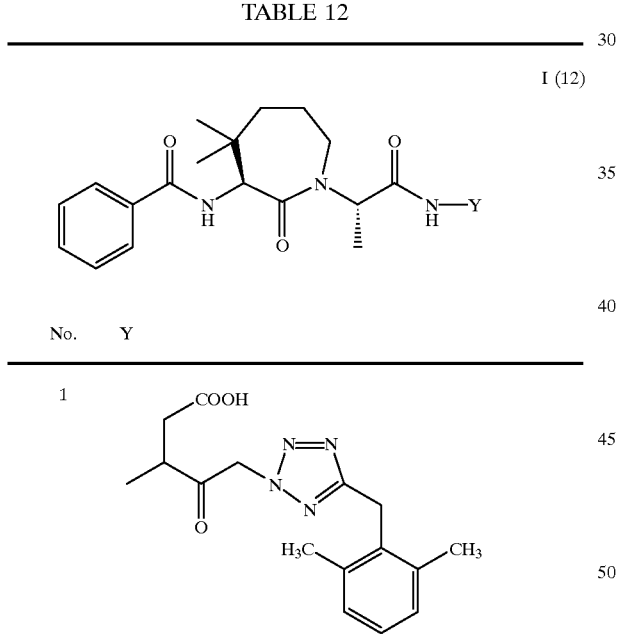
| No. | Y |
|---|---|
| 1 | 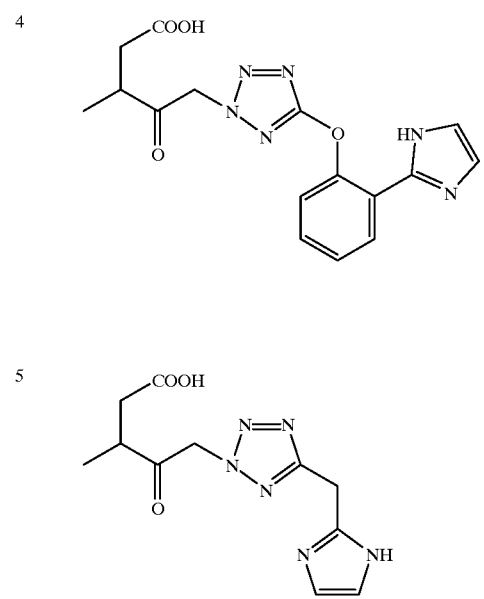 |
| 2 | 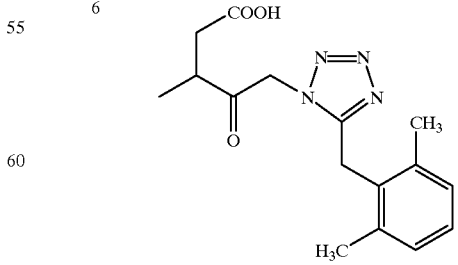 |
TABLE 12-continued
I (12)
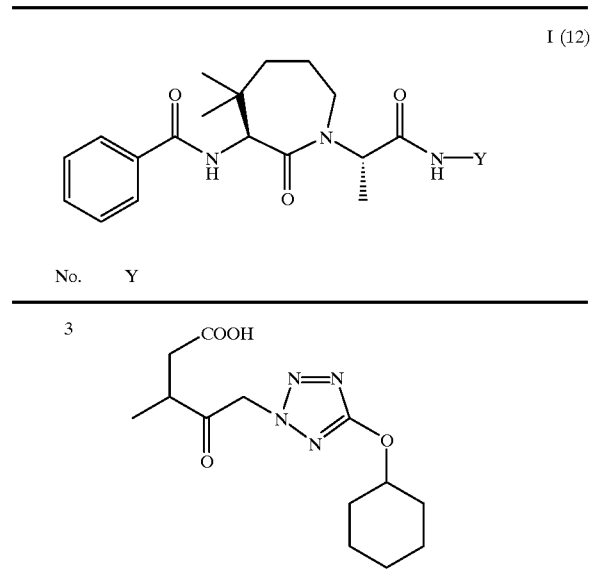
| No. | Y |
|---|---|
| 3 | 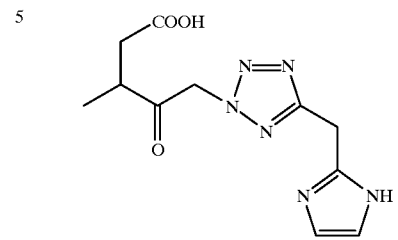 |
| 4 | |
| 5 | |
| 6 | |

TABLE 12-continued
I (12)
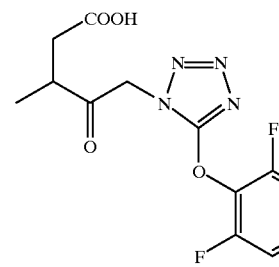
| No. | Y |
|---|---|
| 7 | 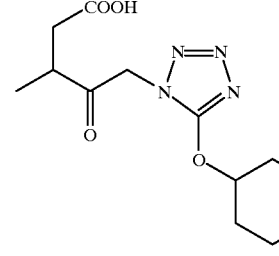 |
| 8 | 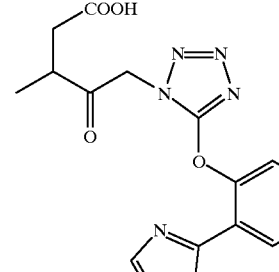 |
| 9 | 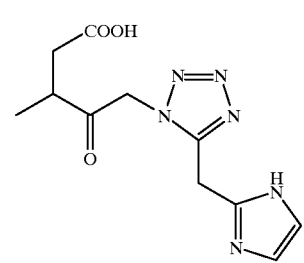 |
| 10 | 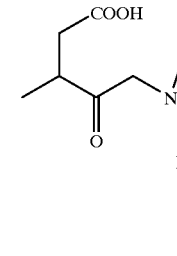 |
TABLE 13
I (13)
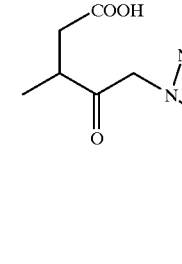
| No. | Y |
|---|---|
| 1 | 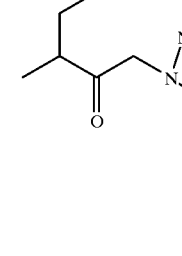 |
| 2 | 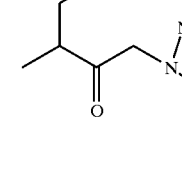 |
| 3 | |
| 4 | |

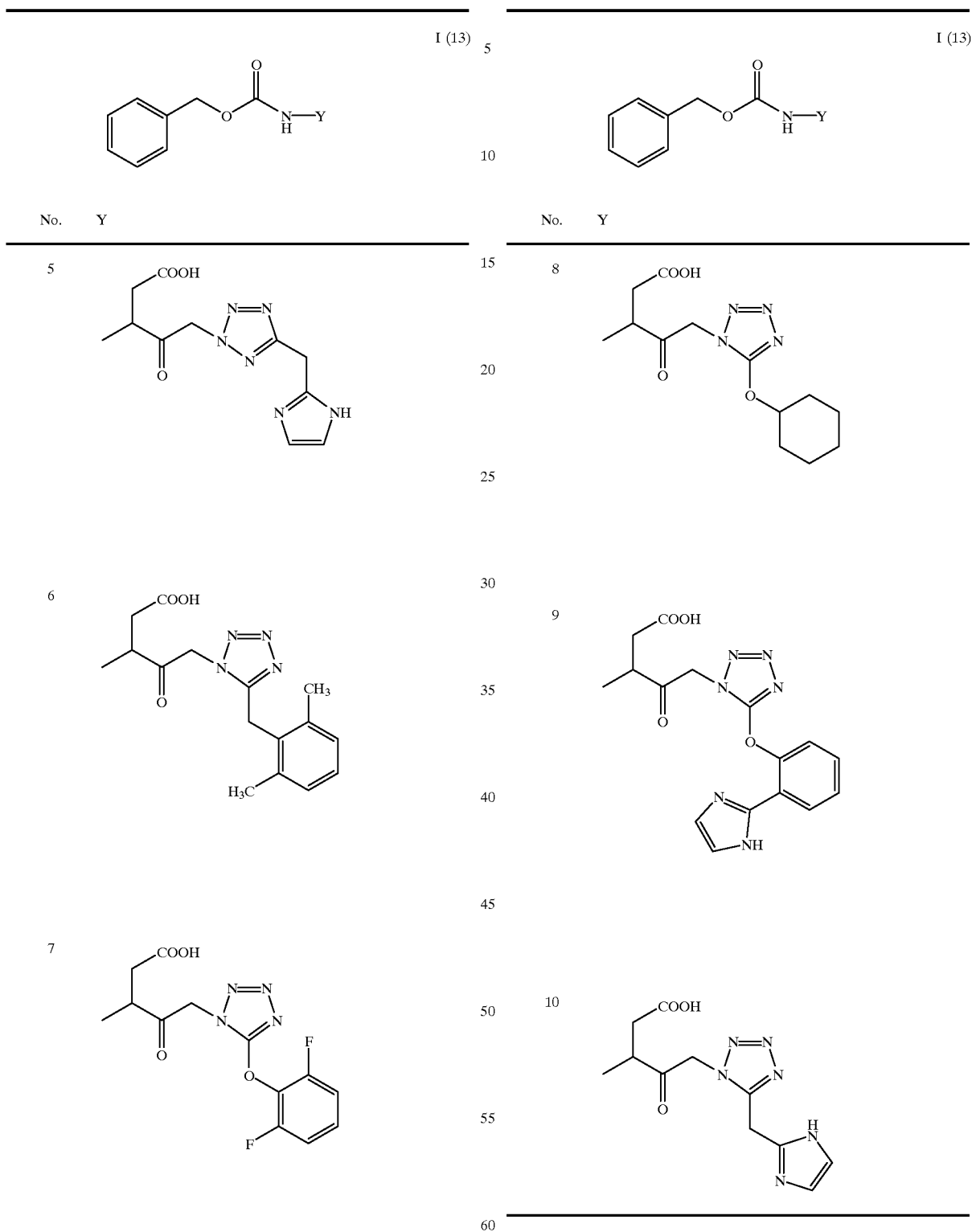

TABLE 14
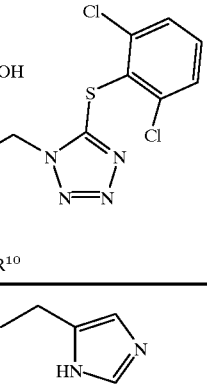
| No. | R⁴ | R⁹ | R¹⁰ |
|---|---|---|---|
| 1 | i-Pr | H | 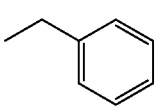 |
| 2 | i-Pr | H | —CH₂—OH |
| 3 | i-Pr | H | 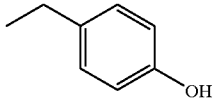 |
| 4 | i-Pr | Me | Me |
| 5 | i-Pr | | —(CH₂)₃— |
| 6 | i-Pr | | —CH₂CH═CHCH₂— |
| 7 | Me | H | Me |
| 8 | i-Bu | H | Me |
| 9 | 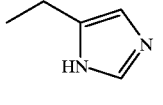 | H | Me |
| 10 | 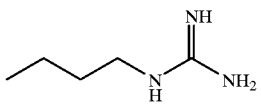 | H | Me |
| 11 | 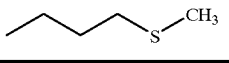 | H | Me |
| 12 |  | H | Me |

TABLE 15

I (15)

[Structure: Ph-CH2-CH2-C(=O)-NH-CH(R4)-C(=O)-N(R9)-CH(R10)-C(=O)-NH-CH(CH2-COOH)-C(=O)-CH2-tetrazole-S-(2,6-dichlorophenyl)]

| No. | R⁴ | R⁹ | R¹⁰ |
|---|---|---|---|
| 1 | i-Pr | H | -CH2-(1H-imidazol-4-yl) |
| 2 | i-Pr | H | —CH₂—OH |
| 3 | i-Pr | H | -CH2-phenyl |
| 4 | i-Pr | Me | Me |
| 5 | i-Pr | | —(CH₂)₃— |
| 6 | i-Pr | | —CH₂CH=CHCH₂— |
| 7 | Me | H | Me |
| 8 | i-Bu | H | Me |
| 9 | -CH2-(4-hydroxyphenyl) | H | Me |
| 10 | -CH2-(1H-imidazol-4-yl) | H | Me |
| 11 | -(CH2)3-NH-C(=NH)-NH2 | H | Me |
| 12 | -(CH2)3-S-CH3 | H | Me |

TABLE 16

I (16)

[Structure: benzyl-O-C(=O)-NH-CH(R⁴)-C(=O)-N(R⁹)-CH(R¹⁰)-C(=O)-NH-CH(CH₂COOH)-C(=O)-CH₂-N(tetrazole-S-(2,6-dichlorophenyl))]

| No. | R⁴ | R⁹ | R¹⁰ |
|---|---|---|---|
| 1 | i-Pr | H | 4-ethyl-1H-imidazole |
| 2 | i-Pr | H | —CH₂—OH |
| 3 | i-Pr | H | —CH₂—C₆H₅ |
| 4 | i-Pr | Me | Me |
| 5 | i-Pr |  | —(CH₂)₃— |
| 6 | i-Pr |  | —CH₂CH=CHCH₂— |
| 7 | Me | H | Me |
| 8 | i-Bu | H | Me |
| 9 | 4-hydroxybenzyl | H | Me |
| 10 | (4-ethyl-1H-imidazol-yl) | H | Me |
| 11 | —(CH₂)₃—NH—C(=NH)—NH₂ | H | Me |
| 12 | —(CH₂)₃—S—CH₃ | H | Me |

TABLE 17
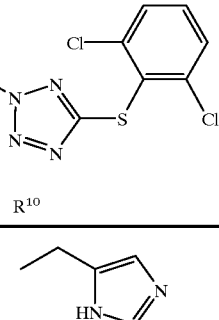
| No. | R⁴ | R⁹ | R¹⁰ |
|---|---|---|---|
| 1 | i-Pr | H | 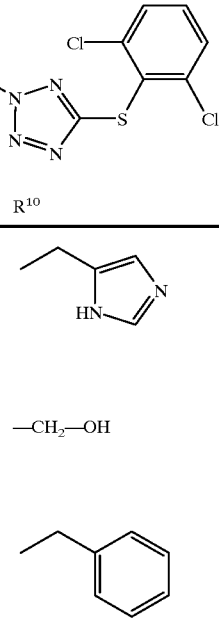 (4-ethyl-1H-imidazole) |
| 2 | i-Pr | H | —CH₂—OH |
| 3 | i-Pr | H | benzyl (—CH₂—C₆H₅) |
| 4 | i-Pr | Me | Me |
| 5 | i-Pr |  | —(CH₂)₃— |
| 6 | i-Pr |  | —CH₂CH=CHCH₂— |
| 7 | Me | H | Me |
| 8 | i-Bu | H | Me |
| 9 | 4-hydroxybenzyl | H | Me |
| 10 | (1H-imidazol-4-yl)methyl | H | Me |
| 11 | 4-guanidinobutyl | H | Me |
| 12 | 3-(methylthio)propyl | H | Me |

TABLE 18
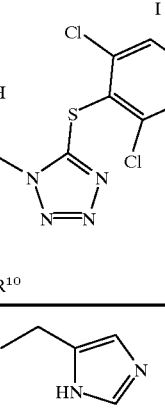
I (18)
| No. | R⁴ | R⁹ | R¹⁰ |
|---|---|---|---|
| 1 | i-Pr | H | (4-ethyl-1H-imidazole) |
| 2 | i-Pr | H | —CH₂—OH |
| 3 | i-Pr | H | (benzyl) |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | (4-hydroxybenzyl) | H | Me |
| 10 | (4-ethyl-1H-imidazole) | H | Me |
| 11 | (butyl guanidine) | H | Me |
| 12 | (butyl-S-CH₃) | H | Me |
TABLE 19
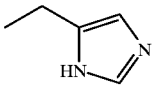
I (19)
| No. | R⁴ | R⁹ | R¹⁰ |
|---|---|---|---|
| 1 | i-Pr | H | (4-ethyl-1H-imidazole) |

TABLE 19-continued
I (19)
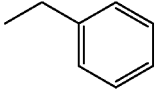
| No. | R⁴ | R⁹ | R¹⁰ |
|---|---|---|---|
| 2 | i-Pr | H | —CH₂—OH |
| 3 | i-Pr | H | 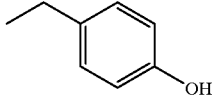 |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | 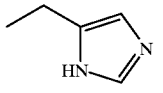 | H | Me |
| 10 | 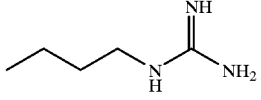 | H | Me |
| 11 | 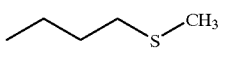 | H | Me |
| 12 |  | H | Me |

TABLE 20
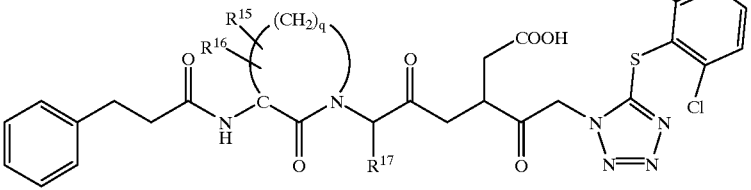
| No. | | R[17] | No. | | R[17] |
|---|---|---|---|---|---|
| 1 | 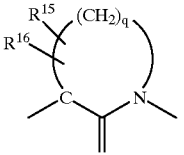 | Me | 7 | 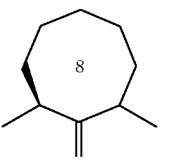 | Me |
| 2 | 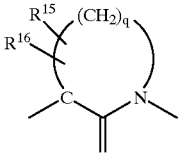 | Me | 8 | 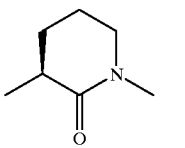 | Me |
| 3 | 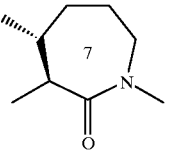 | Me | 9 | 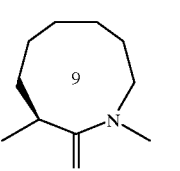 | Me |
| 4 | 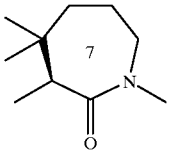 | Me | 10 | 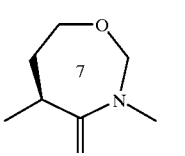 | Me |
| 5 | 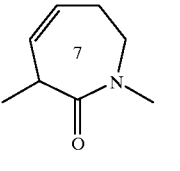 | Me | 11 | 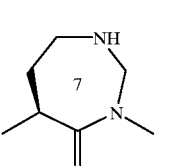 | Me |

TABLE 20-continued
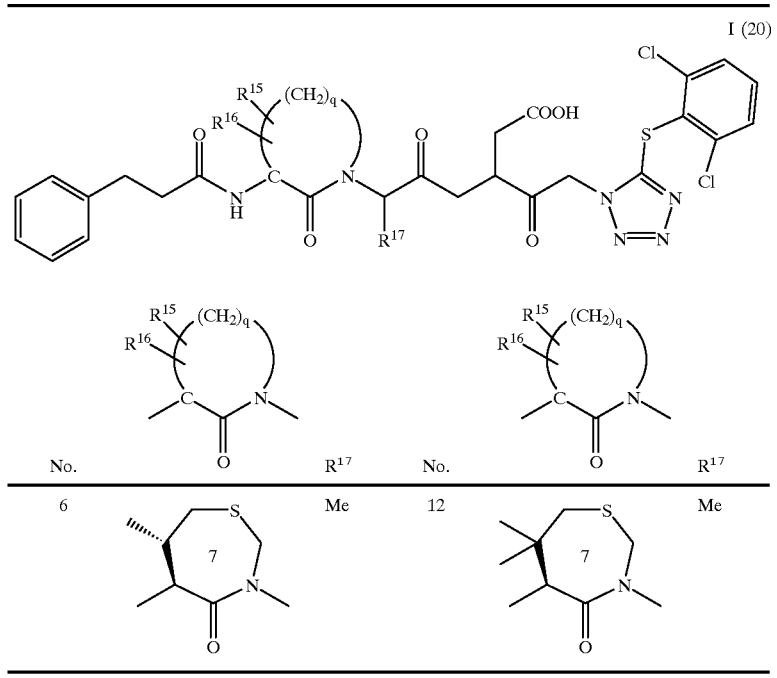
TABLE 21
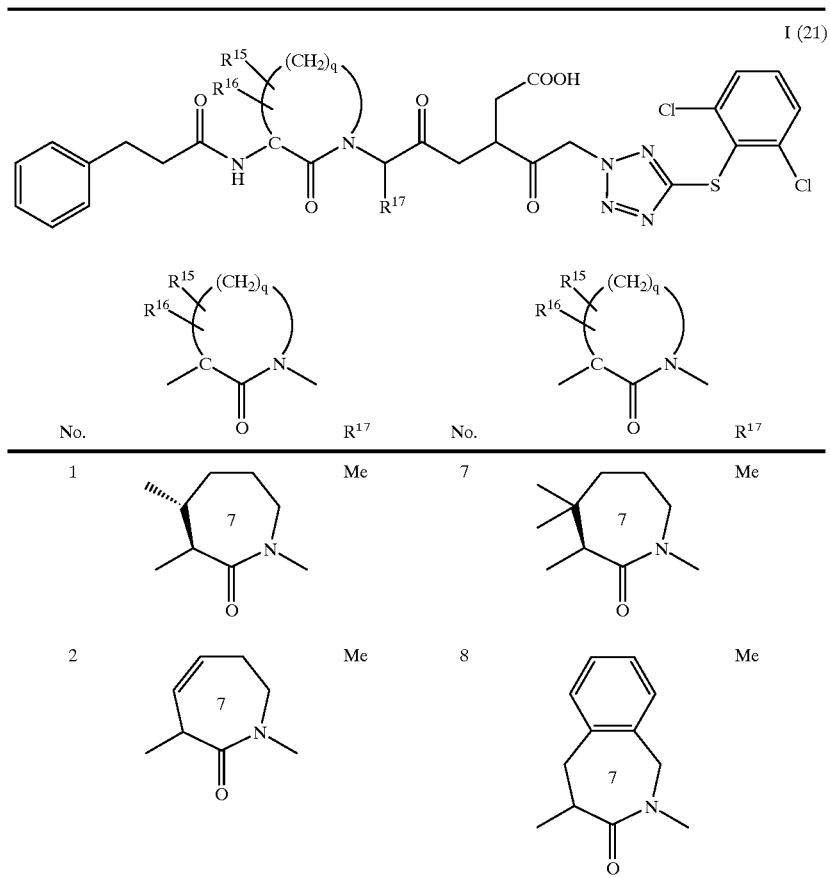

TABLE 21-continued
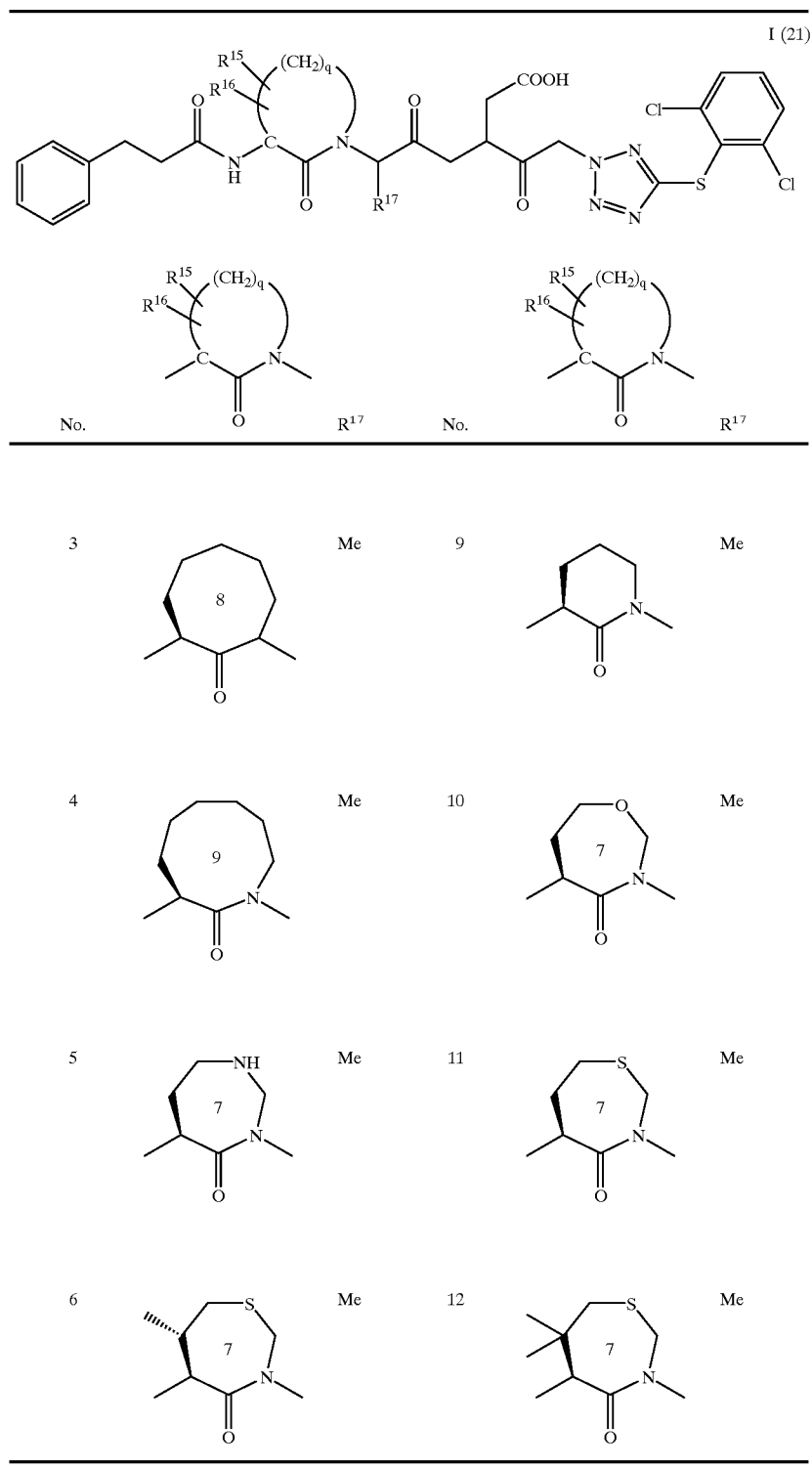

TABLE 22
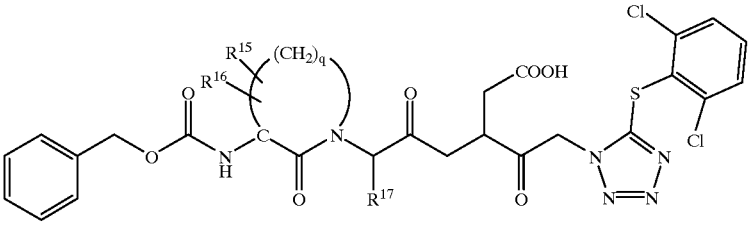
| No. | | R[17] | No. | | R[17] |
|---|---|---|---|---|---|
| 1 | 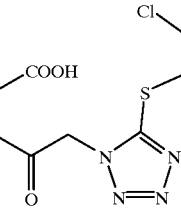 | Me | 7 | 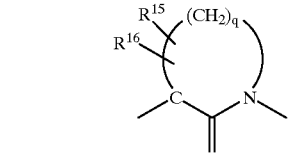 | Me |
| 2 | 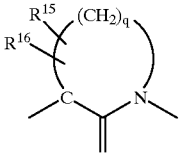 | Me | 8 | 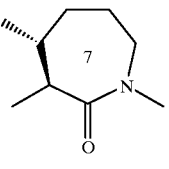 | Me |
| 3 | 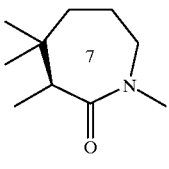 | Me | 9 | 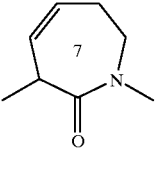 | Me |
| 4 | 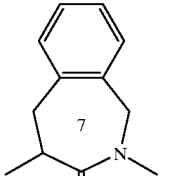 | Me | 10 | 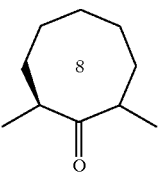 | Me |
| 5 | 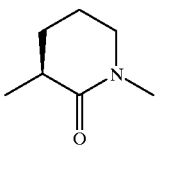 | Me | 11 | 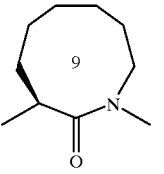 | Me |

TABLE 22-continued
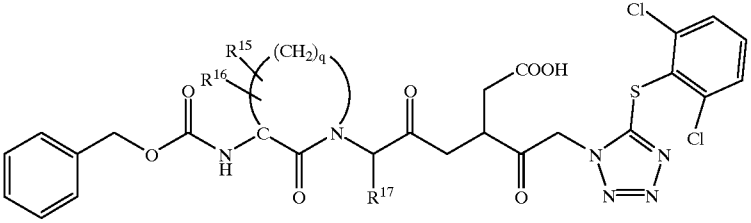
TABLE 23
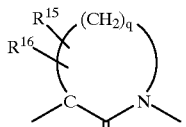

TABLE 23-continued
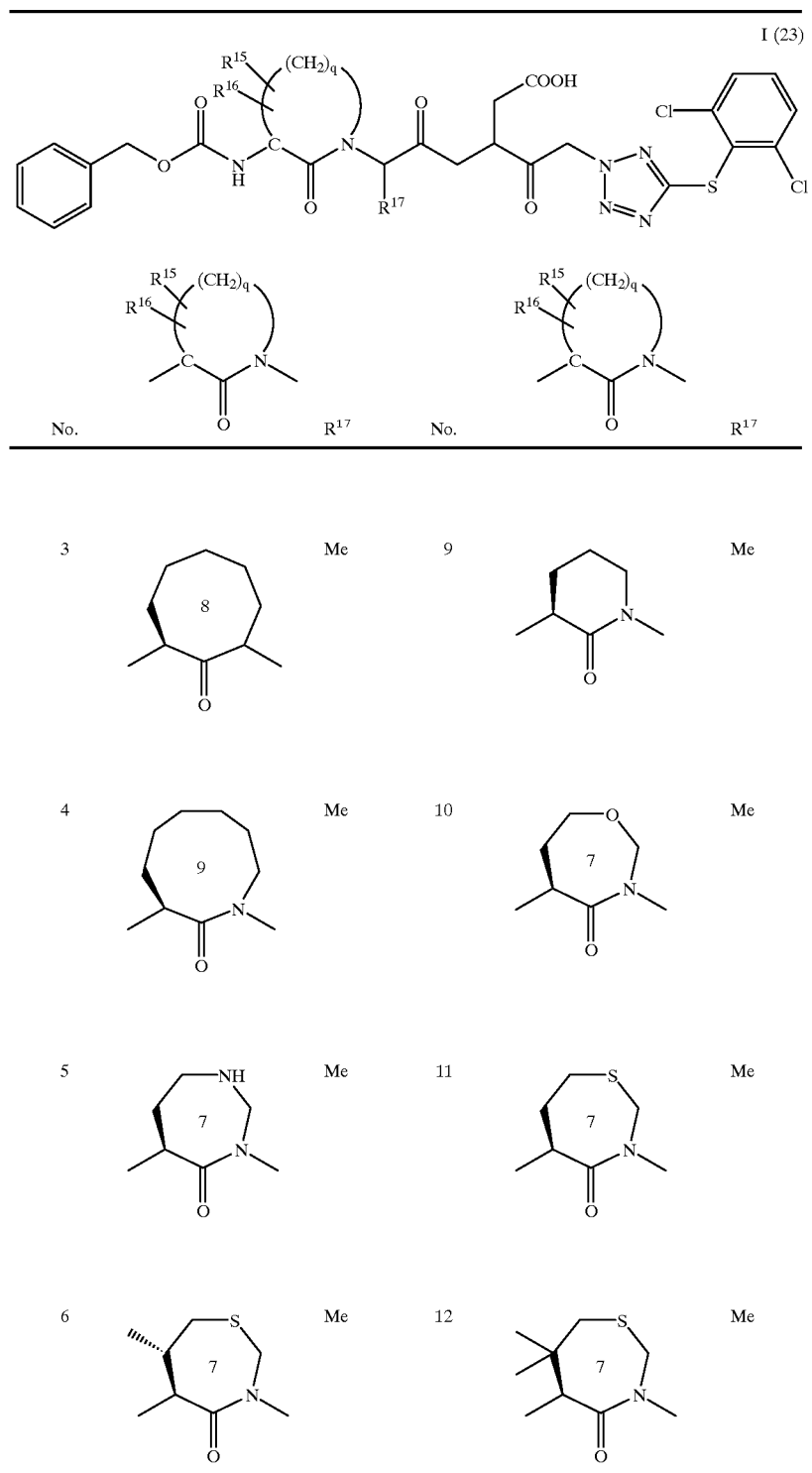

TABLE 24

TABLE 24-continued
I (24)
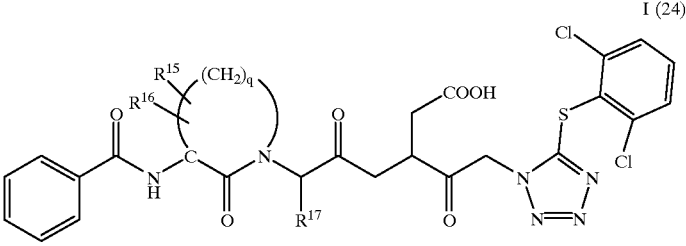
| No. | 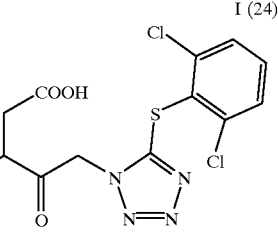 | R[17] | No. | 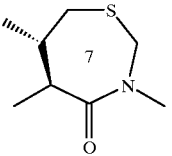 | R[17] |
|---|---|---|---|---|---|
| 6 | 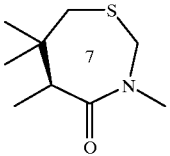 | Me | 12 | 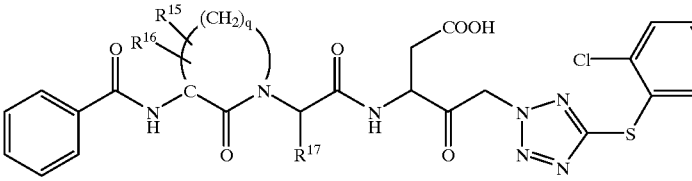 | Me |
TABLE 25
I (25)
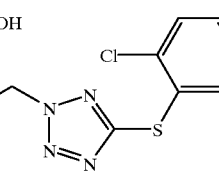
| No. | 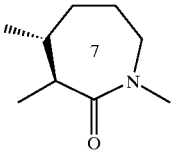 | R[17] | No. | 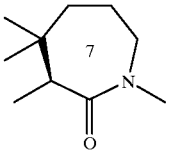 | R[17] |
|---|---|---|---|---|---|
| 1 | 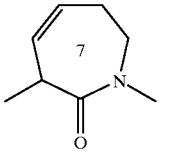 | Me | 7 | 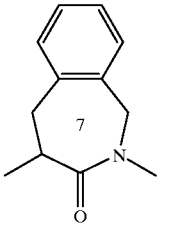 | Me |
| 2 | | Me | 8 | | Me |

TABLE 25-continued

TABLE 26
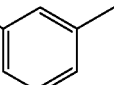
I (26)
| No. | R¹ | No. | R¹ |
|---|---|---|---|
| 1 | Me | 10 | 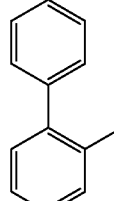 |
| 2 | 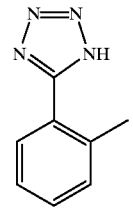 | 11 | 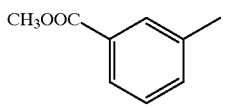 |
| 3 | 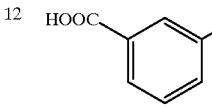 | 12 | 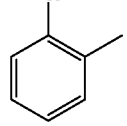 |
| 4 | 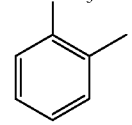 | 13 | 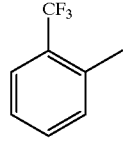 |
| 5 | 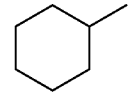 | 14 | 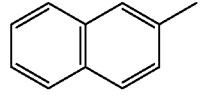 |
| 6 | 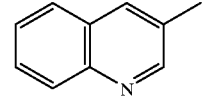 | 15 | 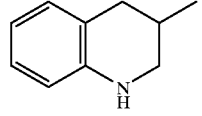 |
| 7 | 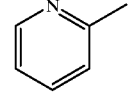 | 16 | 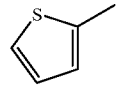 |
| 8 | 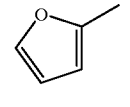 | 17 | 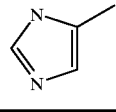 |
| 9 | 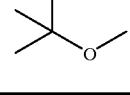 | 18 | 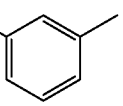 |
TABLE 27
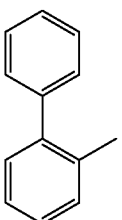
I (27)
| No. | R¹ | No. | R¹ |
|---|---|---|---|
| 1 | Me | 10 | 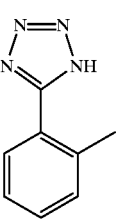 |
| 2 | 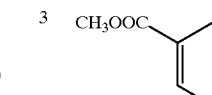 | 11 | 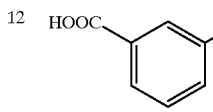 |
| 3 | 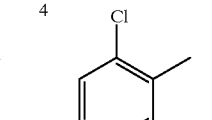 | 12 | 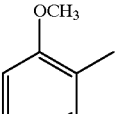 |
| 4 | 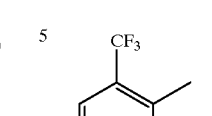 | 13 | 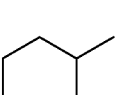 |
| 5 | 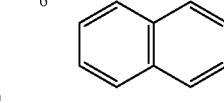 | 14 | 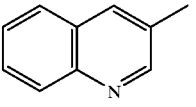 |
| 6 | 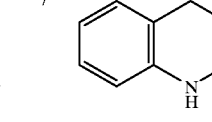 | 15 | 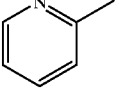 |
| 7 | 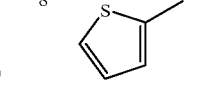 | 16 | 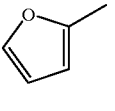 |
| 8 | 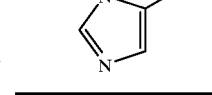 | 17 | 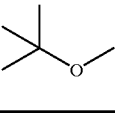 |

TABLE 28
I (28)
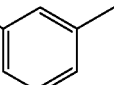
| No. | R¹ | No. | R¹ |
|---|---|---|---|
| 1 | Me | 10 | 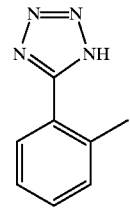 |
| 2 | 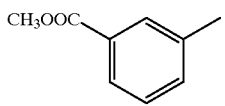 | 11 | 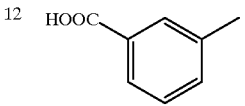 |
| 3 | 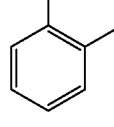 | 12 | 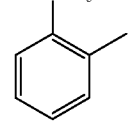 |
| 4 | 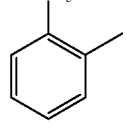 | 13 | 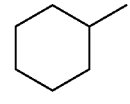 |
| 5 | 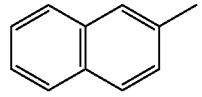 | 14 | 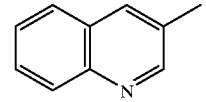 |
| 6 | 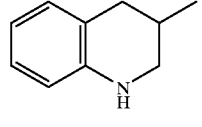 | 15 | 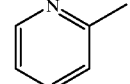 |
| 7 | 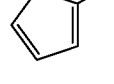 | 16 | 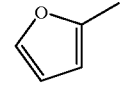 |
| 8 | 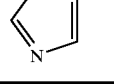 | 17 | 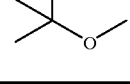 |
| 9 | 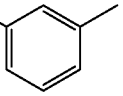 | 18 | 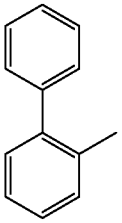 |
TABLE 29
I (29)
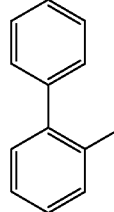
| No. | R¹ | No. | R¹ |
|---|---|---|---|
| 1 | Me | 10 | 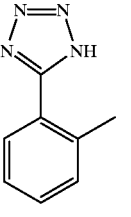 |
| 2 | 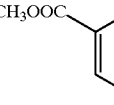 | 11 | 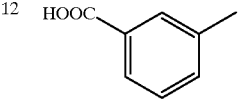 |
| 3 | 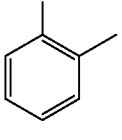 | 12 | 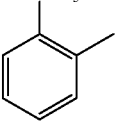 |
| 4 | 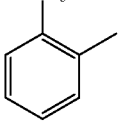 | 13 | 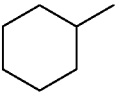 |
| 5 | 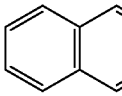 | 14 | 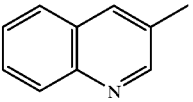 |
| 6 | 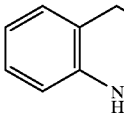 | 15 | 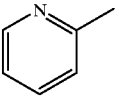 |
| 7 | 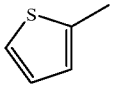 | 16 | 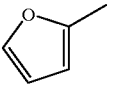 |
| 8 | 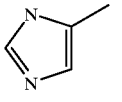 | 17 | 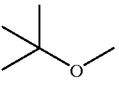 |
| 9 | | 18 | |

TABLE 30
I (30)
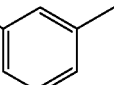
| No. | R¹ | No. | R¹ |
|---|---|---|---|
| 1 | Me | 10 | 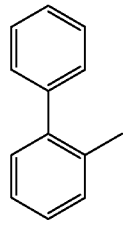 |
| 2 | 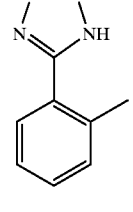 | 11 | 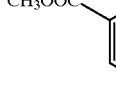 |
| 3 | 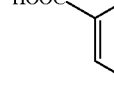 | 12 | 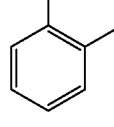 |
| 4 | 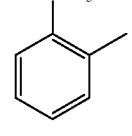 | 13 | 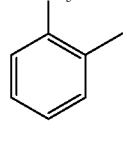 |
| 5 | 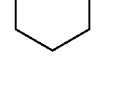 | 14 | 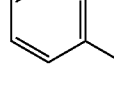 |
| 6 | 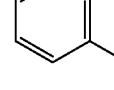 | 15 | 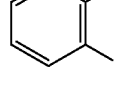 |
| 7 | 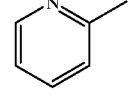 | 16 | 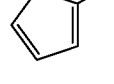 |
| 8 | 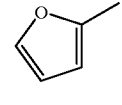 | 17 | 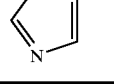 |
| 9 | 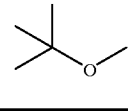 | 18 | 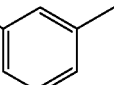 |
TABLE 31
I (31)
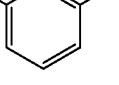
| No. | R¹ | No. | R¹ |
|---|---|---|---|
| 1 | Me | 10 | 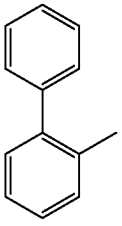 |
| 2 | 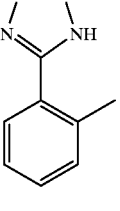 | 11 | 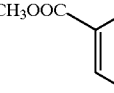 |
| 3 | 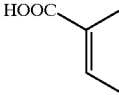 | 12 | 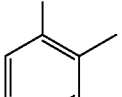 |
| 4 | 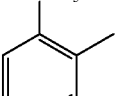 | 13 | 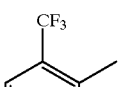 |
| 5 | 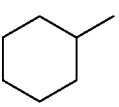 | 14 | 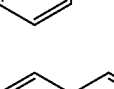 |
| 6 | 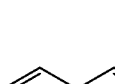 | 15 | 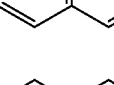 |
| 7 | 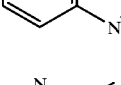 | 16 | 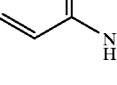 |
| 8 | 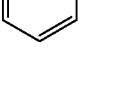 | 17 | 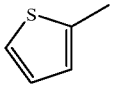 |
| 9 |  | 18 | |

TABLE 32

I (32)

| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-(carboxy)phenyl |
| 4 | 2-chlorophenyl | 13 | 2-methoxyphenyl |
| 5 | 2-(trifluoromethyl)phenyl | 14 | cyclohexyl |
| 6 | 2-naphthyl | 15 | 3-quinolinyl |
| 7 | 1,2,3,4-tetrahydroquinolin-3-yl | 16 | 2-pyridinyl |
| 8 | 2-thienyl | 17 | 2-furyl |
| 9 | 4-imidazolyl | 18 | tert-butoxymethyl |

TABLE 33

I (33)

| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-(carboxy)phenyl |
| 4 | 2-chlorophenyl | 13 | 2-methoxyphenyl |
| 5 | 2-(trifluoromethyl)phenyl | 14 | cyclohexyl |
| 6 | 2-naphthyl | 15 | 3-quinolinyl |
| 7 | 1,2,3,4-tetrahydroquinolin-3-yl | 16 | 2-pyridinyl |
| 8 | 2-thienyl | 17 | 2-furyl |
| 9 | 4-imidazolyl | 18 | tert-butoxymethyl |

TABLE 34
I (34)
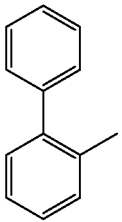
| No. | R¹ | No. | R¹ |
|---|---|---|---|
| 1 | Me | 10 | 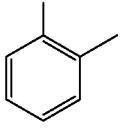 |
| 2 | 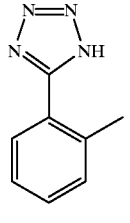 | 11 | 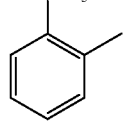 |
| 3 | 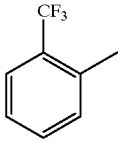 | 12 | 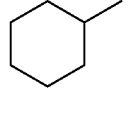 |
| 4 | 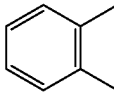 | 13 | 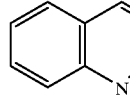 |
| 5 | 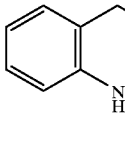 | 14 | 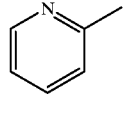 |
| 6 | 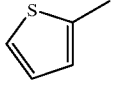 | 15 | 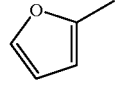 |
| 7 |  | 16 |  |
| 8 | 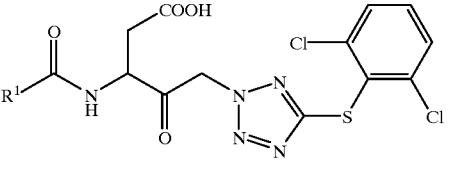 | 17 | 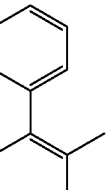 |
TABLE 34-continued
I (34)
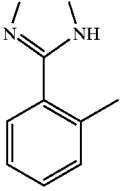
| No. | R¹ | No. | R¹ |
|---|---|---|---|
| 9 | 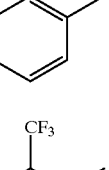 | 18 |  |
TABLE 35
I (35)
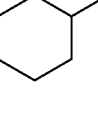
| No. | R¹ | No. | R¹ |
|---|---|---|---|
| 1 | Me | 10 | 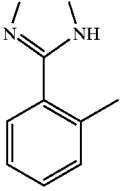 |
| 2 | 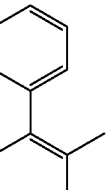 | 11 | 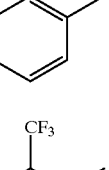 |
| 3 | 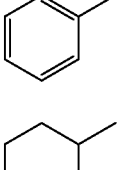 | 12 |  |
| 4 | | 13 | |
| 5 | | 14 | |

TABLE 35-continued

I (35)

| No. | R¹ | No. | R¹ |
|---|---|---|---|
| 6 | 2-naphthyl-methyl | 15 | 3-quinolinyl-methyl |
| 7 | 1,2,3,4-tetrahydroquinolin-3-yl-methyl | 16 | 2-pyridyl-methyl |
| 8 | 2-thienyl-methyl | 17 | 2-furyl-methyl |
| 9 | 4-imidazolyl-methyl | 18 | tert-butoxy-methyl |

TABLE 36

I (36)

| No. | Y |
|---|---|
| 1 | (2,6-dimethylbenzyl)-tetrazolyl derivative |
| 2 | (2,6-difluorophenoxy)-tetrazolyl derivative |
| 3 | (cyclohexyloxy)-tetrazolyl derivative |
| 4 | [2-(imidazol-2-yl)phenoxy]-tetrazolyl derivative |
| 5 | [(imidazol-2-yl)methyl]-tetrazolyl derivative |
| 6 | (2,6-dimethylbenzyl)-tetrazolyl derivative |

TABLE 36-continued
I (36)
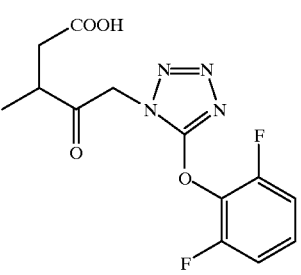
| No. | Y |
|---|---|
| 7 | 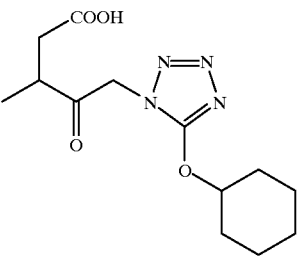 |
| 8 | 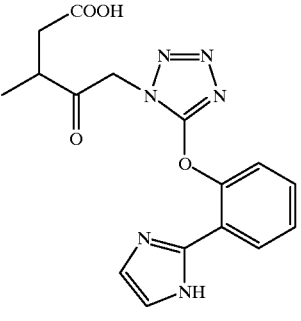 |
| 9 | 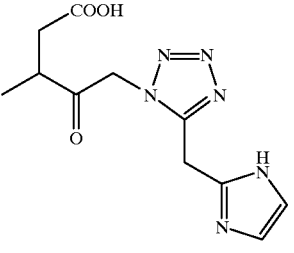 |
| 10 | 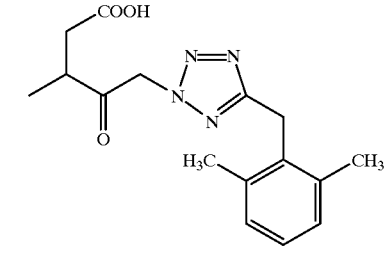 |
TABLE 37
I (37)
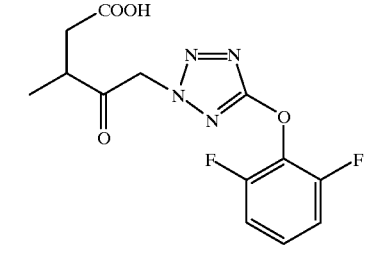
| No. | Y |
|---|---|
| 1 | 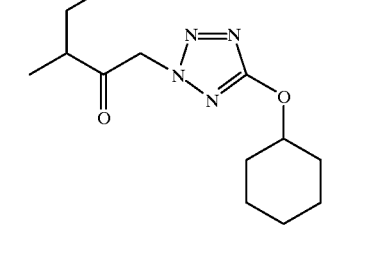 |
| 2 | 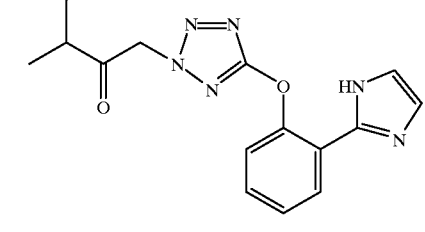 |
| 3 | 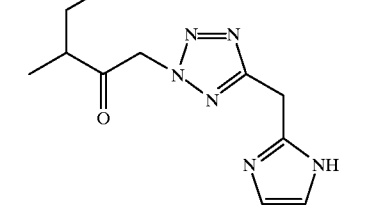 |
| 4 | |
| 5 | |

TABLE 37-continued

I (37)

| No. | Y |
|-----|---|
| 6 | (3-methyl-4-oxo-5-(5-(2,6-dimethylbenzyl)tetrazol-1-yl)pentanoic acid group) |
| 7 | (3-methyl-4-oxo-5-(5-(2,6-difluorophenoxy)tetrazol-1-yl)pentanoic acid group) |
| 8 | (3-methyl-4-oxo-5-(5-cyclohexyloxytetrazol-1-yl)pentanoic acid group) |
| 9 | (3-methyl-4-oxo-5-(5-(2-(1H-imidazol-2-yl)phenoxy)tetrazol-1-yl)pentanoic acid group) |

TABLE 37-continued

I (37)

| No. | Y |
|-----|---|
| 10 | (3-methyl-4-oxo-5-(5-((1H-imidazol-2-yl)methyl)tetrazol-1-yl)pentanoic acid group) |

TABLE 38

I (38)

| No. | Y |
|-----|---|
| 1 | (3-methyl-4-oxo-5-(5-(2,6-dimethylbenzyl)tetrazol-2-yl)pentanoic acid group) |
| 2 | (3-methyl-4-oxo-5-(5-(2,6-difluorophenoxy)tetrazol-1-yl)pentanoic acid group) |

TABLE 38-continued
I (38)
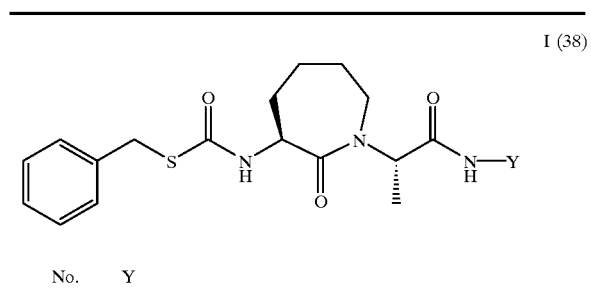
| No. | Y |
|---|---|
| 3 | 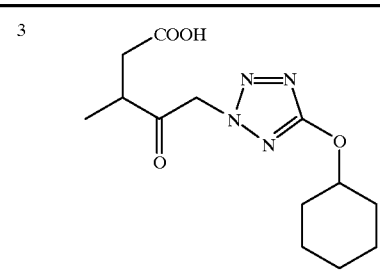 |
| 4 | 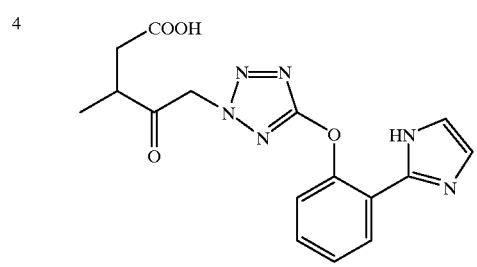 |
| 5 | 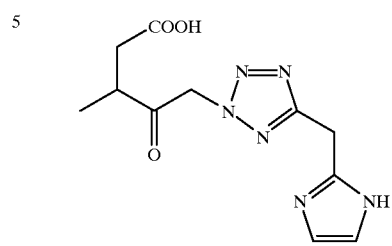 |
| 6 | 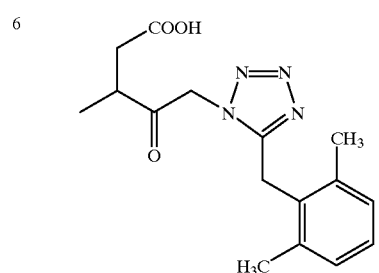 |
TABLE 38-continued
I (38)
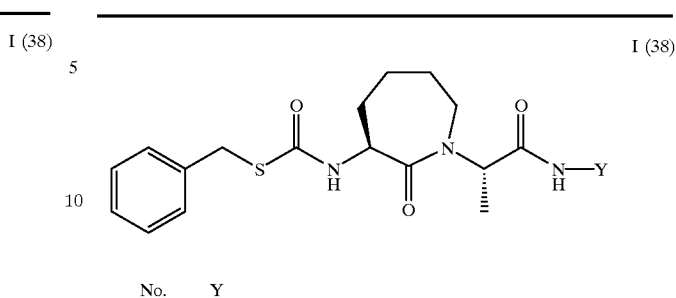
| No. | Y |
|---|---|
| 7 | 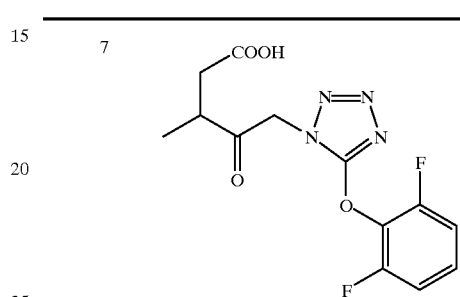 |
| 8 | 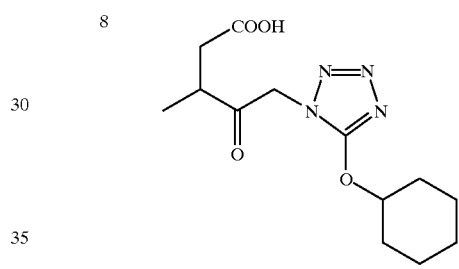 |
| 9 | 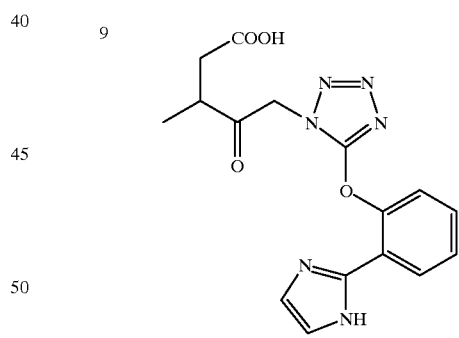 |
| 10 | 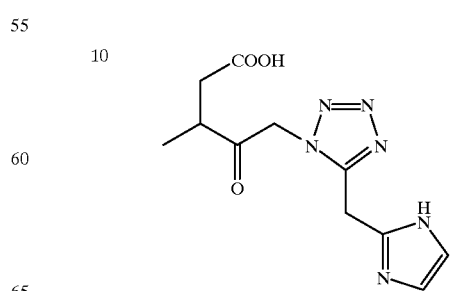 |

TABLE 39

I (39)

| No. | Y |
|-----|---|
| 1 | tetrazole with CH₂ linker to 2,6-dimethylphenyl; 3-methyl-4-oxo-pentanoic acid substituent with COOH |
| 2 | tetrazole with O linker to 2,6-difluorophenyl; 3-methyl-4-oxo-pentanoic acid substituent with COOH |
| 3 | tetrazole with O-cyclohexyl; 3-methyl-4-oxo-pentanoic acid substituent with COOH |
| 4 | tetrazole with O linker to 2-(1H-imidazol-2-yl)phenyl; 3-methyl-4-oxo-pentanoic acid substituent with COOH |
| 5 | tetrazole with CH₂ linker to 1H-imidazol-2-yl; 3-methyl-4-oxo-pentanoic acid substituent with COOH |

TABLE 39-continued

I (39)

| No. | Y |
|-----|---|
| 6 | tetrazole (N1-linked) with CH₂ to 2,6-dimethylphenyl; 3-methyl-4-oxo-pentanoic acid with COOH |
| 7 | tetrazole (N1-linked) with O to 2,6-difluorophenyl; 3-methyl-4-oxo-pentanoic acid with COOH |
| 8 | tetrazole (N1-linked) with O-cyclohexyl; 3-methyl-4-oxo-pentanoic acid with COOH |
| 9 | tetrazole (N1-linked) with O to 2-(1H-imidazol-2-yl)phenyl; 3-methyl-4-oxo-pentanoic acid with COOH |

TABLE 39-continued
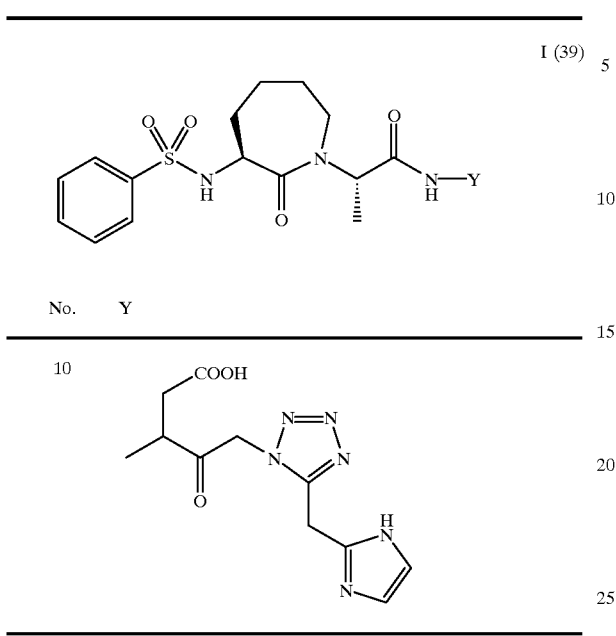
I (39)
| No. | Y |
|---|---|
| 10 | 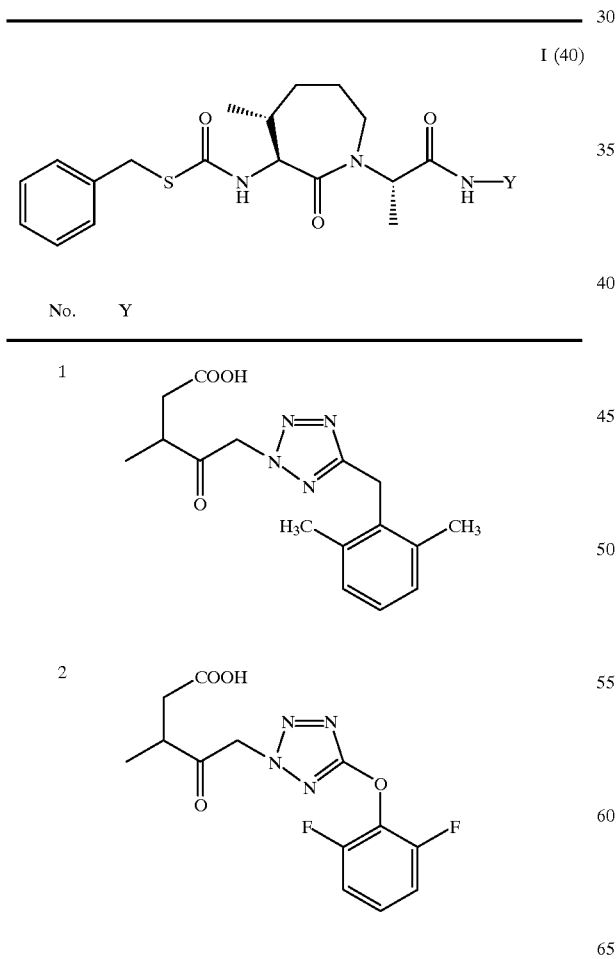 |
TABLE 40
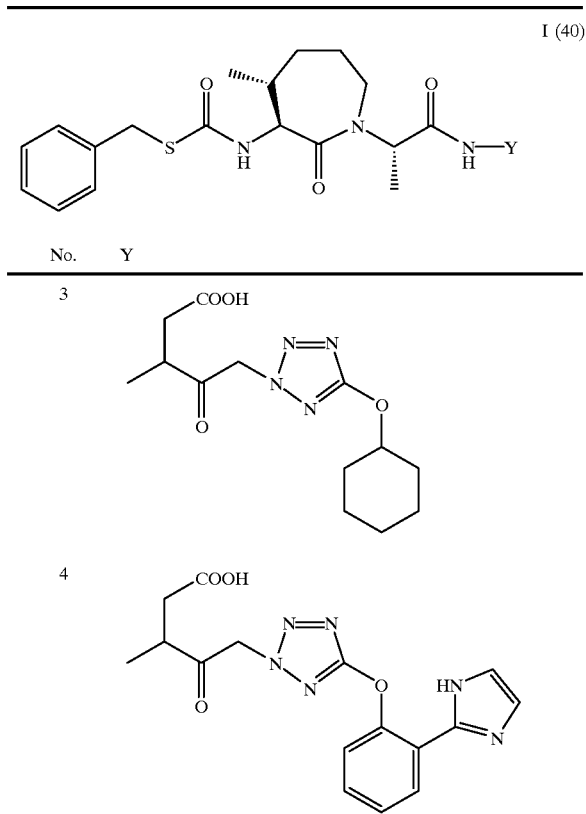
I (40)
| No. | Y |
|---|---|
| 1 | 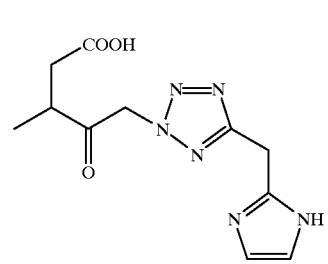 |
| 2 | 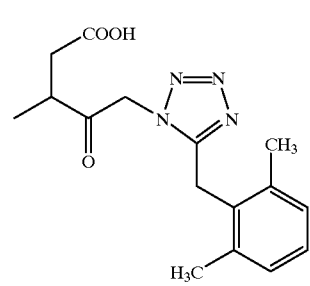 |
| 3 | (structure with cyclohexyloxy) |
| 4 | (structure with phenyl-imidazole) |
| 5 | (structure with imidazole) |
| 6 | (structure with dimethylphenyl) |
| 7 | 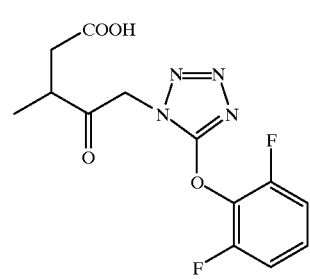 |

TABLE 40-continued

I (40)

No.    Y

8    [structure: COOH-CH(CH3)-CH2-C(O)-CH2-tetrazole-O-cyclohexyl]

9    [structure: COOH-CH(CH3)-CH2-C(O)-CH2-tetrazole-phenyl-imidazole]

10   [structure: COOH-CH(CH3)-CH2-C(O)-CH2-tetrazole-CH2-imidazole]

TABLE 41

I (41)

| No. | Y |
|---|---|
| 1 | [structure: COOH-CH(CH3)-CH2-C(O)-CH2-tetrazole-CH2-(2,6-dimethylphenyl)] |
| 2 | [structure: COOH-CH(CH3)-CH2-C(O)-CH2-tetrazole-O-(2,6-difluorophenyl)] |
| 3 | [structure: COOH-CH(CH3)-CH2-C(O)-CH2-tetrazole-O-cyclohexyl] |
| 4 | [structure: COOH-CH(CH3)-CH2-C(O)-CH2-tetrazole-O-phenyl-imidazole] |
| 5 | [structure: COOH-CH(CH3)-CH2-C(O)-CH2-tetrazole-CH2-imidazole] |

TABLE 41-continued

I (41)

| No. | Y |
|-----|---|
| 6 | 3-methyl-4-oxo-4-[5-(2,6-dimethylbenzyl)tetrazol-1-yl]butyl with COOH |
| 7 | 3-methyl-4-oxo-4-[5-(2,6-difluorophenoxy)tetrazol-1-yl]butyl with COOH |
| 8 | 3-methyl-4-oxo-4-[5-cyclohexyloxytetrazol-1-yl]butyl with COOH |
| 9 | 3-methyl-4-oxo-4-[5-(2-(1H-imidazol-2-yl)phenoxy)tetrazol-1-yl]butyl with COOH |
| 10 | 3-methyl-4-oxo-4-[5-(1H-imidazol-2-yl)methyltetrazol-1-yl]butyl with COOH |

TABLE 42

I (42)

| No. | Y |
|-----|---|
| 1 | 3-methyl-4-oxo-4-[5-(2,6-dimethylbenzyl)tetrazol-1-yl]butyl with COOH |
| 2 | 3-methyl-4-oxo-4-[5-(2,6-difluorophenoxy)tetrazol-1-yl]butyl with COOH |

TABLE 42-continued
I (42)
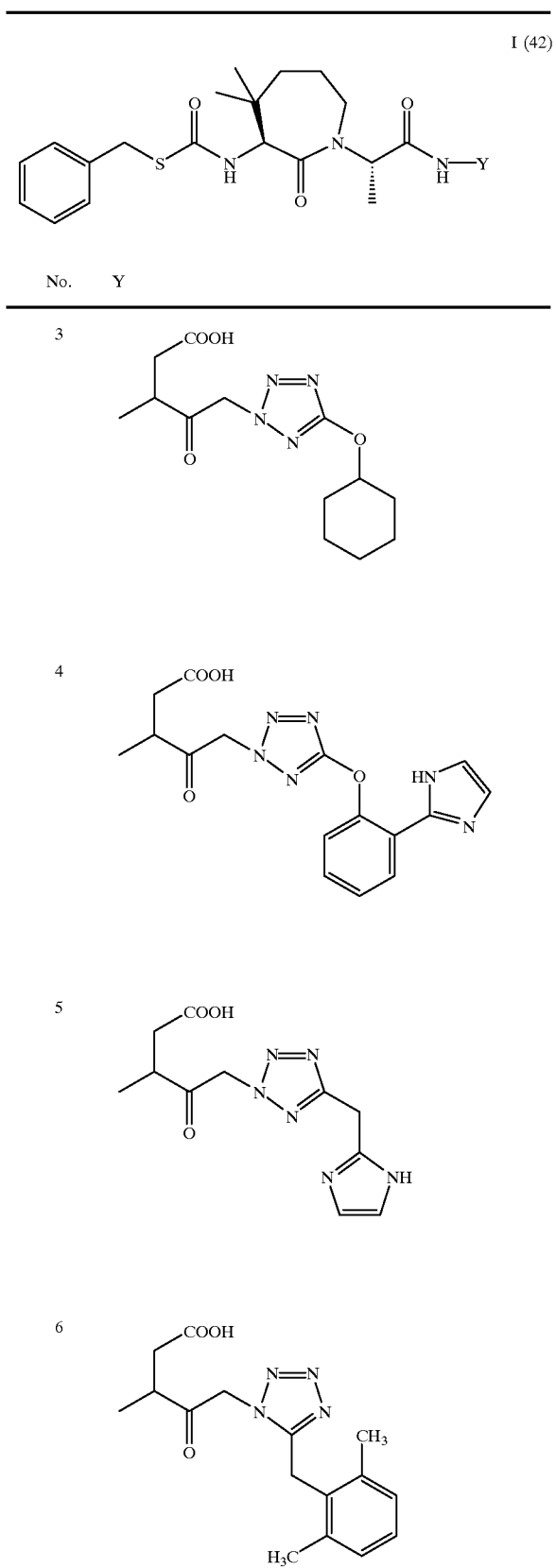
| No. | Y |
|---|---|
| 3 | |
| 4 | |
| 5 | |
| 6 | |
TABLE 42-continued
I (42)
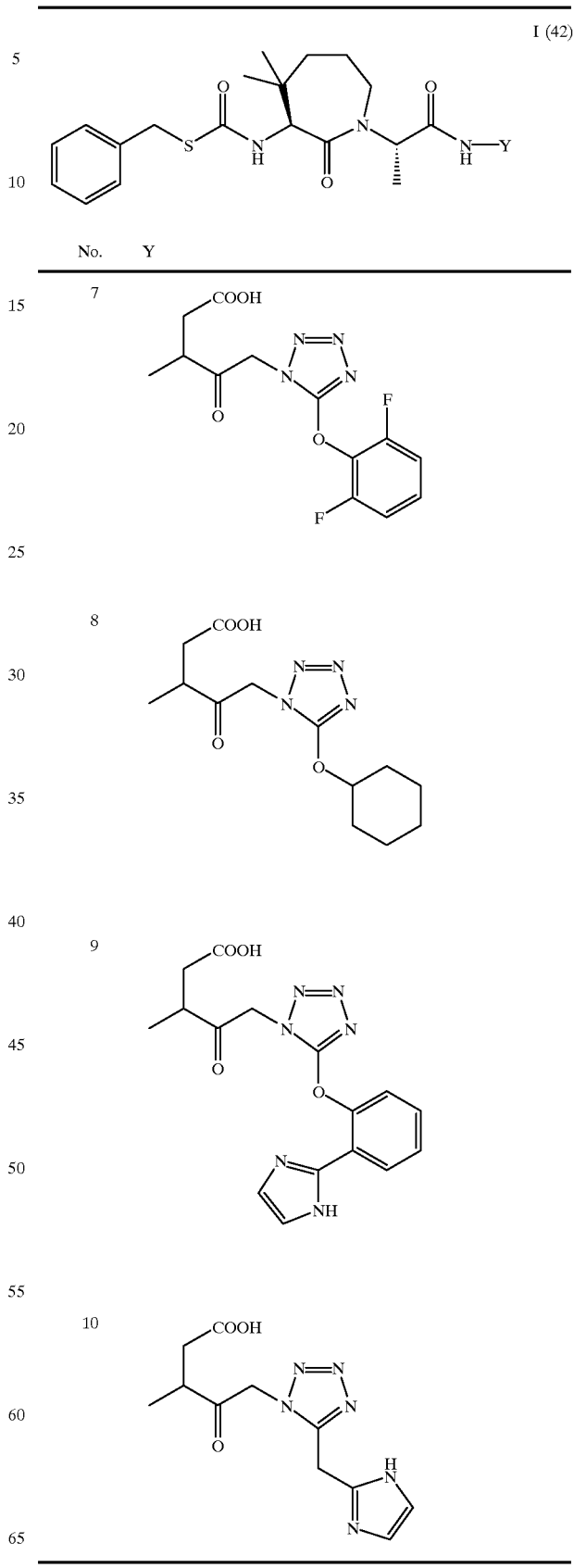
| No. | Y |
|---|---|
| 7 | |
| 8 | |
| 9 | |
| 10 | |

TABLE 43
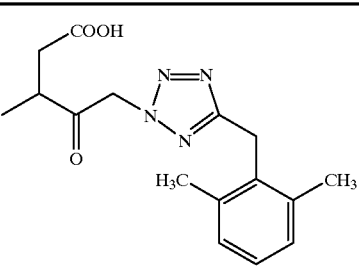
I (43)
| No. | Y |
|---|---|
| 1 | 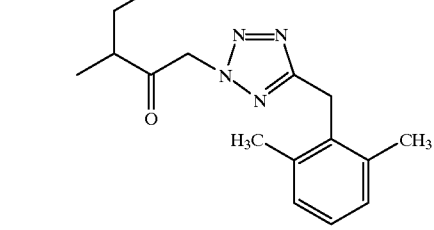 |
| 2 | 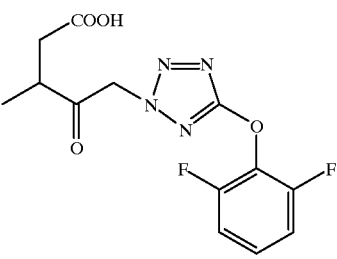 |
| 3 | 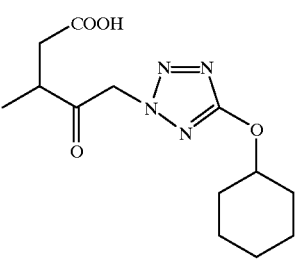 |
| 4 | 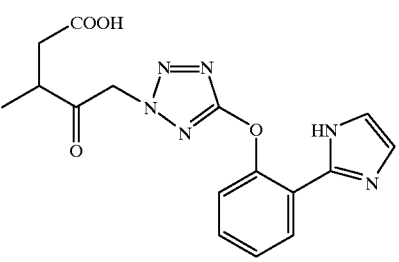 |
| 5 | 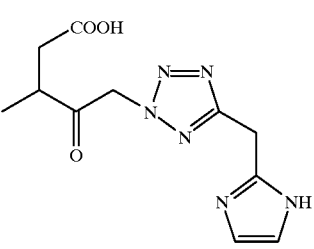 |
TABLE 43-continued
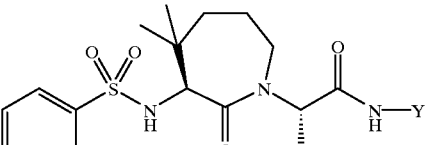
I (43)
| No. | Y |
|---|---|
| 6 |  |
| 7 | 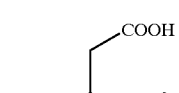 |
| 8 | 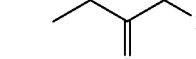 |
| 9 | 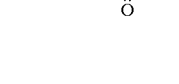 |

TABLE 43-continued

I (43)

No. Y

10 [structure: 3-methyl-4-oxo-5-(tetrazolyl-methyl-imidazole) pentanoic acid derivative]

TABLE 44

I (44)

| No. | R⁴ | R⁹ | R¹⁰ |
|-----|------|----|-----|
| 1 | i-Pr | H | [4-ethyl-1H-imidazole] |
| 2 | i-Pr | H | —CH₂—OH |
| 3 | i-Pr | H | [benzyl/phenethyl] |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | [4-hydroxyphenylethyl] | H | Me |
| 10 | [4-ethyl-1H-imidazole] | H | Me |

TABLE 44-continued
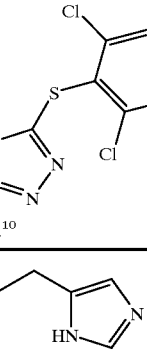
I (44)
| No. | R⁴ | R⁹ | R¹⁰ |
|---|---|---|---|
| 11 | ![propyl-guanidine] | H | Me |
| 12 | ![propyl-SCH₃] | H | Me |
TABLE 45
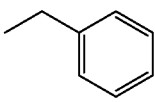
I (45)
| No. | R⁴ | R⁹ | R¹⁰ |
|---|---|---|---|
| 1 | i-Pr | H | ![ethyl-imidazole] |
| 2 | i-Pr | H | —CH₂—OH |
| 3 | i-Pr | H | ![ethyl-phenyl] |
| 4 | i-Pr | Me | Me |
| 5 | i-Pr | | —(CH₂)₃— |
| 6 | i-Pr | | —CH₂CH=CHCH₂— |
| 7 | Me | H | Me |
| 8 | i-Bu | H | Me |
| 9 | ![ethyl-phenol] | H | Me |
| 10 | ![ethyl-imidazole] | H | Me |
| 11 | ![propyl-guanidine] | H | Me |

TABLE 45-continued
I (45)
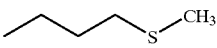
| No. | R⁴ | R⁹ | R¹⁰ |
|---|---|---|---|
| 12 | 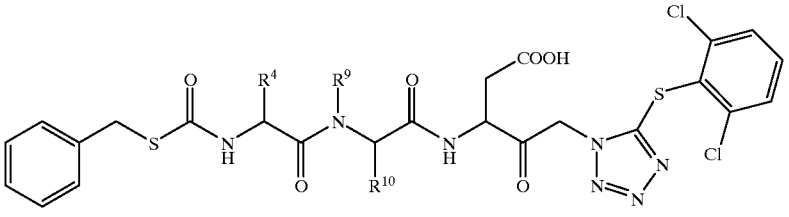 | H | Me |
TABLE 46
I (46)
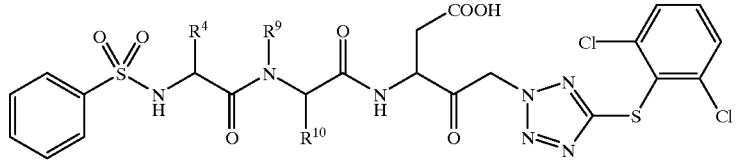
| No. | R⁴ | R⁹ | R¹⁰ |
|---|---|---|---|
| 1 | i-Pr | H | 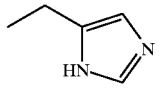 |
| 2 | i-Pr | H | —CH₂—OH |
| 3 | i-Pr | H | 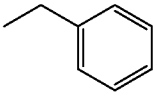 |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | 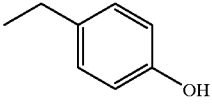 | H | Me |
| 10 | 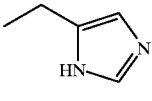 | H | Me |
| 11 | 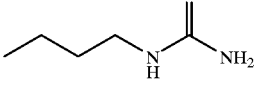 | H | Me |
| 12 |  | H | Me |

TABLE 47

I (47)

[Structure: PhSO2-NH-CH(R4)-C(=O)-N(R9)-CH(R10)-C(=O)-NH-CH(CH2COOH)-C(=O)-CH2-N(tetrazole-S-2,6-dichlorophenyl)]

| No. | R⁴ | R⁹ | R¹⁰ |
|---|---|---|---|
| 1 | i-Pr | H | 4-ethyl-1H-imidazole |
| 2 | i-Pr | H | —CH₂—OH |
| 3 | i-Pr | H | —CH₂—C₆H₅ |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | 4-hydroxybenzyl (−CH₂CH₂−C₆H₄−OH) | H | Me |
| 10 | 4-ethyl-1H-imidazole | H | Me |
| 11 | −(CH₂)₃−NH−C(=NH)−NH₂ | H | Me |
| 12 | −(CH₂)₃−S−CH₃ | H | Me |

TABLE 48

I (48)

| No. | ring | R17 | No. | ring | R17 |
|---|---|---|---|---|---|
| 1 | 7-membered lactam with methyl substituents | Me | 7 | 7-membered lactam with gem-dimethyl | Me |
| 2 | 7-membered unsaturated lactam | Me | 8 | benzo-fused 7-membered lactam | Me |
| 3 | 8-membered lactam | Me | 9 | 6-membered lactam (piperidinone) | Me |
| 4 | 9-membered lactam | Me | 10 | 7-membered oxa-lactam | Me |
| 5 | 7-membered lactam with NH | Me | 11 | 7-membered thia-lactam | Me |
| 6 | 7-membered thia-lactam | Me | 12 | 7-membered thia-lactam with gem-dimethyl | Me |

TABLE 49
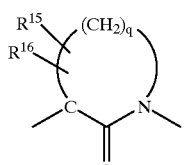
| No. | | R[17] | No. | | R[17] |
|---|---|---|---|---|---|
| 1 | 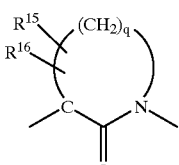 | Me | 7 | 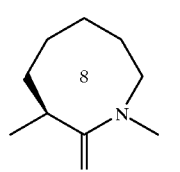 | Me |
| 2 |  | Me | 8 | 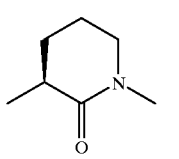 | Me |
| 3 | 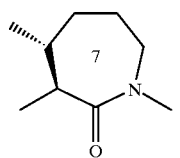 | Me | 9 | 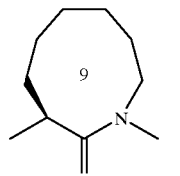 | Me |
| 4 | 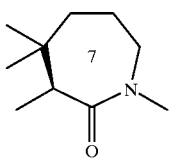 | Me | 10 | 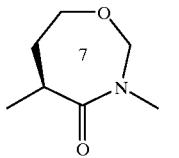 | Me |
| 5 | 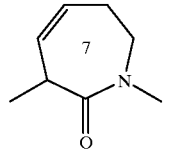 | Me | 11 | 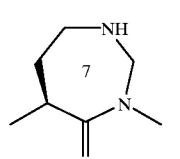 | Me |

TABLE 49-continued

I (49)

| No. | [structure] | R¹⁷ | No. | [structure] | R¹⁷ |
|---|---|---|---|---|---|
| 6 | [7-membered ring with S, N-Me, =O, methyl substituents] | Me | 12 | [7-membered ring with S, N-Me, =O, gem-dimethyl and methyl substituents] | Me |

TABLE 50

I (50)

| No. | [structure] | R¹⁷ | No. | [structure] | R¹⁷ |
|---|---|---|---|---|---|
| 1 | [7-membered lactam ring, N-Me, with methyl substituents] | Me | 7 | [7-membered lactam ring, N-Me, gem-dimethyl and methyl] | Me |
| 2 | [7-membered unsaturated lactam, N-Me, methyl] | Me | 8 | [benzo-fused 7-membered lactam, N-Me, methyl] | Me |

TABLE 50-continued
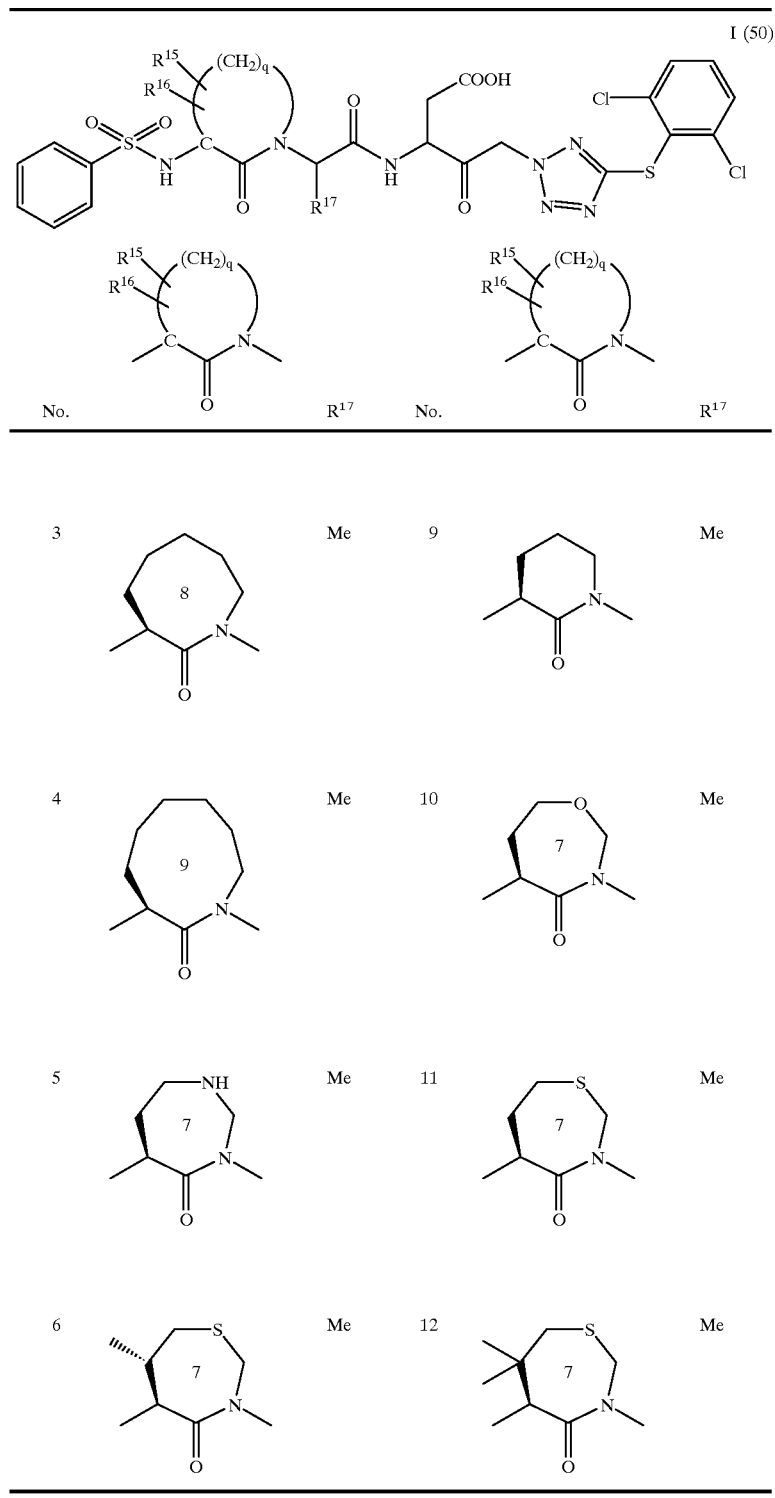

TABLE 51

Structure I(51): A complex molecule containing a phenylsulfonamide group connected to a cyclic amide (with substituents R15, R16, (CH2)q), an R17-bearing amino acid, an aspartic acid derivative with a COOH group, and a tetrazole linked to a 2,6-dichlorophenylthio group.

| No. | Ring structure | R17 | No. | Ring structure | R17 |
|---|---|---|---|---|---|
| 1 | 7-membered lactam with methyl substituents (one wedge) | Me | 7 | 7-membered lactam with gem-dimethyl and methyl | Me |
| 2 | 7-membered unsaturated lactam with methyl | Me | 8 | benzo-fused 7-membered lactam | Me |
| 3 | 8-membered lactam with methyl | Me | 9 | 6-membered lactam (piperidinone) with methyl | Me |
| 4 | 9-membered lactam with methyl | Me | 10 | 7-membered lactam containing O | Me |
| 5 | 7-membered lactam containing NH | Me | 11 | 7-membered lactam containing S | Me |

TABLE 51-continued
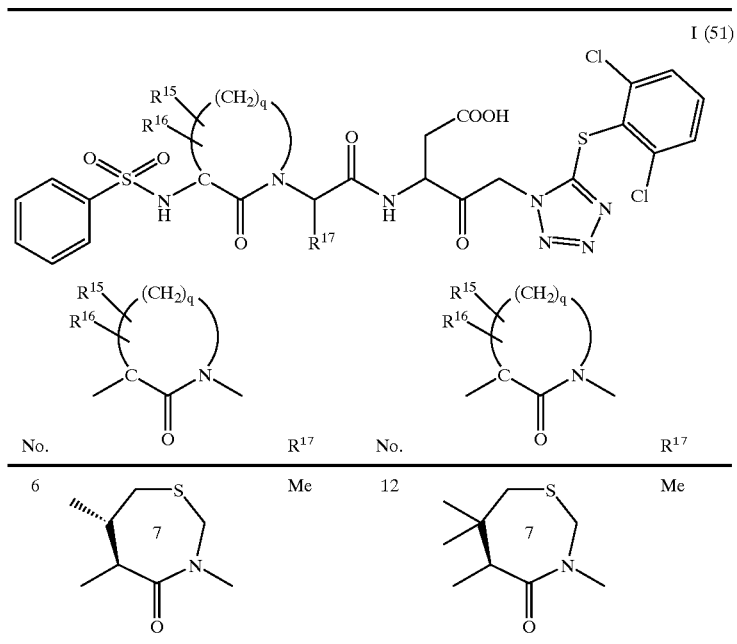
| No. | | $R^{17}$ | No. | | $R^{17}$ |
|---|---|---|---|---|---|
| 6 | | Me | 12 | | Me |
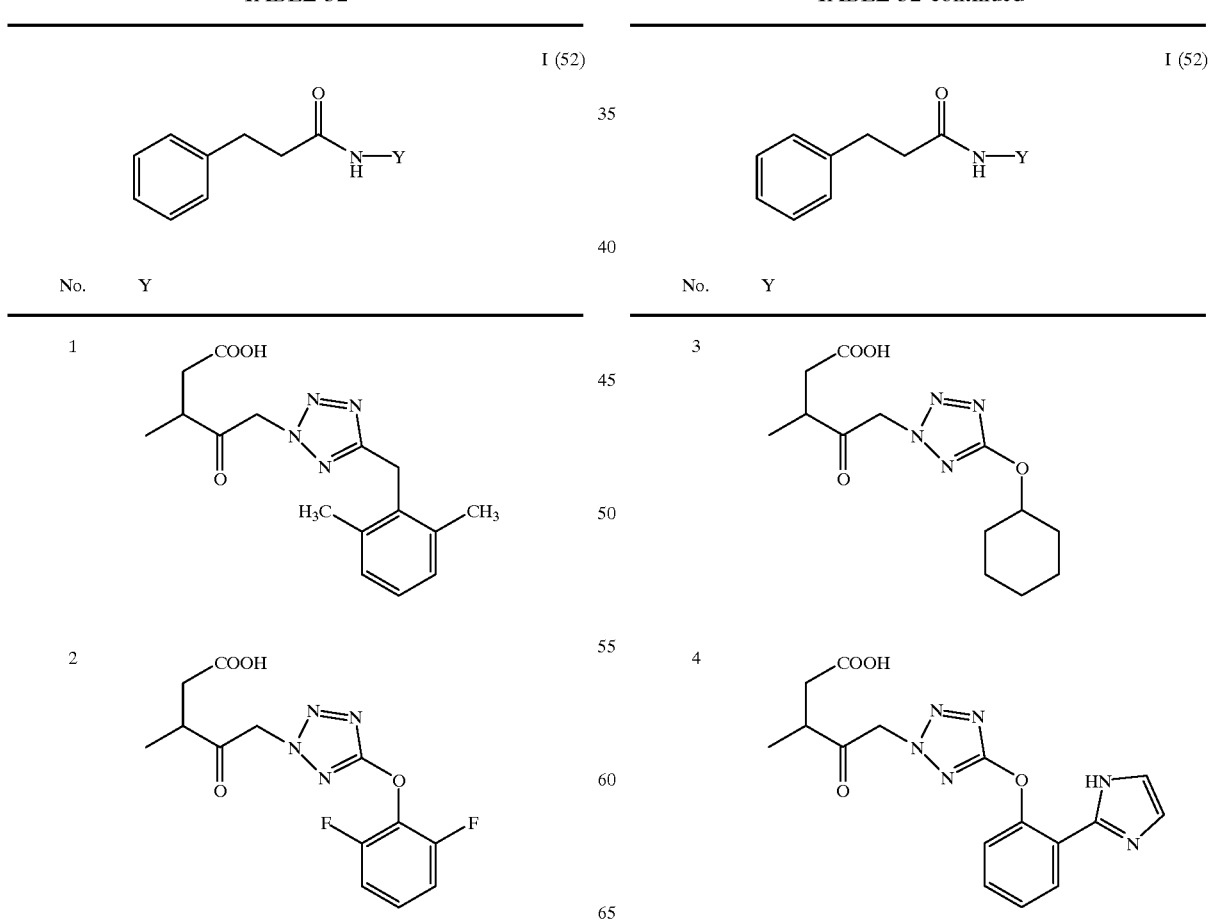

TABLE 52-continued
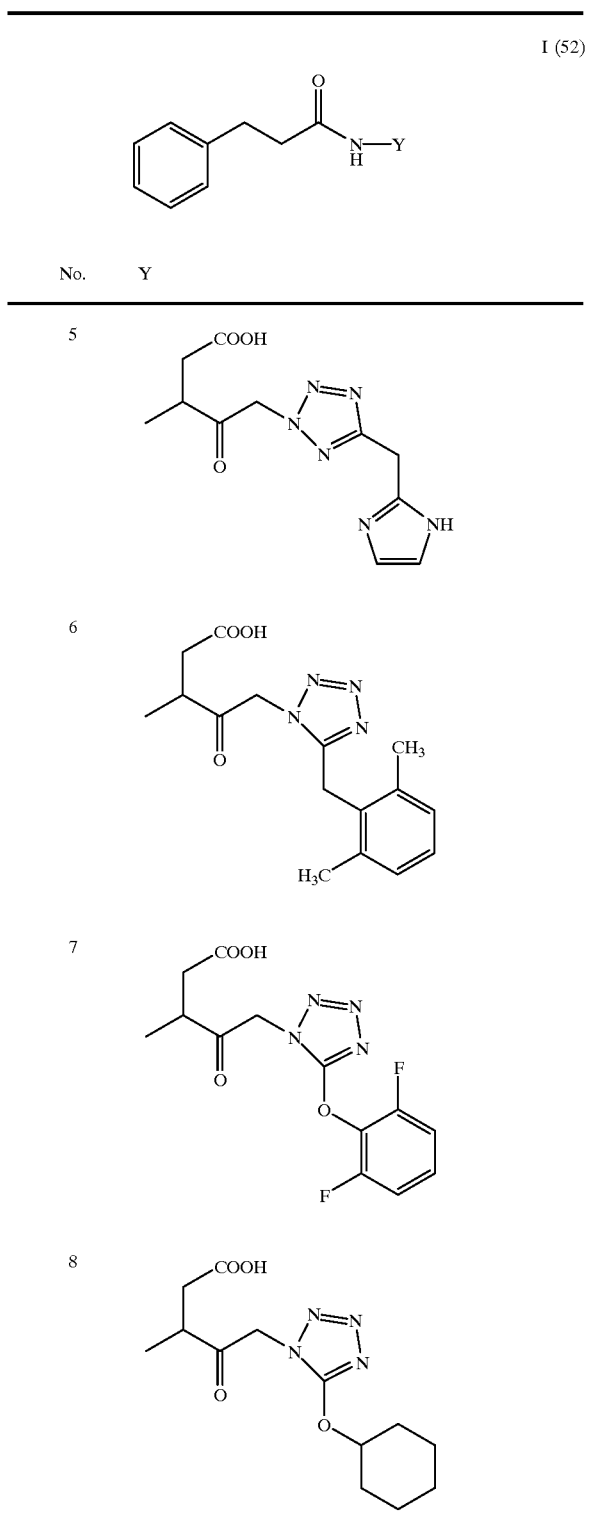
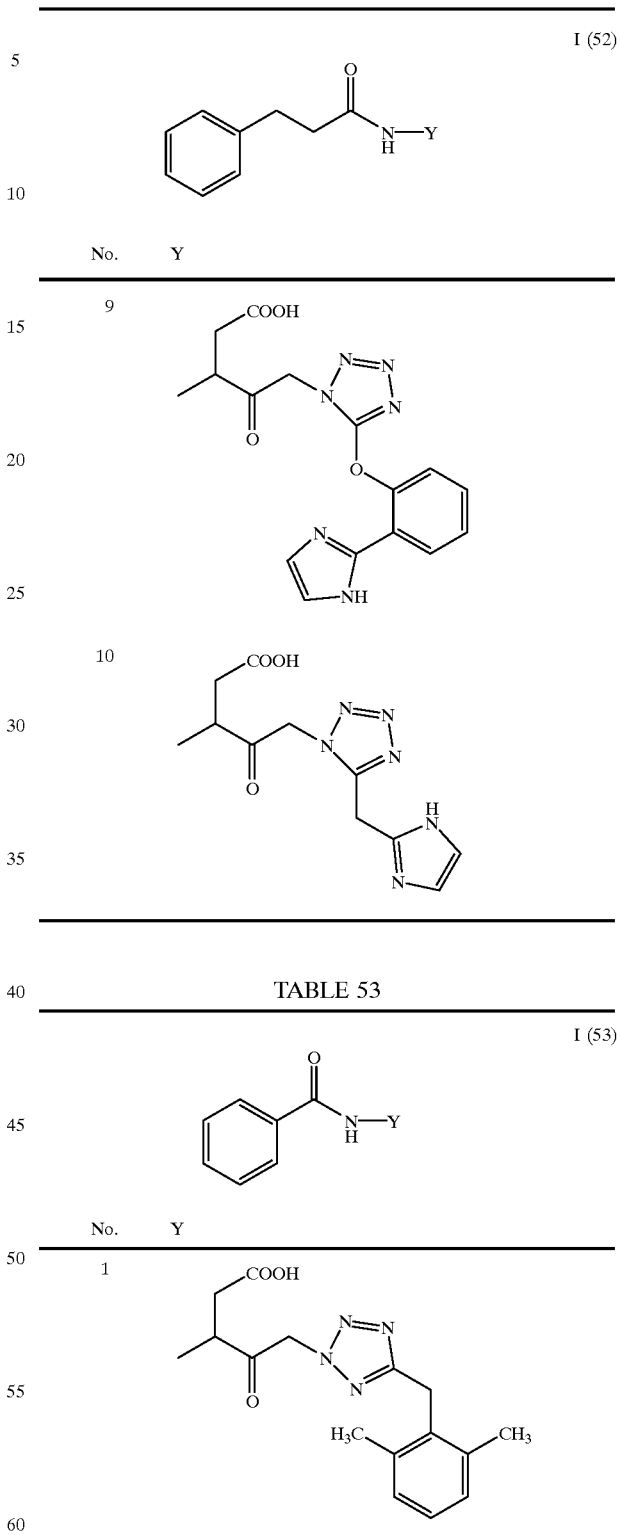
TABLE 53

TABLE 53-continued

I (53)

| No. | Y |
|---|---|
| 2 | 3-methyl-4-oxo-5-[2-(2,6-difluorophenoxy)tetrazol-2-yl]pentanoic acid derivative |
| 3 | 3-methyl-4-oxo-5-[2-(cyclohexyloxy)tetrazol-2-yl]pentanoic acid derivative |
| 4 | 3-methyl-4-oxo-5-[2-(2-(1H-imidazol-2-yl)phenoxy)tetrazol-2-yl]pentanoic acid derivative |
| 5 | 3-methyl-4-oxo-5-[2-((1H-imidazol-2-yl)methyl)tetrazol-2-yl]pentanoic acid derivative |
| 6 | 3-methyl-4-oxo-5-[1-(2,6-dimethylbenzyl)tetrazol-5-yl]pentanoic acid derivative |
| 7 | 3-methyl-4-oxo-5-[1-(2,6-difluorophenoxy)tetrazol-1-yl]pentanoic acid derivative |
| 8 | 3-methyl-4-oxo-5-[1-(cyclohexyloxy)tetrazol-1-yl]pentanoic acid derivative |
| 9 | 3-methyl-4-oxo-5-[1-(2-(1H-imidazol-2-yl)phenoxy)tetrazol-1-yl]pentanoic acid derivative |
| 10 | 3-methyl-4-oxo-5-[1-((1H-imidazol-2-yl)methyl)tetrazol-1-yl]pentanoic acid derivative |

TABLE 54
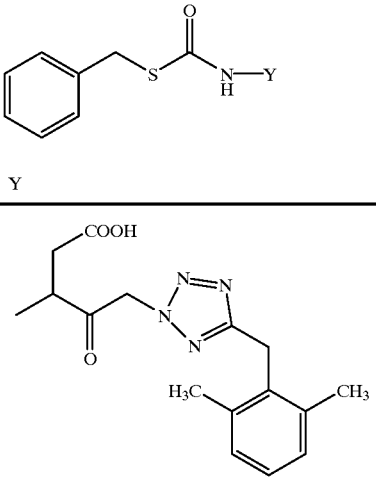
I (54)
| No. | Y |
|---|---|
| 1 | 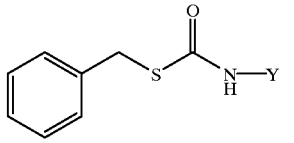 |
| 2 | 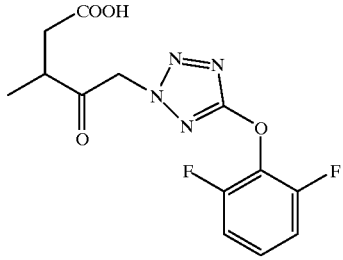 |
| 3 | 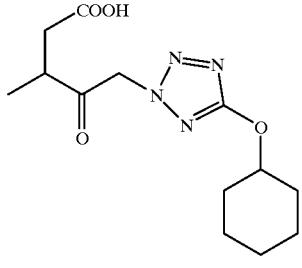 |
| 4 | 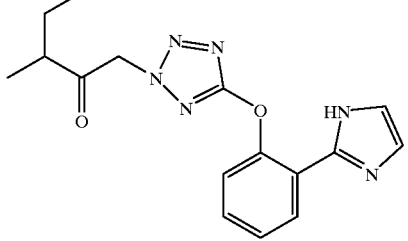 |
| 5 | 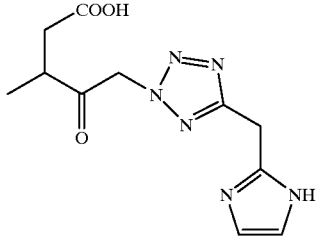 |
TABLE 54-continued
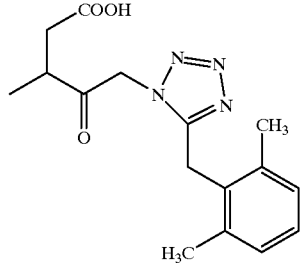
I (54)
| No. | Y |
|---|---|
| 6 | 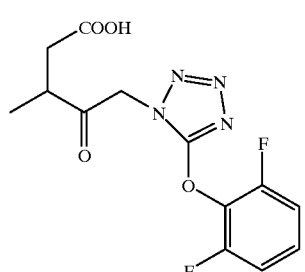 |
| 7 | 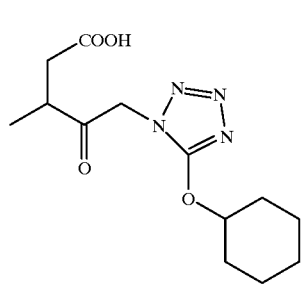 |
| 8 | 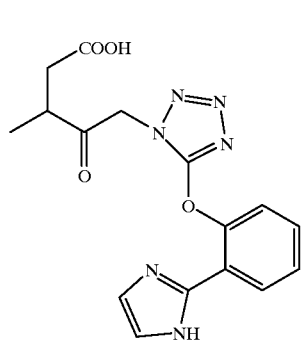 |
| 9 | |

TABLE 54-continued

| No. | Y |
|---|---|
| 10 | (structure: 3-methyl-4-oxo-5-(5-((1H-imidazol-2-yl)methyl)tetrazol-1-yl)pentanoic acid) |

TABLE 55

I (55)

| No. | Y |
|---|---|
| 1 | (structure: 3-methyl-4-oxo-5-(5-(2,6-dimethylbenzyl)tetrazol-2-yl)pentanoic acid) |
| 2 | (structure: 3-methyl-4-oxo-5-(5-(2,6-difluorophenoxy)tetrazol-2-yl)pentanoic acid) |
| 3 | (structure: 3-methyl-4-oxo-5-(5-cyclohexyloxytetrazol-2-yl)pentanoic acid) |
| 4 | (structure: 3-methyl-4-oxo-5-(5-(2-(1H-imidazol-2-yl)phenoxy)tetrazol-2-yl)pentanoic acid) |
| 5 | (structure: 3-methyl-4-oxo-5-(5-((1H-imidazol-2-yl)methyl)tetrazol-2-yl)pentanoic acid) |
| 6 | (structure: 3-methyl-4-oxo-5-(5-(2,6-dimethylbenzyl)tetrazol-1-yl)pentanoic acid) |
| 7 | (structure: 3-methyl-4-oxo-5-(5-(2,6-difluorophenoxy)tetrazol-1-yl)pentanoic acid) |
| 8 | (structure: 3-methyl-4-oxo-5-(5-cyclohexyloxytetrazol-1-yl)pentanoic acid) |

TABLE 55-continued

I (55)

No. Y 9, 10 (structures)

TABLE 56

I (56)

No. Y

1–6 (structures)

TABLE 56-continued

I (56)

[Structure: phenyl-(CH2)3-C(=O)-NH-Y]

| No. | Y |
|---|---|
| 7 | 3-methyl-4-oxo-4-[5-(2,6-difluorophenoxy)tetrazol-1-yl]butanoic acid derivative (CH2COOH, CH(CH3), C(=O), CH2-tetrazole-O-2,6-difluorophenyl) |
| 8 | 3-methyl-4-oxo-4-[5-(cyclohexyloxy)tetrazol-1-yl]butanoic acid derivative |
| 9 | 3-methyl-4-oxo-4-[5-(2-(imidazol-2-yl)phenoxy)tetrazol-1-yl]butanoic acid derivative |
| 10 | 3-methyl-4-oxo-4-[5-((imidazol-2-yl)methyl)tetrazol-1-yl]butanoic acid derivative |

TABLE 57

I (57)

[Structure: phenyl-CH2CH2-O-C(=O)-NH-Y]

| No. | Y |
|---|---|
| 1 | 3-methyl-4-oxo-4-[5-((2,6-dimethylphenyl)methyl)tetrazol-2-yl]butanoic acid derivative |
| 2 | 3-methyl-4-oxo-4-[5-(2,6-difluorophenoxy)tetrazol-2-yl]butanoic acid derivative |
| 3 | 3-methyl-4-oxo-4-[5-(cyclohexyloxy)tetrazol-2-yl]butanoic acid derivative |
| 4 | 3-methyl-4-oxo-4-[5-(2-(imidazol-2-yl)phenoxy)tetrazol-2-yl]butanoic acid derivative |
| 5 | 3-methyl-4-oxo-4-[5-((imidazol-2-yl)methyl)tetrazol-2-yl]butanoic acid derivative |

TABLE 57-continued

I (57)

[Structure: phenethyl-O-C(=O)-NH-Y]

| No. | Y |
|---|---|
| 6 | 3-methyl-4-oxo-4-[5-(2,6-dimethylbenzyl)-tetrazol-1-yl]butanoic acid moiety |
| 7 | 3-methyl-4-oxo-4-[5-(2,6-difluorophenoxy)-tetrazol-1-yl]butanoic acid moiety |
| 8 | 3-methyl-4-oxo-4-[5-cyclohexyloxy-tetrazol-1-yl]butanoic acid moiety |
| 9 | 3-methyl-4-oxo-4-[5-(2-(1H-imidazol-2-yl)phenoxy)-tetrazol-1-yl]butanoic acid moiety |

TABLE 57-continued

I (57)

[Structure: phenethyl-O-C(=O)-NH-Y]

| No. | Y |
|---|---|
| 10 | 3-methyl-4-oxo-4-[5-((1H-imidazol-2-yl)methyl)-tetrazol-1-yl]butanoic acid moiety |

TABLE 58

I (58)

[Structure: phenethyl-S-C(=O)-NH-Y]

| No. | Y |
|---|---|
| 1 | 3-methyl-4-oxo-4-[5-(2,6-dimethylbenzyl)-tetrazol-2-yl]butanoic acid moiety |
| 2 | 3-methyl-4-oxo-4-[5-(2,6-difluorophenoxy)-tetrazol-2-yl]butanoic acid moiety |
| 3 | 3-methyl-4-oxo-4-[5-cyclohexyloxy-tetrazol-2-yl]butanoic acid moiety |

TABLE 58-continued
I (58)
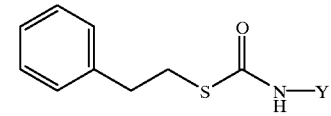
| No. | Y |
|---|---|
| 4 | (structure) |
| 5 | (structure) |
| 6 | (structure) |
| 7 | (structure) |
| 8 | (structure) |
TABLE 58-continued
I (58)
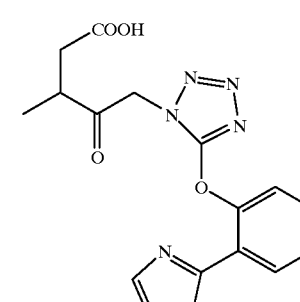
| No. | Y |
|---|---|
| 9 | (structure) |
| 10 | (structure) |
TABLE 59
I (59)
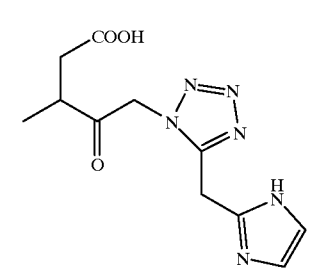
| No. | Y |
|---|---|
| 1 | (structure) |

TABLE 59-continued

I (59)

| No. | Y |
|---|---|
| 2 | 3-methyl-4-oxo-4-[5-(2,6-difluorophenoxy)tetrazol-2-yl]butyl — COOH chain |
| 3 | 3-methyl-4-oxo-4-[5-cyclohexyloxytetrazol-2-yl]butyl — COOH chain |
| 4 | 3-methyl-4-oxo-4-[5-(2-(1H-imidazol-2-yl)phenoxy)tetrazol-2-yl]butyl — COOH chain |
| 5 | 3-methyl-4-oxo-4-[5-((1H-imidazol-2-yl)methyl)tetrazol-2-yl]butyl — COOH chain |
| 6 | 3-methyl-4-oxo-4-[5-(2,6-dimethylbenzyl)tetrazol-1-yl]butyl — COOH chain |
| 7 | 3-methyl-4-oxo-4-[5-(2,6-difluorophenoxy)tetrazol-1-yl]butyl — COOH chain |
| 8 | 3-methyl-4-oxo-4-[5-cyclohexyloxytetrazol-1-yl]butyl — COOH chain |
| 9 | 3-methyl-4-oxo-4-[5-(2-(1H-imidazol-2-yl)phenoxy)tetrazol-1-yl]butyl — COOH chain |

TABLE 59-continued
I (59)
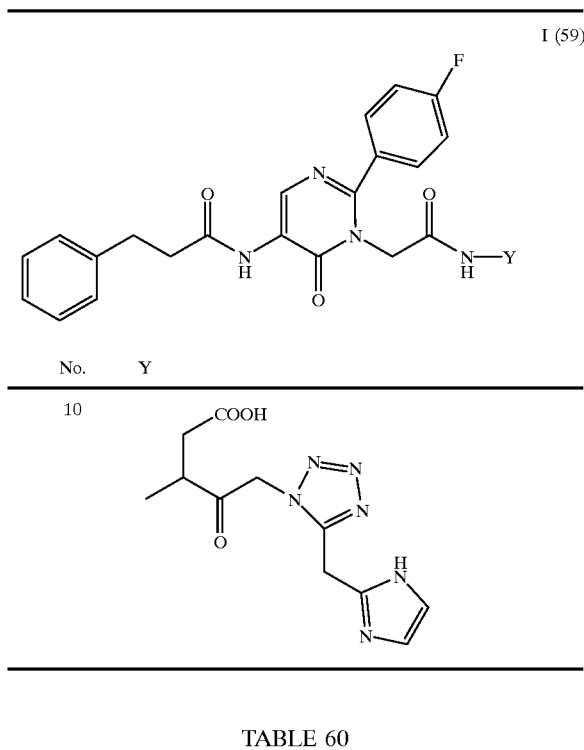
| No. | Y |
|---|---|
| 10 | |
TABLE 60
I (60)
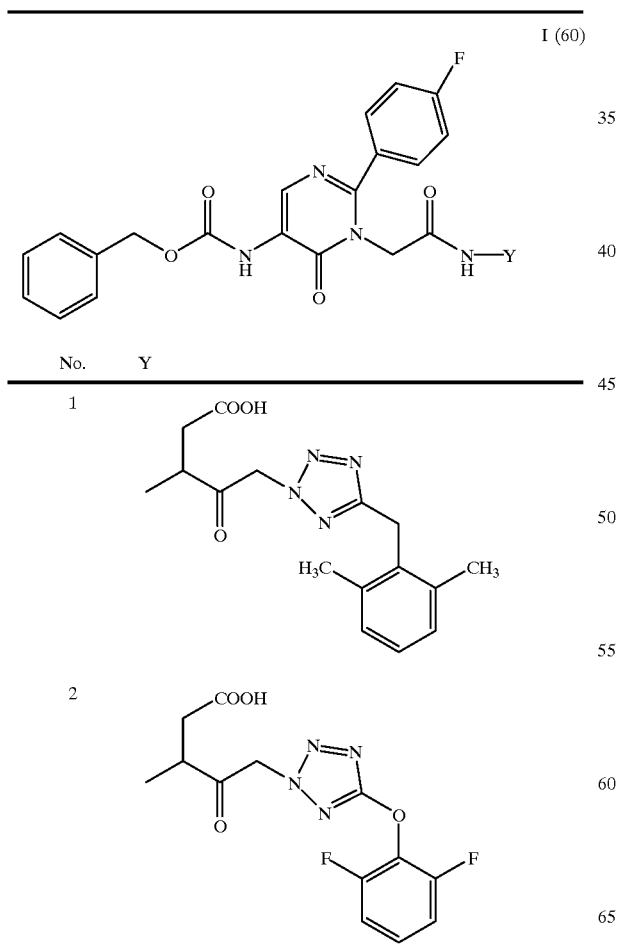
| No. | Y |
|---|---|
| 1 | |
| 2 | |
TABLE 60-continued
I (60)
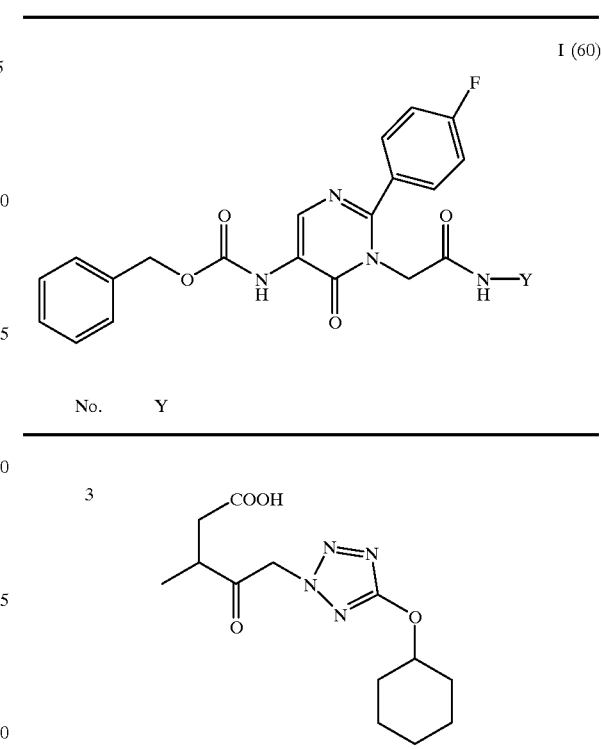
| No. | Y |
|---|---|
| 3 | |
| 4 | |
| 5 | |
| 6 | |
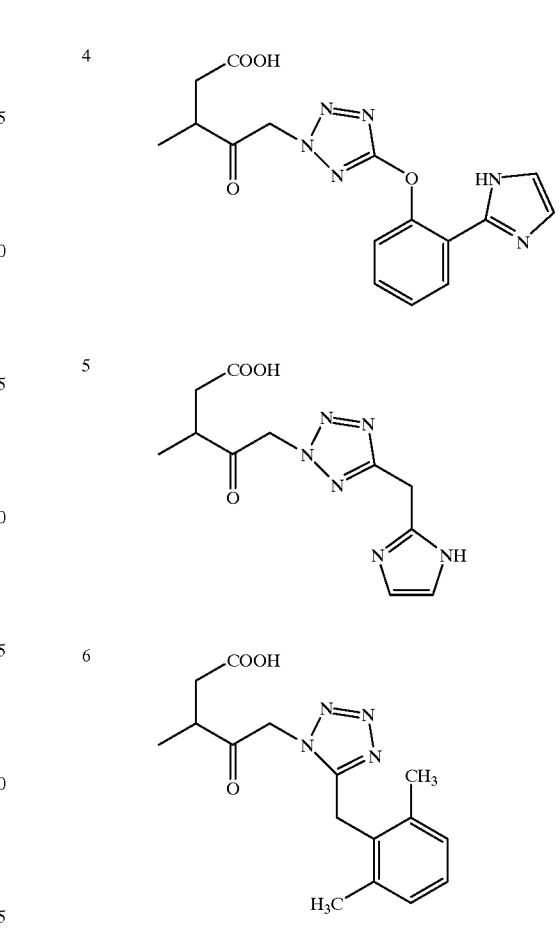

TABLE 60-continued

I (60)

| No. | Y |
|---|---|
| 7 | (3-methyl-4-oxo-5-(1H-tetrazol-1-yl)pentanoic acid with 2,6-difluorophenoxy tetrazole substituent) |
| 8 | (3-methyl-4-oxo-5-(tetrazol-1-yl)pentanoic acid with cyclohexyloxy tetrazole substituent) |
| 9 | (3-methyl-4-oxo-5-(tetrazol-1-yl)pentanoic acid with 2-(1H-imidazol-2-yl)phenoxy tetrazole substituent) |
| 10 | (3-methyl-4-oxo-5-(tetrazol-1-yl)pentanoic acid with 1H-imidazol-2-ylmethyl tetrazole substituent) |

TABLE 61

I (61)

| No. | Y |
|---|---|
| 1 | (3-methyl-4-oxo-5-(tetrazol-2-yl)pentanoic acid with 2,6-dimethylbenzyl tetrazole substituent) |
| 2 | (3-methyl-4-oxo-5-(tetrazol-2-yl)pentanoic acid with 2,6-difluorophenoxy tetrazole substituent) |
| 3 | (3-methyl-4-oxo-5-(tetrazol-2-yl)pentanoic acid with cyclohexyloxy tetrazole substituent) |
| 4 | (3-methyl-4-oxo-5-(tetrazol-2-yl)pentanoic acid with 2-(1H-imidazol-2-yl)phenoxy tetrazole substituent) |

TABLE 61-continued
I (61)
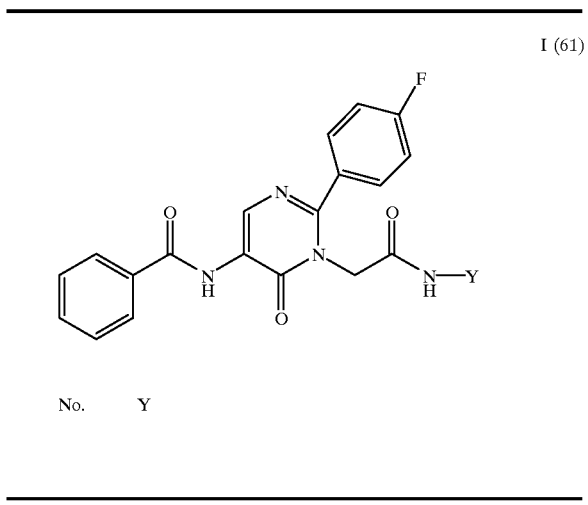
No.    Y
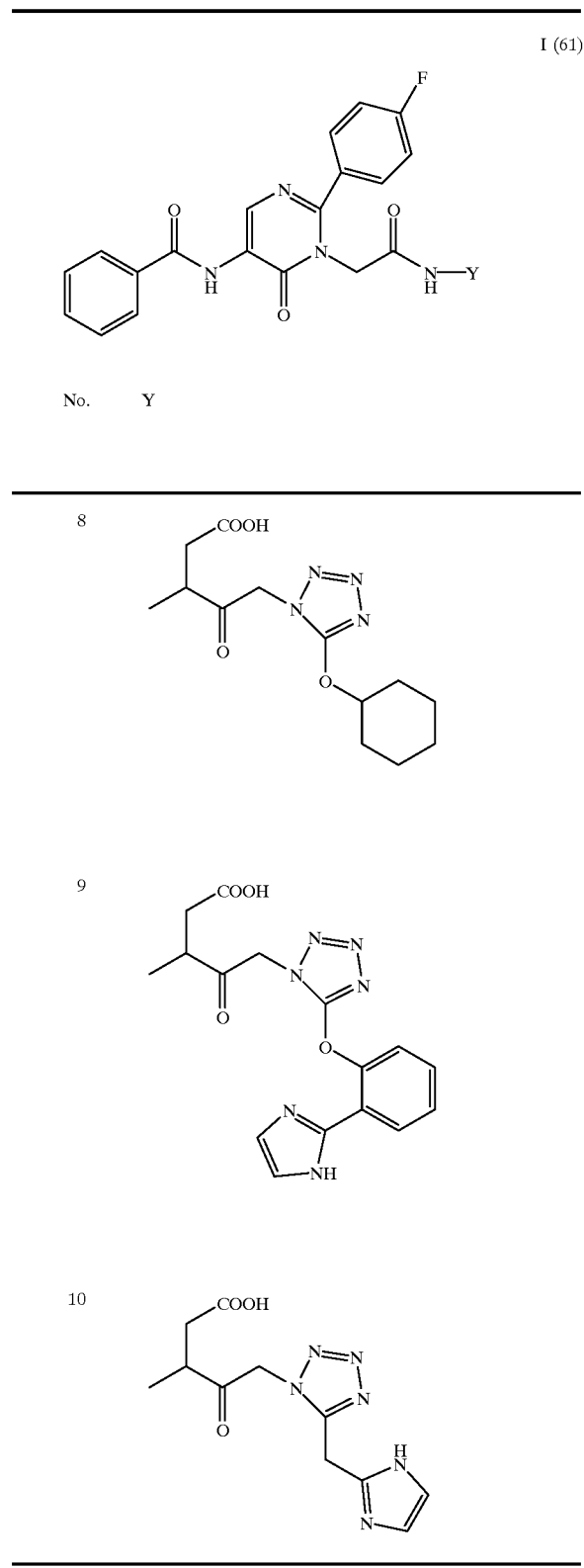

TABLE 62
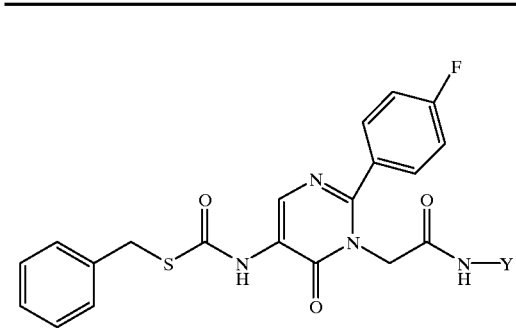
I (62)
No. Y
1 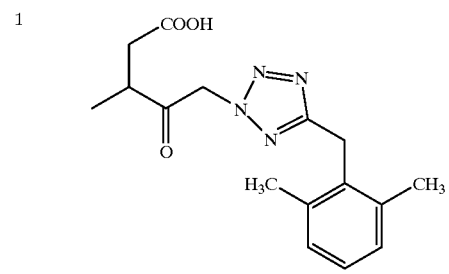
2 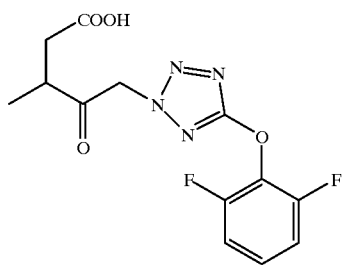
3 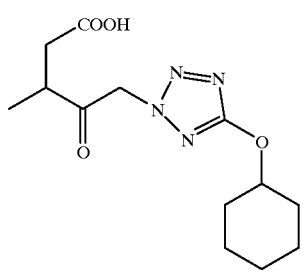
TABLE 62-continued
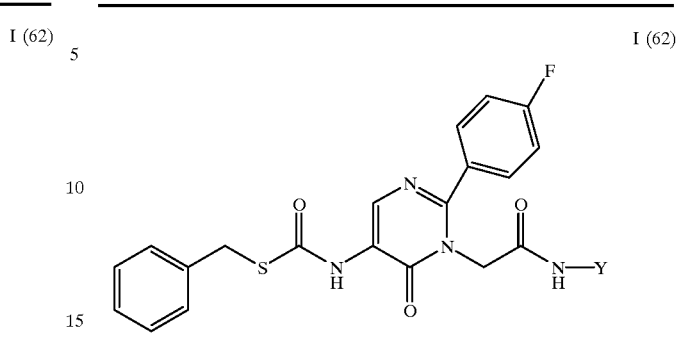
I (62)
No. Y
4 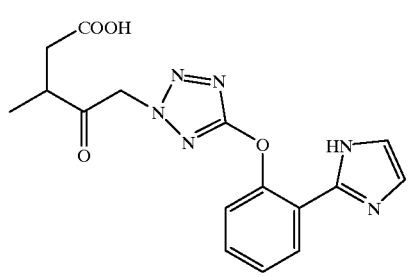
5 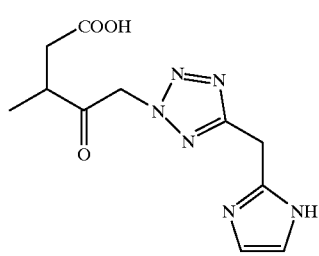
6 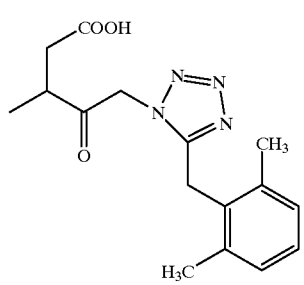

TABLE 62-continued
I (62)
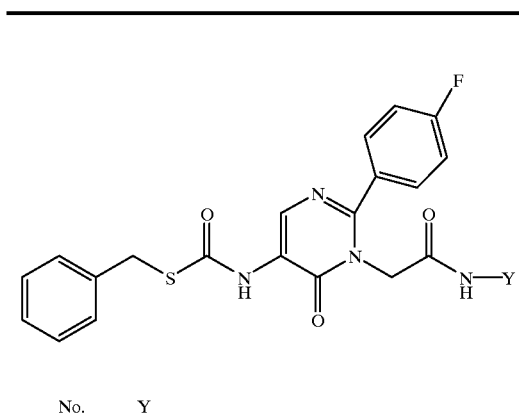
No. Y
| 7 | 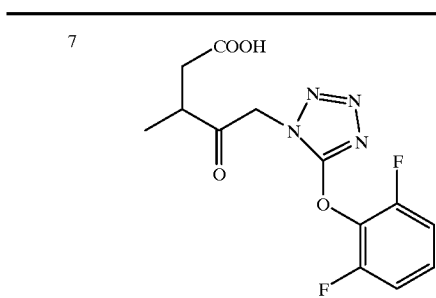 |
| --- | --- |
| 8 | 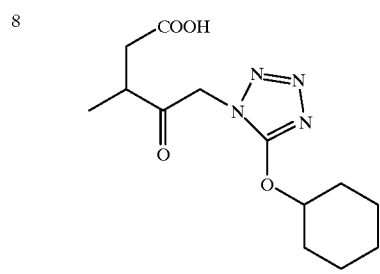 |
| 9 | 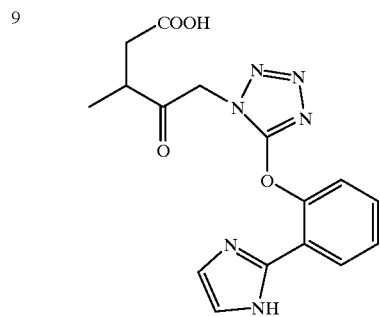 |
TABLE 62-continued
I (62)
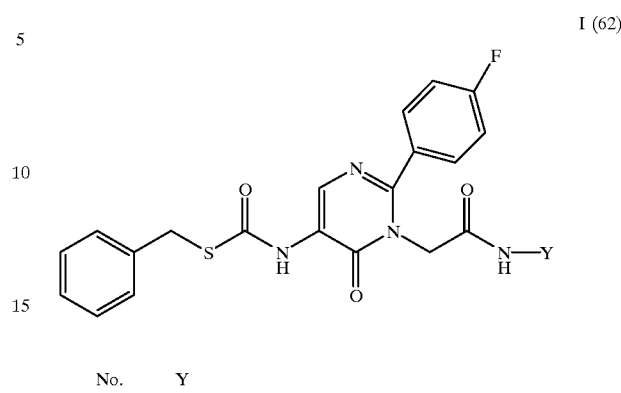
No. Y
| 10 | 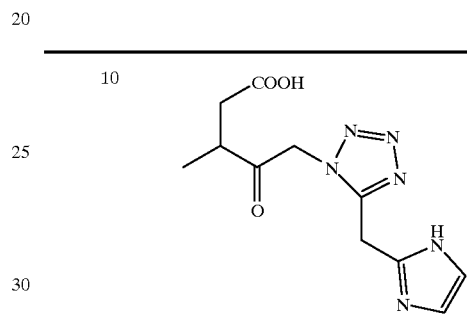 |
| --- | --- |
TABLE 63
I (63)
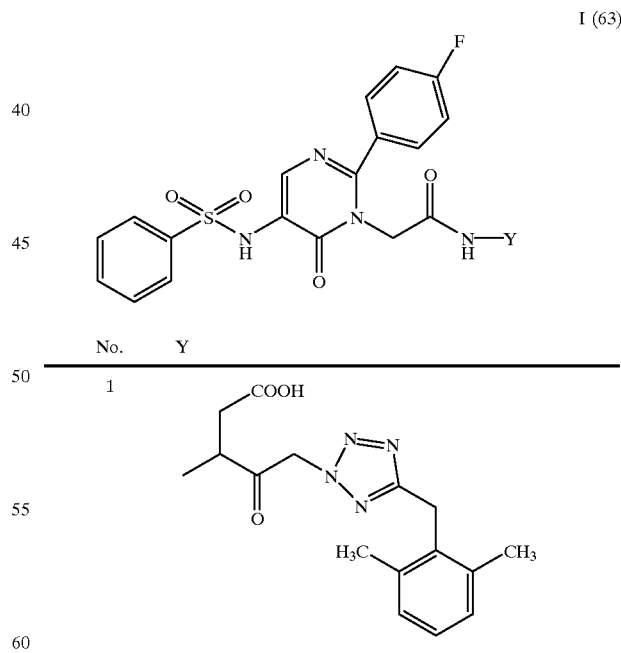
No. Y
| 1 | 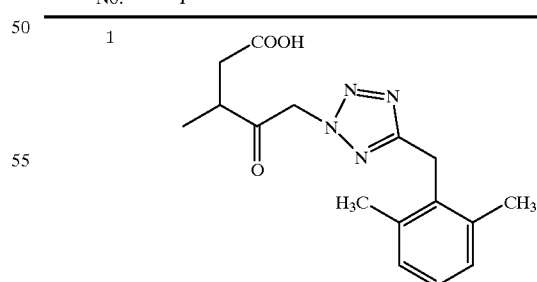 |
| --- | --- |

TABLE 63-continued
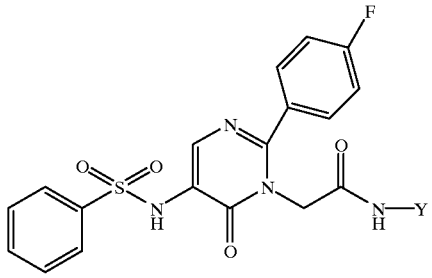
I (63)
| No. | Y |
|---|---|
| 2 | 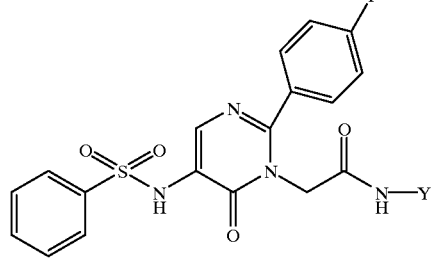 |
| 3 | 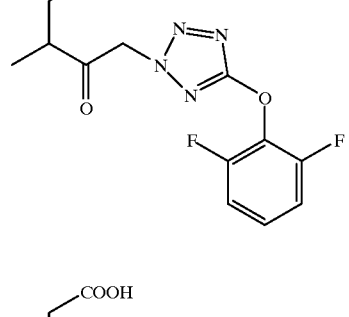 |
| 4 | 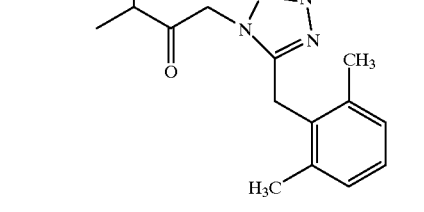 |
| 5 | 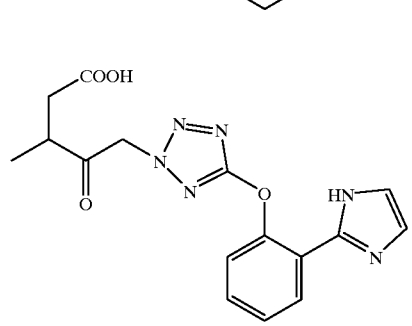 |
TABLE 63-continued
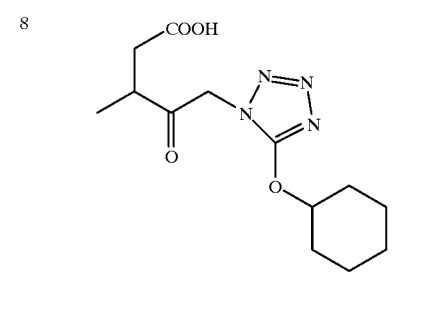
I (63)
| No. | Y |
|---|---|
| 6 | 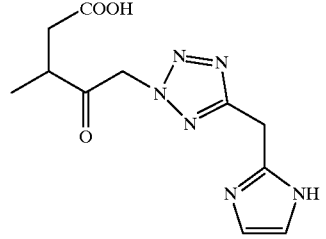 |
| 7 | 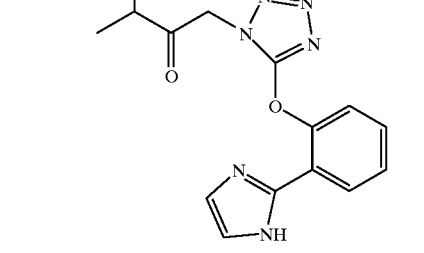 |
| 8 | |
| 9 | |

TABLE 63-continued

I (63)

| No. | Y |
|---|---|
| 10 | (3-methyl-4-oxo-5-(1H-imidazol-2-ylmethyl)tetrazol-1-yl)... COOH group |

TABLE 64

I (64)

| No. | R¹ |
|---|---|
| 1 | Me |
| 2 | 2-phenylphenyl |
| 3 | 3-(methoxycarbonyl)phenyl |
| 4 | 2-chlorophenyl |
| 5 | 2-(trifluoromethyl)phenyl |
| 6 | 2-naphthyl |
| 7 | 1,2,3,4-tetrahydroquinolin-3-yl |
| 8 | 2-thienyl |
| 9 | 4-methylimidazol-5-yl |
| 10 | 3-hydroxyphenyl |
| 11 | 2-(1H-tetrazol-5-yl)phenyl |
| 12 | 3-carboxyphenyl |
| 13 | 2-methoxyphenyl |

TABLE 64-continued

I (64)

| No. | R¹ |
|---|---|
| 14 | cyclohexyl-CH₂- |
| 15 | quinolin-3-yl-CH₂- |
| 16 | pyridin-2-yl-CH₂- |
| 17 | furan-2-yl-CH₂- |
| 18 | tert-butoxy-CH₂- (t-BuO-CH₂-) |

TABLE 65

I (65)

| No. | R¹ |
|---|---|
| 1 | Me |
| 2 | 2-biphenylyl-CH₂- |
| 3 | 3-(CH₃OOC)-C₆H₄-CH₂- |

TABLE 65-continued

I (65)

| No. | R¹ |
|---|---|
| 4 | 2-Cl-C₆H₄-CH₂- |
| 5 | 2-CF₃-C₆H₄-CH₂- |
| 6 | naphthalen-2-yl-CH₂- |
| 7 | 1,2,3,4-tetrahydroquinolin-3-yl-CH₂- |
| 8 | thiophen-2-yl-CH₂- |
| 9 | imidazol-4-yl-CH₂- |
| 10 | 3-HO-C₆H₄-CH₂- |
| 11 | 2-(1H-tetrazol-5-yl)-C₆H₄-CH₂- |
| 12 | 3-HOOC-C₆H₄-CH₂- |

TABLE 65-continued
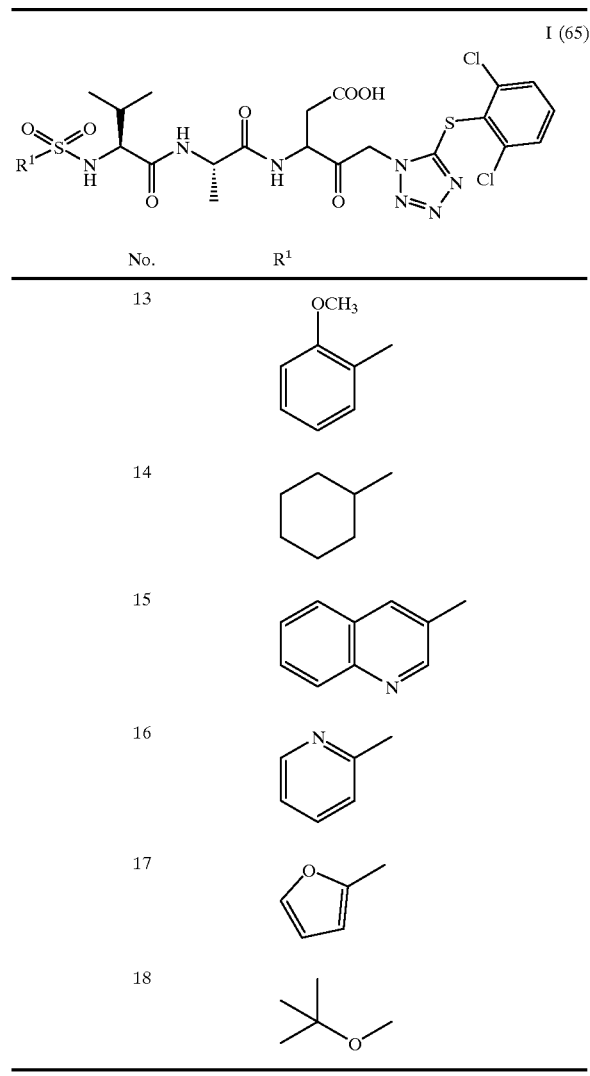
| No. | R[1] |
|---|---|
| 13 | 2-methoxyphenyl |
| 14 | cyclohexyl |
| 15 | quinolin-3-yl |
| 16 | pyridin-2-yl |
| 17 | furan-2-yl |
| 18 | tert-butoxymethyl |
TABLE 66
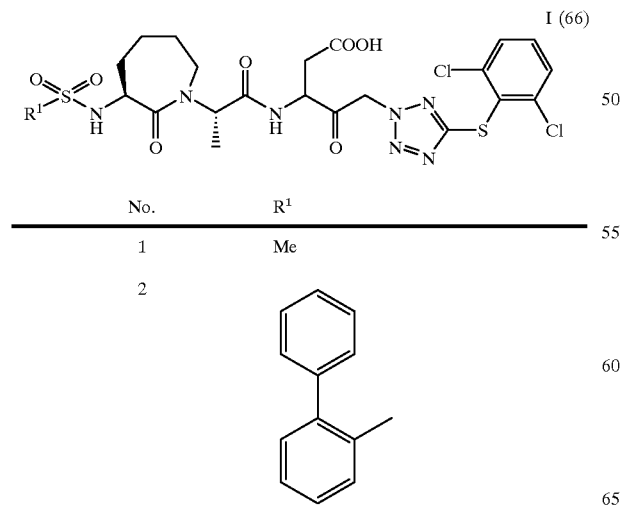
| No. | R[1] |
|---|---|
| 1 | Me |
| 2 | 2-biphenyl |
TABLE 66-continued
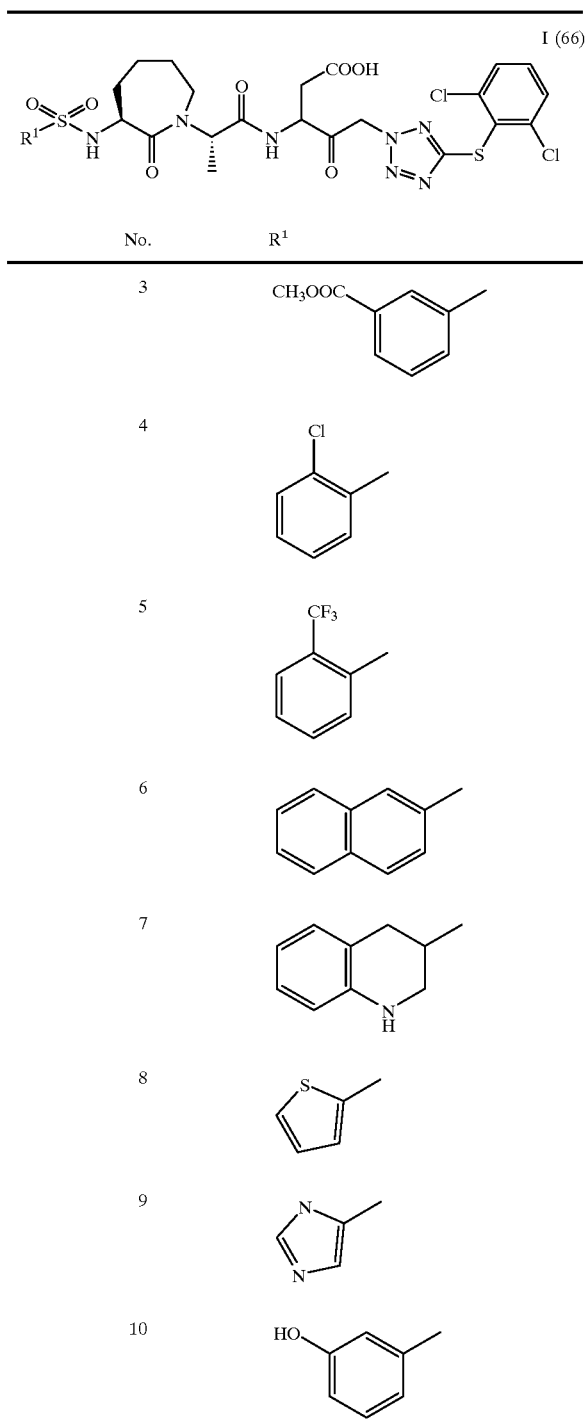
| No. | R[1] |
|---|---|
| 3 | 3-(methoxycarbonyl)phenyl |
| 4 | 2-chlorophenyl |
| 5 | 2-(trifluoromethyl)phenyl |
| 6 | naphthalen-2-yl |
| 7 | 1,2,3,4-tetrahydroquinolin-3-yl |
| 8 | thiophen-2-yl |
| 9 | imidazol-4-yl |
| 10 | 3-hydroxyphenyl |
| 11 | 2-(1H-tetrazol-5-yl)phenyl |

TABLE 66-continued
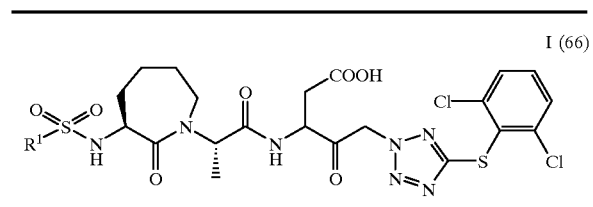
I (66)
| No. | R¹ |
|---|---|
| 12 | 3-carboxyphenyl (HOOC-C₆H₄-) |
| 13 | 2-methoxyphenyl (OCH₃-C₆H₄-) |
| 14 | cyclohexyl |
| 15 | quinolin-3-yl |
| 16 | pyridin-2-yl |
| 17 | furan-2-yl |
| 18 | tert-butoxymethyl (tBuO-CH₂-) |
TABLE 67
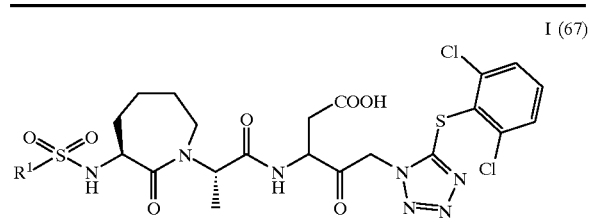
I (67)
| No. | R¹ |
|---|---|
| 1 | Me |
| 2 | biphenyl-2-yl |
| 3 | 3-(methoxycarbonyl)phenyl (CH₃OOC-C₆H₄-) |
| 4 | 2-chlorophenyl |
| 5 | 2-(trifluoromethyl)phenyl (CF₃-C₆H₄-) |
| 6 | naphthalen-2-yl |
| 7 | 1,2,3,4-tetrahydroquinolin-3-yl |
| 8 | thiophen-2-yl |
| 9 | imidazol-4-yl |
| 10 | 3-hydroxyphenyl (HO-C₆H₄-) |

TABLE 67-continued

I (67)

| No. | R¹ |
|---|---|
| 11 | 5-(2-methylphenyl)-1H-tetrazole |
| 12 | 3-methylbenzoic acid |
| 13 | 2-methylanisole |
| 14 | methylcyclohexane |
| 15 | 3-methylquinoline |
| 16 | 2-methylpyridine |
| 17 | 2-methylfuran |
| 18 | tert-butyl methyl ether |

TABLE 68

I (68)

| No. | R¹ |
|---|---|
| 1 | Me |
| 2 | 2-methylbiphenyl |
| 3 | methyl 3-methylbenzoate |
| 4 | 2-chlorotoluene |
| 5 | 2-(trifluoromethyl)toluene |
| 6 | 2-methylnaphthalene |
| 7 | 3-methyl-1,2,3,4-tetrahydroquinoline |
| 8 | 2-methylthiophene |
| 9 | 5-methylimidazole |
| 10 | 3-methylphenol |

TABLE 68-continued

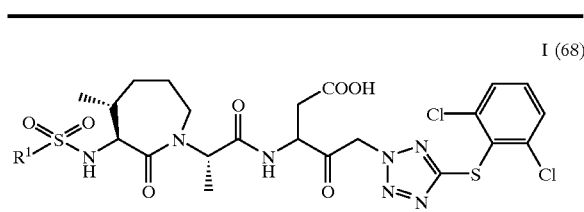

I (68)

| No. | R¹ |
|---|---|
| 11 | 2-(1H-tetrazol-5-yl)phenyl-methyl |
| 12 | 3-carboxyphenyl-methyl |
| 13 | 2-methoxyphenyl-methyl |
| 14 | cyclohexyl-methyl |
| 15 | quinolin-3-yl-methyl |
| 16 | pyridin-2-yl-methyl |
| 17 | furan-2-yl-methyl |
| 18 | tert-butoxymethyl |

TABLE 69

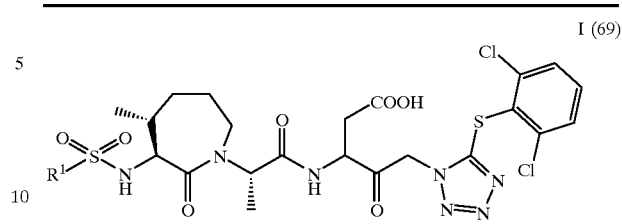

I (69)

| No. | R¹ |
|---|---|
| 1 | Me |
| 2 | 2-phenylphenyl-methyl |
| 3 | 3-(methoxycarbonyl)phenyl-methyl |
| 4 | 2-chlorophenyl-methyl |
| 5 | 2-(trifluoromethyl)phenyl-methyl |
| 6 | naphthalen-2-yl-methyl |
| 7 | 1,2,3,4-tetrahydroquinolin-3-yl-methyl |
| 8 | thiophen-2-yl-methyl |
| 9 | imidazol-4-yl-methyl |
| 10 | 3-hydroxyphenyl-methyl |

TABLE 69-continued
I (69)
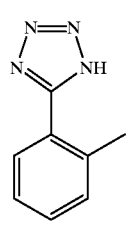
| No. | R¹ |
|---|---|
| 11 | 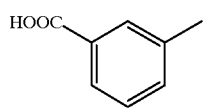 |
| 12 | 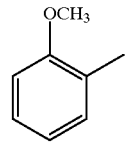 |
| 13 | 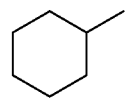 |
| 14 | 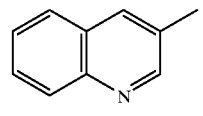 |
| 15 | 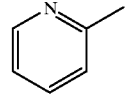 |
| 16 | 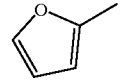 |
| 17 | 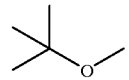 |
| 18 | 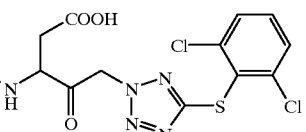 |
TABLE 70
I (70)
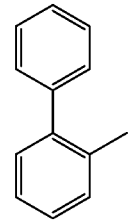
| No. | R¹ |
|---|---|
| 1 | Me |
| 2 | 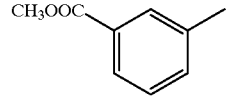 |
| 3 | 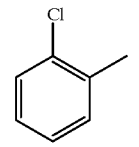 |
| 4 | 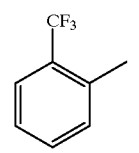 |
| 5 | 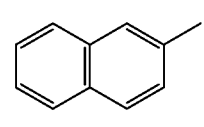 |
| 6 | 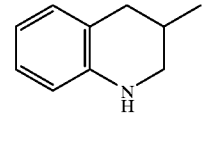 |
| 7 | 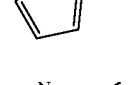 |
| 8 | 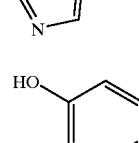 |
| 9 |  |
| 10 |  |

TABLE 70-continued
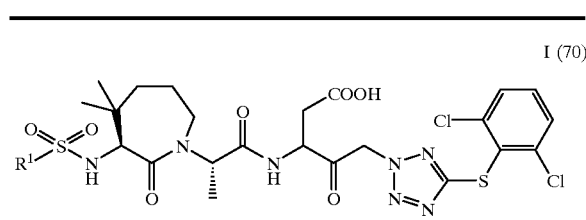
| No. | R¹ |
|---|---|
| 11 | 2-(1H-tetrazol-5-yl)phenyl |
| 12 | 3-carboxyphenyl |
| 13 | 2-methoxyphenyl |
| 14 | cyclohexyl |
| 15 | quinolin-3-yl |
| 16 | pyridin-2-yl |
| 17 | furan-2-yl |
| 18 | tert-butoxymethyl |
TABLE 71
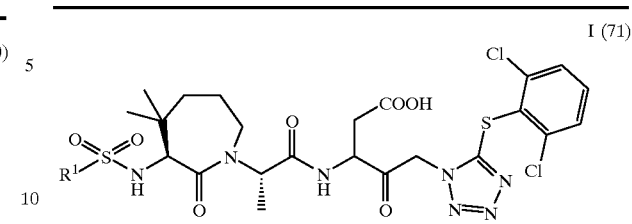
| No. | R¹ |
|---|---|
| 1 | Me |
| 2 | biphenyl-2-yl |
| 3 | 3-(methoxycarbonyl)phenyl |
| 4 | 2-chlorophenyl |
| 5 | 2-(trifluoromethyl)phenyl |
| 6 | naphthalen-2-yl |
| 7 | 1,2,3,4-tetrahydroquinolin-3-yl |
| 8 | thiophen-2-yl |
| 9 | imidazol-4-yl |
| 10 | 3-hydroxyphenyl |

TABLE 71-continued
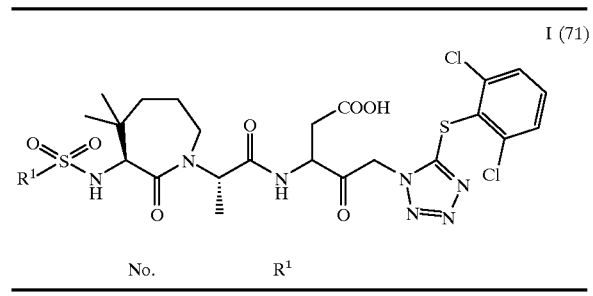
I (71)
| No. | R¹ |
|---|---|
| 11 | 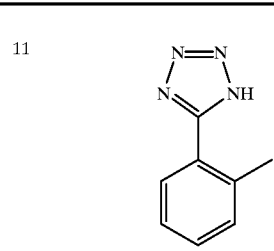 |
| 12 | 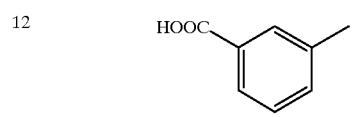 |
| 13 | 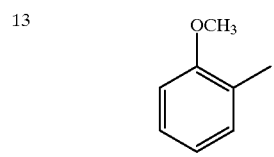 |
| 14 | 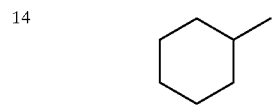 |
| 15 | 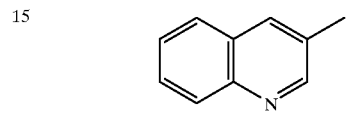 |
| 16 | 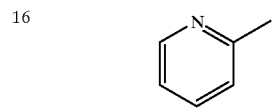 |
| 17 |  |
TABLE 71-continued
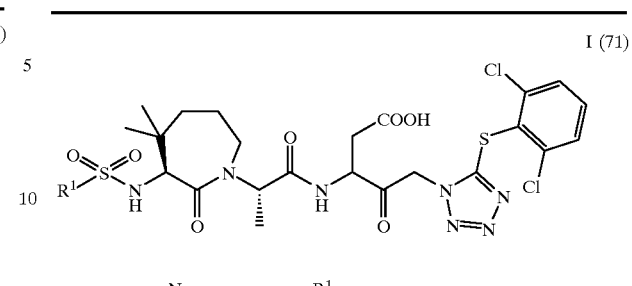
I (71)
| No. | R¹ |
|---|---|
| 18 | 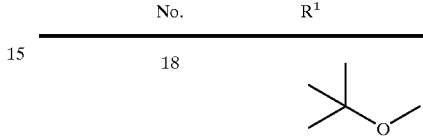 |
TABLE 72
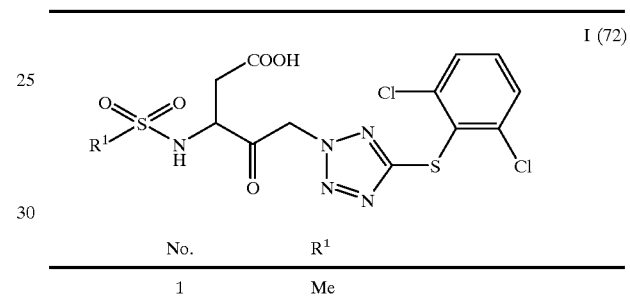
I (72)
| No. | R¹ |
|---|---|
| 1 | Me |
| 2 | 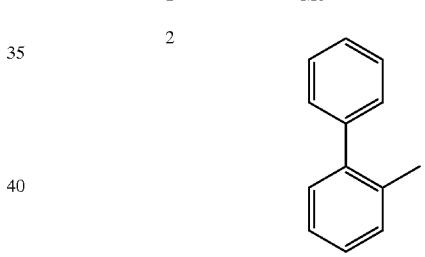 |
| 3 | 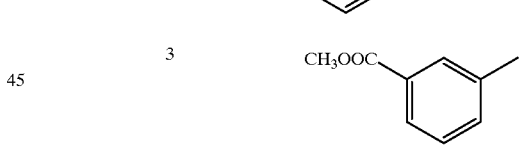 |
| 4 | 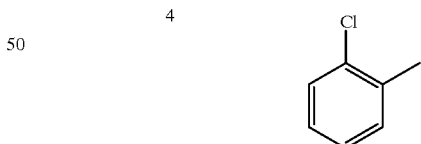 |
| 5 | 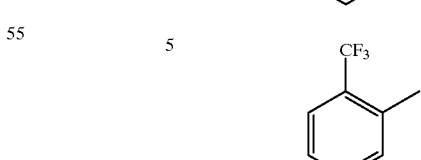 |
| 6 | 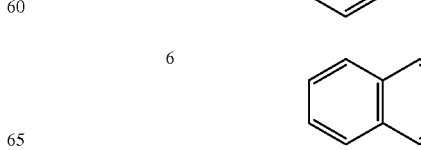 |

TABLE 72-continued
I (72)
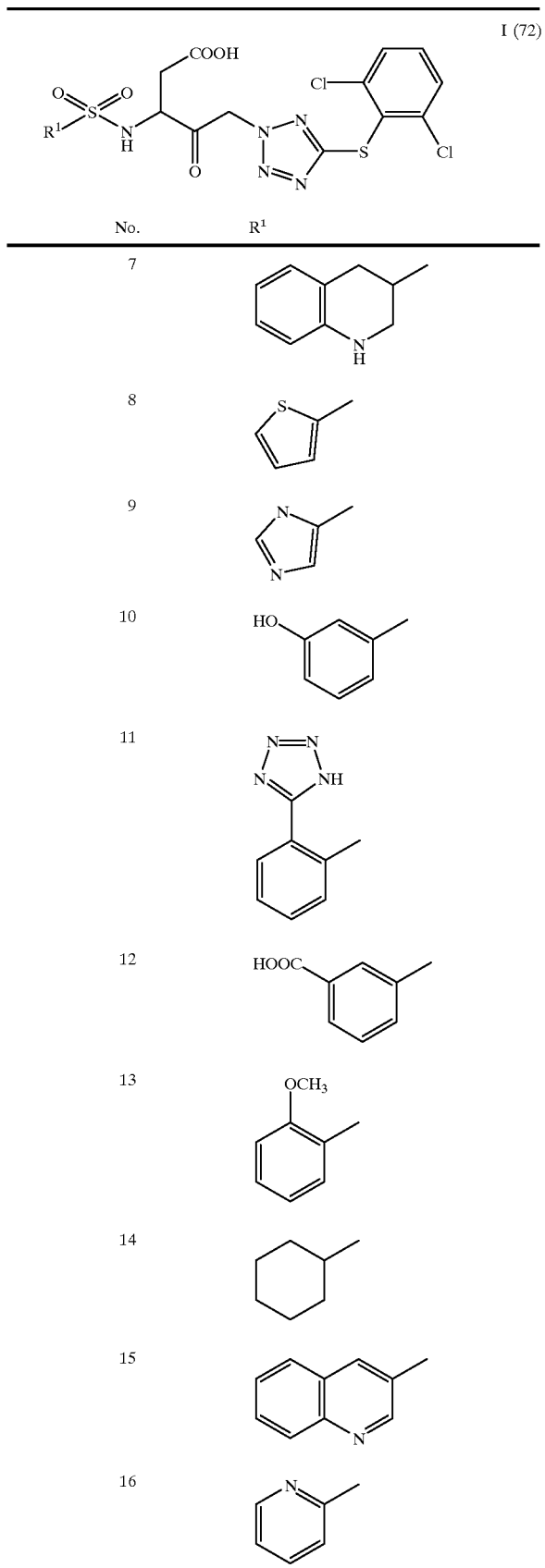
TABLE 72-continued
I (72)
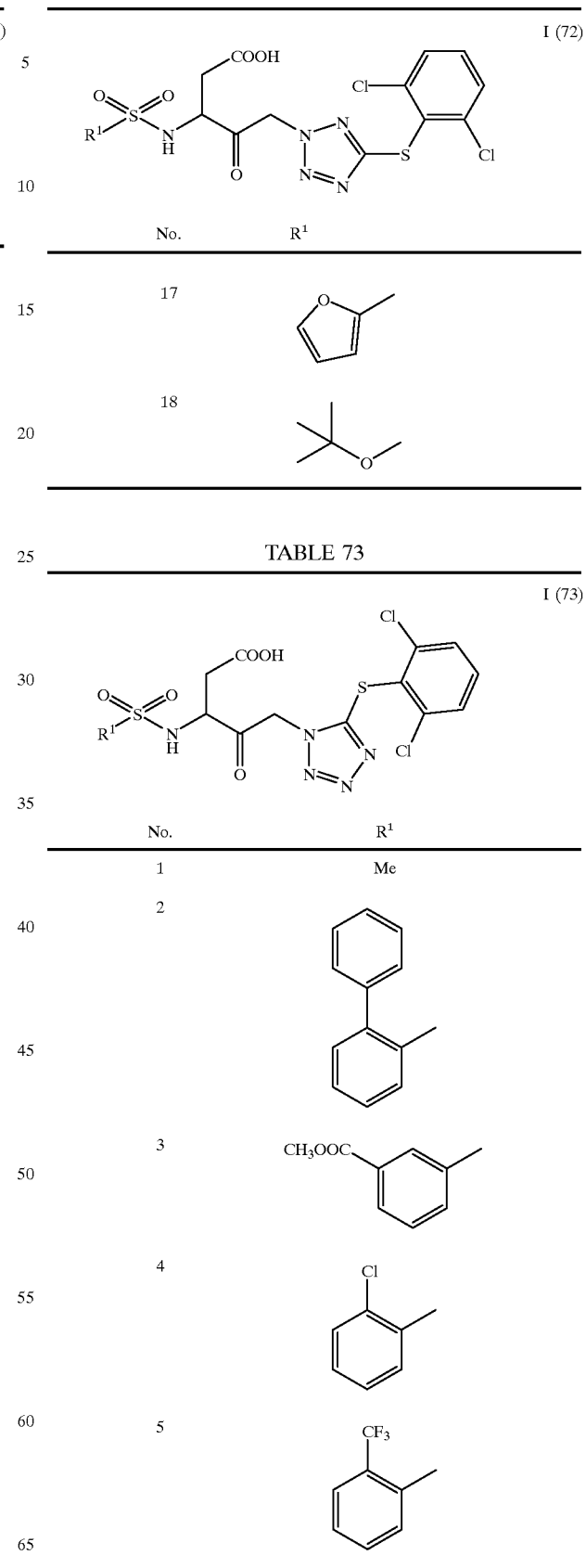

TABLE 73-continued
I (73)
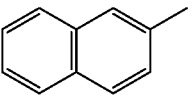
| No. | R¹ |
|---|---|
| 6 | 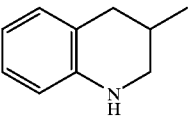 |
| 7 | 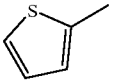 |
| 8 | 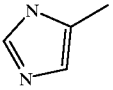 |
| 9 | 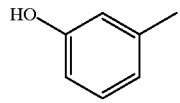 |
| 10 | 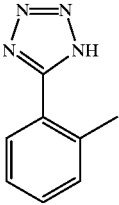 |
| 11 | 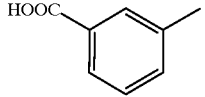 |
| 12 | 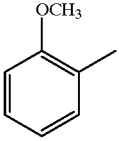 |
| 13 | 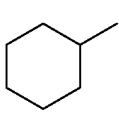 |
| 14 | 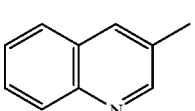 |
TABLE 73-continued
I (73)
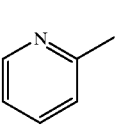
| No. | R¹ |
|---|---|
| 15 | 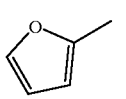 |
| 16 | 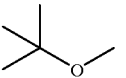 |
| 17 | 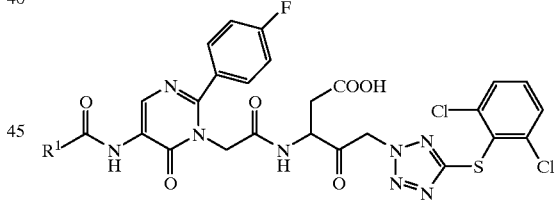 |
| 18 | 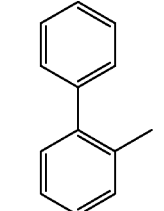 |
TABLE 74
I (74)
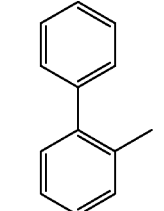
| No. | R¹ |
|---|---|
| 1 | Me |
| 2 |  |
| 3 |  |

TABLE 74-continued

I (74)

[Structure: R¹-NH-C(=O)- attached to 5-position of a pyrimidinone ring bearing 2-(4-fluorophenyl); N1 of pyrimidinone bears CH₂-C(=O)-NH-CH(CH₂COOH)-C(=O)-CH₂-[tetrazole-N]; tetrazole 5-position bears S-(2,6-dichlorophenyl)]

| No. | R¹ |
|---|---|
| 4 | 2-chlorophenyl |
| 5 | 2-(trifluoromethyl)phenyl |
| 6 | 2-naphthyl |
| 7 | 1,2,3,4-tetrahydroquinolin-3-yl |
| 8 | thiophen-2-yl |
| 9 | 1H-imidazol-4-yl |
| 10 | 3-hydroxyphenyl |
| 11 | 2-(1H-tetrazol-5-yl)phenyl |
| 12 | 3-carboxyphenyl |
| 13 | 2-methoxyphenyl |
| 14 | cyclohexyl |
| 15 | quinolin-3-yl |
| 16 | pyridazin-3-yl |
| 17 | isoxazol-5-yl |
| 18 | tert-butoxymethyl |

TABLE 75

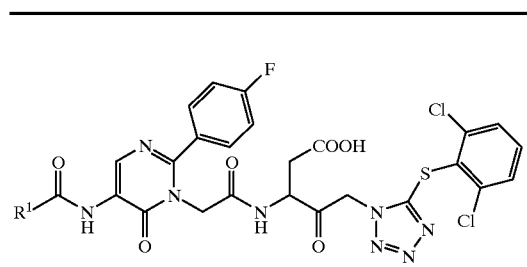

I (75)

| No. | R[1] |
|---|---|
| 1 | Me |
| 2 | (2-phenylphenyl)methyl |
| 3 | (3-(methoxycarbonyl)phenyl)methyl |
| 4 | (2-chlorophenyl)methyl |
| 5 | (2-(trifluoromethyl)phenyl)methyl |
| 6 | (naphthalen-2-yl)methyl |
| 7 | (3-methyl-1,2,3,4-tetrahydroquinolin-3-yl) |
| 8 | (thiophen-2-yl)methyl |
| 9 | (1H-imidazol-4-yl)methyl |

TABLE 75-continued

I (75)

| No. | R[1] |
|---|---|
| 10 | (3-hydroxyphenyl)methyl |
| 11 | (2-(1H-tetrazol-5-yl)phenyl)methyl |
| 12 | (3-carboxyphenyl)methyl |
| 13 | (2-methoxyphenyl)methyl |
| 14 | cyclohexylmethyl |
| 15 | (quinolin-3-yl)methyl |
| 16 | (pyridin-2-yl)methyl |
| 17 | (furan-2-yl)methyl |
| 18 | tert-butoxymethyl |

TABLE 76

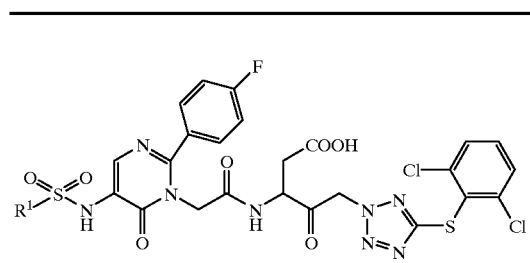

| No. | R¹ |
|---|---|
| 1 | Me |
| 2 | (2-phenylphenyl)methyl |
| 3 | (3-(methoxycarbonyl)phenyl)methyl |
| 4 | (2-chlorophenyl)methyl |
| 5 | (2-(trifluoromethyl)phenyl)methyl |
| 6 | (naphthalen-2-yl)methyl |
| 7 | (1,2,3,4-tetrahydroquinolin-3-yl)methyl |
| 8 | (thiophen-2-yl)methyl |
| 9 | (imidazol-4-yl)methyl |

TABLE 76-continued

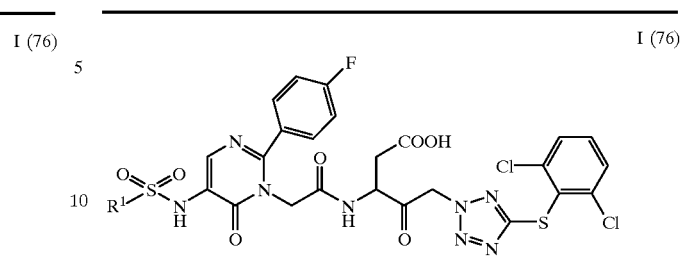

| No. | R¹ |
|---|---|
| 10 | (3-hydroxyphenyl)methyl |
| 11 | (2-(1H-tetrazol-5-yl)phenyl)methyl |
| 12 | (3-carboxyphenyl)methyl |
| 13 | (2-methoxyphenyl)methyl |
| 14 | cyclohexylmethyl |
| 15 | (quinolin-3-yl)methyl |
| 16 | (pyridin-2-yl)methyl |
| 17 | (furan-2-yl)methyl |
| 18 | tert-butoxymethyl |

TABLE 77
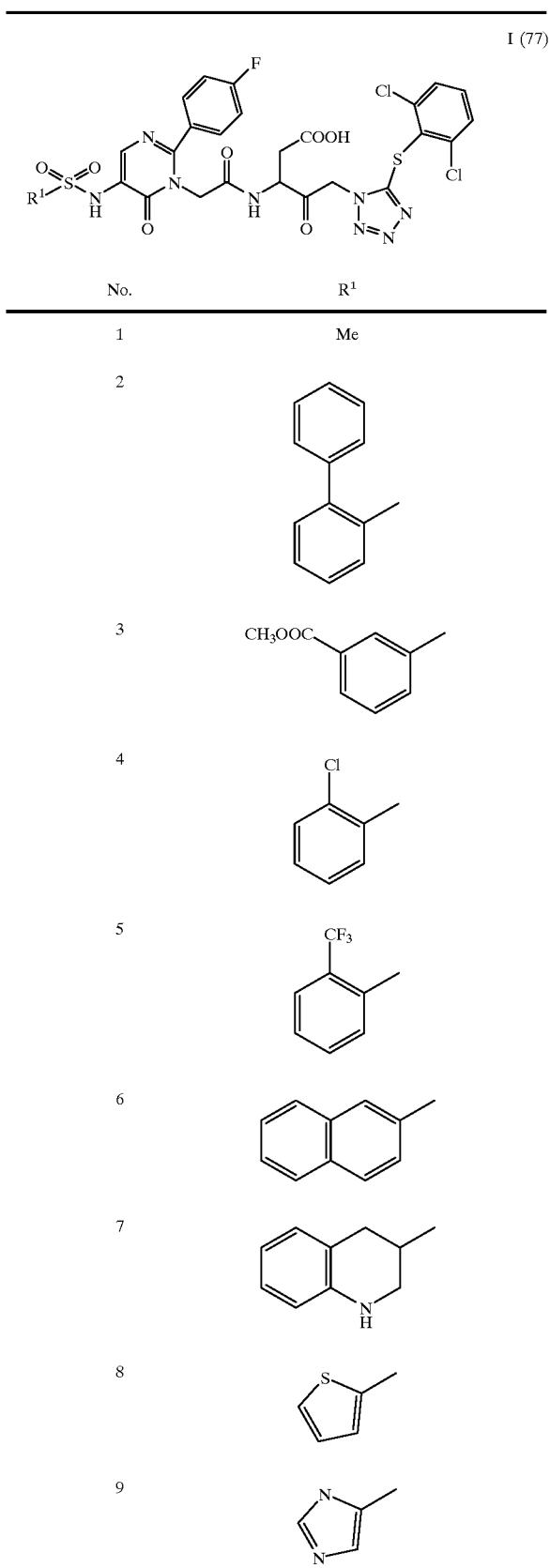
TABLE 77-continued
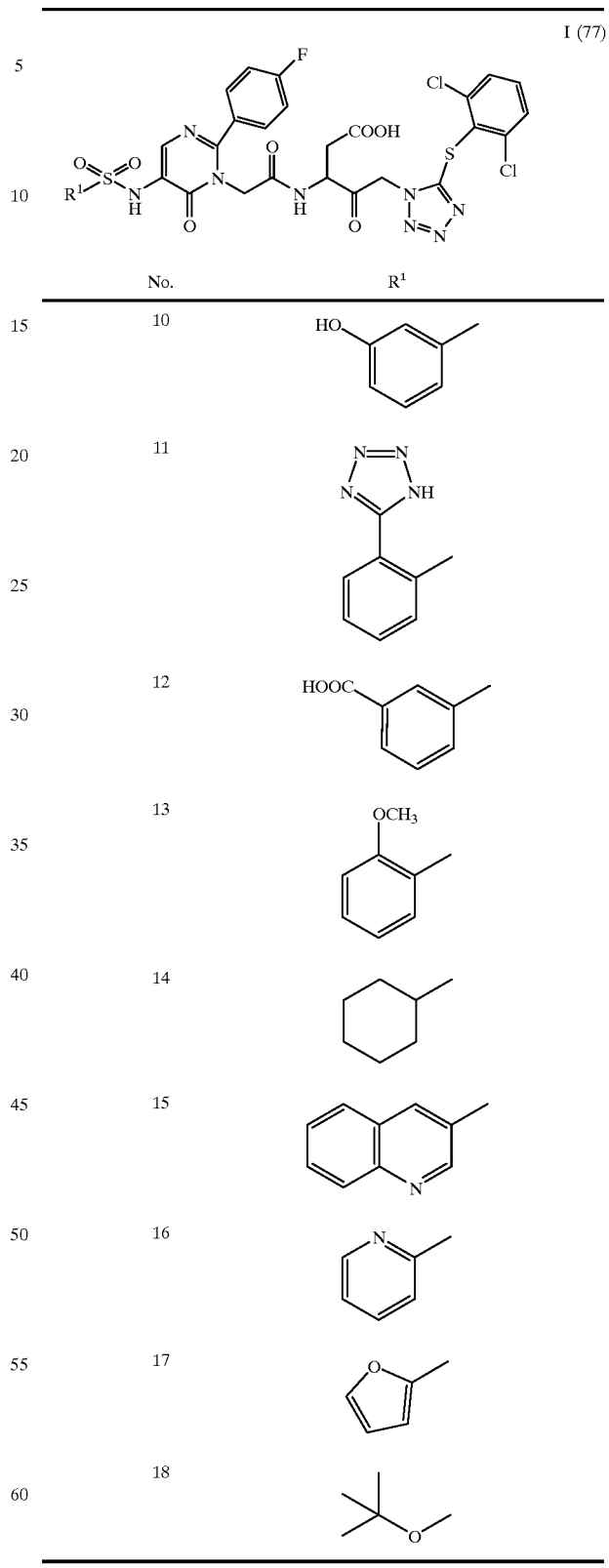
PROCESSES FOR THE PREPARATION
For compounds of formula (I) of the present invention, those in which R does not contain a COOH group, $AA^1$ does not contain a COOH group, $AA^2$ does not contain a COOH group and Y does not contain a COOH group, i.e., the compounds of formula (I-A)

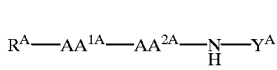
(I-A)

wherein $R^A$, $AA^{1A}$, $AA^{2A}$ and $Y^A$ have the same meaning as hereinbefore defined for R, $AA^1$, $AA^2$ and Y, respectively, provided that all of $R^A$, $AA^{1A}$, $AA^{2A}$ and $Y^A$ do not contain a COOH group may be prepared by methods (a) to (b) as follows.

(a) For compounds of formula (I-A) of the present invention, those in which $R^A$ does not contain an amino group, $AA^{1A}$ does not contain an amino group, $AA^{2A}$ does not contain an amino group, $Y^A$ does not contain an amino group and —Z—E group is bonded directly to a carbon atom of tetrazole of $Y^A$, i.e., the compounds of formula (I-A-a)

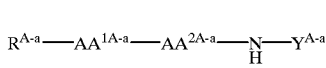
(I-A-a)

wherein $R^{A-a}$, $AA^{1A-a}$, $AA^{2A-a}$ and $Y^{A-a}$ have the same meaning as hereinbefore defined for $R^A$, $AA^{1A}$, $AA^{2A}$ and $Y^A$, respectively, provided that all of $R^{A-a}$, $AA^{1A-a}$, $AA^{2A-a}$ and $Y^{A-a}$ do not contain an amino group and —Z—E group is bonded directly to a carbon atom of tetrazole of $y^{A-a}$ may be prepared by methods (a-1), (a-2), (a-3) or (a-4) as follows.

(a-1) For compounds of formula (I-A-a) of the present invention, those in which —Z—E do not tri(C1–4 alkyl)silyl, i.e., the compounds of formula (I-A-a-1)

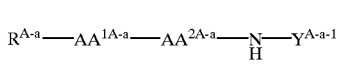
(I-A-a-1)

wherein $Y^{A-a-1}$ have the same meaning as hereinbefore defined for $Y^{A-a}$, provided that of $Y^{A-a-1}$ do not tri(C1–4 alkyl)silyl, the other symbols are the same meaning as hereinbefore defined may be prepared by reacting a compound of formula (II-a-1)

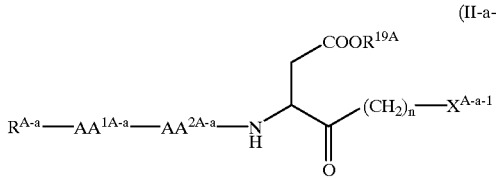
(II-a-1)

wherein $R^{19A}$ is C1–8 alkyl, phenyl or C1–4 alkyl substituted with phenyl, $X^{A-a-1}$ is a leaving group known per se (e.g., chlorine, bromine or iodine atom, mesyl, tosyl group etc.) and the other symbols have the same meaning as hereinbefore defined with a compound of formula (III-a-1)

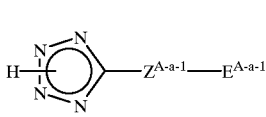
(III-a-1)

wherein $Z^{A-a-1}$ and $E^{A-a-1}$ has the same meaning as hereinbefore defined for Z and E, provided that —$Z^{A-a-1}$—$E^{A-a-1}$ do not contain COOH, amino groups and tri(C1–4 alkyl) silyl group.

This reaction is known per se, and may be carried out, for example, in an organic solvent (e.g., N,N-dimethylformamide etc.), in the presence of potassium fluoride etc., at a temperature of from 20° C. to 40° C.

(a-2) For compounds of formula (I-A-a) of the present invention, those in which —Z—E represent tri(C1–4 alkyl) silyl, i.e., the compounds of formula (I-A-a-2)

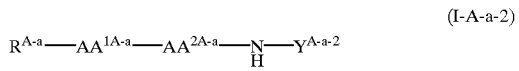
(I-A-a-2)

wherein $Y^{A-a-2}$ have the same meaning as hereinbefore defined for $Y^{A-a}$, provided that of —Z—E group in $Y^{A-a-2}$ represent tri(C1–4 alkyl)silyl, the other symbols are the same meaning as hereinbefore defined may be prepared by reacting a compound of formula (II-a-2)

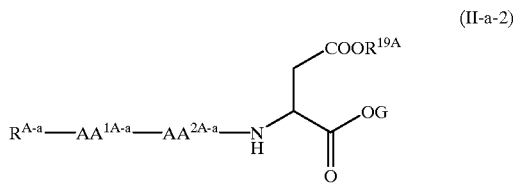
(II-a-2)

wherein G is C1–4 alkyl and the other symbols have the same meaning as hereinbefore defined with a compound of formula (III-a-2)

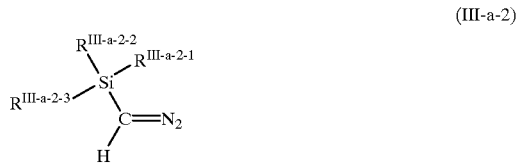
(III-a-2)

wherein $R^{III-a-2-1}$, $R^{III-a-2-2}$ and $R^{III-a-2-3}$ is each independently C1–4 alkyl.

This reaction is known per se, and may be carried out, for example, the same method described in Chem. Pharm. Bull., 30, 3450–3452 (1982). For example, this reaction carried out by reacting the compound of the formula (III-a-2) with alkylaminolithium (e.g., lithium diisobutylamide [LDA], etc.) in an inert organic solvent (e.g., diethyl ether, tetrahydrofuran etc.) under an atmoshere inert gas (e.g., argon, nitrogen, etc.) at a temperature of from –20° C. to 0° C., and then by reacting the obtained lithium compound with the compound of the formula (II-a-2) at a temperature of from –20° C. to 0° C.

(a-3) For compounds of formula (I-A-a) of the present invention, those in which $R^{A-a}$ and NH group in $AA^{1A-a}$ or $AA^{2A-a}$ bonded to form amide bond, sulfonamide bond or sulfonylurea bond, i.e., the compounds of formula (I-A-a-3)

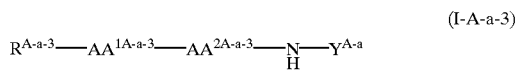
(I-A-a-3)

wherein $R^{A-a-3}$, $AA^{1A-a-3}$ and $AA^{2A-a-3}$ have the same meaning as hereinbefore defined for $R^{A-a}$, $AA^{1A-a}$ and $AA^{2A-a}$, provided that of $R^{A-a-3}$ and NH group in $AA^{1A-a-3}$, $AA^{2A-a-3}$ and $Y^{A-a}$ bonded to form amide bond, sulfonamide bond or sulfonylurea bond, the other symbols are the same meaning as hereinbefore defined may be prepared by reacting a compound of formula (II-a-3)

$R^{A-a}-AA^{1A-a}-AA^{2A-a}-X^{A-a-3}$ (II-a-3)

wherein $X^{A-a-3}$ is a leaving group (e.g., chlorine, bromine or iodine atom etc.) or a hydroxy group and the other symbols have the same meaning as hereinbefore defined with a compound of formula (III-a-3)

$H_2N-Y^{A-a}$ (III-a-3)

wherein all the symbols have the same meaning as hereinbefore defined.

The reaction can be carried out as an amidation reaction, sulfonamidation reaction, sulfonylurea reaction and the like.

Amidation reactions are known per se and can be carried out by, for example:

(1) using an acid halide,
(2) using a mixed acid anhydride,
(3) using a condensing agent etc.

Each of those methods can be carried out, for example, as follows:

(1) the method using an acid halide may be carried out, for example, by reacting a carboxylic acid with an acid halide (e.g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with an amine in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C., (2) the method using a mixed acid anhydride may be carried out, for example, by reacting a carboxylic acid and an acid halide (e.g., pivaloyl chloride, tosyl chloride, mesyl chloride etc.) or an acid derivative (e.g., ethyl chloroformate, isobutyl chloroformate etc.) in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.) or without a solvent at a temperature of from 0° C. to 40° C., and then by reacting the mixture of acid anhydride obtained with an amine in an inert organic solvent (e.g., chloroform, methylene chloride, diethyl ether, tetrahydrofuran etc.), at a temperature of from 0° C. to 40° C., or (3) the method using a condensing agent (e.g., 1,3-dicyclohexyl carbodiimide (DCC), 1-ethyl-3-[3-(dimethylamino)propyl]carbodiimide (EDC), 2-chloro-1-methylpyridinium iodide etc.) may be carried out, for example, by reacting a carboxylic acid with an amine using a condensing agent in the presence or absence of a tertiary amine (e.g., pyridine, triethylamine, dimethylaniline, dimethylaminopyridine etc.) in an inert organic solvent (e.g., chloroform, methylene chloride, dimethyl formamide, diethyl ether etc.) or without a solvent at a temperature of from 0° C. to 40° C.

The reactions (1), (2) and (3) hereinbefore described preferably may be carried out in an atmosphere of inert gas (e.g., argon, nitrogen etc.) under anhydrous conditions.

Sulfonamidation reactions are known pre se, and can be carried out, for example, by reacting a sulfonic acid derivatives with an acid halide (e.g., oxalyl chloride, thionyl chloride, phosphous trichloride, phosphous pentachloride etc.) in an inert organic solvent (e.g., chloroform, methylene chloride, diethyl ether, tetrahydrofuran etc.) or without a solvent at from −20° C. to the reflux temperature of the solvent, and then by reacting the sulfonyl halide obtained with an amine in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C.

Formation of sulfonylurea reactions are known pre se, and can be carried out, for example, by reacting a aminosulfonic acid derivatives with an acid halide (e.g., oxalyl chloride, thionyl chloride, phosphous trichloride, phosphous pentachloride etc.) in an inert organic solvent (e.g., chloroform, methylene chloride, diethyl ether, tetrahydrofuran etc.) or without a solvent at from −20° C. to the reflux temperature of the solvent, and then by reacting the aminosulfonyl halide obtained with an amine in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C.

(a-3) For compounds of formula (I-A-a) of the present invention, those in which $R^{A-a}$ and NH group in $AA^{1A-a}$ or $AA^{2A-a}$ bonded to form urea bond, i.e., the compounds of formula (I-A-a-4)

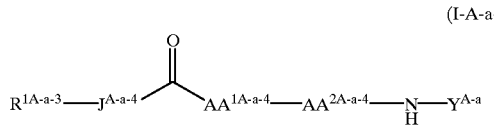

(I-A-a-4)

wherein $R^{1A-a-3}$, $J^{A-a-4}$, $AA^{1A-a-4}$ and $AA^{2A-a-4}$ have the same meaning as hereinbefore defined for $R^1$, J, $AA^{1A-a}$ and $AA^{2A-a}$, provided that of $R^{1A-a-4}-J^{A-a-4}$ group do not contain an COOH, amino group, and carbonyl bonded to NH group in $R^{1A-a-4}-J^{A-a-4}$, the other symbols are the same meaning as hereinbefore defined may be prepared by reacting a compound of formula (II-a-4)

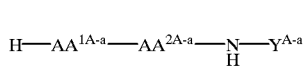

(II-a-4)

wherein all the symbols have the same meaning as hereinbefore defined with a compound of formula (III-a-4)

$R^{1A-a-4}-J^{A-a-4}-H$ (III-a-4)

wherein all the symbols have the same meaning as hereinbefore defined.

Formation of urea reactions are known pre se, and can be carried out, for example, in an inert organic solvent (e.g., dimethylformamide, dichloromethane, tetrahydrofuran etc.), using N,N'-carbodiimidazole, an amine in the presence or absence of a tertiary amine (e.g., pyridine, triethylamine, dimethylaniline, dimethylaminopyridine etc.), at a temperature of from 0° C. to 80° C.

(b) For compounds of formula (I-A) of the present invention, those in which at least one of $R^A$, $AA^{1A}$, $AA^{2A}$ and $Y^A$ represent contains an amino group i.e., the compounds of formula (I-A-b)

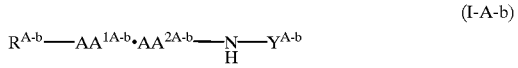

(I-A-b)

wherein $R^{A-b}$, $AA^{1A-b}$, $AA^{2A-b}$ and $Y^{A-b}$ have the same meaning as hereinbefore defined for $R^A$, $AA^{1A}$, $AA^{2A}$ and $Y^A$, respectively, provided that at least one of $R^{A-b}$, $AA^{1A-b}$, $AA^{2A-b}$ and $Y^{A-b}$ represent contains an amino group may be prepared by methods (b-1) or (b-2) as follows.

(b-1) For compounds of formula (I-A-b) of the present invention may be prepared by subjecting the amino protecting group to elimination, the compound prepared by the same methods (a-1), (a-2), (a-3) or (a-4) above and protecting an amino group as known per se (e.g., t-butyloxycarbonyl, benzyloxycarbonyl, triphenylmethyl, 2-(trimethylsilyl)ethoxymethyl or trifluoroacetyl etc.), i.e., the compound of formula (II-b-1)

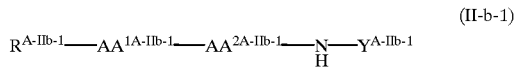

(II-b-1)

wherein $R^{A-IIb-1}$, $AA^{1A-IIb-1}$, $AA^{2A-IIb-1}$ and $Y^{A-IIb-1}$ have the same meaning as hereinbefore defined for $R^{A-b}$, $AA^{1A-b}$, $AA^{2A-b}$ and $Y^{A-b}$, respectively, provided that at least one of $R^{A-IIb-1}$, $AA^{1A-IIb-1}$, $AA^{2A-IIb-1}$, and $Y^{A-IIb-1}$ represent contains a protected amino group with a known protecting group (e.g., t-butyloxycarbonyl, benzyloxycarbonyl, triphenylmethyl, 2-(trimethylsilyl) ethoxymethyl or trifluoroacetyl etc.)

The elimination of an amino protecting group May be carried out by methods known per se, and depends on the protecting group. For example, when the protecting group is t-butoxycarbonyl, triphenylmethyl or 2-(trimethylsilyl) ethoxymethyl, the reaction may be carried out in a water-miscible organic solvent (e.g., methanol, tetrahydrofuran, dioxane, acetone etc.) in the presence of aqueous solution of organic acid (e.g., acetic acid, trifluoroacetic acid etc.) or inorganic acid (hydrochloric acid, sulfuric acid etc.) or a mixture of them, at a temperature of from 0° C. to 100° C.

When the protecting group is a benzyloxycarbonyl group, the elimination of the protecting group can be carried out by hydrogenation. The hydrogenation reaction is known per se, and may be carried out, for example, in an inert solvent [ether (e.g., tetrahydrofuran, dioxane, diethoxyethane, diethyl ether etc.), alcohol (e.g., methanol, ethanol etc.), benzene analogues (e.g., benzene, toluene etc.), ketone (e.g., acetone, methyl ethyl ketone etc.), nitrile (e.g., acetonitrile etc.), amide (e.g., dimethylformamide etc.), water, ethyl acetate, acetic acid, mixture of two or more of them etc.], in the presence of a catalyst of hydrogenation (e.g., palladium on activated carbon, palladium black, palladium, palladium hydroxide on carbon, platinum oxide, nickel, Raney nickel (registered trade mark) etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonic acid, oxalic acid, trifluoroacetic acid, formic acid etc.), at ordinary or additional pressure under an atmosphere of hydrogen, at a temperature of from 0° C. to 200° C. When using an acid, its salt may be used at the same time.

Furthermore, when the protecting group is a trifluoroacetyl group, may be carried out, for example, in a water-miscible organic solvent (e.g., methanol, tetrahydrofuran, dioxan, acetone etc.), using a hydroxide of an alkali metal (e.g., sodium hydroxide, potassium hydroxide, etc.), hydroxide of an alkaline earth metal (e.g., barium hydroxide, calcium hydroxide, etc.), or a carbonate of an alkali metal (e.g., sodium carbonate, potassium carbonate, etc.), or aqueous solution thereof, at a temperature of from 0° C. to 40° C.

It should be easily understood by those skilled in the art, that other amino protecting groups that can be used in the present invention are available and the choices are not limited only to t-butyloxycarbonyl, benzyloxycarbonyl, triphenylmethyl, 2-(trimethylsilyl) ethoxymethyl or trifluoroacetyl groups. Any group which can be easily and selectively eliminated essentially can be used. For example, a protecting group may be one described in Protective Groups in Organic Synthesis (T. W. Greene, Wiley, New York (1991)). The proposed compounds of the present invention may be easily prepared with those protecting group practicing known methods.

(b-2) For compounds of formula (I-A-b) of the present invention may be prepared by subjecting reduction, the compound prepared by the same methods (a-1), (a-2), (a-3) or (a-4) above and having nitro group, i.e., the compound of formula (II-b-2)

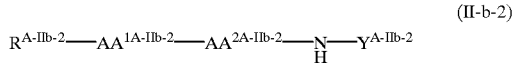

(II-b-2)

wherein $R^{A-IIb-2}$, $AA^{1A-IIb-2}$, $AA^{2A-IIb-2}$, and $Y^{A-IIb-2}$, have the same meaning as hereinbefore defined for $R^{A-b}$, $AA^{1A-b}$, $AA^{2A-b}$ and $Y^{A-b}$, respectively, provided that at least one of $R^{A-IIb-2}$, $AA^{1A-IIb-2}$, $AA^{2A-IIb-2}$ and $Y^{A-IIb-2}$ contains a nitro group.

Reduction of nitro group is known per se, and may be carried out, hydrogenation or reduction by using organic metal.

Hydrogenation may be carried out by the same method as hereinbefore described.

Reduction by using organic metal is known per se, and may be carried out, for example, in a water-miscible organic solvent (e.g., ethanol, methanol etc.), in the presence or absence of an aqueous solution of hydrochloric acid, by using organic metal (e.g., zinc, iron, tin, tin chloride, iron chloride, etc.), at a temperature of from 50° C. to 150° C.

For compounds of formula (I) of the present invention, those in which at least one of R, $AA^1$, $AA^2$ and Y represent contain a COOH group, i.e., the compounds of formula (I-B)

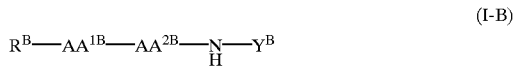

(I-B)

wherein $R^B$, $AA^{1B}$, $AA^{2B}$ and $Y^B$ have the same meaning as hereinbefore defined for R, $AA^1$, $AA^2$ and Y, respectively, provided that at least one of $R^B$, $AA^{1B}$, $AA^{2B}$ and $Y^B$ represent contains a COOH group may be prepared by, for example, hydrolysis of a t-butylester, hydrogenation, hydrolysis of an ester or a cleavage reaction of a 2,2,2-trichloroethylester group of a compound having at least one COOH group derivatized to contain a t-butylester, benzylester, alkylester or 2,2,2-trichloroethylester i.e., the compound of formula (I-A-1)

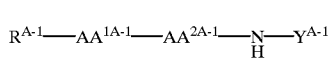
(I-A-1)

wherein $R^{A-1}$, $AA^{1A-1}$, $AA^{2A-1}$ and $Y^{A-1}$ have the same meaning as hereinbefore defined for $R^A$, $AA^{1A}$, $AA^{2A}$ and $Y^A$, respectively, provided that at least one of $R^{A-1}$, $AA^{1A-1}$, $AA^{2A-1}$ and $Y^{A-1}$ represent contains a t-butylester, benzylester, alkylester or 2,2,2-trichloroethylester group.

Hydrolysis of t-butylester is known per se, and may be carried out, for example, in an inert organic solvent (e.g., dichloromethane, chloroform, methanol, dioxane, ethyl acetate, anisole etc.) in the presence of an organic acid (e.g., trifluoroacetic acid etc.), or inorganic acid (e.g., hydrochloric acid etc.) or a mixture of them, at a temperature of from 0° C. to 90° C.

Hydrogenation may be carried out by the same method as hereinbefore described.

Hydrolysis of an ester is known per se, and may be carried out, for example, by hydrolysis in acid or under alkaline conditions. Hydrolysis under alkaline conditions may be carried out, for example, in an appropriate organic solvent (e.g., methanol, dimethoxyethane etc.), using a hydroxide or a carbonate of an alkali metal or alkaline earth metal, at a temperature of from 0° C. to 40° C. Hydrolysis under acidic conditions may be carried out by the same method as for hydrolysis of a t-butylester.

Cleavage of 2,2,2-trichloroethylester is known per se, and may be carried out, for example, in an acidic solvent (e.g., acetic acid, buffer of pH4.2–7.2 or a mixture of organic solvent (e.g. tetrahydrofuran etc.) and solution thereof etc.), in the presence of zinc powder, sonicated or not sonicated, at a temperature of from 0° C. to 40° C.

It should be easily understood by those skilled in the art that the carboxyl protecting group of the present invention are not to only t-butylester, benzylester or 2,2,2-trichloroethylester but any group which can be easily and selectively eliminated can be used in the present invention. For example, a protecting group described in Protective Groups in Organic Synthesis (T. W. Greene, Wiley, N.Y. (1991)) may be used. The proposed compounds of the present invention may be easily prepared using those protecting groups and practicing known methods.

For compounds of formula (I) of the present invention, those in which R does not contain a COOH and amino group, $AA^1$ does not contain a COOH and amino group, $AA^2$ does not contain a COOH and amino group, Y does not contain a COOH and amino group and Z or $R^{20}$ group in Y represent amide group, i.e., the compounds of formula (I-C)

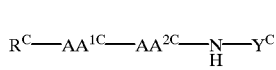
(I-C)

wherein $R^C$, $AA^{1C}$, $AA^{2C}$ and $Y^C$ have the same meaning as hereinbefore defined for R, $AA^1$, $AA^2$ and Y, respectively, provided that all of $R^C$, $AA^{1C}$, $AA^{2C}$ and $Y^C$ do not contain a COOH and amino group, and Z or $R^{20}$ group in $Y^C$ represent amide group may be prepared by subjecting the amidation, the compound prepared by the same methods (I-B) above and Z or $R^{20}$ selectively represent —COOH, methylester or ethylester, i.e., the compound of formula (I-B-1)

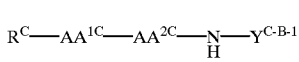
(I-B-1)

wherein $Y^{C-B-1}$ has the same meaning as hereinbefore defined for $Y^C$, provided that Z or $R^{20}$ in $Y^C$ represent COOH with an amine compound of formula (III-C-1)

(III-C-1)

wherein all the symbols are the same meaning as hereinbefore defined.

Amidation of —COOH group and amine may be carried out by the same method as hereinbefore described.

Amidation of -methylester or ethylester and amine may be carried out, for example, in a water-miscible organic solvent (e.g., methanol, ethanol etc.), an aqueous solution of an amine compound of the formula (III-C-1), at room temperature.

For compounds of formula (I) of the present invention, those in which at least one of R, $AA^1$, $AA^2$ and Y represent contain a COOH and amino group and Z or $R^{20}$ group in Y represent amide group, may be prepared by subjecting the amino protecting group to elimination hereinbefore described or the carboxy protecting group to elimination hereinbefore described, the compound prepared by the same methods (I-C) above.

A compound of formula (II-a-1) may be prepared by methods known per se. For example, the compound may be produced by methods described in the literature of J. Med. Chem., 37, 563 (1994) or in EP 0623592.

The products of such synthesis reactions may be purified in a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

The starting materials and each reagents used in the process for the preparation of the present invention are known per se or may be easily prepared by known methods.
Effect It has been confirmed that the compounds of formula (I) of the present invention have inhibitory activities on IL-1β converting enzyme. For example, in laboratory tests the following results were obtained.
Method (1) Assay for IL-1β converting enzyme The reaction mixture contains, for example, 20 mM of HEPES-NaOH pH7.4, 10 mM of KOH, 1.5 mM of $MgCl_2$, 0.1 mM of EDTA and 10% glycerol. Various concentrations of test compounds (50 μl), human ICE solution (50 μl) and various concentrations of substrate (Ac-Tyr-Val-Ala-Asp-MCA) were mixed and incubated at 37° C. Fluorescence intensity was measured at En=355 nm and Ex=460 nm. The compounds of the present invention have ICE inhibitory values less than 1 μM (for example, in Example 2(1), the compound has an $IC_{50}$ of 0.03 μM).

In the aboved example method,

HEPES is 4-(2-Hydroxyethyl)-1-piperazineethanesulfonic acid,

EDTA is Ethylenediamine tetraacetate, and

Ac-Tyr-Val-Ala-Asp-MCA is Acetyl-L-tyrosyl-L-valyl-L-alanyl-L-asparaginic acid 4-methyl-coumarinyl-7-amide.

Toxicity

The compounds of the present invention are substantially non-toxic. Therefore, the compounds of the present invention may be considered sufficiently safe and suitable for pharmaceutical use.

Application for Pharmaceuticals

Compounds of the present invention have an inhibitory activity on ICE in animals, including humans. Therefore the compounds are useful for prevention and/or treatment of insulin dependent diabetes (type I), multiple sclerosis, acute or delayed type hypersensitivity, infectious diseases, infection complications, septic shock, arthritis, colitis, glomerular nephritis, hepatitis, hepatic cirrhosis, pancreatitis, reperfusion injury, cholangeitis, encephalitis, endocarditis, myocarditis, vasculitis, Alzheimer's disease, Parkinson's disease, dementia, cerebral vascular disturbance, neurodegenerative diseases, bone or cartilage-resorption diseases, AIDS, ARC (AIDS related complex), adult T cell leukemia, hairy cell (pilocytic) leukemia, myelosis, respiratory dysfunction, arthropathy, uveitis, neoplasm, diffuse collagen diseases such as systemic lupus erythematosis or rheumatoid arthritis, ulcerative colitis, Sjogren's syndrome, primary biliary cirrhosis, idiopathic thrombocytopnic purpura, autoimmonohaemolytic anemia, severe myasthenia, osteodisplasia syndrome, periodic thrombocytopenia, aplastic anemia, idiopathic thrombocytopenia, various diseases accompanied with thrombocytopenia such as disseminated intravascular coagulation, adult dyspnea syndrome, hyperplasia of the prostae gland, myoma of the uterus, asthma bronchiole, arteriosclerosis, various kinds of teratoma, nephritis, senile cataract, chronic fatigue syndrome, myodystrophy, peripheral nervous disturbance, Crohn's diseases and osteo arthritics etc. essentially disorders arising from or influenced by IL-1β activity.

For the purpose above described, the compounds of formula (I) of the present invention, non-toxic salts thereof, acid additional salts thereof and hydrates thereof may be normally administered systemically or partially, usually by oral or parenteral administration.

The doses to be administered are determined depending on age, body weight, symptom, the desired therapeutic effect, the route of administration, the duration of the treatment etc. In the human adult, the dose per person is generally between 1 mg and 1000 mg, by oral administration, up to several times per day, and between 0.1 mg and 100 mg, by parenteral administration, up to several times per day, or continuous administration between 1 and 24 hrs. per day intravenously.

As mentioned above, the doses to be used depend on various conditions. Therefore, there are cases in which doses lower than or greater than the ranges specified above may be used.

The compounds of the present invention can be administered as solid compositions, liquid compositions or other compositions for oral administration, as injections, liniments or suppositories etc. for parenteral administration.

Solid compositions for oral administration include compressed tablets, pills, capsules, dispersible powders and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate etc.). The compositions also may comprise, as is normal practice, additional substances other than inert diluents: e.g. lubricating agents (such as magnesium stearate etc.), disintegrating agents (such as cellulose calcium glycolate etc.), stabilizing agents (such as lactose etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phthalate etc.), or be coated with more than two films. Further, the coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (purified water, ethanol etc.). Besides inert diluents, such compositions also may comprise adjuvants (such as wetting agents, suspending agents etc.), sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid etc.). For preparation of such spray compositions, for example, the method described in the U.S. Pat. Nos. 2,868,691 or 3,095,355 (herein incorporated in their entirety by reference) may be used.

Injections for parenteral administration include sterile aqueous or non-aqueous solutions, suspensions and emulsions. In such compositions, one more of active compound (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark) etc.).

Injections may comprise other inert diluents: e.g. preserving agents, wetting agents, emulsifying agents, dispersing agents, stabilizing agent (lactose etc.), assisting agents, such as assisting agents for dissolving (glutamic acid, asparaginic acid etc.) etc.

They may be sterilized for example, by filtration through a bacteria-retaining filter, by incorporation of sterilizing agents in the compositions or by irradiation. They may also be manufactured in the form of sterile, solid compositions, for example, by freeze-drying, which may be dissolved in sterile water or some other sterile diluent(s) for injection immediately before use.

Other compositions for parenteral administration include liquids for external use, and endermic liniments, ointments, suppositories and pessaries which comprise one or more of the active compound(s) and may be prepared by per se known methods.

BEST MODE TO PRACTICE THE INVENTION

The following reference examples and examples illustrate the present invention, but should not be construed to limit the present invention.

The solvents in the parentheses show the developing or eluting solvents and the ratios of the solvents used are by volume in chromatographic separations, TLC and HPTLC.

NMR in the parentheses show measured solvents. The TLC plate used was Merck 5715, and the HPTLC plate used was Merck 05642. Silica gel used was Merck 7734, except for specifically case.

EXAMPLE 1

N-((N-(3-phenylpropionyl)-L-valyl)-L-alanyl)-3-amino-4-oxo-5-(5-(2,6-dichlorophenylmethyl)tetrazol-1-yl)pentanoic acid•t-butylester (1) and N-((N-(3-phenylpropionyl)-L-valyl)-L-alanyl)-3-amino-4-oxo-5-(5-(2,6-dichlorophenylmethyl)tetrazol-2-yl)pentanoic acid•t-butylester (2)

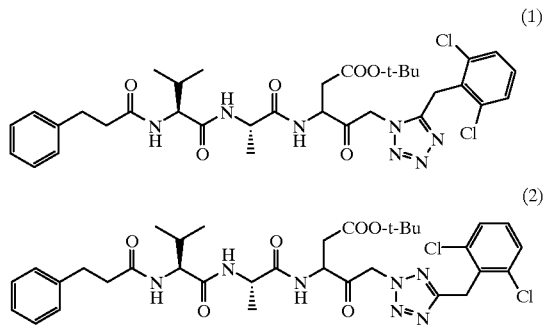

To a solution of N-((N-(3-phenylpropionyl)-L-valyl)-L-alanyl)-3-amino-4-oxo-5-bromopentanoic acid•t-butylester [The compound prepared by the method of J. Med. Chem., 37, 563 (1994)] (298 mg) in N,N-dimethylformamide (5 ml) was successively added potassium fluoride (144 mg) and 5-(2,6-dichlorophenylmethyl)tetrazole (249 mg). The reaction mixture was stirred for 1 days at room temperature. The mixture was quenched by addition of water and extracted with ethyl acetate. The extract was washed with a saturated aqueous solution of sodium chloride, dried over anhydrous sodium sulfate and concentrated. The residue was purified by column chromatography on NAM-600M silica gel (Nam research institute, registered trade mark) (chloroform:methanol=100:1→50:1) to give the compounds of example 1(1) (37 mg) and example 1(2) (147 mg) having the following physical dataly.

Example 1(1)

HPTLC: Rf 0.33 and 0.30 (chloroform:methanol=19:1); NMR (DMSO-$d_6$): δ 8.89 and 8.66 (total 1H, each d, J=7.9 Hz), 8.29 and 8.28 (total 1H, each d, J=7.9 Hz), 7.83 and 7.81 (total 1H, each d, J=7.9 Hz), 7.53 (2H, d, J=9.0 Hz), 7.41 (1H, t, J=9.0 Hz), 7.26–7.11 (5H, m), 5.86, 5.83, 5.79 and 5.75 (total 2H, each d, J=18.0 Hz), 4.85 and 4.64 (total 1H, each dt, J=7.9 Hz, 6.7 Hz), 4.35–4.06 (4H, m), 2.87–2.72, 2.72–2.57 and 2.57–2.35 (total 8H, m), 1.94–1.80 (1H, m), 1.40 and 1.39 (total 9H, each s), 1.28 and 1.25 (total 3H, each d, J=9.0 Hz), 0.80, 0.76 and 0.71 (total 6H, each d, J=6.7 Hz).

Example 1(2)

HPTLC: Rf 0.40 (chloroform:methanol=19:1); NMR (DMSO-$d_6$): δ 8.80 and 8.53 (total 1H, each d, J=7.9 Hz), 8.29 and 8.27 (total 1H, each d, J=7.9 Hz), 7.88 and 7.84 (total 1H, each d, J=7.9 Hz), 7.51 (2H, d, J=9.0 Hz), 7.36 (1H, t, J=9.0 Hz), 7.28–7.12 (5H, m), 5.89, 5.83, 5.79 and 5.71 (total 2H, each d, J=18.0 Hz), 4.78 and 4.56 (total 1H, each dt, J=7.9 Hz, 6.7 Hz), 4.50 and 4.49 (total 1H, each s), 4.22 and 4.21 (1H, each dq, J=9.0 Hz, 7.9 Hz), 4.16 and 4.14 (1H, each dd, J=9.0 Hz, 7.9 Hz), 2.83–2.70 and 2.70–2.36 (total 8H, m), 1.95–1.80 (1H, m), 1.36 and 1.37 (total 9H, each s), 1.24 and 1.22 (total 3H, each d, J=9.0 Hz), 0.82, 0.81 and 0.76 (total 6H, each d, J=6.7 Hz).

EXAMPLES 1(3)–1(6)

By the same procedure as provided in example 1, using corresponding tetrazole compounds instead of 5-(2,6-dichlorophenylmethyl)tetrazole, compounds of the present invention having the following physical data were obtained.

Example 1(3)

N-((N-(3-phenylpropionyl)-L-valyl)-L-alanyl)-3-amino-4-oxo-5-(5-(4-methylphenoxy)tetrazol-1-yl)pentanoic acid•t-butylester

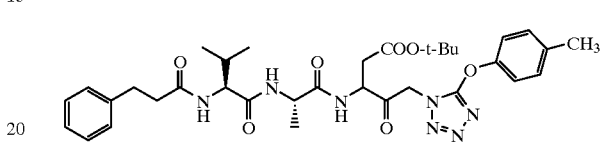

HPTLC: Rf 0.21 (chloroform:methanol=19:1); NMR (CDCl$_3$): δ 7.64–7.54 (1H, m), 7.35–7.12 (10H, m), 6.72–6.61 (1H, m), 6.07–6.00 (1H, m) 5.57 (1H, d, J=18.5 Hz), 5.25 (1H, d, J=18.5 Hz), 4.98–4.81 (1H, m), 4.50–4.30 (1H, m), 4.21–4.07 (1H, m), 3.03–2.84, 2.84–2.63 and 2.63–2.52 (total 8H, m), 2.34 (3H, s), 2.15–1.95 (1H, m), 1.42 (3H, d, J=8.0 Hz), 1.40 (9H, s), 0.87 and 0.82 (each 3H, each d, J=6.8 Hz).

Example 1(4)

N-((N-(3-phenylpropionyl)-L-valyl)-L-alanyl)-3-amino-4-oxo-5-(5-(4-methylphenoxy)tetrazol-2-yl)pentanoic acid•t-butylester

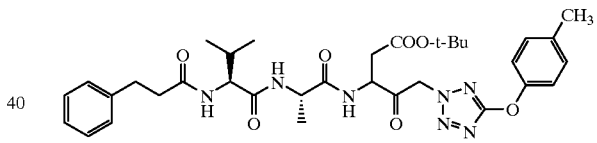

HPTLC: Rf 0.27 (chloroform:methanol=19:1); NMR (CDCl$_3$): δ 7.79–7.67 (1H, m), 7.31–6.98 (10H, m), 6.40–6.29 (1H, m), 5.69 and 5.68 (total 1H, each d, J=17.0 Hz), 5.46 and 5.45 (total 1H, each d, J=17.0 Hz), 4.92–4.75 (1H, m), 4.59–4.38 (1H, m), 4.32–4.19 (1H, m), 3.01–2.83, 2.83–2.65 and 2.65–2.49 (total 8H, m), 2.33 (3H, s), 2.11–1.80 (1H, m), 1.41 (9H, s), 1.38 (3H, d, J=8.4 Hz), 0.92–0.73 (6H, m).

Example 1(5)

N-((N-(3-phenylpropionyl)-L-valyl)-L-alanyl)-3-amino-4-oxo-5-(5-trifluoromethyltetrazol-2-yl)pentanoic acid•t-butylester

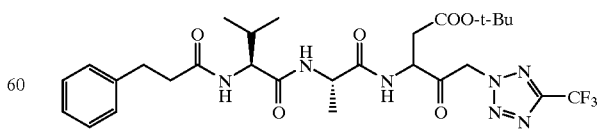

HPTLC: Rf 0.13 (chloroform:methanol=19:1); NMR (DMSO-$d_6$): δ 9.02–8.92 and 8.66–8.55 (total 1H, m), 8.36–8.24 (1H, m), 7.91–7.75 (1H, m), 7.30–7.05 (5H, m), 6.17–6.04 (2H, m), 4.91–4.74 and 4.68–4.50 (total 1H, m), 4.32–4.05 (2H, m), 2.90–2.65 and 2.65–2.27 (total 8H, m), 2.00–1.75 (1H, m) 1.38 and 1.37 (total 9H, each s), 1.28–1.12 (3H, m), 0.92–0.67 (6H, m).

Example 1(6)

N-((N-(3-phenylpropionyl)-L-valyl)-L-alanyl)-3-amino-4-oxo-5-(5-(N,N-dimethylamino)tetrazol-2-yl)pentanoic acid•t-butylester

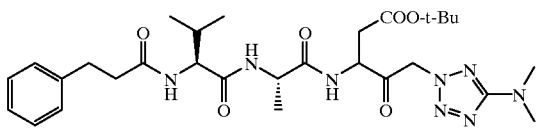

TLC: Rf 0.31 (chloroform:methanol=15:1); NMR (DMSO-d$_6$): δ 8.78 and 8.54 (total 1H, each m), 8.29 (1H, m), 7.88 (1H, m), 7.21 (5H, m), 5.61 (2H, m), 4.79 and 4.58 (total 1H, each m), 4.19 (2H, m), 2.94 (6H, s), 2.88–2.35 (total 6H, m), 1.90 (1H, m), 1.40 (9H, s), 1.23 (3H, m), 0.80 (6H, m).

Example 2(1)

N-((N-(3-phenylpropionyl)-L-valyl)-L-alanyl)-3-amino-4-oxo-5-(5-(2,6-dichlorophenylmethyl)tetrazol-1-yl)pentanoic acid

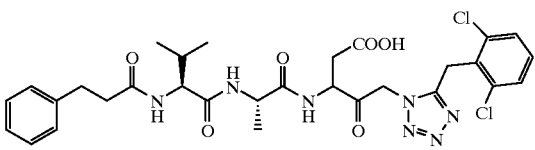

To a solution of compound (1) prepared in example 1 (23 mg) in thioanisole (0.17 ml) and m-cresole (0.1 5 ml) was added trifluoroacetic acid (2 ml). The reaction mixture was stirred for 30 min at room temperature. To the reaction mixture was added toluene, and then the mixture was concentrated. The residue was washed with diethyl ether, and dried over to give the compound of the present invention (17 mg) having the following physical data.

TLC: Rf 0.31 (chloroform:methanol:acetic acid=18:1:1); NMR (DMSO-d$_6$): δ 8.93–8.82 and 8.75–8.64 (total 1H, m), 8.33–8.20 (1H, m), 7.87–7.75 (1H, m), 7.65–7.32 and 7.32–7.05 (total 8H, m), 5.98–5.67 (2H, m), 4.83–4.57 (1H, m), 4.41–4.00 (2H, m), 2.95–2.66 and 2.66–2.25 (total 6H, m), 2.00–1.74 (1H, m), 1.35–1.15 (3H, m), 0.90–0.62 (6H, m).

EXAMPLES 2(2)–2(6)

By the same procedure as provided in example 2(1), and if necessary, by known methods converted to accommodate the corresponding salts, using the compounds of examples 1(2)–1(6) instead of compound (1) prepared in example 1, compounds of the present invention having the following physical data were obtained.

Example 2(2)

N-((N-(3-phenylpropionyl)-L-valyl)-L-alanyl)-3-amino-4-oxo-5-(5-(2,6-dichlorophenylmethyl)tetrazol-2-yl) pentanoic acid

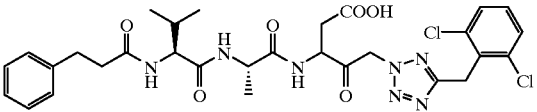

TLC: Rf 0.43 (chloroform:methanol:acetic acid=18:1:1); NMR (DMSO-d$_6$): δ 8.86–8.71 and 8.64–8.52 (total 1H, m), 8.33–8.18 (1H, m), 7.92–7.80 (1H, m), 7.57–7.43 and 7.43–7.30 (3H, m), 7.30–7.07 (5H, m), 6.00–5.75 (2H, m), 4.79–4.63 and 4.63–4.40 (total 1H, m), 4.50 (2H, s), 4.27–4.05 (2H, m), 2.78–2.66 and 2.66–2.25 (total 6H, m), 1.97–1.75 (1H, m), 1.31–1.15 (3H, m), 0.88–0.68 (6H, m).

Example 2(3)

N-((N-(3-phenylpropionyl)-L-valyl)-L-alanyl)-3-amino-4-oxo-5-(5-(4-methylphenoxy)tetrazol-1-yl)pentanoic acid

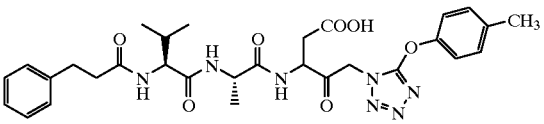

TLC: Rf 0.34 (chloroform:methanol:acetic acid=18:1:1); NMR (DMSO-d$_6$): δ 8.78–8.67 and 8.67–8.54 (1H, m), 8.32–8.16 (1H, m), 7.92–7.80 (1H, m), 7.33–7.08 (9H, m), 5.65–5.30 (2H, m), 4.77–4.55 (1H, m), 4.35–4.03 (2H, m), 2.77–2.66 and 2.66–2.37 (total 6H), 2.32 (3H, s), 1.98–1.75 (1H, m), 1.30–1.15 (3H, m), 0.87–0.67 (6H, m).

Example 2(4)

N-((N-(3-phenylpropionyl)-L-valyl)-L-alanyl)-3-amino-4-oxo-5-(5-(4-methylphenoxy)tetrazol-2-yl)pentanoic acid

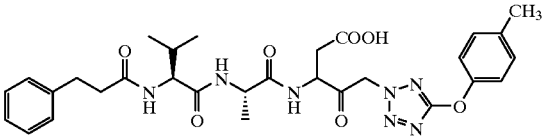

TLC: Rf 0.51 (chloroform:methanol:acetic acid=18:1:1); NMR (DMSO-d$_6$): δ 8.86–8.71 and 8.62–8.52 (1H, m), 8.32–8.18 (1H, m), 7.93–7.79 (1H, m), 7.32–7.07 (9H, m), 5.91–5.58 (2H, m), 4.78–4.65 and 4.65–4.49 (1H, m), 4.30–4.06 (2H, m), 2.80–2.68 (2H, m), 2.68–2.34 (4H, m), 2.31 (3H, s), 2.00–1.75 (1H, m), 1.32–1.15 (3H, m),0.87–0.70 (6H, m).

Example 2(5)

N-((N-(3-phenylpropionyl)-L-valyl)-L-alanyl)-3-amino-4-oxo-5-(5-trifluoromethyltetrazol-2-yl)pentanoic acid

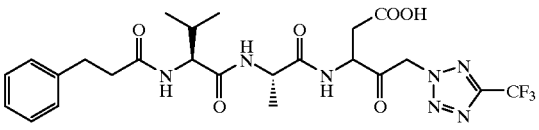

TLC: Rf 0.28 (chloroform:methanol:acetic acid=18:1:1); NMR (DMSO-d$_6$): δ 8.98–8.84 and 8.71–8.59 (total 1H, m), 8.35–8.22 (1H, m), 7.92–7.77 (1H, m) 7.32–7.06 (5H, m), 6.26–5.90 (2H, m), 4.81–4.54 (1H, m), 4.35–4.07 (2H, m), 2.92–2.30 (6H, m) 2.01–1.85 (1H, m), 1.34–1.15 (3H, m), 0.93–0.69 (each 3H, m).

Example 2(6)

N-((N-(3-phenylpropionyl)-L-valyl)-L-alanyl)-3-amino-4-oxo-5-(5-(N,N-dimethylamino)tetrazol-2-yl)pentanoic acid•trifluoroacetic acid salt

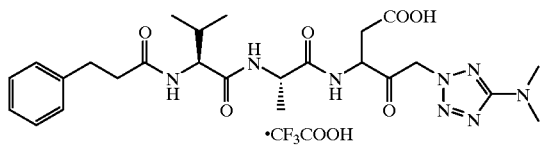

TLC: Rf 0.24 (chloroform:methanol:acetic acid=15:1:1); NMR (DMSO-$d_6$): δ 8.71 and 8.54 (total 1H, each d, J=10 Hz), 8.28 and 8.21 (total 1H, each d, J=6 Hz), 7.88 and 7.84 (total 1H, each d, J=10 Hz), 7.20 (5H, m), 5.70–5.46 (2H, m), 4.70 and 4.55 (total 1H, each m), 4.20 and 4.15 (total 2H, each m), 2.93 (6H, s), 2.80–2.40 (total 6H, m), 1.90 (1H, m), 1.23 (3H, m), 0.80 (6H, m).

EXAMPLES 3(1)–3(7)

By the same procedure as example 1, using corresponding tetrazole compound and 3-(N-(2-(hexahydro-2-oxo-3S-(phenylcarbonylamino)azepin-1-yl))propionyl)amino-4-oxo-5-bromopentanoic acid•t-butylester [The compound was prepared by the method of J. Med. Chem., 37, 563 (1994)] instead of N-((N-(3-phenylpropionyl)-L-valyl)-L-alanyl)-3-amino-4-oxo-5-bromopentanoic acid•t-butylester, compounds of the present invention having the following physical data were obtained.

Example 3(1)

3-(N-(2-(hexahydro-2-oxo-3S-(phenylcarbonylamino)azepin-1-yl))propionyl)amino-4-oxo-5-(5-(2,6-dichlorophenylmethyl)tetrazol-1-yl)pentanoic acid•t-butylester

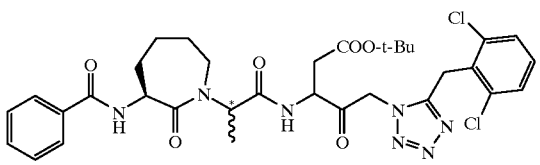

(wherein * represents R or S stereochemistry. The stereostructure has not been identified yet. However, the above compound has the opposite stereoconfiguration as the compound of example 3(3))

HPTLC: Rf 0.24 (benzene:ethyl acetate=1:1); NMR (CDCl$_3$): δ 7.80 and 7.64–7.13 (total 10H, m), 5.82, 5.78, 5.60 and 5.52 (total 2H, each d, J=18.0 Hz), 5.06–4.78 (3H, m), 4.34 and 4.30 (total 2H, each s), 3.56 (2H, m), 3.12–2.61 (2H, m), 2.33–1.10 (9H, m), 1.42 and 1.41 (total 9H, each s).

Example 3(2)

3-(N-(2-(hexahydro-2-oxo-3S-(phenylcarbonylamino)azepin-1-yl))propionyl)amino-4-oxo-5-(5-(2,6-dichlorophenylmethyl)tetrazol-2-yl)pentanoic acid•t-butylester

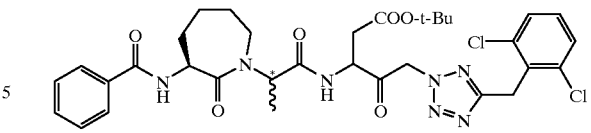

(wherein * represents R or S stereochemistry. The stereostructure has not been identified yet. However, the above compound has the opposite stereoconfiguration as the compound of example 3(4))

HPTLC: Rf 0.32 (benzene:ethyl acetate=1:1); NMR (CDCl$_3$): δ 7.82 and 7.68–7.10 (total 10H, m), 5.85–5.50 (2H, m), 5.13–4.75 (3H, m), 4.60 and 4.57 (total 2H, each s), 3.51 (2H, m), 3.02–2.50 (2H, m), 2.30–1.20 (9H, m), 1.42 and 1.40 (total 9H, each s).

Example 3(3)

3-(N-(2-(hexahydro-2-oxo-3S-(phenylcarbonylamino)azepin-1-yl))propionyl)amino-4-oxo-5-(5-(2,6-dichlorophenylmethyl)tetrazol-1-yl)pentanoic acid•t-butylester

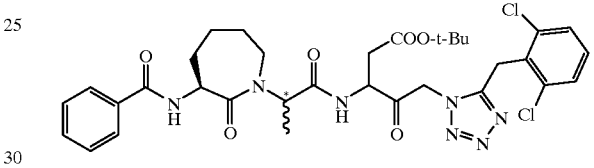

(wherein * represents R or S stereochemistry. The stereostructure has not been identified yet. However, the above compound has the opposite stereoconfiguration as the compound of example 3(1))

HPTLC: Rf 0.29 (benzene:ethyl acetate=1:1); NMR (CDCl$_3$): δ 7.86–7.08 (10H, m), 5.85–5.38 (2H, m), 5.06 (1H, m), 4.96–4.72 (2H, m), 4.60, 4.57, 4.33 and 4.28 (total 2H, each s), 3.65–3.30 (2H, m), 3.02–2.50 (2H, m), 2.28–1.20 (18H, m).

Example 3(4)

3-(N-(2-(hexahydro-2-oxo-3S-(phenylcarbonylamino)azepin-1-yl))propionyl)amino-4-oxo-5-(5-(2,6-dichlorophenylmethyl)tetrazol-2-yl)pentanoic acid•t-butylester

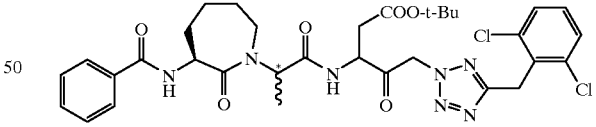

(wherein * represents R or S stereochemistry. The stereostructure has not been identified yet. However, the above compound has the opposite stereoconfiguration as the compound of example 3(2))

HPTLC: Rf 0.42 (benzene:ethyl acetate=1:1); NMR (CDCl$_3$): δ 7.85–7.10 (10H, m), 5.80–5.43 (2H, m), 5.10 (1H, m), 4.82 (2H, m), 4.56 (2H, s), 3.60–3.28 (2H, m), 2.87–2.54 (2H, m), 2.29–1.20 (6H, m), 1.46 (3H, d, J=8.0 Hz), 1.33 and 1.32 (total 9H, each s).

Example 3(5)

3-(N-(2-(hexahydro-2-oxo-3S-(phenylcarbonylamino)azepin-1-yl))propionyl)amine-4-oxo-5-(5-trifluoromethyltetrazol-2-yl)pentanoic acid•t-butylester

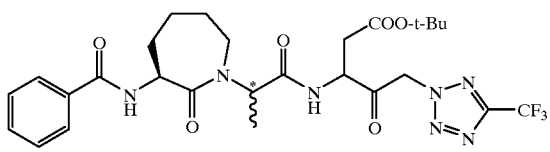

(wherein * represents R or S stereochemistry. The stereostructure has not been identified yet. However, the above compound has the opposite stereoconfiguration as the compound of example 3(6))

HPTLC: Rf 0.39 (hexane:ethyl acetate=1:1); NMR (CDCl$_3$): δ 7.89–7.32 (5H, m), 6.05, 5.95, 5.76 and 5.69 (total 2H, each d, J=17.5 Hz), 5.15–4.75 (3H, m), 3.55 (2H, m), 3.08–2.56 (2H, m), 2.32–1.20 (6H, m), 1.48 (3H, d, J=7.5 Hz), 1.42 (9H, s).

Example 3(6)

3-(N-(2-(hexahydro-2-oxo-3S-(phenylcarbonylamino) azepin-1-yl))propionyl)amino-4-oxo-5-(5-trifluoromethyltetrazol-2-yl)pentanoic acid•t-butylester

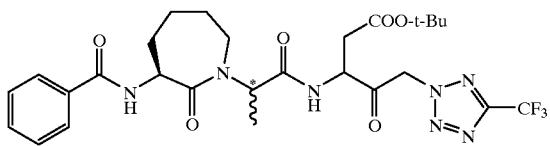

(wherein * represents R or S stereochemistry. The stereostructure has not been identified yet. However, the above compound has the opposite stereoconfiguration as the compound of example 3(5))

HPTLC: Rf 0.27 (hexane:ethyl acetate=1:1); NMR (CDCl$_3$): δ 7.79 and 7.62–7.28 (total 5H, m), 6.06, 6.03, 5.84 and 5.76 (total 2H, each d, J=17.5 Hz), 5.01–4.74 (3H, m), 3.55 (2H, m), 3.08–2.56 (2H, m), 2.32–1.20 (6H, m), 1.48 (3H, d, J=7.5 Hz), 1.42 (9H, s).

Example 3(7)

3-(N-(2-(hexahydro-2-oxo-3S-(phenylcarbonylamino) azepin-1-yl))propionyl)amino-4-oxo-5-(5-phenylmethyltetrazol-1-yl)pentanoic acid•t-butylester

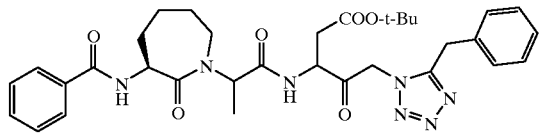

TLC: Rf 0.33 (chloroform:methanol=19:1); NMR (DMSO-d$_6$): δ 8.77–8.47 (1H, m), 8.22 (1H, d, J=6.6 Hz), 7.79 (2H, m), 7.46 (3H, m), 7.26 (5H, m), 5.65 (2H, m), 5.19–4.62 (3H, m), 4.10 (2H, m), 3.50 (2H, m), 2.80 (1H, m), 2.56 (1H, m), 1.99–1.50 (6H, m), 1.40 (9H, s), 1.36 (3H, m).

EXAMPLES 4(1)–4(7)

By the same procedure as provided in example 2(1), using the compounds of examples 3(1)–3(7) instead of compound (1) prepared in example 1, compounds of the present invention having the following physical data were obtained.

Example 4(1)

3-(N-(2-(hexahydro-2-oxo-3S-(phenylcarbonylamino) azepin-1-yl))propionyl)amino-4-oxo-5-(5-(2,6-dichlorophenylmethyl)tetrazol-1-yl)pentanoic acid

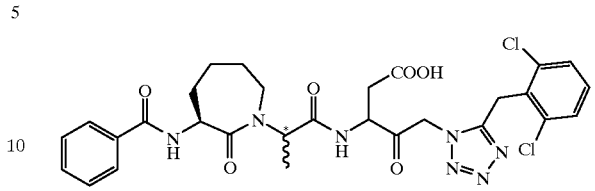

(wherein * represents R or S stereochemistry. The stereostructure has not been identified yet. However, the above compound has the opposite stereoconfiguration as the compound of example 4(3))

HPTLC: Rf 0.34 and 0.30 (chloroform:methanol=4:1); NMR (DMSO-d$_6$): δ 8.57–8.22 (2H, m), 7.80 (2H, m), 7.60–7.30 (6H, m), 5.89 (2H, m), 5.00–4.55 (3H, m), 4.32 (2H, m), 3.51 (2H, m), 2.60 (2H, m), 2.00–1.43 (6H, m), 1.31 (3H, m).

Example 4(2)

3-(N-(2-(hexahydro-2-oxo-3S-(phenylcarbonylamino) azepin-1-yl))propionyl)amino-4-oxo-5-(5-(2,6-dichlorophenylmethyl)tetrazol-2-yl)pentanoic acid

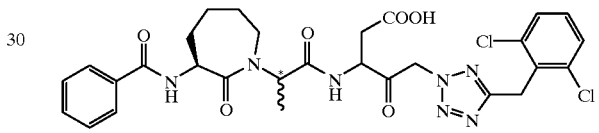

(wherein * represents R or S stereochemistry. The stereostructure has not been identified yet. However, the above compound has the opposite stereoconfiguration as the compound of example 4(4))

HPTLC: Rf 0.41 and 0.32 (chloroform:methanol=4:1); NMR (DMSO-d$_6$): δ 8.46–8.26 (2H, m), 7.79 (2H, m), 7.60–7.29 (6H, m), 6.06–5.66 (2H, m), 4.96–4.54 (3H, m), 4.49 and 4.43 (total 2H, s), 3.50 (2H, m), 2.61–2.36 (2H, m), 1.98–1.45 (6H, m), 1.29 (3H, m).

Example 4(3)

3-(N-(2-(hexahydro-2-oxo-3S-(phenylcarbonylamino) azepin-1-yl))propionyl)amino-4-oxo-5-(5-(2,6-dichlorophenylmethyl)tetrazol-1-yl)pentanoic acid

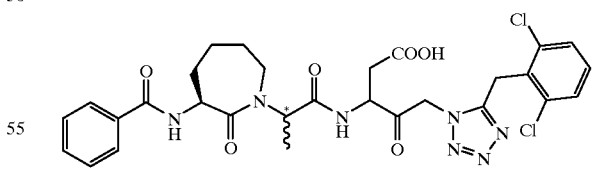

(wherein * represents R or S stereochemistry. The stereostructure has not been identified yet. However, the above compound has the opposite stereoconfiguration as the compound of example 4(1))

HPTLC: Rf 0.37 (chloroform:methanol=4:1); NMR (DMSO-d$_6$): δ 8.53–8.26 (2H, m), 7.84 (2H, m), 7.48 (6H, m), 5.86 (2H, m), 5.15 (1H, m), 4.86 (1H, m), 4.66 (1H, m), 4.34 (total 2H, s), 3.5 (2H, m), 2.59 (2H, m), 2.02–1.53 (6H, m), 1.33 (3H, m).

Example 4(4)
3-(N-(2-(hexahydro-2-oxo-3S-(phenylcarbonylamino)azepin-1-yl))propionyl)amino-4-oxo-5-(5-(2,6-dichlorophenylmethyl)tetrazol-2-yl)pentanoic acid

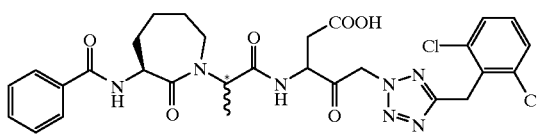

(wherein * represents R or S stereochemistry. The stereostructure has not been identified yet. However, the above compound has the opposite stereoconfiguration as the compound of example 4(2))

HPTLC: Rf 0.43 (chloroform:methanol=4:1); NMR (DMSO-$d_6$): δ 5 8.51–8.21 (2H, m), 7.86 (2H, m), 7.60–7.28 (6H, m), 6.00–5.68 (2H, m), 5.11 (1H, m), 4.89 (1H, m), 4.68 (1H, m), 4.50 and 4.48 (total 2H, s), 3.50 (2H, m), 2.53 (2H, m), 2.00–1.55 (6H, m), 1.33 (3H, m).

Example 4(5)
3-(N-(2-(hexahydro-2-oxo-3S-(phenylcarbonylamino)azepin-1-yl))propionyl)amino-4-oxo-5-(5-trifluoromethyltetrazol-2-yl)pentanoic acid

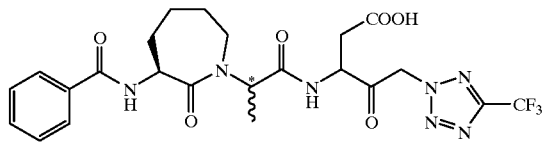

(wherein * represents R or S stereochemistry. The stereostructure has not been identified yet. However, the above compound has the opposite stereoconfiguration as the compound of example 4(6))

HPTLC: Rf 0.35 (chloroform:methanol=4:1); NMR (DMSO-$d_6$): δ 8.59–8.16 (2H, m), 8.00–7.76 and 7.65–7.40 (total 5H, m), 6.29–6.00 (2H, m), 5.13, 4.89 and 4.70 (total 3H, m), 3.6–3.1 (2H, m), 2.66–2.39 (2H, m), 2.00–1.51 and 1.48–1.05 (total 9H, m).

Example 4(6)
3-(N-(2-(hexahydro-2-oxo-3S-(phenylcarbonylamino)azepin-1-yl))propionyl)amino-4-oxo-5-(5-trifluoromethyltetrazol-2-yl)pentanoic acid

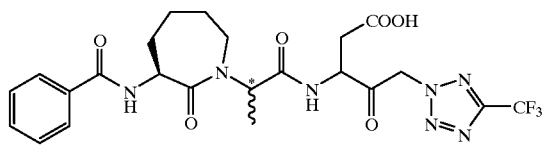

(wherein * represents R or S stereochemistry. The stereostructure has not been identified yet. However, the above compound has the opposite stereoconfiguration as the compound of example 4(5))

HPTLC: Rf 0.30 and 0.24 (chloroform:methanol=4:1); NMR (DMSO-$d_6$): δ 8.60–8.30 (2H, m), 8.00–7.70 and 7.60–7.30 (total 5H, m), 6.36–5.99 (2H, m), 4.95–4.50 (3H, m), 3.6–3.1 (2H, m), 2.65–2.40 (2H, m), 1.98–1.20 (9H, m).

Example 4(7)
3-(N-(2-(hexahydro-2-oxo-3S-(phenylcarbonylamino)azepin-1-yl))propionyl)amino-4-oxo-5-(5-phenylmethyltetrazol-1-yl)pentanoic acid

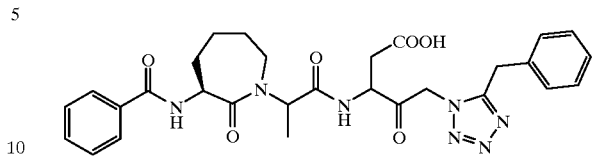

HPTLC: Rf 0.70 (chloroform:methanol water=6:4:1); NMR (DMSO-$d_6$): δ 8.40 (2H, m), 7.85 (2H, m), 7.50 (3H, m), 7.27 (5H, s), 5.72 (2H, m), 5.22–4.58 (3H, m), 4.14 (2H, m), 3.45 (4H, m), 2.59 (2H, m), 1.96–1.50 (6H, m), 1.31 (3H, m).

Reference Example 1
5-(ethoxycarbonylmethyl)tetrazole

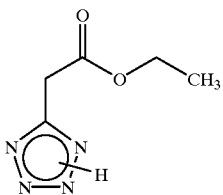

The mixture of ethylcyanoacetate (1.53 g), trimethyltinazaide [$(CH_3)_3SnN_3$] (3.67 g) and toluene (20 ml) was refluxed for 14 h. After the reaction mixture was concentrated under reduced pressure, the residue was dissolved in ethanol (300 ml). To the thus obtained solution was added a 1N aqueous solution of hydrochloric acid (150 ml), and the mixture was stirred for 3 h at room temperature. To the reaction mixture was added a 1N aqueous solution of sodium hydroxide until a pH 3 or 4 was obtained, and the mixture was concentrated under reduced pressure. To the residue was added water, and the mixture was added chloroform and methanol, the precipitate solid was filtered, dried to give the title compound (783 mg) having the following physical data.

TLC: Rf 0.23 (chloroform:methanol=4:1); NMR (CD$_3$OD): δ 4.22 (2H, q, J=7.0 Hz), 4.12 (2H, s), 1.27 (2H, t, J=7.0 Hz).

Reference Example 1(1)
5-styryltetrazole

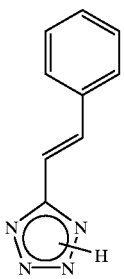

By the same procedure as provided in reference example 1, using the compounds of cinnamonitrile instead of ethylcyanoacetate, compound having the following physical data was obtained.

TLC: Rf 0.25 (chloroform:methanol=19:1); NMR (CD$_3$OD): δ 7.74–7.55 (3H, m), 7.50–7.32 (3H, m), 7.20 (1H, d, J=16.8 Hz).

Reference Example 2
5-phenylethyltetrazole

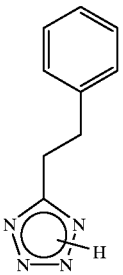

The mixture of the compound prepared in reference example 1(1) (1.0 g), 10% palladium on activated carbon (200 mg) and ethanol (40 ml) was stirred at room temperature for 4 h under an atmosphere of hydrogen gas. The reaction mixture was filtered through Celite (trade mark) and the filtrate was concentrated to give the title compound having the following physical data.

TLC: Rf 0.25 (chloroform:methanol=19:1); NMR (DMSO-$d_6$): δ 7.38–7.10 (5H, m), 3.26–3.12 (2H, m), 3.11–2.97 (2H, m).

Reference Example 3
1-(4-methoxyphenylmethyl)tetrazole

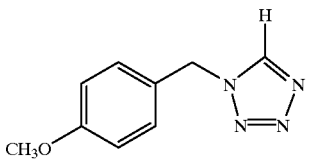

The mixture of 4-methoxybenzylamine (27 g), trimethylorthoformate (52.4 ml), sodium azide (19.2 g) and acetic acid (176 ml) was stirred at 80° C. for 14 h. The reaction mixture was concentrated under reduced pressure, the residue was dissolved in water and extracted with ethyl acetate. The extract was washed with a 1N aqueous solution of hydrochloric acid, water, a saturated aqueous solution of sodium hydrocarbonate and a saturated aqueous solution of sodium chloride, successively, dried over anhydrous sodium sulfate and concentrated. The residue was purified by column chromatography on silica gel (hexane:ethyl acetate=1:1) to give the title compound (17.6 g) having the following physical data.

TLC: Rf 0.34 (hexane:ethyl acetate=1:1); NMR (CDCl$_3$): δ 8.46 (1H, s), 7.26 (2H, d, J=8.5 Hz), 6.92 (2H, d, J=8.5 Hz), 5.52 (2H, s), 3.81 (3H, s).

Reference Example 4
1-(4-methoxyphenylmethyl)-5-bromotetrazole

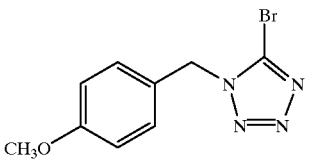

To a solution of the compound prepared in reference example 3 (5.0 g) in tetrahydrofuran (112 ml) and N,N,N', N'-tetramethylethylenediamine (11 ml) was added 1.67 M of n-butyllithium in hexane solution (15.8 ml) at −68° C. under an atmosphere of argon. After the mixture was stirred for 10 min, to the mixture was added dropwise the solution of bromine (1.36 ml) in tetrahydrofuran (8 ml) at same temperature. The mixture was stirred for 30 min at −78° C., and the mixture was warmed up at 0° C. The mixture was concentrated under reduced pressure, the residue was dissolved in water and extracted with ethyl acetate. The extract was washed with a saturated aqueous solution of sodium chloride, dried over anhydrous magnesium sulfate and concentrated. The residue was purified by column chromatography on silica gel (hexane:ethyl acetate=2:1) to give the title compound (2.28 g) having the following physical data.

TLC: Rf 0.63 (hexane:ethyl acetate=1:1); NMR (CDCl$_3$): δ 7.29 (2H, d, J=8.5 Hz), 6.87 (2H, d, J=8.5 Hz), 5.48 (2H, s), 3.80 (3H, s).

Reference Example 5
1-(4-methoxyphenylmethyl)-5-methoxytetrazole

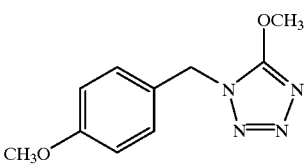

To a solution of the compound prepared in reference example 4 (507 mg) in methanol (5 ml) was added sodium methoxide (509 mg) at 0° C. The mixture was stirred for 4 h at 0° C. The mixture was concentrated under reduced pressure, the residue was dissolved in ice and a 1N aqueous solution of hydrochloric acid and extracted with ethyl acetate. The extract was washed with water and a saturated aqueous solution of sodium chloride, dried over anhydrous magnesium sulfate and concentrated. The residue was purified by column chromatography on NAM-600M silica gel (Nam research institute, registered trade mark) (hexane:ethyl acetate=2:1) to give the title compound (335 mg) having the following physical data.

TLC: Rf 0.53 (hexane:ethyl acetate=1:1); NMR (CDCl$_3$): δ 7.24 (2H, d, J=8.5 Hz), 6.87 (2H, d, J=8.5 Hz), 5.18 (2H, s), 4.22 (3H, s), 3.79 (3H, s).

Reference Example 6
5-methoxytetrazole

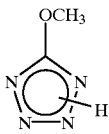

To a solution of the compound prepared in reference example 5 (335 mg) in acetonitrile (8 ml) was added ammonium cerium nitrate [CAN] (4.41 g) in water (6 ml) at 0° C. The mixture was stirred for 1 h at room temperature. The reaction mixture was poured into a saturated aqueous solution of sodium chloride and extracted with ethyl acetate. The extract was washed with a saturated aqueous solution of sodium chloride, dried over anhydrous sodium sulfate and concentrated. The residue was washed with diethylether to give the title compound (66 mg) having the following physical data.

TLC: Rf 0.20 (chloroform:methanol=4:1); NMR (CD$_3$OD): δ 4.15 (3H, s).

Reference Example 7

5-phenylmethyltetrazole

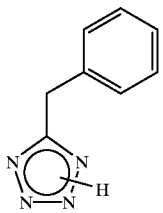

The mixture of 5-(2,6-dichlorophenylmethyl)tetrazole (355 mg), 5% palladium on activated carbon (93 mg) and methanol (8 ml) was stirred for 1 h room temperature under an atmosphere of hydrogen gas. The reaction mixture was filtered through Celite (trade mark) and the filtrate was concentrated to give the title compound having the following physical data.

TLC: Rf 0.50 (chloroform:methanol:acetic acid=18:1:1).

EXAMPLES 5(1)–5(160)

By the same procedure as example 1, using N-benzyloxycarbonyl-3-amino-4-oxo-5-bromopentanoic acid•t-butylester [see EP 0623592, Example 1] instead of N-((N-(3-phenylpropionyl)-L-valyl)-L-alanyl)-3-amino-4-oxo-5-bromopentanoic acid•t-butylester and the corresponding tetrazole compounds (for example the compounds prepared in reference example 1, reference example 1(1), reference example 2, reference example 6 or reference example 7), the compounds of the present invention having the following physical data were obtained.

Example 5(1)

N-benzyloxycarbonyl-3-amino-4-oxo-5-(5-(2,6-dichlorophenylmethyl)tetrazol-1-yl)pentanoic acid•t-butylester

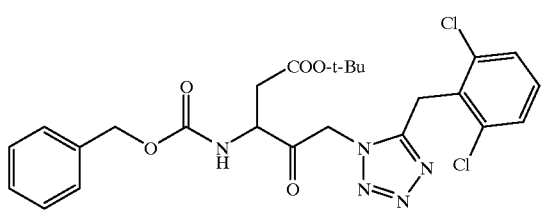

TLC: Rf 0.45 (hexane:ethyl acetate=3:2); NMR (CDCl$_3$): δ 7.44–7.15 (8H, m), 5.86 (1H, d, J=8.0 Hz), 5.69 (1H, d, J=18.7 Hz), 5.55 (1H, d, J=18.7 Hz), 5.20 (2H, s), 4.70–4.54 (1H, m), 4.33 (1H, d, J=16.4 Hz), 4.23 (1H, d, J=16.4 Hz), 3.10 (1H, dd, J=17.6, 4.4 Hz), 2.76 (1H, dd, J=17.6, 5.0 Hz), 1.41 (9H, s).

Example 5(2)

N-benzyloxycarbonyl-3-amino-4-oxo-5-(5-(2,6-dichlorophenylmethyl)tetrazol-2-yl)pentanoic acid•t-butylester

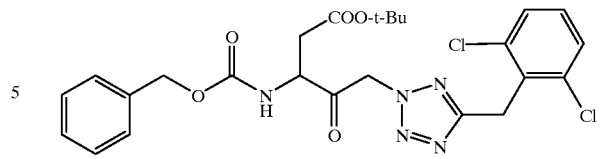

TLC: Rf 0.66 (hexane:ethyl acetate=3:2); NMR (CDCl$_3$): δ 7.40–7.10 (8H, m), 5.92 (1H, d, J=8.4 Hz), 5.76 (1H, d, J=17.7 Hz), 5.58 (1H, d, J=17.7 Hz), 5.16 (2H, s), 4.70–4.55 (3H, m), 2.99 (1H, dd, J=17.5, 5.0 Hz), 2.69 (1H, dd, J=17.5, 4.8 Hz), 1.41 (9H, s).

Example 5(3)

N-benzyloxycarbonyl-3-amino-4-oxo-5-(5-phenylmethyltetrazol-1-yl)pentanoic acid•t-butylester

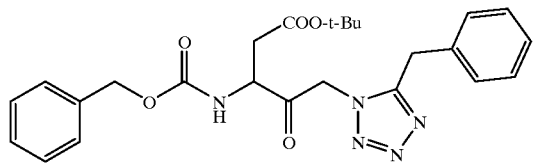

TLC: Rf 0.14 (hexane:ethyl acetate=2:1); NMR (CDCl$_3$): δ 7.41–7.14 (10H, m), 5.87–5.73 (1H, m), 5.32 (2H, s), 5.15 (2H, s), 4.60–4.44 (1H, m), 4.25 and 4.04 (each 1H, d, J=17.0 Hz), 3.03 and 2.71 (each 1H, dd, J=17.0 Hz, 5.0 Hz), 1.43 (9H, s).

Example 5(4)

N-benzyloxycarbonyl-3-amino-4-oxo-5-(5-phenylmethyltetrazol-2-yl)pentanoic acid•t-butylester

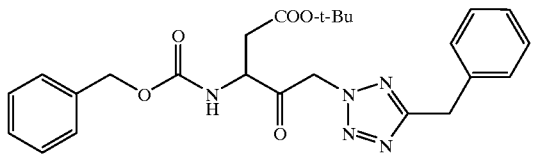

TLC: Rf 0.36 (hexane:ethyl acetate=2:1); NMR (CDCl$_3$): δ 7.42–7.16 (10H, m), 6.05–5.90 (1H, m), 5.78 and 5.60 (each 1H, d, J=18.0 Hz), 5.16 (2H, s), 4.73–4.56 (1H, m), 4.26 (2H, s), 2.98 (1H, dd, J=17.4 Hz, 4.4 Hz), 2.70 (1H, dd, J=17.4 Hz, 5.0 Hz), 1.41 (9H, s).

Example 5(5)

N-benzyloxycarbonyl-3-amino-4-oxo-5-(5-(4-methylphenoxy)tetrazol-1-yl)pentanoic acid•t-butylester

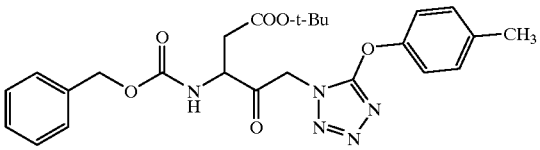

NMR (CDCl$_3$): δ 7.39 (5H, brs), 7.21 (4H, brs), 5.97 (1H, d, J=8.9 Hz), 5.53 (1H, d, J=18.3 Hz), 5.32 (1H, d, J=18.3 Hz), 5.20 (2H, s), 4.78–4.56 (1H, m), 3.07 (1H, dd, J=17.5, 4.2 Hz), 2.72 (1H, dd, J=17.5, 4.9 Hz), 2.36 (3H, s), 1.39 (9H, s).

Example 5(6)

N-benzyloxycarbonyl-3-amino-4-oxo-5-(5-(4-methylphenoxy)tetrazol-2-yl)pentanoic acid•t-butylester

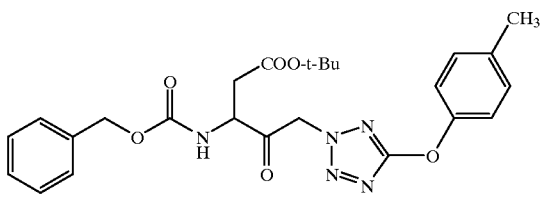

NMR (CDCl$_3$): δ 7.38 (5H, brs), 7.18 (4H, brs), 5.95 (1H, d, J=9.0 Hz), 5.71 (1H, d, J=17.4 Hz), 5.54 (1H, d, J=17.4 Hz), 5.18 (2H, s), 4.76–4.58 (1H, m), 3.02 (1H, dd, J=17.6, 4.8 Hz), 2.70 (1H, dd, J=17.6, 4.8 Hz), 2.35 (3H, s), 1.42 (9H, s).

Example 5(7)

N-benzyloxycarbonyl-3-amino-4-oxo-5-(5-(3-butylphenoxy)tetrazol-1-yl)pentanoic acid•t-butylester

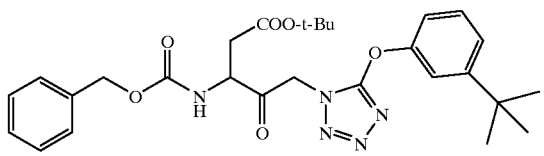

NMR (CDCl$_3$): δ 7.42–7.08 (9H, m), 5.97 (1H, J=8.8 Hz), 5.54 (1H, d, J=18.0 Hz), 5.33 (1H, d, J=18.0 Hz), 5.19 (2H, s), 4.74–4.60 (1H, m), 3.08 (1H, dd, J=18.0, 4.0 Hz), 2.72 (1H, dd, J=18.0, 4.0 Hz), 1.37 (9H, s), 1.31 (9H, s).

Example 5(8)

N-benzyloxycarbonyl-3-amino-4-oxo-5-(5-(3-t-butylphenoxy)tetrazol-2-yl)pentanoic acid•t-butylester

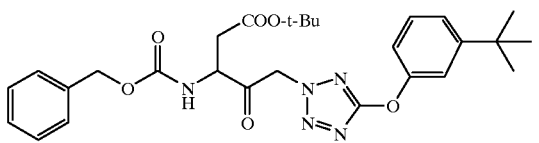

NMR (CDCl$_3$): δ 7.42–7.20 (8H, m), 7.06 (1H, 6 J=8.0 Hz), 5.95 (1H, d, J=9.4 Hz), 5.71 (1H, d, J=17.7 Hz), 5.55 (1H, d, J=17.7 Hz), 5.17 (2H, s), 4.73–4.55 (1H, m), 3.02 (1H, dd, J=17.5, 4.6 Hz), 2.71 (1H, dd, J=17.5, 4.9 Hz), 1.41 (9H, s), 1.31 (9H, s).

Example 5(9)

N-benzyloxycarbonyl-3-amino-4-oxo-5-(5-styryltetrazol-1-yl)pentanoic acid•t-butylester

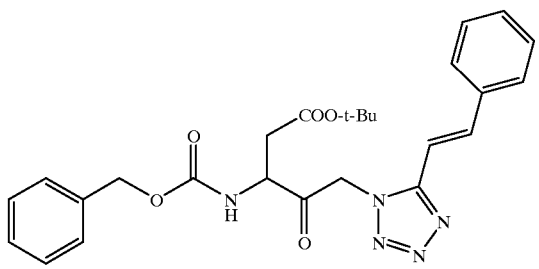

NMR (CDCl$_3$): δ 7.93 (1H, δ J=15.9 Hz), 7.59 (2H, brs), 7.54–7.18, (8H, m), 6.80 (1H, d, J=15.9 Hz), 5.80 (1H, d, J=8.6 Hz), 5.63 (2H, brs), 5.20 (2H, s), 4.66 (1H, brs), 3.24–3.00 (1H, m), 2.93–2.79 (1H, m), 1.41 (9H, s).

Example 5(10)

N-benzyloxycarbonyl-3-amino-4-oxo-5-(5-styryltetrazol-2-yl)pentanoic acid•t-butylester

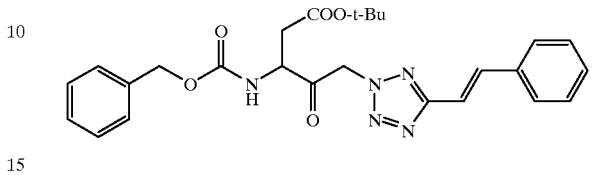

NMR (CDCl$_3$): δ 7.76 (1H, δ J=16.5 Hz), 7.68–7.31 (10H, m), 7.16 (1H, d, J=16.5 Hz) 5.98 (1H, d, J=9.6 Hz), 5.84 (1H, d, J=17.9 Hz), 5.67 (1H, d, J=17.9 Hz), 5.19 (2H, s), 4.80–4.62 (1H, m), 3.04 (1H, dd, J=17.4, 4.4 Hz), 2.74 (1H, dd, J=7.4, 4.9 Hz), 1.44 (9H, s).

Example 5(11)

N-benzyloxycarbonyl-3-amino-4-oxo-5-(5-phenylethyltetrazol-1-yl)pentanoic acid•t-butylester

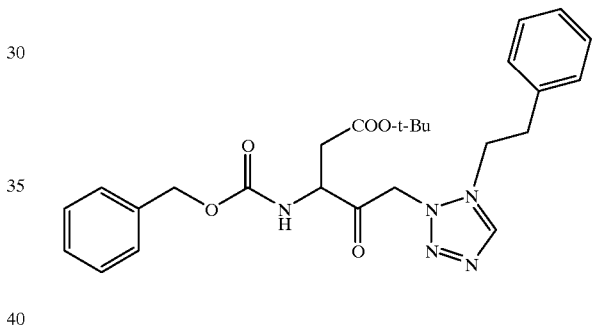

NMR (CDCl$_3$): δ 7.64–7.05 (10H, m), 5.72 (1H, d, J=9.1 Hz), 5.21 (1H, d, J=18.7 Hz), 5.18 (2H, s), 5.08 (1H, d, J=18.7 Hz), 4.65–4.45 (1H, m), 3.20–2.85 (5H, m), 2.71 (1H, dd, J=17.7, 5.0 Hz), 1.38 (9H, s).

Example 5(12)

N-benzyloxycarbonyl-3-amino-4-oxo-5-(5-phenylethyltetrazol-1-yl)pentanoic acid•t-butylester

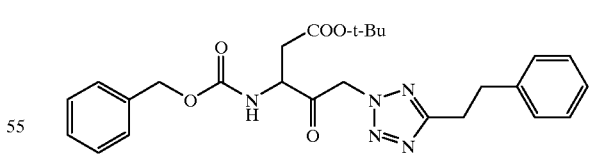

NMR (CDCl$_3$): δ 7.65–7.10 (10H, m), 5.94 (1H, d, J=9.1 Hz), 5.79 (1H, d, J=17.8 Hz), 5.62 (1H, d, J=17.8 Hz), 5.19 (2H, s), 4.77–4.57 (1H, m), 3.30 3.06 (4H, m), 3.01 (1H, dd, J=17.5, 4.5 Hz), 2.72 (1H, dd, J=17.5, 4.8 Hz), 1.43 (9H, s).

Example 5(13)

N-benzyloxycarbonyl-3-amino-4-oxo-5-(5-methoxytetrazol-1-yl)pentanoic acid•t-butylester

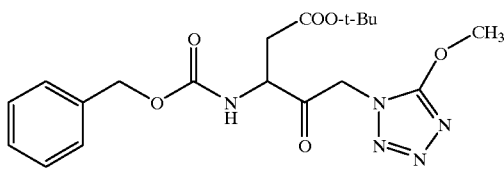

HPTLC: Rf 0.10 (hexane:ethyl acetate=2:1); NMR (CDCl$_3$): δ 7.38 (5H, m), 5.95 (1H, brs), 5.35 and 5.13 (each 1H, each d, J=18.0 Hz), 5.18 (2H, s), 4.62 (1H, m), 4.18 (3H, s), 3.03 (1H, dd, J=17.0, 4.5 Hz), 2.70 (1H, dd, J=17.0, 5.0 Hz), 1.42 (9H, s).

Example 5(14)

N-benzyloxycarbonyl-3-amino-4-oxo-5-(5-methoxytetrazol-2-yl)pentanoic acid•t-butylester

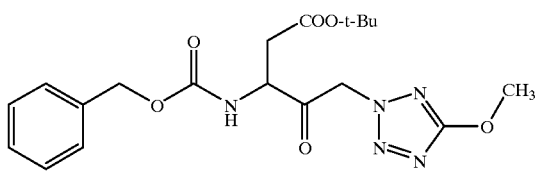

HPTLC: Rf 0.33 (hexane:ethyl acetate=2:1); NMR (CDCl$_3$): δ 7.38 (5H, m), 5.93 (1H, brs), 5.67 and 5.50 (each 1H, each d, J=18.5 Hz), 5.16 (2H, s), 4.65 (1H, m), 4.09 (3H, s), 3.02 (1H, dd, J=17.0, 4.5 Hz), 2.71 (1H, dd, J=17.0, 5.0 Hz), 1.42 (9H, s).

Example 5(15)

N-benzyloxycarbonyl-3-amino-4-oxo-5-(5-(N,N-dibenzylamino)tetrazol-2-yl)pentanoic acid•t-butylester

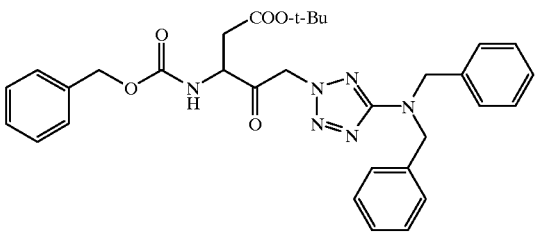

TLC: Rf 0.65 (hexane:ethyl acetate=2:1); NMR (CDCl$_3$): δ 7.23–7.15 (15H, m), 5.93 (1H, d, J=10.0 Hz), 5.61 and 5.45 (each 1H, d, J=17.5 Hz), 5.16 (2H, s), 4.72–4.50 (1H, m), 4.61 (4H, s), 2.99 and 2.70 (each 1H, dd, J=17.5 Hz, 5.0 Hz), 1.42 (9H, s).

Example 5(16)

N-benzyloxycarbonyl-3-amino-4-oxo-5-(5-trifluoromethyltetrazol-1-yl)pentanoic acid•t-butylester

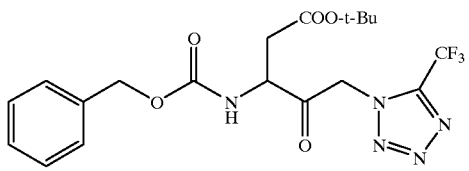

HPTLC: Rf 0.39 (hexane:ethyl acetate=2:1); NMR (CDCl$_3$): δ 7.39 (5H, m), 6.04–5.60 (3H, m), 5.20 (2H, s), 4.67 (1H, m), 3.09 (1H, dd, J=18.0, 4.5 Hz), 2.73 (1H, dd, J=18.0, 5.0 Hz), 1.42 (9H, s).

Example 5(17)

N-benzyloxycarbonyl-3-amino-4-oxo-5-(5-trifluoromethyltetrazol-2-yl)pentanoic acid•t-butylester

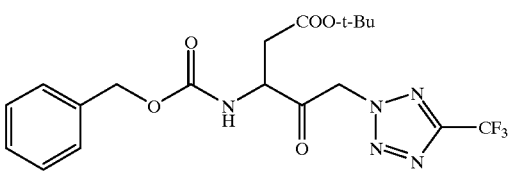

HPTLC: Rf 0.43 (hexane:ethyl acetate=2:1); NMR (CDCl$_3$): δ 7.39 (5H, m), 6.04–5.68 (3H, m), 5.19 (2H, s), 4.69 (1H, m), 3.07 (1H, dd, J=18.0, 4.5 Hz), 2.73 (1H, dd, J=18.0, 5.0 Hz), 1.43 (9H, s).

Example 5(18)

N-benzyloxycarbonyl-3-amino-4-oxo-5-(5-(ethoxycarbonylmethyl)tetrazol-2-yl)pentanoic acid•t-butylester

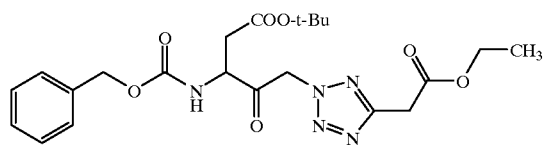

HPTLC: Rf 0.36 (hexane:ethyl acetate=2:1); NMR (CDCl$_3$): δ 7.44–7.32 (5H, m), 5.94 (1H, d, J=8.0 Hz), 5.82 and 5.68 (each 1H, both d, J=18.0 Hz), 5.18 (2H, s), 4.66 (1H, m), 4.20 (2H, q, J=7.0 Hz), 4.00 (2H, s), 3.00 (1H, dd, J=18.0, 4.0 Hz), 2.73 (1H, dd, J=18.0, 5.0 Hz), 1.42 (9H, s), 1.27 (3H, t, J=7.0 Hz).

Example 5(19)

N-benzyloxycarbonyl-3-amino-4-oxo-5-(5-ethylthiotetrazol-1-yl)pentanoic acid•t-butylester

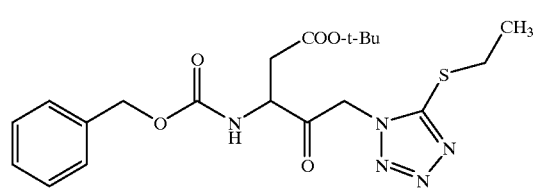

TLC: Rf 0.38 (hexane:ethyl acetate=3:2); NMR (CDCl$_3$): δ 7.39 (5H, m), 5.95 (1H, m), 5.50 (1H, d, J=16 Hz), 5.30 (1H, d, J=16 Hz), 5.20 (2H, s), 4.63 (1H, m), 3.30 (2H, q, J=7 Hz), 3.05 (1H, dd, J=17.5, 5 Hz), 2.70 (1H, dd, J=17.5, 5 Hz), 1.42 (12H, m).

Example 5(20)

N-benzyloxycarbonyl-3-amino-4-oxo-5-(5-ethylthiotetrazol-2-yl)pentanoic acid•t-butylester

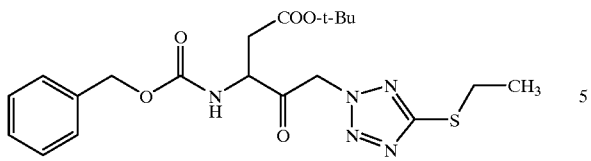

TLC: Rf 0.54 (hexane:ethyl acetate=3:2); NMR (CDCl$_3$): δ 7.39 (5H, m), 5.95 (1H, m), 5.80 (1H, d, J=16 Hz), 5.60 (1H, d, J=16 Hz), 5.16 (2H, s), 4.63 (1H, m), 3.20 (2H, q, J=7 Hz), 3.01 (1H, dd, J=17.5, 5 Hz), 2.70 (1H, dd, J=17.5, 5 Hz), 1.41 (12H, m).

Example 5(21)

N-benzyloxycarbonyl-3-amino-4-oxo-5-(5-(ethoxycarbonylmethyl)tetrazol-1-yl)pentanoic acid•t-butylester

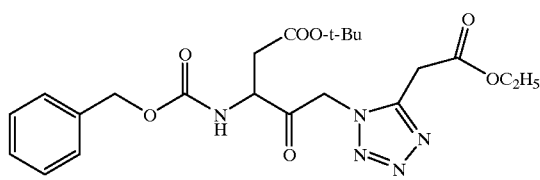

HPTLC: Rf 0.26 (hexane:ethyl acetate=2:1); NMR (CDCl$_3$): δ 7.44–7.30 (5H, m), 5.89–5.58 (3H, m), 5.17 (2H, s), 4.62 (1H, m), 4.18 (2H, q, J=7.0 Hz), 4.03 and 3.82 (each 1H, each d, J=17.0 Hz), 3.09 and 2.77 (each 1H, each dd, J=17.0, 5.0 Hz), 1.42 (9H, s), 1.27 (3H, t, J=7.0 Hz).

Example 5(22)

N-benzyloxycarbonyl-3-amino-4-oxo-5-(5-((4-chlorophenyl)thiomethyl)tetrazol-2-yl)pentanoic acid•t-butylester

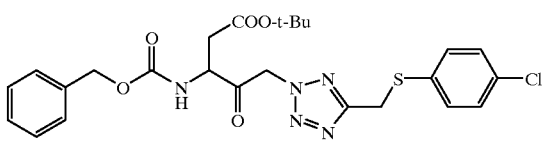

TLC: Rf 0.62 (hexane:ethyl acetate=3:2); NMR (CDCl$_3$): δ 7.38 (5H, m), 7.30 and 7.22 (total 4H, each d, J=9.0 Hz), 5.94 (1H, d, J=10.0 Hz), 5.79 (1H, d, J=17.5 Hz), 5.60 (1H, d, J=17.5 Hz), 5.18 (2H, s), 4.64 (1H, m), 4.28 (2H, s), 3.00 (1H, dd, J=17.5 Hz and 5.0 Hz), 2.70 (1H, dd, J=17.5 Hz and 5.0 Hz), 1.40 (9H, s).

Example 5(23)

N-benzyloxycarbonyl-3-amino-4-oxo-5-(5-((4-chlorophenyl)thiomethyl)tetrazol-1-yl)pentanoic acid•t-butylester

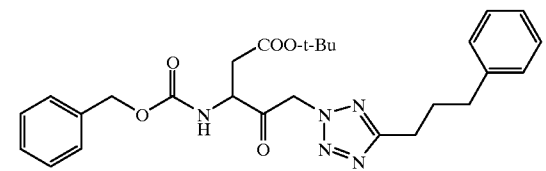

TLC: Rf 0.46 (hexane:ethyl acetate=3:2); NMR (CDCl$_3$): δ 7.38 (5H, m), 7.22 (4H, m), 5.80 (1H, d, J=10.0 Hz), 5.75 (1H, d, J=17.5 Hz), 5.60 (1H, d, J=17.5 Hz), 5.20 (2H, s), 4.64 (1H, m), 4.28 and 4.08 (total 2H, each d, J=15.0 Hz), 3.10 (1H, dd, J=17.5 Hz and 5.0 Hz), 2.78 (1H, dd, J=17.5 Hz and 5.0 Hz), 1.40 (9H, s).

Example 5(24)

N-benzyloxycarbonyl-3-amino-4-oxo-5-(5-(3-phenylpropyl)tetrazol-2-yl)pentanoic acid•t-butylester

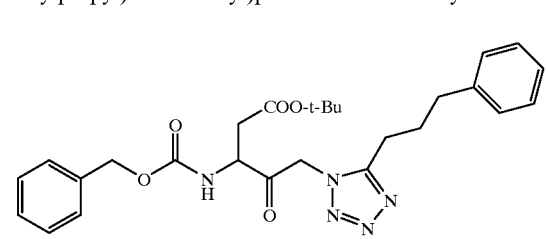

TLC: Rf 0.36 (hexane:ethyl acetate=2:1); NMR (CDCl$_3$): δ 7.98 (1H, d, J=9.5 Hz), 7.42–7.10 (10H, m), 5.91 (2H, s), 5.10 (2H, s), 4.75–4.57 (1H, m) 2.92–2.55 (6H, m), 2.10–1.90 (2H, m), 1.38 (9H, s).

Example 5(25)

N-benzyloxycarbonyl-3-amino-4-oxo-5-(5-(3-phenylpropyl)tetrazol-1-yl)pentanoic acid•t-butylester TLC: Rf 0.14 (hexane:ethyl acetate=2:1); NMR (CDCl$_3$): δ 8.07 (1H, d, J=9.5 Hz), 7.42–7.08 (10H, m), 5.71 (2H, s), 5.11 (2H, s), 4.72–4.57 (1H, m), 2.87–2.54 (6H, m), 2.05–1.84 (2H, m), 1.38 (9H, s).

Example 5(26)

N-benzyloxycarbonyl-3-amino-4-oxo-5-(5-(2,6-dichlorophenyloxy)tetrazol-2-yl)pentanoic acid•t-butylester

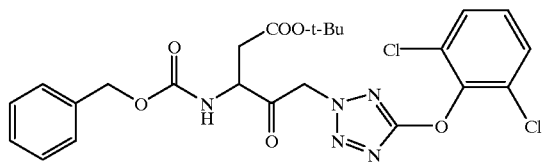

HPTLC: Rf 0.55 (hexane:ethyl acetate=2:1); NMR (CDCl$_3$): δ 7.44–7.12 (8H, m), 5.92 (1H, m), 5.70 and 5.53 (each 1H, each d, J=17.5 Hz), 5.16 (2H, s), 4.63 (1H, m), 3.01 and 2.69 (each 1H, each dd, J=17.0, 5.0 Hz), 1.41 (9H, s).

Example 5(27)

N-benzyloxycarbonyl-3-amino-4-oxo-5-(5-(2,6-dichlorophenyloxy)tetrazol-1-yl)pentanoic acid•t-butylester

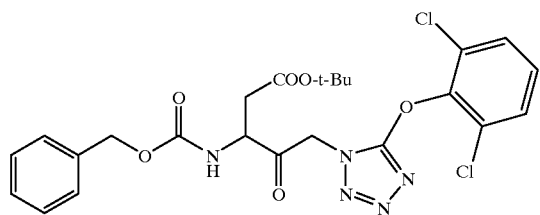

HPTLC: Rf 0.44 (hexane:ethyl acetate=1:1); NMR (CDCl$_3$): δ 7.47–7.14 (8H, m), 6.00 (1H, m), 5.69–5.26 (2H, m), 5.19 (2H, brs), 4.69 (1H, br), 3.08 and 2.73 (each 1H, each m), 1.40 (9H, s).

Example 5(28)

N-benzyloxycarbonyl-3-amino-4-oxo-5-(5-(2-chlorophenyloxymethyl)tetrazol-2-yl)pentanoic acid•t-butylester

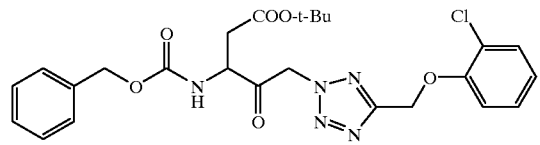

TLC: Rf 0.62 (hexane:ethyl acetate=3:2); NMR (CDCl$_3$): δ 7.38 (6H, m), 7.20 (1H, d, J=6.0 Hz), 7.10 (1H, d, J=6.0 Hz), 6.94 (1H, m), 5.95 (1H, d, J=10.0 Hz), 5.88 (1H, d, J=17.5 Hz), 5.70 (1H, d, J=17.5 Hz), 5.42 (2H, s), 5.18 (2H, s), 4.65 (1H, m), 3.01 (1H, dd, J=17.5 Hz and 5.0 Hz), 2.70 (1H, dd, J=17.5 Hz and 5.0 Hz), 1.42 (9H, s).

Example 5(29)

N-benzyloxycarbonyl-3-amino-4-oxo-5-(5-(2-chlorophenyloxymethyl)tetrazol-1-yl)pentanoic acid•t-butylester


TLC: Rf 0.48 (hexane:ethyl acetate=3:2); NMR (CDCl$_3$): δ 7.38 (6H, m), 7.20 (1H, d, J=6.0 Hz), 6.98 (2H, m), 6.08 (1H, d, J=19.0 Hz), 5.88 (1H, d, J=10.0 Hz), 5.75 (1H, d, J=19.0 Hz), 5.50 and 5.30 (total 2H, each d, J=12.5 Hz), 5.18 (2H, s), 4.68 (1H, m), 3.01 (1H, dd, J=117.5 Hz and 5.0 Hz), 2.68 (1H, dd, J=17.5 Hz and 5.0 Hz), 1.25 (9H, s).

Example 5(30)

N-benzyloxycarbonyl-3-amino-4-oxo-5-(5-(2-methoxycarbonylethyl)tetrazol-2-yl)pentanoic acid•t-butylester

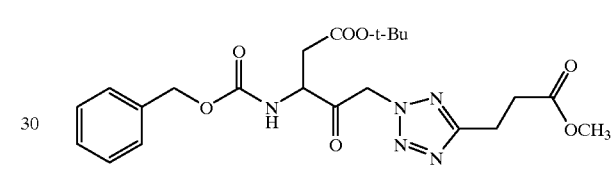

TLC: Rf 0.50 (hexane:ethyl acetate=1:1); NMR (CDCl$_3$): δ 7.45–7.30 (5H, m), 5.94 (1H, d, J=10.0 Hz), 5.76 (1H, d, J=17.0 Hz), 5.61 (1H, d, J=17.0 Hz), 5.18 (2H, s), 4.75–4.50 (1H, m), 3.70 (3H, s), 3.23 (2H, t, J=6.5 Hz), 3.00 (1H, dd, J=16.0 and 4.5 Hz), 2.86 (2H, t, J=6.5 Hz), 2.70 (1H, dd, J=16.0 and 5.0 Hz), 1.42 (9H, s).

Example 5(31)

N-benzyloxycarbonyl-3-amino-4-oxo-5-(5-(2-methoxycarbonylethyl)tetrazol-1-yl)pentanoic acid•t-butylester

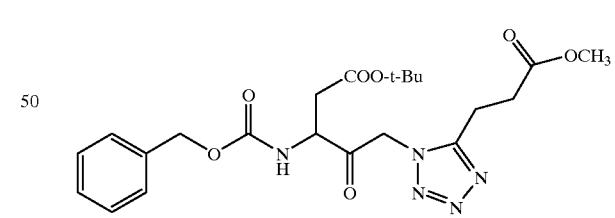

TLC: Rf 0.25 (hexane:ethyl acetate=1:1); NMR (CDCl$_3$): δ 7.43–7.29 (5H, m), 5.96 (1H, d, J=9.0 Hz), 5.68 (1H, d, J=19.5 Hz), 5.55 (1H, d, J=19.5 Hz), 5.19 (2H, s), 4.72–4.51 (1H, m), 3.65 (3H, s), 3.06 (1H, dd, J=16.5 and 5.0 Hz), 2.92 (4H, brs), 2.73 (1H, dd, J=16.5 and 5.5 Hz), 1.42 (9H, s).

Example 5(32)

N-benzyloxycarbonyl-3-amino-4-oxo-5-(5-(1-methylpyrrol-2-ylmethyl)tetrazol-2-yl)pentanoic acid•t-butylester

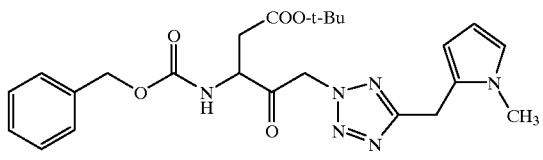

TLC: Rf 0.65 (hexane:ethyl acetate=1:1); NMR (CDCl$_3$): δ 7.46–7.28 (5H, m), 6.51 (1H, m), 5.98 (1H, m), 5.87 (1H, d, J=9.0 Hz), 5.73 (1H, d, J=17.8 Hz), 5.55 (1H, d, J=17.8 Hz), 5.11 (2H, s), 4.75–4.54 (1H, m), 4.18 (2H, s), 3.51 (3H, s), 2.94 (1H, dd, J=17.2 and 4.4 Hz), 2.64 (1H, dd, J=17.2 Hz and 4.8 Hz), 1.36 (9H, s).

Example 5(33)

N-benzyloxycarbonyl-3-amino-4-oxo-5-(5-(1-methylpyrrol-2-ylmethyl)tetrazol-1-yl)pentanoic acid•t-butylester

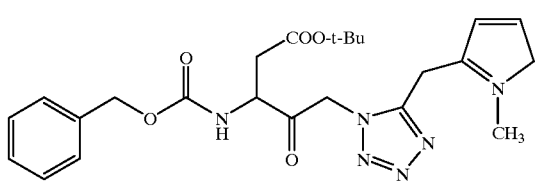

TLC: Rf 0.51 (hexane:ethyl acetate=3:1); NMR (CDCl$_3$): δ 7.48–7.30 (5H, m), 6.56 (1H, m), 6.18–5.92 (2H, m), 5.83 (1H, d, J=9.1 Hz), 5.44 (1H, d, J=18.4 Hz), 5.30 (1H, d, J=18.4 Hz), 5.18 (2H, s), 4.64–4.45 (1H, m), 4.31 (1H, d, J=16.8 Hz), 4.12 (1H, d, J=16.8 Hz), 3.44 (3H, s), 2.97 (1H, dd, J=17.5 and 4.6 Hz), 2.66 (1H, dd, J=17.5 and 4.8 Hz), 1.43 (9H, s).

Example 5(34)

N-benzyloxycarbonyl-3-amino-4-oxo-5-(5-(pyridin-2-ylmethyl)tetrazol-2-yl)pentanoic acid•t-butylester

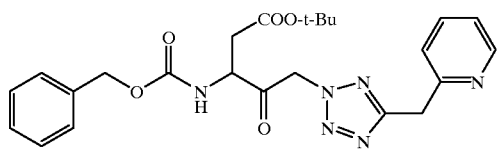

TLC: Rf 0.16 (hexane:ethyl acetate=1:1); NMR (CDCl$_3$): δ 8.60–8.46 (1H, m), 7.71–7.54 (1H, m), 7.52–7.07 (7H, m), 5.99 (1H, d, J=8.8 Hz), 5.80 (1H, d, J=17.8 Hz), 5.65 (1H, dd, J=17.8 Hz), 5.16 (2H, s), 4.75–4.50 (1H, m), 4.48 (2H, s), 3.00 (1H, dd, J=17.6 and 4.8 Hz), 2.72 (1H, dd, 17.6 and 5.0 Hz), 1.41 (9H, s).

Example 5(35)

N-benzyloxycarbonyl-3-amino-4-oxo-5-(5-(pyridin-2-ylmethyl)tetrazol-1-yl)pentanoic acid•t-butylester

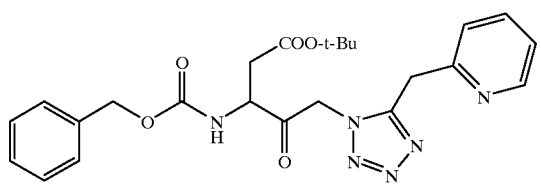

TLC: Rf 0.07 (hexane:ethyl acetate=1:1); NMR (CDCl$_3$): δ 8.50–8.36 (1H, m), 7.71–7.56 (1H, m), 7.52–7.07 (7H, m), 6.00 (1H, d, J=8.2 Hz), 5.93 (1H, d, J=18.4 Hz), 5.70 (1H, d, J=18.4 Hz), 5.17 (2H, s), 4.77–4.54 (1H, m), 4.33 (2H, s), 3.03 (1H, dd, J=22.1 and 4.6 Hz), 2.74 (1H, dd, J=22.1 and 5.0 Hz), 1.39 (9H, s).

Example 5(36)

N-benzyloxycarbonyl-3-amino-4-oxo-5-(5-(pyridin-3-ylmethyl)tetrazol-2-yl)pentanoic acid•t-butylester

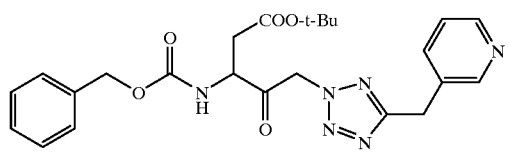

TLC: Rf 0.61 (chloroform:methanol:acetic acid=18:1:1); NMR (CDCl$_3$): δ 8.80–8.30 (2H, m), 7.70–7.60 (1H, m), 7.50–7.21 (1H, m), 5.98 (1H, d, J=9.2 Hz), 5.80 (1H, d, J=17.7 Hz), 5.63 (1H, d, J=17.7 Hz), 5.17 (2H, s), 4.75–4.56 (1H, m), 4.27 (2H, s), 3.01 (1H, dd, J=17.4, 4.6 Hz), 2.71 (1H, dd, J=17.4, 4.9 Hz), 1.42 (9H, s).

Example 5(37)

N-benzyloxycarbonyl-3-amino-4-oxo-5-(5-(pyridin-3-ylmethyl)tetrazol-1-yl)pentanoic acid•t-butylester

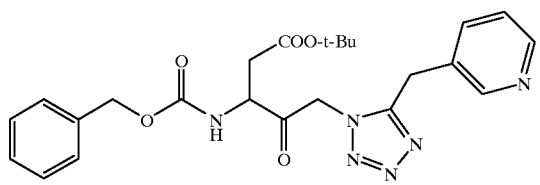

TLC: Rf 0.50 (chloroform:methanol:acetic acid=18:1:1); NMR (CDCl$_3$): δ 8.75–8.35 (2H, m), 7.65–7.56 (1H, m), 7.50–7.04 (1H, m), 5.80 (1H, d, J=8.5 Hz), 5.47 (2H, s), 5.18 (2H, s), 4.66–4.52 (1H, m), 4.20 (1H, d, J=16.4 H), 4.02 (1H, d, J=16.4 Hz), 3.09 (1H, dd, J=17.6, 4.5 Hz), 2.77 (1H, dd, J=17.6, 5.2 Hz), 1.43 (9H, s).

Example 5(38)

N-benzyloxycarbonyl-3-amino-4-oxo-5-(5-(2,6-difluorophenylmethyl)tetrazol-2-yl)pentanoic acid•t-butylester

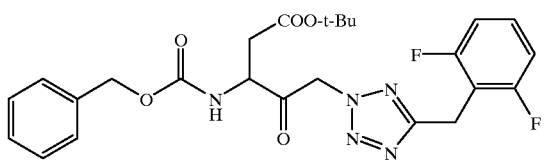

TLC: Rf 0.45 (hexane:ethyl acetate=2:1); NMR (CDCl$_3$): δ 7.70–7.15 (6H, m), 7.03–6.70 (2H, m), 5.92 (1H, d, J=9.2

Hz), 5.76 (1H, d, J=17.9 Hz), 5.58 (1H, d, J=17.9 Hz), 5.16 (2H, s), 4.73–4.52 (1H, m), 4.31 (2H, s), 2.99 (1H, dd, J=17.3, 4.6 Hz), 2.69 (1H, dd, J=17.3, 4.9 Hz), 1.41 (9H, s).

Example 5(39)

N-benzyloxycarbonyl-3-amino-4-oxo-5-(5-(2,6-difluorophenylmethyl)tetrazol-1-yl)pentanoic acid•t-butylester

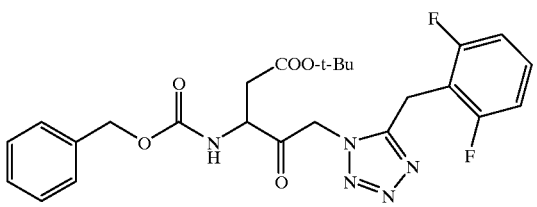

TLC: Rf 0.25 (hexane:ethyl acetate=2:1); NMR (CDCl$_3$): δ 7.60–7.10 (6H, m), 7.00–6.85 (2H, m), 5.88 (1H, d, J=8.4 Hz), 5.66 (1H, d, J=18.7 Hz), 5.49 (1H, d, J=18.7 Hz), 5.19 (2H, s), 4.74–4.53 (1H, m), 4.07 (2H, s), 3.07 (1H, dd, J=17.5, 4.6 Hz), 2.75 (1H, dd, J=17.5, 4.9 Hz), 1.41 (9H, s).

Example 5(40)

N-benzyloxycarbonyi-3-amino-4-oxo-5-(5-(phenylthio)tetrazol-2-yl)pentanoic acid•t-butylester

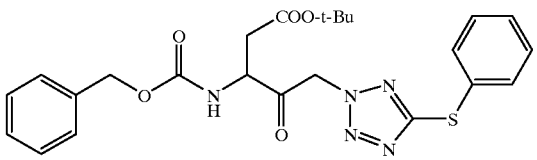

TLC: Rf 0.26 (hexane:ethyl acetate=2:1); NMR (CDCl$_3$): δ 7.62–7.49 and 7.43–7.29 (total 10H, m), 5.93 (1H, d, J=8.5 Hz), 5.79 and 5.62 (each 1H, each d, J=17.5 Hz), 5.16 (2H, s), 4.63 (1H, m), 3.00 and 2.70 (each 1H, each dd, J=17.5, 5.0 Hz), 1.40 (9H, s).

Example 5(41)

N-benzyloxycarbonyl-3-amino-4-oxo-5-(5-(phenylthio)tetrazol-1-yl)pentanoic acid•t-butylester

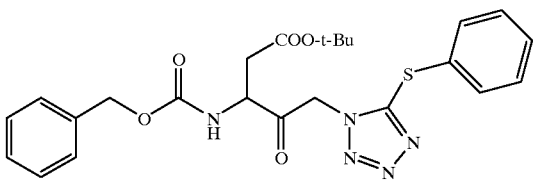

TLC: Rf 0.19 (hexane:ethyl acetate=2:1); NMR (CDCl$_3$): δ 7.58–7.28 (10H, m), 5.94 (1H, d, J=8.0 Hz), 5.58 and 5.42 (each 1H, each d, J=17.5 Hz), 5.19 (2H, s), 4.60 (1H, m), 3.04 and 2.70 (each 1H, each dd, J=17.5, 5.0 Hz), 1.41 (9H, s).

Example 5(42)

N-benzyloxycarbonyl-3-amino-4-oxo-5-(5-(2,6-dichlorophenylthio)tetrazol-2-yl)pentanoic acid•t-butylester

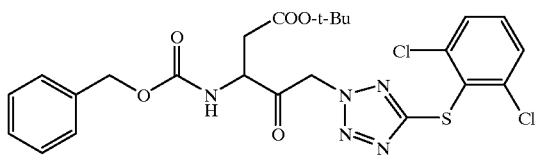

HPTLC: Rf 0.42 (hexane:ethyl acetate=2:1); NMR (CDCl$_3$): δ 7.50–7.23 (8H, m), 5.93 (1H, d, J=8.0 Hz), 5.77 and 5.58 (each 1H, each d, J=17.5 Hz), 5.16 (2H, s), 4.62 (1H, m), 3.00 and 2.69 (each 1H, each dd, J=17.5, 5.0 Hz), 1.39 (9H, s).

Example 5(43)

N-benzyloxycarbonyl-3-amino-4-oxo-5-(5-(2,6-dichlorophenylthio)tetrazol-1-yl)pentanoic acid•t-butylester

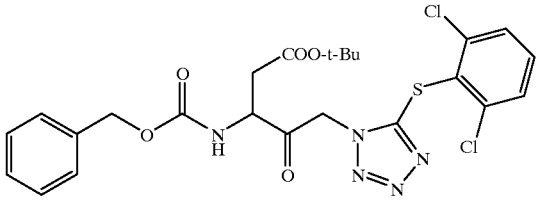

HPTLC: Rf 0.30 (hexane:ethyl acetate=2:1); NMR (CDCl$_3$): δ 7.50–7.25 (8H, m), 5.98 (1H, d, J=8.0 Hz), 5.69 and 5.52 (each 1H, each d, J=17.5 Hz), 5.21 (2H, s), 4.68 (1H, m), 3.10 and 2.75 (each 1H, each dd, J=17.5, 5.0 Hz), 1.43 (9H, s).

Example 5(44)

N-benzyloxycarbonyl-3-amino-4-oxo-5-(5-(2,6-dimethylphenylmethyl)tetrazol-2-yl)pentanoic acid•t-butylester

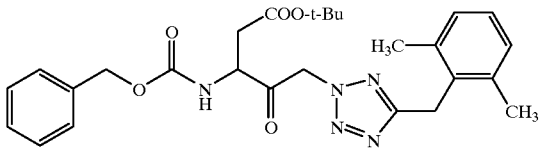

TLC: Rf 0.71 (hexane:ethyl acetate=3:2); NMR (CDCl$_3$): δ 7.46–7.20 (5H, m), 7.13–6.92 (2H, m), 5.93 (1H, d, J=8.6 Hz), 5.73 (1H, d, J=18.0 Hz), 5.55 (1H, d, J=18.0 Hz), 5.15 (2H, s), 4.72–4.64 (1H, m), 4.25 (2H, s), 2.98 (1H, dd, J=17.3, 4.4 Hz), 2.67 (1H, dd, J=17.3, 4.8 Hz), 2.38 (6H, s), 1.41 (9H, s).

Example 5(45)

N-benzyloxycarbonyl-3-amino-4-oxo-5-(5-(2,6-dimethylphenylmethyl)tetrazol-1-yl)pentanoic acid•t-butylester

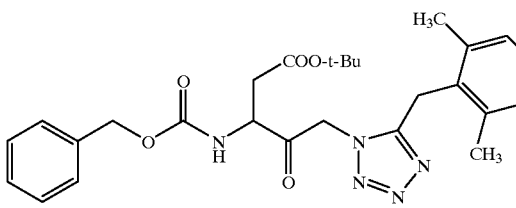

TLC: Rf 0.40 (hexane:ethyl acetate=3:2); NMR (CDCl₃): δ 7.50–7.25 (5H, m), 7.18–6.95 (2H, m), 5.80 (1H, d, J=8.6 Hz), 5.45 (1H, d, J=18.6 Hz), 5.31 (1H, d, J=18.6 Hz), 5.17 (2H, s), 4.51–4.35 (1H, m), 4.05 (2H, s), 2.98 (1H, dd, J=17.7, 4.6 Hz), 2.69 (1H, dd, J=17.7, 4.9 Hz), 2.18 (6H, s), 1.40 (9H, s).

Example 5(46)
N-benzyloxycarbonyl-3-amino-4-oxo-5-(5-(cyclohexylmethyl)tetrazol-2-yl)pentanoic acid•t-butylester

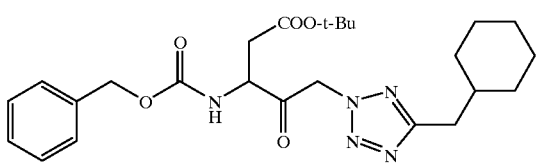

TLC: Rf 0.72 (hexane:ethyl acetate=3:2); NMR (CDCl₃): δ 7.42–7.30 (5H, m), 5.95 (1H, d, J=9.0 Hz), 5.78 (1H, d, J=17.8 Hz), 5.61 (1H, d, J=17.8 Hz), 5.17 (2H, s), 4.72–4.50 (1H, m), 3.00 (1H, dd, J=17.4, 4.4 Hz), 2.84–2.62 (3H, m), 2.00–1.50 (6H, m), 1.42 (9H, s), 1.36–0.85 (5H, m).

Example 5(47)
N-benzyloxycarbonyl-3-amino-4-oxo-5-(5-(cyclohexylmethyl)tetrazol-1-yl)pentanoic acid•t-butylester

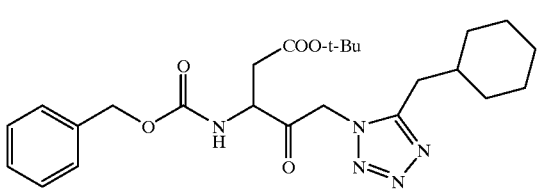

TLC: Rf 0.46 (hexane:ethyl acetate=3:2); NMR (CDCl₃): δ 7.45–7.30 (5H, m), 5.85 (1H, d, J=8.8 Hz), 5.49 (2H, s), 5.19 (2H, s), 4.68–4.54 (1H, m), 3.09 (1H, dd, J=17.4, 4.4 Hz), 2.75 (1H, dd, J=17.4, 5.2 Hz), 2.54 (2H, d, J=7.2 Hz), 2.00–1.51 (6H, m), 1.43 (9H, s), 1.37–0.80 (5H, m).

Example 5(48)
N-benzyloxycarbonyl-3-amino-4-oxo-5-(5-(4-methylphenylthio)tetrazol-2-yl)pentanoic acid•t-butylester

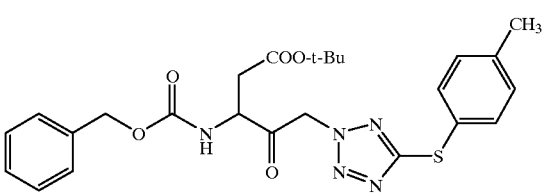

TLC: Rf 0.65 (hexane:ethyl acetate=3:2); NMR (CDCl₃): δ 7.48 (2H, d, J=8.0 Hz), 7.42–7.30 (5H, m), 7.17 (2H, d, J=8.0 Hz), 5.93 (1H, d, J=9.0 Hz), 5.77 (1H, d, J=17.8 Hz), 5.59 (1H, d, J=17.8 Hz), 5.16 (2H, s), 4.71–4.56 (1H, m), 3.00 (1H, dd, J=17.4, 4.4 Hz), 2.69 (1H, dd, J=17.4, 4.9 Hz), 2.35 (3H, s), 1.41 (9H, s).

Example 5(49)
N-benzyloxycarbonyl-3-amino-4-oxo-5-(5-(4-methylphenylthio)tetrazol-1-yl)pentanoic acid•t-butylester

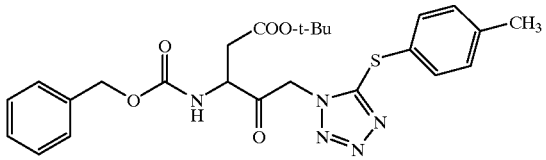

TLC: Rf 0.52 (hexane:ethyl acetate=3:2); NMR (CDCl₃): δ 7.53–7.28 (7H, m), 7.18 (2H, d, J=8.0 Hz), 5.95 (1H, d, J=8.7 Hz), 5.57 (1H, d, J=18.4 Hz), 5.40 (1H, d, J=18.4 Hz), 5.19 (2H, s), 4.73–4.52 (1H, m), 3.04 (1H, dd, J=17.7, 4.6 Hz), 2.70 (1H, dd, J=17.7, 4.9 Hz), 2.35 (6H, s), 1.43 (9H, s).

Example 5(50)
N-benzyloxycarbonyl-3-amino-4-oxo-5-(5-(4-chlorophenylthio)tetrazol-2-yl)pentanoic acid•t-butylester

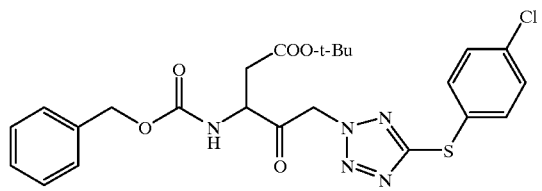

TLC: Rf 0.63 (hexane:ethyl acetate=3:2); NMR (CDCl₃): δ 7.50 (2H, d, J=8.6 Hz), 7.42–7.30 (5H, m), 7.33 (2H, d, J=8.6 Hz), 5.93 (1H, d, J=8.8 Hz), 5.80 (1H, d, J=17.6 Hz), 5.62 (1H, d, J=17.6 Hz), 5.17 (2H, s), 4.72–4.56 (1H, m), 3.02 (1H, dd, J=17.4, 4.4 Hz), 2.70 J=17.6 Hz), 5.17 (2H, s), 4.72–4.56 (1H, m), 3.02 (1H, dd, J=17.4, 4.4 Hz), 2.70 (1H, dd, J=17.4, 4.7 Hz), 1.41 (9H, s).

Example 5(51)
N-benzyloxycarbonyl-3-amino-4-oxo-5-(5-(4-chlorophenylthio)tetrazol-1-yl)pentanoic acid•t-butylester

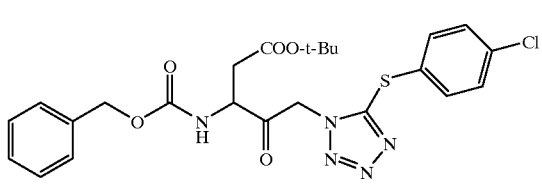

TLC: Rf 0.51 (hexane:ethyl acetate=3:2); NMR (CDCl₃): δ 7.48 (2H, d, J=8.6 Hz), 7.43–7.28 (7H, m), 5.94 (1H, d, J=9.0 Hz), 5.60 (1H, d, J=18.3 Hz), 5.44 (1H, d, J=18.3 Hz), 5.20 (2H, s), 4.70–4.54 (1H, m), 3.06 (1H, dd, J=17.6, 4.2 Hz), 2.71 (1H, dd, J=17.6, 4.7 Hz), 1.43 (9H, s).

Example 5(52)
N-benzyloxycarbonyl-3-amino-4-oxo-5-(5-(pyridin-4-yl)tetrazol-2-yl)pentanoic acid•t-butylester

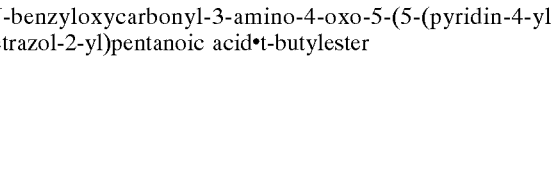

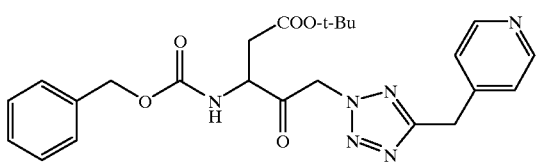

TLC: Rf 0.55 (ethyl acetate); NMR (CDCl₃): δ 8.58–8.48 (2H, m), 7.38 (5H, m), 7.27–7.18 (2H, m), 5.95 (1H, d, J=8.4 Hz), 5.83 (1H, d, J=17.6 Hz), 5.65 (1H, d, J=17.6 Hz), 5.18 (2H, s), 4.77–4.50 (1H, m), 4.27 (2H, s), 3.04 (1H, dd, J=17.4 and 4.6 Hz), 2.71 (1H, dd, J=17.4 and 4.8 Hz), 1.42 (9H, s).

Example 5(53)
N-benzyloxycarbonyl-3-amino-4-oxo-5-(5-(pyridin-4-yl)tetrazol-1-yl)pentanoic acid•t-butylester

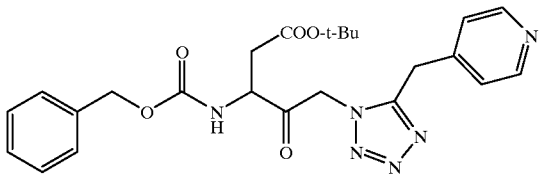

TLC: Rf 0.37 (ethyl acetate); NMR (CDCl₃): δ 8.64–8.50 (2H, m), 7.38 (5H, brs), 7.25–7.11 (2H, m), 5.75–5.65 (1H, m), 5.58–5.31 (2H, m), 5.17 (2H, s), 4.69–4.45 (1H, m), 4.20 (1H, d, J=16.6 Hz), 4.01 (1H, d, J=16.6 Hz), 3.19–2.67 (2H, m), 1.43 (9H, s).

Example 5(54)
N-benzyloxycarbonyl-3-amino-4-oxo-5-(5-(3,5-dichlorophenylthio)tetrazol-2-yl)pentanoic acid•t-butylester

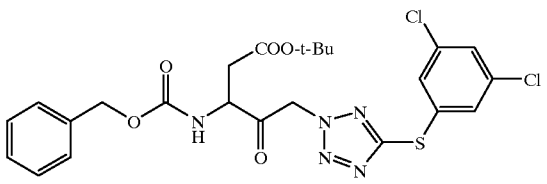

HPTLC: Rf 0.59 (hexane:ethyl acetate=2:1); NMR (CDCl₃): δ 7.45–7.28 (8H, m), 5.94 (1H, d, J=8.5 Hz), 5.84 and 5.68 (each 1H, each d, J=17.5 Hz), 5.17 (2H, s), 4.66 (1H, m), 3.03 and 2.71 (each 1H, each dd, J=17.5, 5.0 Hz), 1.40 (9H, s).

Example 5(55)
N-benzyloxycarbonyl-3-amino-4-oxo-5-(5-(3,5-dichlorophenylihio)tetrazol-1-yl)pentanoic acid•t-butylester

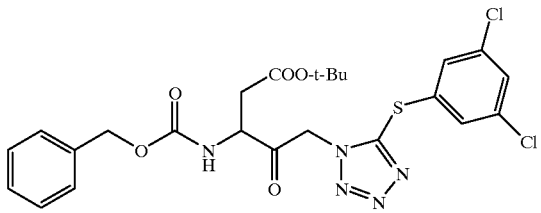

HPTLC: Rf 0.46 (hexane:ethyl acetate=2:1); NMR (CDCl₃): δ 7.46–7.30 (8H, m), 5.92 (1H, d, J=8.5 Hz), 5.64 and 5.48 (each 1H, each d, J=17.5 Hz), 5.19 (2H, s), 4.63 (1H, m), 3.07 and 2.73 (each 1H, each dd, J=17.5, 5.0 Hz), 1.42 (9H, s).

Example 5(56)
N-benzyloxycarbonyl-3-amino-4-oxo-5-(5-(1-methylpyrimidin-2,4-dion-3-ylmethyl)tetrazol-2-yl)pentanoic acid•t-butylester

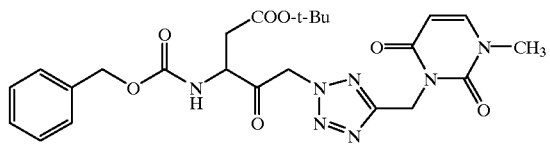

TLC: Rf 0.38 (chloroform:methanol=20:1); NMR (CDCl₃): δ 7.38 (5H, m), 7.15 (1H, d, J=8 Hz), 6.00 (1H, d, J=10 Hz), 5.79 (1H, d, J=8 Hz), 5.72 (1H, d, J=17 Hz), 5.62 (1H, d, J=17 Hz), 5.43 (2H, s), 5.18 (2H, s), 4.61 (1H, m), 3.40 (3H, s), 2.93 (1H, dd, J=18 and 5 Hz), 2.71 (1H, dd, J=15 and 5 Hz), 1.40 (9H, s).

Example 5(57)
N-benzyloxycarbonyl-3-amino-4-oxo-5-(5-(1-methylpyrimidin-2,4-dion-3-ylmethyl)tetrazol-1-yl)pentanoic acid•t-butylester

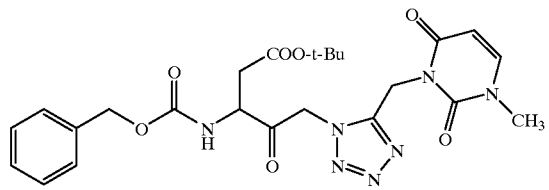

TLC: Rf 0.32 (chloroform:methanol=20:1); NMR (CDCl₃): δ 7.40 (5H, m), 7.13 (1H, d, J=8 Hz), 5.93 (1H, d, J=10 Hz), 5.92 (1H, d, J=17 Hz), 5.75 (1H, d, J=17 Hz), 5.72 (1H, d, J=8 Hz), 5.30 (1H, d, J=16 Hz), 5.20 (2H, s), 5.09 (1H, d, J=16 Hz), 4.68 (1H, m), 3.39 (3H, s), 3.03 (1H, dd, J=17 and 5 Hz), 2.78 (1H, dd, J=17 and 5 Hz), 1.40 (9H, s).

Example 5(58)
N-benzyloxycarbonyl-3-amino-4-oxo-5-(5-(2-chloroethyl)tetrazol-2-yl)pentanoic acid•t-butylester

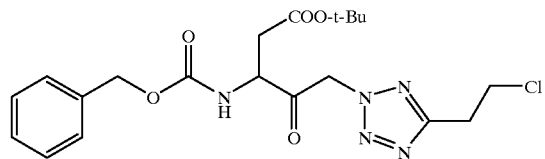

TLC: Rf 0.68 (hexane:ethyl acetate=1:1); NMR (CDCl₃): δ 7.39 (5H, m), 5.94 (1H, d, J=8.8 Hz), 5.82 (1H, d, J=17.8 Hz), 5.65 (1H, d, J=17.8 Hz), 5.18 (2H, s), 4.72–4.60 (1H, m), 3.92 (2H, t, J=7.0 Hz), 3.39 (2H, t, J=7.0 Hz), 3.02 (1H, dd, J=17.4 and 4.2 Hz), 2.72 (1H, dd, J=17.4 and 4.8 Hz), 1.43 (9H, s).

Example 5(59)
N-benzyloxycarbonyl-3-amino-4-oxo-5-(5-(2-chloroethyl)tetrazol-1-yl)pentanoic acid•t-butylester

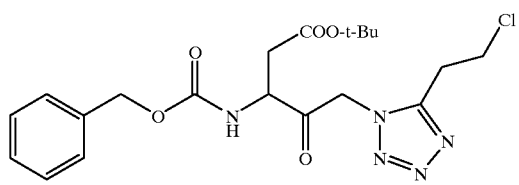

TLC: Rf 0.46 (hexane:ethyl acetate=1:1); NMR (CDCl$_3$): δ 7.39 (5H, m), 5.79 (1H, d, J=8.2 Hz), 5.74–5.49 (2H, m), 5.20 (2H, s), 4.70–4.52 (1H, m), 3.92 (2H, t, J=7.0 Hz), 3.24–3.02 (3H, m), 277 (1H, dd, J=17.4 and 5.2 Hz), 1.44 (9H, s).

Example 5(60)
N-benzyloxycarbonyl-3-amino-4-oxo- 5-(5-(phenylcarbonyl)tetrazol-2-yl)pentanoic acid•t-butylester

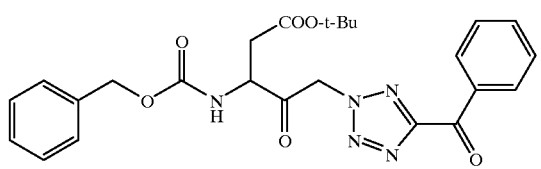

HPTLC: Rf 0.35 (hexane:ethyl acetate=2:1); NMR (CDCl$_3$): δ 8.36 (2H, d, J=7.0 Hz), 7.73–7.29 (3H, m), 7.37 (5H, m), 6.11–5.74 (3H, m), 5.18 (2H, s), 4.73 (1H, m), 3.05 and 2.77 (each 1H, each dd, J=17.0, 5.0 Hz), 1.42 (9H, s).

Example 5(61)
N-benzyloxycarbonyl-3-amino-4-oxo-5-(5-(phenylcarbonyl)tetrazol-1-yl)pentanoic acid•t-butylester

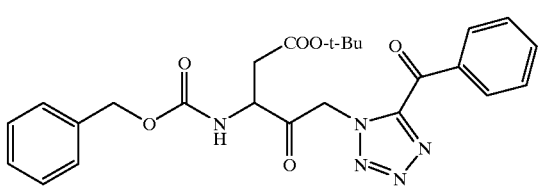

HPTLC: Rf 0.47 (hexane:ethyl acetate=2:1); NMR (CDCl$_3$): δ 8.42 (2H, d, J=7.0 Hz), 7.70 (1H, t, J=7.0 Hz), 7.54 (2H, t, J=7.0 Hz), 7.46–7.29 (5H, m), 6.12–5.74 (3H, m), 5.20 (2H, s), 4.78 (1H, m), 2.97 and 2.71 (each 1H, each dd, J=17.5, 5.0 Hz), 1.36 (9H, s).

Example 5(62)
N-benzyloxycarbonyl-3-amino-4-oxo-5-(5-(2-chloro-6-fluorophenylmethyl)tetrazol-2-yl)pentanoic acid•t-butylester

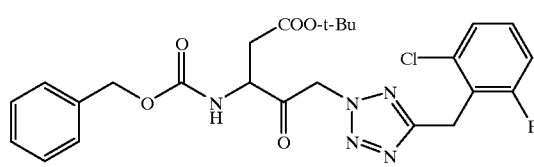

TLC: Rf 0.74 (hexane:ethyl acetate=1:1); NMR (CDCl$_3$): δ 7.46–7.30 (5H, m), 7.25–7.18 (2H, m), 7.10–6.95 (1H, m), 5.94 (1H, d, J=8.6 Hz), 5.77 (1H, d, J=17.8 Hz), 5.58 (1H, d, J=17.8 Hz), 5.16 (2H, s), 4.70–4.55 (1H, m), 4.44 (2H, s), 2.99 (1H, dd, J=17.4, 4.5 Hz), 2.68 (1H, dd, J=17.4, 4.8 Hz), 1.41 (9H,s).

Example 5(63)
N-benzyloxycarbonyl-3-amino-4-oxo-5-(5-(2-chloro-6-fluorophenylmethyl)tetrazol-1-yl)pentanoic acid•t-butylester

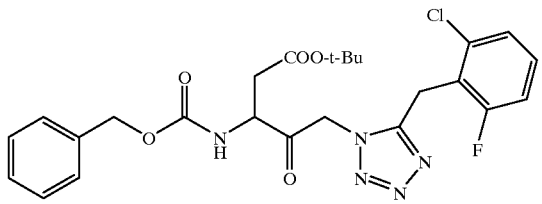

TLC: Rf 0.51 (hexane:ethyl acetate=1:1); NMR (CDCl$_3$): δ 7.50–7.30 (5H, m), 7.30–7.16 (2H, m), 7.10–6.94 (1H, m), 5.88 (1H, d, J=9.1 Hz), 5.68 (1H, d, J=18.7 Hz), 5.52 (1H, d, J=18.7 Hz), 5.19 (2H, s), 4.70–4.55 (1H, m), 3.10 (1H, dd, J=17.6, 4.6 Hz), 2.76 (1H, dd, J=17.6, 4.8 Hz), 1.41 (9H, s).

Example 5(64)
N-benzyloxycarbonyl-3-amino-4-oxo- 5-(5-(cyclohexylthio)tetrazol-2-yl)pentanoic acid•t-butylester

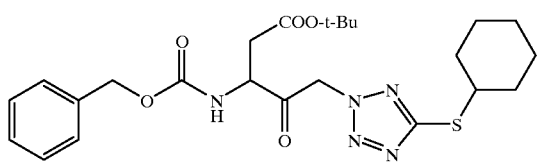

TLC: Rf 0.42 (hexane:ethyl acetate=1:1); NMR (CDCl$_3$): δ 7.44–7.30 (5H, m), 5.95 (1H, d, J=9.4 Hz), 5.79 (1H, d, J=17.8 Hz), 5.61 (1H, d, J=17.8 Hz), 5.18 (2H, s), 4.75–4.60 (1H, m), 3.72–3.50 (1H, m), 3.03 (1H, dd, J=17.4, 4.4 Hz), 2.71 (1H, dd, J=17.4, 4.8 Hz), 2.20–1.30 (10H, m), 1.42 (9H, s).

Example 5(65)
N-benzyloxycarbonyl-3-amino-4-oxo-5-(5-(cyclohexylthio)tetrazol-1-yl)pentanoic acid•t-butylester

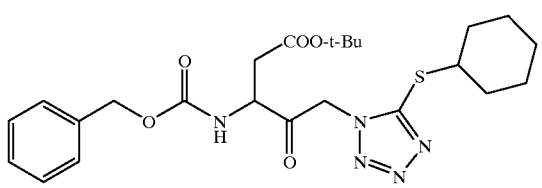

TLC: Rf 0.28 (hexane:ethyl acetate=1:1); NMR (CDCl$_3$): δ 7.48–7.30 (5H, m), 5.96 (1H, d, J=8.4 Hz), 5.49 (1H, d, J=18.3 Hz), 5.31 (1H, d, J=18.3 Hz), 5.19 (2H, s), 4.72–4.57 (1H, m), 3.91–3.72 (1H, m), 3.06 (1H, dd, J=17.6, 4.3 Hz), 2.70 (1H, dd, J=17.6, 4.9 Hz), 2.20–1.20 (10H, m), 1.43 (9H, s).

Example 5(66)
N-benzyloxycarbonyl-3-amino-4-oxo-5-(5-(4-methoxyphenylthio)tetrazol-2-yl)pentanoic acid•t-butylester

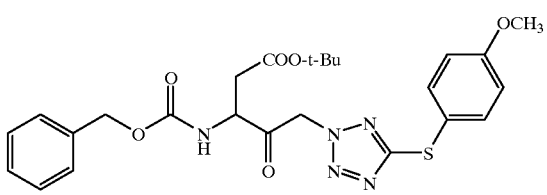

TLC: Rf 0.50 (hexane:ethyl acetate=1:1); NMR (CDCl$_3$): δ 7.56 (2H, d, J=8.9 Hz), 7.45–7.30 (5H, m), 6.90 (2H, d, J=8.9 Hz), 5.93 (1H, d, J=9.2 Hz), 5.75 (1H, d, J=17.8 Hz), 5.58 (1H, d, J=17.8 Hz), 5.16 (2H, s), 4.72–4.55 (1H, m), 3.81 (3H, s), 2.97 (1H, dd, J=17.3 4.3 Hz), 2.68 (1H, dd, J=17.3, 4.9 Hz), 1.41 (9H, s).

Example 5(67)

N-benzyloxycarbonyl-3-amino-4-oxo-5-(5-(4-methoxyphenylthio)tetrazol-1-yl)pentanoic acid•t-butylester

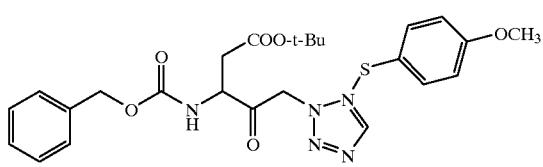

TLC: Rf 0.43 (hexane:ethyl acetate=1:1); NMR (CDCl$_3$): δ 7.51 (2H, d, J=8.9 Hz), 7.45–7.32 (5H, m), 6.90 (2H, d, J=8.9 Hz), 5.97 (1H, d, J=9.2 Hz), 5.57 (1H, d, J=18.4 Hz), 5.40 (1H, d, J=18.4 Hz), 5.20 (2H, s), 4.71–4.55 (1H, m), 3.81 (3H, s), 3.05 (1H, dd, J=17.5, 4.4 Hz), 2.75 (1H, dd, J=17.5, 4.9 Hz), 1.43 (9H, s).

Example 5(68)

N-benzyloxycarbonyl-3-amino-4-oxo-5-(5-(2-chlorophenylthio)tetrazol-2-yl)pentanoic acid•t-butylester

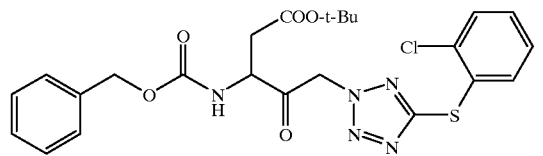

TLC: Rf 0.52 (hexane:ethyl acetate=2:1); NMR (CDCl$_3$): δ 7.51–7.16 (9H, m), 5.93 (1H, d, J=9.4 Hz), 5.84 (1H, d, J=17.8 Hz), 5.66 (1H, d, J=17.8 Hz), 5.18 (2H, s), 4.73–4.54 (1H, m), 3.03 (1H, dd, J=17.4 and 4.8 Hz), 2.71 (1H, dd, 17.4 and 4.6 Hz), 1.42 (9H, s).

Example 5(69)

N-benzyloxycarbonyl-3-amino-4-oxo-5-(5-(2-chlorophenylthio)tetrazol-1-yl)pentanoic acid•t-butylester

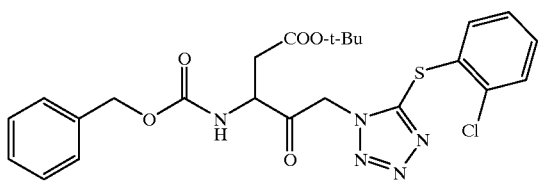

TLC: Rf 0.40 (hexane:ethyl acetate=2:1); NMR (CDCl$_3$): δ 7.58–7.00 (9H, m), 5.95 (1H, d, J=9.0 Hz), 5.67 (J=18.4 Hz), 5.50 (1H, d, J=18.4 Hz), 5.20 (2H, s), 4.74–4.52 (1H, m), 3.05 (1H, dd, J=17.6 and 4.2 Hz), 2.71 (1H, dd, 17.6 and 5.0 Hz), 1.41 (9H, s).

Example 5(70)

N-benzyloxycarbonyl-3-amino-4-oxo-5-(5-(2,4-dichlorophenylthio)tetrazol-2-yl)pentanoic acid•t-butylester

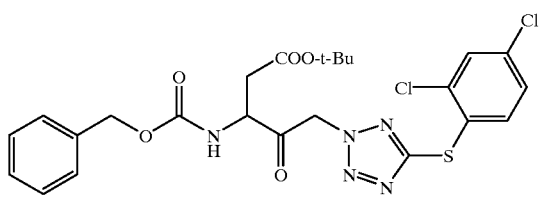

TLC: Rf 0.30 (hexane:ethyl acetate=4:1); NMR (CDCl$_3$): δ 7.48 (1H, d, J=2.2 Hz), 7.46–7.31 (6H, m), 7.23 (1H, dd, J=8.4 and 2.2 Hz), 5.93 (1H, d, J=9.0 Hz), 5.84 (1H, d, J=17.8 Hz), 5.66 (1H, d, J=17.8 Hz), 5.18 (2H, s), 4.75–4.52 (1H, m), 3.03 (1H, dd, J=17.6 and 4.4 Hz), 2.71 (1H, dd, J=17.6 and 4.8 Hz), 1.42 (9H, s).

Example 5(71)

N-benzyloxycarbonyl-3-amino-4-oxo-5-(5-(2,4-dichlorophenylthio)tetrazol-1-yl)pentanoic acid•t-butylester

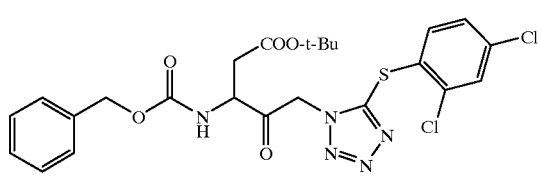

TLC: Rf 0.23 (hexane:ethyl acetate=4:1); NMR (CDCl$_3$): δ 7.53 (1H, d, J=8.4 Hz), 7.47 (1H, d, J=2.4 Hz), 7.45–7.32 (5H, m), 7.27 (1H, dd, J=8.4 and 2.4 Hz), 5.94 (1H, d, J=9.6 Hz), 5.68 (1H, d, J=18.6 Hz), 5.51 (1H, d, J=18.6 Hz), 5.20 (2H, s), 4.76–4.52 (1H, m), 3.07 (1H, dd, J=17.6 and 4.6 Hz), 2.72 (1H, dd, J=17.6 and 4.6 Hz), 1.41 (9H, s).

Example 5(72)

N-benzyloxycarbonyl-3-amino- 4-oxo-5-(5-(2-chloro-6-methylphenylthio)tetrazol-2-yl)pentanoic acid•t-butylester

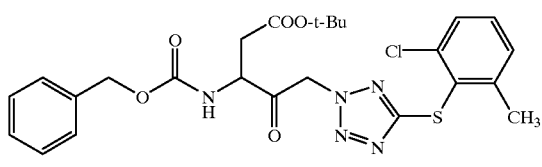

TLC: Rf 0.71 (benzene:diethylether=2:1); NMR (CDCl$_3$): δ 7.39–7.20 (8H, m), 5.92 (1H, d, J=8.8 Hz), 5.74 (1H, d, J=17.4 Hz), 5.55 (1H, d, J=17.4 Hz), 4.65–4.55 (1H, m), 3.00 (1H, dd, J=4.4, 17.4 Hz), 2.69 (1H, dd, J=4.6, 17.4 Hz), 2.52 (3H, s), 1.40 (9H, s).

Example 5(73)

N-benzyloxycarbonyl-3-amino-4-oxo-5-(5-(2-chloro-6-methylphenylthio)tetrazol-1-yl)pentanoic acid•t-butylester

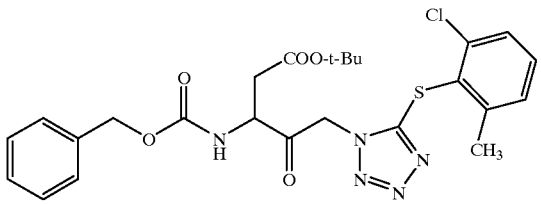

TLC: Rf 0.55 (benzene:diethylether=2:1); NMR (CDCl₃): δ 7.43–7.23 (8H, m), 5.97 (1H, d, J=9.4 Hz), 5.66 (1H, d, J=18.6 Hz), 5.49 (1H, d, J=18.6 Hz), 4.70–4.60 (1H, m), 3.08 (1H, dd, J=4.4, 17.2 Hz), 2.74 (1H, dd, J=4.6, 17.2 Hz), 2.58 (3H, s), 1.43 (9H, s).

Example 5(74)
N-benzyloxycarbonyl-3-amino-4-oxo-5-(5-(4-trifluoromethylphenylthio)tetrazol-2-yl)pentanoic acid•t-butylester

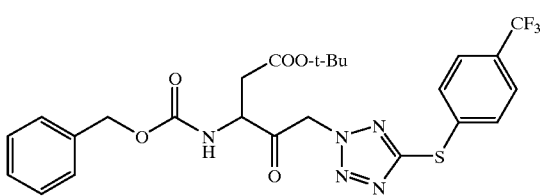

TLC: Rf 0.59 (hexane:ethyl acetate=2:1); NMR (CDCl₃): δ 7.60 (s, 4H), 7.38 (s, 5H), 6.0–5.6 (m, 3H), 5.18 (s, 2H), 4.7–4.6 (m, 1H), 3.05 (dd, J=4.3, 17.5 Hz, 1H), 2.72 (dd, J=4.8, 17.5 Hz, 1H), 1.42 (s, 9H).

Example 5(75)
N-benzyloxycarbonyl-3-amino-4-oxo-5-(5-(4-trifluoromethylphenylthio)tetrazol-1-yl)pentanoic acid•t-butylester

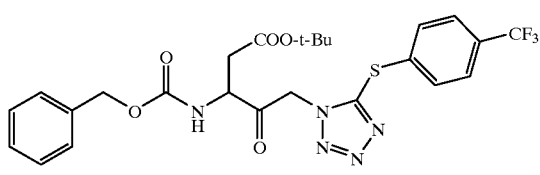

TLC: Rf 0.43 (hexane:ethyl acetate=3:1); NMR (CDCl₃): δ 7.61 (s, 4H), 7.38 (s, 5H), 6.0–5.9 (m, 1H), 5.7–5.4 (m, 2H), 5.20 (s, 2H), 4.7–4.6 (m, 1H), 3.07 (dd, J=4.3, 17.6 Hz, 1H), 2.71 (dd, J=4.0, 17.5 Hz, 1H), 1.41 (s, 9H).

Example 5(76)
N-benzyloxycarbonyl-3-amino-4-oxo-5-(5-(naphthalen-2-ylthio)tetrazol-2-yl)pentanoic acid•t-butylester

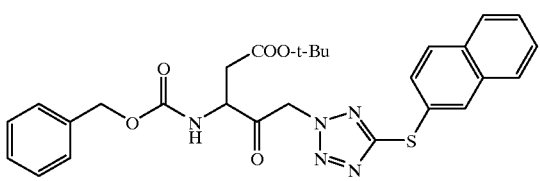

TLC: Rf 0.47 (hexane:ethyl acetate=7:3); NMR (CDCl₃): δ 8.08 (1H, d, J=1.5 Hz), 7.87–7.73 (3H, m), 7.62–7.43 (3H, m), 7.41–7.25 (5H, m), 5.93 (1H, d, J=8.6 Hz), 5.79 (1H, d, J=17.7 Hz), 5.62 (1H, d, J=17.7 Hz), 5.15 (2H, s), 4.71–4.56 (1H, m), 3.00 (1H, dd, J=17.5, 4.4 Hz), 2.69 (1H, dd, J=17.5, 4.9 Hz), 1.39 (9H, s).

Example 5(77)
N-benzyloxycarbonyl-3-amino-4-oxo-5-(5-(naphthalen-2-ylthio)tetrazol-1-yl)pentanoic acid•t-butylester

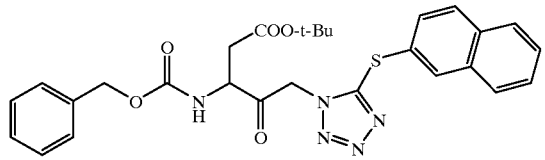

TLC: Rf 0.35 (hexane:ethyl acetate=7:3); NMR (CDCl₃): δ 8.06 (1H, s), 7.88–7.75 (3H, m), 7.61–7.46 (3H, m), 7.43–7.30 (5H, m), 5.92 (1H, d, J=8.8 Hz), 5.59 (1H, d, J=18.3 Hz), 5.44 (1H, d, J=18.3 Hz), 5.17 (2H, s), 4.65–4.52 (1H, m), 2.98 (1H, dd, J=17.5, 4.4 Hz), 2.66 (1H, dd, J=17.5, 4.9 Hz), 1.42 (9H, s).

Example 5(78)
N-benzyloxycarbonyl-3-amino-4-oxo-5-(5-(4-t-butylphenylthio)tetrazol-2-yl)pentanoic acid•t-butylester

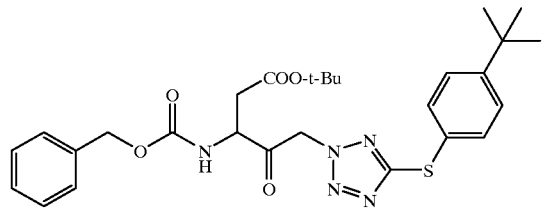

TLC: Rf 0.49 (hexane:ethyl acetate=7:3); NMR (CDCl₃): δ 7.51 (2H, d, J=8.6 Hz), 7.45–7.30 (7H, m), 5.94 (1H, d, J=8.8 Hz), 5.78 (1H, d, J=17.8 Hz), 5.60 (1H, d, J=17.8 Hz), 5.16 (2H, s), 4.70–4.56 (1H, m), 3.01 (1H, dd, J=17.4, 4.4 Hz), 2.69 (1H, dd, J=17.4, 4.8 Hz), 1.41 (9H, s), 1.30 (9H, s).

Example 5(79)
N-benzyloxycarbonyl-3-amino-4-oxo-5-(5-(4-t-butylphenylthio)tetrazol-1-yl)pentanoic acid•t-butylester

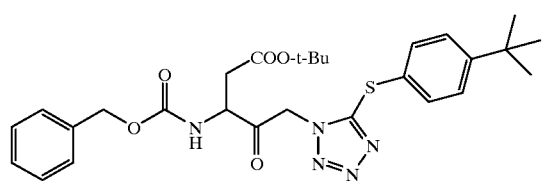

TLC: Rf 0.34 (hexane:ethyl acetate=7:3); NMR (CDCl₃): δ 7.47 (2H, d, J=8.7 Hz), 7.42–7.30 (7H, m), 5.95 (1H, d, J=9.2 Hz), 5.57 (1H, d, J=18.4 Hz), 5.41 (1H, d, J=18.4 Hz), 5.19 (2H, s), 4.68–4.53 (1H, m), 3.03 (1H, dd, J=17.4, 4.4 Hz), 2.69 (1H, dd, J=17.4, 4.9 Hz), 1.42 (9H, s), 1.30 (9H, s).

Example 5(80)
N-benzyloxycarbonyl-3-amino-4-oxo-5-(5-(4-trifluoromethyloxyphenylthio)tetrazol-1-yl)pentanoic acid•t-butylester

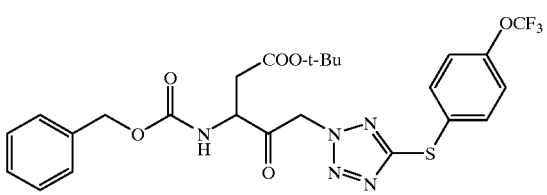

TLC: Rf 0.31 (hexane:ethyl acetate=3:1); NMR (CDCl$_3$): δ 7.7–7.5 (m, 2H), 7.5–7.3 (m, 5H), 7.3–7.2 (m, 2H), 5.94 (d, J=8.5 Hz, 1H), 5.63 (d, J=18.4 Hz, 1H), 5.46 (d, J=18.4 Hz, 1H), 5.20 (s, 2H), 4.7–4.6 (m, 1H), 3.10 (dd, J=4.4, 17.6 Hz, 1H), 2.71 (dd, J=4.9, 17.6 Hz, 1H), 1.42 (s, 9H).

Example 5(81)
N-benzyloxycarbonyl-3-amino-4-oxo-5-(5-(4-trifluoromethyloxyphenylthio)tetrazol-2-yl)pentanoic acid•t-butylester

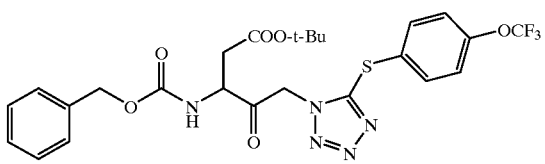

TLC: Rf 0.37 (hexane:ethyl acetate=3:1); NMR (CDCl$_3$): δ 7.7–7.5 (m, 2H), 7.5–7.3 (m, 5H), 7.3–7.2 (m, 2H), 6.0–5.9 (m, 1H), 5.86 (d, J=17.7 Hz, 1H), 5.68 (d, J=17.7 Hz, 1H), 5.17 (s, 2H), 4.7–4.6 (m, 1H), 3.00 (dd, J=4.4, 17.5 Hz, 1H), 2.70 (dd, J=4.8, 17.5 Hz, 1H), 1.41 (s, 9H).

Example 5(82)
N-benzyloxycarbonyl-3-amino-4-oxo-5-(5-(2,3,6-trichlorophenylthio)tetrazol-2-yl)pentanoic acid•t-butylester

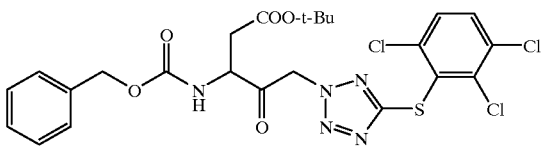

TLC: Rf 0.55 (benzene:diethylether=10:1); NMR (CDCl$_3$): δ 7.51–7.35 (7H, m), 5.92 (1H, d, J=8.8 Hz), 5.78 (1H, d, J=17.8 Hz), 5.59 (1H, d, J=17.8 Hz), 5.17 (2H, s), 4.63–4.60 (1H, m), 3.08 (1H, dd, J=4.8, 17.6 Hz), 2.71 (1H, dd, J=5.0, 17.6 Hz), 1.41 (9H, s).

Example 5(83)
N-benzyloxycarbonyl-3-amino-4-oxo-5-(5-(2,3,6-trichlorophenylthio)tetrazol-1-yl)pentanoic acid•t-butylester

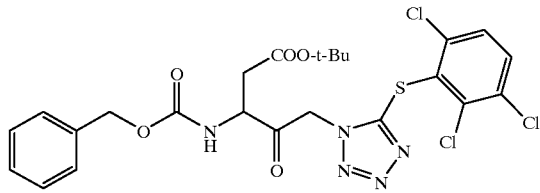

TLC: Rf 0.37 (benzene:diethylether=10:1); NMR (CDCl$_3$): δ 7.53–7.33 (7H, m), 5.98 (1H, d, J=9.4 Hz), 5.70 (1H, d, J=18.4 Hz), 5.54 (1H, d, J=18.4 Hz), 5.21 (2H, s), 4.76–4.64 (1H, m), 3.12 (1H, dd, J=4.4, 17.6 Hz), 2.76 (1H, dd, J=5.0, 17.6 Hz), 1.43 (9H, s).

Example 5(84)
N-benzyloxycarbonyl-3-amino-4-oxo-5-(5-(2,4-dimethylphenylthio)tetrazol-2-yl)pentanoic acid•t-butylester

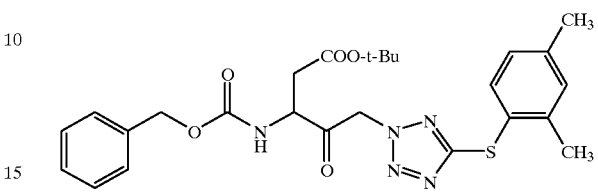

TLC: Rf 0.53 (hexane:ethyl acetate=7:3); NMR (CDCl$_3$): δ 7.49 (1H, d, J=7.9 Hz), 7.45–7.30 (5H, m), 7.11 (1H, s), 7.01 (1H, d, J=7.9 Hz), 5.94 (1H, d, J=9.1 Hz), 5.76 (1H, d, J=17.8 Hz), 5.57 (1H, d, J=17.8 Hz), 5.16 (2H, s), 4.72–4.55 (1H, m), 3.01 (1H, dd, J=17.8, 4.4 Hz), 2.68 (1H, dd, J=17.8, 4.7 Hz), 2.39 (3H, s), 2.33 (3H, s), 1.41 (9H, s).

Example 5(85)
N-benzyloxycarbonyl-3-amino-4-oxo-5-(5-(2,4-dimethylphenylthio)tetrazol-1-yl)pentanoic acid•t-butylester

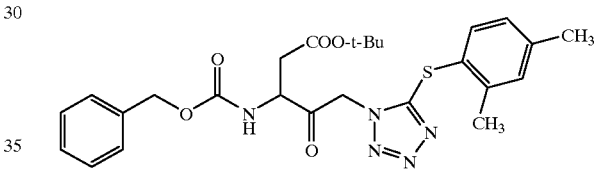

TLC: Rf 0.36 (hexane:ethyl acetate=7:3); NMR (CDCl$_3$): δ 7.46–7.31 (6H, m), 7.13 (1H, s), 7.02 (1H, d, J=7.7 Hz), 5.96 (1H, d, J=9.2 Hz), 5.56 (1H, d, J=18.4 Hz), 5.39 (1H, d, J=18.4 Hz), 5.20 (2H, s), 4.70–4.54 (1H, m), 3.05 (1H, dd, J=17.5, 4.4 Hz), 2.70 (1H, dd, J=17.5, 4.8 Hz), 2.37 (3H, s), 2.32 (3H, s), 1.42 (9H, s).

Example 5(86)
N-benzyloxycarbonyl-3-amino-4-oxo-5-(5-(2,5-dichlorophenylthio)tetrazol-2-yl)pentanoic acid•t-butylester

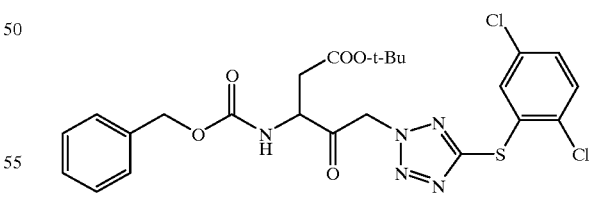

TLC: Rf 0.72 (hexane:ethyl acetate=3:2); NMR (CDCl$_3$): δ 7.55–7.30 (6H, m), 7.30–7.17 (2H, m), 5.94 (1H, d, J=9.0 Hz), 5.87 (1H, d, J=17.5 Hz), 5.69 (1H, d, J=17.5 Hz), 5.18 (2H, s), 4.73–4.59 (1H, m), 3.05 (1H, dd, J=17.6, 4.0 Hz), 2.71 (1H, dd, J=17.6, 4.8 Hz), 1.42 (9H, s).

Example 5(87)
N-benzyloxycarbonyl-3-amino-4-oxo-5-(5-(2,5-dichlorophenylthio)tetrazol-1-yl)pentanoic acid•t-butylester

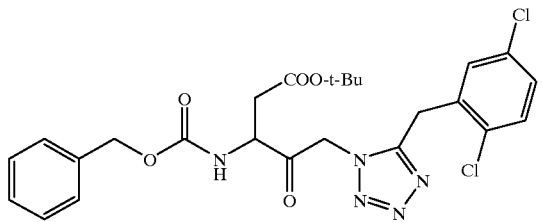

TLC: Rf 0.72 (hexane:ethyl acetate=3:2); NMR (CDCl₃): δ 7.53 (1H, d, J=7.2 Hz 7.45–7.32 (5H, m) 7.30–7.24 (2H, m), 5.94 (1H, d, J=9.2 Hz), 5.69 (1H, d, J=18.3 Hz), 5.52 (1H, d, J=18.3 Hz), 5.20 (2H, s), 4.74–4.58 (1H, m), 3.08 (1H, dd, J=17.5, 4.3 Hz), 2.72 (1H, dd, J=17.5, 4.8 Hz), 1.42 (9H, s).

Example 5(88)
N-benzyloxycarbonyl-3-amino-4-oxo-5-(5-(4-bromophenylthio)tetrazol-2-yl)pentanoic acid•t-butylester

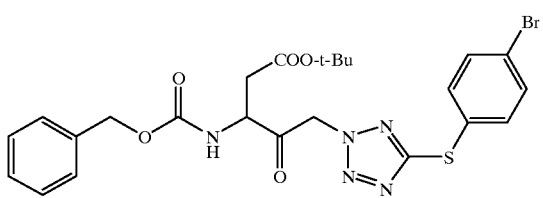

TLC: Rf 0.35 (hexane:ethyl acetate=4:1).

Example 5(89)
N-benzyloxycarbonyl-3-amino-4-oxo-5-(5-(4-bromophenylthio)tetrazol-1-yl)pentanoic acid•t-butylester

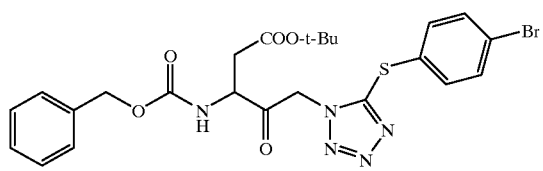

TLC: Rf 0.31 (hexane:ethyl acetate=3:1).

Example 5(90)
N-benzyloxycarbonyl-3-amino-4-oxo-5-(5-(2,6-dichloro-4-methylphenylthio)tetrazol-2-yl)pentanoic acid•t-butylester

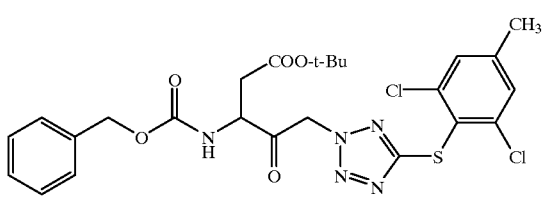

TLC: Rf 0.47 (hexane:ethyl acetate=7:3); NMR (CDCl₃): δ 7.42–7.29 (5H, m), 7.27 (2H, d, J=1.4 Hz), 5.92 (1H, d, J=8.8 Hz), 5.75 (1H, d, J=17.6 Hz), 5.57 (1H, d, J=17.6 Hz), 5.16 (2H, s), 4.70–4.55 (1H, m), 3.00 (1H, dd, J=17.4, 4.3 Hz), 2.69 (1H, dd, J=17.4, 4.8 Hz), 2.34 (3H, s), 1.42 (9H, s).

Example 5(91)
N-benzyloxycarbonyl-3-amino-4-oxo-5-(5-(2,6-dichloro-4-methylphenylthio)tetrazol-1-yl)pentanoic acid•t-butylester

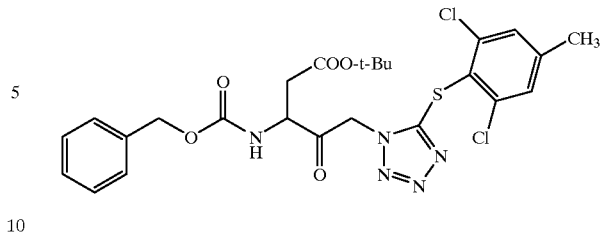

TLC: Rf 0.34 (hexane:ethyl acetate=7:3); NMR (CDCl₃): δ 7.45–7.31 (5H, m), 7.26 (2H, s), 5.98 (1H, d, J=9.1 Hz), 5.67 (1H, d, J=18.4 Hz), 5.50 (1H, d, J=18.4 Hz), 5.21 (2H, s), 4.75–4.62 (1H, m), 3.09 (1H, dd, J=17.5, 4.5 Hz), 2.74 (1H, dd, J=17.5, 4.8 Hz), 2.34 (3H, s), 1.43 (9H, s).

Example 5(92)
N-benzyloxycarbonyl-3-amino-4-oxo-5-(5-(3,4-dichlorophenylthio)tetrazol-2-yl)pentanoic acid•t-butylester

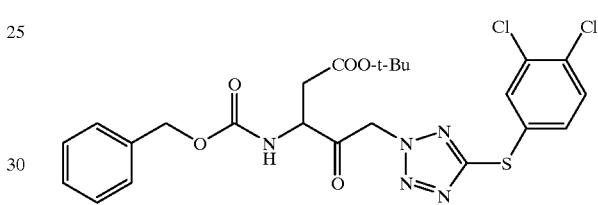

TLC: Rf 0.72 (benzene:diethylether=2:1); NMR (CDCl₃): δ 7.65 (1H, d, J=1.8 Hz), 7.45–7.33 (7H, m), 5.94 (1H, d, J=9.6 Hz), 5.83 (1H, d, J=18.0 Hz), 5.65 (1H, d, J=18.0 Hz), 5.17 (2H, s), 4.70–4.61 (1H, m), 3.04 (1H, dd, J=4.2, 17.4 Hz), 2.72 (1H, dd, J=4.6, 17.4 Hz), 1.41 (9H, s).

Example 5(93)
N-benzyloxycarbonyl-3-amino-4-oxo-5-(5-(3,4-dichlorophenylthio)tetrazol-1-yl)pentanoic acid•t-butylester

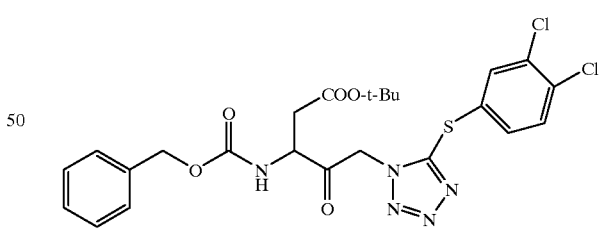

TLC: Rf 0.53 (benzene:diethylether=2:1); NMR (CDCl₃): δ 7.65 (1H, d, J=2.0 Hz), 7.47–7.34 (7H, m), 5.94 (1H, d, J=8.6 Hz), 5.63 (1H, d, J=18.6 Hz), 5.47 (1H, d, J=18.6 Hz), 5.20 (2H, s), 4.69–4.60 (1H, m), 3.09 (1H, dd, J=4.4, 17.6 Hz), 2.75 (1H, dd, J=5.0, 17.6 Hz), 1.43 (9H, s).

Example 5(94)
N-benzyloxycarbonyl-3-amino-4-oxo-5-(5-bromotetrazol-2-yl)pentanoic acid•t-butylester

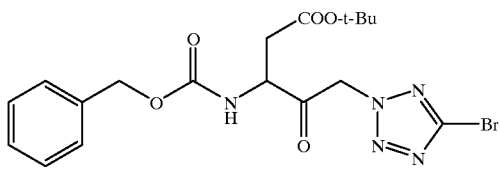

TLC: Rf 0.26 (hexane:ethyl acetate=3:1); NMR (CDCl$_3$): δ 7.39 (5H, m), 5.93 (1H, d, J=10.2 Hz), 5.86 (1H, d, J=17.6 Hz), 5.68 (1H, d, J=17.6 Hz), 5.18 (2H, s), 4.78–4.55 (1H, m), 3.04 (1H, dd, J=17.4 Hz, and 4.6 Hz), 2.72 (1H, dd, J=17.4 Hz and 4.8 Hz), 1.43 (9H, s).

Example 5(95)
N-benzyloxycarbonyl-3-amino-4-oxo-5-(5-(4-nitrophenylthio)tetrazol-2-yl)pentanoic acid•t-butylester

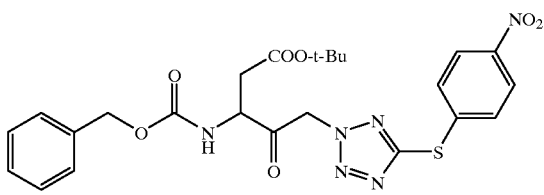

TLC: Rf 0.40 (hexane:ethyl acetate=2:1); NMR (CDCl$_3$): δ 8.24–8.09 (2H, m), 7.62–7.48 (2H, m), 7.45–7.28 (5H, m), 5.94 (1H, d, J=8.4 Hz), 5.91 (1H, d, J=17.8 Hz), 5.72 (1H, d, J=17.8 Hz), 5.18 (2H, s), 4.78–4.58 (1H, m), 3.06 (1H, dd, J=17.6 and 4.4 Hz), 2.73 (1H, dd, J=17.6 and 4.8 Hz), 1.42 (9H, s).

Example 5(96)
N-benzyloxycarbonyl-3-amino-4-oxo-5-(5-(4-nitrophenylthio)tetrazol-1-yl)pentanoic acid•t-butylester

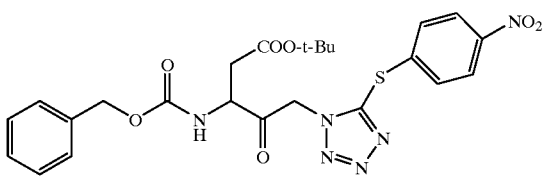

TLC: Rf 0.23 (hexane:ethyl acetate=2:1); NMR (CDCl$_3$): δ 8.26–8.11 (2H, m), 7.69–7.50 (2H, m), 7.46–7.28 (5H, m), 5.90 (1H, d, J=9.0 Hz), 5.68 (1H, d, J=18.2 Hz), 5.51 (1H, d, J=18.2 Hz), 5.19 (2H, s), 4.75–4.48 (1H, m), 3.06 (1H, dd, J=17.6 and 4.4 Hz), 2.71 (1H, dd, J=17.6 and 5.0 Hz), 1.41 (9H, s).

Example 5(97)
N-benzyloxycarbonyl-3-amino-4-oxo-5-(5-(naphthalen-1-ylthio)tetrazol-2-yl)pentanoic acid•t-butylester

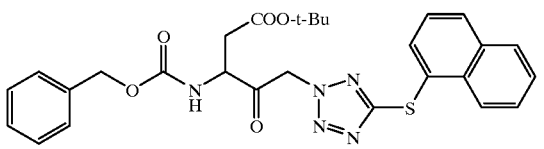

TLC: Rf 0.77 (hexane:ethyl acetate=1:1); NMR (CDCl$_3$): δ 8.39 (1H, d, J=7.0 Hz), 7.94–7.85 (3H, m), 7.59–7.43 (3H, m), 7.40–7.30 (5H, m), 5.89 (1H, d, J=9.0 Hz), 5.70 (1H, d, J=18.0 Hz), 5.52 (1H, d, J=18.0 Hz), 5.13 (2H, s), 4.71–4.56 (1H, m), 2.96 (1H, dd, J=17.0, 4.0 Hz), 2.65 (1H, dd, J=17.0, 5.0 Hz), 1.38 (9H, s).

Example 5(98)
N-benzyloxycarbonyl-3-amino-4-oxo-5-(5-(naphthalen-1-ylthio)tetrazol-1-yl)pentanoic acid•t-butylester

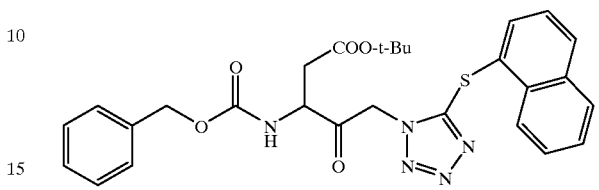

TLC: Rf 0.70 (hexane:ethyl acetate=1:1); NMR (CDCl$_3$): δ 8.32 (1H, d, J=8.0 Hz), 7.96–7.86 (3H, m), 7.64–7.47 (3H, m), 7.44–7.31 (5H, m), 5.92 (1H, d, J=9.0 Hz), 5.59 (1H, d, J=18.0 Hz), 5.43 (1H, d, J=18.0 Hz), 5.19 (2H, s), 4.65–4.52 (1H, m), 3.02 (1H, dd, J=17.0, 4.0 Hz), 2.69 (1H, dd, J=17.0, 4.0 Hz), 1.42 (9H, s).

Example 5(99)
N-benzyloxycarbonyl-3-amino-4-oxo-5-(5-(2,4-di-t-butylphenylthio)tetrazol-2-yl)pentanoic acid•t-butylester

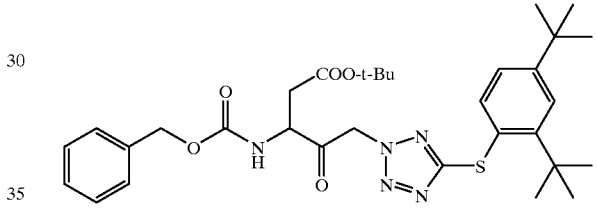

TLC: Rf 0.48 (benzene:diethylether=8:1); NMR (CDCl$_3$): δ 7.50 (1H, d, J=2.2 Hz), 7.44 (1H, d, J=8.2 Hz), 7.38–7.35 (5H, m), 7.17 (1H, dd, J=2.2 and 8.2 Hz), 5.94 (1H, d, J=8.4 Hz), 5.76 and 5.59 (each 1H, each d, J=17.4 Hz), 5.16 (2H, s), 4.69–4.59 (1H, m), 2.99 (1H, dd, J=4.6 and 17.4 Hz), 2.69 (1H, dd, J=4.8 and 17.4 Hz), 1.53 (9H, s), 1.41 (9H, s), 1.31 (9H, s).

Example 5(100)
N-benzyloxycarbonyl-3-amino-4-oxo-5-(5-(2,4-di-t-butylphenylthio)tetrazol-1-yl)pentanoic acid•t-butylester

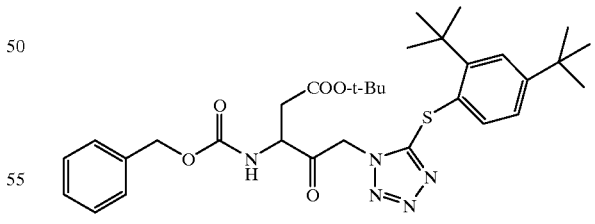

TLC: Rf 0.31 (benzene:diethylether=8:1); NMR (CDCl$_3$): δ 7.52 (1H, d-like), 7.41–7.34 (5H, m), 7.28–7.16 (2H, m), 5.95 (1H, d, J=8.8 Hz), 5.60 and 5.43 (each 1H, each d, J=18.4 Hz), 5.19 (2H, s), 4.69–4.59 (1H, m), 3.06 (1H, dd, J=4.6 and 17.4 Hz), 2.71 (1H, dd, J=4.6 and 17.4 Hz), 1.51 (9H, s), 1.42 (9H, s), 1.31 (9H, s).

Example 5(101)
N-benzyloxycarbonyl-3-amino-4-oxo-5-(5-(imidazol-1-ylmethyl)tetrazol-2-yl)pentanoic acid•t-butylester

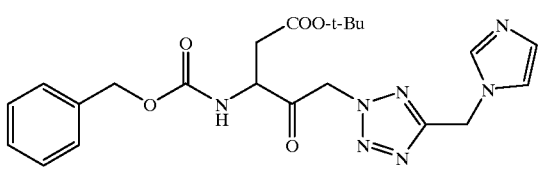

TLC: Rf 0.50 (chloroform:methanol=10:1); NMR (CDCl$_3$): δ 7.62 (1H, s), 7.40–7.30 (5H, m), 7.07 (1H, s), 7.05 (1H, s), 5.88 (1H, m), 5.84 (1H, d, J=18 Hz), 5.66 (1H, d, J=18 Hz), 5.39 (2H, s), 5.17 (2H, s), 4.64 (1H, m), 3.03 (1H, dd, J=4.4, 17 Hz), 2.71 (1H, dd, J=4.6, 17 Hz), 1.42 (9H, s).

Example 5(102)
N-benzyloxycarbonyl-3-amino-4-oxo-5-(5-(imidazol-1-ylmethyl)tetrazol-1-yl)pentanoic acid•t-butylester

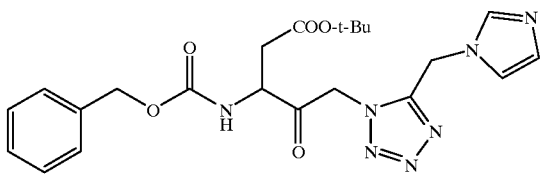

TLC: Rf 0.44 (chloroform:methanol=10:1); NMR (CDCl$_3$): δ 7.68 (1H, s), 7.40–7.30 (5H, m), 7.08 (1H, s), 7.00 (1H, s), 5.84 (1H, m), 5.60–5.26 (4H, m), 5.39 (2H, s), 5.18 (2H, s), 4.60 (1H, m), 3.10 (1H, dd, J=4.8, 18 Hz), 2.80 (1H, dd, J=5.0, 18 Hz), 1.42 (9H, s).

Example 5(103)
N-benzyloxycarbonyl-3-amino-4-oxo-5-(5-(2-methoxyphenylthio)tetrazol-2-yl)pentanoic acid•t-butylester

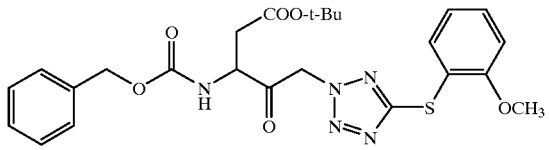

TLC: Rf 0.53 (benzene:diethylether=2:1); NMR (CDCl$_3$): δ 7.48–7.30 (7H, m), 6.98–6.90 (2H, m), 5.93 (1H, d, J=9.6 Hz), 5.78 (1H, d, J=17.8 Hz), 5.60 (1H, d, J=17.8 Hz), 5.16 (2H, s), 4.89–4.60 (1H, m), 3.81 (3H, s), 3.00 (1H, dd, J=4.4, 17.4 Hz), 2.70 (1H, dd, J=4.8, 17.4 Hz), 1.41 (9H, s).

Example 5(104)
N-benzyloxycarbonyl-3-amino-4-oxo-5-(5-(2-methoxyphenylthio)tetrazol-1-yl)pentanoic acid•t-butylester

TLC: Rf 0.38 (benzene:diethylether=2:1); NMR (CDCl$_3$): δ 7.52–7.31 (7H, m), 6.99–6.85 (2H, m), 5.96 (1H, d, J=8.8 Hz), 5.64 (1H, d, J=18.2 Hz), 5.45 (1H, d, J=18.2 Hz), 5.19 (2H, s), 4.64–4.55 (1H, m), 3.75 (3H, s), 3.01 (1H, dd, J=4.4, 17.4 Hz), 2.70 (1H, dd, J=4.8, 17.4 Hz), 1.42 (9H, s).

Example 5(105)
N-benzyloxycarbonyl-3-amino-4-oxo-5-(5-(2,6-dichloro-4-dimethylaminophenylthio)tetrazol-2-yl)pentanoic acid•t-butylester

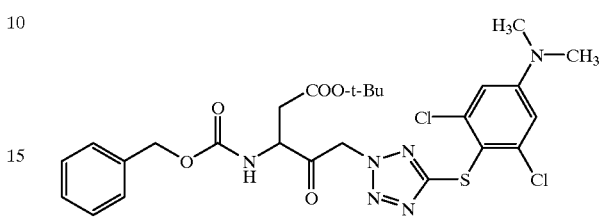

TLC: Rf 0.59 (hexane:ethyl acetate=1:1); NMR (CDCl$_3$): δ 7.40–7.30 (5H, m), 6.72 (2H, s), 5.95 (1H, d, J=8.8 Hz), 5.72 (1H, d, J=18 Hz), 5.57 (1H, d, J=18 Hz), 5.16 (2H, s), 4.63 (1H, m), 3.02–2.93 (7H, m), 2.69 (1H, dd, J=4.6, 17 Hz), 1.41 (9H, s).

Example 5(106)
N-benzyloxycarbonyl-3-amino-4-oxo-5-(5-(2,6-dichloro-4-dimethylaminophenylthio)tetrazol-1-yl)pentanoic acid•t-butylester

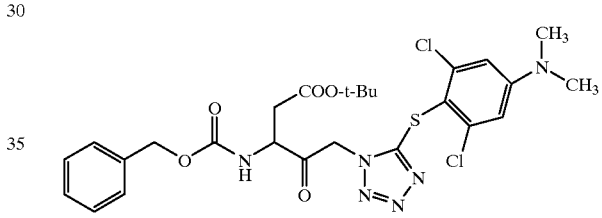

TLC: Rf 0.50 (hexane:ethyl acetate=1:1); NMR (CDCl$_3$): δ 7.42–7.30 (5H, m), 6.69 (2H, s), 5.99 (1H, d, J=8.8 Hz), 5.62 (1H, d, J=18 Hz), 5.47 (1H, d, J=18 Hz), 5.20 (2H, s), 4.65 (1H, m), 3.12–2.98 (7H, m), 2.72 (1H, dd, J=4.8, 17 Hz), 1.43 (9H, s).

Example 5(107)
N-benzyloxycarbonyl-3-amino-4-oxo-5-(5-(thiophen-2-yl)tetrazol-2-yl)pentanoic acid•t-butylester

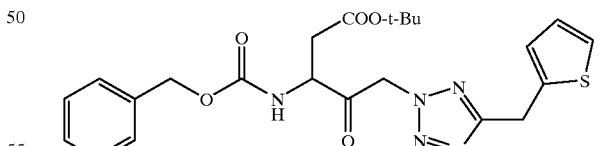

TLC: Rf 0.27 (benzene:diethylether=8:1); NMR (CDCl$_3$): δ 7.40–7.32 (5H, m), 7.19–7.16 (1H, m), 6.94–6.90 (2H, m), 5.97 (1H, d, J=8.4 Hz), 5.80 and 5.63 (each 1H, each d, J=17.6 Hz), 5.17 (2H, s), 4.71–4.62 (1H, m), 4.46 (2H, s), 3.00 (1H, dd, J=4.6 and 17.4 Hz), 2.71 (1H, dd, J=4.8 and 17.4 Hz), 1.42 (9H, s).

Example 5(108)
N-benzyloxycarbonyl-3-amino-4-oxo-5-(5-(thiophen-2-yl)tetrazol-1-yl)pentanoic acid•t-butylester

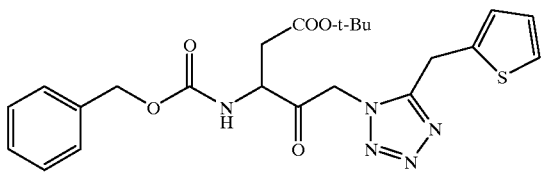

TLC: Rf 0.12 (benzene:diethylether=8:1); NMR (CDCl₃): δ 7.37 (5H, m), 7.22–7.19 (1H, m), 6.95–6.92 (2H, m), 5.84 (1H, d, J=8.4 Hz), 5.45 and 5.34 (each 1H, each d, J=18.6 Hz), 5.16 (2H, s), 4.62–4.53 (1H, m), 4.43 and 4.27 (each 1H, each d, J=16.6 Hz), 3.06 (1H, dd, J=4.4 and 17.6 Hz), 2.74 (1H, dd, J=4.8 and 17.6 Hz), 1.44 (9H, s).

Example 5(109)
N-benzyloxycarbonyl-3-amino-4-oxo-5-(5-(thiophen-3-yl)tetrazol-2-yl)pentanoic acid•t-butylester

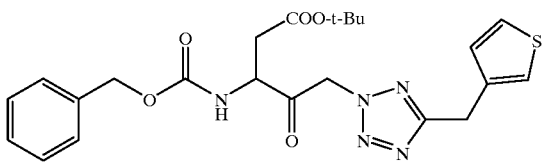

TLC: Rf 0.23 (benzene:diethylether=8:1); NMR (CDCl₃): δ 7.40–7.31 (5H, m), 7.28–7.24 (1H, m), 7.12–7.10 (1H, m), 7.03 (1H, dd, J=1.2 and 5.0 Hz), 5.97 (1H, d, J=9.2 Hz), 5.80 and 5.62 (each 1H, each d, J=17.6 Hz), 5.17 (2H, s), 4.71–4.62 (1H, m), 4.28 (2H, s), 3.00 (1H, dd, J=4.4 and 17.6 Hz), 2.71 (1H, dd, J=5.0 and 17.6 Hz), 1.42 (9H, s).

Example 5(110)
N-benzyloxycarbonyl-3-amino-4-oxo-5-(5-(thiophen-3-yl)tetrazol-1-yl)pentanoic acid•t-butylester

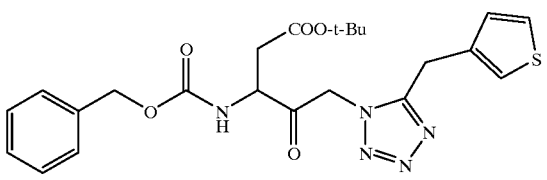

TLC: Rf 0.09 (benzene:diethylether=8:1); NMR (CDCl₃): δ 7.40–7.33 (5H, m), 7.31–7.27 (1H, m), 7.18 (1H, brs), 6.94–6.91 (1H, m), 5.82 (1H, d, J=8.8 Hz), 5.35 (2H, s), 5.16 (2H, s), 4.59–4.50 (1H, m), 4.24 and 4.07 (each 1H, each d, J=16.2 Hz), 3.05 (1H, dd, J=4.4 and 17.4 Hz), 2.73 (1H, dd, J=5.0 and 17.4 Hz), 1.44 (9H, s).

Example 5(111)
N-benzyloxycarbonyl-3-amino-4-oxo-5-(5-(3-imidazol-1-ylpropyl)tetrazol-2-yl)pentanoic acid•t-butylester

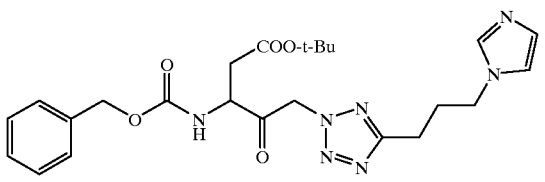

TLC: Rf 0.44 (chloroform:methanol=9:1); NMR (CDCl₃): δ 7.49 (1H, s), 7.40–7.30 (5H, m), 7.05 (1H, s), 6.94 (1H, s), 6.10 (1H, d, J=8.8 Hz), 5.81 (1H, d, J=18 Hz), 5.64 (1H, d, J=18 Hz), 5.18 (2H, s), 4.67 (1H, m), 4.03 (2H, t, J=7.0 Hz), 3.02 (1H, dd, J=4.6, 17 Hz), 2.90 (2H, t, J=7.0 Hz), 2.72 (1H, dd, J=5.0, 17 Hz), 2.27 (2H, m), 1.42 (9H, s).

Example 5(112)
N-benzyloxycarbonyl-3-amino-4-oxo-5-(5-(3-imidazol-1-ylpropyl)tetrazol-1-yl)pentanoic acid•t-butylester

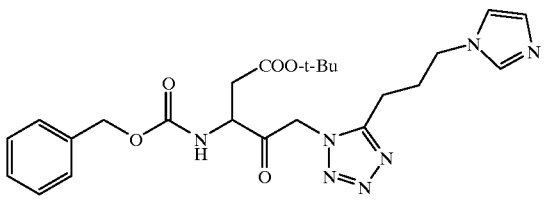

TLC: Rf 0.36 (chloroform:methanol=9:1); NMR (CDCl₃): δ 7.45 (1H, s), 7.40–7.30 (5H, m), 7.04 (1H, s), 6.92 (1H, s), 6.10 (1H, d, J=8.8 Hz), 5.46 (2H, s), 5.18 (2H, s), 4.60 (1H, m), 4.09 (2H, t, J=6.8 Hz), 3.03 (1H, dd, J=4.4, 18 Hz), 2.78 (1H, dd, J=5.4, 18 Hz), 2.57 (2H, t, J=6.8 Hz), 2.27 (2H, m), 1.41 (9H, s).

Example 5(113)
N-benzyloxycarbonyl-3-amino-4-oxo-5-(5-(2,3-dichlorophenylthio)tetrazol-2-yl)pentanoic acid•t-butylester

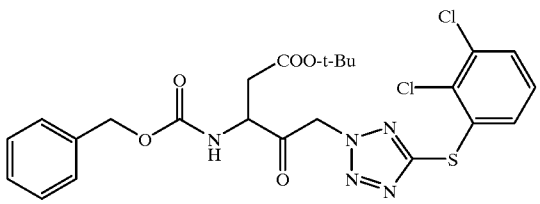

TLC: Rf 0.60 (hexane:ethyl acetate=2:1); NMR (CDCl₃): δ 7.44–7.11 (8H, m), 5.94 (1H, d, J=10.8 Hz), 5.86 (1H, d, J=17.8 Hz), 5.68 (1H, d, J=17.8 Hz), 4.73–4.62 (1H, m), 3.04 (1H, dd, J=4.0, 17.2 Hz), 2.73 (1H, dd, J=4.8, 17.2 Hz), 1.42 (9H, s).

Example 5(114)
N-benzyloxycarbonyl-3-amino-4-oxo-5-(5-(2,3-dichlorophenylthio)tetrazol-1-yl)pentanoic acid•t-butylester

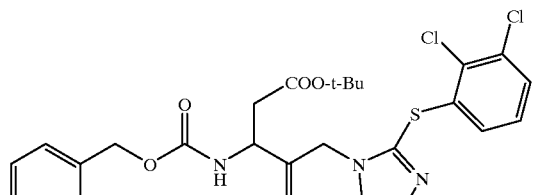

TLC: Rf 0.49 (hexane:ethyl acetate=2:1); NMR (CDCl₃): δ 7.48–7.15 (8H, m), 5.94 (1H, d, J=10.6 Hz), 5.69 (1H, d, J=18.4 Hz), 5.52 (1H, d, J=18.4 Hz), 4.73–4.63 (1H, m), 3.06 (1H, dd, J=4.4, 17.6 Hz), 2.73 (1H, dd, J=4.8, 17.6 Hz), 1.41 (9H, s).

Example 5(115)
N-benzyloxycarbonyl-3-amino-4-oxo-5-(5-(2,6-dimethylphenylthio)tetrazol-2-yl)pentanoic acid•t- butylester

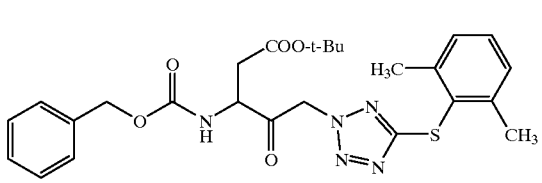

TLC: Rf 0.56 (hexane:ethyl acetate=3:2); NMR (CDCl₃): δ 7.37 (5H, s), 7.25–7.10 (3H, m), 5.91 (1H, d, J=9.1 Hz), 5.73 (1H, d, J=17.8 Hz), 5.54 (1H, d, J=17.8 Hz), 5.16 (2H, s), 4.70–4.55 (1H, m), 2.99 (1H, dd, J=17.5, 4.5 Hz), 2.67 (1H, dd, J=17.5, 4.8 Hz), 2.48 (6H, s), 1.41 (9H, s).

Example 5(116)

N-benzyloxycarbonyl-3-amino-4-oxo-5-(5-(2,6-dimethylphenylthio)tetrazol-1-yl)pentanoic acid•t-butylester

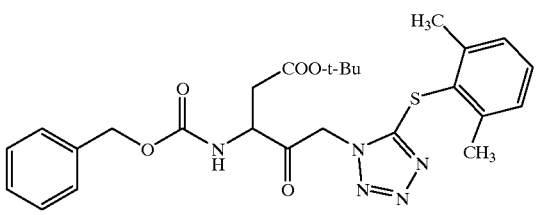

TLC: Rf 0.44 (hexane:ethyl acetate=3:2); NMR (CDCl₃): δ 7.45–7.35 (5H, m), 7.31–7.14 (3H, m), 5.96 (1H, d, J=9.1 Hz), 5.56 (1H, d, J=18.5 Hz), 5.38 (1H, d, J=18.5 Hz), 5.21 (2H, s), 4.70–4.54 (1H, m), 3.06 (1H, dd, J=17.5, 4.4 Hz), 2.71 (1H, dd, J=17.5, 4.9 Hz), 2.42 (6H, s), 1.42 (9H, s).

Example 5(117)

N-benzyloxycarbonyl-3-amino-4-oxo-5-(5-(2-chloro-4-t-butylphenylthio)tetrazol-2-yl)pentanoic acid•t-butylester

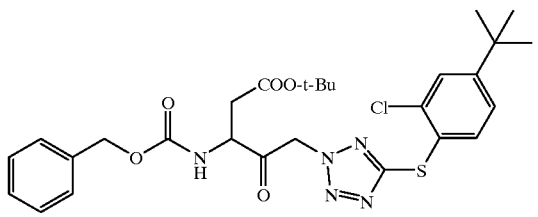

TLC: Rf 0.65 (hexane:ethyl acetate=3:2); NMR (CDCl₃): δ 87.46 (1H, d, J=2.1 Hz), 7.43–7.30 (6H, m), 7.25 (1H, dd, J=8.3, 2.1 Hz), 5.94 (1H, d, J=9.3 Hz), 5.82 (1H, d, J=17.8 Hz), 5.64 (1H, d, J=17.8 Hz), 5.17 (2H, s), 4.73–4.58 (1H, m), 3.02 (1H, dd, J=17.4, 4.4 Hz), 2.70 (1H, dd, J=17.4, 4.9 Hz), 1.42 (9H, s), 1.30 (9H, s).

Example 5(118)

N-benzyloxycarbonyl-3-amino-4-oxo-5-(5-(2-chloro-4-t-butylphenylthio)tetrazol-1-yl)pentanoic acid•t-butylester

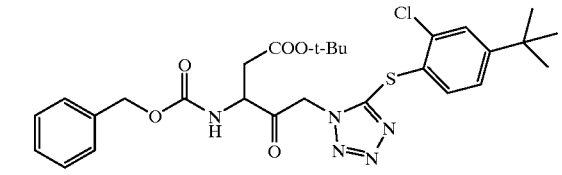

TLC: Rf 0.55 (hexane:ethyl acetate=3:2); NMR (CDCl₃): δ 7.53 (1H, d, J=8.4 Hz), 7.45 (1H, d, J=2.2 Hz), 7.43–7.33 (5H, m), 7.29 (1H, dd, J=8.4, 2.2 Hz), 5.96 (1H, d, J=9.2 Hz), 5.67 (1H, d, J=18.4 Hz), 5.49 (1H, d, J=18.4 Hz), 5.20 (2H, s), 4.72–4.60 (1H, m), 3.05 (1H, dd, J=17.5, 4.4 Hz), 2.71 (1H, dd, J=17.5, 4.9 Hz), 1.43 (9H, s), 1.30 (9H, s).

Example 5(119)

N-benzyloxycarbonyl-3-amino-4-oxo-5-(5-(2,2,6,6-tetramethylpiperidin-2-ylmethyl)tetrazol-2-yl)pentanoic acid•t-butylester

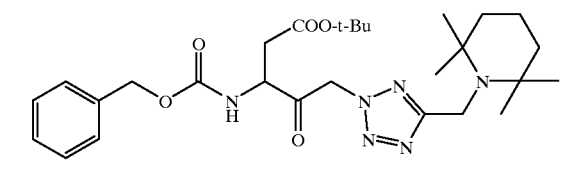

TLC: Rf 0.52 (hexane:ethyl acetate=2:1); NMR (CDCl₃): δ 7.40–7.30 (5H, m), 5.98 (1H, d, J=8.6 Hz), 5.79 (1H, d, J=18 Hz), 5.61 (1H, d, J=18 Hz), 5.17 (2H, s), 4.66 (1H, m), 4.00 (2H, s), 2.99 (1H, dd, J=4.2, 17 Hz), 2.70 (1H, dd, J=4.6, 17 Hz), 1.60–1.44 (6H, m), 1.42 (9H, s), 1.07 (12H, s).

Example 5(120)

N-benzyloxycarbonyl-3-amino-4-oxo-5-(5-(2,2,6,6-tetramethylpiperidin-1-ylmethyl)tetrazol-1-yl)pentanoic acid•t-butylester

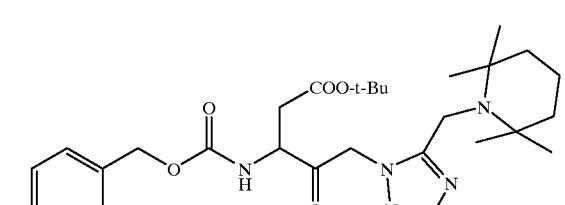

TLC: Rf 0.31 (hexane:ethyl acetate=2:1); NMR (CDCl₃): δ 7.40–7.30 (5H, m), 6.04 (1H, d, J=9.0 Hz), 5.95 (1H, d, J=18 Hz), 5.76 (1H, d, J=18 Hz), 5.20 (2H, s), 4.68 (1H, m), 4.01 (2H, s), 3.05 (1H, dd, J=4.4, 17 Hz), 2.73 (1H, dd, J=4.8, 17 Hz), 1.62–1.46 (6H, m), 1.43 (9H, s), 0.99 and 0.94 (total 12H, each s).

Example 5(121)

N-benzyloxycarbonyl-3-amino-4-oxo-5-(5-(N-phenyl-N-methylamino)tetrazol-2-yl)pentanoic acid•t-butylester

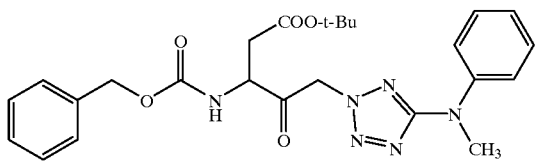

TLC: Rf 0.17 (benzene:diethylether=8:1); NMR (CDCl$_3$): δ 7.47–7.31 (9H, m), 7.12–7.05 (1H, m), 5.96 (1H, d-like), 5.66 and 5.49 (each 1H, each d, J=17.6 Hz), 5.16 (2H, s), 4.70–4.60 (1H, m), 3.56 (3H, s), 3.00 (1H, dd, J=4.4 and 17.4 Hz), 2.70 (1H, dd, J=5.0 and 17.4 Hz), 1.42 (9H, s).

Example 5(122)

N-benzyloxycarbonyl-3-amino-4-oxo-5-(5-(N-phenyl-N-methylamino)tetrazol-1-yl)pentanoic acid•t-butylester

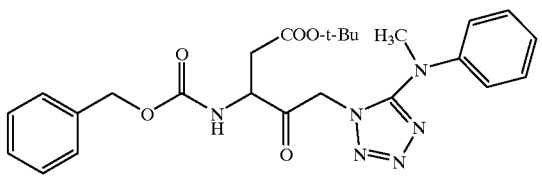

TLC: Rf 0.04 (benzene:diethylether=8:1); NMR (CDCl$_3$): δ 7.41–7.19 (8H, m), 6.98–6.94 (2H, m), 5.60 (1H, d-like), 5.08 (2H, s), 4.89 and 4.69 (each 1H, each d, J=18.6 Hz), 4.11–3.99 (1H, m), 3.49 (3H, s), 2.74 (1H, dd, J=4.6 and 17.4 Hz), 2.49 (1H, dd, J=4.8 and 17.4 Hz), 1.40 (9H, s).

Example 5(123)

N-benzyloxycarbonyl-3-amino-4-oxo-5-(5-(2,6-diisopropylphenylthio)tetrazol-2-yl)pentanoic acid•t-butylester

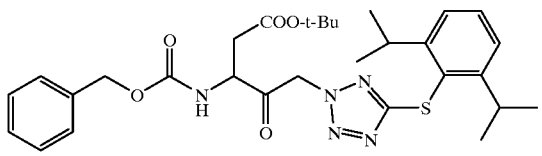

TLC: Rf 0.41 (benzene:diethylether=8:1); NMR (CDCl$_3$): δ 7.46–7.31 (6H, m), 7.25–7.21 (2H, m), 5.91 (1H, d, J=9.4 Hz), 5.71 and 5.52 (each 1H, each d, J=18.2 Hz), 5.15 (2H, s), 4.65–4.55 (1H, m), 3.84–3.70 (2H, m), 2.97 (1H, dd, J=4.4 and 17.4 Hz), 2.66 (1H, dd, J=5.0 and 17.4 Hz), 1.39 (9H, s), 1.17 (12H, d, J=6.8 Hz).

Example 5(124)

N-benzyloxycarbonyl-3-amino-4-oxo-5-(5-(2,6-diisopropylphenylthio)tetrazol-1-yl)pentanoic acid•t-butylester

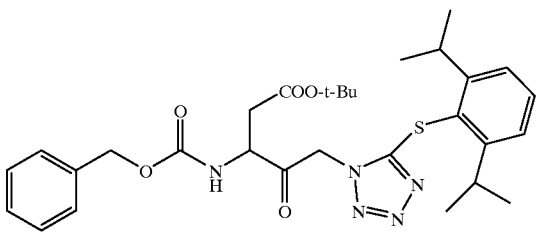

TLC: Rf 0.24 (benzene:diethylether=8:1); NMR (CDCl$_3$): δ 7.50–7.35 (6H, m), 7.28–7.25 (2H, m), 5.98 (1H, d-like), 5.60 and 5.44 (each 1H, each d, J=18.2 Hz), 5.21 (2H, s), 4.75–4.64 (1H, m), 3.60–3.47 (2H, m), 3.11 (1H, dd, J=4.4 and 17.6 Hz), 2.75 (1H, dd, J=5.0 and 17.6 Hz), 1.44 (9H, s), 1.19 and 1.16 (each 6H, each d, J=6.8 Hz).

Example 5(125)

N-benzyloxycarbonyl-3-amino-4-oxo-5-(5-(2-methyl-4-t-butylphenylthio)tetrazol-2-yl)pentanoic acid•t-butylester

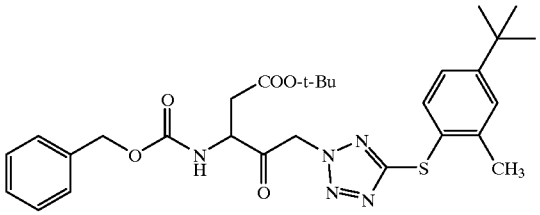

TLC: Rf 0.52 (hexane:ethyl acetate=7:3); NMR (CDCl$_3$): δ 7.50 (1H, d, J=8.2 Hz), 7.43–7.3,2 (5H, m), 7.29 (1H, d, J=2.2 Hz), 7.21 (1H, dd, J=8.2, 2.2 Hz), 5.94 (1H, d, J=9.0 Hz), 5.77 (1H, d, J=17.8 Hz), 5.58 (1H, d, J=17.8 Hz), 5.16 (2H, s), 4.72–4.56 (1H, m), 3.00 (1H, dd, J=17.3, 4.4 Hz), 2.69 (1H, dd, J=17.3, 4.8 Hz), 2.43 (3H, s), 1.41 (9H, s), 1.30 (9H, s).

Example 5(126)

N-benzyloxycarbonyl-3-amino-4-oxo-5-(5-(2-methyl-4-t-butylphenylthio)tetrazol-1-yl)pentanoic acid•t-butylester

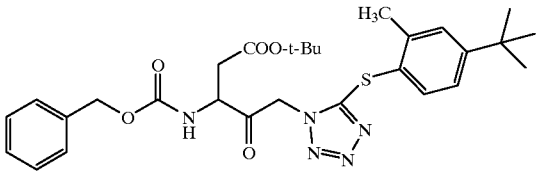

TLC: Rf 0.42 (hexane:ethyl acetate=7:3); NMR (CDCl$_3$): δ 7.55–7.15 (8H, m), 5.94 (1H, d, J=9.0 Hz), 5.57 (1H, d, J=18.6 Hz), 5.40 (1H, d, J=18.6 Hz), 5.20 (2H, s), 4.68–4.52 (1H, m), 3.03 (1H, dd, J=17.6, 4.4 Hz), 2.69 (1H, dd, J=17.6, 4.8 Hz), 2.41 (3H, s), 1.42 (9H, s), 1.30 (9H, s).

Example 5(127)

N-benzyloxycarbonyl-3-amino-4-oxo-5-(5-(2,6-dimethyl-4-t-butylphenylthio)tetrazol-2-yl)pentanoic acid•t-butylester

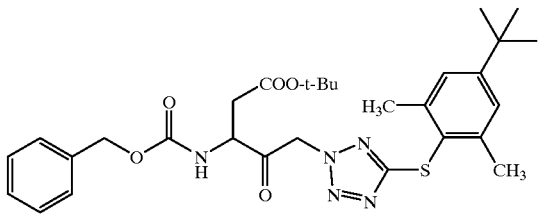

TLC: Rf 0.63 (hexane:ethyl acetate=7:3); NMR (CDCl₃): δ 7.37 (5H, s), 7.16 (2H, s), 5.93 (1H, d, J=9.1 Hz), 5.73 (1H, d, J=17.7 Hz), 5.55 (1H, d, J=17.7 Hz), 5.15 (2H, s), 4.70–4.56 (1H, m), 2.99 (1H, dd, J=17.3, 4.4 Hz), 2.68 (1H, dd, J=17.3, 4.8 Hz), 2.48 (6H, s), 1.41 (9H, s), 1.30 (9H, s).

Example 5(128)

N-benzyloxycarbonyl-3-amino-4-oxo-5-(5-(2,6-dimethyl-4-t-butylphenylthio)tetrazol-1-yl)pentanoic acid•t-butylester

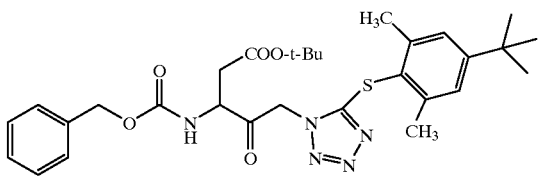

TLC: Rf 0.50 (hexane:ethyl acetate=7:3); NMR (CDCl₃): δ 7.45–7.32 (5H, m), 7.18 (2H, s), 5.97 (1H, d, J=9.2 Hz), 5.57 (1H, d, J=18.5 Hz), 5.39 (1H, d, J=18.5 Hz), 5.20 (2H, s), 4.68–4.54 (1H, m), 3.06 (1H, dd, J=17.5, 4.3 Hz), 2.71 (1H, dd, J=17.5, 4.9 Hz), 2.41 (3H, s), 1.43 (9H, s), 1.30 (9H, s).

Example 5(129)

N-benzyloxycarbonyl-3-amino-4-oxo-5-(5-(2,6-dimethyl-4-dimethylaminophenylthio)tetrazol-2-yl)pentanoic acid•t-butylester

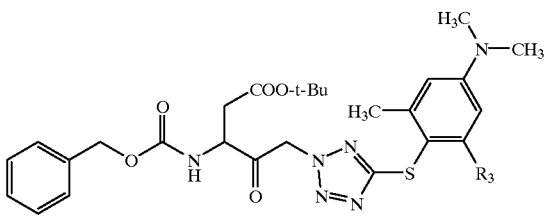

TLC: Rf 0.56 (hexane:ethyl acetate=3:2); NMR (CDCl₃): δ 7.40–7.30 (5H, m), 6.49 (2H, s), 5.93 (1H, d, J=9.0 Hz), 5.71 (1H, d, J=18 Hz), 5.53 (1H, d, J=18 Hz), 5.15 (2H, s), 4.62 (1H, m), 3.02–2.92 (7H, m), 2.67 (1H, dd, J=5.0, 17 Hz), 2.44 (6H, s), 1.40 (9H, s).

Example 5(130)

N-benzyloxycarbonyl-3-amino-4-oxo-5-(5-(2,6-dimethyl-4-dimethylaminophenylthio)tetrazol-1-yl)pentanoic acid•t-butylester

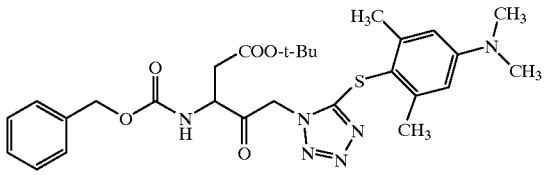

TLC: Rf 0.43 (hexane:ethyl acetate=3:2); NMR (CDCl₃): δ 7.42–7.32 (5H, m), 6.48 (2H, s), 5.96 (1H, d, J=8.8 Hz), 5.51 (1H, d, J=18 Hz), 5.33 (1H, d, J=18 Hz), 5.20 (2H, s), 4.61 (1H, m), 3.07–2.96 (7H, m), 2.70 (1H, dd, J=4.8, 18 Hz), 2.37 (6H, s), 1.43 (9H, s).

Example 5(131)

N-benzyloxycarbonyl-3-amino-4-oxo-5-(5-(benzoimizazol-2-ylmethyl)tetrazol-2-yl)pentanoic acid•t-butylester

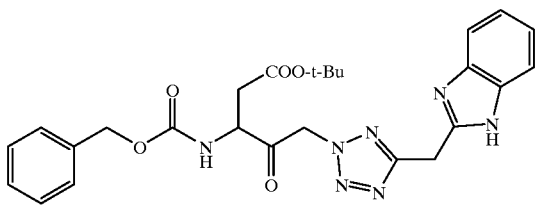

TLC: Rf 0.16 (hexane:ethyl acetate=1:1); NMR (CDCl₃): δ 11.70–10.25 (1H, br), 7.73–7.11 (9H, m), 6.36–6.15 (1H, m), 5.90 (1H, d, J=18.6 Hz), 5.67 (1H, d, J=18.6 Hz), 5.18 (2H, s), 4.82–4.58 (1H, m), 4.54 (2H, s), 2.96 (1H, dd, J=17.2 and 5.0 Hz), 2.72 (1H, dd, J=17.2 and 5.0 Hz), 1.34 (9H, s).

Example 5(132)

N-benzyloxycarbonyl-3-amino-4-oxo-5-(5-(benzoimizazol-2-ylmethyl)tetrazol-1-yl)pentanoic acid•t-butylester

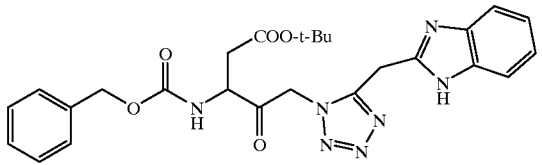

TLC: Rf 0.11 (hexane:ethyl acetate=1:1); NMR (CDCl₃): δ 10.80–9.90 (1H, br), 7.94–7.08 (9H, m), 6.05 (1H, d, J=9.8 Hz), 5.73 (2H, brs), 5.15 (2H, s), 4.80–4.52 (1H, m), 4.66 (2H, s), 3.03 (1H, dd, J=17.8 and 5.0 Hz), 2.70 (1H, dd, J=17.8 and 5.0 Hz), 1.42 (9H, s).

Example 5(133)

N-benzyloxycarbonyl-3-amino-4-oxo-5-(5-(4-isopropylphenylthio)tetrazol-2-yl)pentanoic acid•t-butylester

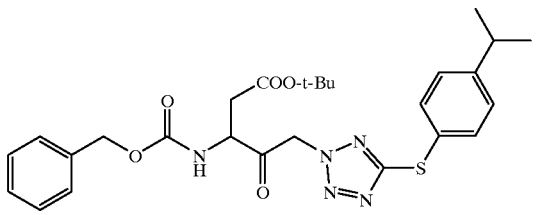

TLC: Rf 0.45 (hexane:ethyl acetate=3:1); NMR (CDCl$_3$): δ 7.50 (2H, d, J=10.6 Hz), 7.40–7.30 (5H, m), 7.23 (2H, d, J=10.6 Hz), 5.94 (1H, d, J=9.0 Hz), 5.79 (1H, d, J=17.6 Hz), 5.61 (1H, d, J=17.6 Hz), 5.17 (2H, s), 4.70–4.60 (1H, m), 3.06–2.83 (2H, m), 2.71 (1H, dd, J=4.8, 17.2 Hz), 1.41 (9H, s), 1.24 (6H, d, J=7.0 Hz).

Example 5(134)
N-benzyloxycarbonyl-3-amino-4-oxo-5-(5-(4-isopropylphenylthio)tetrazol- 1-yl)pentanoic acid•t-butylester

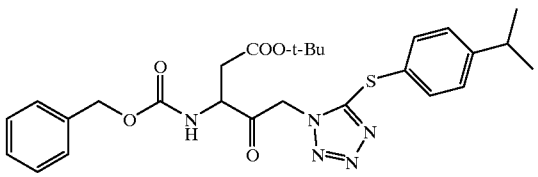

TLC: Rf 0.32 (hexane:ethyl acetate=3:1); NMR (CDCl$_3$): δ 7.49–7.34 (7H, m), 7.23 (2H, d, J=8.4 Hz), 5.96 (1H, d, J=9.0 Hz), 5.58 (1H, d, J=18.4 Hz), 5.42 (1H, d, J=18.4 Hz), 5.20 (2H, s), 4.68–4.58 (1H, m), 3.09–2.83 (2H, m), 2.69 (1H, dd, J=4.8, 17.6 Hz), 1.43 (9H, s), 1.23 (6H, d, J=6.8 Hz).

Example 5(135)
N-benzyloxycarbonyl-3-amino-4-oxo-5-(5-(benzothiazol-2-ylmethyl)tetrazol-2-yl)pentanoic acid•t-butylester

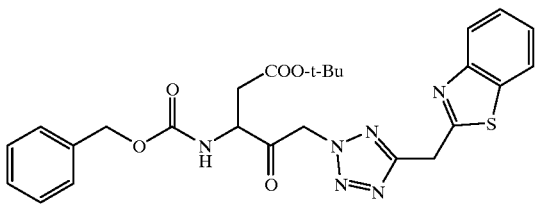

TLC: Rf 0.60 (hexane:ethyl acetate=1:1); NMR (CDCl$_3$): δ 8.09–7.94 (1H, m), 7.92–7.74 (1H, m), 7.53–7.28 (7H, m), 5.98 (1H, d, J=9.6 Hz), 5.85 (1H, d, J=17.8 Hz), 5.68 (1H, d, J=17.8 Hz), 5.17 (2H, s), 4.80 (2H, s), 4.74–4.57 (1H, m), 3.01 (1H, dd, J=17.6 Hz and 4.6 Hz), 2.72 (1H, dd, J=17.6 and 4.8 Hz), 1.41 (9H, s).

Example 5(136)
N-benzyloxycarbonyl-3-amino-4-oxo-5-(5-(benzothiazol-2-ylmethyl)tetrazol-1-yl)pentanoic acid•t-butylester

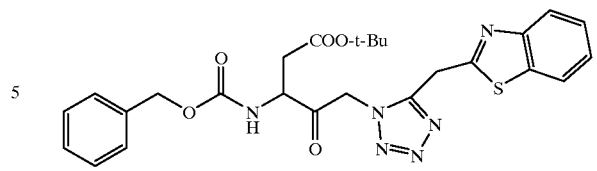

TLC: Rf 0.54 (hexane:ethyl acetate=1:1); NMR (CDCl$_3$): δ 8.02–7.76 (2H, m), 7.54–7.22 (7H, m), 6.04–5.08 (1H, m), 5.96 (1H, d, J=18.6 Hz), 5.73 (1H, d, J=18.6 Hz), 5.12 (2H, s), 4.80–4.51 (3H, m), 3.01 (1H, dd, J=17.6 Hz and 5.0 Hz), 2.74 (1H, dd, J=17.6 and 4.8 Hz), 1.38 (9H, s).

Example 5(137)
N-benzyloxycarbonyl-3-amino-4-oxo-5-(5-(thiazol-2-ylthio)tetrazol-2-yl)pentanoic acid•t-butylester

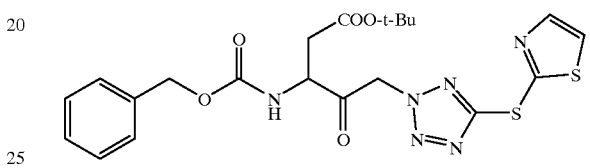

TLC: Rf 0.70 (hexane:ethyl acetate=1:1); NMR (CDCl$_3$): δ 7.80 (1H, d, J=3.4 Hz), 7.42 (1H, d, J=3.4 Hz), 7.38 (5H, m), 6.00 (1H, d, J=9 Hz), 5.87 (1H, d, J=18.0 Hz), 5.70 (1H, d, J=18.0 Hz), 5.20 (2H, m), 5.67 (1H, m), 3.03 (1H, dd, J=17.4 Hz, 4.2 Hz), 2.72 (1H, dd, J=17.4 Hz, 4.8 Hz), 1.42 (9H, s).

Example 5(138)
N-benzyloxycarbonyl-3-amino-4-oxo-5-(5-(thiazol-2-ylthio)tetrazol-1-yl)pentanoic acid•t-butylester

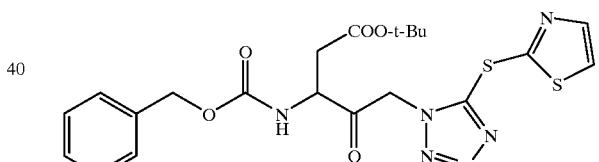

TLC: Rf 0.56 (hexane:ethyl acetate=1:1); NMR (CDCl$_3$): δ 7.75 (1H, d, J=3.4 Hz), 7.46 (1H, d, J=3.4 Hz), 7.38 (5H, m), 6.00 (1H, d, J=8.8 Hz), 5.81 (1H, d, J=18.4 Hz), 5.64 (1H, d, J=18.4 Hz,), 5.19 (2H, m), 4.72 (1H, m), 3.03 (1H, dd, J=17.6 Hz, 4.2 Hz), 2.74 (1H, dd, J=17.4 Hz, 4.8 Hz), 1.42 (9H, s).

Example 5(139)
N-benzyloxycarbonyl-3-amino-4-oxo-5-(5-(2,4,6-trichlorophenylthio)tetrazol-2-yl)pentanoic acid•t-butylester

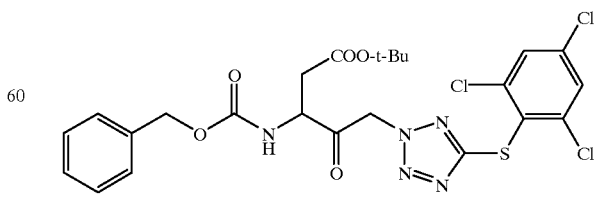

TLC: Rf 0.48 (hexane:ethyl acetate=7:3); NMR (CDCl$_3$): δ 7.47 (2H, s), 7.37 (5H, brs), 5.82 (1H, d, J=8.8 Hz), 5.76

(1H, d, J=17.6 Hz), 5.58 (1H, d, J=17.6 Hz), 5.16 (2H, s), 4.70–4.54 (1H, m), 3.06 (1H, dd, J=17.5, 4.4 Hz), 2.69 (1H, dd, J=17.5, 5.0 Hz), 1.41 (9H, s).

Example 5(140)

N-benzyloxycarbonyl-3-amino-4-oxo-5-(5-(2,4,6-trichlorophenylthio)tetrazol-1-yl)pentanoic acid•t-butylester

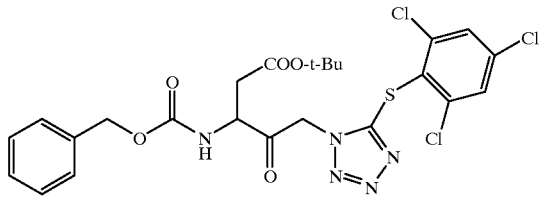

TLC: Rf 0.31 (hexane:ethyl acetate=7:3); NMR (CDCl₃): δ 7.47 (2H, s), 7.39 (5H, brs), 5.96 (1H, d, J=8.4 Hz), 5.67 (1H, d, J=18.3 Hz), 5.50 (1H, d, J=18.3 Hz), 5.21 (2H, s), 4.75–4.60 (1H, m), 3.01 (1H, dd, J=17.6, 4.3 Hz), 2.74 (1H, dd, J=17.6, 4.9 Hz), 1.43 (9H, s).

Example 5(141)

N-benzyloxycarbonyl-3-amino-4-oxo-5-(5-(2,6-dichloro-4-(1,1-dimethylpropyl)phenylthio)tetrazol-2-yl)pentanoic acid•t-butylester

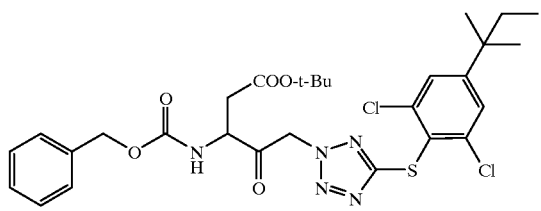

TLC: Rf 0.51 (hexane:ethyl acetate=7:3); NMR (CDCl₃): δ 7.42–7.30 (7H, m), 5.92 (1H, d, J=8.8 Hz), 5.76 (1H, d, J=17.7 Hz), 5.57 (1H, d, J=17.7 Hz), 5.16 (2H, s), 4.70–4.55 (1H, m), 2.99 (1H, dd, J=17.2, 4.6 Hz), 2.69 (1H, dd, J=17.2, 4.6 Hz), 1.63 (2H, q, J=7.5 Hz), 1.41 (9H, s), 1.27 (6H, s), 0.72 (3H, t, J=7.5 Hz).

Example 5(142)

N-benzyloxycarbonyl-3-amino-4-oxo-5-(5-(2,6-dichloro-4-(1,1-dimethylpropyl)phenylthio)tetrazol-1-yl)pentanoic acid•t-butylester

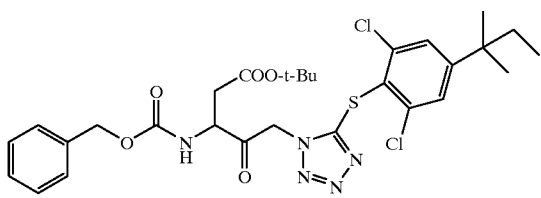

TLC: Rf 0.42 (hexane:ethyl acetate=7:3); NMR (CDCl₃): δ 7.43–7.28 (7H, m), 5.97 (1H, d, J=8.8 Hz), 5.68 (1H, d, J=18.1 Hz), 5.51 (1H, d, J=18.1 Hz), 5.21 (2H, s), 4.75–4.60 (1H, m), 3.08 (1H, dd, J=17.6, 4.5 Hz), 2.73 (1H, dd, J=17.6, 4.7 Hz), 1.62 (2H, q, J=7.5 Hz), 1.43 (9H, s), 1.26 (6H, s), 0.72 (3H, t, J=7.5 Hz).

Example 5(143)

N-benzyloxycarbonyl-3-amino-4-oxo-5-(5-(1,1-diphenylmethyl)tetrazol-2-yl)pentanoic acid•t-butylester

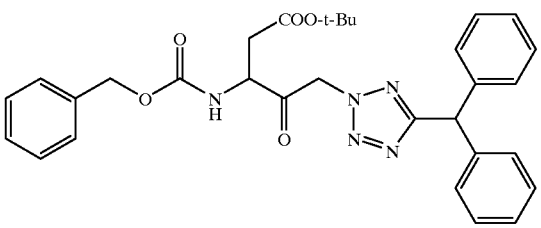

TLC: Rf 0.31 (hexane:ethyl acetate=3:1); NMR (CDCl₃): δ 7.47–7.15 (15H, m), 5.95 (1H, d, J=8.6 Hz), 5.83 (1H, s), 5.82 (1H, d, J=17.4 Hz), 5.46 (1H, d, J=17.4 Hz), 5.16 (2H, s), 4.76–4.56 (1H, m), 3.01 (1H, dd, J=17.4 and 4.4 Hz), 2.70 (1H, dd, J=17.4 and 4.8 Hz), 1.41 (9H, s).

Example 5(144)

N-benzyloxycarbonyl-3-amino-4-oxo-5-(5-(1,1-diphenylmethyl)tetrazol-1-yl)pentanoic acid•t-butylester

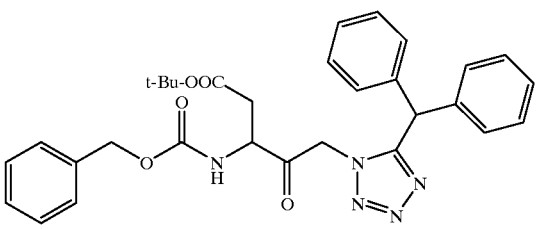

TLC: Rf 0.21 (hexane:ethyl acetate=3:1); NMR (CDCl₃): δ 7.46–7.13 (15H, m), 5.72 (1H, d, J=9.0 Hz), 5.55–5.26 (3H, m), 5.15 (2H, s), 4.68–4.45 (1H, m), 3.11 (1H, dd, J=17.2 and 3.8 Hz), 2.75 (1H, dd, J=17.2 and 4.6 Hz), 1.42 (9H, s).

Example 5(145)

N-benzyloxycarbonyl-3-amino-4-oxo-5-(5-(2-chloro-4-fluorophenylthio)tetrazol-2-yl)pentanoic acid•t-butylester

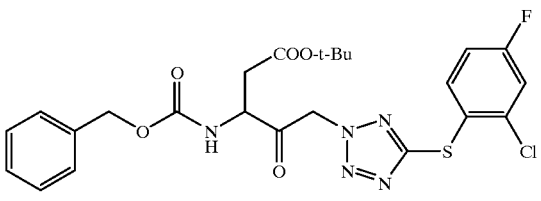

TLC: Rf 0.35 (hexane:ethyl acetate=3:1); NMR (CDCl₃): δ 7.58 (1H, dd, J=8.8 and 5.8 Hz), 7.48–7.27 (5H, m), 7.27–7.17 (1H, m), 7.07–6.92 (1H, m), 5.95 (1H, d, J=9.2 Hz), 5.81 (1H, d, J=17.6 Hz), 5.63 (1H, d, J=17.6 Hz), 5.17 (2H, s), 4.76–4.54 (1H, m), 3.03 (1H, dd, J=17.4 and 4.8 Hz), 2.70 (1H, dd, J=17.4 and 5.0 Hz), 1.41 (9H, s).

Example 5(146)

N-benzyloxycarbonyl-3-amino-4-oxo-5-(5-(2-chloro-4-fluorophenylthio)tetrazol-1-yl)pentanoic acid•t-butylester

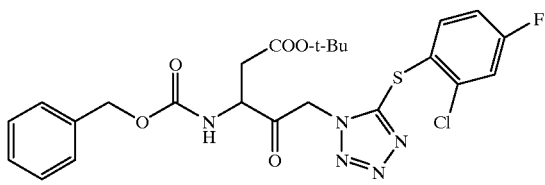

TLC: Rf 0.25 (hexane:ethyl acetate=3:1); NMR (CDCl$_3$): δ 7.68 (1H, dd, J=8.8 and 5.6 Hz), 7.52–7.27 (5H, m), 7.23 (1H, dd, J=8.4 and 2.8 Hz), 7.12–6.95 (1H, m), 5.97 (1H, d, J=9.4 Hz), 5.68 (1H, d, J=18.2 Hz), 5.50 (1H, d, J=18.2 Hz), 5.20 (2H, s), 4.79–4.52 (1H, m), 3.07 (1H, dd, J=17.6 and 4.4 Hz), 2.73 (1H, dd, J=17.6 and 4.8 Hz), 1.42 (9H, s).

Example 5(147)

N-benzyloxycarbanyl-3-amino-4-oxo-5-(5-(5-imidazol-1-ylpentyl)tetrazol-2-yl)pentanoic acid•t-butylester

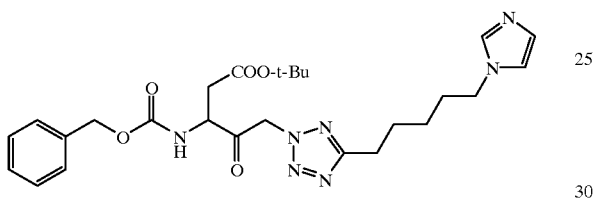

TLC: Rf 0.40 (chloroform:methanol=9:1); NMR (CDCl$_3$): δ 7.44 (1H, s), 7.48–7.25 (5H, m), 7.03 (1H, s), 6.88 (1H, s), 6.38 (1H, d, J=9.2 Hz), 5.79 (1H, d, J=17.6 Hz), 5.62 (1H, d, J=17.6 Hz), 5.18 (2H, s), 4.78–4.60 (1H, m), 3.92 (2H, t, J=7.2 Hz), 3.07–2.83 (3H, m), 2.75 (1H, dd, J=17.4 and 5.4 Hz), 1.97–1.57 (6H, m), 1.42 (9H, s).

Example 5(148)

N-benzyloxycarbonyl-3-amino-4-oxo-5-(5-(5-imidazol-1-ylpentyl)tetrazol-1-yl)pentanoic acid•t-butylester

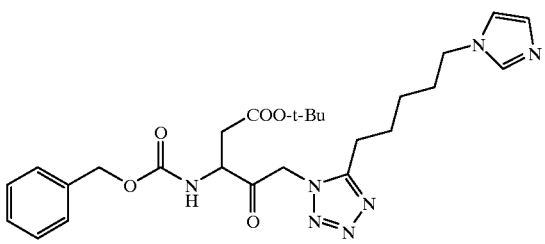

TLC: Rf 0.31 (chloroform:methanol=9:1); NMR (CDCl$_3$): δ 7.46 (1H, s), 7.45–7.20 (5H, m), 7.03 (1H, s), 6.89 (1H, s), 6.22 (1H, d, J=8.6 Hz), 5.49 (2H, brs), 5.18 (2H, s), 4.72–4.52 (1H, m), 3.93 (2H, t, J=7.2 Hz), 3.12 (1H, dd, J=17.6 and 4.8 Hz), 2.78 (1H, dd, J=17.4 and 5.2 Hz), 2.61 (2H, t, J=7.2 Hz), 1.96–1.57 (6H, m), 1.42 (9H, s).

Example 5(149)

N-benzyloxycarbonyl-3-amino-4-oxo-5-(5-(2-dimethylaminoethyl)tetrazol-2-yl)pentanoic acid•t-butylester

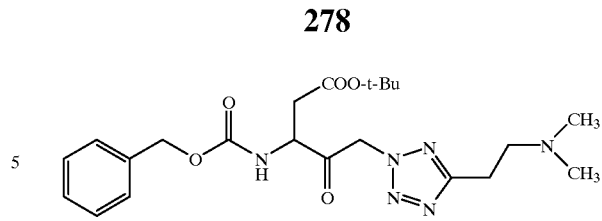

TLC: Rf 0.43 (chloroform:methanol=9:1).

Example 5(150)

N-benzyloxycarbonyl-3-amino-4-oxo-5-(5-(2-dimethylaminoethyl)tetrazol-1-yl)pentanoic acid•t-butylester

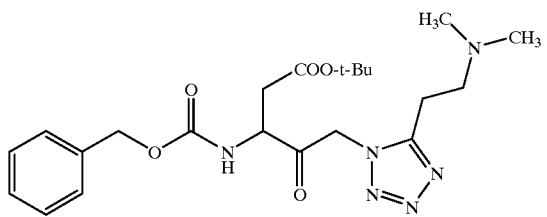

TLC: Rf 0.43 (chloroform:methanol=9:1).

Example 5(151)

N-benzyloxycarbonyl-3-amino-4-oxo-5-(5-(4-(4-fluorophenyl)thiazol-2-ylmethyl)tetrazol-2-yl)pentanoic acid•t-butylester

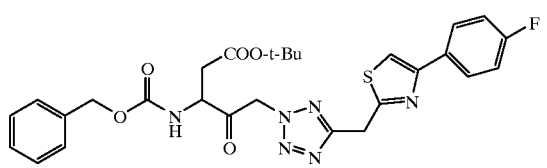

TLC: Rf 0.30 (hexane:ethyl acetate=2:1); NMR (CDCl$_3$): δ 7.92–7.76 (2H, m), 7.46–7.28 (5H, m), 7.34 (1H, s), 7.17–7.01 (2H, m), 5.95 (1H, d, J=9.2 Hz), 5.85 (1H, d, J=17.6 Hz), 5.68 (1H, d, J=17.6 Hz), 5.18 (2H, s), 4.77–4.60 (1H, m), 4.73 (2H, s), 3.02 (1H, dd, J=17.6 and 4.6 Hz), 2.72 (1H, dd, J=17.6 and 4.8 Hz), 1.42 (9H, s).

Example 5(152)

N-benzyloxycarbonyl-3-amino-4-oxo-5-(5-(4-(4-fluorophenyl)thiazol-2-ylmethyl)tetrazol-1-yl)pentanoic acid•t-butylester

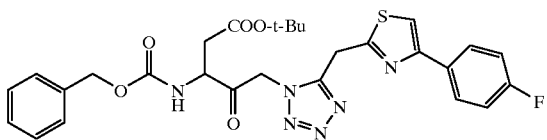

TLC: Rf 0.16 (hexane:ethyl acetate=2:1); NMR (CDCl$_3$): δ 7.89–7.68 (2H, m), 7.44–7.24 (5H, m), 7.36 (1H, s), 7.16–7.00 (2H, m), 5.85 (1H, d, J=8.6 Hz), 5.98 (1H, d, J=18.6 Hz), 5.75 (1H, d, J=18.6 Hz), 5.22–4.99 (2H, m), 4.76–4.46 (3H, m), 3.00 (1H, dd, J=17.6 and 4.6 Hz), 2.71 (1H, dd, J=17.6 and 4.8 Hz), 1.39 (9H, s).

Example 5(153)

N-benzyloxycarbonyl-3-amino-4-oxo-5-(5-(4-(4-chlorophenyl)thiazol-2-ylmethyl)tetrazol-2-yl)pentanoic acid•t-butylester

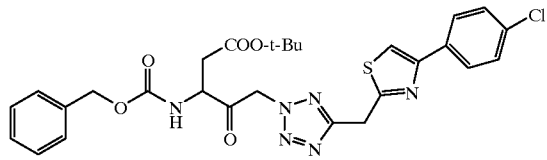

TLC: Rf 0.36 (hexane:ethyl acetate=2:1); NMR (CDCl₃): δ 7.86–7.74 (2H, m), 7.46–7.28 (8H, m), 5.96 (1H, d, J=9.2 Hz), 5.85 (1H, d, J=17.8 Hz), 5.68 (1H, d, J=17.8 Hz), 5.17 (2H, s), 4.78–4.58 (1H, m), 4.73 (2H, s), 3.02 (1H, dd, J=17.4 and 4.4 Hz), 2.72 (1H, dd, J=17.4 and 4.8 Hz), 1.42 (9H, s).

Example 5(154)

N-benzyloxycarbonyl-3-amino-4-oxo-5-(5-(4-(4-chlorophenyl)thiazol-2-ylmethyl)tetrazol-1-yl)pentanoic acid•t-butylester

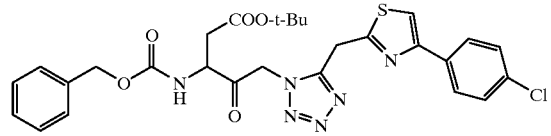

TLC: Rf 0.20 (hexane:ethyl acetate=2:1); NMR (CDCl₃): δ 7.84–7.74 (2H, m), 7.49–7.21 (8H, m), 5.98 (1H, d, J=18.6 Hz), 5.87 (1H, d, J=9.0 Hz), 5.75 (1H, d, J=18.6 Hz), 5.14 (1H, d, J=12.2 Hz), 5.06 (1H, d, J=2.2 Hz), 4.76–4.44 (3H, m), 3.01 (1H, dd, J=17.6 and 4.6 Hz), 2.72 (1H, dd, J=17.6 and 5.0 Hz), 1.39 (9H, s).

Example 5(155)

N-benzyloxycarbonyl-3-amino-4-oxo-5-(5-(4-(3-nitrophenyl)thiazol-2-ylmethyl)tetrazol-2-yl)pentanoic acid•t-butylester

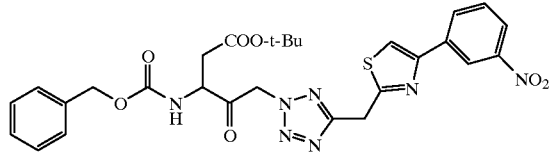

TLC: Rf 0.27 (hexane:ethyl acetate=2:1); NMR (CDCl₃): δ 8.76–8.66 (1H, m), 8.30–8.06 (2H, m), 7.66–7.50 (2H, m), 7.46–7.22 (5H, m), 5.97 (1H, d, J=8.8 Hz), 5.87 (1H, d, J=17.6 Hz), 5.70 (1H, d, J=17.6 Hz), 5.18 (2H, s), 4.80–4.56 (1H, m), 4.76 (2H, s), 3.03 (1H, dd, J=17.6 and 4.4 Hz), 2.73 (1H, dd, J=7.6 and 5.0 Hz), 1.42 (9H, s).

Example 5(156)

N-benzyloxycarbonyl-3-amino-4-oxo-5-(5-(4-(3-nitrophenyl)thiazol-2-ylmethyl)tetrazol-1-yl)pentanoic acid•t-butylester

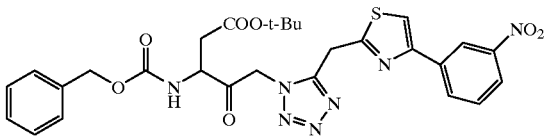

TLC: Rf 0.18 (hexane:ethyl acetate=2:1); NMR (CDCl₃): δ 8.73 (1H, brs), 8.23–8.04 (2H, m), 7.64–7.44 (2H, m), 7.44–7.14 (5H, m), 6.06 (1H, d, J=18.8 Hz), 5.94 (1H, d, J=8.0 Hz), 5.76 (1H, d, J=18.8 Hz), 5.08 (2H, brs), 4.77–4.46 (3H, m), 3.09 (1H, dd, J=17.6 and 4.4 Hz, 2.78 (1H, dd, J=17.6 and 5.0 Hz), 1.41 (9H, s).

Example 5(157)

N-benzyloxycarbonyl-3-amino-4-oxo-5-(5-(4-trifluoromethylcarbonylaminophenylthio)tetrazol-2-yl)pentanoic acid•t-butylester

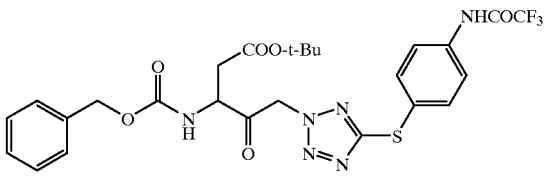

TLC: Rf 0.64 (hexane:ethyl acetate=1:1); NMR (CDCl₃): δ 8.01 (1H, brs), 7.53 (4H, brs), 7.37 (5H, brs), 5.96 (1H, d, J=9.0 Hz), 5.81 (1H, d, J=17.8 Hz), 5.63 (1H, d, J=17.8 Hz), 5.16 (2H, s), 4.76–4.52 (1H, m), 3.00 (1H, dd, J=17.6 and 4.4 Hz), 2.71 (1H, dd, J=17.6 and 5.0 Hz), 1.41 (9H, s).

Example 5(158)

N-benzyloxycarbonyl-3-amino-4-oxo-5-(5-(4-trifluoromethylcarbonylaminophenylthio)tetrazol-1-yl)pentanoic acid•t-butylester

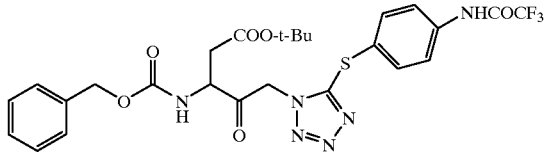

TLC: Rf 0.08 (hexane:ethyl acetate=3:1); NMR (CDCl₃): δ 8.81–8.62 (1H, br), 7.65–7.25 (9H, m), 5.94 (1H, d, J=8.8 Hz), 5.62 (1H, d, J=18.4 Hz), 5.46 (1H, d, J=18.4 Hz), 5.20 (2H, s), 4.75–4.50 (1H, m), 3.07 (1H, dd, J=18.0 and 4.4 Hz), 2.73 (1H, dd, J=18.0 and 5.2 Hz), 1.43 (9H, s).

Example 5(159)

N-benzyloxycarbonyl-3-amino-4-oxo-5-(5-(imizazol-4-ylmethyl)tetrazol-2-yl)pentanoic acid•t-butylester

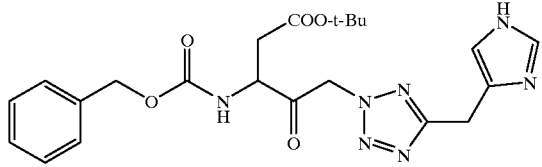

TLC: Rf 0.35 (chloroform:methanol=9:1); NMR (CDCl₃): δ 7.50 (1H, s), 7.38–7.30 (5H, m), 6.85 (1H, s), 6.32 (1H, d, J=9.0 Hz), 5.74 (1H, d, J=18 Hz), 5.63 (1H, d, J=18 Hz), 5.14 (2H, s), 4.68 (1H, m), 4.24 (2H, s), 2.93 (1H, dd, J=4.8, 17 Hz), 2.73 (1H, dd, J=5.0, 17 Hz), 1.40 (9H, s).

Example 5(160)

N-benzyloxycarbonyl-3-amino-4-oxo-5-(5-(imizazol-4-ylmethyl)tetrazol-1-yl)pentanoic acid•t-butylester

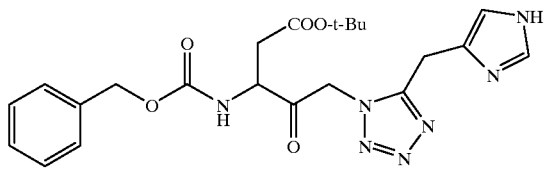

TLC: Rf 0.35 (chloroform:methanol=9:1); NMR (CDCl$_3$): δ 7.41 (1H, s), 7.38–7.30 (5H, m), 6.86 (1H, s), 6.43 (1H, d, J=8.8 Hz), 5.74 (1H, d, J=19 Hz), 5.53 (1H, d, J=19 Hz), 5.16 (2H, s), 4.69 (1H, m), 4.11 (2H, s), 2.98 (1H, dd, J=5.0, 17 Hz), 2.76 (1H, dd, J=5.4, 17 Hz), 1.40 (9H, s).

Example 6(1)

N-benzyloxycarbonyl-3-amino-4-oxo-5-(5-(2,6-dichlorophenylmethyl)tetrazol-1-yl)pentanoic acid

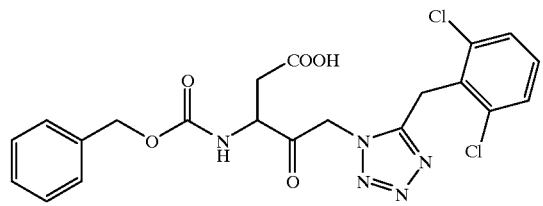

To a solution of compound prepared in example 5(1) (119 mg) in m-cresole (0.9 ml) was added trifluoroacetic acid (9 ml). The reaction mixture was stirred for 1 h at room temperature. To the reaction mixture was added toluene, and then the mixture was concentrated. The residue was purified by column chromatography on silica gel (chloroform:methanol:acetic acid=30:1:1) to give the compound of the present invention (68 mg) having the following physical data.

TLC: Rf 0.22 (chloroform:methanol:acetic acid=28:1:1); NMR (CDCl$_3$): δ 7.67 (1H, brs), 7.40–7.00 (8H, m), 6.31 (1H, brs), 5.54 (1H, brd, J=17 Hz), 5.34 (1H, d, J=17 Hz), 5.10 (2H, s), 4.52 (1H, brs), 4.24 (2H, brs) 2.94 (1H, brd, J=16 Hz), 2.65 (1H, brd, J=16 Hz).

EXAMPLES 6(2)–6(160)

By the same procedure as provided in example 6(1), and if necessary, by known methods converting the same to a corresponding salt, using the compound prepared in examples 5(2)–5(160), compounds of the present invention having the following physical data were obtained.

Example 6(2)

N-benzyloxycarbonyl-3-amino-4-oxo-5-(5-(2,6-dichlorophenylmethyl)tetrazol-2-yl)pentanoic acid

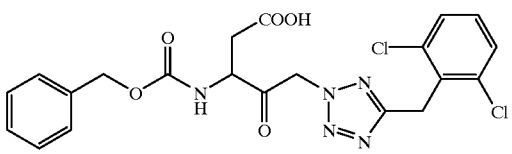

TLC: Rf 0.37 (chloroform:methanol:acetic acid=28:1:1); NMR (CDCl$_3$): δ 8.53 (1H, brs), 7.60–7.10 (8H, m), 6.20 (1H, brs), 5.90–5.30 (2H, m), 5.08 (2H, s), 4.73–4.35 (3H, m), 2.97 (1H, brd, J=17 Hz), 2.69 (1H, brd, J=17 Hz).

Example 6(3)

N-benzyloxycarbonyl-3-amino-4-oxo-5-(5-phenylmethyltetrazol-1-yl)pentanoic acid

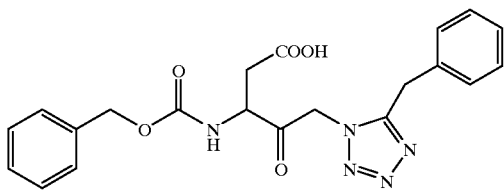

TLC: Rf 0.44 (chloroform:methanol:acetic acid=18:1:1); NMR (DMSO-d$_6$): δ 8.05–7.95 (1H, m), 7.42–7.17 (10H, m), 5.81–5.60 (2H, m), 5.09 (2H, s), 4.67–4.52 (1H, m), 4.13 (2H, s), 2.87–2.56 (2H, m).

Example 6(4)

N-benzyloxycarbonyl-3-amino-4-oxo-5-(5-phenylmethyltetrazol-2-yl)pentanoic acid

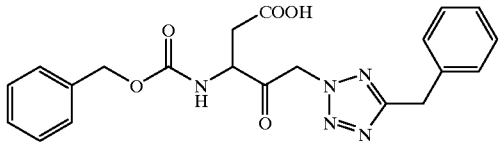

TLC: Rf 0.60 (chloroform:methanol:acetic acid=18:1:1); NMR (DMSO-d$_6$): δ 7.98–7.86 (1H, m), 7.41–7.12 (10H, m), 5.96–5.74 (2H, m), 5.07 (2H, s), 4.67–4.50 (1H, m), 4.23 (2H, s), 2.85–2.53 (2H, m).

Example 6(5)

N-benzyloxycarbonyl-3-amino-4-oxo-5-(5-(4-methylphenoxy)tetrazol-1-yl)pentanoic acid

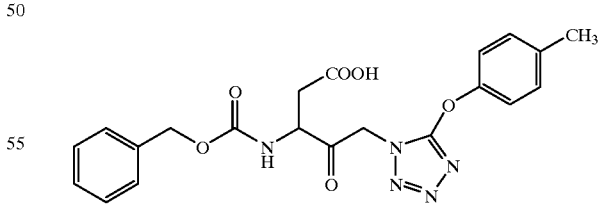

TLC: Rf 0.30 (chloroform:methanol:acetic acid=30:1:1); NMR (CDCl$_3$): δ 7.41–7.22 (5H, m), 7.20–7.03 (4H, m), 6.20 (1H, brs), 5.46 (1H, d, J=18 Hz), 5.20–4.98 (3H, m), 4.67–4.52 (1H, m), 3.06 (1H, brd, J=18 Hz), 2.74 (1H, brd, J=18 Hz), 2.31 (3H, s).

Example 6(6)

N-benzyloxycarbonyl-3-amino-4-oxo-5-(5-(4-methylphenoxy)tetrazol-2-yl)pentanoic acid

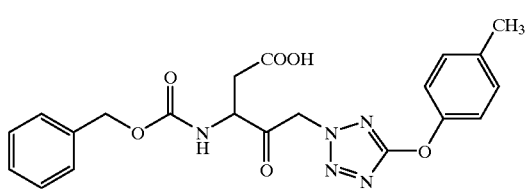

TLC: Rf 0.34 (chloroform:methanol:acetic acid=30:1:1); NMR (CDCl$_3$): δ 7.43–7.23 (5H, m), 7.22–7.00 (4H, m), 6.06 (1H, brs), 5.57 (1H, d, J=18 Hz), 5.38 (1H, d, J=18 Hz), 5.11 (2H, s), 4.72–4.55 (1H, m), 3.05 (1H, brd, J=18 Hz), 2.73 (1H, brd, J=18 Hz), 2.31 (3H, s).

Example 6(7)

N-benzyloxycarbonyl-3-amino-4-oxo-5-(5-(3-t-butylphenoxy)tetrazol-1-yl)pentanoic acid

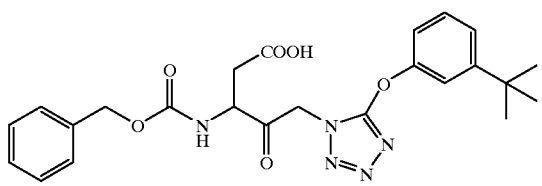

TLC: Rf 0.38 (chloroform:methanol:acetic acid=30:1:1); NMR (CDCl$_3$): δ 7.35–7.18 (8H, m), 7.15–6.98 (1H, m), 6.30–6.13 (1H, m), 5.48 (1H, d, J=18 Hz), 5.25–4.95 (3H, m), 4.71–4.55 (1H, m), 2.98 (1H, brd, J=18 Hz), 2.77 (1H, brd, J=18 Hz), 1.29 (9H, s).

Example 6(8)

N-benzyloxycarbonyl-3-amino-4-oxo-5-(5-(3-t-butylphenoxy)tetrazol-2-yl)pentanoic acid

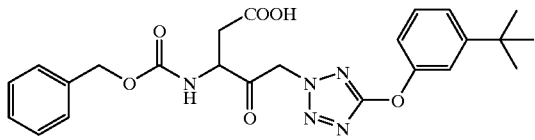

TLC: Rf 0.43 (chloroform:methanol:acetic acid=18:1:1); NMR (CDCl$_3$): δ 7.40–7.16 (8H, m), 7.03 (1H, d, J=8.0 Hz), 5.88 (1H, brs), 5.42 (2H, brs), 5.14 (2H, s), 4.73–4.58 (1H, m), 3.09 (1H, dd, J=18.0, 6.0 Hz), 2.76 (1H, dd, J=18.0, 6.0 Hz), 1.29 (9H, s).

Example 6(9)

N-benzyloxycarbonyl-3-amino-4-oxo-5-(5-styryltetrazol-1-yl)pentanoic acid

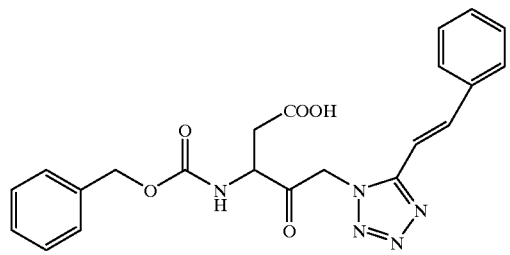

TLC: Rf 0.33 (chloroform:methanol:acetic acid=20:1:1); NMR (DMSO-d$_6$): δ 8.14 (1H, d, J=8.0 Hz), 7.85–7.68 (3H, m), 7.50–7.24 (8H, m), 7.16 (1H, d, J=16.2 Hz), 5.90 (2H, s), 5.13 (2H, s), 4.76–4.58 (1H, m), 2.84 (1H, dd, J=16.0, 6.0 Hz), 2.70 (1H, dd, J=16.0, 6.6 Hz).

Example 6(10)

N-benzyloxycarbonyl-3-amino-4-oxo-5-(5-styryltetrazol-2-yl)pentanoic acid

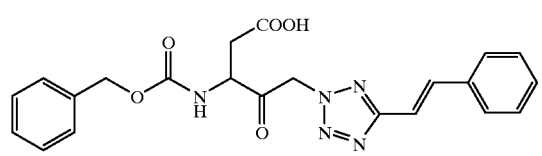

TLC: Rf 0.45 (chloroform:methanol:acetic acid=20:1:1); NMR (DMSO-d$_6$): δ 7.94–7.51 (3H, m), 7.51–7.13 (10H, m), 5.98 (2H, s), 5.09 (2H, s), 4.67–4.50 (1H, m), 2.65 (2H, d, J=5.5 Hz).

Example 6(11)

N-benzyloxycarbonyl-3-amino-4-oxo-5-(5-phenylethyltetrazol-1-yl)pentanoic acid

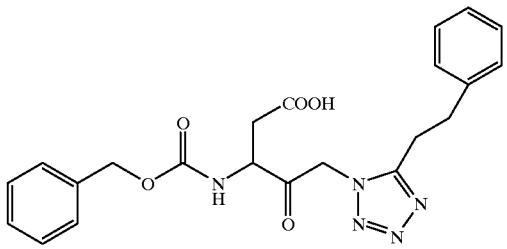

TLC: Rf 0.26 (chloroform:methanol:acetic acid=28:1:1); NMR (DMSO-d$_6$): δ 8.03 (1H, d, J=7.4 Hz), 7.40–7.10 (10H, m), 5.64 (2H, s), 5.07 (2H, s), 4.67–4.52 (1H, m), 2.99 (4H, s), 2.80 (1H, dd, J=17.0, 6.0 Hz), 2.66 (1H, dd, J=17.0, 6.8 Hz).

Example 6(12)

N-benzyloxycarbonyl-3-amino-4-oxo-5-(5-phenylethyltetrazol-1-yl)pentanoic acid

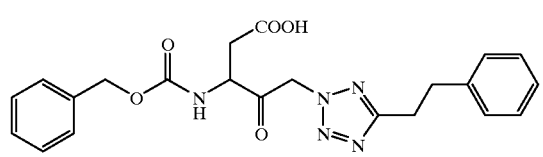

TLC: Rf 0.42 (chloroform:methanol:acetic acid=28:1:1); NMR (DMSO-d$_6$): δ 7.91 (1H, d, J=7.2 Hz), 7.45–7.08 (10H, m), 5.88 (2H, s), 5.09 (2H, s), 4.66–4.50 (1H, m), 3.20–2.96 (4H, m), 2.76 (1H, dd, J=16.8, 6.0 Hz), 2.63 (1H, dd, J=16.8, 7.2 Hz).

Example 6(13)

N-benzyloxycarbonyl-3-amino-4-oxo-5-(5-methoxytetrazol-1-yl)pentanoic acid

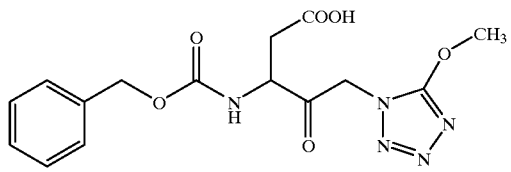

TLC: Rf 0.25 (chloroform:methanol=4:1); NMR (DMSO-$d_6$): δ 7.55 (1H, m), 7.38 (5H, m), 5.55–5.27 (2H, m), 5.08 (2H, s), 4.49 (1H, m), 4.10 (3H, s), 2.56 (2H, m).

Example 6(14)
N-benzyloxycarbonyl-3-amino-4-oxo-5-(5-methoxytetrazol-2-yl)pentanoic acid

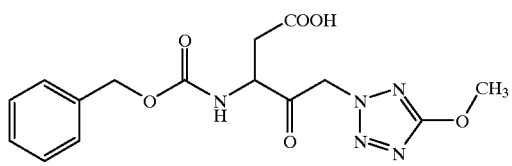

TLC: Rf 0.31 (chloroform:methanol=4:1); NMR (DMSO-$d_6$): δ 7.94 (1H, m), 7.37 (5H, m), 5.82 (2H, brs), 5.09 (2H, s), 4.60 (1H, m), 4.03 (3H, s), 2.88–2.55 (2H, m).

Example 6(15)
N-benzyloxycarbonyl-3-amino-4-oxo-5-(5-(N,N-dibenzylamino)tetrazol-2-yl)pentanoic acid•hydrochloric acid salt

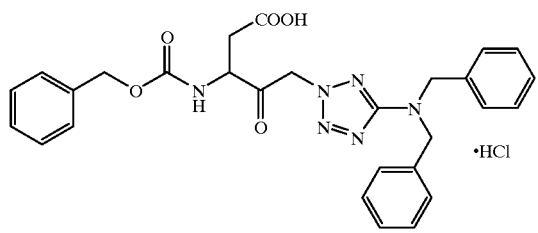

TLC: Rf 0.34 (chloroform:methanol:acetic acid=18:1:1); NMR (DMSO-$d_6$): δ 8.01–7.87 (1H, m), 7.42–7.12 (15H, m), 5.80–5.65 (2H, m), 5.70 (2H, s), 4.70–4.50 (1H, m), 4.57 (4H, s), 2.90–2.52 (2H, m).

Example 6(16)
N-benzyloxycarbonyl-3-amino-4-oxo-5-(5-trifluoromethyltetrazol-1-yl)pentanoic acid

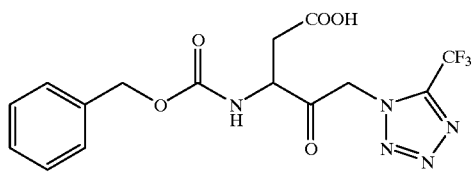

HPTLC: Rf 0.28 (chloroform:methanol=4:1); NMR (CDCl$_3$): δ 7.35 (5H, m), 5.96 (1H, m), 5.88–5.43 (2H, m), 5.17 (2H, s), 4.70 (1H, m), 4.0 (1H, brs), 3.25–3.03 and 2.96–2.73 (total 2H, m).

Example 6(17)
N-benzyloxycarbonyl-3-amino-4-oxo-5-(5-trifluoromethyltetrazol-2-yl)pentanoic acid

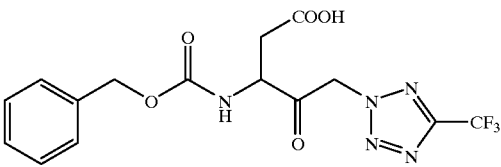

HPTLC: Rf 0.38 (chloroform:methanol=4:1); NMR (DMSO-$d_6$): δ 7.62 (1H, m), 7.37 (5H, m), 6.24 (2H, brs), 5.08 (2H, s), 4.56 (1H, m), 2.61 (2H, m).

Example 6(18)
N-benzyloxycarbonyl-3-amino-4-oxo-5-(5-(ethoxycarbonylmethyl)tetrazol-2-yl)pentanoic acid

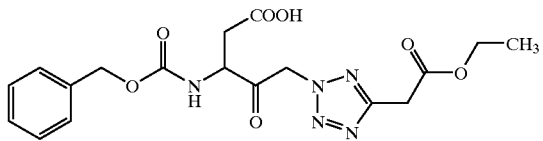

TLC: Rf 0.35 (chloroform:methanol=4:1); NMR (DMSO-$d_6$): δ 7.67 (1H, m), 7.36 (5H, m), 5.97 (2H, brs), 5.07 (2H, s), 4.52 (1H, m), 4.19–3.96 (4H, m), 2.60 (2H, d, J=5.0 Hz), 1.20 (3H, t, J=7.0 Hz).

Example 6(19)
N-benzyloxycarbonyl-3-amino-4-oxo-5-(5-ethylthiotetrazol-1-yl)pentanoic acid

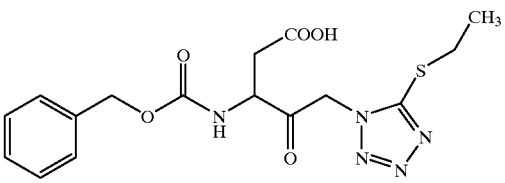

TLC: Rf 0.27 (chloroform:methanol:acetic acid=30:1:1); NMR (DMSO-$d_6$): δ 7.99 (1H, m), 7.36 (5H, m), 5.56 (2H, m), 5.10 (2H, s), 4.60 (1H, m), 3.20 (2H, q, J=7.5 Hz), 2.72 (2H, m), 1.31 (3H, t, J=7.5 Hz).

Example 6(20)
N-benzyloxycarbonyl-3-amino-4-oxo-5-(5-ethylthiotetrazol-2-yl)pentanoic acid

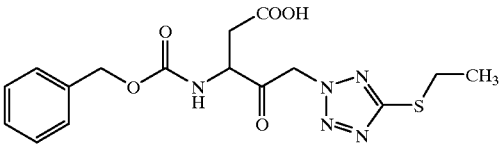

TLC: Rf 0.41 (chloroform:methanol:acetic acid=30:1:1); NMR (DMSO-$d_6$): δ 7.98 (1H, m), 7.38 (5H, m), 5.93 (2H, m), 5.09 (2H, s), 4.63 (1H, m), 3.19 (2H, q, J=7.5 Hz), 2.73 (2H, m), 1.34 (3H, t, J=7.5 Hz).

Example 6(21)
N-benzyloxycarbonyl-3-amino-4-oxo-5-(5-(ethoxycarbonylmethyl)tetrazol-1-yl)pentanoic acid

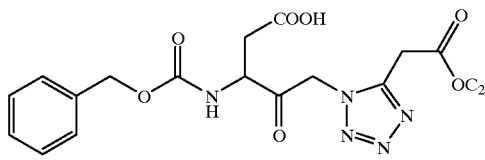

TLC: Rf 0.56 (chloroform:ethanol:acetic acid=8:1:1); NMR (DMSO-$d_6$): δ 7.66 (1H, m), 7.37 (5H, m), 5.79 (2H, brs), 5.07 (2H, s), 4.49 (1H, m), 4.23–3.94 (4H, m), 2.61 (2H, m), 1.18 (3H, t, J=6.5 Hz).

Example 6(22)
N-benzyloxycarbonyl-3-amino-4-oxo-5-(5-((4-chlorophenyl)thiomethyl)tetrazol-2-yl)pentanoic acid

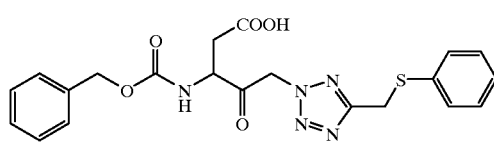

TLC: Rf 0.55 (chloroform:methanol:acetic acid=15:1:1); NMR (DMSO-$d_6$): δ 7.94 (1H, m), 7.38 (9H, m), 5.90 (2H, m), 5.10 (2H, s), 4.60 (1H, m), 4.52 (2H, s), 2.70 (2H, m).

Example 6(23)
N-benzyloxycarbonyl-3-amino-4-oxo-5-(5-((4-chlorophenyl)thiomethyl)tetrazol-1-yl)pentanoic acid

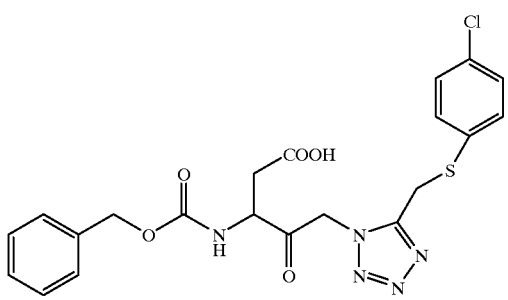

TLC: Rf 0.43 (chloroform:methanol:acetic acid=15:1:1); NMR (DMSO-$d_6$): δ 7.98 (1H, m), 7.38 (9H, m), 5.79 (2H, m), 5.10 (2H, s), 4.60 (1H, m), 4.48 (2H, m), 2.74 (2H, m).

Example 6(24)
N-benzyloxycarbonyl-3-amino-4-oxo-5-(5-(3-phenylpropyl)tetrazol-2-yl)pentanoic acid

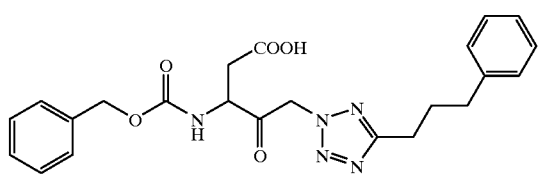

TLC: Rf 0.51 (chloroform:methanol:acetic acid=18:1:1); NMR (DMSO-$d_6$): δ 8.05–7.90 (1H, m), 7.43–7.09 (10H, m), 6.01–5.78 (2H, m), 5.09 (2H, s), 4.68–4.53 (1H, m), 2.90–2.72 and 2.72–2.54 (4H, m), 2.07–1.88 (2H, m).

Example 6(25)
N-benzyloxycarbonyl-3-amino-4-oxo-5-(5-(3-phenylpropyl)tetrazol-1-yl)pentanoic acid

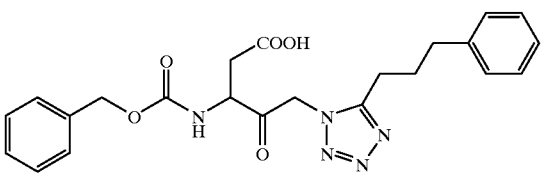

TLC: Rf 0.38 (chloroform:methanol:acetic acid=18:1:1); NMR (DMSO-$d_6$): δ 8.10–8.00 (1H, m), 7.43–7.08 (10H, m), 5.77–5.58 (2H, m), 5.10 (2H, s), 4.69–4.53 (1H, m), 2.88–2.54 (4H, m), 2.03–1.92 (2H, m).

Example 6(26)
N-benzyloxycarbonyl-3-amino-4-oxo-5-(5-(2,6-dichlorophenyloxy)tetrazol-2-yl)pentanoic acid

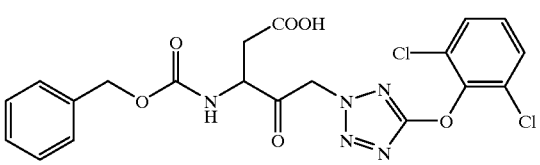

HPTLC: Rf 0.38 (chloroform:methanol=4:1); NMR (DMSO-$d_6$): δ 7.92 (1H, br), 7.67 (2H, d, J=7.5 Hz), 7.51–7.24 (6H, m), 5.88 (2H, br), 5.08 (2H, s), 4.59 (1H, m), 2.87–2.54 (2H, m).

Example 6(27)
N-benzyloxycarbonyl-3-amino-4-oxo-5-(5-(2,6-dichlorophenyloxy)tetrazol-1-yl)pentanoic acid

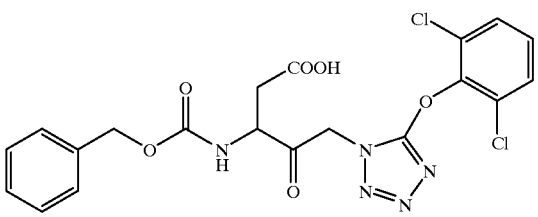

HPTLC: Rf 0.30 (chloroform:methanol=4:1); NMR (DMSO-$d_6$): δ 8.00 (1H, m), 7.79 and 7.58–7.16 (total 8H, m), 5.73 (2H, br), 5.08 (2H, brs), 4.66 (1H, m), 2.96–2.60 (2H, m).

Example 6(28)
N-benzyloxycarbonyl-3-amino-4-oxo-5-(5-(2-chlorophenyloxymethyl)tetrazol-2-yl)pentanoic acid

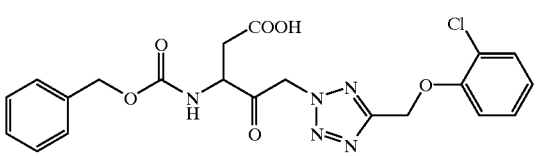

TLC: Rf 0.58 (chloroform:methanol:acetic acid=15:1:1); NMR (DMSO-$d_6$): δ 8.00 (1H, m), 7.38 (8H, m), 7.00 (1H, m), 6.01 (2H, br), 5.50 (2H, s), 5.10 (2H, s), 4.64 (1H, m), 2.74 (2H, m).

Example 6(29)
N-benzyloxycarbonyl-3-amino-4-oxo-5-(5-(2-chlorophenyloxymethyl)tetrazol-1-yl)pentanoic acid

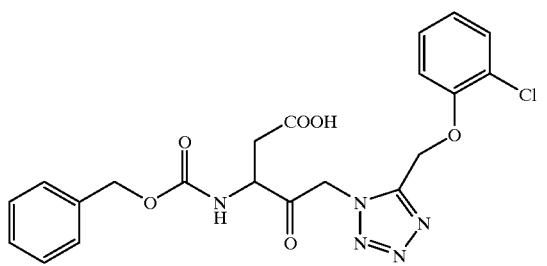

TLC: Rf 0.53 (chloroform:methanol:acetic acid=15:1:1); NMR (DMSO-$d_6$): δ 8.08 (1H, m), 7.34 (8H, m), 7.02 (1H, m), 5.88 (2H, br), 5.48 (2H, s), 5.01 (2H, s), 4.62 (1H, m), 2.72 (2H, m).

Example 6(30)

N-benzyloxycarbonyl-3-amino-4-oxo-5-(5-(2-methoxycarbonylethyl)tetrazol-2-yl)pentanoic acid

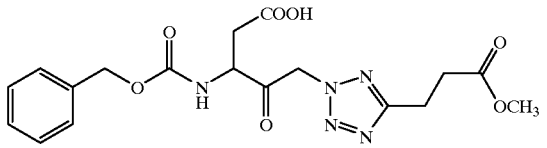

TLC: Rf 0.63 (chloroform:methanol:acetic acid=18:1:1); NMR (DMSO-$d_6$): δ 7.92 (1H, d, J=7.2 Hz), 7.46–7.23 (5H, m), 5.88 (2H, s), 5.09 (2H, s), 4.68–4.49 (1H, m), 3.60 (3H, s), 3.12 (2H, t, J=7.0 Hz), 2.93–2.51 (4H, m).

Example 6(31)

N-benzyloxycarbonyl-3-amino-4-oxo-5-(5-(2-methoxycarbonylethyl)tetrazol-1-yl)pentanoic acid

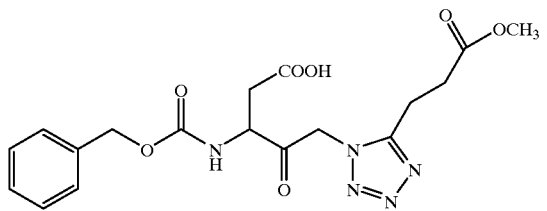

TLC: Rf 0.46 (chloroform:methanol:acetic acid=18:1:1); NMR (DMSO-$d_6$): δ 7.87–7.69 (1H, m), 7.48–7.24 (5H, m), 5.75 (2H, s), 5.09 (2H, s), 4.64–4.45 (1H, m), 3.60 (3H, s), 3.05–2.56 (6H, m).

Example 6(32)

N-benzyloxycarbonyl-3-amino-4-oxo-5-(5-(1-methoxylpyrrol-2-ylmethyl)tetrazol-2-yl)pentanoic acid

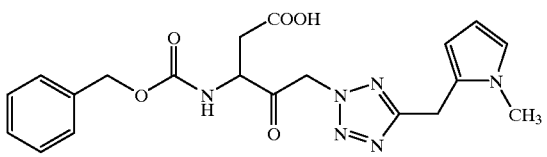

TLC: Rf 0.50 (chloroform:methanol:acetic acid=20:1:1); NMR (DMSO-$d_6$): δ 13.10–11.90 (1H, br), 8.00 (1H, d-like, J=7.0 Hz), 7.50–7.21 (5H, m), 6.68–6.60 (1H, m), 6.06–5.71 (4H, m), 5.09 (2H, s), 4.74–4.52 (2H, s), 3.53 (3H, s), 2.91–2.54 (2H, m).

Example 6(33)

N-benzyloxycarbonyl-3-amino-4-oxo-5-(5-(1-methoxylpyrrol-2-ylmethyl)tetrazol-2-yl)pentanoic acid

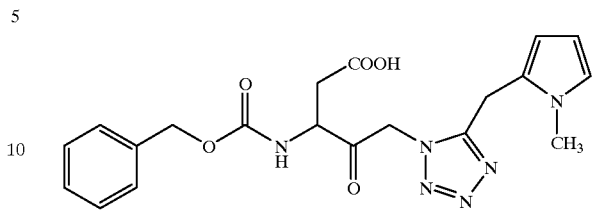

TLC: Rf 0.38 (chloroform:methanol:acetic acid=20:1:1); NMR (DMSO-$d_6$): δ 13.22–11.20 (1H, br), 8.06–7.92 (1H, m), 7.46–7.16 (6H, m), 6.87 (1H, brs), 6.28 (1H, brs), 5.06 (3H, brs), 4.51 (1H, d, J=17.0 Hz), 4.20 (1H, d, J=17.0 Hz), 3.69 (3H, s), 2.74–2.46 (2H, m).

Example 6(34)

N-benzyloxycarbonyl-3-amino-4-oxo-5-(5-(pyridin-2-ylmethoxyl)tetrazol-2-yl)pentanoic acid•hydrochloric acid salt

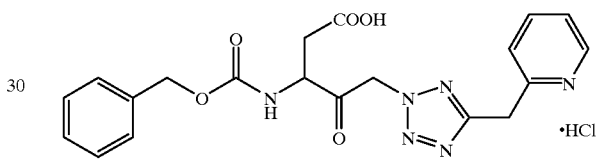

TLC: Rf 0.29 (chloroform:methanol:acetic acid=20:1:1); NMR (DMSO-$d_6$): δ 8.71 (1H, d, J=4.4 Hz), 8.27–8.09 (1H, m), 8.03 (1H, d, J=7.8 Hz), 7.77–7.55 (2H, m), 7.48–7.20 (5H, m), 5.98 (2H, s), 5.09 (2H, s), 4.64 (3H, brs), 2.83 (1H, dd, J=16.8 and 5.8 Hz), 2.64 (1H, dd, J=16.8 and 6.8 Hz).

Example 6(35)

N-benzyloxycarbonyl-3-amino-4-oxo-5-(5-(pyridin-2-ylmethyl)tetrazol-1-yl)pentanoic acid•hydrochloric acid salt

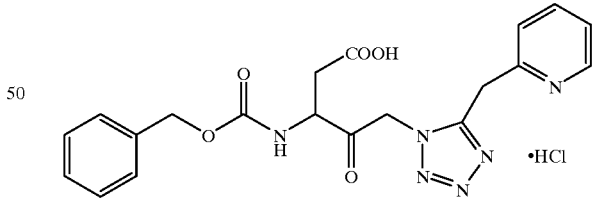

TLC: Rf 0.14 (chloroform:methanol:acetic acid=20:1:1); NMR (DMSO-$d_6$): δ 8.64–8.52 (1H, m), 8.13 (1H, d, J=7.8 Hz), 8.00 (1H, td, J=7.8 and 1.8 Hz), 7.65–7.44 (2H, m), 7.44–7.23 (5H, m), 5.90 (2H, s), 5.06 (2H, s), 4.78–4.55 (1H, m), 4.47 (2H, s), 2.83 (1H, dd, J=17.0 and 6.0 Hz), 2.67 (1H, dd, J=17.0 and 6.8 Hz).

Example 6(36)

N-benzyloxycarbonyl-3-amino-4-oxo-5-(5-(pyridin-3-ylmethyl)tetrazol-2-yl)pentanoic acid•hydrochloric acid salt

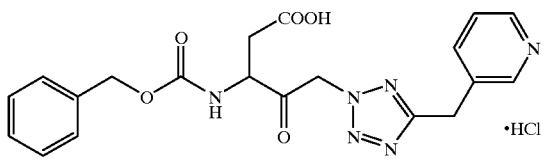

TLC: Rf 0.37 (chloroform:methanol:acetic acid= 89:10:1); NMR (DMSO-$d_6$): δ 8.76 (1H, brs), 8.72–8.61 (1H, m), 8.19–8.05 (1H, m), 8.05–7.96 (1H, m), 7.78–7.64 (1H, m), 7.50–7.22 (5H, m), 5.95 (2H, s), 5.08 (2H, s), 4.70–4.52 (1H, m), 4.45 (2H, s), 2.90–2.50 (2H, m).

Example 6(37)
N-benzyloxycarbonyl-3-amino-4-oxo-5-(5-(pyridin-3-ylmethyl)tetrazol-1-yl)pentanoic acid•hydrochloric acid salt

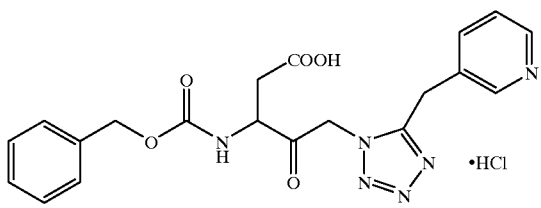

TLC: Rf 0.18 (chloroform:methanol:acetic acid= 89:10:1); NMR (DMSO-$d_6$): δ 8.70–8.52 (2H, m), 8.20–8.09 (1H, m), 7.92–7.78 (1H, m), 7.55–7.43 (1H, m), 7.43–7.21 (5H, m), 5.86 (2H, s), 5.10 (2H, s), 4.70–4.58 (1H, m), 4.21 (2H, s), 2.95–2.60 (2H, m).

Example 6(38)
N-benzyloxycarbonyl-3-amino-4-oxo-5-(5-(2,6-difluorophenylmethyl) tetrazol-2-yl)pentanoic acid

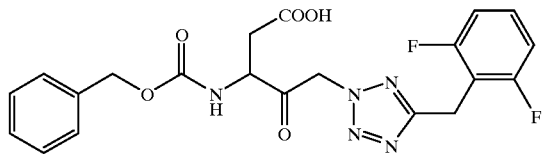

TLC: Rf 0.54 (chloroform:methanol:acetic acid=18:1:1); NMR (DMSO-$d_6$): δ 8.10–7.90 (1H, m), 7.63–7.03 (8H, m), 5.93 (2H, brs), 5.08 (2H, s), 4.72–4.53 (1H, m), 4.27 (2H, s), 2.90–2.55 (2H, m).

Example 6(39)
N-benzyloxycarbonyl-3-amino-4-oxo-5-(5-(2,6-difluorophenylmethyl) tetrazol-1-yl)pentanoic acid

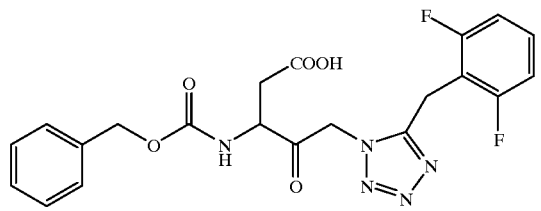

TLC: Rf 0.36 (chloroform:methanol:acetic acid=18:1:1); NMR (DMSO-$d_6$): δ 8.07 (1H, brs), 7.60–7.08 (8H, m), 5.84 (2H, brs), 5.10 (2H, s), 4.73–4.56 (1H, m), 4.13 (2H, s), 2.90–2.60 (2H, m).

Example 6(40)
N-benzyloxycarbonyl-3-amino-4-oxo-5-(5-(phenylthio) tetrazol-2-yl) pentanoic acid

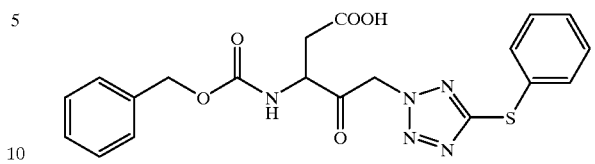

TLC: Rf 0.39 (chloroform:methanol=4:1); NMR (DMSO-$d_6$): δ 7.76 (1H, m), 7.58–7.22 (10H, m), 6.00 (2H, brs), 5.06 (2H, s), 4.54 (1H, m), 2.62 (2H, m).

Example 6(41)
N-benzyloxycarbonyl-3-amino-4-oxo-5-(5-(phenylthio) tetrazol-1-yl) pentanoic acid

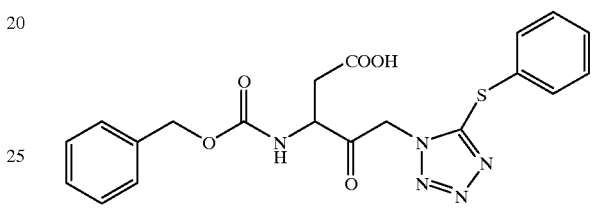

TLC: Rf 0.33 (chloroform:methanol=4:1); NMR (DMSO-$d_6$): δ 7.99 (1H, br), 7.60–7.23 (total 10H, m), 5.73 (2H, brs), 5.09 (2H, s), 4.60 (1H, m), 2.71 (2H, m).

Example 6(42)
N-benzyloxycarbonyl-3-amino-4-oxo-5-(5-(2,6-dichlorophenylthio) tetrazol-2-yl)pentanoic acid

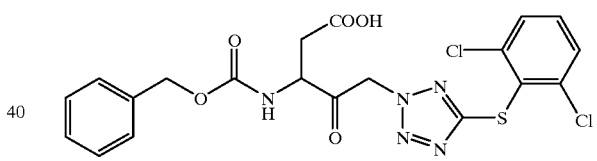

TLC: Rf 0.41 (chloroform:methanol=4:1); NMR (DMSO-$d_6$): δ 7.98 (1H, d, J=7.5 Hz), 7.69 and 7.68 (each 1H, each d, J=9.0, 7.5 Hz), 7.55 (1H, dd, J=9.0, 7.5 Hz), 7.44–7.24 (5H, m), 5.98 (2H, brs), 5.07 (2H, s), 4.61 (1H, m), 2.80 and 2.62 (each 1H, each dd, J=16.5, 6.0 Hz).

Example 6(43)
N-benzyloxycarbonyl-3-amino-4-oxo-5-(5-(2,6-dichlorophenylthio) tetrazol-1-yl)pentanoic acid

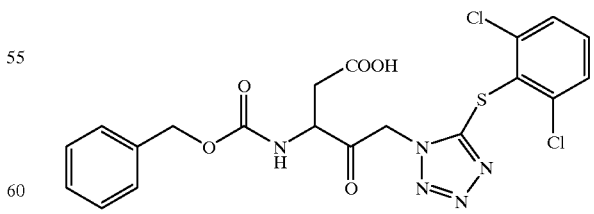

TLC: Rf 0.32 (chloroform:methanol=4:1); NMR (DMSO-$d_6$): δ 7.78 (1H, m), 7.67 and 7.66 (each 1H, each d, J=9.0, 7.0 Hz), 7.56 (1H, dd, J=9.0, 7.5 Hz), 7.41–7.17 (5H, m), 5.80 (2H, br), 5.13 and 5.03 (each 1H, each d, J=12.0 Hz), 4.54 (1H, m), 2.63 (2H, m).

Example 6(44)

N-benzyloxycarbonyl-3-amino-4-oxo-5-(5-(2,6-dimethylphenylmethyl) tetrazol-2-yl)pentanoic acid

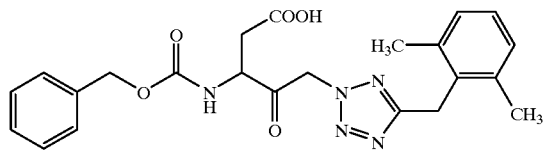

TLC: Rf 0.33 (chloroform:methanol:acetic acid=95:4:1); NMR (DMSO-$d_6$): δ 12.47 (1H, brs), 8.02–7.88 (1H, m), 7.56–7.15 (5H, m), 7.10–6.80 (3H, m), 5.88 (2H, brs), 5.07 (2H, s), 4.70–4.47 (1H, m), 4.20 (2H, s), 2.88–2.50 (2H, m), 2.33 (6H, s).

Example 6(45)

N-benzyloxycarbonyl-3-amino-4-oxo-5-(5-(2,6-dimethylphenylmethyl) tetrazol-1-yl)pentanoic acid

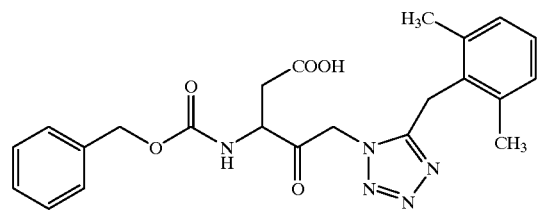

TLC: Rf 0.09 (chloroform:methanol:acetic acid=95:4:1); NMR (DMSO-$d_6$): δ 8.05 (1H, d, J=8.0 Hz), 7.42–7.20 (5H, m), 7.16–6.92 (3H, m), 5.82 (2H, brs), 5.10 (2H, s), 4.72–4.55 (1H, m), 3.98 (2H, s) 2.90–2.63 (2H, m), 2.12 (6H, s).

Example 6(46)

N-benzyloxycarbonyl-3-amino-4-oxo-5-(5-(cyclohexylmethyl)tetrazol-2-yl)pentanoic acid

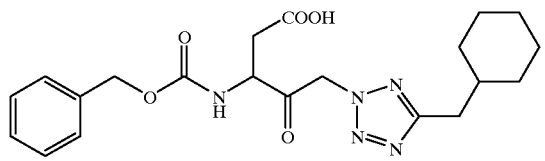

TLC: Rf 0.26 (chloroform:methanol:acetic acid=95:4:1); NMR (DMSO-$d_6$): δ 12.50 (1H, brs), 7.94 (1H, brs), 7.60–7.10 (5H, m), 5.88 (2H, brs), 5.09 (2H, s), 4.70–4.51 (1H, m), 2.89–2.47 (4H, m), 1.82–1.40 (6H, m), 1.35–0.74 (5H, m).

Example 6(47)

N-benzyloxycarbonyl-3-amino-4-oxo-5-(5-(cyclohexylmethyl)tetrazol-1-yl)pentanoic acid

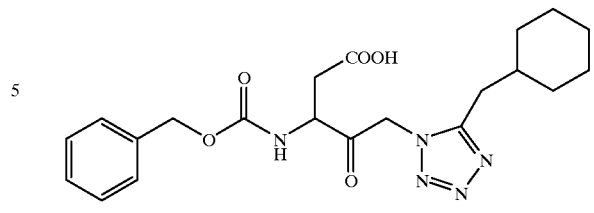

TLC: Rf 0.11 (chloroform:methanol:acetic acid=95:4:1); NMR (DMSO-$d_6$): δ 8.04 (1H, d, J=7.4 Hz), 7.41–7.23 (5H, m), 5.67 (2H, brs), 5.09 (2H, s), 4.67–4.50 (1H, m), 2.88–2.60 (2H, m), 2.58 (2H, d, J=6.6 Hz) 1.82–1.41 (6H, m), 1.36–0.78 (5H, m).

Example 6(48)

N-benzyloxycarbonyl-3-amino-4-oxo-5-(5-(4-methylphenylthio) tetrazol-2-yl)pentanoic acid


TLC: Rf 0.24 (chloroform:methanol:acetic acid=95:4:1); NMR (DMSO-$d_6$): δ 7.95 (1H, brs), 7.60–7.10 (9H, m), 5.93 (2H, brs), 5.08 (2H, s), 4.73–4.51 (1H, m), 2.83–2.54 (2H, m), 2.31 (3H, s).

Example 6(49)

N-benzyloxycarbonyl-3-amino-4-oxo-5-(5-(4-methylphenylthio) tetrazol-1-yl)pentanoic acid

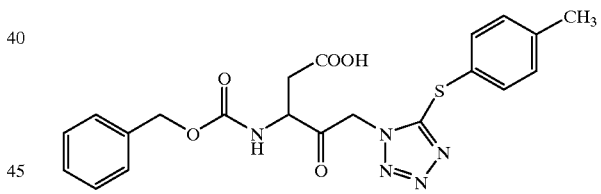

TLC: Rf 0.14 (chloroform:methanol:acetic acid=95:4:1); NMR (DMSO-$d_6$): δ 8.10–7.93 (1H, brs), 7.47–7.16 (9H, m), 5.72 (2H, brs), 5.11 (2H, s), 4.73–4.55 (1H, m), 2.90–2.59 (2H, m), 2.32 (3H, s).

Example 6(50)

N-benzyloxycarbonyl-3-amino-4-oxo-5-(5-(4-chlorophenylthio) tetrazol-2-yl)pentanoic acid

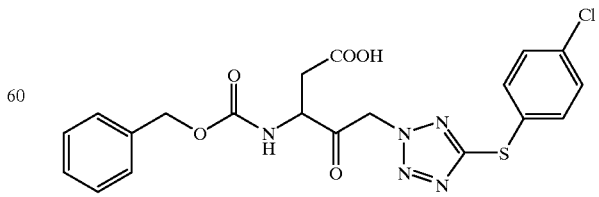

TLC: Rf 0.26 (chloroform:methanol:acetic acid=95:4:1); NMR (DMSO-$d_6$): δ 12.50 (1H, brs), 8.01 (1H, d, J=7.4 Hz), 7.60–7.42 (4H, m), 7.42–7.23 (5H, m), 6.03 (2H, s), 5.09 (2H, s), 4.78–4.48 (1H, m), 2.90–2.57 (2H, m).

Example 6(51)

N-benzyloxycarbonyl-3-amino-4-oxo-5-(5-(4-chlorophenylthio) tetrazol-1-yl)pentanoic acid

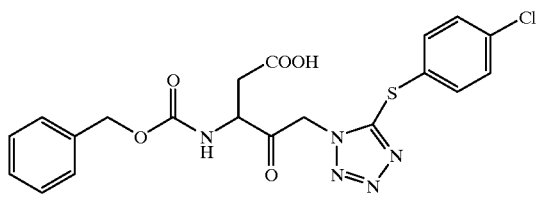

TLC: Rf 0.22 (chloroform:methanol:acetic acid=95:4:1); NMR (DMSO-$d_6$): δ 12.47 (1H, brs), 8.15–7.96 (1H, m), 7.70–7.41 (4H, m), 7.41–7.23 (5H, m), 5.77 (2H, s), 5.10 (2H, s), 4.75–4.52 (1H, m), 2.90–2.55 (2H, m).

Example 6(52)

N-benzyloxycarbonyl-3-amino-4-oxo-5-(5-(pyridin-4-yl) tetrazol-2-yl) pentanoic acid•hydrochloric acid salt

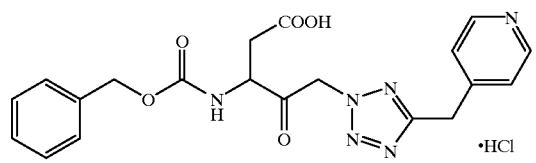

TLC: Rf 0.35 (chloroform:methanol:acetic acid=10:1:1); NMR (DMSO-$d_6$): δ 13.36–11.90 (1H, br), 8.81 (2H, d, J=5.3 Hz), 8.08 (1H, d, J=7.5 Hz), 7.82 (2H, d, J=5.3 Hz), 7.52–7.14 (5H, m), 6.00 (2H, s), 5.09 (2H, s), 4.80–4.45 (3H, m), 2.97–2.57 (2H, m).

Example 6(53)

N-benzyloxycarbonyl-3-amino-4-oxo-5-(5-(pyridin-4-yl) tetrazol-1-yl) pentanoic acid•hydrochloric acid salt

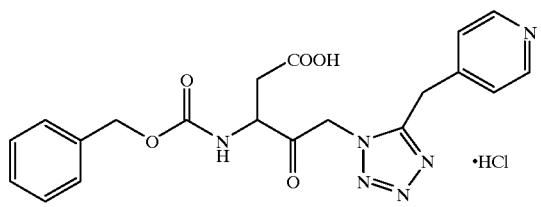

TLC: Rf 0.11 (chloroform:methanol:acetic acid=10:1:1); NMR (DMSO-$d_6$): δ 8.85 (2H, d, J=6.4 Hz), 8.17 (1H, d, J=7.4 Hz), 7.88 (2H, d, J=6.4 Hz), 7.52–7.09 (5H, m), 6.06–5.74 (2H, m), 5.11 (2H, s), 4.73–4.56 (1H, m), 4.51 (2H, s), 2.92–2.59 (2H, m).

Example 6(54)

N-benzyloxycarbonyl-3-amino-4-oxo-5-(5-(3,5-dichlorophenylthio) tetrazol-2-yl)pentanoic acid

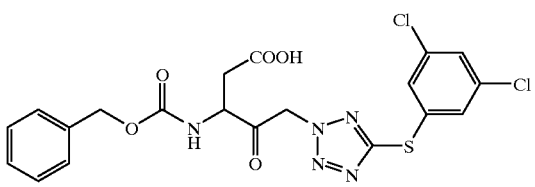

TLC: Rf 0.40 (chloroform:methanol=4:1); NMR (DMSO-$d_6$): δ 8.01 (1H, m), 7.64 (1H, d, J=1.5 Hz), 7.52 (2H, d, J=1.5 Hz), 7.37 (5H, m), 6.08 (2H, br), 5.08 (2H, s), 4.64 (1H, m), 2.89–2.56 (2H, m).

Example 6(55)

N-benzyloxycarbonyl-3-amino-4-oxo-5-(5-(3,5-dichlorophenylthio) tetrazol-1-yl)pentanoic acid

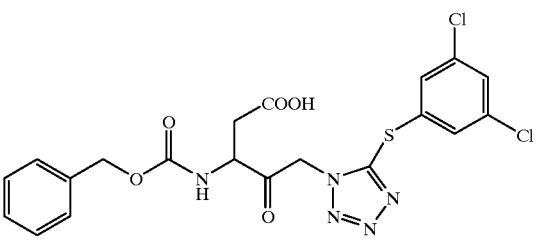

TLC: Rf 0.30 (chloroform:methanol=4:1); NMR (DMSO-$d_6$): δ 8.06 (1H, m), 7.69 (1H, d, J=1.5 Hz), 7.58 (2H, brs), 7.36 (5H, m), 5.82 (2H, br), 5.10 (2H, s), 4.64 (1H, m), 2.75 (2H, m).

Example 6(56)

N-benzyloxycarbonyl-3-amino-4-oxo-5-(5-(1-methylpyrimidin-2,4-dion-3-ylmethyl)tetrazol-2-yl) pentanoic acid

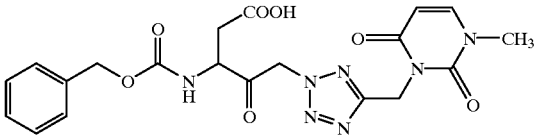

TLC: Rf 0.36 (chloroform:methanol:acetic acid=20:2:1); NMR (DMSO-$d_6$): δ 7.82 (1H, d, J=8 Hz), 7.76 (1H, d, J=8 Hz), 7.38 (5H, m), 5.92 (2H, br), 5.75 (1H, d, J=8 Hz), 5.22 (2H, s), 5.08 (2H, s), 4.58 (1H, q, J=8 Hz), 3.28 (3H, s), 2.82–2.50 (2H, m).

Example 6(57)

N-benzyloxycarbonyl-3-amino-4-oxo-5-(5-(1-methylpyrimidin-2,4-dion-3-ylmethyl)tetrazol-1-yl) pentanoic acid

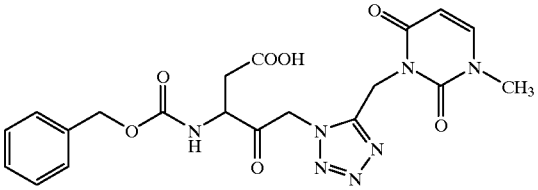

TLC: Rf 0.18 (chloroform:methanol:acetic acid=20:2:1); NMR (DMSO-$d_6$): δ 7.78 (1H, d, J=8 Hz), 7.60 (1H, d, J=8

Hz), 7.36 (5H, m), 6.00 (1H, d, J=17 Hz), 5.88 (1H, d, J=17 Hz), 5.56 (1H, d, J=8 Hz), 5.20–4.96 (4H, m), 4.46 (1H, J=8 Hz), 3.30 (3H, s), 2.80–2.55 (2H, m).

Example 6(58)

N-benzyloxycarbonyl-3-amino-4-oxo-5-(5-(2-chloroethyl)tetrazol-2-yl) pentanoic acid

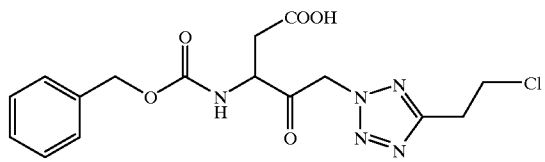

TLC: Rf 0.52 (chloroform:methanol:acetic acid=20:1:1); NMR (DMSO-$d_6$): δ 7.84–7.61 (1H, m), 7.52–7.16 (5H, m), 6.07–5.80 (2H, m), 5.08 (2H, s), 4.63–4.42 (1H, m), 3.99 (2H, t, J=6.6 Hz), 3.35 (2H, t, J=6.6 Hz), 2.62 (2H, d-like, J=5.6 Hz).

Example 6(59)

N-benzyloxycarbonyl-3-amino-4-oxo-5-(5-(2-chloroethyl)tetrazol-1-yl) pentanoic acid

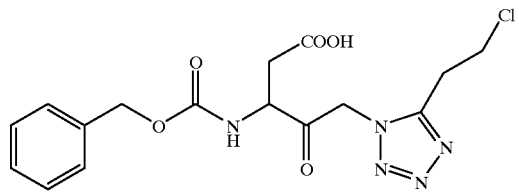

TLC: Rf 0.22 (chloroform:methanol:acetic acid=20:1:1); NMR (DMSO-$d_6$): δ 8.06–7.86 (1H, m), 7.56–7.20 (5H, m), 5.76 (2H, brs), 5.10 (2H, s), 4.68–4.49 (1H, m), 3.94 (2H, t, J=6.8 Hz), 3.25 (2H, t, J=6.8 Hz), 2.85–2.60 (2H, m).

Example 6(60)

N-benzyloxycarbonyl-3-amino-4-oxo-5-(5-(phenylcarbonyl)tetrazol-2-yl)pentanoic acid

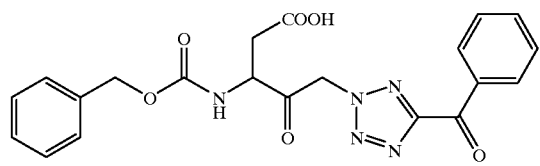

TLC: Rf 0.37 (chloroform:ethanol:acetic acid=18:1:1); NMR (DMSO-$d_6$): δ 8.21 (2H, d, J=7.0 Hz), 7.84–7.56 (4H, m), 7.35 (5H, m), 6.21 (2H, br), 5.08 (2H, s), 4.58 (1H, m), 2.64 (2H, br).

Example 6(61)

N-benzyloxycarbonyl-3-amino-4-oxo-5-(5-(phenylcarbonyl)tetrazol-1-yl)pentanoic acid

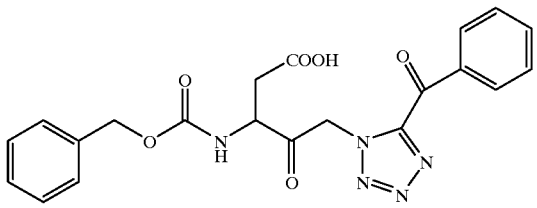

TLC: Rf 0.45 (chloroform:ethanol:acetic acid=18:1:1); NMR (DMSO-$d_6$): δ 8.25 (2H, d, J=7.0 Hz), 8.00–7.58 (4H, m), 7.48–7.20 (5H, m), 6.09–5.81 (2H, m), 5.10 (2H, s), 4.65 (1H, m), 2.66 (2H, m).

Example 6(62)

N-benzyloxycarbonyl-3-amino-4-oxo-5-(5-(2-chloro-6-fluorophenylmethyl)tetrazol-2-yl)pentanoic acid

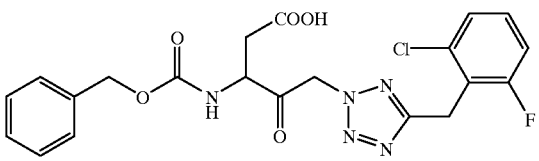

TLC: Rf 0.49 (chloroform:methanol:acetic acid=45:4:1); NMR (DMSO-$d_6$): δ 12.45 (1H, brs), 8.02–7.78 (1H, m), 7.50–7.20 (8H, m), 5.90 (2H, s), 5.07 (2H, s), 4.70–4.50 (1H, m), 4.36 (2H, s), 2.90–2.53 (2H, m).

Example 6(63)

N-benzyloxycarbonyl-3-amino-4-oxo-5-(5-(2-chloro-6-fluorophenylmethyl)tetrazol-1-yl)pentanoic acid

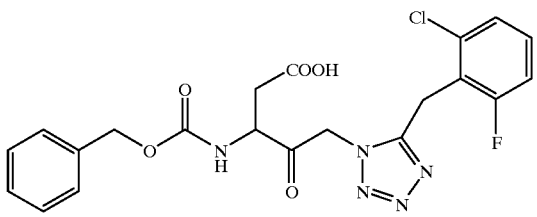

TLC: Rf 0.39 (chloroform:methanol:acetic acid=45:4:1); NMR (DMSO-$d_6$): δ 12.40 (1H, brs), 8.13–7.99 (1H, m), 7.50–7.15 (8H, m), 5.85 (2H, s), 5.10 (2H, s), 4.74–4.56 (1H, m), 4.19 (2H, s), 2.90–2.60 (2H, m).

Example 6(64)

N-benzyloxycarbonyl-3-amino-4-oxo-5-(5-(cyclohexylthio)tetrazol-2-yl) pentanoic acid

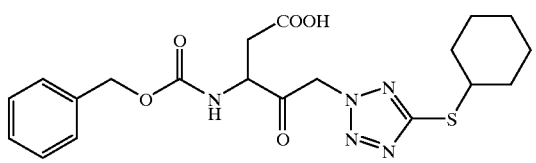

TLC: Rf 0.63 (chloroform:methanol:acetic acid=18:1:1); NMR (DMSO-$d_6$): δ 12.50 (1H, brs), 8.05–7.90 (1H, m), 7.63–7.42 (5H, m), 5.95 (2H, s), 5.09 (2H, s), 4.70–4.57 (1H, m), 3.63–3.45 (1H, m), 2.90–2.60 (2H, m), 2.10–1.10 (10H, m).

Example 6(65)

N-benzyloxycarbonyl-3-amino-4-oxo-5-(5-(cyclohexylthio) tetrazol-1-yl) pentanoic acid

TLC: Rf 0.54 (chloroform:methanol:acetic acid=18:1:1);
NMR (DMSO-$d_6$): δ 12.43 (1H, brs), 8.07–7.91 (1H, m), 7.42–7.21 (5H, m), 5.60 (2H, s), 5.10 (2H, s), 4.70–4.51 (1H, m), 3.70–3.52 (1H, m), 2.89–2.53 (2H, m), 2.10–1.11 (10H, m).

Example 6(66)

N-benzyloxycarbonyl-3-amino-4-oxo-5-(5-(4-methoxyphenylthio) tetrazol-2-yl)pentanoic acid

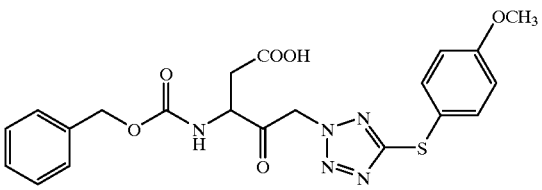

TLC: Rf 0.55 (chloroform:methanol:acetic acid=45:4:1);
NMR (DMSO-$d_6$): δ 12.49 (1H, brs), 8.04–7.83 (1H, m), 7.52 (2H, d, J=8.5 Hz), 7.45–7.22 (5H, m), 7.00 (2H, d, J=8.5 Hz), 5.94 (2H, s), 5.07 (2H, s), 4.70–4.50 (1H, m), 3.78 (3H, s), 2.90–2.53 (2H, m).

Example 6(67)

N-benzyloxycarbonyl-3-amino-4-oxo-5-(5-(4-methoxyphenylthio) tetrazol-1-yl)pentanoic acid

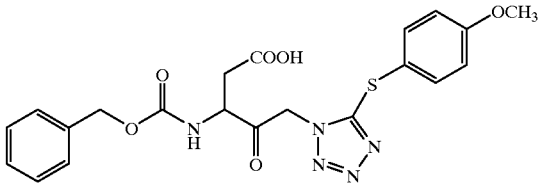

TLC: Rf 0.49 (chloroform:methanol:acetic acid=45:4:1);
NMR (DMSO-$d_6$): δ 8.08–7.97 (1H, m), 7.51 (2H, d, J=8.9 Hz), 7.42–7.25 (5H, m), 6.92 (2H, d, J=8.5 Hz), 5.69 (2H, s), 5.11 (2H, s), 4.71–4.53 (1H, m), 3.78 (3H, s), 2.90–2.53 (2H, m).

Example 6(68)

N-benzyloxycarbonyl-3-amino-4-oxo-5-(5-(2-chlorophenylthio) tetrazol-2-yl)pentanoic acid

TLC: Rf 0.53 (chloroform:methanol:acetic acid=20:1:1);
NMR (DMSO-$d_6$): δ 12.52 (1H, brs), 8.02 (1H, d, J=8 Hz), 7.70–7.52 (1H, m), 7.52–7.20 (8H, m), 6.06 (2H, s), 5.09 (2H, s), 4.78–4.49 (1H, m), 2.83 (1H, dd, J=17 and 6 Hz), 2.65 (1H, dd, J=17 and 7 Hz).

Example 6(69)

N-benzyloxycarbonyl-3-amino-4-oxo-5-(5-(2-chlorophenylthio) tetrazol-1-yl)pentanoic acid

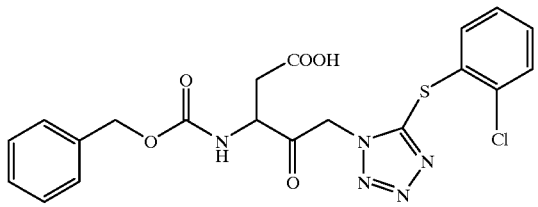

TLC: Rf 0.33 (chloroform:methanol:acetic acid=20:1:1);
NMR (DMSO-$d_6$): δ 8.07–7.79 (1H, m), 7.75–7.12 (9H, m), 5.78 (2H, brs), 5.08 (2H, s), 4.71–4.41 (1H, m), 2.87–2.55 (2H, m).

Example 6(70)

N-benzyloxycarbonyl-3-amino-4-oxo-5-(5-(2,4-dichlorophenylthio) tetrazol-2-yl)pentanoic acid

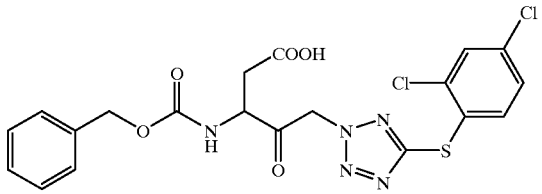

TLC: Rf 0.57 (chloroform:methanol:acetic acid=18:1:1);
NMR (DMSO-$d_6$): δ 12.85–12.15 (1H, br), 8.10 (1H, d, J=7 Hz), 7.82 (1H, d, J=7 Hz), 7.58–7.20 (7H, m), 6.05 (2H, s), 5.09 (2H, s), 4.82–4.46 (1H, m), 2.82 (1H, dd, J=17 and 6 Hz), 2.65 (1H, dd, J=17 and 7 Hz).

Example 6(71)

N-benzyloxycarbonyl-3-amino-4-oxo-5-(5-(2,4-dichlorophenylthio) tetrazol-1-yl)pentanoic acid

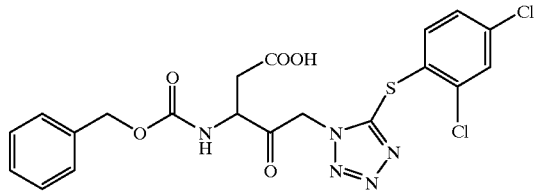

TLC: Rf 0.53 (chloroform:methanol:acetic acid=18:1:1);
NMR (DMSO-$d_6$): δ 8.03 (1H, d, J=7 Hz), 7.82 (1H, s-like), 7.66–7.12 (7H, m), 5.76 (2H, brs), 5.09 (2H, s), 4.78–4.44 (1H, m), 2.95–2.53 (2H, m).

Example 6(72)

N-benzyloxycarbonyl-3-amino-4-oxo-5-(5-(2-chloro-6-methylphenylthio)tetrazol-2-yl)pentanoic acid

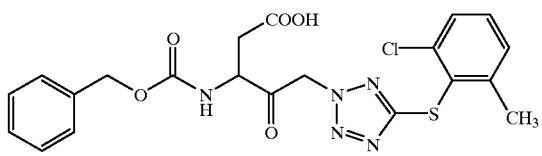

TLC: Rf 0.56 (chloroform:methanol:acetic acid=18:1:1); NMR (DMSO-d$_6$): δ 12.5 (1H, brs), 7.96 (1H, d, J=7.6 Hz), 7.51–7.28 (8H, m), 5.95 (2H, brs), 5.08 (2H, s), 4.67–4.56 (1H, m), 2.80 (1H, dd, J=5.4, 17 Hz), 2.63 (1H, dd, J=7.0, 17 Hz), 2.47 (3H, s).

Example 6(73)

N-benzyloxycarbonyl-3-amino-4-oxo-5-(5-(2-chloro-6-methylphenylthio)tetrazol-1-yl)pentanoic acid

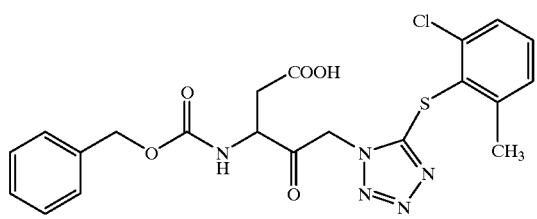

TLC: Rf 0.49 (chloroform:methanol:acetic acid=18:1:1); NMR (DMSO-d$_6$): δ 12.5 (1H, brs), 8.08 (1H, d, J=9.6 Hz), 7.51–7.23 (8H, m), 5.75 (2H, brs), 5.12 (2H, s), 4.71–4.61 (1H, m), 2.92–2.67 (2H, m), 2.46 (3H, s).

Example 6(74)

N-benzyloxycarbonyl-3-amino-4-oxo-5-(5-(4-trifluoromethylphenylthio) tetrazol-2-yl)pentanoic acid

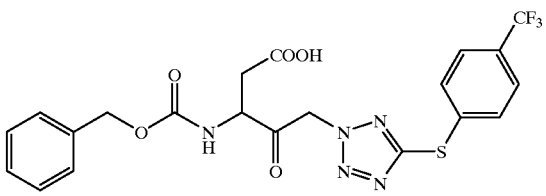

TLC: Rf 0.40 (chloroform:methanol:acetic acid=40:1:1); NMR (DMSO-d$_6$): δ 7.99 (d, J=8.0 Hz, 1H), 7.76 (d, J=8.6 Hz, 2H), 7.62 (d, J=8.6 Hz, 2H), 7.4–7.2 (m, 5H), 6.07 (s, 2H), 5.09 (s, 2H), 4.8–4.6 (m, 1H), 2.78 (dd, J=6.0, 17.0 Hz, 1H), 2.65 (dd, J=7.0,17.0 Hz, 1H).

Example 6(75)

N-benzyloxycarbonyl-3-amino-4-oxo-5-(5-(4-trifluoromethylphenylthio) tetrazol-1-yl)pentanoic acid

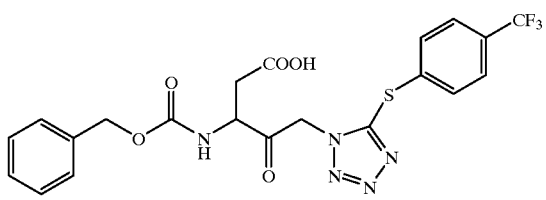

TLC: Rf 0.45 (chloroform:methanol:acetic acid=40:1:1); NMR (DMSO-d$_6$): δ 8.0–7.9 (m, 1H), 7.78 (d, J=8.5 Hz, 2H), 7.67 (d, J=8.5 Hz, 2H), 7.4–7.3 (m, 5H), 5.79 (s, 2H), 5.09 (s, 2H), 4.7–4.5 (m, 1H), 2.8–2.6 (m, 2H).

Example 6(76)

N-benzyloxycarbonyl-3-amino-4-oxo-5-(5-(naphthalen-2-ylthio) tetrazol-2-yl)pentanoic acid

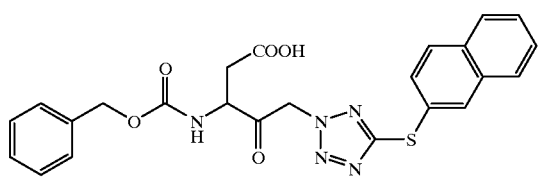

TLC: Rf 0.43 (chloroform:methanol:acetic acid=46:3:1); NMR (DMSO-d$_6$): δ 12.50 (1H, brs), 8.12 (1H, s), 8.00–7.86 (4H, m), 7.62–7.45 (3H, m), 7.43–7.20 (5H, m), 5.99 (2H, s), 5.07 (2H, s), 4.73–4.53 (1H, m), 2.90–2.55 (2H, m).

Example 6(77)

N-benzyloxycarbonyl-3-amino-4-oxo-5-(5-(naphthalen-2-ylthio) tetrazol-1-yl)pentanoic acid

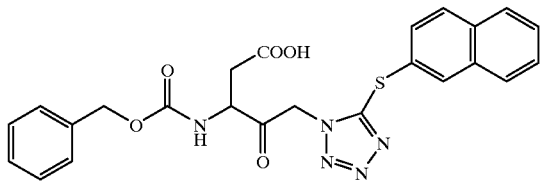

TLC: Rf 0.31 (chloroform:methanol:acetic acid=46:3:1); NMR (DMSO-d$_6$): δ 12.57 (1H, brs), 8.15 (1H, s), 8.10–7.87 (4H, m), 7.69–7.44 (3H, m), 7.42–7.23 (5H, m), 5.78 (2H, s), 5.10 (2H, s), 4.73–4.5 (1H, m), 2.90–2.55 (2H, m).

Example 6(78)

N-benzyloxycarbonyl-3-amino-4-oxo-5-(5-(4-t-butylphenylthio)tetrazol-2-yl)pentanoic acid

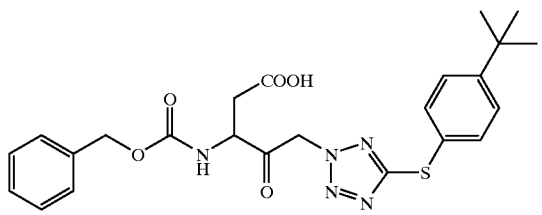

TLC: Rf 0.49 (chloroform:methanol:acetic acid=46:3:1); NMR (DMSO-d$_6$): δ 12.48 (1H, brs), 7.96 (1H, brs), 7.60–7.40 (9H, m), 5.98 (2H, brs), 5.06 (2H, s), 4.70–4.50 (1H, m), 2.88–2.53 (2H, m), 1.26 (9H, s).

Example 6(79)

N-benzyloxycarbonyl-3-amino-4-oxo-5-(5-(4-t-butylphenylthio)tetrazol-1-yl)pentanoic acid

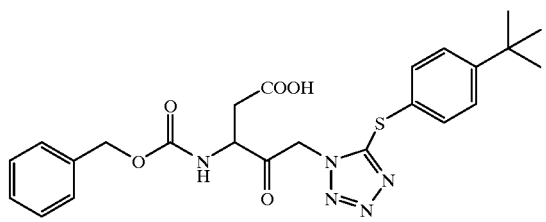

TLC: Rf 0.43 (chloroform:methanol:acetic acid=46:3:1); NMR (DMSO-d$_6$): δ 8.10–7.90 (1H, m), 7.60–7.25 (9H, m), 5.70 (2H, brs), 5.09 (2H, s), 4.70–4.53 (1H, m), 2.90–2.53 (2H, m), 1.27 (9H, s).

Example 6(80)

N-benzyloxycarbonyl-3-amino-4-oxo-5-(5-(4-trifluoromethyloxyphenylthio)tetrazol-1-yl)pentanoic acid

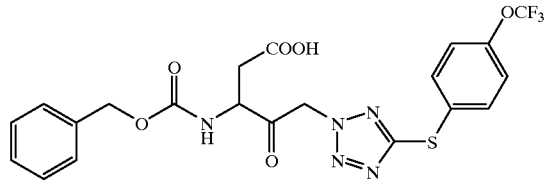

TLC: Rf 0.33 (chloroform:methanol:acetic acid=30:1:1); NMR (DMSO-d$_6$): δ 8.1–8.0 (m, 1H), 7.66 (d, J=8.8 Hz, 2H), 7.43 (d, J=8.8 Hz, 2H), 7.5–7.3 (m, 5H), 5.76 (brs, 2H), 5.10 (s, 2H), 4.7–4.6 (m, 1H), 2.9–2.6 (m, 2H).

Example 6(81)

N-benzyloxycarbonyl-3-amino-4-oxo-5-(5-(4-trifluoromethyloxyphenylthio)tetrazol-2-yl)pentanoic acid

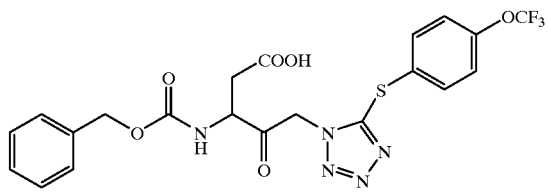

TLC: Rf 0.33 (chloroform:methanol:acetic acid=15:1:1); NMR (DMSO-d$_6$): δ 8.1–7.9 (m, 1H), 7.63 (d, J=8.8 Hz, 2H), 7.43 (d, J=8.8 Hz, 2H), 7.5–7.2 (m, 5H), 6.2–5.9 (m, 2H), 5.09 (s, 2H), 4.7–4.5 (m, 1H), 2.9–2.6 (m, 2H).

Example 6(82)

N-benzyloxycarbonyl-3-amino-4-oxo-5-(5-(2,3,6-trichlorophenylthio) tetrazol-2-yl)pentanoic acid

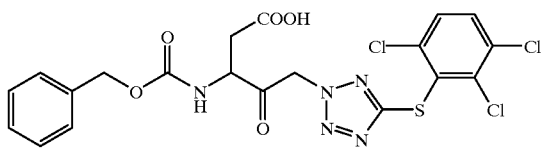

TLC: Rf 0.61 (chloroform:methanol:acetic acid=18:1:1); NMR (DMSO-d$_6$): δ 11.9 (1H, brs), 7.96 (1H, d, J=7.8 Hz), 7.84 (1H, d, J=8.8 Hz), 7.71 (1H, d, J=8.8 Hz), 7.39–7.30 (5H, m), 5.97 (2H, brs), 5.09 (2H, s), 4.68–4.58 (1H, m), 2.80 (1H, dd, J=5.6, 16.6 Hz), 2.64 (1H, dd, J=7.0, 16.6 Hz).

Example 6(83)

N-benzyloxycarbonyl-3-amino-4-oxo-5-(5-(2,3,6-trichlorophenylthio) tetrazol-1-yl)pentanoic acid

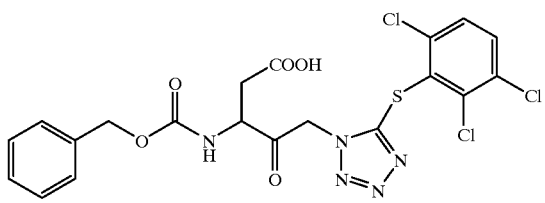

TLC: Rf 0.48 (chloroform:methanol:acetic acid=18:1:1); NMR (DMSO-d$_6$): δ 8.08 (1H, d, J=7.4 Hz), 7.86 (1H, d, J=8.8 Hz), 7.71 (1H, d, J=8.8 Hz), 7.42–7.26 (5H, m), 5.78 (2H, brs), 5.12 (2H, s), 4.75–4.60 (1H, m), 2.93–2.70 (2H, m).

Example 6(84)

N-benzyloxycarbonyl-3-amino-4-oxo-5-(5-(2,4-dimethylphenylthio) tetrazol-2-yl)pentanoic acid

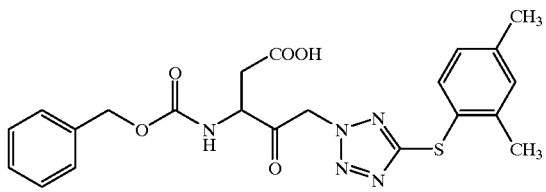

TLC: Rf 0.38 (chloroform:methanol:acetic acid=94:3:3); NMR (DMSO-d$_6$): δ 8.02–7.89 (1H, m), 7.43–7.22 (6H, m), 7.19 (1H, s), 7.06 (1H, d, J=8.0 Hz), 5.92 (2H, brs), 5.07 (2H, s), 4.70–4.50 (1H, m), 2.90–2.53 (2H, m), 2.32 (3H, s), 2.29 (3H, s).

Example 6(85)

N-benzyloxycarbonyl-3-amino-4-oxo-5-(5-(2,4-dimethylphenylthio) tetrazol-1-yl)pentanoic acid

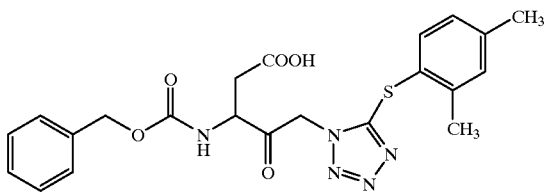

TLC: Rf 0.29 (chloroform:methanol:acetic acid=94:3:3); NMR (DMSO-d$_6$): δ 8.10–7.96 (1H, m), 7.43–7.25 (6H, m), 7.20 (1H, s), 7.07 (1H, d, J=7.4 Hz), 5.69 (2H, brs), 5.10 (2H, s), 4.70–4.53 (1H, m), 2.90–2.53 (2H, m), 2.30 (6H, s).

Example 6(86)

N-benzyloxycarbonyl-3-amino-4-oxo-5-(5-(2,5-dichlorophenylthio) tetrazol-2-yl)pentanoic acid

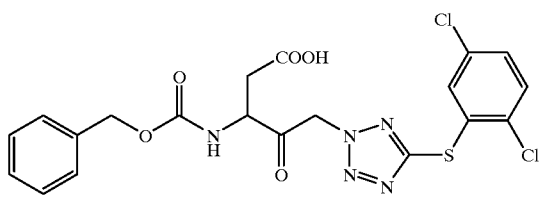

TLC: Rf 0.48 (chloroform:methanol:acetic acid=96:3:1); NMR (DMSO-d$_6$): δ 8.08–7.90 (1H, m), 7.65 (1H, dd, J=8.7, 2.9 Hz), 7.48 (1H, d, J=8.7 Hz), 7.42–7.23 (6H, m), 6.05 (2H, brs), 5.09 (2H, s), 4.70–4.52 (1H, m), 2.90–2.55 (2H, m).

Example 6(87)

N-benzyloxycarbonyl-3-amino-4-oxo-5-(5-(2,5-dichlorophenylthio) tetrazol-1-yl)pentanoic acid

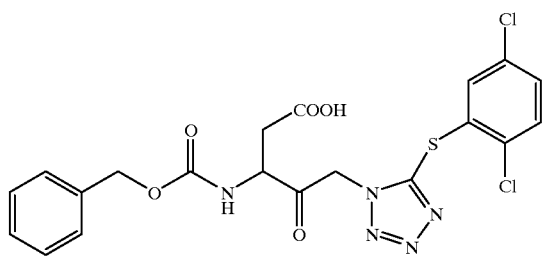

TLC: Rf 0.40 (chloroform:methanol:acetic acid=96:3:1); NMR (DMSO-d$_6$): δ 8.05 (1H, brs), 7.70–7.58 (1H, m), 7.55–7.45 (2H, m), 7.45–7.21 (5H, m), 5.83 (2H, brs), 5.09 (2H, s), 4.75–4.55 (1H, m), 2.90–2.55 (2H, m).

Example 6(88)

N-benzyloxycarbonyl-3-amino-4-oxo-5-(5-(4-bromophenylthio) tetrazol-2-yl)pentanoic acid

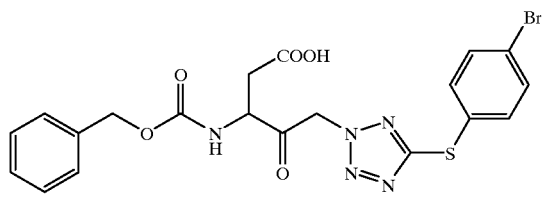

TLC: Rf 0.43 (chloroform:methanol:acetic acid=30:1:1); NMR (DMSO-d$_6$): δ 12.53 (brs, 1H), 8.00 (d, J=8.0 Hz, 1H), 7.62 (d, J=8.6 Hz, 2H), 7.46 (d, J=8.6 Hz, 2H), 7.5–7.3 (s, 4H), 6.03 (s, 2H), 5.09 (s, 2H), 4.8–4.6 (m, 1H), 3.0–2.6 (m, 2H).

Example 6(89)

N-benzyloxycarbonyl-3-amino-4-oxo-5-(5-(4-bromophenylthio) tetrazol-1-yl)pentanoic acid

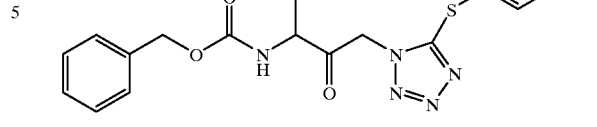

TLC: Rf 0.26 (chloroform:methanol:acetic acid=30:1:1); NMR (DMSO-d$_6$): δ 12.57 (brs, 1H), 8.07 (d, J=7.4 Hz, 1H),7.63 (d, J=8.6 Hz, 2H), 7.46 (d, J=8.6 Hz, 2H), 7.5–7.2 (m, 4H), 5.79 (s, 2H), 5.11 (s, 2H), 4.8–4.6 (m, 1H), 3.0–2.6 (m, 2H).

Example 6(90)

N-benzyloxycarbonyl-3-amino-4-oxo-5-(5-(2,6-dichloro-4-methylphenylthio)tetrazol-2-yl)pentanoic acid

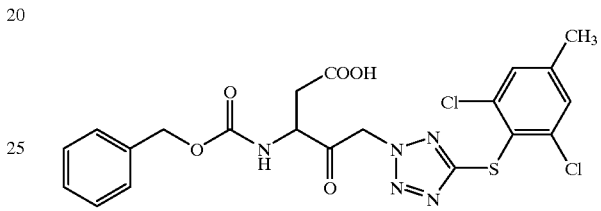

TLC: Rf 0.60 (chloroform:methanol:acetic acid=96:3:1); NMR (DMSO-d$_6$): δ 7.95 (1H, d, J=7.6 Hz), 7.53 (2H, s), 7.40–7.25 (5H, m), 5.96 (2H, s), 5.08 (2H, s), 4.70–4.50 (1H, m), 2.79 (1H, dd, J=16.8, 6.0 Hz), 2.61 (1H, dd, J=16.8, 6.8 Hz), 2.36 (3H, s).

Example 6(91)

N-benzyloxycarbonyl-3-amino-4-oxo-5-(5-(2,6-dichloro-4-methylphenylthio)tetrazol-1-yl)pentanoic acid

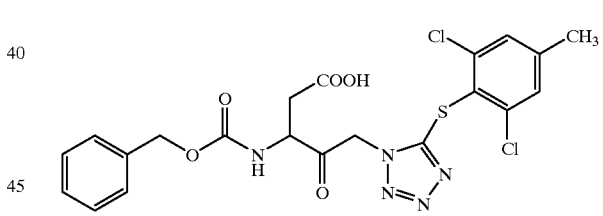

TLC: Rf 0.50 (chloroform:methanol:acetic acid=96:3:1); NMR (DMSO-d$_6$): δ 8.04 (1H, brs), 7.52 (2H, s), 7.45–7.20 (5H, m), 5.74 (2H, s), 5.11 (2H, s), 4.76–4.56 (1H, m), 2.90–2.65 (2H, m), 2.36 (3H, s).

Example 6(92)

N-benzyloxycarbonyl-3-amino-4-oxo-5-(5-(3,4-dichlorophenylthio) tetrazol-2-yl)pentanoic acid

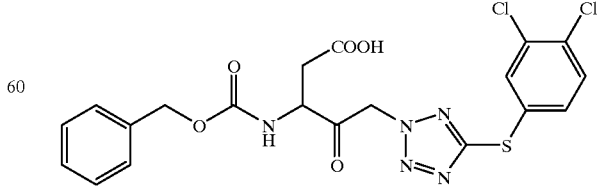

TLC: Rf 0.48 (chloroform:methanol:acetic acid=36:1:1); NMR (CDCl$_3$): δ 7.99 (1H, d, J=7.6 Hz), 7.75 (1H, d, J=2.2

Hz), 7.67 (1H, d, J=8.6 Hz), 7.46 (1H, dd, J=2.2, 8.6 Hz), 7.40–7.30 (5H, m), 6.00 (2H, brs), 5.09 (2H, s), 4.69–4.59 (1H, m), 2.87–2.61 (2H, m).

Example 6(93)
N-benzyloxycarbonyl-3-amino-4-oxo-5-(5-(3,4-dichlorophenylthio)tetrazol-1-yl)pentanoic acid

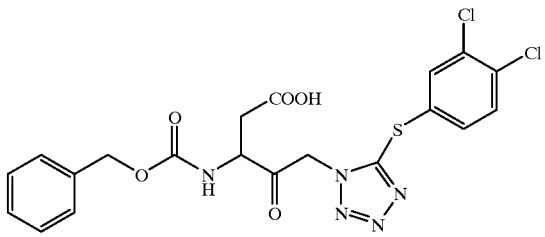

TLC: Rf 0.33 (chloroform:methanol:acetic acid=36:1:1); NMR (CDCl$_3$): δ 8.06 (1H, d, J=7.4 Hz), 7.80 (1H, d, J=2.2 Hz), 7.68 (1H, d, J=8.6 Hz), 7.50 (1H, dd, J=2.2, 8.6 Hz), 7.40–7.29 (5H, m), 5.77 (2H, br s), 5.11 (2H, s), 4.69–4.59 (1H, m), 2.88–2.64 (2H, m).

Example 6(94)
N-benzyloxycarbonyl-3-amino-4-oxo-5-(5-bromotetrazol-2-yl) pentanoic acid

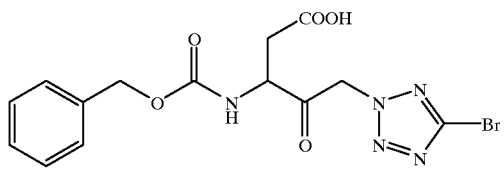

TLC: Rf 0.51 (chloroform:methanol:acetic acid=18:1:1); NMR (DMSO-d$_6$): δ 7.93 (1H, d, J=7.4 Hz), 7.56–7.13 (5H, m), 6.01 (2H, brs), 5.09 (2H, s), 4.73–4.49 (1H, m), 2.92–2.52 (2H, m).

Example 6(95)
N-benzyloxycarbonyl-3-amino-4-oxo-5-(5-(4-nitrophenylthio)tetrazol-2-yl)pentanoic acid

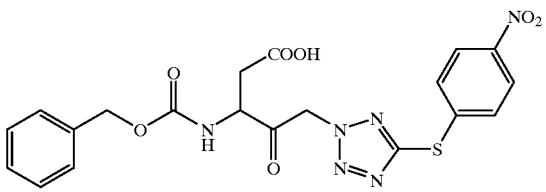

TLC: Rf 0.53 (chloroform:methanol:acetic acid=18:1:1); NMR (DMSO-d$_6$): δ 12.80–10.36 (1H, br), 8.22 (2H, d, J=9.0 Hz), 8.00 (1H, d, J=7.8 Hz), 7.61 (2H, d, J=9.0 Hz), 7.47–7.18 (5H, m), 6.05 (2H, brs), 5.09 (2H, s), 4.80–4.52 (1H, m), 2.93–2.56 (2H, m).

Example 6(96)
N-benzyloxycarbonyl-3-amino-4-oxo-5-(5-(4-nitrophenylthio)tetrazol-1-yl)pentanoic acid

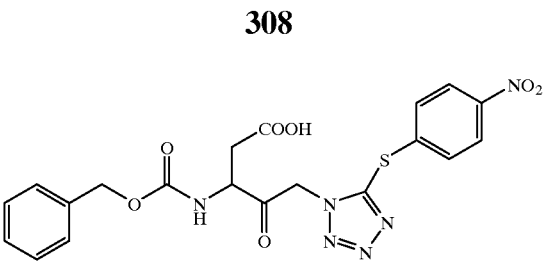

TLC: Rf 0.37 (chloroform:methanol:acetic acid=18:1:1); NMR (DMSO-d$_6$): δ 8.22 (2H, d, J=9.0 Hz), 7.98 (1H, d, J=7.8 Hz), 7.66 (2H, d, J=9.0 Hz), 7.46–7.19 (5H, m), 5.79 (2H, brs), 5.09 (2H, s), 4.74–4.46 (1H, m), 2.87–2.54 (2H, m).

Example 6(97)
N-benzyloxycarbonyl-3-amino-4-oxo-5-(5-(naphthalen-1-ylthio) tetrazol-2-yl)pentanoic acid

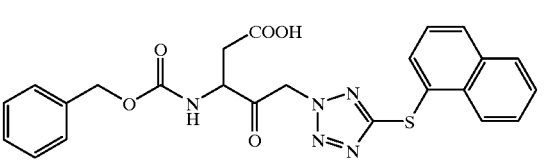

TLC: Rf 0.47 (chloroform:methanol:acetic acid=96:3:1); NMR (DMSO-d$_6$): δ 12.43 (1H, brs), 8.26 (1H, d, J=8.6 Hz), 8.16–7.80 (4H, m), 7.74–7.47 (3H, m), 7.42–7.22 (5H, m), 5.94 (2H, s), 5.06 (2H, s), 4.75–4.50 (1H, m), 2.87–2.52 (2H, m).

Example 6(98)
N-benzyloxycarbonyl-3-amino-4-oxo-5-(5-(naphthalen-1-ylthio) tetrazol-1-yl)pentanoic acid

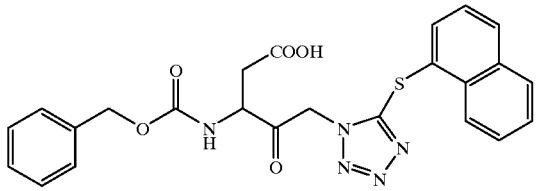

TLC: Rf 0.37 (chloroform:methanol:acetic acid=96:3:1); NMR (DMSO-d$_6$): δ 12.56 (1H, brs), 8.32–7.97 (4H, m), 7.93 (1H, d, J=7.0 Hz), 7.70–7.49 (3H, m) 7.41–7.10 (5H, m), 5.86 (2H, brs), 5.12 (2H, s), 4.78–4.58 (1H, m), 2.94–2.62 (2H, m).

Example 6(99)
N-benzyloxycarbonyl-3-amino-4-oxo-5-(5-(2,4-di-t-butylphenylthio) tetrazol-2-yl)pentanoic acid

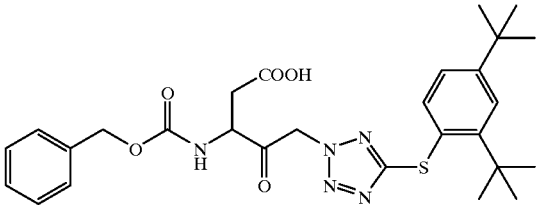

TLC: Rf 0.26 (chloroform:methanol:acetic acid= 90:10:1); NMR (DMSO-d$_6$): δ 7.60 (1H, d, J=7 Hz), 7.46

(1H, d, J=2 Hz), 7.37–7.19 (7H, m), 5.97 (2H, dd, J=17 and 24 Hz), 5.04 (2H, s), 4.48 (1H, m), 2.65–2.52 (2H, m), 1.49 and 1.27 (each 9H, each s).

Example 6(100)

N-benzyloxycarbonyl-3-amino-4-oxo-5-(5-(2,4-di-t-butylphenylthio) tetrazol-1-yl)pentanoic acid

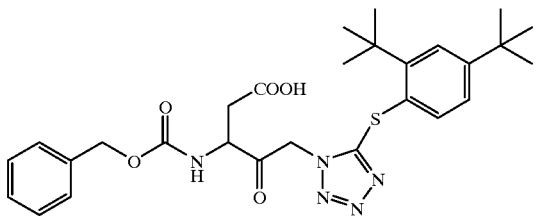

TLC: Rf 0.24 (chloroform:methanol:acetic acid= 90:10:1); NMR (DMSO-d$_6$): δ 7.79 (1H, d, J=8 Hz), 7.48 (1H, s), 7.35–7.18 (7H, m), 5.77 (2H, brs), 5.06 (2H, s), 4.52 (1H, m), 2.61 (2H, d-like), 1.46 and 1.29 (each 9H, each s).

Example 6(101)

N-benzyloxycarbonyl-3-amino-4-oxo-5-(5-(imidazol-1-ylmethyl) tetrazol-2-yl)pentanoic acid•hydrochloric acid salt

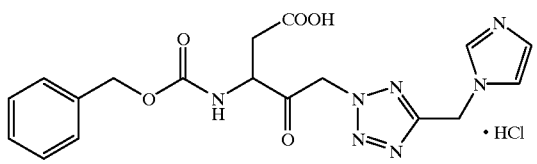

TLC: Rf 0.44 (chloroform:methanol:acetic acid=10:5:1); NMR (DMSO-d$_6$): δ 9.28 (1H, s), 8.02 (1H, d, J=7.0 Hz), 7.80 (1H, s), 7.71 (1H, s), 7.42–7.30 (5H, m), 6.04 (2H, s), 5.91 (2H, s), 5.09 (2H, s), 4.62 (1H, m), 2.90–2.58 (2H, m).

Example 6(102)

N-benzyloxycarbonyl-3-amino-4-oxo-5-(5-(imidazol-1-ylmethyl) tetrazol-1-yl)pentanoic acid•hydrochloric acid salt

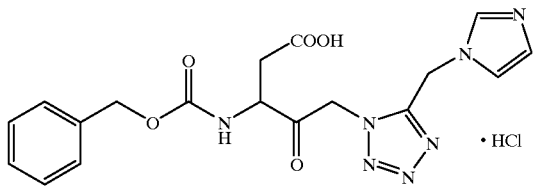

TLC: Rf 0.38 (chloroform:methanol:acetic acid=10:5:1); NMR (DMSO-d$_6$): δ 9.22 (1H, s), 8.20 (1H, d, J=7.0 Hz), 7.72 (1H, s), 7.68 (1H, s), 7.40–7.26 (5H, m), 6.10–5.88 (2H, m), 5.81 (2H, s), 5.12 (2H, s), 4.72 (1H, m), 2.92–2.62 (2H, m).

Example 6(103)

N-benzyloxycarbonyl-3-amino-4-oxo-5-(5-(2-methoxyphenylthio) tetrazol-2-yl)pentanoic acid

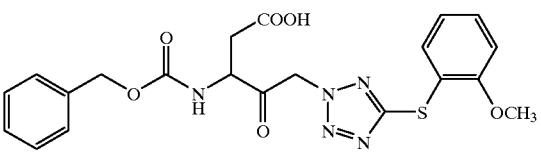

TLC: Rf 0.34 (chloroform:methanol:acetic acid=36:1:1); NMR (DMSO-d$_6$): δ 7.98 (1H, d, J=7.6 Hz), 7.42–7.30 (6H, m), 7.25 (1H, d, J=7.4 Hz), 7.10 (1H, d, J=7.4 Hz), 7.00–6.92 (1H, m), 5.97 (2H, brs), 5.09 (2H, s), 4.68–4.58 (1H, m), 3.80 (3H, s), 2.87–2.60 (2H, m).

Example 6(104)

N-benzyloxycarbonyl-3-amino-4-oxo-5-(5-(2-methoxyphenylthio) tetrazol-1-yl)pentanoic acid

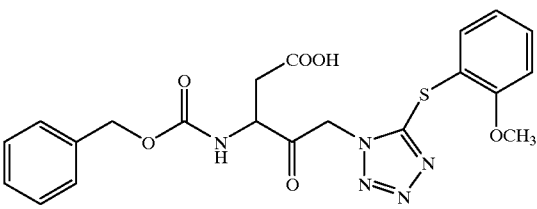

TLC: Rf 0.29 (chloroform:methanol:acetic acid=36:1:1); NMR (DMSO-d$_6$): δ 8.03 (1H, d, J=6.8 Hz), 7.46–7.31 (7H, m), 7.09 (1H, d, J=7.8 Hz), 7.03–6.95 (1H, m), 5.72 (2H, brs), 5.10 (2H, s), 4.68–4.58 (1H, m), 3.75 (3H, s), 2.87–2.62 (2H, m).

Example 6(105)

N-benzyloxycarbonyl-3-amino-4-oxo-5-(5-(2,6-dichloro-4-dimethylaminophenylthio)tetrazol-2-yl)pentanoic acid•hydrochloric acid salt

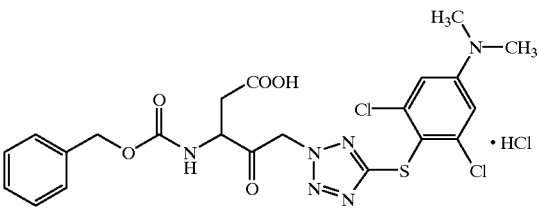

TLC: Rf 0.38 (chloroform:methanol:water=50:10:1); NMR (DMSO-d$_6$): δ 7.97 (1H, d, J=7.8 Hz), 7.40–7.26 (5H, m), 6.88 (2H, s), 5.95 (2H, brs), 5.08 (2H, s), 4.60 (1H, m), 2.77 (6H, s), 2.84–2.72 (2H, m).

Example 6(106)

N-benzyloxycarbonyl-3-amino-4-oxo-5-(5-(2,6-dichloro-4-dimethylaminophenylthio)tetrazol-1-yl)pentanoic acid•hydrochloric acid salt

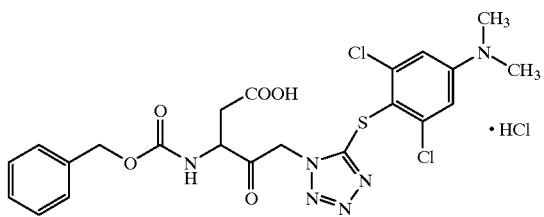

TLC: Rf 0.29 (chloroform:methanol:water=50:10:1); NMR (DMSO-d$_6$): δ 8.02 (1H, m), 7.40–7.24 (5H, m), 6.87 (2H, s), 5.73 (2H, brs), 5.11 (2H, s), 4.62 (1H, m), 3.00 (6H, s), 2.92–2.62 (2H, m).

Example 6(107)

N-benzyloxycarbonyl-3-amino-4-oxo-5-(5-(thiophen-2-yl) tetrazol-2-yl) pentanoic acid

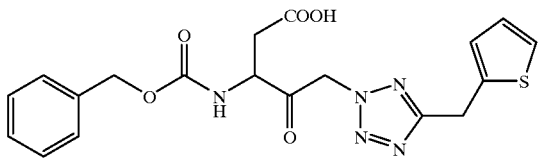

TLC: Rf 0.46 (chloroform:methanol:water=40:10:1); NMR (DMSO-d$_6$): δ 7.61 (1H, d, J=8 Hz), 7.40–7.32 (6H, m), 6.96–6.94 (2H, m), 5.96 (2H, brs), 5.07 (2H, s), 4.57–4.47 (1H, m), 4.46 (2H, s), 2.60 (2H, d-like).

Example 6(108)

N-benzyloxycarbonyl-3-amino-4-oxo-5-(5-(thiophen-2-yl) tetrazol-1-yl) pentanoic acid

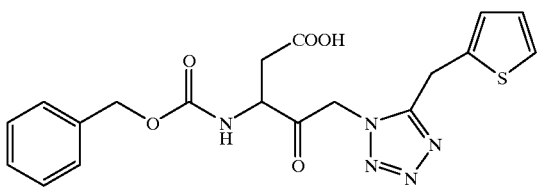

TLC: Rf 0.34 (chloroform:methanol:water=40:10:1); NMR (DMSO-d$_6$): δ 8.08 (1H, d, J=8 Hz), 7.43–7.37 (6H, m), 6.97–6.94 (2H, m), 5.77 (2H, s), 5.10 (2H, s), 4.64 (1H, m), 4.38 (2H, s), 2.76 (2H, m).

Example 6(109)

N-benzyloxycarbonyl-3-amino-4-oxo-5-(5-(thiophen-3-yl) tetrazol-2-yl) pentanoic acid

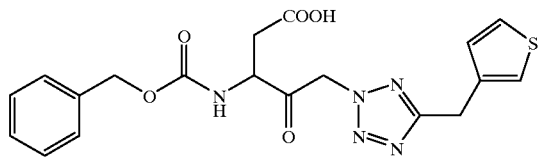

TLC: Rf 0.49 (chloroform:methanol:water=40:10:1); NMR (DMSO-d$_6$): δ 7.97 (1H, d, J=7 Hz), 7.48 (1H, dd, J=3 and 5 Hz), 7.37–7.33 (5H, m), 7.28–7.26 (1H, m), 7.02 (1H, d, J=5 Hz), 5.90 (2H, brs), 5.09 (2H, s), 4.67–4.57 (1H, m), 4.25 (2H, s), 2.81 and 2.64 (each 1H, each dd, J=7 and 17 Hz).

Example 6(110)

N-benzyloxycarbonyl-3-amino-4-oxo-5-(5-(thiophen-3-yl) tetrazol-1-yl) pentanoic acid

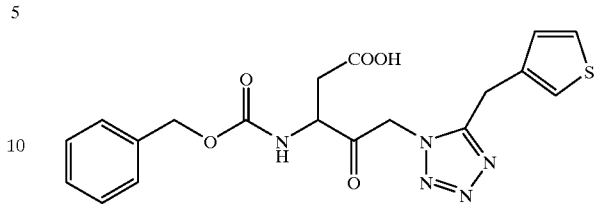

TLC: Rf 0.37 (chloroform:methanol:water=40:10:1); NMR (DMSO-d$_6$): δ 8.06 (1H, d, J=7 Hz), 7.48 (1H, dd, J=3 and 5 Hz), 7.40–7.31 (6H, m), 6.98 (1H, d, J=5 Hz), 5.72 (2H, brs), 5.10 (2H, s), 4.67–4.58 (1H, m), 4.14 (2H, s), 2.81 and 2.69 (each 1H, each dd, J=7 and 17 Hz).

Example 6(111)

N-benzyloxycarbonyl-3-amino-4-oxo-5-(5-(3-imidazol-1-ylpropyl) tetrazol-2-yl)pentanoic acid

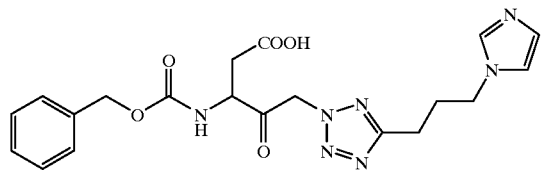

TLC: Rf 0.50 (chloroform:methanol:acetic acid=10:3:1); NMR (DMSO-d$_6$): δ 7.97 (1H, d, J=7.8 Hz), 7.62 (1H, brs), 7.40–7.30 (5H, m), 7.19 (1H, brs), 6.92 (1H, brs), 5.87 (2H, s), 5.09 (2H, s), 4.61 (1H, m), 4.04 (2H, t, J=7.0 Hz), 2.88–2.58 (4H, m), 2.14 (2H, m).

Example 6(112)

N-benzyloxycarbonyl-3-amino-4-oxo-5-(5-(3-imidazol-1-ylpropyl) tetrazol-1-yl)pentanoic acid

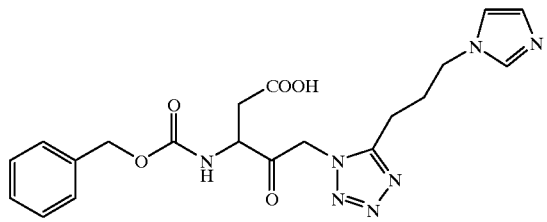

TLC: Rf 0.38 (chloroform:methanol:acetic acid=10:3:1); NMR (DMSO-d$_6$): δ 8.04 (1H, d, J=7.8 Hz), 7.62 (1H, brs), 7.40–7.30 (5H, m), 7.17 (1H, s), 6.89 (1H, s), 5.69 (2H, s), 5.10 (2H, s), 4.60 (1H, m), 4.10–3.98 (2H, m), 2.90–2.62 (4H, m), 2.10 (2H, m).

Example 6(113)

N-benzyloxycarbonyl-3-amino-4-oxo-5-(5-(2,3-dichlorophenylthio) tetrazol-2-yl)pentanoic acid

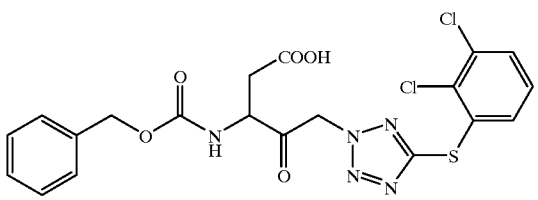

TLC: Rf 0.19 (chloroform:methanol:acetic acid=36:1:1);
NMR (DMSO-d$_6$): δ 7.99 (1H, d, J=7.4 Hz), 7.64 (1H, d, J=8.0 Hz), 7.40–7.31 (6H, m), 7.24 (1H, d, J=8.0 Hz), 6.05 (2H, brs), 5.10 (2H, s), 4.70–4.60 (1H, m), 2.89–2.62 (2H, m).

Example 6(114)
N-benzyloxycarbonyl-3-amino-4-oxo-5-(5-(2,3-dichlorophenylthio) tetrazol-1-yl)pentanoic acid

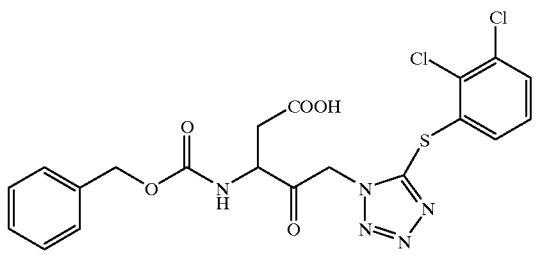

TLC: Rf 0.16 (chloroform:methanol:acetic acid=36:1:1);
NMR (DMSO-d$_6$): δ 8.05 (1H, d, J=7.6 Hz), 7.71–7.66 (1H, m), 7.41–7.18 (7H, m), 5.81 (2H, brs), 5.09 (2H, s), 4.69–4.59 (1H, m), 2.88–2.63 (2H, m).

Example 6(115)
N-benzyloxycarbonyl-3-amino-4-oxo-5-(5-(2,6-dimethylphenylthio) tetrazol-2-yl)pentanoic acid

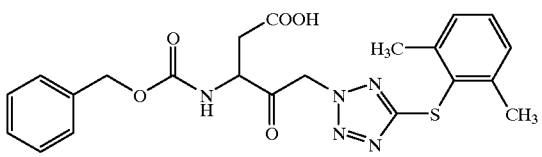

TLC: Rf 0.48 (chloroform:methanol:acetic acid=46:3:1);
NMR (DMSO-d$_6$): δ 12.40 (1H, brs), 7.92 (1H, d, J=8.8 Hz), 7.40–7.05 (8H, m) 5.90 (2H, brs), 5.05 (2H, s), 4.70–4.50 (1H, m), 2.84–2.50 (2H, m), 2.40 (6H, s).

Example 6(116)
N-benzyloxycarbonyl-3-amino-4-oxo-5-(5-(2,6-dimethylphenylthio) tetrazol-1-yl)pentanoic acid

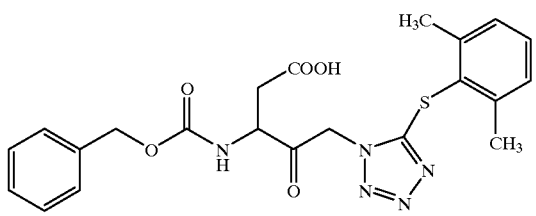

TLC: Rf 0.41 (chloroform:methanol:acetic acid=46:3:1);
NMR (DMSO-d$_6$): δ 8.04 (1H, d, J=8.6 Hz), 7.42–7.10 (8H, m) 5.70 (2H, brs), 5.11 (2H, s), 4.70–4.52 (1H, m), 2.91–2.60 (2H, m), 2.35 (6H, s).

Example 6(117)
N-benzyloxycarbonyl-3-amino-4-oxo-5-(5-(2-chloro-4-t-butylphenylthio)tetrazol-2-yl)pentanoic acid

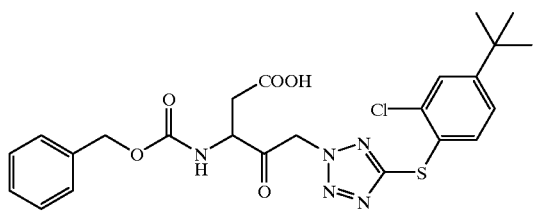

TLC: Rf 0.25 (chloroform:methanol:acetic acid=46:3:1);
NMR (DMSO-d$_6$): δ 7.98 (1H, d, J=8.0 Hz), 7.56 (1H, d, J=1.6 Hz), 7.43–7.20 (7H, m) 6.02 (2H, brs), 5.07 (2H, s), 4.70–4.55 (1H, m), 2.80 (1H, dd, J=16.6, 5.7 Hz), 2.62 (1H, dd, J=16.6, 6.6 Hz), 1.26 (9H, s).

Example 6(118)
N-benzyloxycarbonyl-3-amino-4-oxo-5-(5-(2-chloro-4-t-butylphenylthio)tetrazol-1-yl)pentanoic acid

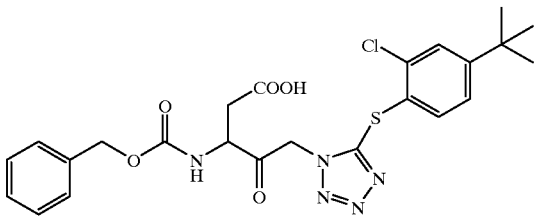

TLC: Rf 0.19 (chloroform:methanol:acetic acid=46:3:1);
NMR (DMSO-d$_6$): δ 8.10–7.95 (1H, m), 7.58 (1H, d, J=1.4 Hz), 7.53–7.21 (7H, m) 5.76 (2H, brs), 5.10 (2H, s), 4.70–4.54 (1H, m), 2.90–2.60 (2H, m), 1.29 (9H, s).

Example 6(119)
N-benzyloxycarbonyl-3-amino-4-oxo-5-(5-(2,2,6,6-tetramethylpiperidin-2-ylmethyl)tetrazol-2-yl)pentanoic acid•hydrochloric acid salt

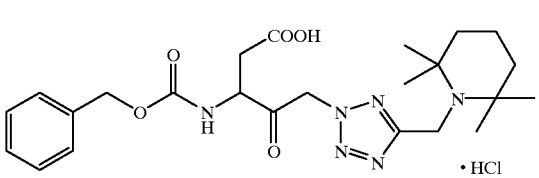

TLC: Rf 0.45 (chloroform:methanol:acetic acid=10:2:1);
NMR (DMSO-d$_6$): δ 9.32 (1H, brs), 8.08 (1H, d, J=7.6 Hz), 7.40–7.30 (5H, m), 6.07 (2H, s), 5.10 (2H, s), 4.80–4.58 (3H, m), 2.92–2.58 (2H, m), 2.10–1.40 (18H, m).

Example 6(120)
N-benzyloxycarbonyl-3-amino-4-oxo-5-(5-(2,2,6,6-tetramethylpiperidin-1-ylmethyl)tetrazol-1-yl)pentanoic acid•hydrochloric acid salt

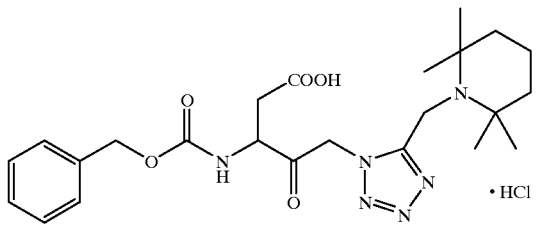

TLC: Rf 0.66 (chloroform:methanol:acetic acid=10:2:1); NMR (DMSO-d$_6$): δ 8.36 (1H, d, J=7.4 Hz), 7.40–7.24 (5H, m), 6.20–5.90 (2H, m), 5.11 (2H, s), 4.80–4.60 (3H, m), 2.96–2.60 (2H, m), 2.00–1.20 (18H, m).

Example 6(121)
N-benzyloxycarbonyl-3-amino-4-oxo-5-(5-(N-phenyl-N-methylamino) tetrazol-2-yl)pentanoic acid•hydrochloric acid salt

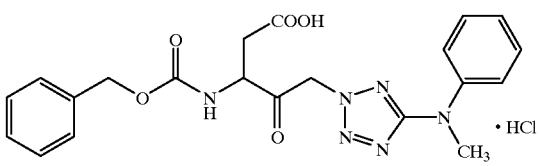

TLC: Rf 0.25 (chloroform:methanol:water=90:10:1); NMR (DMSO-d$_6$): δ 7.96 (1H, d, J=8 Hz), 7.48–7.32 (9H, m), 7.08 (1H, t, J=7 Hz), 5.81 (2H, s), 5.09 (2H, s), 4.67–4.57 (1H, m), 3.49 (3H, s), 2.82 and 2.62 (each 1H, each dd, J=7 and 17 Hz).

Example 6(122)
N-benzyloxycarbonyl-3-amino-4-oxo-5-(5-(N-phenyl-N-methylamino) tetrazol-1-yl)pentanoic acid•hydrochloric acid salt

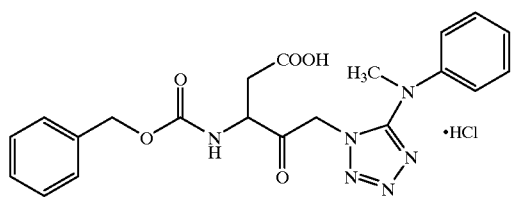

TLC: Rf 0.19 (chloroform:methanol:acetic acid= 90:10:1); NMR (DMSO-d$_6$): δ 7.79 (1H, d, J=8 Hz), 7.42–7.28 (7H, m), 7.17–7.09 (1H, m), 6.96 (2H, d, J=8 Hz), 5.06 (2H, q-like), 5.01 (2H, s), 4.26–4.16 (1H, m), 3.30 (3H, s), 2.64–2.37 (2H, m).

Example 6(123)
N-benzyloxycarbonyl-3-amino-4-oxo-5-(5-(2,6-diisopropylphenylthio) tetrazol-2-yl)pentanoic acid

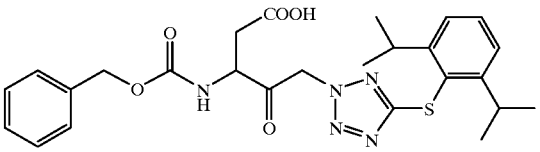

TLC: Rf 0.24 (chloroform:methanol:water=90:10:1); NMR (DMSO-d$_6$): δ 7.90 (1H, d, J=8 Hz), 7.51–7.27 (8H, m), 5.87 (2H, brs), 5.07 (2H, s), 4.62–4.52 (1H, m), 3.75–3.62 (2H, m), 2.97–2.62 (2H, m), 1.13 (12H, d, J=7 Hz).

Example 6(124)
N-benzyloxycarbonyl-3-amino-4-oxo-5-(5-(2,6-diisopropylphenylthio) tetrazol-1-yl)pentanoic acid

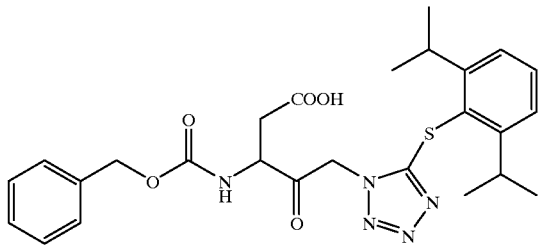

TLC: Rf 0.21 (chloroform:methanol:water=90:10:1); NMR (DMSO-d$_6$): δ 8.06 (1H, d, J=7 Hz), 7.55–7.28 (8H, m), 5.73 (2H, brs), 5.11 (2H, s), 4.71–4.61 (1H, m), 3.60–3.42 (2H, m), 3.04–2.66 (2H, m), 1.11 (12H, d, J=7 Hz).

Example 6(125)
N-benzyloxycarbonyl-3-amino-4-oxo-5-(5-(2-methyl-4-t-butylphenylthio)tetrazol-2-yl)pentanoic acid

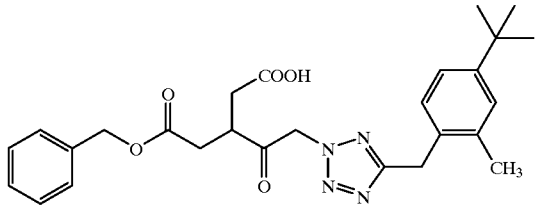

TLC: Rf 0.40 (chloroform:methanol:acetic acid=46:3:1); NMR (DMSO-d$_6$): δ 12.47 (1H, brs), 7.98 (1H, J=7.6 Hz), 7.60–7.10 (8H, m) 5.98 (2H, s), 5.08 (2H, s), 4.70–4.50 (1H, m), 2.81 (1H, dd, J=16.8, 5.8 Hz), 2.62 (1H, dd, J=16.8, 6.8 Hz), 2.36 (3H, s), 1.28 (9H, s).

Example 6(126)
N-benzyloxycarbonyl-3-amino-4-oxo-5-(5-(2-methyl-4-t-butylphenylthio)tetrazol-1-yl)pentanoic acid

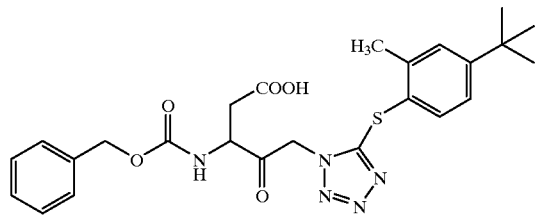

TLC: Rf 0.32 (chloroform:methanol:acetic acid=46:3:1); NMR (DMSO-d$_6$): δ 12.57 (1H, brs), 8.08 (1H, d, J=7.4 Hz), 7.60–7.10 (8H, m) 5.75 (2H, s), 5.11 (2H, s), 4.70–4.55 (1H, m), 2.86 (1H, dd, J=17.6, 5.8 Hz), 2.68 (1H, dd, J=17.6, 7.0 Hz), 2.35 (3H, s), 1.28 (9H, s).

Example 6(127)
N-benzyloxycarbonyl-3-amino-4-oxo-5-(5-(2,6-dimethyl-4-t-butylphenylthio)tetrazol-2-yl)pentanoic acid

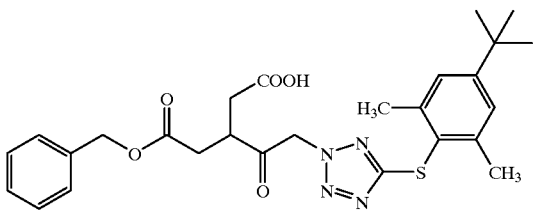

TLC: Rf 0.48 (chloroform:methanol:acetic acid=47:2:1); NMR (DMSO-d$_6$): δ 12.48 (1H, brs), 7.94 (1H, d, J=7.6 Hz), 7.35 (5H, brs), 7.24 (2H, s), 5.92 (2H, s), 5.07 (2H, s), 4.70–4.50 (1H, m), 2.90–2.50 (2H, m), 2.41 (6H, s), 1.28 (9H, s).

Example 6(128)

N-benzyloxycarbonyl-3-amino-4-oxo-5-(5-(2,6-dimethyl-4-t-butylphenylthio)tetrazol-1-yl)pentanoic acid

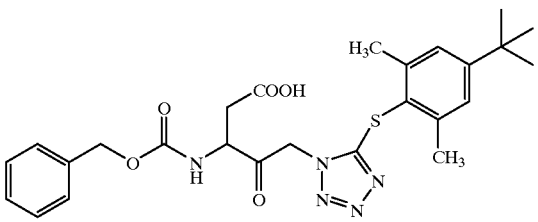

TLC: Rf 0.43 (chloroform:methanol:acetic acid=47:2:1); NMR (DMSO-d$_6$): δ 12.50 (1H, brs), 8.11–7.90 (1H, m), 7.46–7.20 (5H, m), 7.25 (2H, s), 5.71 (2H, s), 5.11 (2H, s), 4.72–4.53 (1H, m), 2.93–2.57 (2H, m), 2.35 (6H, s), 1.29 (9H, s).

Example 6(129)

N-benzyloxycarbonyl-3-amino-4-oxo-5-(5-(2,6-dimethyl-4-dimethylaminophenylthio)tetrazol-2-yl)pentanoic acid•hydrochloric acid salt

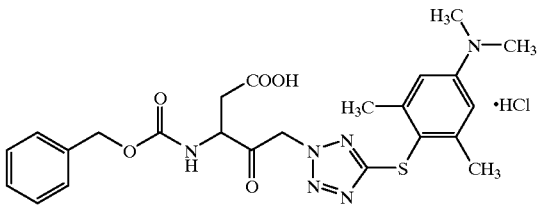

TLC: Rf 0.39 (chloroform:methanol:water=50:10:1); NMR (DMSO-d$_6$): δ 7.99 (1H, d, J=7.8 Hz), 7.40–7.30 (5H, m), 6.79 (2H, s), 5.92 (2H, s), 5.07 (2H, s), 4.60 (1H, m), 2.96 (6H, s), 2.88–2.54 (2H, m), 2.38 (6H, s).

Example 6(130)

N-benzyloxycarbonyl-3-amino-4-oxo-5-(5-(2,6-dimethyl-4-dimethylaminophenylthio)tetrazol-1-yl)pentanoic acid•hydrochloric acid salt

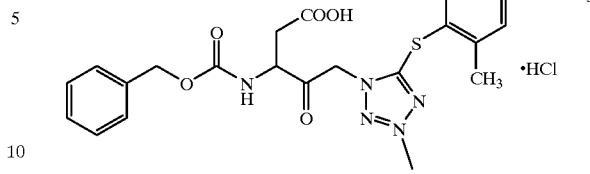

TLC: Rf 0.36 (chloroform:methanol:water=50:10:1); NMR (DMSO-d$_6$): δ 8.10 (1H, d, J=7.8 Hz), 7.40–7.26 (5H, m), 6.74 (2H, s), 5.69 (2H, s), 5.11 (2H, s), 4.62 (1H, m), 2.97 (6H, s), 2.92–2.62 (2H, m), 2.30 (6H, s).

Example 6(131)

N-benzyloxycarbonyl-3-amino-4-oxo-5-(5-(benzoimizazol-2-ylmethyl) tetrazol-2-yl)pentanoic acid•hydrochloric acid salt

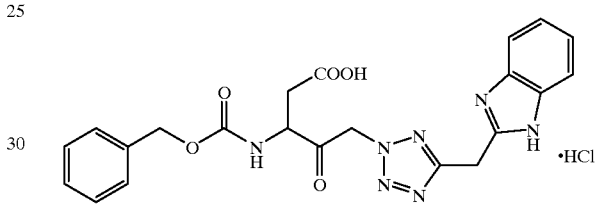

TLC: Rf 0.30 (chloroform:methanol:acetic acid=20:1:1); NMR (DMSO-d$_6$): δ 8.28–8.01 (1H, m), 7.62 (2H, dd, J=5.8 and 3.0 Hz), 7.50–7.28 (7H, m), 5.97 (2H, brs), 5.02 (2H, s), 4.67 (3H, brs), 2.92–2.54 (2H, m).

Example 6(132)

N-benzyloxycarbonyl-3-amino-4-oxo-5-(5-(benzoimizazol-2-ylmethyl) tetrazol-1-yl)pentanoic acid•hydrochloric acid salt

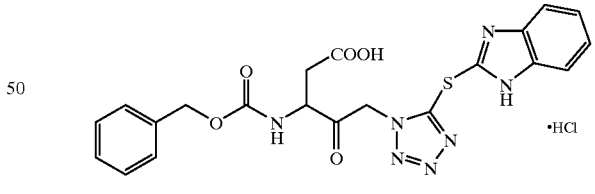

TLC: Rf 0.20 (chloroform:methanol:acetic acid=20:1:1); NMR (DMSO-d$_6$): δ 8.04 (1H, d, J=7.6 Hz), 7.79 (2H, dd, J=6.0 and 3.2 Hz), 7.51 (2H, dd, J=6.0 and 3.2 Hz), 7.42–7.20 (5H, m), 6.04 (2H, s), 5.08 (2H, s), 4.95 (2H, s), 4.77–4.99 (1H, m), 2.84 (1H, dd, J=16.8 and 6.4 Hz), 2.65 (1H, dd, J=16.8 and 6.8 Hz).

Example 6(133)

N-benzyloxycarbonyl-3-amino-4-oxo-5-(5-(4-isopropylphenylthio) tetrazol-2-yl)pentanoic acid

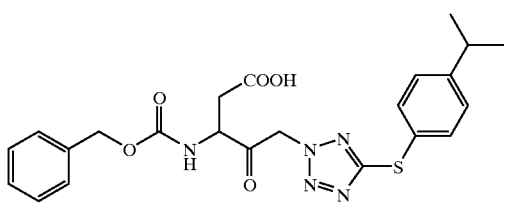

TLC: Rf 0.34 (chloroform:methanol:acetic acid=36:1:1); NMR (DMSO-d$_6$): δ 7.99 (1H, d, J=6.4 Hz), 7.47–7.25 (9H, m), 5.99 (2H, brs), 5.09 (2H, s), 4.69–4.58 (1H, m), 2.98–2.60 (3H, m), 1.20 (6H, d, J=6.8 Hz).

Example 6(134)
N-benzyloxycarbonyl-3-amino-4-oxo-5-(5-(4-isopropylphenylthio) tetrazol-1-yl)pentanoic acid

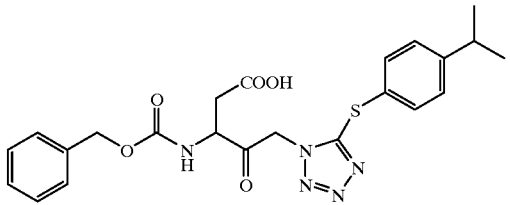

TLC: Rf 0.27 (chloroform:methanol:acetic acid=36:1:1); NMR (DMSO-d$_6$): δ 8.05 (1H, d, J=7.0 Hz), 7.49–7.28 (9H, m), 5.72 (2H, brs), 5.12 (2H, s), 4.69–4.59 (1H, m), 2.98–2.63 (3H, m), 1.21 (6H, d, J=6.8 Hz).

Example 6(135)
N-benzyloxycarbonyl-3-amino-4-oxo-5-(5-(benzothiazol-2-ylmethyl) tetrazol-2-yl)pentanoic acid

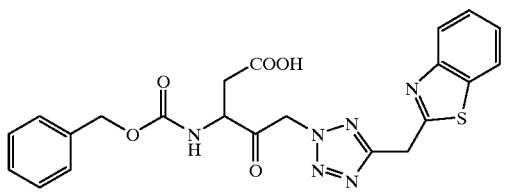

TLC: Rf 0.15 (chloroform:methanol:acetic acid=50:1:1); NMR (DMSO-d$_6$): δ 13.80–11.40 (1H, br), 8.20–7.86 (3H, m), 7.62–7.22 (7H, m), 6.29–5.68 (2H, brs), 5.09 (2H, s), 4.87 (2H, s), 4.78–4.46 (1H, m), 2.82 (1H, dd, J=17.0 and 6.5 Hz), 2.65 (1H, dd, J=17.0 and 7.0 Hz).

Example 6(136)
N-benzyloxycarbonyl-3-amino-4-oxo-5-(5-(benzothiazol-2-ylmethyl) tetrazol-1-yl)pentanoic acid

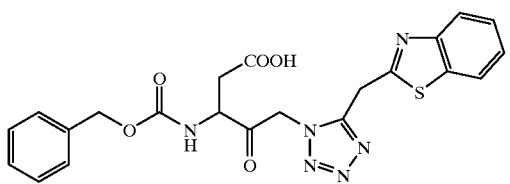

TLC: Rf 0.10 (chloroform:methanol:acetic acid=50:1:1); NMR (DMSO-d$_6$): δ 13.50–11.40 (1H, br), 8.19–7.84 (3H, m), 7.70–7.18 (7H, m), 6.15–5.60 (2H, brs), 5.03 (2H, s), 4.98–4.50 (3H, m), 2.90–2.57 (2H, m).

Example 6(137)
N-benzyloxycarbonyl-3-amino-4-oxo-5-(5-(thiazol-2-ylthio)tetrazol-2-yl)pentanoic acid

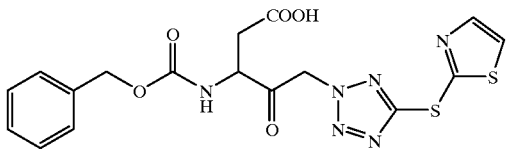

TLC: Rf 0.29 (chloroform:methanol:water=40:10:1); NMR (DMSO-d$_6$): δ 7.89 (2H, m), 7.78 (1H, m), 7.36 (5H, s), 6.07 (2H, s), 5.08 (2H, s), 4.55 (1H, m), 2.66 (2H, m).

Example 6(138)
N-benzyloxycarbonyl-3-amino-4-oxo-5-(5-(thiazol-2-ylthio)tetrazol-1-yl)pentanoic acid

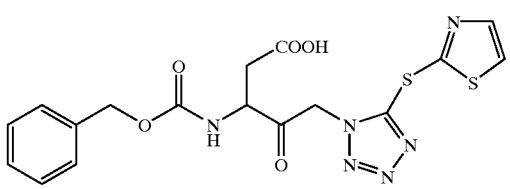

TLC: Rf 0.24 (chloroform:methanol:water=40:10:1); NMR (DMSO-d$_6$): δ 7.89 (2H, m), 7.73 (1H, m), 7.35 (5H, s), 5.87 (2H, s), 5.07 (2H, s), 4.53 (1H, m), 2.61 (2H, m).

Example 6(139)
N-benzyloxycarbonyl-3-amino-4-oxo-5-(5-(2,4,6-trichlorophenylthio) tetrazol-2-yl)pentanoic acid

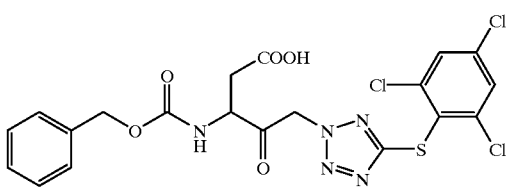

TLC: Rf 0.24 (chloroform:methanol:acetic acid=48:1:1); NMR (DMSO-d$_6$): δ 12.49 (1H, brs), 8.05–7.84 (3H, m), 7.45–7.20 (5H, m), 5.98 (2H, s), 5.07 (2H, s), 4.70–4.50 (1H, m), 2.90–2.50 (2H, m).

Example 6(140)
N-benzyloxycarbonyl-3-amino-4-oxo-5-(5-(2,4,6-trichlorophenylthio) tetrazol-1-yl)pentanoic acid

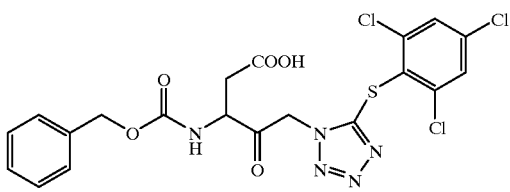

TLC: Rf 0.17 (chloroform:methanol:acetic acid=48:1:1); NMR (DMSO-d$_6$): δ 12.57 (1H, brs), 8.10–8.00 (1H, m), 7.93 (2H, s), 7.43–7.20 (5H, m), 5.80 (2H, s), 5.10 (2H, s), 4.80–4.55 (1H, m), 2.93–2.65 (2H, m).

Example 6(141)

N-benzyloxycarbonyl-3-amino-4-oxo-5-(5-(2,6-dichloro-4-(1,1-dimethylpropyl)phenylthio)tetrazol-2-yl)pentanoic acid

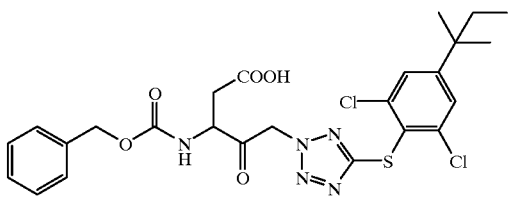

TLC: Rf 0.26 (chloroform:methanol:acetic acid=48:1:1); NMR (DMSO-$d_6$): δ 12.50 (1H, brs), 7.96 (1H, d, J=8.5 Hz), 7.59 (2H, s), 7.35 (5H, s), 5.98 (2H, s), 5.07 (2H, s), 4.70–4.52 (1H, m), 2.90–2.50 (2H, m), 1.63 (2H, q, J=7.5 Hz), 1.25 (6H, s), 0.64 (3H, t, J=7.5 Hz).

Example 6(142)

N-benzyloxycarbonyl-3-amino-4-oxo-5-(5-(2,6-dichloro-4-(1,1-dimethylpropyl)phenylthio)tetrazol-1-yl)pentanoic acid

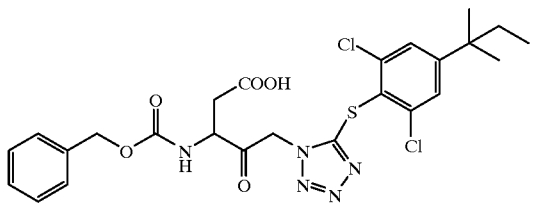

TLC: Rf 0.17 (chloroform:methanol:acetic acid=48:1:1); NMR (DMSO-$d_6$): δ 12.56 (1H, brs), 8.09 (1H, d, J=8.5 Hz), 7.59 (2H, s), 7.42–7.08 (5H, s), 5.80 (2H, s), 5.10 (2H, s), 4.75–4.60 (1H, m), 2.90–2.50 (2H, m), 1.63 (2H, q, J=7.5 Hz), 1.25 (6H, s), 0.64 (3H, t, J=7.5 Hz).

Example 6(143)

N-benzyloxycarbonyl-3-amino-4-oxo-5-(5-(1,1-diphenylmethyl) tetrazol-2-yl)pentanoic acid

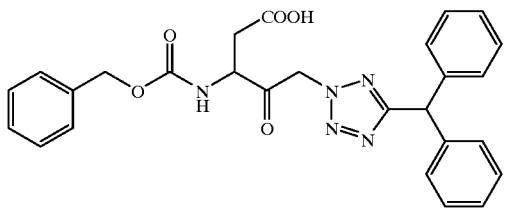

TLC: Rf 0.29 (chloroform:methanol:acetic acid=38:1:1); NMR (DMSO-$d_6$): δ 7.94 (1H, d, J=7.0 Hz), 7.50–7.12 (15H, m), 5.93 (3H, m), 5.08 (2H, s), 4.72–4.51 (1H, m), 2.92–2.53 (2H, m).

Example 6(144)

N-benzyloxycarbonyl-3-amino-4-oxo-5-(5-(1,1-diphenylmethyl) tetrazol-1-yl)pentanoic acid

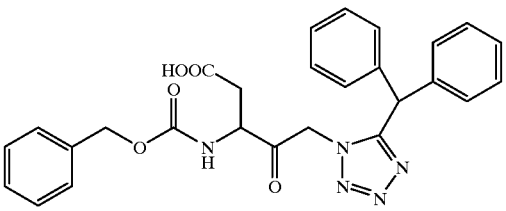

TLC: Rf 0.16 (chloroform:methanol:acetic acid=38:1:1); NMR (DMSO-$d_6$): δ 8.05 (1H, d, J=7.0 Hz,), 7.53–7.08 (15H, m), 5.92–5.57 (3H, m), 5.10 (2H, s), 4.72–4.46 (1H, m), 2.94–2.55 (2H, m).

Example 6(145)

N-benzyloxycarbonyl-3-amino-4-oxo-5-(5-(2-chloro-4-fluorophenylthio)tetrazol-2-yl)pentanoic acid

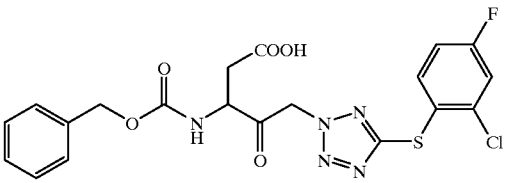

TLC: Rf 0.40 (chloroform:methanol:acetic acid=38:1:1); NMR (DMSO-$d_6$): δ 12.80–12.10 (1H, br), 7.99 (1H, d, J=8.0 Hz), 7.75–7.52 (2H, m), 7.52–7.18 (6H, m), 6.02 (2H, brs), 5.09 (2H, s), 4.80–4.45 (1H, m), 2.95–2.52 (2H, m).

Example 6(146)

N-benzyloxycarbonyl-3-amino-4-oxo-5-(5-(2-chloro-4-fluorophenylthio)tetrazol-1-yl)pentanoic acid

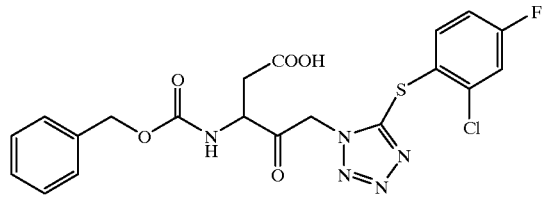

TLC: Rf 0.28 (chloroform:methanol:acetic acid=38:1:1); NMR (DMSO-$d_6$): δ 8.02 (1H, d, J=7.0 Hz,), 7.82–7.54 (2H, m), 7.54–7.16 (6H, m), 5.76 (2H, brs), 5.10 (2H, s), 4.75–4.45 (1H, m), 2.92–2.55 (2H, m).

Example 6(147)

N-benzyloxycarbonyl-3-amino-4-oxo-5-(5-(5-imidazol-1-ylpentyl) tetrazol-2-yl)pentanoic acid•hydrochloric acid salt

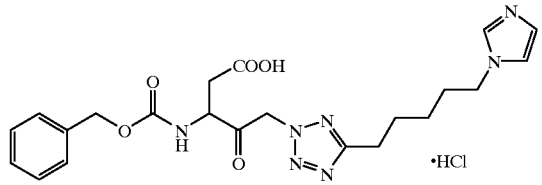

TLC: Rf 0.39 (chloroform:methanol:water=90:10:1); NMR (DMSO-$d_6$): δ 9.08 (1H, s), 8.15 (1H, d, J=7.0 Hz), 7.75 (1H, s), 7.59 (1H, s), 7.80–6.90 (5H, brs), 5.91 (2H, brs), 5.12 (2H, s), 4.88–4.51 (1H, m), 4.40–4.00 (2H, m), 3.05–2.60 (4H, m), 2.08–1.47 (4H, m), 1.47–1.04 (2H, m).

Example 6(148)
N-benzyloxycarbonyl-3-amino-4-oxo-5-(5-(5-imidazol-1-ylpentyl) tetrazol-1-yl)pentanoic acid•hydrochloric acid salt

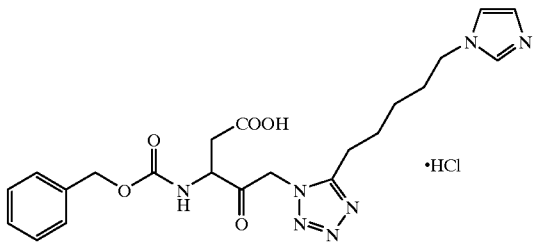

TLC: Rf 0.13 (chloroform:methanol=9:1); NMR (DMSO-d$_6$): δ 9.21 (1H, s), 8.14 (1H, d, J=7.0 Hz), 7.79 (1H, s), 7.67 (1H, s), 7.52–7.20 (5H, brs), 5.74 (2H, brs), 5.10 (2H, s), 4.79–4.48 (1H, m), 4.33–4.03 (2H, m), 3.00–2.56 (4H, m), 2.04–1.48 (4H, m), 1.48–1.08 (2H, m).

Example 6(149)
N-benzyloxycarbonyl-3amino-4-oxo-5-(5-(2-dimethylaminoethyl) tetrazol-2-yl)pentanoic acid•hydrochloric acid salt

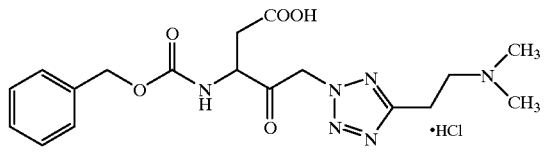

TLC: Rf 0.29 (chloroform:methanol:water=24:8:1); NMR (DMSO-d$_6$): δ 11.80–9.42 (1H, br), 8.26–8.05 (1H, m), 7.49–7.24 (5H, m), 5.98–5.70 (2H, br), 5.11 (2H, s), 4.80–4.50 (1H, m), 3.55–3.05 (4H, m), 2.96–2.60 (2H, m), 2.82 (6H, s).

Example 6(150)
N-benzyloxycarbonyl-3-amino-4-oxo-5-(5-(2-dimethylaminoehtyl)tetrazol-1-yl)pentanoic acid•hydrochloric acid salt

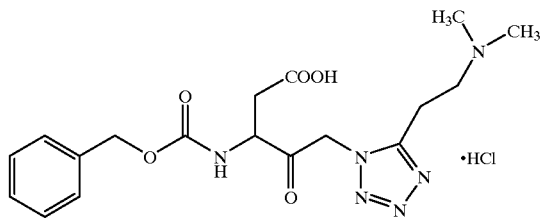

TLC: Rf 0.18 (chloroform:methanol:water=24:8:1); NMR (DMSO-d$_6$): δ 13.30–11.65 (1H, br), 11.10–10.60 (1H, br), 8.05 (1H, d, J=8.0 Hz), 7.55–7.20 (5H, m), 5.99 (2H, s), 5.10 (2H, s), 4.70–4.50 (1H, m), 3.60–3.30 (4H, m), 2.96–2.55 (2H, m), 2.82 (6H, s).

Example 6(151)
N-benzyloxycarbonyl-3-amino-4-oxo-5-(5-(4-(4-fluorophenyl)thiazol-2-ylmethyl)tetrazol-2-yl)pentanoic acid

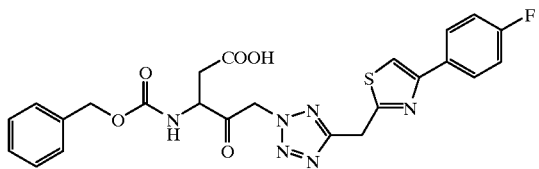

TLC: Rf 0.28 (chloroform:methanol:acetic acid=38:1:1); NMR (DMSO-d$_6$): δ 13.40–11.50 (1H, br), 8.04 (1H, s), 8.19–7.94 (3H, m), 7.48–7.14 (7H, m), 6.00 (2H, brs), 5.09 (2H, s), 4.77 (2H, s), 4.80–4.47 (1H, m), 2.94–2.53 (2H, m).

Example 6(152)
N-benzyloxycarbonyl-3-amino-4-oxo-5-(5-(4-(4-fluorophenyl)thiazol-2-ylmethyl)tetrazol-1-yl)pentanoic acid

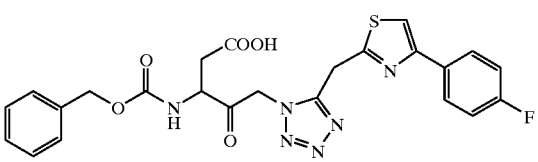

TLC: Rf 0.21 (chloroform:methanol:acetic acid=38:1:1); NMR (DMSO-d$_6$): δ 8.07 (1H, s), 8.24–7.80 (3H, m), 7.46–7.15 (7H, m), 5.92 (2H, brs), 5.04 (2H, s), 4.84–4.51 (3H, m), 2.93–2.55 (2H, m).

Example 6(153)
N-benzyloxycarbonyl-3-amino-4-oxo-5-(5-(4-(4-chlorophenyl)thiazol-2-ylmethyl)tetrazol-2-yl)pentanoic acid

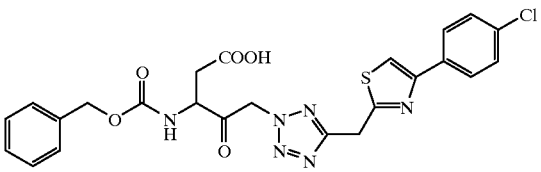

TLC: Rf 0.20 (chloroform:methanol:acetic acid=50:1:1); NMR (DMSO-d$_6$): δ 13.10–11.30 (1H, br), 8.11 (1H, s), 8.12–7.80 (3H, m), 7.58–7.20 (7H, m), 6.01 (2H, brs), 5.09 (2H, s), 4.78 (2H, s), 4.77–4.46 (1H, m), 2.92–2.53 (2H, m).

Example 6(154)
N-benzyloxycarbonyl-3-amino-4-oxo-5-(5-(4-(4-chlorophenyl)thiazol-2-ylmethyl)tetrazol-1-yl)pentanoic acid

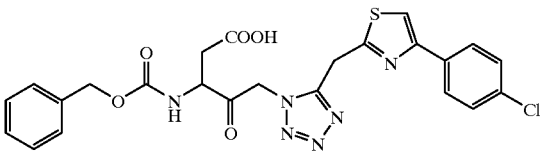

TLC: Rf 0.16 (chloroform:methanol:acetic acid=50:1:1); NMR (DMSO-d$_6$): δ 12.90–11.20 (1H, br), 8.15 (1H, s), 8.11 (1H, d, J=8.0 Hz), 7.93 (2H, d, J=8.5 Hz), 7.48 (2H, d, J=8.5 Hz), 7.44–7.16 (5H, m), 5.92 (2H, brs), 5.04 (2H, s), 4.87–4.50 (3H, m), 2.92–2.58 (2H, m).

Example 6(155)

N-benzyloxycarbonyl-3-amino-4-oxo-5-(5-(4-(3-nitrophenyl)thiazol-2-ylmethyl)tetrazol-2-yl)pentanoic acid

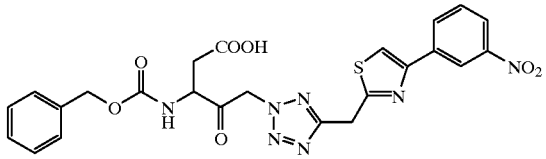

TLC: Rf 0.28 (chloroform:methanol:acetic acid=50:1:1); NMR (DMSO-$d_6$): δ 13.30–11.70 (1H, br), 8.74 (1H, t, J=2.0 Hz), 8.40 (1H, s), 8.46–8.29 (1H, m), 8.27–8.10 (1H, m), 8.09–7.91 (1H, m), 7.74 (1H, t, J=8.0 Hz), 7.50–7.15 (5H, m), 6.00 (2H, brs), 5.09 (2H, s), 4.83 (2H, s), 4.78–4.50 (1H, m), 2.94–2.55 (2H, m).

Example 6(156)

N-benzyloxycarbonyl-3-amino-4-oxo-5-(5-(4-(3-nitrophenyl)thiazol-2-ylmethyl)tetrazol-1-yl)pentanoic acid

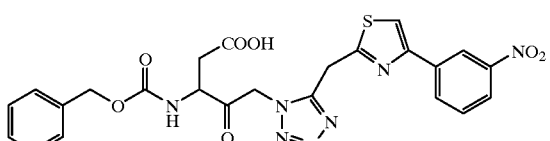

TLC: Rf 0.13 (chloroform:methanol:acetic acid=50:1:1); NMR (DMSO-$d_6$): δ 8.72 (1H, t, J=2.0 Hz), 8.43 (1H, s), 8.45–8.29 (1H, m), 8.25–8.02 (2H, m), 7.73 (1H, t, J=8.0 Hz), 7.50–7.12 (5H, m), 5.90 (2H, brs), 5.05 (2H, s), 4.90–4.50 (3H, m), 2.95–2.55 (2H, m).

Example 6(157)

N-benzyloxycarbonyl-3-amino-4-oxo-5-(5-(4-trifluoromethylcarbonylaminophenylthio)tetrazol-2-yl)pentanoic acid

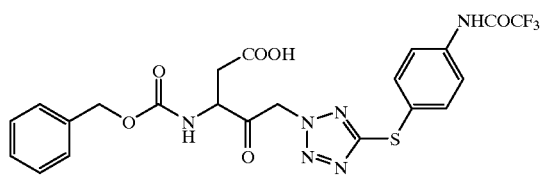

TLC: Rf 0.40 (chloroform:methanol:acetic acid=18:1:1); NMR (DMSO-$d_6$): δ 12.10–10.50 (1H, br), 7.90 (1H, d, J=7.2 Hz), 7.75 (2H, d, J=8.8 Hz), 7.55 (2H, d, J=8.8 Hz), 7.48–7.38 (6H, m), 5.94 (2H, brs), 5.09 (2H, s), 4.70–4.47 (1H, m), 2.90–2.53 (2H, m).

Example 6(158)

N-benzyloxycarbonyl-3-amino-4-oxo-5-(5-(4-trifluoromethylcarbonylaminophenylthio)tetrazol-1-yl)pentanoic acid

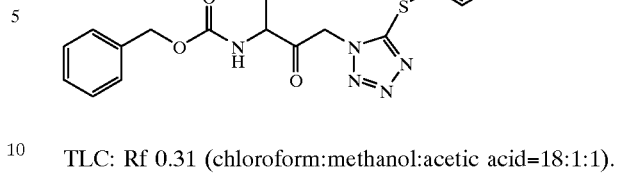

TLC: Rf 0.31 (chloroform:methanol:acetic acid=18:1:1).

Example 6(159)

N-benzyloxycarbonyl-3-amino-4-oxo-5-(5-(imizazol-4-ylmethyl) tetrazol-2-yl)pentanoic acid•hydrochloric acid salt

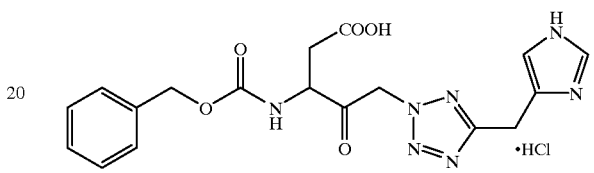

TLC: Rf 0.37 (chloroform:methanol:acetic acid=10:3:1); NMR (DMSO-$d_6$): δ 9.07 (1H, s), 8.02 (1H, d, J=8.6 Hz), 7.51 (1H, s), 7.40–7.30 (5H, m), 5.98 (2H, s), 5.09 (2H, s), 4.62 (1H, m), 4.43 (2H, s), 2.90–2.60 (2H, m).

Example 6(160)

N-benzyloxycarbonyl-3-amino-4-oxo-5-(5-(imizazol-4-ylmethyl) tetrazol-1-yl)pentanoic acid•hydrochloric acid salt

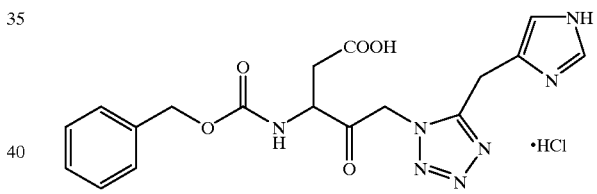

TLC: Rf 0.40 (chloroform:methanol:acetic acid=10:3:1); NMR (DMSO-$d_6$): δ 9.04 (1H, s), 8.13 (1H, d, J=8.6 Hz), 7.52 (1H, s), 7.40–7.30 (5H, m), 5.86 (2H, brs), 5.11 (2H, s), 4.67 (1H, m), 4.31 (2H, s), 2.94≧2.84 (2H, m).

Example 7

N-benzyloxycarbonyl-3-amino-4-oxo-5-(5-(carboxymethyl)tetrazol-2-yl)pentanoic acid

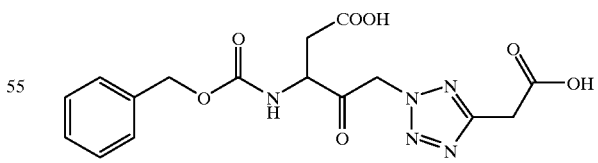

To a solution of the compound prepared in example 5(18) (59 mg) in dimethoxyethane (1 ml) was added a 1N aqueous solution of sodium hydroxide (0.36 ml). The reaction mixture was stirred for 4 h at room temperature. The reaction mixture was quenched by addition of a 1N aqueous solution of hydrochloric acid, and extracted with ethyl acetate. The extract was washed with water and a saturated aqueous solution of sodium chloride, dried over anhydrous sodium sulfate and concentrated. The residue was purified by column chromatography on silica gel (chloroform:methanol:acetic acid=18:1:1) to give the compound of the present invention (32 mg) having the following physical data.

TLC: Rf 0.32 (chloroform:ethanol:acetic acid=8:1:1); NMR (DMSO-$d_6$): δ 7.99 (1H, m), 7.42–7.24 (5H, m), 5.97 (2H, brs), 5.09 (2H, s), 4.62 (1H, m), 3.94 (2H, s), 2.91–2.54 (2H, m).

EXAMPLES 7(1)–7(3)

By the same procedure as provided in example 7, using the compounds prepared in examples 5(21), 5(30) or 5(31) instead of the compound prepared in example 5(18), compounds of the present invention having the following physical data were obtained.

Example 7(1)
N-benzyloxycarbonyl-3-amino-4-oxo-5-(5-(carboxymethyl)tetrazol-1-yl)pentanoic acid

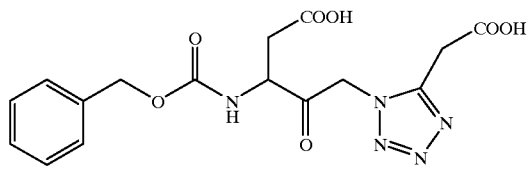

TLC: Rf 0.30 (chloroform:ethanol:acetic acid=4:1:1); NMR (DMSO-$d_6$): δ 8.07 (1H, m), 7.45–7.17 (5H, m), 5.73 (2H, br), 5.09 (2H, s), 4.63 (1H, m), 4.10–3.85 (2H, m), 2.88–2.58 (2H, m).

Example 7(2)
N-benzyloxycarbonyl-3-amino-4-oxo-5-(5-(2-carboxyethyl)tetrazol-2-yl)pentanoic acid

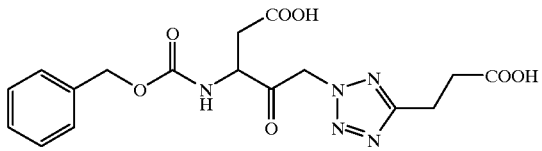

TLC: Rf 0.54 (chloroform:methanol:acetic acid=10:1:1); NMR (DMSO-$d_6$): δ 13.50–11.12 (2H, br), 7.96 (1H, d, J=7.6 Hz), 7.44–7.21 (5H, m), 5.89 (2H, brs), 5.10 (2H, s), 4.74–4.52 (1H, m), 3.07 (2H, t, J=7.2 Hz), 2.88–2.54 (4H, m).

Example 7(3)
N-benzyloxycarbonyl-3-amino-4-oxo-5-(5-(2-carboxyethyl)tetrazol-1-yl)pentanoic acid

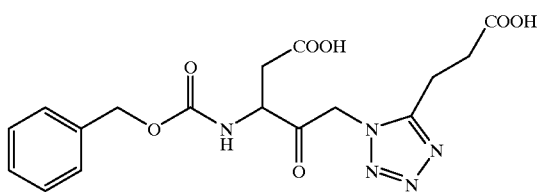

TLC: Rf 0.44 (chloroform:methanol:acetic acid=10:1:1); NMR (DMSO-$d_6$): δ 8.03–7.82 (1H, m), 7.52–7.17 (5H, m), 5.90–5.56 (2H, m), 5.10 (2H, s), 4.71–4.40 (1H, m), 3.05–2.80 (2H, m), 2.80–2.37 (4H, M).

Example 8(1)
N-benzyloxycarbonyl-3-amino-4-oxo-5-(5-ethylsulfinyltetrazol-1-yl) pentanoic acid•t-butylester

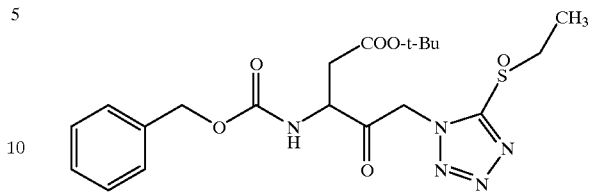

To a solution of the compound prepared in example 5(19) (50 mg) in methanol (2.1 ml) and water (0.4 ml) was added a 20% aqueous solution of titanium (III) chloride (0.2 ml). To the mixture was added dropwise a solution of a 30% aqueous solution of hydrogen peroxide (0.1 ml) in methanol (0.5 ml). The reaction mixture was stirred for 15 min at room temperature. The reaction mixture was quenched by addition of water, and extracted with chloroform. The extract was dried over anhydrous magnesium sulfate and concentrated. The residue was purified by column chromatography on silica gel (hexane:ethyl acetate=4:1→1:1) to give the compound of the present invention (38 mg) having the following physical data.

TLC: Rf 0.39 (hexane:ethyl acetate=1:1); NMR (CDCl$_3$): δ 7.39 (5H, m), 6.05–5.60 (3H, m), 5.19 (2H, s), 4.75 (1H, m), 3.35 (2H, m), 2.98 (1H, m), 2.74 (1H, m), 1.35 (12H, m).

EXAMPLES 8(2)–8(4)

By the same procedure as provided in example 8(1), using the compounds prepared in examples 5(20), 5(22) or 5(23) instead of the compound prepared in example 5(19), compounds of the present invention having the following physical data were obtained.

Example 8(2)
N-benzyloxycarbonyl-3-amino-4-oxo-5-(5-ethylsulfinyltetrazol-2-yl) pentanoic acid•t-butylester

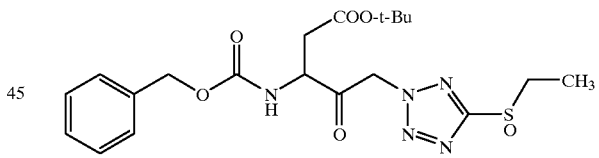

TLC: Rf 0.25 (hexane:ethyl acetate=1:1); NMR (CDCl$_3$): δ 7.39 (5H, m), 6.01 (1H, m), 5.88 (2H, m), 5.18 (2H, s), 4.69 (1H, m), 3.33 (2H, m), 3.03 (1H, m), 2.73 (1H, m), 1.38 (12H, m).

Example 8(3)
N-benzyloxycarbonyl-3-amino-4-oxo-5-(5-(4-chlorophenylsulfinylmethyl)tetrazol-2-yl)pentanoic acid•t-butylester

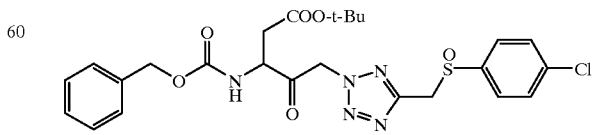

TLC: Rf 0.12 (hexane:ethyl acetate=3:2); NMR (CDCl$_3$): δ 7.40 (9H, m), 5.98 (1H, d, J=10.0 Hz), 5.82 (1H, m), 5.64

(1H, m), 5.18 (2H, s), 4.65 (1H, m), 4.44 (1H, d, J=17.5 Hz), 4.32 (1H, d, J=17.5 Hz), 3.01 (1H, m), 2.72 (1H, m), 1.42 (9H, m).

Example 8(4)
N-benzyloxycarbonyl-3-amino-4-oxo-5-(5-(4-chlorophenylsulfinylmethyl)tetrazol-1-yl)pentanoic acid•t-butylester

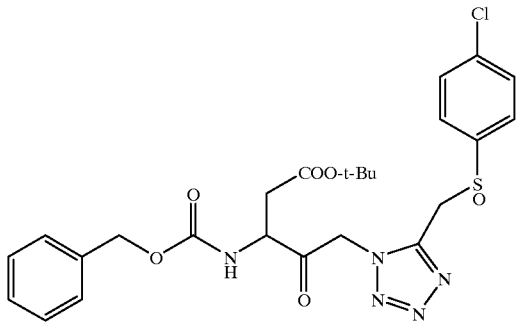

TLC: Rf 0.23 (hexane:ethyl acetate=3:2); NMR (CDCl$_3$): δ 7.40 (9H, m), 6.05–5.68 (3H, m), 5.20 (2H, s), 4.62 (1H, m), 4.40 (1H, m), 4.12 (1H, m), 3.06 (1H, m), 2.79 (1H, m), 1.42 and 1.38 (total 9H, each s).

Example 9(1)
N-benzyloxycarbonyl-3-amino-4-oxo-5-(5-ethylsulfonyltetrazol-1-yl) pentanoic acid•t-butylester

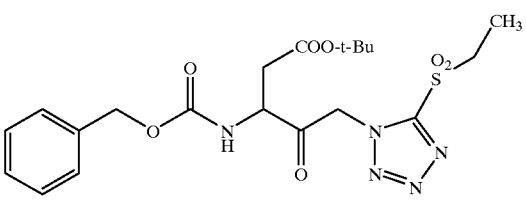

To a solution of the compound prepared in example 5(19) (50 mg) in dichloromethane (3 ml) and chloroform (3 ml) was added 80% m-chloroperbenzoic acid (48 mg) at 0° C. The reaction mixture was stirred for 18 h at room temperature. The reaction mixture was quenched by addition of water (10 ml), and extracted with chloroform. The extract was washed with a saturated aqueous solution of sodium hydrocarbonate, water and a saturated aqueous solution of sodium chloride, successively, dried over anhydrous magnesium sulfate and concentrated. The residue was purified by column chromatography on silica gel (hexane:ethyl acetate=4:1→1:1) to give the compound of the present invention (25 mg) having the following physical data.

TLC: Rf 0.69 (hexane:ethyl acetate=1:1); NMR (CDCl$_3$): δ 7.39 (5H, m), 6.01 (1H, m), 5.95 (1H, d, J=16 Hz), 5.74 (1H, d, J=16 Hz), 5.20 (2H, s), 4.73 (1H, m), 3.50 (2H, q, J=7 Hz), 3.00 (1H, dd, J=17.5, 5 Hz), 2.73 (1H, dd, J=17.5, 5 Hz), 1.42 (12H, m).

EXAMPLES 9(2)–9(4)

By the same procedure as provided in example 9(1), using the compounds prepared in examples 5(20), 5(22) or 5(23) instead of the compound prepared in example 5(19), compounds of the present invention having the following physical data were obtained.

Example 9(2)
N-benzyloxycarbonyl-3-amino-4-oxo-5-(5-ethylsulfonyltetrazol-2-yl) pentanoic acid•t-butylester

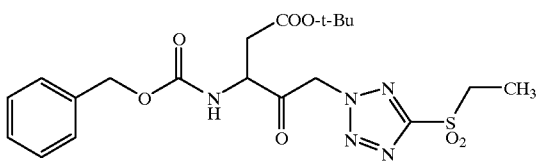

TLC: Rf 0.73 (hexane:ethyl acetate=1:1); NMR (CDCl$_3$): δ 7.40 (5H, m), 6.00 (1H, d, J=16 Hz), 5.95 (1H, m), 5.80 (1H, d, J=16 Hz), 5.18 (2H, s), 4.69 (1H, m), 3.46 (2H, q, J=7 Hz), 3.05 (1H, dd, J=17.5, 5 Hz), 2.73 (1H, dd, J=17.5, 5 Hz), 1.41 (12H, m).

Example 9(3)
N-benzyloxycarbonyl-3-amino-4-oxo-5-(5-(4-chlorophenylsulfonylmethyl)tetrazol-2-yl)pentanoic acid•t-butylester

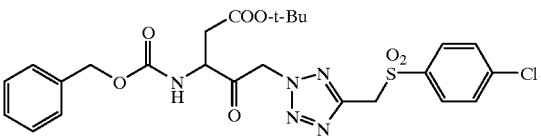

TLC: Rf 0.30 (hexane:ethyl acetate=3:2); NMR (CDCl$_3$): δ 7.68 (2H, d, J=9.0 Hz), 7.48 (2H, d, J=9.0 Hz), 7.40 (5H, m), 5.92 (1H, d, J=10.0 Hz), 5.88 (1H, d, J=17.5 Hz), 5.66 (1H, d, J=17.5 Hz), 5.20 (2H, s), 4.70 (2H, s), 4.65 (1H, m), 3.01 (1H, dd, J=17.5 Hz and 5.0 Hz), 2.72 (1H, dd, J=17.5 Hz and 5.0 Hz), 1.42 (9H, s).

Example 9(4)
N-benzyloxycarbonyl-3-amino-4-oxo-5-(5-(4-chlorophenylsulfonylmethyl)tetrazol-1-yl)pentanoic acid•t-butylester

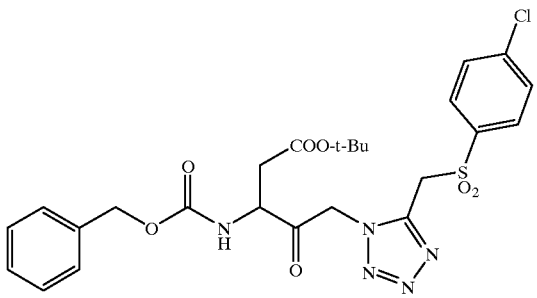

TLC: Rf 0.39 (hexane:ethyl acetate=3:2); NMR (CDCl$_3$): δ 7.60–7.30 (9H, m), 6.10–5.75 (3H, m), 5.20 (2H, s), 4.65 (3H, m), 3.10 (1H, dd, J=17.5 Hz and 5.0 Hz), 2.82 (1H, dd, J=17.5 Hz and 5.0 Hz), 1.42 (9H, s).

EXAMPLES 10(1)–10(8)

By the same procedure as provided in example 6(1), using the compounds prepared in examples 8(1)–8(4) or 9(1)–9(4), compounds of the present invention having the following physical data were obtained.

Example 10(1)
N-benzyloxycarbonyl-3-amino-4-oxo-5-(5-ethylsulfinyltetrazol-1-yl) pentanoic acid

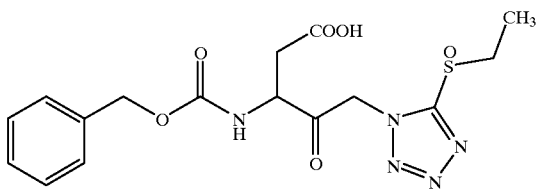

TLC: Rf 0.54 (chloroform:methanol:acetic acid=15:1:1); NMR (DMSO-d$_6$): δ 7.90 (1H, m), 7.35 (5H, m), 5.90 (2H, m), 5.10 (2H, s), 4.60 (1H, m), 3.35 (2H, m), 2.70 (2H, m), 1.20 (3H, m).

Example 10(2)
N-benzyloxycarbonyl-3-amino-4-oxo-5-(5-ethylsulfonyltetrazol-1-yl) pentanoic acid

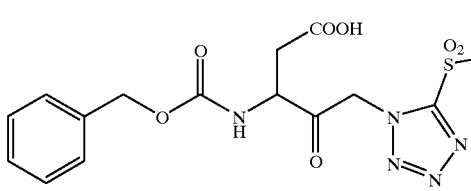

TLC: Rf 0.58 (chloroform:methanol:acetic acid=15:1:1); NMR (DMSO-d$_6$): δ 7.90 (1H, m), 7.38 (5H, m), 5.95 (2H, m), 5.10 (2H, s), 4.60 (1H, m), 3.70 (2H, m), 2.70 (2H, m), 1.25 (3H, m).

Example 10(3)
N-benzyloxycarbonyl-3-amino-4-oxo-5-(5-ethylsulfinyltetrazol-2-yl) pentanoic acid

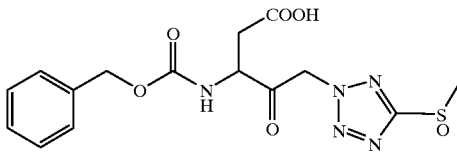

TLC: Rf 0.43 (chloroform:methanol:acetic acid=15:1:1); NMR (DMSO-d$_6$): δ 7.98 (1H, m), 7.35 (5H, m), 6.10 (2H, brs), 5.10 (2H, s), 4.63 (1H, m), 3.35 (2H, m), 2.70 (2H, m), 1.19 (3H, m).

Example 10(4)
N-benzyloxycarbonyl-3-amino-4-oxo-5-(5-ethylsulfonyltetrazol-2-yl) pentanoic acid

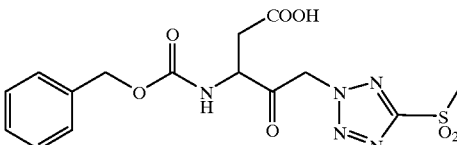

TLC: Rf 0.49 (chloroform:methanol:acetic acid=15:1:1); NMR (DMSO-d$_6$): δ 8.00 (1H, m), 7.35 (5H, m), 6.15 (2H, brs), 5.10 (2H, s), 4.65 (1H, m), 3.64 (2H, m), 2.74 (2H, m), 1.21 (3H, m).

Example 10(5)
N-benzyloxycarbonyl-3-amino-4-oxo-5-(5-(4-chlorophenylsulfinylmethyl)tetrazol-2-yl)pentanoic acid

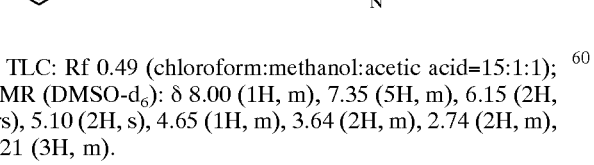

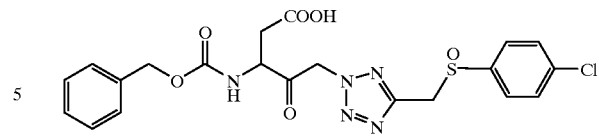

TLC: Rf 0.41 (chloroform:methanol:acetic acid=15:1:1); NMR (DMSO-d$_6$): δ 7.73 (1H, m), 7.60 (4H, m), 7.38 (5H, m), 5.99 (2H, br), 5.08 (2H, s), 4.60 (3H, m), 2.64 (2H, m).

Example 10(6)
N-benzyloxycarbonyl-3-amino-4-oxo-5-(5-(4-chlorophenylsulfinylmethyl)tetrazol-1-yl)pentanoic acid

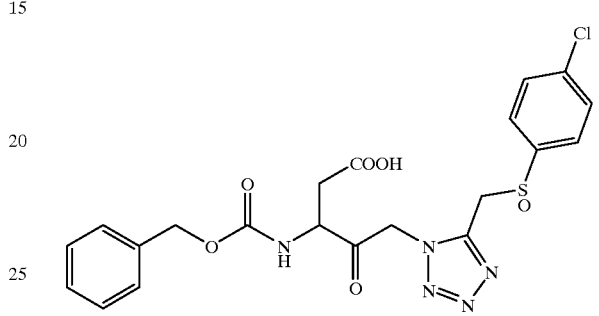

TLC: Rf 0.41 (chloroform:methanol:acetic acid=15:1:1); NMR (DMSO-d$_6$): δ 7.75 (1H, m), 7.60 (4H, m), 7.38 (5H, m), 5.85 (2H, m), 5.08 (2H, m), 4.90 (1H, m), 4.58 (2H, m), 2.61 (2H, m).

Example 10(7)
N-benzyloxycarbonyl-3-amino-4-oxo-5-(5-(4-chlorophenylsulfonylmethyl)tetrazol-2-yl)pentanoic acid

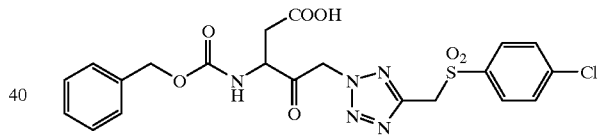

TLC: Rf 0.48 (chloroform:methanol:acetic acid=15:1:1); NMR (DMSO-d$_6$): δ 7.73 (4H, m), 7.60 (1H, m), 7.38 (5H, m), 6.01 (2H, br), 5.21 (2H, s), 5.08 (2H, s), 4.55 (1H, m), 2.60 (2H, m).

Example 10(8)
N-benzyloxycarbonyl-3-amino-4-oxo-5-(5-(4-chlorophenylsulfonylmethyl)tetrazol-1-yl)pentanoic acid

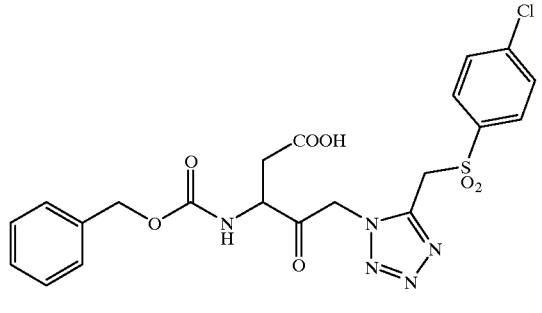

TLC: Rf 0.51 (chloroform:methanol:acetic acid=15:1:1); NMR (DMSO-d$_6$): δ 7.79 (5H, m), 7.35 (5H, m), 5.88 (2H, m), 5.40 (2H, m), 5.08 (2H, s), 4.52 (1H, m), 2.65 (2H, m).

Example 11

N-benzyloxycarbonyl-3-amino-4-oxo-5-(5-trimethylsilyltetrazol-2-yl) pentanoic acid•t-butylester

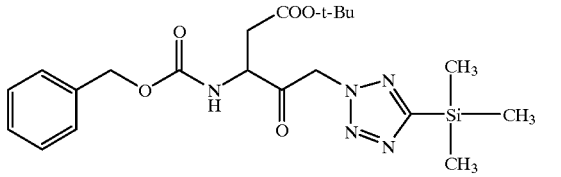

To a solution of (S)-N-benzyloxycarbonyl-3-amino-3-methoxycarbonyl propanic acid•t-butylester (1.69 g) in tetrahydrofuran (10 ml) was added dropwise a 2M lithium diisopropylamide [LDA] in heptane/tetrahydrofuran/ethylbenzene solution (2.5 ml) at 0° C. under an atmosphere of argon. To the mixture was added dropwise the solution prepared in the mixture of trimethyldiazomethane (in 10% hexane solution, 13.7 g) and 2M lithium diisopropylamide in heptane/tetrahydrofuran/ethylbenzene solution (6 ml) at 0° C. under an atmosphere of argon using cannula. The reaction mixture was stirred for 3.5 h at 0° C. The mixture was poured into ice water, and extracted with diethylether. The extract was washed with water and a saturated aqueous solution of sodium chloride, successively, dried over anhydrous sodium sulfate and concentrated. The residue was purified by column chromatography on silica gel (hexane:ethyl acetate=2:1) to give the compound of the present invention (633 mg) having the following physical data.

TLC: Rf 0.55 (hexane:ethyl acetate=2:1); NMR (CDCl$_3$): δ 7.36 (5H, m), 5.97 (1H, m), 5.87 and 5.68 (each 1H, both d, J=17.5 Hz), 5.16 (2H, brs), 4.67 (1H, m), 3.00 (1H, dd, J=16.0, 4.5 Hz), 2.70 (1H, dd, J=16.0, 5.0 Hz), 1.41 (9H, s), 0.39 (9H, s).

Example 12

N-benzyloxycarbonyl-3-amino-4-oxo-5-(5-trimethylsilyltetrazol-2-yl) pentanoic acid

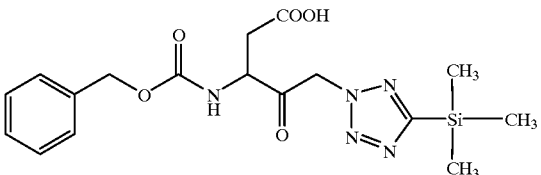

By the same procedure as provided in example 6(1), using the compound prepared in example 11, compound of the present invention having the following physical data was obtained.

TLC: Rf 0.29 (chloroform:methanol=4:1); NMR (DMSO-d$_6$): δ 7.56 (1H, m), 7.34 (5H, m), 5.98 (2H, m), 5.06 (2H, s), 4.52 (1H, m), 2.58 (2H, m), 0.34 (9H, s).

Reference Example 8

N-benzyoxycarbonyl-3-amino-4-oxo-5-(5-(2-(1-(2-(trimethylsilyl) ethoxymethyl)imidazol-2-yl)ethenyl)tetrazol-2-yl)pentanoic acid•t-butylester (1) and N-benzyloxycarbonyl-3-amino-4-oxo-5-(5-(2-(1-(2-(trimethylsilyl) ethoxymethyl)imidazol-2-yl)ethenyl)tetrazol-1-yl)pentanoic acid•t-butylester (2)

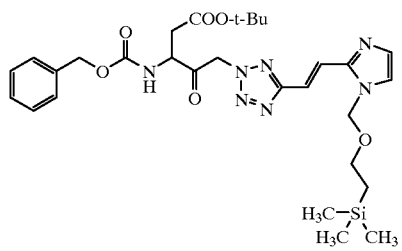

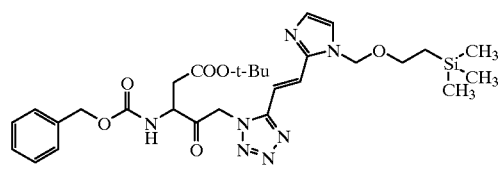

To a solution of N-benzyloxycarbonyl-3-amino-4-oxo-5-bromopentanoic acid•t-butylester (300 mg) in N,N-dimethylformamide (5 ml) was added potassium carbonate (414 mg) and 5-(2-(1-(2-(trimethylsilyl) ethoxymethyl) imidazol-2-yl)ethenyl)tetrazole (438 mg). The reaction mixture was stirred for 4 h at room temperature. The reaction mixture was quenched by addition of a saturated aqueous solution of sodium hydrocarbonate, and extracted with ethyl acetate. The extract was washed with a saturated aqueous solution of sodium chloride, dried over anhydrous sodium sulfate and concentrated. The residue was purified by column chromatography on silica gel (hexane:ethyl acetate=1:1) to give the compound of reference example 8(1) (297 mg) and reference example 8(2) (110 mg), respectively.

Reference Example 8(1)

TLC: Rf 0.61 (hexane:ethyl acetate=1:4); NMR (CDCl$_3$): δ 7.67 (1H, d, J=16 Hz), 7.61 (1H, d, J=16 Hz), 7.38 (5H, m), 7.17 (1H, d, J=1.2 Hz), 7.07 (1H, d, J=1.2 Hz), 5.99 (1H, d, J=8.8 Hz), 5.83 (1H, d, J=18 Hz), 5.67 (1H, d, J=18 Hz), 5.38 (2H, s), 5.19 (2H, s), 4.66 (1H, m), 3.53 (2H, t, J=8.0 Hz), 3.03 (1H, dd, J=4.6, 18 Hz), 2.73 (1H, dd, J=4.8, 18 Hz), 1.43 (9H, s), 0.91 (2H, t, J=8.0 Hz), −0.03 (9H, s).

Reference Example 8(2)

TLC: Rf 0.50 (hexane:ethyl acetate=1:4); NMR (CDCl$_3$): δ 7.83 (1H, d, J=16 Hz), 7.40–7.08 (8H, m), 6.02 (1H, d, J=9.0 Hz), 5.73 (1H, d, J=19 Hz), 5.52 (1H, d, J=19 Hz), 5.38 (2H, s), 5.21 (2H, s), 4.70 (1H, m), 3.51 (2H, t, J=8.2 Hz), 3.06 (1H, dd, J=4.8, 17 Hz), 2.74 (1H, dd, J=4.8, 17 Hz), 1.39 (9H, s), 0.91 (2H, t, J=8.2 Hz), −0.03 (9H, s).

Reference Example 8(3)–8(12)

By the same procedure as provided in reference example 8, using the corresponding tetrazole compound instead of 5-(2-(1-(2-(trimethylsilyl) ethoxymethyl)imidazol-2-yl) ethenyl)tetrazole, the title compounds having the following physical data were obtained.

Reference Example 8(3)

N-benzyloxycarbonyl-3-amino-4-oxo-5-(5-(2-(1-(2-(trimethylsilyl) ethoxymethyl)imidazol-2-yl)ethyl)tetrazol-2-yl)pentanoic acid•t-butylester

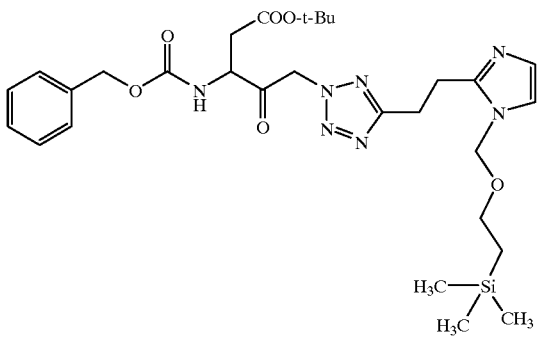

TLC: Rf 0.58 (chloroform:t-butanol=10:1); NMR (CDCl$_3$): δ 7.38 (5H, m), 6.94 (1H, d, J=1.2 Hz), 6.90 (1H, d, J=1.2 Hz), 6.29 (1H, d, J=8.6 Hz), 5.71 (1H, d, J=18 Hz), 5.61 (1H, d, J=18 Hz), 5.21 (2H, s), 5.17 (2H, s), 4.60 (1H, m), 3.54–3.38 (4H, m), 3.30–3.18 (2H, m), 2.96 (1H, dd, J=4.6, 17 Hz), 2.75 (1H, dd, J=4.8, 17 Hz), 1.42 (9H, s), 0.90 (2H, t), J=8.2 Hz), −0.02 (9H, s).

Reference Example 8(4)
N-benzyloxycarbonyl-3-amino-4-oxo-5-(5-(2-(1-(2-(trimethylsilyl) ethoxymethyl)imidazol-2-yl)ethyl)tetrazol-1-yl)pentanoic acid•t-butylester

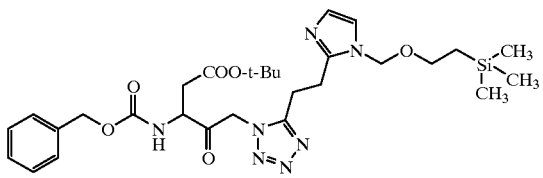

TLC: Rf 0.50 (chloroform:t-butanol=10:1); NMR (CDCl$_3$): δ 7.38 (5H, m), 6.85 (1H, d, J=1.2 Hz), 6.82 (1H, d, J=1.2 Hz), 6.17 (1H, d, J=9.0 Hz), 5.81 (1H, d, J=19 Hz), 5.60 (1H, d, J=19 Hz), 5.20 (2H, s), 5.16 (2H, s), 4.66 (1H, m), 3.44 (2H, t, J=8.2 Hz), 3.30–3.18 (4H, m), 3.03 (1H, dd, J=4.8, 17 Hz), 2.74 (1H, dd, J=4.8, 17 Hz), 1.40 (9H, s), 0.88 (2H, t, J=8.2 Hz), −0.02 (9H, s).

Reference Example 8(5)
N-benzyloxycarbonyl-3-amino-4-oxo-5-(5-(3-(1-(2-(trimethylsilyl) ethoxymethyl)imidazol-2-yl)phenylmethyl)tetrazol-2-yl)pentanoic acid•t-butylester

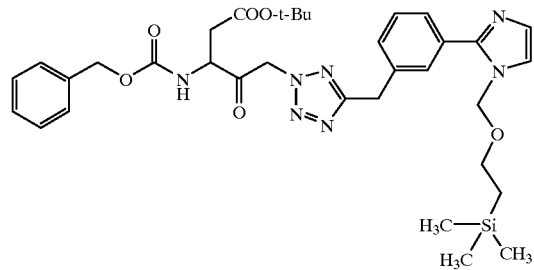

TLC: Rf 0.45 (chloroform:t-butanol=15:1); NMR (CDCl$_3$): δ 7.70–7.60 (2H, m), 7.40–7.28 (7H, m), 7.12–7.08 (2H, m), 6.04 (1H, m), 5.80–5.74 (2H, m,), 5.25 (2H, s), 5.16 (2H, s), 4.32 (1H, m), 4.32 (2H, s), 3.54 (2H, t, J=8.0 Hz), 3.04–2.62 (2H, m), 1.41 (9H, s), 0.91 (2H, t, J=8.0 Hz), 0.00 (9H, s).

Reference Example 8(6)
N-benzyloxycarbonyl-3-amino-4-oxo-5-(5-(3-(1-(2-(trimethylsilyl) ethoxymethyl)imidazol-2-yl)phenylmethyl)tetrazol-1-yl)pentanoic acid•t-butylester

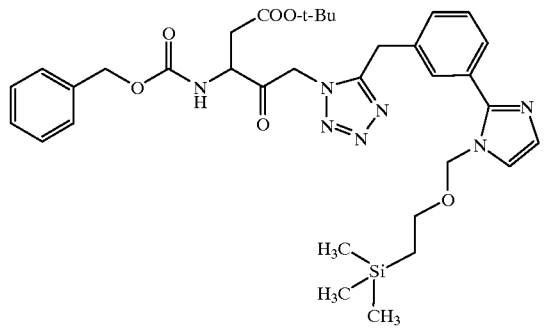

TLC: Rf 0.38 (chloroform:t-butanol:acetic acid=15:1); NMR (CDCl$_3$): δ 7.86 (1H, m), 7.70–7.60 (2H, m), 7.42–7.28 (7H, m), 7.10 (2H, m), 5.44–5.20 (4H, m), 5.13 (2H, s), 4.64 (1H, m), 4.23 (2H, s), 3.56 (2H, t, J=8.0 Hz), 2.80–2.70 (2H, m), 1.40 (9H, s), 0.93 (2H, t, J=8.0 Hz), 0.00 (9H, s).

Reference Example 8(7)
N-benzyloxycarbonyl-3-amino-4-oxo-5-(5-(4-(1-(2-(trimethylsilyl) ethoxymethyl)imidazol-2-yl)phenylmethyl)tetrazol-2-yl)pentanoic acid•t-butylester

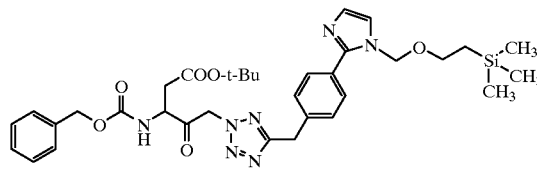

TLC: Rf 0.51 (chloroform:methanol=15:1); NMR (CDCl$_3$): δ 7.73 (2H, d, J=8.2 Hz), 7.40–7.32 (7H, m), 7.12 (1H, d, J=1.4 Hz), 7.09 (1H, d, J=1.4 Hz), 6.02 (1H, d, J=9.2 Hz), 5.78 (1H, d, J=18 Hz), 5.63 (1H, d, J=18 Hz), 5.25 (2H, s), 5.16 (2H, s), 4.64 (1H, m), 4.31 (2H, s), 3.56 (2H, t, J=8.2 Hz), 3.05 (1H, dd, J=4.4, 17 Hz), 2.96 (1H, dd, J=4.4, 17 Hz), 1.42 (9H, s), 0.90 (2H, t, J=8.2 Hz), −0.02 (9H, s).

Reference Example 8(8)
N-benzyloxycarbonyl-3-amino-4-oxo-5-(5-(4-(1-(2-(trimethylsilyl) ethoxymethyl)imidazol-2-yl)phenylmethyl)tetrazol-1-yl)pentanoic acid•t-butylester

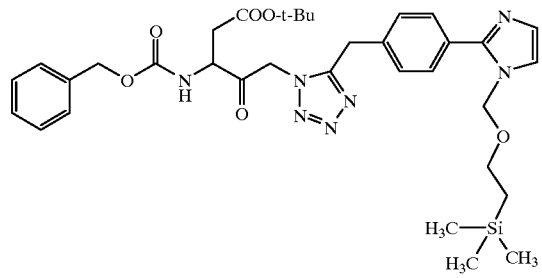

TLC: Rf 0.46 (chloroform:methanol=15:1); NMR (CDCl$_3$): δ 7.77 (2H, d, J=8.2 Hz), 7.40–7.29 (7H, m), 7.13 (1H, d, J=1.2 Hz), 7.10 (1H, d, J=1.2 Hz), 5.81 (1H, d, J=9.2

Hz), 5.38 (2H, s), 5.24 (2H, s), 5.14 (2H, s), 4.58 (1H, m), 4.26 (1H, d, J=16 Hz), 4.09 (1H, d, J=16 Hz), 3.58 (2H, t, J=8.2 Hz), 3.07 (1H, dd, J=4.4, 18 Hz), 2.74 (1H, dd, J=4.4, 17 Hz), 1.43 (9H, s), 0.92 (2H, t, J=8.2 Hz), −0.01 (9H, s).

Reference Example 8(9)

N-benzyloxycarbonyl-3-amino-4-oxo-5-(5-(2-(1-(2-(trimethylsilyl) ethoxymethyl)imidazol-2-yl)phenylmethyl) tetrazol-2-yl)pentanoic acid•t-butylester

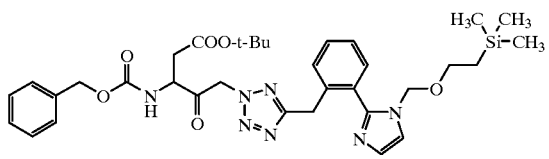

TLC: Rf 0.51 (chloroform:methanol=15:1); NMR (CDCl₃): δ 7.54–7.20 (11H, m), 6.36 (1H, m), 5.80–5.44 (2H, m), 5.15 (2H, s), 5.02–4.96 (2H, m), 4.62 (1H, m), 4.50–4.40 (2H, m), 3.54 (2H, t, J=8.2 Hz), 2.98–2.74 (2H, m), 1.41 (9H, s), 0.90 (2H, t, J=8.2 Hz), 0.00 (9H, s).

Reference Example 8(10)

N-benzyloxycarbonyl-3-amino-4-oxo-5-(5-(2-(1-(2-(trimethylsilyl) ethoxymethyl)imidazol-2-yl)phenylmethyl) tetrazol-1-yl)pentanoic acid•t-butylester

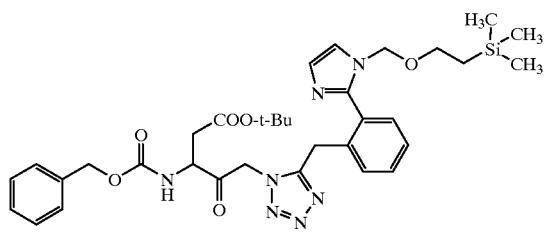

TLC: Rf 0.64 (chloroform:methanol=15:1); NMR (CDCl₃): δ 7.62–7.15 (11H, m), 6.90 (1H, m), 5.86–5.46 (2H, m), 5.23–5.20 (4H, m), 4.84 (1H, m), 4.60–4.20 (2H, m), 3.66 (2H, t, J=8.2 Hz), 3.02–2.78 (2H, m), 1.41 (9H, s), 0.98 (2H, t, J=8.2 Hz), 0.02 (9H, s).

Reference Example 8(11)

N-benzyloxycarbonyl-3-amino-4-oxo-5-(5-(1-(2-(trimethylsilyl) ethoxymethyl)imidazol-2-ylmethyl)tetrazol-2-yl)pentanoic acid•t-butylester

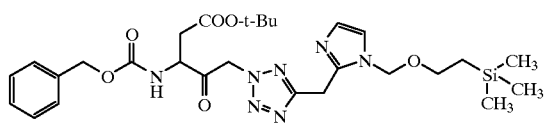

TLC: Rf 0.47 (chloroform:methanol=15:1); NMR (CDCl₃): δ 7.40–7.30 (5H, m), 6.95 (2H, br-s), 6.10 (1H, d, J=8.0 Hz), 5.80–5.58 (2H, m), 5.30 (2H, s), 5.15 (2H, s), 4.60 (1H, m), 4.47 (2H, s), 3.48 (2H, t, J=8.2 Hz), 2.96 (1H, dd, J=4.8, 17 Hz), 2.71 (1H, dd, J=5.0, 17 Hz), 1.41 (9H, s), 0.88 (2H, t, J=8.2 Hz), −0.01 (9H, s).

Reference Example 8(12)

N-benzyloxycarbonyl-3-amino-4-oxo-5-(5-(1-(2-(trimethylsilyl) ethoxymethyl)imidazol-2-ylmethyl)tetrazol-1-yl)pentanoic acid•t-butylester

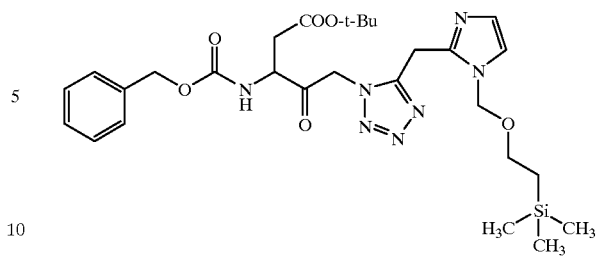

TLC: Rf 0.57 (chloroform:methanol=15:1); NMR (CDCl₃): δ 7.40–7.30 (5H, m), 6.92 (1H, d, J=1.2 Hz), 6.87 (1H, d, J=1.2 Hz), 6.38 (1H, d, J=8.0 Hz), 5.82 (1H, d, J=18 Hz), 5.82 (1H, d, J=18 Hz), 5.36–5.18 (4H, m), 4.76 (1H, m), 4.40 (2H, s), 3.43 (2H, t, J=8.2 Hz), 2.93 (1H, dd, J=4.6, 17 Hz), 2.72 (1H, dd, J=5.2, 17 Hz), 1.40 (9H, s), 0.87 (2H, t, J=8.2 Hz), −0.02 (9H, s).

Example 13(1)

N-benzyloxycarbonyl-3-amino-4-oxo-5-(5-(2-(imidazol-2-yl)ethenyl) tetrazol-2-yl)pentanoic acid•hydrochloric acid salt

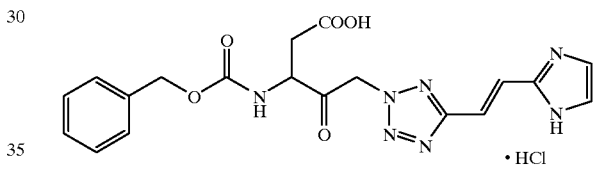

By the same procedure as provided in example 6(1), using the compound prepared in reference example 8(1), compound of the present invention having the following physical data was obtained.

TLC: Rf 0.28 (chloroform:methanol:acetic acid=10:2:1); NMR (DMSO-d₆): δ 8.18–8.04 (2H, m), 7.69 (2H, s), 7.63 (1H, d, J=17 Hz), 7.42–7.30 (5H, m), 6.07 (2H, s), 5.10 (2H, s), 4.64 (1H, m), 2.92–2.60 (2H, m).

EXAMPLES 13(2)–13(12)

By the same procedure as provided in reference example 8→example 13(1), and if necessary, by known methods converted to accommodate the corresponding salts, using the corresponding tetrazole compound instead of 5-(2-(1-((2-trimethylsilyl)ethoxymethyl)imidazol-2-yl)ethenyl) tetrazole, compounds of the present invention having the following physical data were obtained.

Example 13(2)

N-benzyloxycarbonyl-3-amino-4-oxo-5-(5-(2-(imidazol-2-yl)ethenyl) tetrazol-1-yl)pentanoic acid•hydrochloric acid salt

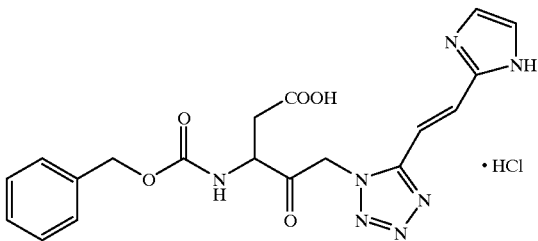

TLC: Rf 0.50 (chloroform:methanol:acetic acid=10:2:1); NMR (DMSO-d$_6$): δ 8.16–8.02 (2H, m), 7.70–7.60 (3H, m), 7.42–7.30 (5H, m), 6.02–5.80 (2H, m), 5.12 (2H, s), 4.84 (1H, m), 3.00–2.60 (2H, m).

Example 13(3)
N-benzyloxycarbonyl-3-amino-4-oxo-5-(5-(2-(imidazol-2-yl)ethyl) tetrazol-2-yl)pentanoic acid•hydrochloric acid salt

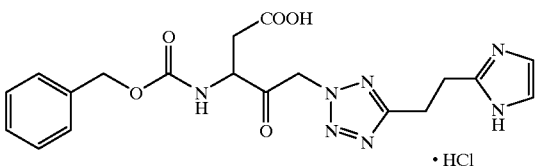

TLC: Rf 0.29 (chloroform:methanol:acetic acid=10:3:1); NMR (DMSO-d$_6$): δ 8.02 (1H, m), 7.53 (2H, s), 7.40–7.30 (5H, m), 5.82 (2H, brs), 5.09 (2H, s), 4.60 (1H, m), 3.50–3.40 (4H, m), 2.90–2.60 (2H, m).

Example 13(4)
N-benzyloxycarbonyl-3-amino-4-oxo-5-(5-(2-(imidazol-2-yl)ethyl) tetrazol-1-yl)pentanoic acid•hydrochloric acid salt

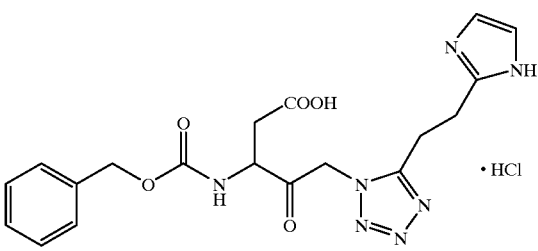

TLC: Rf 0.40 (chloroform:methanol:acetic acid=10:3:1); NMR (DMSO-d$_6$): δ 8.10 (1H, d, J=8.6 Hz), 7.52 (2H, s), 7.40–7.30 (5H, m), 5.79 (2H, brs), 5.09 (2H, s), 4.64 (1H, m), 3.42–3.32 (4H, m), 2.92–2.60 (2H, m).

Example 13(5)
N-benzyloxycarbonyl-3-amino-4-oxo-5-(5-(3-(imidazol-2-yl) phenylmethyl)tetrazol-2-yl)pentanoic acid•hydrochloric acid salt

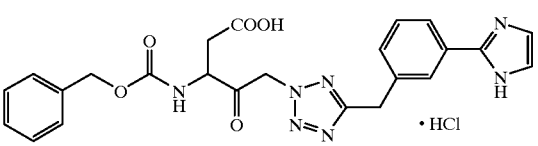

TLC: Rf 0.51 (chloroform:methanol:acetic acid=10:3:1); NMR (DMSO-d$_6$): δ 8.04–7.96 (3H, m), 7.52–7.28 (9H, m), 5.90 (2H, m), 5.08 (2H, s), 4.60 (1H, m), 4.32 (2H, s), 2.90–2.60 (2H, m).

Example 13(6)
N-benzyloxycarbonyl-3-amino-4-oxo-5-(5-(3-(imidazol-2-yl) phenylmethyl)tetrazol-1-yl)pentanoic acid•hydrochloric acid salt

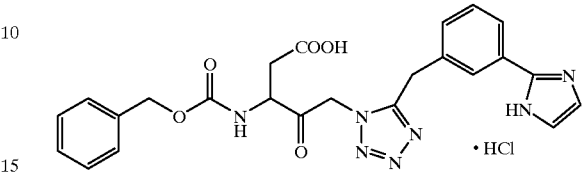

TLC: Rf 0.60 (chloroform:methanol:acetic acid=10:3:1); NMR (DMSO-d$_6$): δ 8.12 (1H, m), 8.02–7.90 (2H, m), 7.50–7.20 (9H, m), 5.79 (2H, m), 5.09 (2H, s), 4.64 (1H, m), 4.20 (2H, s), 2.90–2.62 (2H, m).

Example 13(7)
N-benzyloxycarbonyl-3-amino-4-oxo-5-(5-(4-(imidazol-2-yl) phenylmethyl)tetrazol-2-yl)pentanoic acid•hydrochloric acid salt

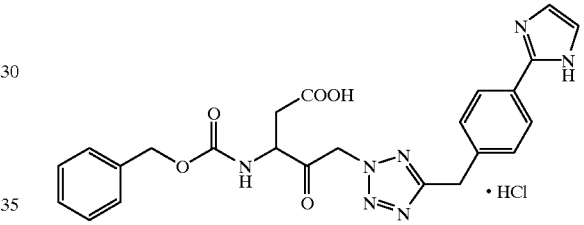

TLC: Rf 0.46 (chloroform:methanol:acetic acid=10:4:1); NMR (DMSO-d$_6$): δ 8.18 (2H, d, J=8.6 Hz), 8.04 (1H, d, J=7.8 Hz), 7.77 (2H, s), 7.54 (2H, d, J=8.6 Hz), 7.42–7.26 (5H, m), 5.70 (2H, brs), 5.09 (2H, s), 4.62 (1H, m), 4.39 (2H, brs), 2.90–2.56 (2H, m).

Example 13(8)
N-benzyloxycarbonyl-3-amino-4-oxo-5-(5-(4-(imidazol-2-yl) phenylmethyl)tetrazol-1-yl)pentanoic acid•hydrochloric acid salt

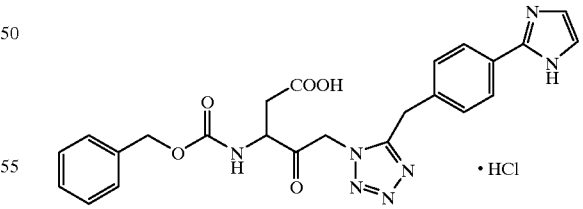

TLC: Rf 0.40 (chloroform:methanol:acetic acid=10:4:1); NMR (DMSO-d$_6$): δ 8.22–8.12 (3H, m), 7.77 (2H, s), 7.52 (2H, d, J=8.6 Hz), 7.42–7.30 (5H, m), 5.86 (2H, brs), 5.10 (2H, s), 4.64 (1H, m), 4.25 (2H, brs), 2.92–2.64 (2H, m).

Example 13(9)
N-benzyloxycarbonyl-3-amino-4-oxo-5-(5-(2-(imidazol-2-yl) phenylmethyl)tetrazol-2-yl)pentanoic acid•hydrochloric acid salt

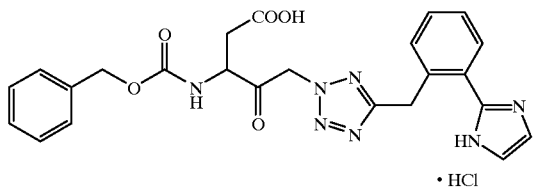

TLC: Rf 0.44 (chloroform:methanol:acetic acid=10:3:1); NMR (DMSO-d₆): δ 8.02 (1H, m), 7.72–7.24 (11H, m), 5.85 (2H, brs), 5.08 (2H, s), 4.62–4.52 (3H, m), 2.88–2.58 (2H, m).

Example 13(10)

N-benzyloxycarbonyl-3-amino-4-oxo-5-(5-(2-(imidazol-2-yl) phenylmethyl)tetrazol-1-yl)pentanoic acid•hydrochloric acid salt

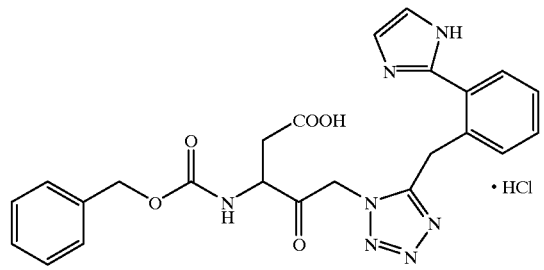

TLC: Rf 0.58 (chloroform:methanol:acetic acid=10:3:1); NMR (DMSO-d₆): δ 8.12 (1H, m), 7.68–7.30 (11H, m), 5.82 (2H, brs), 5.11 (2H, s), 4.70–4.58 (3H, m), 2.92–2.60 (2H, m).

Example 13(11)

N-benzyloxycarbonyl-3-amino-4-oxo-5-(5-(imidazol-2-ylmethyl) tetrazol-2-yl)pentanoic acid•hydrochloric acid salt

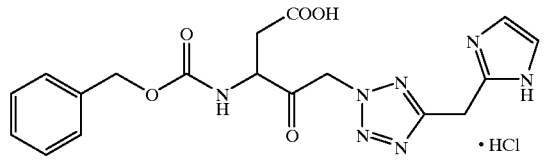

TLC: Rf 0.41 (chloroform:methanol:water=10:5:1); NMR (DMSO-d₆): δ 8.04 (1H, m), 7.59 (2H, s), 7.40–7.30 (5H, m), 6.01 (2H, brs), 5.08 (2H, s), 4.73 (2H, s), 4.62 (1H, m), 2.92–2.58 (2H, m).

Example 13(12)

N-benzyloxycarbonyl-3-amino-4-oxo-5-(5-(imidazol-2-ylmethyl) tetrazol-1-yl)pentanoic acid•hydrochloric acid salt

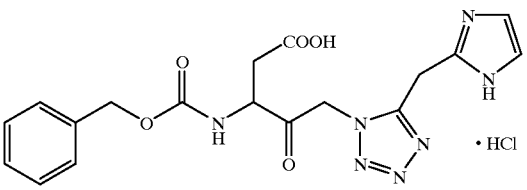

TLC: Rf 0.55 (chloroform:methanol:water=10:5:1); NMR (DMSO-d₆): δ 8.14 (1H, m), 7.60 (2H, s), 7.40–7.30 (5H, m), 5.91 (2H, brs,), 5.11 (2H, s,), 4.80–4.60 (3H, m), 2.92–2.62 (2H, m).

EXAMPLES 14(1)–14(106)

By the same procedure as provided in example 1, using the corresponding tetrazole compounds and the corresponding bromo compounds instead of N-((N-(3-phenylpropionyl)-L-valyl)-L-alanyl)-3-amino-4-oxo-5-bromopentanoic acid•t-butylester, compounds of the present invention having the following physical data were obtained.

Example 14(1)

N-(benzylthio)carbonyl-3-amino-4-oxo-5-(2,6-dichlorophenylmethyl)tetrazol-2-yl)pentanoic acid•t-butylester

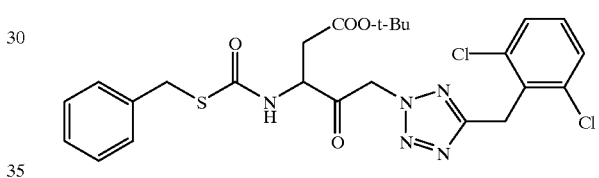

TLC: Rf 0.36 (hexane:ethyl acetate=3:1); NMR (CDCl₃): δ 7.40–7.12 (8H, m), 6.62 (1H, d, J=9.5 Hz), 5.69 and 5.49 (each 1H, d, J=17.8 Hz), 4.95–4.78 (1H, m), 4.60 (4H, s), 4.19 (2H, s), 2.98 (1H, dd, J=17.5 Hz, 4.4 Hz), 2.66 (1H, dd, J=17.5 Hz, 4.8 Hz), 1.41 (3H, s).

Example 14(2)

N-(benzylthio)carbonyl-3-amino-4-oxo-5-(5-(2,6-dichlorophenylmethyl)tetrazol-1-yl)pentanoic acid•t-butylester

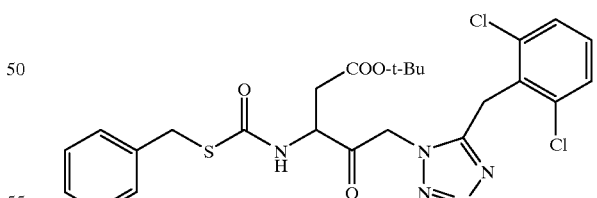

TLC: Rf 0.15 (hexane:ethyl acetate=3:1); NMR (CDCl₃): δ 7.41–7.15 (8H, m), 6.52 (1H, d, J=9.5 Hz), 5.58 and 5.46 (each 1H, d, J=18.0 Hz), 4.92–4.74 (1H, m), 4.33 and 4.23 (each 1H, d, J=17.5 Hz), 4.22 (2H, s), 3.07 (1H, dd, J=17.5 Hz, 5.0 Hz), 2.75 (1H, dd, J=17.5 Hz, 5.5 Hz), 1.41 (3H, s).

Example 14(3)

N-(benzylthio)carbonyl-3-amino-4-oxo-5-(5-(2,6-dichlorophenylthio) tetrazol-2-yl)pentanoic acid•t-butylester

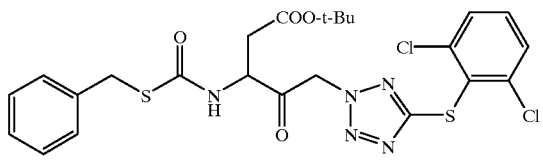

TLC: Rf 0.72 (benzene:diethylether=2:1); NMR (CDCl$_3$): δ 7.45 (2H, d, J=6.8 Hz), 7.35–7.20 (6H, m), 6.61 (1H, d, J=8.8 Hz), 5.67 (1H, d, J=17.8 Hz), 5.48 (1H, d, J=17.8 Hz), 4.90–4.80 (1H, m), 4.19 (2H, s), 2.99 (1H, dd, J=4.4, 17.4 Hz), 2.67 (1H, dd, J=5.0, 17.6 Hz), 1.41 (9H, s).

Example 14(4)

N-(benzylthio)carbonyl-3-amino-4-oxo-5-(5-(2,6-dichlorophenylthio)tetrazol-1-yl)pentanoic acid•t-butylester

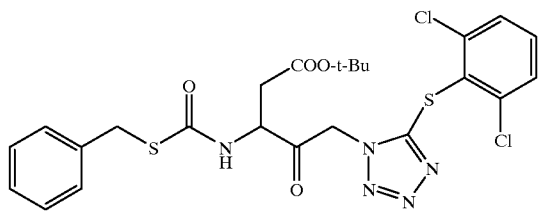

TLC: Rf 0.57 (benzene:diethylether=2:1); NMR (CDCl$_3$): δ 7.47–7.20 (8H, m), 6.66 (1H, d, J=8.8 Hz), 5.58 (1H, d, J=18.2 Hz), 5.42 (1H, d, J=18.2 Hz), 4.95–4.83 (1H, m), 4.23 (2H, s), 3.06 (1H, dd, J=4.4, 17.6 Hz), 2.73 (1H, dd, J=4.6, 17.6 Hz), 1.44 (9H, s).

Example 14(5)

N-(2-phenylethyloxy)carbonyl-3-amino-4-oxo-5-(5-(2,6-dichlorophenylmethyl)tetrazol-2-yl)pentanoic acid•t-butylester

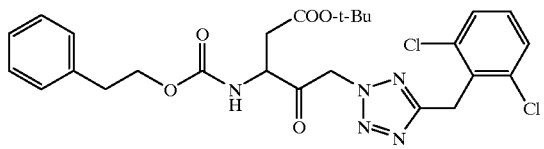

TLC: Rf 0.22 (hexane:ethyl acetate=3:1); NMR (CDCl$_3$): δ 7.37–7.11 (8H, m), 5.80 (1H, d, J=9.4 Hz), 5.65 (1H, d, J=17.9 Hz), 5.44 (1H, d, J=17.9 Hz), 4.61–4.14 (4H, m), 3.05–2.93 (3H, m), 2.65 (1H, dd, J=4.6, 17.2 Hz), 1.41 (9H, s).

Example 14(6)

N-(2-phenylethyloxy)carbonyl-3-amino-4-oxo-5-(5-(2,6-dichlorophenylmethyl)tetrazol-1-yl)pentanoic acid•t-butylester

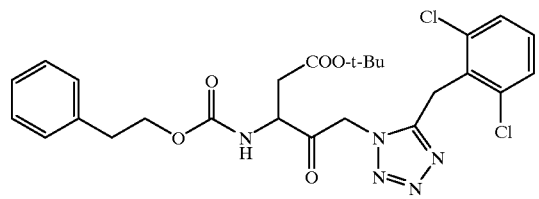

TLC: Rf 0.77 (hexane:ethyl acetate=3:1); NMR (CDCl$_3$): δ 7.39–7.17 (8H, m), 5.74 (1H, d, J=9.0 Hz), 5.59 (1H, d, J=18.8 Hz), 5.43 (1H, d, J=18.8 Hz), 4.54–4.28 (4H, m), 3.14–2.97 (3H, m), 2.73 (1H, dd, J=5.0, 19.0 Hz), 1.42 (9H, s).

Example 14(7)

N-(2-phenylethylthio)carbonyl-3-amino-4-oxo-5-(5-(2,6-dichlorophenylmethyl)tetrazol-2-yl)pentanoic acid•t-butylester

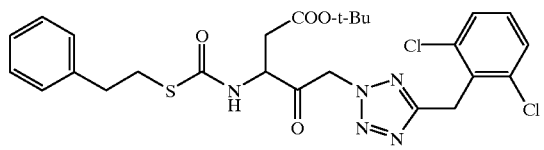

TLC: Rf 0.58 (hexane:ethyl acetate=2:1); NMR (CDCl$_3$): δ 7.37–7.09 (8H, m), 6.58 (1H, d, J=8.8 Hz), 5.67 (1H, d, J=17.8 Hz), 5.45 (1H, d, J=17.8 Hz), 4.89–4.80 (1H, m), 4.61 (2H, s), 3.28–3.19 (2H, m), 3.03–2.87 (3H, m), 2.65 (1H, dd, J=4.6, 17.4 Hz), 1.42 (9H, s).

Example 14(8)

N-(2-phenylethylthio)carbonyl-3-amino-4-oxo-5-(5-(2,6-dichlorophenylmethyl)tetrazol-1-yl)pentanoic acid•t-butylester

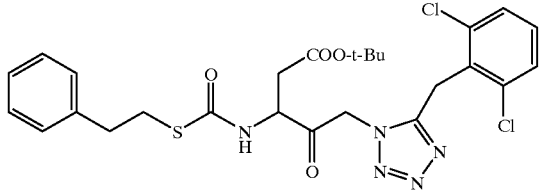

TLC: Rf 0.35 (hexane:ethyl acetate=2:1); NMR (CDCl$_3$): δ 7.39–7.15 (8H, m), 6.53 (1H, d, J=8.6 Hz), 5.61 (1H, d, J=18.7 Hz), 5.46 (1H, d, J=18.7 Hz), 4.87–4.78 (1H, m), 4.37 (1H, d, J=14.9 Hz), 4.26 (1H, d, J=18.7 Hz), 3.31–3.23 (2H, m), 3.13–2.90 (3H, m), 2.74 (1H, dd, J=4.9, 17.6 Hz), 1.43 (9H, s).

Example 14(9)

N-(2,6-dichlorobenzyloxy)carbonyl-3-amino-4-oxo-5-(5-phenylmethyltetrazol-1-yl)pentanoic acid•t-butylester

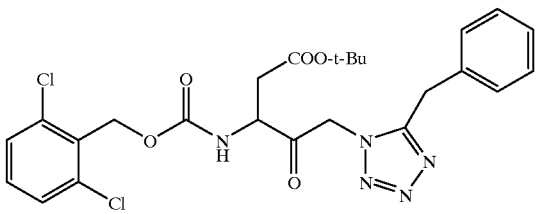

TLC: Rf 0.50 (hexane:ethyl acetate=1:1); NMR (CDCl₃): δ 7.41–7.20 (8H, m), 5.76 (1H, d, J=9.0 Hz), 5.66–5.11 (4H, m), 4.60–4.50 (1H, m), 4.32–4.03 (2H, m), 3.07 (1H, dd, J=4.4, 17.6 Hz), 2.73 (1H, dd, J=4.8, 17.6 Hz), 1.44 (9H, s).

Example 14(10)
N-(2,6-dichlorobenzyloxy)carbonyl-3-amino-4-oxo-5-(5-(2,6-dichlorophenylmethyl)tetrazol-2-yl)pentanoic acid•t-butylester

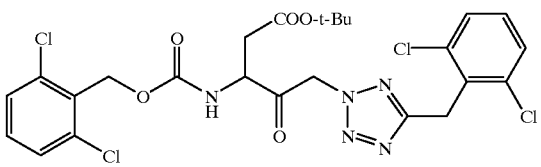

TLC: Rf 0.44 (hexane:ethyl acetate=3:1); NMR (CDCl₃): δ 7.39–7.13 (6H, m), 5.92 (1H, d, J=8.4 Hz), 5.86–5.47 (4H, m), 4.68–4.55 (1H, m), 4.60 (2H, s), 3.03 (1H, dd, J=4.2, 17.0 Hz), 2.71 (1H, dd, J=4.6, 17.0 Hz), 1.40 (9H, s).

Example 14(11)
N-(3-phenylpropyloxy)carbonyl-3-amino-4-oxo-5-(5-(2,6-dichlorophenylmethyl)tetrazol-2-yl)pentanoic acid•t-butylester

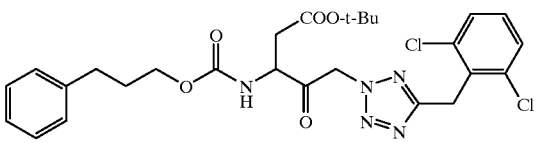

TLC: Rf 0.50 (hexane:ethyl acetate=2:1); NMR (CDCl₃): δ 7.36–7.13 (8H, m), 5.83 (1H, d, J=8.8 Hz), 5.79 (1H, d, J=17.8 Hz), 5.60 (1H, d, J=17.8 Hz), 4.15 (2H, t, J=6.6 Hz), 2.98 (1H, dd, J=4.7, 17.5 Hz), 2.74–2.63 (3H, m), 2.04–1.94 (2H, m), 1.43 (9H, s).

Example 14(12)
N-(3-phenylpropyloxy)carbonyl-3-amino-4-oxo-5-(5-(2,6-dichlorophenylmethyl)tetrazol-1-yl)pentanoic acid•t-butylester

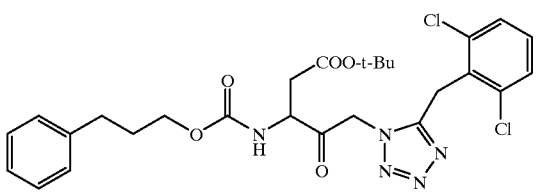

TLC: Rf 0.24 (hexane:ethyl acetate=2:1); NMR (CDCl₃): δ 7.39–7.17 (8H, m), 5.77 (1H, d, J=8.6 Hz), 5.72 (1H, d, J=18.8 Hz), 5.57 (1H, d, J=18.8 Hz), 4.37 (1H, d, J=15.6 Hz), 4.26 (1H, d, J=15.6 Hz), 4.19 (2H, t, J=6.6 Hz), 3.11 (1H, dd, J=4.6, 17.4 Hz), 2.82–2.69 (3H, m), 2.08–1.94 (2H, m), 1.43 (9H, s).

Example 14(13)
N-(4-phenylbutyloxy)carbonyl-3-amino-4-oxo-5-(5-(2,6-dichlorophenylmethyl)tetrazol-2-yl)pentanoic acid•t-butylester

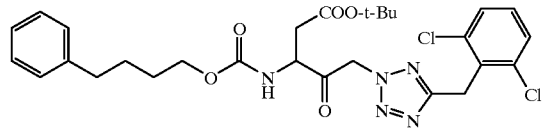

TLC: Rf 0.51 (hexane:ethyl acetate=2:1); NMR (CDCl₃): δ 7.37–7.13 (8H, m), 5.82 (1H, d, J=8.8 Hz), 5.78 (1H, d, J=17.8 Hz), 5.59 (1H, d, J=17.8 Hz), 4.18–4.10 (2H, br), 2.99 (1H, dd, J=4.6, 11.5 Hz), 2.74–2.62 (3H, m), 1.72–1.66 (4H, m), 1.42 (9H, s).

Example 14(14)
N-(4-phenylbutyloxy)carbonyl-3-amino-4-oxo-5-(5-(2,6-dichlorophenylmethyl)tetrazol-1-yl)pentanoic acid•t-butylester

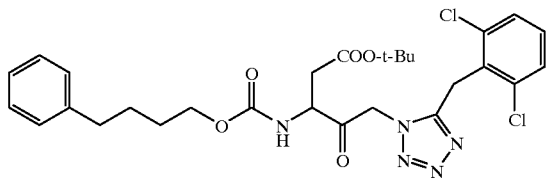

TLC: Rf 0.28 (hexane:ethyl acetate=2:1); NMR (CDCl₃): δ 7.39–7.15 (8H, m), 5.76 (1H, d, J=8.8 Hz), 5.72 (1H, d, J=18.8 Hz), 5.57 (1H, d, J=18.8 Hz), 4.37 (1H, d, J=15.6 Hz), 4.26 (1H, d, J=15.6 Hz), 4.22–4.14 (2H, br), 3.08 (1H, dd, J=4.6, 17.4 Hz), 2.81–2.63 (3H, m), 1.75–1.68 (4H, m), 1.42 (9H, s).

Example 14(15)
N-(2-(thiophen-2-yl)ethyloxy)carbonyl-3-amino-4-oxo-5-(5-(2,6-dichlorophenylmethyl)tetrazol-2-yl)pentanoic acid•t-butylester

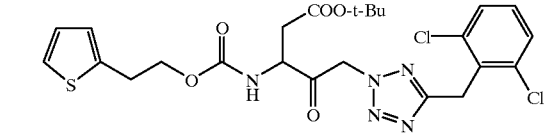

TLC: Rf 0.38 (hexane:ethyl acetate=2:1); NMR (CDCl₃): δ 7.39–7.35 (2H, m), 7.27–7.14 (2H, m), 6.97–6.89 (2H, m), 5.85 (1H, d, J=9.2 Hz), 5.73 (1H, d, J=17.8 Hz), 5.53 (1H, d, J=17.8 Hz), 4.64–4.21 (5H, m), 3.21 (2H, t, J=6.6 Hz), 3.09 (1H, dd, J=4.5, 17.6 Hz), 2.75 (1H, dd, J=4.8, 17.6 Hz), 1.42 (9H, s).

Example 14(16)
N-(2-(thiophen-2-yl)ethyloxy)carbonyl-3-amino-4-oxo-5-(5-( 2,6-dichlorophenylmethyl)tetrazol-1-yl)pentanoic acid•t-butylester

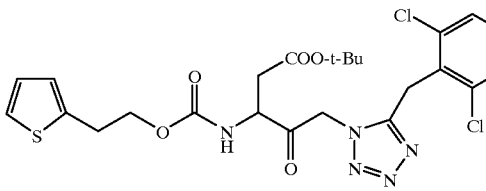

TLC: Rf 0.17 (hexane:ethyl acetate=2:1); NMR (CDCl$_3$): δ 7.39–7.35 (2H, m), 7.26–7.14 (2H, m), 6.97–6.89 (2H, m), 5.85 (1H, d, J=9.2 Hz), 5.67 (1H, d, J=18.8 Hz), 5.51 (1H, d, J=18.8 Hz), 4.64–4.22 (5H, m), 3.21 (2H, t, J=6.6 Hz), 3.09 (1H, dd, J=4.5, 17.6 Hz), 2.75 (1H, dd, J=4.8, 17.6 Hz), 1.42 (9H, s).

Example 14(17)

N-(2-(4-methoxyphenyl)ethyloxy)carbonyl-3-amino-4-oxo-5-(5-(2,6-dichlorophenylmethyl)tetrazol-2-yl)pentanoic acid•t-butylester

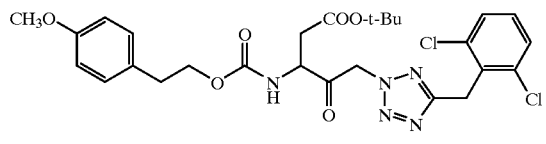

TLC: Rf 0.36 (hexane:ethyl acetate=2:1); NMR (CDCl$_3$): δ 7.37–7.32 (2H, m), 7.21–7.12 (3H, m), 6.86–6.79 (2H, m), 5.82 (1H, d, J=9.2 Hz), 5.69 (1H, d, J=17.9 Hz), 5.49 (1H, d, J=17.9 Hz), 4.61–4.54 (3H, m), 4.45–4.21 (2H, m), 3.73 (3H, s), 3.02–2.86 (3H, m), 2.66 (1H, dd, J=4.6, 17.2 Hz), 1.42 (9H, s).

Example 14(18)

N-(2-(4-methoxyphenyl)ethyloxy)carbonyl-3-amino-4-oxo-5-(5-(2,6-dichlorophenylmethyl)tetrazol-1-yl)pentanoic acid•t-butylester

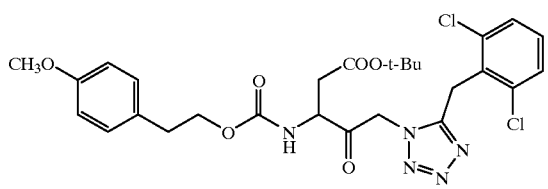

TLC: Rf 0.19 (hexane:ethyl acetate=2:1); NMR (CDCl$_3$): δ 7.39–7.35 (2H, m), 7.26–7.13 (3H, m), 6.88–6.81 (2H, m), 5.76 (1H, d, J=8.4 Hz), 5.62 (1H, d, J=18.8 Hz), 5.45 (1H, d, J=18.8 Hz), 4.64–4.23 (5H, m), 3.74 (3H, s), 2.93 (2H, t, J=7.0 Hz), 3.07 (1H, dd, J=4.4, 17.6 Hz), 2.66 (1H, dd, J=4.6, 17.6 Hz), 1.42 (9H, s).

Example 14(19)

N-(2-(4-fluorophenyl)ethyloxy)carbonyl-3-amino-4-oxo-5-(5-(2,6-dichlorophenylmethyl)tetrazol-2-yl)pentanoic acid•t-butylester

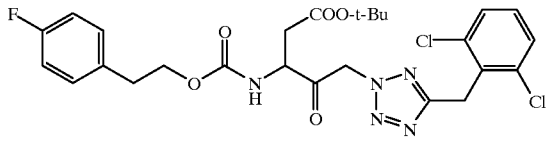

TLC: Rf 0.38 (hexane:ethyl acetate=2:1); NMR (CDCl$_3$): δ 7.37–7.31 (2H, m), 7.21–7.13 (3H, m), 7.02–6.94 (2H, m), 5.81 (1H, d, J=8.6 Hz), 5.71 (1H, d, J=17.8 Hz), 5.53 (1H, d, J=17.8 Hz), 4.61–4.55 (3H, m), 4.43–4.23 (2H, m), 3.01–2.89 (3H, m), 2.66 (1H, dd, J=4.9, 17.6 Hz), 1.42 (9H, s).

Example 14(20)

N-(2-(4-fluorophenyl)ethyloxy)carbonyl-3-amino-4-oxo-5-(5-(2,6-dichlorophenylmethyl)tetrazol-1-yl)pentanoic acid•t-butylester

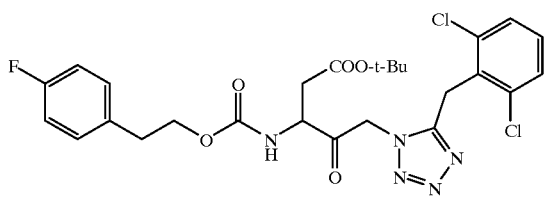

TLC: Rf 0.17 (hexane:ethyl acetate=2:1); NMR (CDCl$_3$): δ 7.39–7.35 (2H, m), 7.24–7.16 (3H, m), 7.05–6.95 (2H, m), 5.76 (1H, d, J=8.4 Hz), 5.66 (1H, d, J=18.8 Hz), 5.51 (1H, d, J=18.8 Hz), 4.65–4.55 (1H, m), 4.43–4.23 (4H, m), 3.12–2.93 (3H, m), 2.74 (1H, dd, J=4.7, 17.5 Hz), 1.42 (9H, s).

Example 14(21)

N-(2-(phenylmethyloxy)ethyloxy)carbonyl-3-amino-4-oxo-5-(5-(2,6-dichlorophenylmethyl)tetrazol-2-yl)pentanoic acid•t-butylester

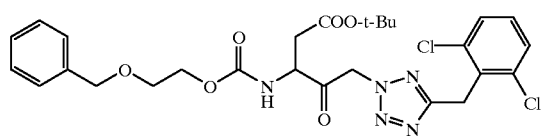

TLC: Rf 0.40 (hexane:ethyl acetate=2:1); NMR (CDCl$_3$): δ 7.36–7.13 (8H, m), 5.95 (1H, d, J=8.7 Hz), 5.79 (1H, d, J=18.0 Hz), 5.57 (1H, d, J=18.0 Hz), 4.66–4.57 (5H, m), 4.37–4.27 (2H, m), 3.69 (2H, t, J=4.6 Hz), 3.01 (1H, dd, J=4.2, 17.5 Hz), 2.67 (1H, dd, J=4.3, 17.5 Hz), 1.42 (9H, s).

Example 14(22)

N-(2-(phenylmethyloxy)ethyloxy)carbonyl-3-amino-4-oxo-5-(5-(2,6-dichlorophenylmethyl)tetrazol-1-yl)pentanoic acid•t-butylester

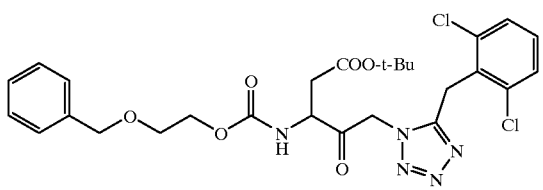

TLC: Rf 0.22 (hexane:ethyl acetate=2:1); NMR (CDCl$_3$): δ 7.39–7.18 (8H, m), 5.90 (1H, d, J=8.8 Hz), 5.71 (1H, d, J=18.8 Hz), 5.56 (1H, d, J=18.8 Hz), 4.65–4.56 (3H, m), 4.38–4.21 (4H, m), 3.73 (2H, t, J=4.4 Hz), 3.14 (1H, dd, J=4.2, 17.7 Hz), 2.75 (1H, dd, J=4.8, 17.7 Hz), 1.42 (9H, s).

Example 14(23)

N-(2-(4-dimethylaminophenyl)ethyloxy)carbonyl-3-amino-4-oxo-5-(5-(2,6-dichlorophenylmethyl)tetrazol-2-yl) pentanoic acid•t-butylester

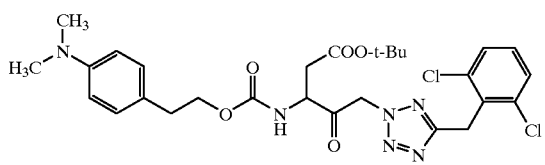

TLC: Rf 0.60 (benzene:diethylether=2:1); NMR (CDCl$_3$): δ 7.36–7.07 (5H, m), 6.65 (2H, d, J=8.8 Hz), 5.80 (1H, d, J=10.2 Hz), 5.67 (1H, d, J=17.8 Hz), 5.45 (1H, d, J=17.8 Hz), 4.60 (2H, s), 4.62–4.55 (1H, m), 4.50–4.18 (2H, m), 2.94–2.60 (4H, m), 2.84 (6H, s), 1.41 (9H, s).

Example 14(24)

N-(2-(4-dimethylaminophenyl)ethyloxy)carbonyl-3-amino-4-oxo-5-(5-(2,6-dichlorophenylmethyl)tetrazol-1-yl) pentanoic acid•t-butylester

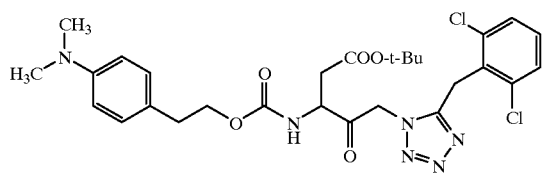

TLC: Rf 0.41 (benzene:diethylether=2:1); NMR (CDCl$_3$): δ 7.38–7.07 (5H, m), 6.68 (2H, d, J=8.8 Hz), 5.80 (1H, d, J=10.2 Hz), 5.67 (1H, d, J=17.8 Hz), 5.45 (1H, d, J=17.8 Hz), 4.60 (2H, s), 4.62–4.55 (1H, m), 4.50–4.18 (2H, m), 2.94–2.60 (4H, m), 2.84 (6H, s), 1.41 (9H, s).

Example 14(25)

N-(benzylthio)carbonyl-3-amino-4-oxo-5-(5-(2,3,6-trichlorophenylthio) tetrazol-2-yl)pentanoic acid•t-butylester

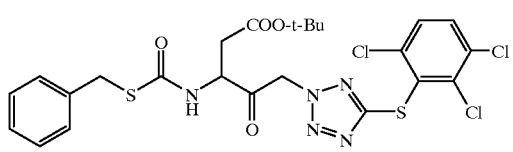

NMR (CDCl$_3$): δ 7.49 (1H, d, J=8.8 Hz), 7.40 (1H, d, J=8.8 Hz), 7.36–7.22 (5H, m), 6.64 (1H, d, J=8.8 Hz), 5.70 (1H, d, J=17.8 Hz), 5.50 (1H, d, J=17.8 Hz), 4.87 (1H, m), 4.20 (2H, s), 2.99 (1H, dd, J=17.4 Hz, 4.5 Hz), 2.68 (1H, dd, J=17.4 Hz, 4.8 Hz), 1.41 (9H, s).

Example 14(26)

N-(benzylthio)carbonyl-3-amino-4-oxo-5-(5-(2,3,6-trichlorophenylthio) tetrazol-1-yl)pentanoic acid•t-butylester

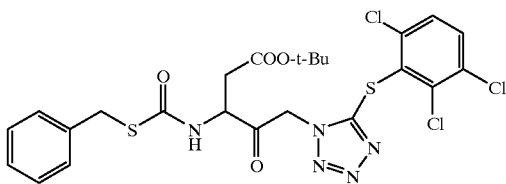

NMR (CDCl$_3$): δ 7.51 (1H, d, J=8.7 Hz), 7.40 (1H, d, J=8.7 Hz), 7.39–7.23 (5H, m), 6.67 (1H, d, J=8.4 Hz), 5.61 (1H, d, J=18.5 Hz), 5.51 (1H, d, J=18.5 Hz), 4.92 (1H, m), 4.24 (2H, s), 3.08 (1H, dd, J=17 Hz, 4.0 Hz), 2.73 (1H, dd, J=17 Hz, 4.8 Hz), 1.44 (9H, s).

Example 14(27)

N-(benzylthio)carbonyl-3-amino-4-oxo-5-(5-(2,6-dichloro-4-methylphenylthio)tetrazol-2-yl)pentanoic acid•t-butylester

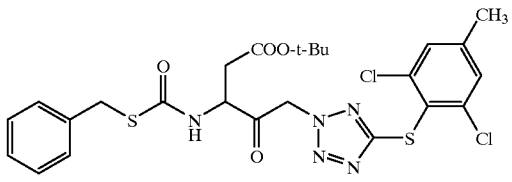

TLC: Rf 0.53 (hexane:ethyl acetate=2:1); NMR (CDCl$_3$): δ 7.36–7.22 (7H, m), 6.64 (1H, d, J=8.5 Hz), 5.68 (1H, d, J=17.8 Hz), 5.49 (1H, d, J=17.8 Hz), 4.88 (1H, m), 4.20 (2H, s), 2.98 (1H, dd, J=17.3 Hz, 4.4 Hz), 2.67 (1H, dd, J=17.3 Hz, 4.7 Hz), 2.34 (3H, s), 1.41 (9H, s).

Example 14(28)

N-(benzylthio)carbonyl-3-amino-4-oxo-5-(5-(2,6-dichloro-4-methylphenylthio)tetrazol-1-yl)pentanoic acid•t-butylester

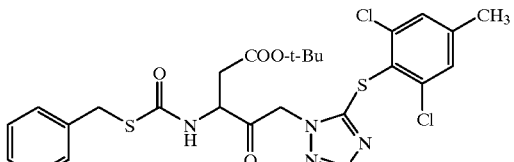

TLC: Rf 0.41 (hexane:ethyl acetate=2:1); NMR (CDCl$_3$): δ 7.39–7.23 (7H, m), 6.69 (1H, d, J=8.7 Hz), 5.58 (1H, d, J=18.4 Hz), 5.42 (1H, d, J=18.4 Hz), 4.91 (1H, m), 4.24 (2H, s), 3.07 (1H, dd, J=17.5 Hz, 4.3 Hz), 2.72 (1H, dd, J=17.5 Hz, 4.7 Hz), 2.34 (3H, s), 1.43 (9H, s).

Example 14(29)

N-(3-phenylpropylthio)carbonyl-3-amino-4-oxo-5-(5-(2,6-dichlorophenylmethyl)tetrazol-2-yl)pentanoic acid•t-butylester

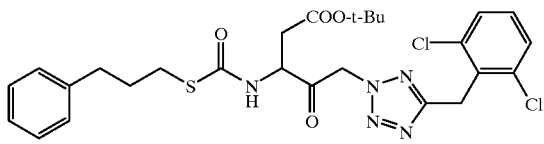

TLC: Rf 0.54 (hexane:ethyl acetate=2:1); NMR (CDCl₃): δ 7.36–7.13 (8H, m), 6.59 (1H, d, J=8.8 Hz), 5.77 (1H, d, J=17.8 Hz), 5.57 (1H, d, J=17.8 Hz), 4.91–4.82 (1H, m), 4.60 (2H, s), 3.04–2.91 (3H, m), 2.75–2.62 (3H, m), 2.05–1.90 (2H, m), 1.42 (9H, s).

Example 14(30)

N-(3-phenylpropylthio)carbonyl-3-amino-4-oxo-5-(5-(2,6-dichlorophenylmethyl)tetrazol-1-yl)pentanoic acid•t-butylester

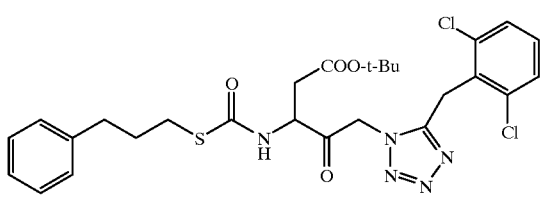

TLC: Rf 0.24 (hexane:ethyl acetate=2:1); NMR (CDCl₃): δ 7.39–7.17 (8H, m), 6.53 (1H, d, J=8.6 Hz), 5.68 (1H, d, J=18.7 Hz), 5.54 (1H, d, J=18.7 Hz), 4.89–4.81 (1H, m), 4.38 (1H, d, J=16.3 Hz), 4.27 (1H, d, J=16.3 Hz), 3.31–2.97 (3H, m), 2.82–2.70 (3H, m), 2.07–1.93 (2H, m), 1.43 (9H, s).

Example 14(31)

N-(benzylthio)carbonyl-3-amino-4-oxo-5-(5-(2,6-dichloro-4-dimethylaminophenylthio)tetrazol-2-yl)pentanoic acid•t-butylester

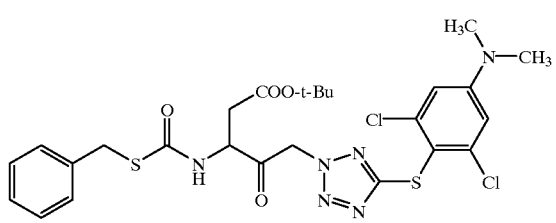

TLC: Rf 0.38 (hexane:ethyl acetate=2:1); NMR (CDCl₃): δ 7.41–7.16 (5H, m), 6.72 (2H, s), 6.66 (1H, d, J=8.6 Hz), 5.66 (1H, d, J=17.6 Hz), 5.48 (1H, d, J=17.6 Hz), 4.95–4.76 (1H, m), 4.19 (2H, s), 2.99 (6H, s), 2.97 (1H, dd, J=17.2 and 4.6 Hz), 2.68 (1H, dd, J=17.2 and 4.8 Hz), 1.41 (9H, s).

Example 14(32)

N-benzylthio)carbonyl-3-amino-4-oxo-5-(5-(2,6-dichloro-4-dimethylaminophenylthio)tetrazol-1-yl)pentanoic acid•t-butylester

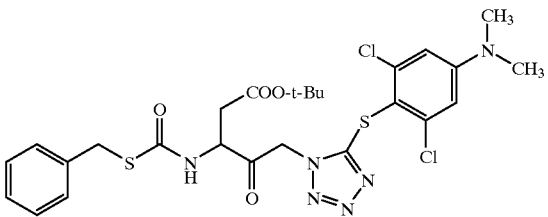

TLC: Rf 0.28 (hexane:ethyl acetate=2:1); NMR (CDCl₃): δ 7.43–7.18 (5H, m), 6.70 (2H, s), 6.76–6.60 (1H, m), 5.55 (1H, d, J=18.2 Hz), 5.37 (1H, d, J=18.2 Hz), 4.99–4.80 (1H, m), 4.24 (2H, s), 3.15–2.96 (2H, m), 2.99 (6H, s), 2.71 (1H, dd, J=17.4 and 4.8 Hz), 1.43 (9H, s).

Example 14(33)

N-(2-phenylethylthio)carbonyl-3-amino-4-oxo-5-(5-(2,3,6-trichlorophenylythio)tetrazol-2-tl)pentanoic acid•t-butylester

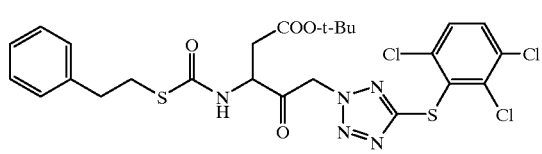

TLC: Rf 0.58 (hexane:ethyl acetate=2:1); NMR (CDCl₃): δ 7.49 (1H, d, J=8.8 Hz), 7.40 (1H, d, J=8.8 Hz), 7.30–7.21 (5H, m), 6.62 (1H, d, J=9 Hz), 5.68 (1J=17.8 Hz), 5.46 (1H, d, J=17.8 Hz), 4.84 (1H, m), 3.30–3.13 (2H, m), 3.05–2.90 (3H, m), 2.80–2.61 (1H, m), 1.42 (9H, s).

Example 14(34)

N-(2-phenylethylthio)carbonyl-3-amino-4-oxo-5-(5-(2,3,6-trichlorophenylthio)tetrazol-1-yl)pentanoic acid•t-butylester

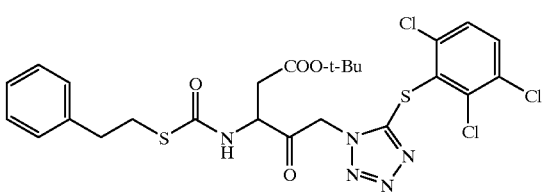

TLC: Rf 0.47 (hexane:ethyl acetate=2:1); NMR (CDCl₃): δ 7.52 (1H, d, J=8.8 Hz), 7.40 (1H, d, J=8.8 Hz), 7.35–7.19 (5H, m), 6.65 (1H, d, J=8.7 Hz), 5.61 (1H, d, J=18.5 Hz), 5.43 (1H, d, J18.5 Hz), 4.91 (1H, m), 3.33–3.25 (2H, m), 3.09 (1H, dd, J=17.6 Hz, 4.7 Hz), 3.01–2.93 (2H, m), 2.72 (1H, dd, J=17.6 Hz, 4.7 Hz), 1.45 (9H, s).

Example 14(35)

N-(2-phenylethylthio)carbonyl-3-amino-4-oxo-5-(5-(2,6-dichloro-4-methylphenylthio)tetrazol-2-yl)pentanoic acid•t-butylester

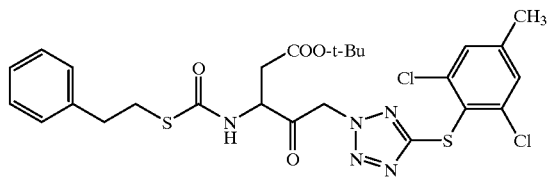

TLC: Rf 0.56 (hexane:ethyl acetate=2:1); NMR (CDCl$_3$):
δ 7.32–7.14 (7H, m), 6.60 (1H, d, J=7.0 Hz), 5.65 (1H, d, J=17.9 Hz), 5.44 (1H, d, J=17.9 Hz), 4.83 (1H, m), 3.29–3.20 (2H, m), 3.04–2.89 (3H, m), 2.65 (1H, dd, J=17.4 Hz, 4.7 Hz), 2.35 (3H, s), 1.42 (9H, s).

Example 14(36)

N-(2-phenylethylthio)carbonyl-3-amino-4-oxo-5-(5-(2,6-dichloro-4-methylphenylthio)tetrazol-1-yl)pentanoic acid•t-butylester

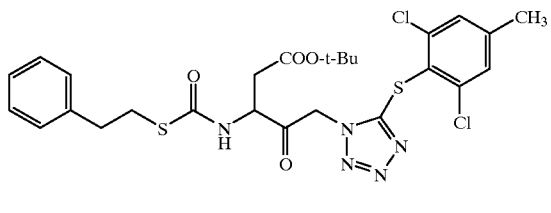

TLC: Rf 0.43 (hexane:ethyl acetate=2:1); NMR (CDCl$_3$):
δ 7.31–7.19 (7H, m), 6.64 (1H, d, J=8.8 Hz), 5.58 (1H, d, J=18.5 Hz), 5.39 (1H, d, J=18.5 Hz), 4.90 (1H, m), 3.33–3.24 (2H, m), 3.12–2.93 (3H, m), 2.71 (1H, dd, J=17.5 Hz, 4.8 Hz), 2.34 (3H, s), 1.44 (9H, s).

Example 14(37)

N-(benzylthio)carbonyl-3-amino-4-oxo-5-(5-(2,6-dimethyl-4-dimethylaminophenylthio)tetrazol-2-yl)pentanoic acid•t-butylester

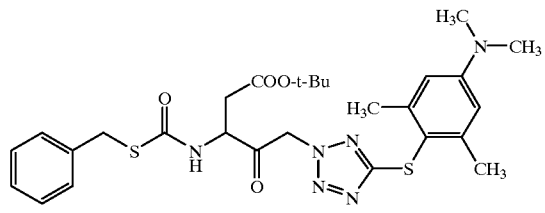

TLC: Rf 0.65 (hexane:ethyl acetate=3:2); NMR (CDCl$_3$):
δ 7.36–7.18 (5H, m), 6.63 (2H, d, J=8.8 Hz), 6.49 (2H, s), 5.64 (1H, d, J=18 Hz), 5.45 (1H, d, J=18 Hz), 4.85 (1H, m), 4.18 (2H, s), 3.01–2.89 (7H, m), 2.65 (1H, dd, J=4.6, 17 Hz), 2.44 (6H, s), 1.40 (9H, s).

Example 14(38)

N-(benzylthio)carbonyl-3-amino-4-oxo-5-(5-(2,6-dimethyl-4-dimethylaminophenylthio)tetrazol-1-yl)pentanoic acid•t-butylester

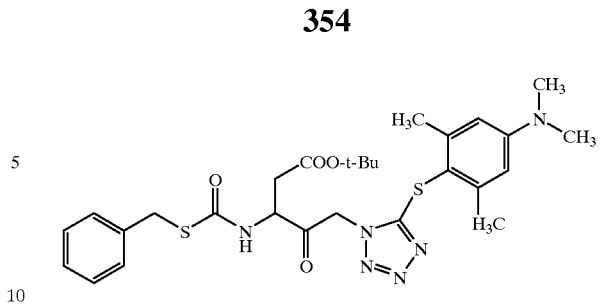

TLC: Rf 0.50 (hexane:ethyl acetate=3:2); NMR (CDCl$_3$):
δ 7.40–7.20 (5H, m), 6.58 (2H, d, J=8.8 Hz), 6.49 (2H, s), 5.41 (1H, d, J=18 Hz), 5.24 (1H, d, J=18 Hz), 4.83 (1H, m), 4.23 (2H, s), 3.05–2.94 (7H, m), 2.67 (1H, dd, J=4.6, 17 Hz), 2.37 (6H, s), 1.43 (9H, s).

Example 14(39)

N-(benzylthio)carbonyl-3-amino-4-oxo-5-(5-(2,6-dimethyl-4-t-butylphenylthio)tetrazol-2-yl)pentanoic acid•t-butylester

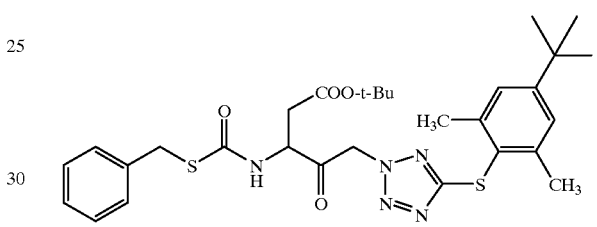

TLC: Rf 0.61 (hexane:ethyl acetate=3:1); NMR (CDCl$_3$):
δ 7.37–7.19 (5H, m), 7.16 (2H, s), 6.62 (1H, d, J=8.8 Hz), 5.65 (1H, d, J=17.7 Hz), 5.46 (1H, d, J=17.7 Hz), 4.94–4.78 (1H, m), 4.19 (2H, s), 2.98 (1H, dd, J=17.5, 4.3 Hz), 2.65 (1H, dd, J=17.5, 4.7 Hz), 2.48 (6H, s), 1.41 (9H, s), 1.30 (9H, s).

Example 14(40)

N-(benzylthio)carbonyl-3-amino-4-oxo-5-(5-(2,6-dimethyl-4-t-butylphenylthio)tetrazol-1-yl)pentanoic acid•t-butylester

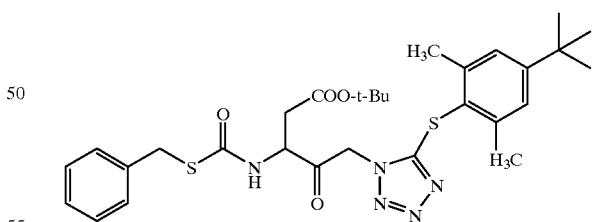

TLC: Rf 0.47 (hexane:ethyl acetate=3:1); NMR (CDCl$_3$):
δ 7.42–7.13 (7H, m), 6.75–6.59 (1H, m), 5.48 (1H, d, J=18.5 Hz), 5.30 (1H, d, J=18.5 Hz), 4.92–4.76 (1H, m), 4.24 (2H, s), 3.04 (1H, dd, J=17.5, 4.3 Hz), 2.68 (1H, dd, J=17.5, 4.5 Hz), 2.41 (3H, s), 1.43 (9H, s), 1.30 (9H, s).

Example 14(41)

N-(2-(pyridin-2-yl)ethyloxy)carbonyl-3-amino-4-oxo-5-(5-(2,6-dichlorophenylmethyl)tetrazol-2-yl)pentanoic acid•t-butylester

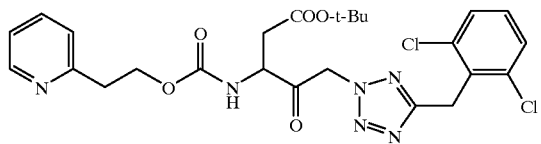

TLC: Rf 0.33 (hexane:ethyl acetate=1:2); NMR (CDCl$_3$): δ 8.53 (1H, d, J=5.0 Hz), 7.64–7.56 (1H, m), 7.36–7.08 (5H, m), 5.85 (1H, d, J=9.2 Hz), 5.74 (1H, d, J=17.8 Hz), 5.53 (1H, d, J=17.8 Hz), 4.68–4.42 (5H, m), 3.14 (2H, t, J=6.4 Hz), 2.97 (1H, dd, J=4.0, 17.4 Hz), 2.67 (1H, dd, J=5.0, 17.4 Hz), 1.40 (9H, s).

Example 14(42)

N-(2-(pyridin-2-yl)ethyloxy)carbonyl-3-amino-4-oxo-5-(5-(2,6-dichlorophenylmethyl)tetrazol-1-yl)pentanoic acid•t-butylester

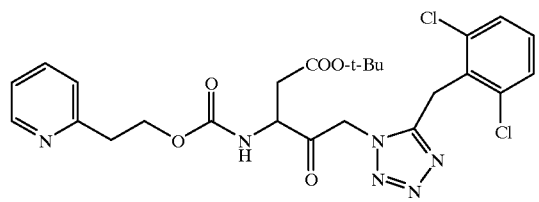

TLC: Rf 0.22 (hexane:ethyl acetate=1:2); NMR (CDCl$_3$): δ 8.55 (1H, d, J=5.0 Hz), 7.68–7.60 (1H, m), 7.39–7.12 (5H, m), 5.82 (1H, d, J=8.0 Hz), 5.69 (1H, d, J=18.8 Hz), 5.53 (1H, d, J=18.8 Hz), 4.75–4.45 (3H, m), 4.40–4.20 (2H, m), 3.17 (2H, t, J=6.6 Hz), 3.13–3.02 (1H, m), 2.75 (1H, dd, J=4.8, 17.4 Hz), 1.41 (9H, s).

Example 14(43)

N-(2-phenylethylthio)carbonyl-3-amino-4-oxo-5-(5-(2,6-dichloro-4-dimethylaminophenylthio)tetrazol-2-yl)pentanoic acid•t-butylester

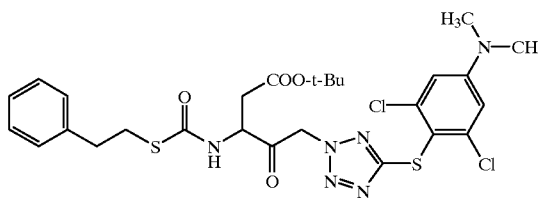

TLC: Rf 0.79 (hexane:ethyl acetate=1:1); NMR (CDCl$_3$): δ 7.38–7.06 (5H, m), 6.73 (2H, s), 6.57 (1H, d, J=8.4 Hz), 5.63 (1H, d, J=17.8 Hz), 5.43 (1H, d, J=17.8 Hz), 4.92–4.72 (1H, m), 3.36–3.12 (2H, m), 3.12–3.09 (3H, m), 2.99 (6H, s), 2.65 (1H, dd, J=17.4 and 4.6 Hz), 1.42 (9H, s).

Example 14(44)

N-(2-phenylethylthio)carbonyl-3-amino-4-oxo-5-(5-(2,6-dichloro-4-dimethylaminophenylthio)tetrazol-1-yl)pentanoic acid•t-butylester

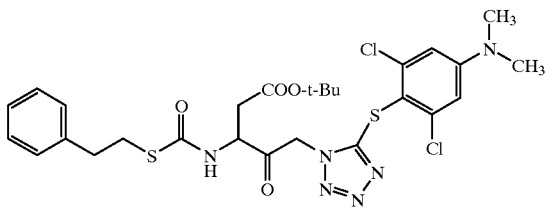

TLC: Rf 0.67 (hexane:ethyl acetate=1:1); NMR (CDCl$_3$): δ 7.41–7.09 (5H, m), 6.70 (2H, s), 6.63 (1H, d, J=8.6 Hz), 5.54 (1H, d, J=18.4 Hz), 5.34 (1H, d, J=18.4 Hz), 4.98–4.74 (1H, m), 3.38–3.15 (2H, m), 3.15–2.80 (3H, m), 2.99 (6H, s), 2.69 (1H, dd, J=17.6 and 4.8 Hz), 1.44 (9H, s).

Example 14(45)

N-(2-(4-methoxyphenyl)ethyloxy)carbonyl-3-amino-4-oxo-5-(5-(2,3,6-trichlorophenylthio)tetrazol-2-yl)pentanoic acid•t-butylester

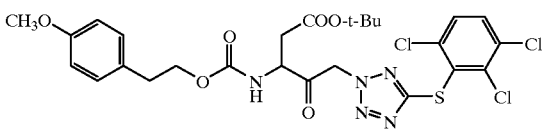

TLC: Rf 0.46 (hexane:ethyl acetate=2:1); NMR (CDCl$_3$): δ 7.49 (1H, d, J=8.7 Hz), 7.39 (1H, d, J=8.7 Hz), 7.15 (2H, d, J=8.7 Hz), 6.83 (2H, d, J=8.7 Hz), 5.82 (1H, d, J=9.2 Hz), 5.73–5.44 (2H, m), 4.58 (1H, m), 4.48–4.22 (2H, m), 3.74 (3H, s), 3.00 (1H, dd, J=17 Hz, 5 Hz), (2H, t, J=6.9 Hz), 2.66 (1H, dd, J=17 Hz, 4.7 Hz), 1.42 (9H, s).

Example 14(46)

N-(2-(4-methoxyphenyl)ethyloxy)carbonyl-3-amino-4-oxo-5-(5-(2,3,6-trichlorophenylthio)tetrazol-1-yl)pentanoic acid•t-butylester

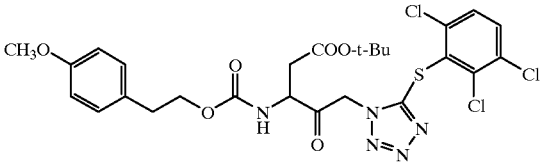

TLC: Rf 0.38 (hexane:ethyl acetate=2:1); NMR (CDCl$_3$): δ 7.51 (1H, d, J=8.8 Hz), 7.39 (1H, d, J=8.8 Hz), 7.16 (2H, d, J=8.6 Hz), 6.85 (2H, d, J=8.6 Hz), 5.86 (1H, d, J=9.4 Hz), 5.66–5.38 (2H, m), 4.63 (1H, m), 4.51–4.26 (2H, m), 3.75 (3H, s), 3.08 (1H, dd, J=18 Hz, 4.0 Hz), 2.93 (2H, t, 6.9 Hz), 2.70 (1H, dd, J=18 Hz, 4.6 Hz), 1.43 (9H, s).

Example 14(47)

N-(2-(4-methoxyphenyl)ethyloxy)carbonyl-3-amino-4-oxo-5-(5-(2,6-dichloro-4-methylphenylthio)tetrazol-2-yl)pentanoic acid•t-butylester

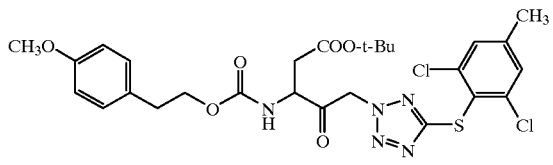

TLC: Rf 0.41 (hexane:ethyl acetate=2:1); NMR (CDCl$_3$): δ 7.21 (2H, s), 7.08 (2H, d, J=8.4 Hz), 6.77 (2H, d, J=8.4 Hz), 5.74 (1H, d, J=9.5 Hz), 5.65–5.36 (2H, m), 4.51 (1H, m), 4.42–416 (2H, m), 3.68 (3H, s), 2.98–2.81 (3H, m), 2.64 (1H, dd, J=17 Hz, 4.8 Hz), 2.28 (3H, s), 1.36 (9H, s).

Example 14(48)

N-(2-(4-methoxyphenyl)ethyloxy)carbonyl-3-amino-4-oxo-5-(5-(2,6-dichloro-4-methylphenylthio)tetrazol-1-yl)pentanoic acid•t-butylester

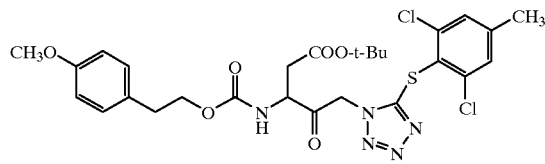

TLC: Rf 0.33 (hexane:ethyl acetate=2:1); NMR (CDCl$_3$): δ 7.27 (2H, s), 7.17 (2H, d, J=8.7 Hz), 6.85 (2H, d, J=8.7 Hz), 5.88 (1H, d, J=9.2 Hz), 5.65–5.36 (2H, m), 4.63 (1H, m), 4.51–4.26 (2H, m), 3.75 (3H, s), 3.06 (1H, dd, J=17.6 Hz, 4.2 Hz), 2.93 (2H, t, J=7.0 Hz), 2.70 (1H, dd, J=17.6 Hz, 4.7 Hz), 2.34 (3H, s), 1.44 (9H, s).

Example 14(49)

N-(2-(4-methoxyphenyl)ethyloxy)carbonyl-3-amino-4-oxo-5-(5-(2,6-dichloro-4-dimethylaminophenylthio)tetrazol-2-yl)pentanoic acid•t-butylester

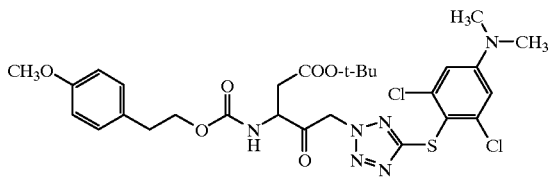

TLC: Rf 0.79 (hexane:ethyl acetate=2:1); NMR (CDCl$_3$): δ 7.14 (2H, d, J=8.5 Hz), 6.83 (2H, d, J=8.5 Hz), 6.72 (2H, s), 5.81 (1H, d, J=9 Hz), 5.62–5.42 (2H, m), 4.57 (1H, m), 4.47–4.21 (2H, m), 3.74 (3H, s), 2.99 (6H, s), 2.90 (3H, m), 2.66 (1H, dd, J=17 Hz, 4.5 Hz), 1.42 (9H, s).

Example 14(50)

N-(2-(4-methoxyphenyl)ethyloxy)carbonyl-3-amino-4-oxo-5-(5-(2,6-dichloro-4-dimethylaminophenylthio)tetrazol-1-yl)pentanoic acid•t-butylester

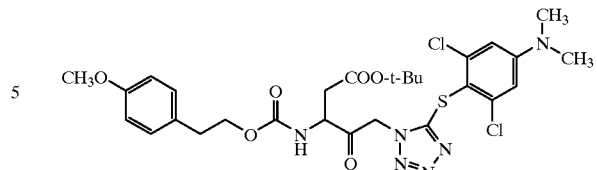

TLC: Rf 0.69 (hexane:ethyl acetate=2:1); NMR (CDCl$_3$): δ 7.16 (2H, d, J=8.4 Hz), 6.85 (2H, d, J=8.4 Hz), 6.70 (2H, s), 5.88 (1H, d, J=9 Hz), 5.61–5.32 (2H, m), 4.62 (1H, m), 4.50–4.26 (2H, m), 3.75 (3H, s), 3.09–2.90 (3H, m), 2.99 (6H, s), 2.70 (1H, dd, J=17 Hz, 4.4 Hz), 1.44 (9H, s).

Example 14(51)

N-(2-(4-methoxyphenyl)ethyloxy)carbonyl-3-amino-4-oxo-5-(5-(2,6-dimethyl-4-dimethylaminophenylthio)tetrazol-2-yl)pentanoic acid•t-butylester

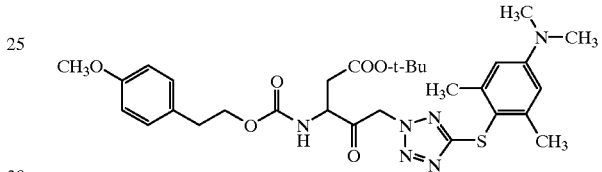

TLC: Rf 0.61 (hexane:ethyl acetate=3:2); NMR (CDCl$_3$): δ 7.13 (2H, d, J=8.6 Hz), 6.81 (2H, d, J=8.6 Hz), 6.49 (2H, s), 5.81 (1H, d, J=9.0 Hz), 5.61 (1H, d, J=17.9 Hz), 5.41 (1H, d, J=17.9 Hz), 4.63–4.15 (3H, m), 3.73 (3H, s), 3.05–2.80 (3H, m), 2.96 (6H, s), 2.64 (1H, dd, J=17.3, 4.7 Hz), 2.44 (6H, s), 1.42 (9H, s).

Example 14(52)

N-(2-(4-methoxyphenyl)ethyloxy)carbonyl-3-amino-4-oxo-5-(5-(2,6-dimethyl-4-dimethylaminophenylthio)tetrazol-1-yl)pentanoic acid•t-butylester

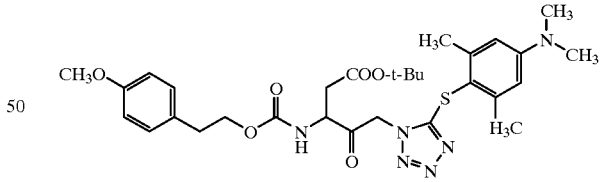

TLC: Rf 0.45 (hexane:ethyl acetate=3:2); NMR (CDCl$_3$): δ 7.16 (2H, d, J=8.7 Hz), 6.84 (2H, d, J=8.7 Hz), 6.49 (2H, s), 5.84 (1H, d, J=9.2 Hz), 5.41 (1H, d, J=18.4 Hz), 5.20 (1H, d, J=18.4 Hz), 4.63–4.20 (3H, m), 3.73 (3H, s), 3.05–2.85 (3H, m), 2.97 (6H, s), 2.65 (1H, dd, J=17.5, 4.8 Hz), 2.38 (6H, s), 1.43 (9H, s).

Example 14(53)

N-(4-(4-methoxyphenyl)butyloxy)carbonyl-3-amino-4-oxo-5-(5-(2,3,6-trichlorophenylthio)tetrazol-2-yl)pentanoic acid•t-butylester

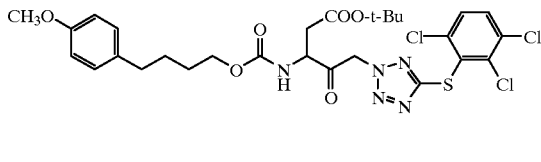

TLC: Rf 0.43 (hexane:ethyl acetate=2:1); NMR (CDCl$_3$): δ 7.49 (1H, d, J=8.8 Hz), 7.39 (1H, d, J=8.8 Hz), 7.09 (2H, d, J=8.5 Hz), 6.82 (2H, d, J=8.5 Hz), 5.80 (1H, d, J=17.9 Hz), 5.80 (1H, m), 5.61 (1H, d, J=17.9 Hz), 4.64 (1H, m), 4.14 (2H, m), 3.78 (3H, s), 3.01 (1H, dd, J=17.5 Hz, 4.4 Hz), 2.69 (1H, dd, J=17.5 Hz, 4.8 Hz), 2.59 (2H, m), 1.65 (4H, m), 1.42 (9H, s).

Example 14(54)

N-(4-(4-methoxyphenyl)butyloxy)carbonyl-3-amino-4-oxo-5-(5-(2,3,6-trichlorophenylthio)tetrazol-2-yl)pentanoic acid•t-butylester

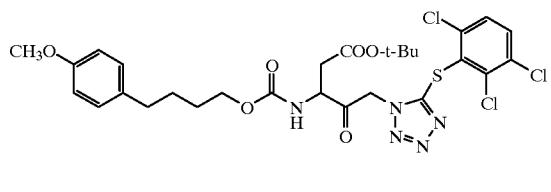

TLC: Rf 0.34 (hexane:ethyl acetate=2:1); NMR (CDCl$_3$): δ 7.52 (1H, d, J=8.8 Hz), 7.40 (1H, d, J=8.8 Hz), 7.10 (2H, d, J=8.4 Hz), 6.83 (2H, d, J=8.4 Hz), 5.88 (1H, d, J=8.4 Hz), 5.73 (1H, d, J=8.4 Hz), 5.56 (1H, d, J=18.9 Hz), 4.68 (1H, m), 4.19 (2H, m), 3.78 (3H, s), 3.10 (1H, dd, J=17.6 Hz, 4.4 Hz), 2.74 (1H, dd, J=17.6 Hz, 4.8 Hz), 2.61 (2H, m), 1.69 (4H, 1.45 (9H, s).

Example 14(55)

N-(4-(4-methoxyphenyl)butyloxy)carbonyl-3-amino-4-oxo-5-(5-(2,6-dichloro-4-dimethylaminophenylthio)tetrazol-2-yl)pentanoic acid•t-butylester

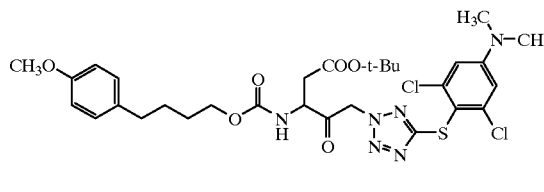

TLC: Rf 0.35 (hexane:ethyl acetate=2:1); NMR (CDCl$_3$): δ 7.09 (2H, d, J=8.6 Hz), 6.82 (2H, d, J=8.6 Hz), 6.72 (2H, s), 5.81 (1H, m), 5.75 (1H, d, J=17.8 Hz), 5.57 (1H, d, J=17.8 Hz), 4.60 (1H, m), 4.14 (2H, m), 3.78 (3H, s), 2.99 (6H, s), 2.95 (1H, m), 2.74–2.66 (1H, m), 2.59 (2H, m), 1.67 (4H, m), 1.42 (9H, s).

Example 14(56)

N-(4-(4-methoxyphenyl)butyloxy)carbonyl-3-amino-4-oxo-5-(5-(2,6-dichloro-4-dimethylaminophenylthio)tetrazol-1-yl)pentanoic acid•t-butylester

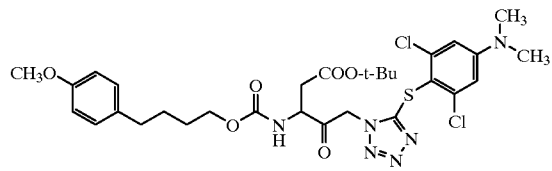

TLC: Rf 0.24 (hexane:ethyl acetate=2:1); NMR (CDCl$_3$): δ 7.10 (2H, d, J=8.6 Hz), 6.82 (2H, d, J=8.6 Hz), 6.70 (2H, s), 5.88 (1H, m), 5.66 (1H, d, J=18.4 Hz), 5.47 (1H, d, J=18.4 Hz), 4.65 (1H, m), 4.14 (2H, m), 3.78 (3H, s), 3.05 (1H, dd, J=17.2 Hz, 4.4 Hz), 2.99 (6H, s), 2.72 (1H, dd, J=17.2 Hz, 4.8 Hz), 2.59 (2H, m), 1.69 (4H, m), 1.44 (9H, s).

Example 14(57)

N-(2-(4-methylthiazol-5-yl)ethyloxy)carbonyl-3-amino-4-oxo-5-(5-(2,6-dichlorophenylthio)tetrazol-2-yl)pentanoic acid•t-butylester

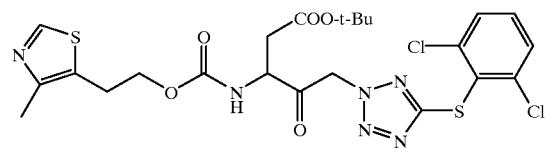

TLC: Rf 0.60 (hexane:ethyl acetate=1:2); NMR (CDDl$_3$): δ 8.59 (1H, s), 7.48–7.28 (3H, m), 5.99 (1H, m), 5.76 (1H, d, J=17.8 Hz), 5.59 (1H, d, J=17.8 Hz), 4.64 (1H, m), 4.29 (2H, t, J=6.6 Hz), 3.12 (2H, t, J=6.6 Hz), 2.97 (1H, dd, J=18 Hz, 4.4 Hz), 2.71 (1H, dd, J=18 Hz, 5.0 Hz), 2.41 (3H, s), 1.42 (9H, s).

Example 14(58)

N-(2-(4-methylthiazol-5-yl)ethyloxy)carbonyl-3-amino-4-oxo-5-(5-(2,6-dichlorophenylthio)tetrazol-1-yl)pentanoic acid•t-butylester

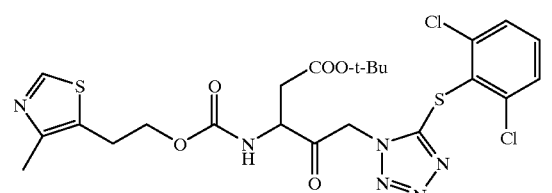

TLC: Rf 0.51 (hexane:ethyl acetate=1:2); NMR (CDCl$_3$): δ 8.60 (1H, s), 7.48–7.27 (3H, m), 5.99 (1H, m), 5.69 (1H, d, J=18.2 Hz), 5.52 (1H, d, J=18.2 Hz), 4.66 (1H, m), 4.36 (2H, t, J=6.2 Hz), 3.16 (2H, t, J=6.2 Hz), 3.08 (1H, dd, J=17.6 Hz, 4.4 Hz), 2.74 (1H, dd, J=17.6 Hz, 5.0 Hz), 2.44 (3H, s), 1.45 (9H, s).

Example 14(59)

N-(2-phenylethylthio)carbonyl-3-amino-4-oxo-5-(5-(2,6-dichlorophenylthio)tetrazol-2-yl)pentanoic acid•t-butylester

361

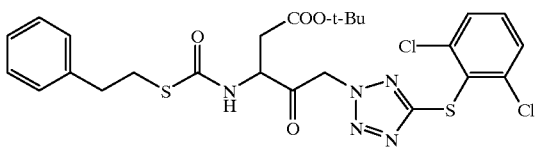

TLC: Rf 0.49 (hexane:ethyl acetate=2:1); NMR (CDCl₃): δ 7.47–7.43 (2H, m), 7.34–7.14 (6H, m), 6.57 (1H, d, J=8.8 Hz), 5.66 (1H, d, J=17.8 Hz), 5.44 (1H, d, J=17.8 Hz), 4.82 (1H, m), 3.29–3.20 (2H, m), 3.04–2.89 (3H, m), 2.65 (1H, dd, J=17.4 Hz, 4.6 Hz), 1.42 (9H, s).

Example 14(60)
N-(2-phenylethylthio)carbonyl-3-amino-4-oxo-5-(5-(2,6-dichlorophenylthio)tetrazol-1-yl)pentanoic acid•t-butylester

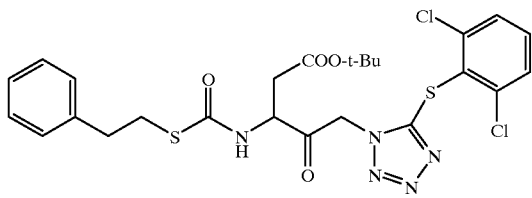

TLC: Rf 0.35 (hexane:ethyl acetate=2:1); NMR (CDCl₃): δ 7.48–7.43 (2H, m), 7.36–7.18 (6H, m), 6.64 (1H, d, J=8 (Hz), 5.60 (1H, d, J=18.6 Hz), 5.41 (1H, d, J=18.6 Hz), 4.89 (1H, m), 3.31–3.24 (2H, m), 3.12–2.93 (3H, m), 2.70 (1H, dd, J=17 Hz, 4.6 Hz), 1.45 (9H, s).

Example 14(61)
N-(2-phenylethylthio)carbonyl-3-amino-4-oxo-5-(5-(4-(pyrrolidin-1-ylmethyl)phenylthio)tetrazol-2-yl)pentanoic acid•t-butylester

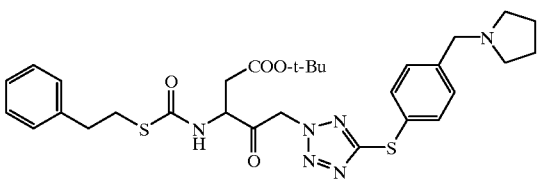

TLC: Rf 0.45 (chloroform:methanol=9:1), NMR (CDCl₃): δ 7.62 (2H, d, J=8.8 Hz), 7.55 (2H, d, J=8.8 Hz), 7.38–7.10 (5H, m), 6.79 (1H, d, J=8.4 Hz), 5.78 (1H, d, J=17.7 Hz), 5.57 (1H, d, J=17.7 Hz), 4.98–4.83 (1H, m), 4.13 (2H, s), 3.30–2.63 (10H, m), 2.23–2.00 (4H, m), 1.44 (9H, s).

Example 14(62)
N-(2-phenylethylthio)carbonyl-3-amino-4-oxo-5-(5-(4-(pyrrolidin-1-ylmethyl)phenylthio)tetrazol-1-yl)pentanoic acid•t-butylester

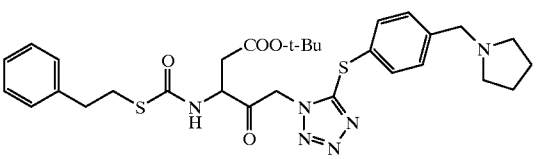

TLC: Rf 0.43 (chloroform:methanol=9:1); NMR (CDCl₃): δ 7.62 (2H, d, J=8.3 Hz), 7.51 (2H, d, J=8.3 Hz), 7.41–7.10 (6H, m), 5.68 (1H, d, J=18.6 Hz), 5.45 (1H, d, J=18.6 Hz), 4.98–4.80 (1H, m), 4.30 (1H, d, J=12.7 Hz), 3.94 (1H, d, J=12.7 Hz), 3.33–2.66 (10H, m), 2.30–2.00 (4H, m), 1.41 (9H, s).

Example 14(63)
N-(2-(4-methylthiazol-5-yl)ethylthio)carbonyl-3-amino-4-oxo-5-(5-(2,6-dichlorophenylthio)tetrazol-2-yl)pentanoic acid•t-butylester

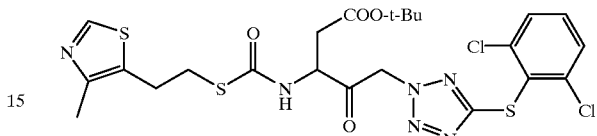

TLC: Rf 0.67 (hexane:ethyl acetate=1:2); NMR (CDCl₃): δ 8.58 (1H, s), 7.47–7.41 (2H, m), 7.34–7.24 (2H, m), 6.69 (1H, d, J=8.8 Hz), 5.74 (1H, d, J=17.6 Hz), 5.56 (1H, d, J=17.6 Hz), 4.86 (1H, m), 3.14 (4H, m), 2.98 (1H, dd, J=17.6 Hz, 4.4 Hz), 2.69 (1H, dd, J=17.6 Hz, 4.8 Hz), 2.43 (1H, s), 1.43 (9H, s).

Example 14(64)
N-(2-(4-methylthiazol-5-yl)ethylthio)carbonyl-3-amino-4-oxo-5-(5-( 2,6-dichlorophenylthio)tetrazol-1-yl)pentanoic acid•t-butylester

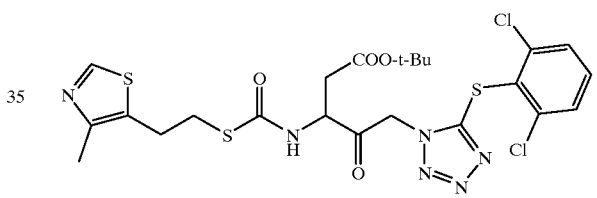

TLC: Rf 0.58 (hexane:ethyl acetate=1:2); NMR (CDCl₃): δ 8.59 (1H, s), 7.48–7.43 (2H, m), 7.37–7.27 (2H, m), 6.83 (1H, d, J=8.8 Hz), 5.67 (1H, d, J=18.6 Hz), 5.50 (1H, d, J=18.6 Hz), 492 (1H, m), 3.18 (4H, m), 3.05 (1H, dd, J=17.4 Hz, 4.6 Hz), 2.76 (1H, dd, J=17.4 Hz, 5.0 Hz), 2.44 (1H, s), 1.43 (9H, s).

Example 14(65)
N-(butylthio)carbonyl-3-amino-4-oxo-5-(5-(2,6-dichlorophenylthio) tetrazol-2-yl)pentanoic acid•t-butylester

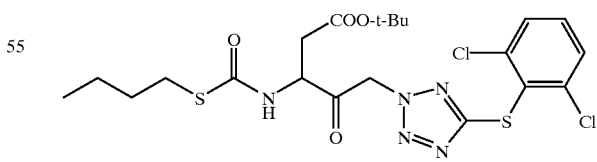

TLC: Rf 0.68 (hexane:ethyl acetate=2:1); NMR (CDCl₃): δ 7.37–7.16 (3H, m), 6.50 (1H, d, J=9.0 Hz), 5.67 (1H, d, J=17.8 Hz), 5.47 (1H, d, J=17.8 Hz), 4.76 (1H, m), 2.89 (1H, dd, J=17.4 Hz, 4.8 Hz), 2.86 (2H, t, J=7.2 Hz), 2.59 (1H, dd, J=17.4 Hz, 4.8 Hz), 1.57 (2H, m), 1.34 (2H, m), 1.33 (9H, s), 0.83 (3H, t, J=7.2 Hz).

Example 14(66)

N-(butylthio)carbonyl-3-amino-4-oxo-5-(5-(2,6-dichlorophenylthio) tetrazol-1-yl)pentanoic acid•t-butylester

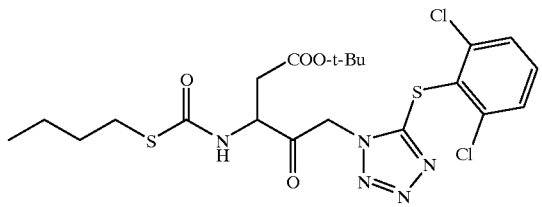

TLC: Rf 0.43 (hexane:ethyl acetate=2:1); NMR (CDCl$_3$): δ 7.39–7.18 (3H, m), 6.59 (1H, d, J=8.6 Hz), 5.61 (1H, d, J=18.2 Hz), 5.44 (1H, d, J=18.2 Hz), 4.85 (1H, m), 3.00 (1H, dd, J=17.4 Hz, 4.6 Hz), 2.93 (2H, t, J=7.3 Hz), 2.66 (1H, dd, J=17.4 Hz, 4.8 Hz), 1.58 (2H, m), 1.41 (2H, m), 1.37 (9H, s), 0.86 (3H, t, J=7.3 Hz).

Example 14(67)

N-(2-(4-methoxyphenyl)ethylthio)carbonyl-3-amino-4-oxo-5-(5-(2,6-dichlorophenylthio)tetrazol-2-yl)pentanoic acid•t-butylester

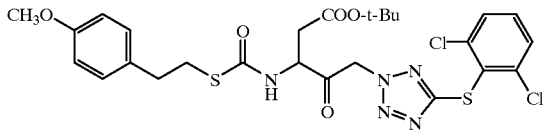

TLC: Rf 0.39 (hexane:ethyl acetate=2:1); NMR (CDCl$_3$): δ 7.48–7.43 (2H, m), 7.34–7.29 (1H, m), 7.14 (2H, d, J=8.6 Hz), 6.83 (2H, d, J=8.6 Hz), 6.58 (1H, d, J=8.6 Hz), 5.70 (1H, d, J=17.8 Hz), 5.49 (1H, J=17.8 Hz), 4.85 (1H, m), 3.75 (3H, s), 3.23–3.09 (2H, m), 3.04–2.86 (3H, m), 2.66 (1H, dd, J=18 Hz, 4.6 Hz), 1.42 (9H, s).

Example 14(68)

N-(2-(4-methoxyphenyl)ethylthio)carbonyl-3-amino-4-oxo-5-(5-(2,6-dichlorophenylthio)tetrazol-1-yl)pentanoic acid•t-butylester

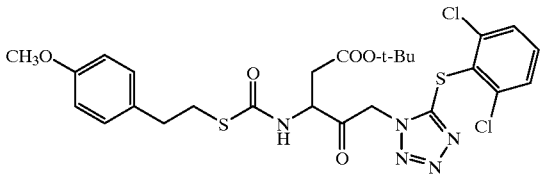

TLC: Rf 0.27 (hexane:ethyl acetate=2:1); NMR (CDCl$_3$): δ 7.48–7.43 (2H, m), 7.36–7.28 (1H, m), 7.16 (2H, d, J=8.8 Hz), 6.84 (2H, d, J=8.8 Hz), 6.13 (1H, d, J=8.8 Hz), 5.63 (1H, d, J=18.4 Hz), 5.45 (1H, d, J=18.4 Hz), 4.90 (1H, m), 3.76 (3H, s), 3.24 (2H, m), 3.07 (1H, dd, J=18 Hz, 4.4 Hz), 2.92 (2H, m), 2.71 (1H, dd, J=18 Hz, 4.6 Hz), 1.45 (9H, s).

Example 14(69)

N-(3-(pyrimidin-2-yl)propyloxy)carbonyl-3-amino-4-oxo-5-(5-(2,6-dichlorophenylthio)tetrazol-2-yl)pentanoic acid•t-butylester

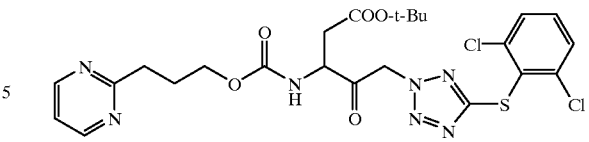

HPTLC: Rf 0.51 (chloroform:t-butanol=20:1); NMR (CDCl$_3$): δ 8.66 (2H, d, J=5.0 Hz), 7.44 (2H, d, J=6.5 Hz), 7.30 (1H, m), 7.14 (1H, t, J=5.0 Hz), 5.92–5.56 (3H, m), 4.60 (1H, m), 4.22 (2H, t, J=6.0 Hz), 3.13–2.85 (3H, m), 2.69 (1H, dd, J=17.0, 5.0 Hz), 2.22 (2H, m), 1.44 (9H, s).

Example 14(70)

N-(3-(pyrimidin-2-yl)propyloxy)carbonyl-3-amino-4-oxo-5-(5-(2,6-dichlorophenylthio)tetrazol-1-yl)pentanoic acid•t-butylester

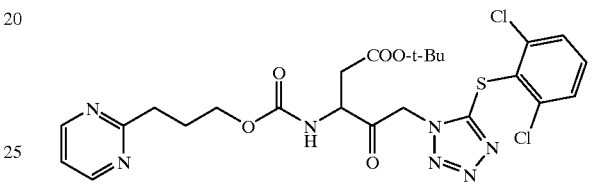

HPTLC: Rf 0.45 (chloroform:t-butanol=20:1); NMR (CDCl$_3$): δ 8.78 (2H, d, J=5.0 Hz), 7.45 (2H, d, J=7.0 Hz), 7.32 (1H, m), 7.15 (1H, t, J=5.0 Hz), 5.93 (1H, d, J=8.5 Hz), 5.75 and 5.59 (each 1H, each d, J=18.0 Hz), 4.66 (1H, m), 4.28 (2H, t, J=6.5 Hz), 3.10 (3H, m), 2.74 (1H, dd, J=17.0, 5.0 Hz), 2.25 (2H, m), 1.46 (9H, s).

Example 14(71)

N-(2-(4-acetylaminophenyl)ethylthio)carbonyl-3-amino-4-oxo-5-(5-(2,6-dichlorophenylthio)tetrazol-2-yl)pentanoic acid•t-butylester

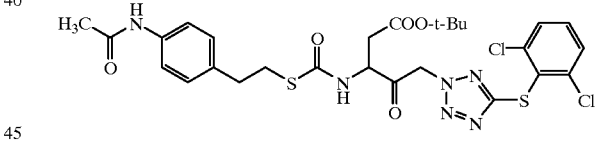

TLC: Rf 0.66 (hexane:ethyl acetate=3:7); NMR (CDCl$_3$): δ 7.53–7.08 (8H, m), 6.58 (1H, d, J=8.6 Hz), 5.64 (1H, d, J=17.7 Hz), 5.44 (1H, d, J=17.7 Hz), 4.86–4.73 (1H, m), 3.30–2.55 (6H, m), 2.14 (3H, s), 1.42 (9H, s).

Example 14(72)

N-(2-(4-acetylaminophenyl)ethylthio)carbonyl-3-amino-4-oxo-5-(5-(2,6-dichlorophenylthio)tetrazol-1-yl)pentanoic acid•t-butylester

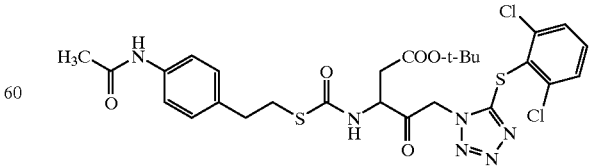

TLC: Rf 0.57 (hexane:ethyl acetate=3:7); NMR (CDCl$_3$): δ 7.54 (1H, s), 7.50–7.23 (5H, m), 7.17 (2H, d, J=8.4 Hz), 6.82 (1H, d, J=8.4 Hz), 5.59 (1H, d, J=18.5 Hz), 5.38

(1H, d, J=18.5 Hz), 4.95–4.81 (1H, m), 3.40–2.62 (6H, m), 2.10 (3H, s), 1.44 (9H, s).

Example 14(73)

N-butyloxycarbonyl-3-amino-4-oxo-5-(5-(2,6-dichlorophenylthio) tetrazol-2-yl)pentanoic acid•t-butylester

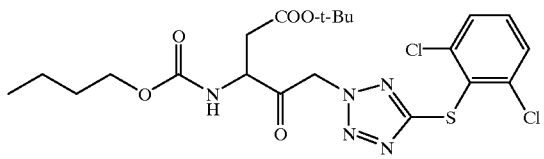

TLC: Rf 0.48 (hexane:ethyl acetate=2:1); NMR (CDCl₃): δ 7.47–7.43 (2H, m), 7.34–7.27 (1H, m), 5.80 (1H, d, J=18.0 Hz), 5.79 (1H, m), 5.61 (1H, d, J=18.0 Hz), 4.62 (1H, m), 4.14 (2H, m), 2.99 (1H, dd, J=17.4 Hz, 4.6 Hz), 2.70 (1H, dd, J=17.4 Hz, 5.0 Hz), 1.64 (2H, m), 1.43 (9H, s), 1.37 (2H, m), 0.94 (3H, t, J=7.4 Hz).

Example 14(74)

N-butyloxycarbonyl-3-amino-4-oxo-5-(5-(2,6-dichlorophenylthio) tetrazol-1-yl)pentanoic acid•t-butylester

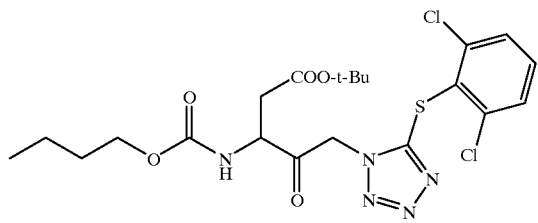

TLC: Rf 0.38 (hexane:ethyl acetate=2:1); NMR (CDCl₃): δ 7.48–7.43 (2H, m), 7.36–7.27 (1H, m), 5.89 (1H, d, J=8.8 Hz), 5.73 (1H, d, J=18.4 Hz), 5.55 (1H, d, J=18.4 Hz), 4.68 (1H, m), 4.20 (2H, m), 3.08 (1H, dd, J=17.6 Hz, 4.4 Hz), 2.75 (1H, dd, J=17.6 Hz, 5.0 Hz), 1.63 (2H, m), 1.45 (9H, s), 1.41 (2H, m), 0.96 (3H, t, J=7.2 Hz).

Example 14(75)

N-(propylthio)carbonyl-3-amino-4-oxo-5-(5-(2,6-dichlorophenylthio) tetrazol-2-yl)pentanoic acid•t-butylester

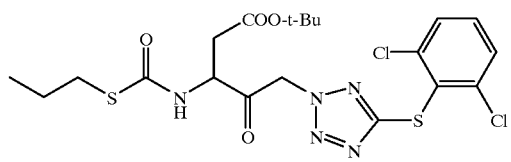

TLC: Rf 0.57 (hexane:ethyl acetate=7:3); NMR (CDCl₃): δ 7.50–7.21 (3H, m), 6.59 (1H, d, J=8.6 Hz), 5.77 (1H, d, J=17.6 Hz), 5.57 (1H, d, J=17.6 Hz), 4.92–4.78 (1H, m), 3.08–2.87 (3H, m), 2.69 (1H, dd, 17.5, 4.7 Hz), 1.80–1.55 (2H, m), 1.43 (9H, s), 1.00 (3H, t, J=7.3 Hz).

Example 14(76)

N-(propylthio)carbonyl-3-amino-4-oxo-5-(5-(2,6-dichlorophenylthio) tetrazol-1-yl)pentanoic acid•t-butylester

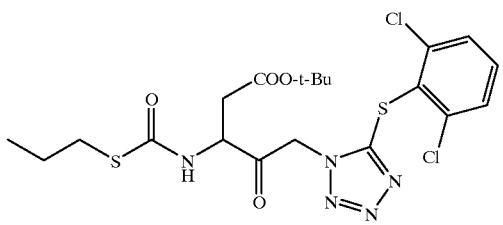

TLC: Rf 0.43 (hexane:ethyl acetate=7:3); NMR (CDCl₃): δ 7.50–7.25 (3H, m), 6.65 (1H, d, J=8.8 Hz), 5.69 (1H, d, J=18.2 Hz), 5.51 (1H, d, J=18.2 Hz), 5.00–4.85 (1H, m), 3.16–2.93 (3H, m), 2.74 (1H, dd, 17.5, 4.9 Hz), 1.81–1.57 (2H, m), 1.45 (9H, s), 1.02 (3H, t, J=7.3 Hz).

Example 14(77)

N-(isopropylthio)carbonyl-3-amino-4-oxo-5-(5-(2,6-dichlorophenylthio) tetrazol-2-yl)pentanoic acid•t-butylester

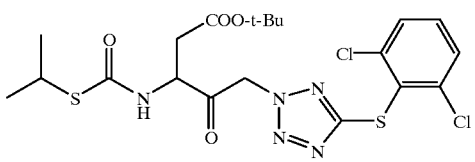

TLC: Rf 0.34 (hexane:ethyl acetate=3:2); NMR (CDCl₃): δ 7.50–7.23 (3H, m), 6.52 (1H, d, J=8.8 Hz), 5.78 (1H, d, J=17.7 Hz), 5.58 (1H, d, J=7.7 Hz), 4.92–4.78 (1H, m), 3.69 (1H, sep, J=6.8 Hz), 2.99 (1H, dd, 17.5, 4.4 Hz), 2.69 (1H, dd, 17.5, 4.7 Hz), 1.43 (9H, s), 1.37 (6H, t, J=6.8 Hz).

Example 14(78)

N-(isopropylthio)carbonyl-3-amino-4-oxo-5-(5-(2,6-dichlorophenylthio) tetrazol-1-yl)pentanoic acid•t-butylester

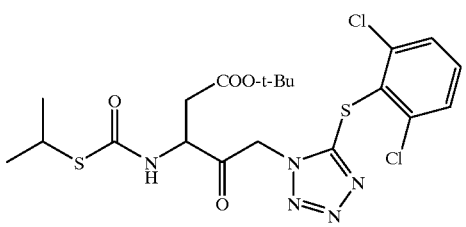

TLC: Rf 0.12 (hexane:ethyl acetate=3:2); NMR (CDCl₃): δ 7.50–7.25 (3H, m), 6.58 (1H, d, J=8.8 Hz), 5.69 (1H, d, J=18.6 Hz), 5.52 (1H, d, J=18.6 Hz), 5.00–4.83 (1H, m), 3.73 (1H, sep, J=7.0 Hz), 3.08 (1H, dd, 17.5, 4.6 Hz), 2.73 (1H, dd, 17.5, 4.9 Hz), 1.45 (9H, s), 1.40 (6H, t, J=6.8 Hz).

Example 14(79)

N-(2-methoxyethyloxy)carbonyl-3-amino-4-oxo-5-(5-(2,6-dichlorophenylthio)tetrazol-2-yl)pentanoic acid•t-butylester

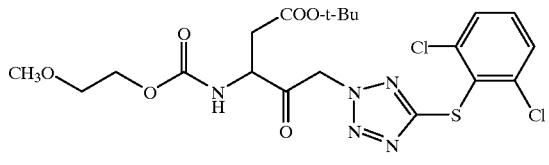

TLC: Rf 0.45 (hexane:ethyl acetate=1:1); NMR (CDCl$_3$): δ 7.47–7.43 (2H, m), 7.34–7.26 (1H, m), 5.96 (1H, d, J=9.2 Hz), 5.81 (1H, d, J=17.8 Hz), 5.62 (1H, d, J=17.8 Hz), 4.60 (1H, m), 4.30 (2H, m), 3.61 (2H, t, J=4.4 Hz), 3.40 (3H, s), 3.02 (1H, dd, J=17.4 Hz, 4.2 Hz), 2.69 (1H, dd, J=17.4 Hz, 4.6 Hz), 1.42 (9H, s).

Example 14(80)

N-(2-methoxyethyloxy)carbonyl-3-amino-4-oxo-5-(5-(2,6-dichlorophenylthio)tetrazol-1-yl)pentanoic acid•t-butylester

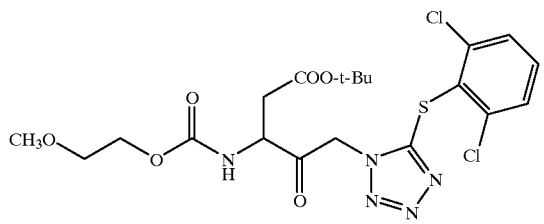

TLC: Rf 0.40 (hexane:ethyl acetate=1:1); NMR (CDCl$_3$): δ 7.48–7.43 (2H, m), 7.37–7.28 (1H, m), 6.06 (1H, d, J=7.6 Hz), 5.75 (1H, d, J=18.0 Hz), 5.57 (1H, d, J=18.0 Hz), 4.68 (1H, m), 4.35 (2H, m), 3.65 (2H, t, J=4.4 Hz), 3.42 (3H, s), 3.12 (1H, dd, J=17.4 Hz, 4.4 Hz), 2.74 (1H, dd, J=17.4 Hz, 4.8 Hz), 1.44 (9H, s).

Example 14(81)

N-(2-cyclohexylethyloxy)carbonyl-3-amino-4-oxo-5-(5-(2,6-dichlorophenylthio)tetrazol-2-yl)pentanoic acid•t-butylester

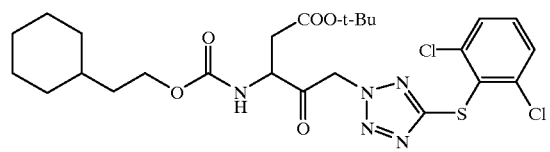

NMR (CDCl$_3$): δ 7.50–7.28 (3H, m), 5.80 (1H, d, J=17.8 Hz), 5.79 (1H, d, J=9.0 Hz), 5.61 (1H, d, J=17.8 Hz), 4.70–4.55 (1H, m), 4.17 (2H, t, J=6.8 Hz), 2.99 (1H, dd, 17.4, 4.4 Hz), 2.70 (1H, dd, 17.4, 4.8 Hz), 1.80–1.46 (7H, m), 1.43 (9H, s), 1.38–0.80 (6H, m).

Example 14(82)

N-(2-cyclohexylethyloxy)carbonyl-3-amino-4-oxo-5-(5-(2,6-dichlorophenylthio)tetrazol-1-yl)pentanoic acid•t-butylester

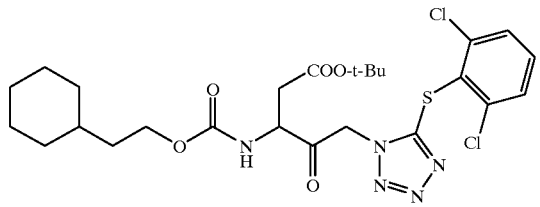

TLC: Rf 0.30 (hexane:ethyl acetate=7:3); NMR (CDCl$_3$): δ 7.50–7.28 (3H, m), 5.86 (1H, d, J=9.0 Hz), 5.73 (1H, d, J=18.5 Hz), 5.55 (1H, d, J=18.5 Hz), 4.75–4.60 (1H, m), 4.22 (2H, t, J=6.8 Hz), 3.08 (1H, dd, 17.5, 4.5 Hz), 2.75 (1H, dd, 17.5, 4.8 Hz), 1.80–1.50 (7H, m), 1.45 (9H, s), 1.40–0.80 (6H, m).

Example 14(83)

N-cyclohexylmethyloxycarbonyl-3-amino-4-oxo-5-(5-(2,6-dichlorophenylthio)tetrazol-2-yl)pentanoic acid•t-butylester

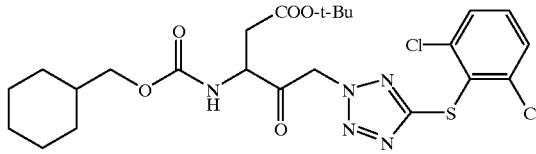

TLC: Rf 0.43 (hexane:ethyl acetate=7:3); NMR (CDCl$_3$): δ 7.50–7.28 (3H, m), 5.81 (1H, d, J=9.4 Hz), 5.80 (1H, d, J=17.8 Hz), 5.61 (1H, d, J=17.8 Hz), 4.70–4.55 (1H, m), 3.94 (2H, d, J=6.4 Hz), 2.99 (1H, dd, 17.4, 4.6 Hz), 2.70 (1H, dd, 17.4, 4.7 Hz), 1.80–1.50 (5H, m), 1.43 (9H, s), 1.40–0.80 (6H, m).

Example 14(84)

N-cyclohexylmethyloxycarbonyl-3-amino-4-oxo-5-(5-(2,6-dichlorophenylthio)tetrazol-1-yl)pentanoic acid•t-butylester

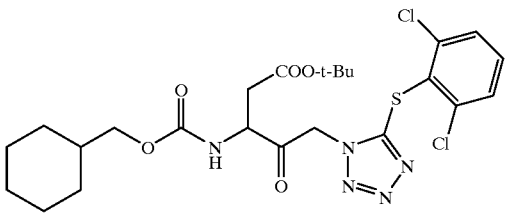

TLC: Rf 0.29 (hexane:ethyl acetate=7:3); NMR (CDCl$_3$): δ 7.50–7.28 (3H, m), 5.87 (1H, d, J=8.8 Hz), 5.73 (1H, d, J=18.4 Hz), 5.55 (1H, d, J=18.4 Hz), 4.75–4.60 (1H, m), 4.30–3.90 (2H, m), 3.08 (1H, dd, 17.3, 4.6 Hz), 2.75 (1H, dd, 17.3, 4.8 Hz), 1.85–1.50 (5H, m), 1.45 (9H, s), 1.40–0.80 (6H, m).

Example 14(85)

N-(2-phenylethyloxy)carbonyl-3-amino-4-oxo-5-(5-(2,6-dichlorophenylthio)tetrazol-2-yl)pentanoic acid•t-butylester

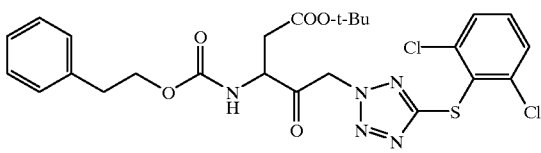

TLC: Rf 0.46 (hexane:ethyl acetate=2:1); NMR (CDCl$_3$): δ 7.44 (2H, d, J=6.8 Hz), 7.33–7.15 (6H, m), 5.86 (1H, d, J=8.8 Hz), 5.64 (1H, d, J=17.8 Hz), 5.34 (1H, d, J=17.8 Hz), 4.58 (1H, m), 4.48–4.25 (2H, m), 2.99–2.87 (3H, m), 2.66 (1H, dd, J=17.6 Hz, 5.0 Hz), 1.41 (9H, s).

Example 14(86)
N-(2-phenylethyloxy)carbonyl-3-amino-4-oxo-5-(5-(2,6-dichlorophenylthio)tetrazol-1-yl)pentanoic acid•t-butylester

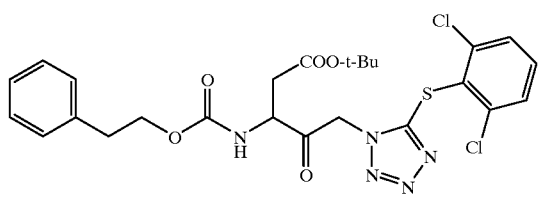

TLC: Rf 0.34 (hexane:ethyl acetate=2:1); NMR (CDCl$_3$): δ 7.47–7.43 (2H, m), 7.36–7.19 (6H, m), 5.91 (1H, d, J=9 Hz), 5.59 (1H, d, J=19.2 Hz), 5.39 (1H, d, J=19.2 Hz), 4.63 (1H, m), 4.50–4.30 (2H, m), 3.11–2.96 (3H, m), 2.70 (1H, dd, J=17 Hz, 4.6 Hz), 1.44 (9H, s).

Example 14(87)
N-butyloxycarbonyl-3-amino-4-oxo-5-(5-(2,6-dichloro-4-acetylaminophenylthio)tetrazol-2-yl)pentanoic acid•t-butylester

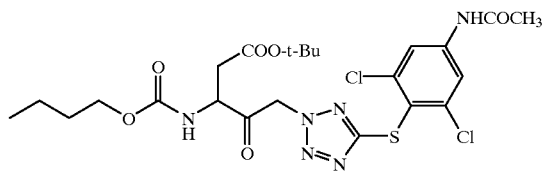

TLC: Rf 0.43 (hexane:ethyl acetate=2:3); NMR (CDCl$_3$): δ 8.47 (1H, s), 7.58 (2H, s), 5.90–5.75 (1H, m), 5.88 (1H, d, J=17.7 Hz), 5.69 (1H, d, J=17.7 Hz), 4.73–4.58 (1H, m), 4.14 (2H, t, J=6.9 Hz), 3.01 (1H, dd, 17.4, 4.6 Hz), 2.73 (1H, dd, 17.4, 4.9 Hz), 2.07 (3H, s), 1.70–1.30 (4H, m), 1.43 (9H, s), 0.95 (3H, t, J=7.2 Hz).

Example 14(88)
N-butyloxycarbonyl-3-amino-4-oxo-5-(5-(2,6-dichloro-4-acetylaminophenylthio)tetrazol-1-yl)pentanoic acid•t-butylester

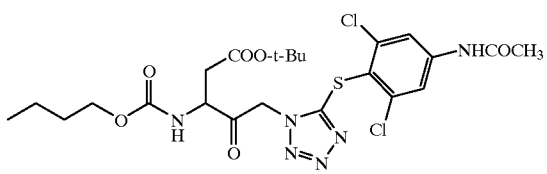

TLC: Rf 0.35 (hexane:ethyl acetate=2:3); NMR (CDCl$_3$): δ 9.44 (1H, s), 7.53 (2H, s), 5.83 (1H, d, J=9.2 Hz), 5.75 (1H, d, J=18.4 Hz), 5.61 (1H, d, J=18.4 Hz), 4.75–4.62 (1H, m), 4.19 (2H, t, J=6.7 Hz), 3.13 (1H, dd, 17.5, 4.5 Hz), 2.77 (1H, dd, 17.5, 4.7 Hz), 2.08 (3H, s), 1.75–1.30 (4H, m), 1.45 (9H, s), 0.96 (3H, t, J=7.3 Hz).

Example 14(89)
N-(2-(4-cyanophenyl)ethyloxy)carbonyl-3-amino-4-oxo-5-(5-(2,6-dichlorophenylthio)tetrazol-2-yl)pentanoic acid•t-butylester

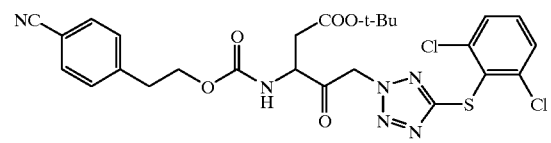

HPTLC: Rf 0.20 (hexane:ethyl acetate=2:1); NMR (CDCl$_3$): δ 7.62 (2H, d, J=8.0 Hz), 7.48–7.24 (5H, m), 5.83 (1H, d, J=8.0 Hz), 5.72 and 5.56 (each 1H, each d, J=18.0 Hz), 4.58 (1H, m), 4.36 (2H, t, J=6.5 Hz), 3.09–2.86 (3H, m), 2.69 (1H, dd, J=17.5, 5.0 Hz), 1.41 (9H, s).

Example 14(90)
N-(2-(4-cyanophenyl)ethyloxy)carbonyl-3-amino-4-oxo-5-(5-(2,6-dichlorophenylthio)tetrazol-1-yl)pentanoic acid•t-butylester

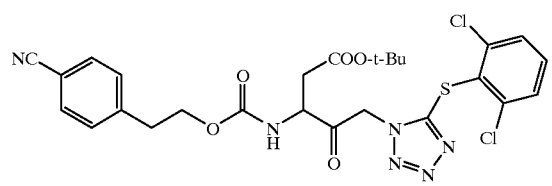

HPTLC: Rf 0.13 (hexane:ethyl acetate=2:1); NMR (CDCl$_3$): δ 7.62 (2H, d, J=8.0 Hz), 7.49–7.23 (5H, m), 5.90 (1H, d, J=8.5 Hz), 5.66 and 5.51 (each 1H, each d, J=17.5 Hz), 4.64 (1H, m), 4.41 (2H, t, J=6.5 Hz), 3.13–2.96 (3H, m), 2.72 (1H, dd, J=17.0, 5.0 Hz), 1.44 (9H, s).

Example 14(91)
N-(2-(4-cyanophenyl)ethyloxy)carbonyl-3-amino-4-oxo-5-(5-(2,6-dichloro-4-methylphenylthio)tetrazol-2-yl)pentanoic acid•t-butylester

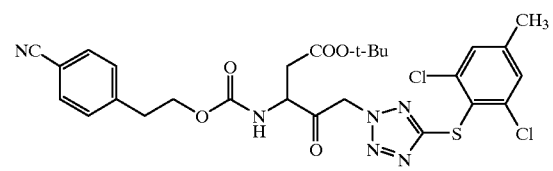

HPTLC: Rf 0.21 (hexane:ethyl acetate=2:1); NMR (CDCl$_3$): δ 7.62 (2H, d, J=8.0 Hz), 7.33 (2H, d, J=8.0 Hz), 7.27 (2H, s), 5.83 (1H, d, J=8.0 Hz), 5.70 and 5.55 (each 1H, each d, J=17.5 Hz), 4.58 (1H, m), 4.36 (2H, t, J=6.5 Hz), 3.08–2.85 (3H, m), 2.67 (1H, dd, J=17.0, 5.0 Hz), 2.34 (3H, s), 1.41 (9H, s).

Example 14(92)
N-(2-(4-cyanophenyl)ethyloxy)carbonyl-3-amino-4-oxo-5-(5-(2,6-dichloro-4-methylphenylthio)tetrazol-1-yl)pentanoic acid•t-butylester

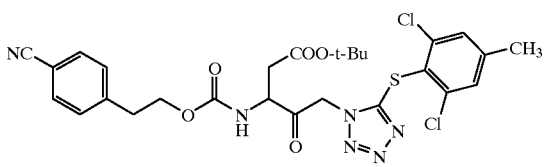

HPTLC: Rf 0.15 (hexane:ethyl acetate=2:1); NMR (CDCl₃): δ 7.62 (2H, d, J=8.0 Hz), 7.36 (2H, d, J=8.0 Hz), 7.28 (2H, s), 5.90 (1H, d, J=7.5 Hz), 5.65 and 5.49 (each 1H, each d, J=18.5 Hz), 4.65 (1H, m), 4.40 (2H, t, J=6.5 Hz), 3.14–2.93 (3H, m), 2.72 (1H, dd, J=17.0, 5.0 Hz), 2.35 (3H, s), 1.44 (9H, s).

Example 14(93)
N-(2-methoxyethylthio)carbonyl-3-amino-4-oxo-5-(5-(2,6-dichlorophenylthio)tetrazol-2-yl)pentanoic acid•t-butylester

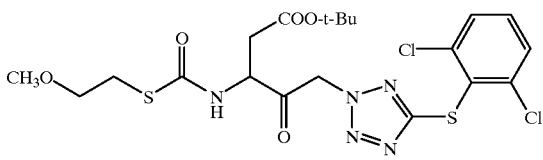

TLC: Rf 0.65 (hexane:ethyl acetate=1:1); NMR (CDCl₃): δ 7.47–7.43 (2H, m), 7.28 (1H, dd, J=6.8 Hz, 2.2 Hz), 6.81 (1H, d, J=8.6 Hz), 5.78 (1H, d, J=18.0 Hz), 5.58 (1H, d, J=18.0 Hz), 4.87 (1H, m), 3.59 (2H, t, J=6.2 Hz), 3.36 (3H, s), 3.17 (2H, t, J=6.2 Hz), 2.98 (1H, dd, J=17.4 Hz, 4.4 Hz), 2.70 (1H, dd, J=17.4 Hz, 4.4 Hz), 1.43 (9H, s).

Example 14(94)
N-(2-methoxyethylthio)carbonyl-3-amino-4-oxo-5-(5-(2,6-dichlorophenylthio)tetrazol-1-yl)pentanoic acid•t-butylester

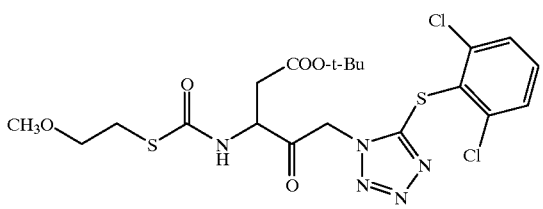

TLC: Rf 0.52 (hexane:ethyl acetate=1:1); NMR (CDCl₃): δ 7.48–7.43 (2H, m), 7.30 (1H, dd, J=9.2 Hz, 2.6 Hz), 6.89 (1H, d, J=8.8 Hz), 5.70 (1H, d, J=18.6 Hz), 5.52 (1H, d, J=18.6 Hz), 4.91 (1H, m) 3.63 (2H, t, J=6.0 Hz), 3.40 (3H, s), 3.18 (2H, t, J=6.0 Hz), 3.08 (1H, dd, J=17.6 Hz, 4.4 Hz), 2.75 (1H, dd, J=17.6 Hz, 4.8 Hz), 1.45 (9H, s).

Example 14(95)
N-(2-(2-methoxyethyloxy)ethyloxy)carbonyl-3-amino-4-oxo-5-(5-(2,6-dichlorophenylthio)tetrazol-2-yl)pentanoic acid•t-butylester

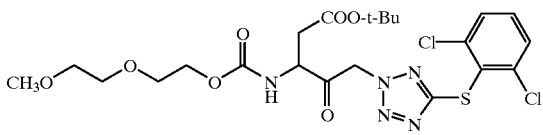

TLC: Rf 0.54 (hexane:ethyl acetate=1:2); NMR (CDCl₃): δ 7.47–7.43 (2H, m), 7.34–7.29 (1H, m), 6.00 (1H, d, J=8.8 Hz), 5.83 (1H, d, J=17.6 Hz), 5.62 (1H, d, J=17.6 Hz), 4.62 (1H, m), 4.30 (2H, m), 3.72 (2H, t, J=4.8 Hz), 3.64 (2H, m), 3.56 (2H, m), 3.36 (3H, s), 3.00 (1H, dd, J=17.6 Hz, 4.6 Hz), 2.70 (1H, dd, J=17.6 Hz, 5.0 Hz), 1.42 (9H, s).

Example 14(96)
N-(2-(2-methoxyethyloxy)ethyloxy)carbonyl-3-amino-4-oxo-5-(5-(2,6-dichlorophenylthio)tetrazol-1-yl)pentanoic acid•t-butylester

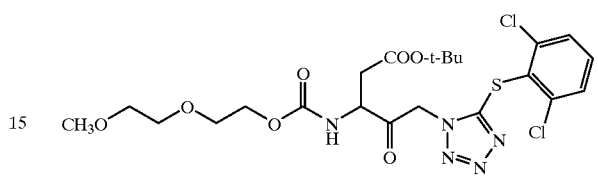

TLC: Rf 0.42 (hexane:ethyl acetate=1:2); NMR (CDCl₃): δ 7.48–7.43 (2H, m), 7.36–7.27 (1H, m), 6.05 (1H, d, J=9.4 Hz), 5.75 (1H, d, J=18.2 Hz), 5.56 (1H, d, J=18.2 Hz), 4.66 (1H, m), 4.34 (2H, m), 3.76 (2H, t, J=4.6 Hz), 3.67 (2H, m), 3.57 (2H, m), 3.38 (3H, s), 3.13 (1H, dd, J=17.4 Hz, 4.0 Hz), 2.74 (1H, dd, J=17.4 Hz, 5.0 Hz), 1.45 (9H, s).

Example 14(97)
N-(2-phenylethylthio)carbonyl-3-amino-4-oxo-5-(5-(2-chlorophenylthio)tetrazol-2-yl)pentanoic acid•t-butylester

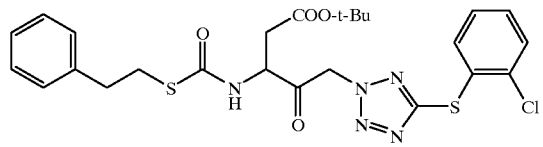

TLC: Rf 0.55 (hexane:ethyl acetate=2:1); NMR (CDCl₃): δ 7.48–7.43 (2H, m), 7.33–7.15 (7H, m), 6.60 (1H, d, J=8.8 Hz), 5.73 (1H, d, J=17.8 Hz), 5.53 (1H, d, J=17.8 Hz), 4.86 (1H, m), 3.24 (2H, m), 3.00 (1H, dd, J=17.4 Hz, 4.4 Hz), 2.97 (2H, m), 2.67 (1H, dd, J=17.4 Hz, 4.8 Hz), 1.43 (9H, s).

Example 14(98)
N-(2-phenylethylthio)carbonyl-3-amino-4-oxo-5-(5-(2-chlorophenylthio)tetrazol-1-yl)pentanoic acid•t-butylester

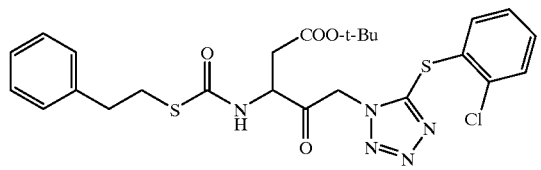

TLC: Rf 0.40 (hexane:ethyl acetate=2:1); NMR (CDCl₃): δ 7.57–7.43 (2H, m), 7.33–7.17 (7H, m), 6.62 (1H, d, J=8.4 Hz), 5.78 (1H, d, J=18.6 Hz), 5.39 (1H, d, J=18.6 Hz), 4.87 (1H, m), 3.26 (2H, m), 3.03 (1H, dd, J=17.4 Hz, 4.4 Hz), 2.97 (2H, m), 2.68 (1H, dd, J=17.4 Hz, 4.8 Hz), 1.43 (9H, s).

Example 14(99)
N-(2-acetylaminoethylthio)carbonyl-3-amino-4-oxo-5-(5-(2,6-dichlorophenylthio)tetrazol-2-yl)pentanoic acid•t-butylester

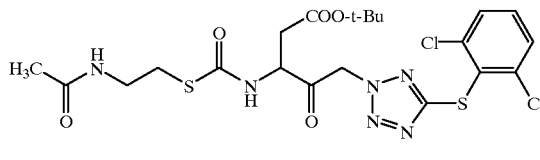

TLC: Rf 0.69 (chloroform:methanol=9:1); NMR (CDCl$_3$): δ 7.50–7.28 (3H, m), 6.89 (1H, d, J=8.0 Hz), 6.25–6.07 (1H, m), 5.76 (1H, d, J=17.7 Hz), 5.60 (1H, d, J=17.7 Hz), 4.93–4.75 (1H, m), 3.48 (2H, q, J=6.2 Hz), 3.08 (2H, t, J=6.2 Hz), 2.95 (1H, dd, 17.4, 4.9 Hz), 2.73 (1H, dd, 17.4, 5.0 Hz), 1.97 (3H, s), 1.43 (9H, s).

Example 14(100)

N-(2-acetylaminoethylthio)carbonyl-3-amino-4-oxo-5-(5-(2,6-dichlorophenylthio)tetrazol-1-yl)pentanoic acid•t-butylester

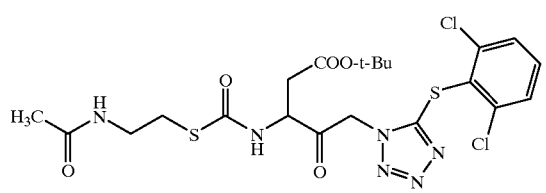

TLC: Rf 0.65 (chloroform:methanol=9:1); NMR (CDCl$_3$): δ 7.50–7.28 (3H, m), 6.93 (1H, d, J=8.8 Hz), 6.20–6.06 (1H, m), 5.70 (1H, d, J=18.4 Hz), 5.53 (1H, d, J=18.4 Hz), 5.00–4.85 (1H, m), 3.52 (2H, q, J=6.4 Hz), 3.12 (2H, t, J=6.4 Hz), 3.06 (1H, dd, 17.4, 4.6 Hz), 2.75 (1H, dd, 17.4, 5.2 Hz), 1.99 (3H, s), 1.45 (9H, s).

Example 14(101)

N-(2-acetylaminoethyloxy)carbonyl-3-amino-4-oxo-5-(5-(2,6-dichlorophenylthio)tetrazol-2-yl)pentanoic acid•t-butylester

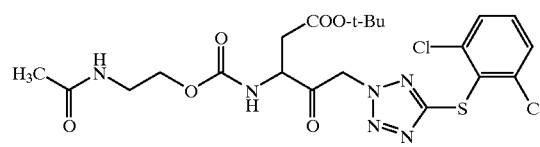

TLC: Rf 0.50 (chloroform:methanol=9:1); NMR (CDCl$_3$): δ 7.48–7.43 (2H, m), 7.35–7.32 (1H, m), 6.16 (1H, brs), 5.01 (1H, d, J=8.6 Hz), 5.78 (1H, d, J=17.6 Hz), 5.63 (1H, d, J=17.6 Hz), 4.60 (1H, m), 4.20 (2H, m), 3.50 (2H, m), 3.00–2.85 (1H, m), 2.75 (1H, dd, J=17.6 Hz, 5.0 Hz), 1.98 (3H, s), 1.43 (9H, s).

Example 14(102)

N-(2-acetylaminoethyloxy)carbonyl-3-amino-4-oxo-5-(5-(2,6-dichlorophenylthio)tetrazol-1-yl)pentanoic acid•t-butylester

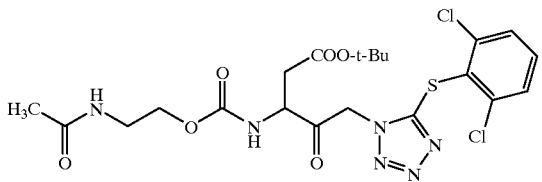

TLC: Rf 0.48 (chloroform:methanol=9:1); NMR (CDCl$_3$): δ 7.49–7.44 (2H, m), 7.37–7.33 (1H, m), 6.06 (2H, m), 5.74 (1H, d, J=18.6 Hz), 5.55 (1H, d, J=18.6 Hz), 4.68 (1H, m), 4.26 (2H, m), 3.54 (2H, m), 3.06 (1H, dd, J=17.6 Hz, 4.4 Hz), 2.77 (1H, dd, J=17.6 Hz, 5.0 Hz), 2.00 (3H, s), 1.45 (9H, s).

Example 14(103)

N-(2-(2-methoxyethyloxy)ethylthio)carbonyl-3-amino-4-oxo-5-(5-( 2,6-dichlorophenylthio)tetrazol-2-yl)pentanoic acid•t-butylester

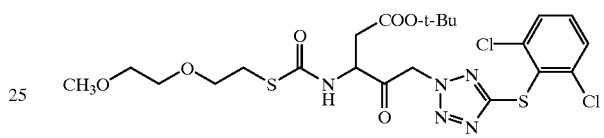

TLC: Rf 0.49 (hexane:ethyl acetate=1:1); NMR (CDCl$_3$): δ 7.50–7.28 (3H, m), 6.76 (1H, d, J=8.4 Hz), 5.77 (1H, d, J=17.8 Hz), 5.58 (1H, d, J=17.8 Hz), 4.90–4.75 (1H, m), 3.80–3.50 (6H, m), 3.37 (3H, s), 3.18 (2H, t, J=6.1 Hz), 2.98 (1H, dd, 17.4, 4.5 Hz), 2.69 (1H, dd, 17.4, 4.9 Hz), 1.43 (9H, s).

Example 14(104)

N-(2-(2-methoxyethyloxy)ethylthio)carbonyl-3-amino-4-oxo-5-(5-(2,6-dichlorophenylthio)tetrazol-1-yl)pentanoic acid•t-butylester

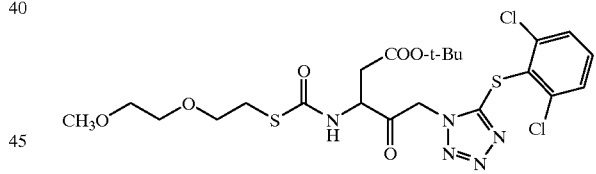

TLC: Rf 0.39 (hexane:ethyl acetate=1:1); NMR (CDCl$_3$): δ 7.50–7.28 (3H, m), 6.83 (1H, d, J=9.0 Hz), 5.69 (1H, d, J=18.4 Hz), 5.51 (1H, d, J=18.4 Hz), 5.00–4.85 (1H, m), 3.80–3.50 (6H, m), 3.38 (3H, s), 3.23 (2H, t, J=6.3 Hz), 3.07 (1H, dd, 17.5, 4.6 Hz), 2.75 (1H, dd, 17.5, 4.9 Hz), 1.45 (9H, s).

Example 14(105)

N-(2-phenylethylthio)carbonyl-3-amino-4-oxo-5-(5-(phenylthio) tetrazol-2-yl)pentanoic acid•t-butylester

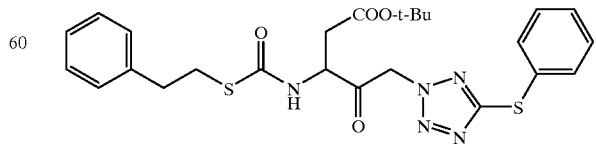

TLC: Rf 0.57 (hexane:ethyl acetate=2:1); NMR (CDCl$_3$): δ 7.59–7.55 (2H, m), 7.37–7.15 (8H, m), 6.62 (1H, d, J=8.8

Hz), 5.71 (1H, d, J=17.8 Hz), 5.50 (1H, d, J=17.8 Hz), 4.85 (1H, m), 3.23 (2H, m), 3.05–2.90 (3H, m), 2.67 (1H, dd, J=17.4 Hz, 4.8 Hz), 1.43 (9H, s).

Example 14(106)
N-(2-phenylethylthio)carbonyl-3-amino-4-oxo-5-(5-(phenylthio) tetrazol-1-yl)pentanoic acid•t-butylester

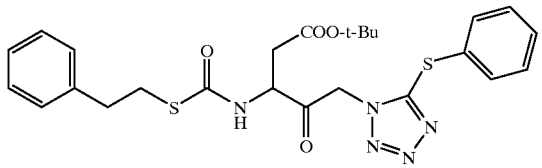

TLC: Rf 0.43 (hexane:ethyl acetate=2:1); NMR (CDCl$_3$): δ 7.57–7.51 (2H, m), 7.39–7.15 (8H, m), 6.63 (1H, d, J=8.6 Hz), 5.49 (1H, d, J=18.4 Hz), 5.30 (1H, d, J=18.4 Hz), 4.82 (1H, m), 3.27 (2H, m), 3.07–2.91 (3H, m), 2.67 (1H, dd, J=17.6 Hz, 4.8 Hz), 1.44 (9H, s).

EXAMPLES 15(1)–15(106)

By the same procedure as provided in example 6(1), and if necessary, by known methods converted to accommodate the corresponding salts, using the compound prepared in examples 14(1)–14(106), compounds of the present invention having the following physical data were obtained.

Example 15(1)
N-(benzylthio)carbonyl-3-amino-4-oxo-5-(5-(2,6-dichlorophenylmethyl)tetrazol-2-yl)pentanoic acid

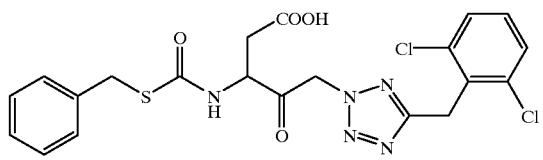

TLC: Rf 0.61 (chloroform:methanol:acetic acid=18:1:1); NMR (DMSO-d$_6$): δ 12.65–12.30 (1H, br), 8.96–8.82 (1H, m), 7.52 (2H, d, J=7.5 Hz), 7.45–7.13 (6H, m), 6.05–5.70 (2H, m), 4.87–4.72 (1H, m), 4.52 (2H, s), 4.11 (2H, s), 2.90–2.55 (2H, m).

Example 15(2)
N-(benzylthio)carbonyl-3-amino-4-oxo-5-(5-(2,6-dichlorophenylmethyl)tetrazol-1-yl)pentanoic acid

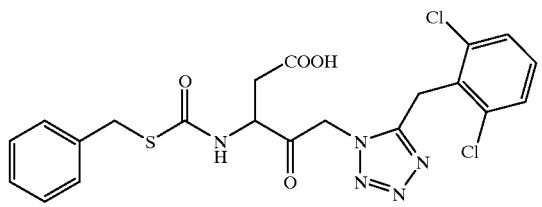

TLC: Rf 0.19 (chloroform:methanol:acetic acid=18:1:1); NMR (DMSO-d$_6$): δ 9.05–8.95 (1H, m), 7.54 (2H, d, J=7.5 Hz), 7.46–7.10 (6H, m), 6.00–5.75 (2H, m), 4.92–4.75 (1H, m), 4.33 (2H, s), 4.11 (2H, s), 2.88–2.70 (2H, m).

Example 15(3)
N-(benzylthio)carbonyl-3-amino-4-oxo-5-(5-(2,6-dichlorophenylthio) tetrazol-2-yl)pentanoic acid

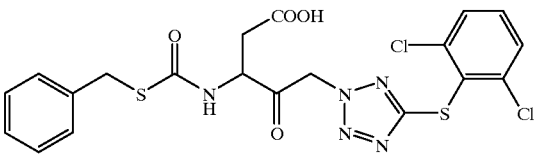

TLC: Rf 0.58 (chloroform:methanol:acetic acid=18:1:1); NMR (DMSO-d$_6$): δ 8.88 (1H, d, J=6.2 Hz), 7.69–7.50 (3H, m), 7.33–7.12 (5H, m), 5.89 (2H, brs), 4.85–4.73 (1H, m), 4.10 (2H, s), 2.80 (1H, dd, J=6.0, 17 Hz), 2.64 (1H, dd, J=7.2, 17 Hz).

Example 15(4)
N-(benzylthio)carbonyl-3-amino-4-oxo-5-(5-(2,6-dichlorophenylthio) tetrazol-1-yl)pentanoic acid

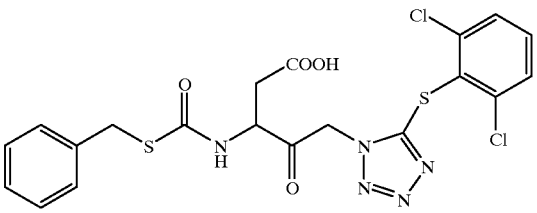

TLC: Rf 0.36 (chloroform:methanol:acetic acid=18:1:1); NMR (DMSO-d$_6$): δ 8.99 (1H, d, J=6.4 Hz), 7.70–7.52 (3H, m), 7.35–7.13 (5H, m), 5.71 (2H, brs), 4.90–4.79 (1H, m), 4.12 (2H, s), 2.92–2.68 (2H, m).

Example 15(5)
N-(2-phenylethoyloxy)carbonyl-3-amino-4-oxo-5-(5-(2,6-dichlorophenylmethy)tetrazol-2-yl)pentanoic acid

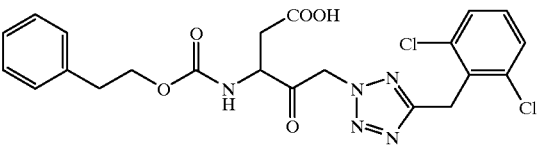

TLC: Rf 0.57 (chloroform:methanol:acetic acid= 19:1:0.1); NMR (CDCl$_3$): δ 12.70–12.10 (10H, br), 7.80 (1H, d, J=6.4 Hz), 7.55–7.15 (8H, m), 5.82 (2H, s), 4.59–451 (3H, m), 4.23 (2H, t, J=7.0 Hz), 2.92–2.48 (4H, m).

Example 15(6)
N-(2-phenylethyloxy)carbonyl-3-amino-4-oxo-5-(5-(2,6-dichlorophenylmethyl)tetrazol-1-yl)pentanoic acid

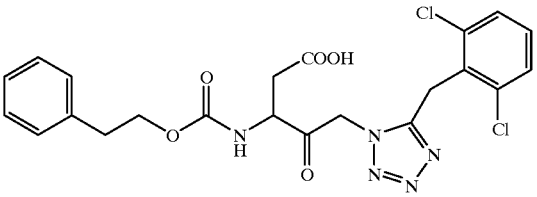

TLC: Rf 0.52 (chloroform:methanol:acetic acid= 19:1:0.1); NMR (CDCl$_3$): δ 7.61–7.15 (9H, m), 5.90 (2H, s), 4.58–4.44 (1H, m), 4.35 (2H, s), 4.30–4.16 (2H, m), 2.88 (2H, t, J=7.5 Hz), 2.63 (2H, d, J=5.6 Hz).

Example 15(7)
N-(2-phenylethylthio)carbonyl-3-amino-4-oxo-5-(5-(2,6-dichlorophenylmethyl)tetrazol-2-yl)pentanoic acid

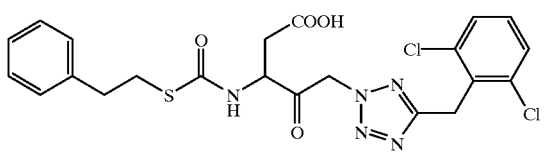

TLC: Rf 0.57 (chloroform:methanol:acetic acid= 90:10:1); NMR (DMSO-d$_6$): δ 8.62 (1H, d, J=6.0 Hz), 7.50 (2H, d, J=7.2 Hz), 7.40–7.09 (6H, m), 5.88 (2H, d, J=2.8 Hz), 4.74–4.63 (1H, m), 4.50 (2H, s), 3.07 (2H, t, J=7.2 Hz), 2.82 (2H, t, J=7.2 Hz), 2.63–2.50 (2H, m).

Example 15(8)
N-(2-phenylethylthio)carbonyl-3-amino-4-oxo-5-(5-(2,6-dichlorophenylmethyl)tetrazol-1-yl)pentanoic acid

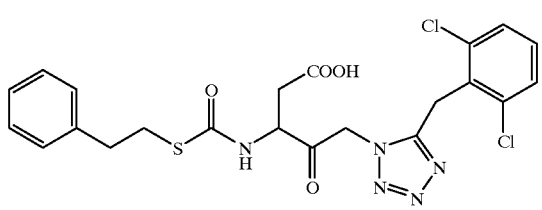

TLC: Rf 0.42 (chloroform:methanol:acetic acid= 90:10:1); NMR (DMSO-d$_6$): δ 8.89 (1H, d, J=6.4 Hz), 7.52 (2H, d, J=7.0 Hz), 7.39 (1H, dd, J=6.6, 9.0 Hz), 7.25–7.13 (5H, m), 5.91 (2H, s), 4.78–4.69 (1H, m), 4.38 (2H, s), 3.17–3.01 (2H, m), 2.82–2.69 (4H, m).

Example 15(9)
N-(2,6-dichlorobenzyloxy)carbonyl-3-amino-4-oxo-5-(5-phenylmethyltetrazol-1-yl)pentanoic acid

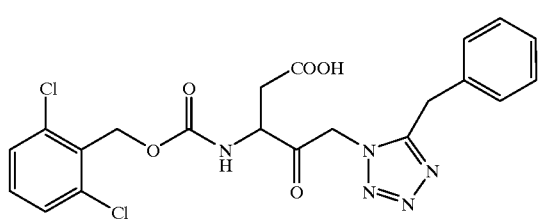

TLC: Rf 0.38 (chloroform:methanol:acetic acid=36:1:1); NMR (DMSO-d$_6$): δ 8.12 (1H, d, J=7.6 Hz), 7.54–7.12 (8H, m), 5.76 (2H, s), 5.34 (2H, s), 4.70–4.58 (1H, m), 4.15 (2H, s), 2.87–2.63 (2H, m).

Example 15(10)
N-(2,6-dichlorobenzyloxy)carbonyl-3-amino-4-oxo-5-(-(2,6-dichlorophenylmethyl)tetrazol-2-yl)pentanoic acid

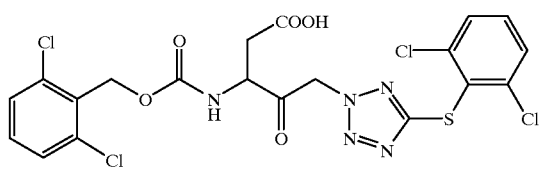

TLC: Rf 0.31 (chloroform:methanol=9:1); NMR (DMSO-d$_6$): δ 7.60 (1H, d, J=7.6 Hz), 7.57–7.31 (6H, m), 6.00–5.80 (2H, m), 5.30 (2H, s), 4.55–4.43 (1H, m), 4.51 (2H, s), 2.60–2.54 (2H, m).

Example 15(11)
N-(3-phenylpropyloxy)carbonyl-3-amino-4-oxo-5-(5-(2,6-dichlorophenylmethyl)tetrazol-2-yl)pentanoic acid

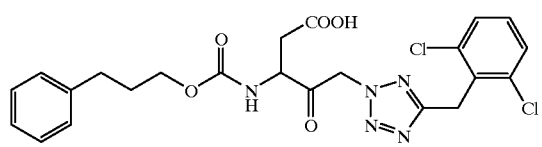

TLC: Rf 0.45 (chloroform:methanol:acetic acid= 90:10:1); NMR (DMSO-d$_6$): δ 7.82 (1H, d, J=7.5 Hz), 7.51 (2H, d, J=7.6 Hz), 7.40–7.14 (6H, m), 6.00–5.76 (2H, br), 4.62–4.51 (3H, m), 3.98 (2H, t, J=3.6 Hz), 2.38–2.5 (4H, m), 1.94–1.80 (2H, m).

Example 15(12)
N-(3-phenylpropyloxy)carbonyl-3-amino-4-oxo-5-(5-(2,6-dichlorophenylmethyl)tetrazol-1-yl)pentanoic acid

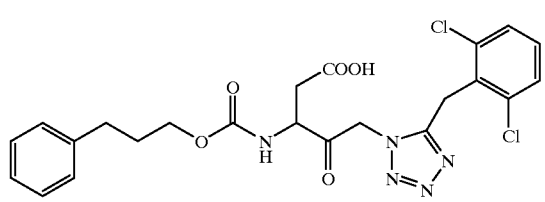

TLC: Rf 0.42 (chloroform:methanol:acetic acid= 90:10:1); NMR (DMSO-d$_6$): δ 7.97 (1H, d, J=7.5 Hz), 7.56–7.12 (8H, m), 5.92–5.83 (2H, br), 4.67–4.58 (1H, m), 4.35 (2H, s), 4.02 (2H, t, J=6.6 Hz), 2.92–2.60 (4H, m), 1.95–1.80 (2H, m).

Example 15(13)
N-(4-phenylbutyloxy)carbonyl-3-amino-4-oxo-5-(5-(2,6-dichlorophenylmethyl)tetrazol-2-yl)pentanoic acid

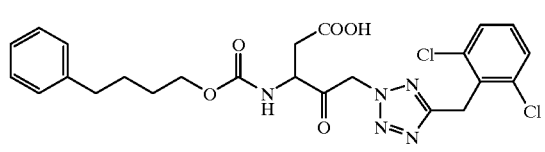

TLC: Rf 0.45 (chloroform:methanol:acetic acid=90:0:1); NMR (DMSO-d$_6$):: δ 7.75 (1H, d, J=7.6 Hz), 7.52 (2H, d, J=7.2 Hz), 7.40–7.10 (6H, m), 5.87 (2H, s), 4.61–4.51 (3H, m), 4.05–3.97 (2H, br),2.77 (1H, dd, J=6.3, 17.0 Hz), 2.64–2.56 (3H, m), 1.65–1.50 (4H, br).

Example 15(14)
N-(4-phenylbutyloxy)carbonyl-3-amino-4-oxo-5-(5-(2,6-dichlorophenylmethyl)tetrazol-1-yl)pentanoic acid

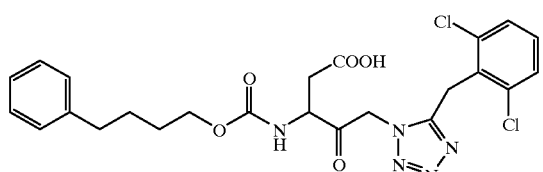

TLC: Rf 0.42 (chloroform:methanol:acetic acid= 90:10:1); NMR (DMSO-d$_6$): δ 7.91 (1H, d, J=6.8 Hz), 7.54 (2H, d, J=6.6 Hz), 7.41 (1H, dd, J=6.6, 9.4 Hz), 7.30–7.16

(5H, m), 5.87 (2H, s), 4.69–4.58 (1H, m), 4.35 (2H, s), 4.08–4.00 (2H, br), 2.91–2.55 (4H, m), 1.68–1.52 (4H, br).

Example 15(15)

N-(2-(thiophen-2-yl)ethyloxy)carbonyl-3-amino-4-oxo-5-(5-(2,6-dichlorophenylmethyl)tetrazol-2-yl)pentanoic acid

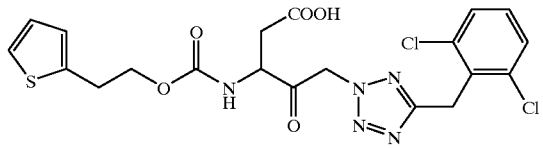

TLC: Rf 0.39 (chloroform:methanol:acetic acid= 19:1:0.1); NMR (DMSO-d$_6$): δ 7.87 (1H, d, J=7.6 Hz), 7.54–7.50 (2H, m), 7.41–7.30 (2H, m), 6.93 (2H, d, J=3.2 Hz), 5.93–5.81 (2H, br), 4.62–4.51 (3H, m), 4.18 (2H, t, J=6.6 Hz), 3.11 (2H, t, J=6.6 Hz), 2.77 (1H, dd, J=6.0, 16.8 Hz), 2.58 (1H, dd, J=7.2, 16.4 Hz).

Example 15(16)

N-(2-(thiophen-2-yl)ethyloxy)carbonyl-3-amino-4-oxo-5-(5-(2,6-dichlorophenylmethyl)tetrazol-1-yl)pentanoic acid

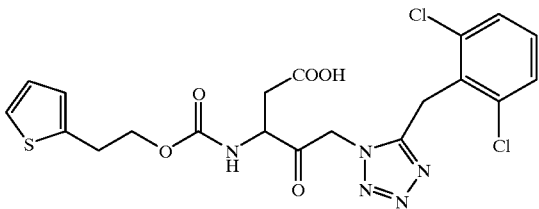

TLC: Rf 0.27 (chloroform:methanol:acetic acid= 19:1:0.1); NMR (DMSO-d$_6$): δ 8.02 (1H, d, J=7.2 Hz), 7.57–7.52 (2H, m), 7.45–7.31 (2H, m), 6.94 (2H, d, J=3.8 Hz), 5.91–5.80 (2H, br), 4.70–4.60 (1H, m), 4.35 (2H, s), 4.18 (2H, t, J=6.6 Hz), 3.13 (2H, t, J=6.6 Hz), 2.84 (1H, dd, J=6.6, 16.6 Hz), 2.70 (1H, dd, J=6.6, 16.6 Hz).

Example 15(17)

N-(2-(4-methoxyphenyl)ethyloxy)carbonyl-3-amino-4-oxo-5-(5-(2,6-dichlorophenylmethyl)tetrazol-2-yl)pentanoic acid

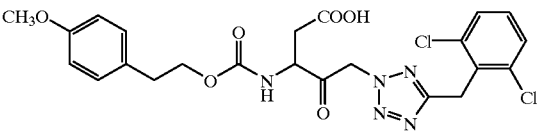

TLC: Rf 0.51 (chloroform:methanol:acetic acid= 90:10:1); NMR (DMSO-d$_6$): δ 7.78 (1H, d, J=6.8 Hz), 7.54–7.50 (2H, m), 7.37 (1H, dd, J=7.1, 9.1 Hz), 7.17 (2H, d, J=8.5 Hz), 6.83 (2H, d, J=8.5 Hz), 5.90–5.85 (2H, br), 4.60–4.51 (3H, m), 4.17 (2H, t, J=6.6 Hz), 3.67 (3H, s), 2.85–2.52 (4H, m).

Example 15(18)

N-(2-(4-methoxyphenyl)ethyloxy)carbonyl-3-amino-4-oxo-5-(5-(2,6-dichlorophenylmethyl)tetrazol-1-yl)pentanoic acid

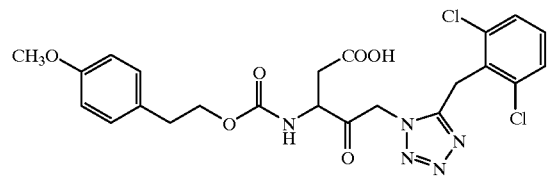

TLC: Rf 0.47 (chloroform:methanol:acetic acid= 90:10:1); NMR (DMSO-d$_6$): δ 7.92 (1H, d, J=6.8 Hz), 7.56–7.52 (2H, m), 7.40 (1H, dd, J=6.8, 9.2 Hz), 7.17 (2H, d, J=8.2 Hz), 6.83 (2H, d, J=8.2 Hz), 5.83 (2H, s), 4.66–4.56 (1H, m), 4.35 (2H, s), 4.19 (2H, t, J=6.9 Hz), 3.69 (3H, s), 2.86–2.63 (4H, m).

Example 15(19)

N-(2-(4-fluorophenyl)ethyloxy)carbonyl-3-amino-4-oxo-5-(5-(2,6-dichlorophenylmethyl)tetrazol-2-yl)pentanoic acid

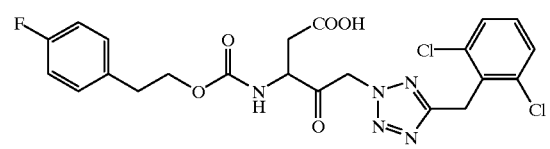

TLC: Rf 0.49 (chloroform:methanol:acetic acid= 90:10:1); NMR (DMSO-d$_6$): δ 7.78 (1H, d, J=8.0 Hz), 7.51 (2H, d, J=7.6 Hz), 7.40–7.26 (3H, m), 7.08 (2H, t, J=9.0 Hz), 5.82 (2H, s), 4.58–4.51 (3H, m), 4.20 (2H, t, J=6.5 Hz), 2.90–2.52 (4H, m).

Example 15(20)

N-(2-(4-fluorophenyl)ethyloxy)carbonyl-3-amino-4-oxo-5-(5-(2,6-dichlorophenylmethyl)tetrazol-1-yl)pentanoic acid

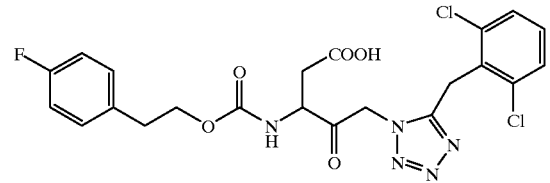

TLC: Rf 0.44 (chloroform:methanol:acetic acid= 90:10:1); NMR (DMSO-d$_6$): δ 7.93 (1H, d, J=7.2 Hz), 7.56–7.25 (5H, m), 7.08 (2H, t, J=9.0 Hz), 5.84 (2H, s), 4.66–4.57 (1H, m), 4.34 (2H, s), 4.21 (2H, t, J=6.9 Hz), 2.92–2.63 (4H, m).

Example 15(21)

N-(2-(phenylmethyloxy)ethyloxy)carbonyl-3-amino-4-oxo-5-(5-(2,6-dichlorophenylmethyl)tetrazol-2-yl)pentanoic acid

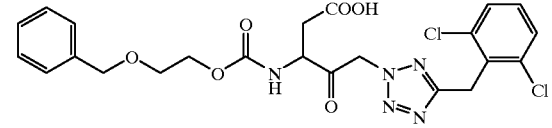

TLC: Rf 0.53 (chloroform:methanol:acetic acid= 90:10:1); NMR (DMSO-d$_6$): δ 7.91 (1H, d, J=7.4 Hz), 7.54–7.50 (2H, m), 7.40–7.23 (6H, m), 5.96–5.74 (2H, br), 4.61–4.50 (5H, m), 4.18 (2H, t, J=4.4 Hz), 3.62 (2H, t, J=4.4 Hz), 2.78 (1H, dd, J=6.0, 17.2 Hz), 2.59 (1H, dd, J=7.0, 16.6 Hz).

Example 15(22)

N-(2-(phenylmethyloxy)ethyloxy)carbonyl-3-amino-4-oxo-5-(5-(2,6-dichlorophenylmethyl)tetrazol-1-yl)pentanoic acid

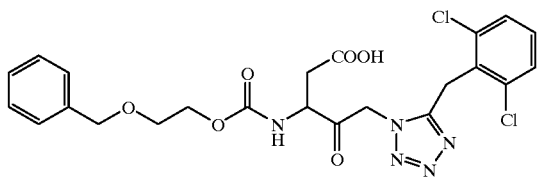

TLC: Rf 0.47 (chloroform:methanol:acetic acid=90:10:1); NMR (DMSO-$d_6$): δ 8.07 (1H, d, J=7.2 Hz), 7.56–7.23 (8H, m), 5.87 (2H, s), 4.69–4.59 (1H, m), 4.50 (2H, s), 4.35 (2H, s), 4.20 (2H, t, J=4.5 Hz), 3.64 (2H, t, J=4.5 Hz), 2.91–2.66 (2H, m).

Example 15(23)

N-(2-(4-dimethylaminophenyl)ethyloxy)carbonyl-3-amino-4-oxo-5-(5-(2,6-dichlorophenylmethyl)tetrazol-2-yl)pentanoic acid•hydrochloric acid salt

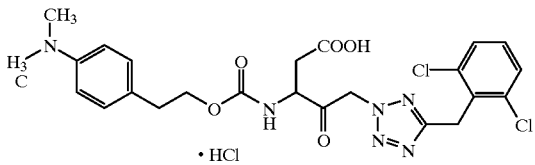

TLC: Rf 0.37 (chloroform:methanol:acetic acid=18:1:1); NMR (DMSO-$d_6$): δ 7.82 (1H, d, J=7.4 Hz), 7.52–7.32 (7H, m), 5.87 (2H, s), 4.59–4.52 (1H, m), 4.52 (2H, s), 4.27–4.19 (2H, m), 3.05 (6H, s), 2.94–2.84 (2H, m), 2.94–2.61 (2H, m).

Example 15(24)

N-(2-(4-dimethylaminophenyl)ethyloxy)carbonyl-3-amino-4-oxo-5-(5-(2,6-dichlorophenylmethyl)tetrazol-1-yl) pentanoic acid•hydrochloric acid salt

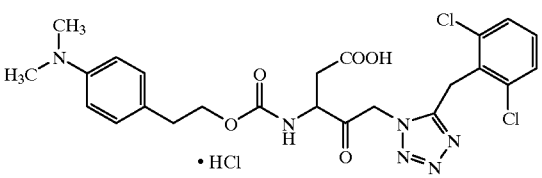

TLC: Rf 0.36 (chloroform:methanol:acetic acid=18:1:1); NMR (DMSO-$d_6$): δ 7.99 (1H, d, J=7.4 Hz), 7.54–7.31 (7H, m), 5.88 (2H, s), 4.66–4.63 (1H, m), 4.36 (2H, m), 4.28–4.20 (2H, m), 3.01 (6H, s), 2.93–2.74 (4H, m).

Example 15(25)

N-(benzylthio)carbonyl-3-amino-4-oxo-5-(5-(2,3,6-trichlorophenylthio) tetrazol-2-yl)pentanoic acid

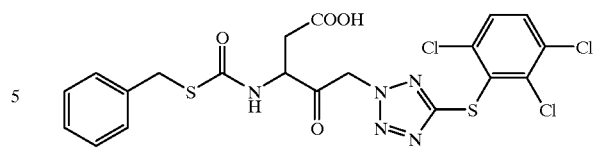

TLC: Rf 0.51 (chloroform:methanol:water=40:10:1); NMR (DMSO-$d_6$): δ 8.70 (1H, d, J=6 Hz), 7.82 (1H, d, J=8.8 Hz), 7.69 (1H, d, J=8.8 Hz), 7.32–7.22 (5H, m), 5.94 (2H, m), 4.73 (1H, m), 4.08 (2H, s), 2.60 (2H, m).

Example 15(26)

N-(benzylthio)carbonyl-3-amino-4-oxo-5-(5-(2,3,6-trichlorophenylthio) tetrazol-1-yl)pentanoic acid

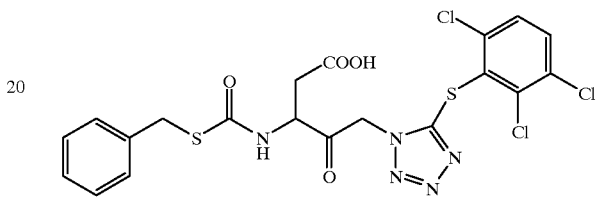

TLC: Rf 0.43 (chloroform:methanol:water=40:10:1); NMR (DMSO-$d_6$): δ 8.83 (1H, d, J=7 Hz), 7.84 (1H, d, J=8.8 Hz), 7.69 (1H, d, J=8.8 Hz), 7.33–7.08 (5H, m), 5.84 (2H, m), 4.75 (1H, m), 4.09 (2H, m), 2.64 (2H, m).

Example 15(27)

N-(benzylthio)carbonyl-3-amino-4-oxo-5-(5-(2,6-dichloro-4-methylphenylthio)tetrazol-2-yl)pentanoic acid

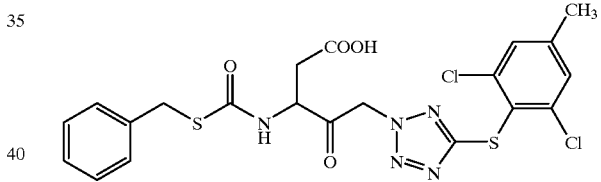

TLC: Rf 0.51 (chloroform:methanol:water=40:10:1); NMR (DMSO-$d_6$): δ 8.69 (1H, d, J=6.4 Hz), 7.52 (2H, s), 7.32–7.19 (5H, m), 5.92 (2H, m), 4.71 (1H, m), 4.08 (2H, s), 2.56 (2H, m), 2.36 (3H, s).

Example 15(28)

N-(benzylthio)carbonyl-3-amino-4-oxo-5-(5-(2,6-dichloro-4-methylphenylthio)tetrazol-1-yl)pentanoic acid

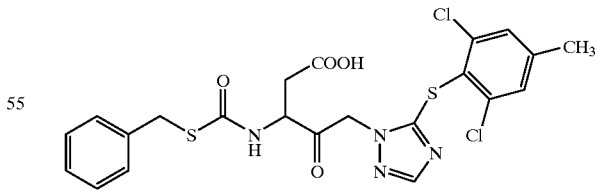

TLC: Rf 0.45 (chloroform:methanol:water=40:10:1); NMR (DMSO-$d_6$): δ 8.77 (1H, m), 7.51 (2H, s), 7.33–7.13 (5H, m), 5.82 (2H, m), 4.75 (1H, m), 4.10 (2H, m), 2.62 (2H, m), 2.37 (3H, s).

Example 15(29)

N-(3-phenylpropylthio)carbonyl-3-amino-4-oxo-5-(5-(2,6-dichlorophenylmethyl)tetrazol-2-yl)pentanoic acid

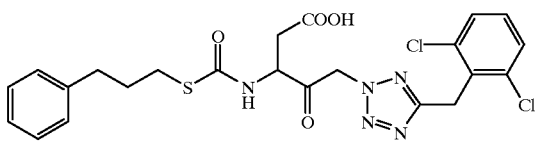

TLC: Rf 0.54 (chloroform:methanol:acetic acid= 19:1:0.1); NMR (DMSO-$d_6$): δ 8.81 (1H, d, J=6.4 Hz), 7.51 (2H, d, J=7.2 Hz), 7.40–7.14 (6H, m), 6.00–5.74 (2H, br), 4.83–4.73 (1H, m), 4.50 (2H, s), 2.87–2.56 (6H, m), 1.91–1.77 (2H, m).

Example 15(30)
N-(3-phenylpropylthio)carbonyl-3-amino-4-oxo-5-(5-(2,6-dichlorophenylmethyl)tetrazol-1-yl)pentanoic acid

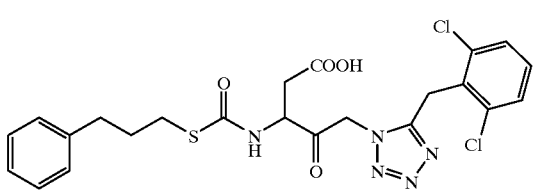

TLC: Rf 0.41 (chloroform:methanol:acetic acid= 19:1:0.1); NMR (DMSO-$d_6$): δ 8.97 (1H, d, J=6.8 Hz), 7.55–7.36 (3H, m), 7.27–7.11 (5H, m), 5.87 (2H, s), 4.87–4.78 (1H, m), 4.34 (2H, s), 2.92–2.58 (6H, 1.91–1.78 (2H, m).

Example 15(31)
N-(benzylthio)carbonyl-3-amino-4-oxo-5-(5-(2,6-dichloro-4-dimethylaminophenylthio)tetrazol-2-yl)pentanoic acid

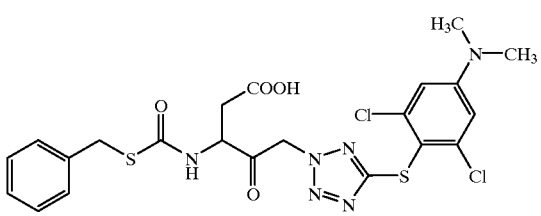

TLC: Rf 0.56 (chloroform:methanol:acetic acid=18:1:1); NMR (DMSO-$d_6$): δ 13.28–11.40 (1H, br), 9.03–8.77 (1H, m), 7.42–7.06 (5H, m), 6.88 (2H, s), 6.10–5.66 (2H, br), 4.90–4.68 (1H, m), 4.11 (2H, s), 3.00 (6H, s), 2.92–2.53 (2H, m).

Example 15(32)
N-(benzylthio)carbonyl-3-amino-4-oxo-5-(5-(2,6-dichloro-4-dimethylaminophenylthio)tetrazol-1-yl)pentanoic acid

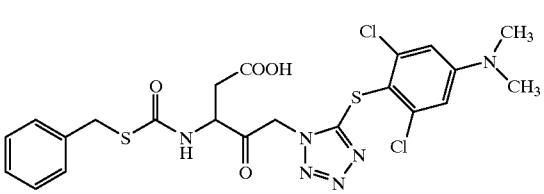

TLC: Rf 0.31 (chloroform:methanol:acetic acid=30:1:1); NMR (DMSO-$d_6$): δ 13.08–11.40 (1H, br), 9.13–8.86 (1H, m), 7.44–7.08 (5H, m), 6.88 (2H, s), 5.90–5.45 (2H, br), 4.95–4.71 (1H, m), 4.13 (2H, s), 3.00 (6H, s), 2.93–2.62 (2H, m).

Example 15(33)
N-(2-phenylethylthio)carbonyl-3-amino-4-oxo-5-(5-(2,3,6-trichlorophenylthio)tetrazol-2-yl)pentanoic acid

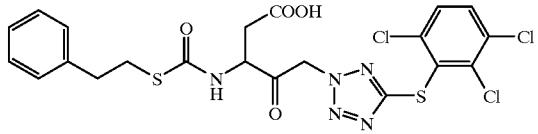

TLC: Rf 0.60 (chloroform:methanol:water=40:10:1); NMR (DMSO-$d_6$): δ 8.69 (1H, m), 7.83 (1H, d, J=8.8 Hz), 7.70 (1H, d, J=8.8 Hz), 7.31–7.15 (5H, m), 5.91 (2H, m), 4.73 (1H, m), 3.06 (2H, m), 2.84 (2H, m), 2.62 (2H, m).

Example 15(34)
N-(2-phenylethylthio)carbonyl-3-amino-4-oxo-5-(5-(2,3,6-trichlorophenylthio)tetrazol-1-yl)pentanoic acid

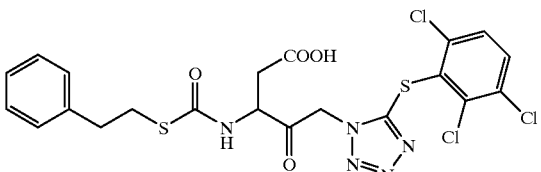

TLC: Rf 0.51 (chloroform:methanol:water=40:10:1); NMR (DMSO-$d_6$): δ 8.87 (1H, m), 7.82 (1H, d, J=8.8 Hz), 7.67 (1H, d, J=8.8 Hz), 7.27–7.14 (5H, m), 5.85 (2H, m), 4.77 (1H, m), 3.05 (2H, m), 2.83 (2H, m), 2.65 (2H, m).

Example 15(35)
N-(2-phenylethylthio)carbonyl-3-amino-4-oxo-5-(5-(2,6-dichloro-4-methylphenylthio)tetrazol-2-yl)pentanoic acid

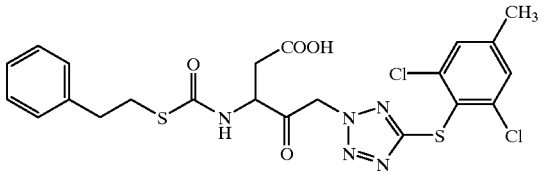

TLC: Rf 0.63 (chloroform:methanol:water=40:10:1); NMR (DMSO-$d_6$): δ 8.56 (1H, d, J=6 Hz), 7.49 (2H, s), 7.26–7.15 (5H, m), 5.92 (2H, m), 4.73 (1H, m), 3.04 (2H, m), 2.84 (2H, m), 2.59 (2H, m), 2.35 (3H, s).

Example 15(36)
N-(2-phenylethylthio)carbonyl-3-amino-4-oxo-5-(5-(2,6-dichloro-4-methylphenylthio)tetrazol-1-yl)pentanoic acid

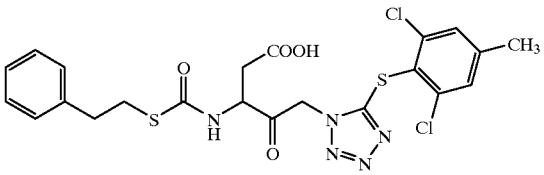

TLC: Rf 0.53 (chloroform:methanol:water=40:10:1); NMR (DMSO-$d_6$): δ 8.82 (1H, d, J=6.8 Hz), 7.49 (2H, s), 7.24–7.14 (5H, m), 5.81 (2H, s), 4.77 (1H, m), 3.05 (2H, m), 2.82 (2H, m), 2.66 (2H, m), 2.34 (3H, s).

Example 15(37)

N-(benzylthio)carbonyl-3-amino-4-oxo-5-(5-(2,6-dimethyl-4-dimethylaminophenylthio)tetrazol-2-yl)pentanoic acid•hydrochloric acid salt

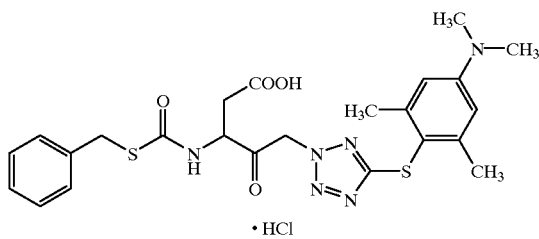

TLC: Rf 0.43 (chloroform:methanol:water=50:10:1); NMR (DMSO-d$_6$): δ 8.96 (1H, d, J=7.0 Hz), 7.34–7.18 (5H, m), 6.79 (2H, s), 5.88 (2H, m), 4.79 (1H, m), 4.10 (2H, s), 2.96 (6H, s), 2.90–2.58 (2H, m), 2.38 (6H, s).

Example 15(38)

N-(benzylthio)carbonyl-3-amino-4-oxo-5-(5-(2,6-dimethyl-4-dimethylaminophenylthio)tetrazol-1-yl)pentanoic acid•hydrochloric acid salt

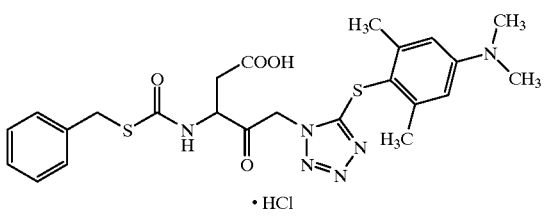

TLC: Rf 0.36 (chloroform:methanol:water=50:10:1); NMR (DMSO-d$_6$): δ 9.05 (1H, d, J=7.0 Hz), 7.38–7.16 (5H, m), 6.71 (2H, s), 5.67 (2H, s), 4.82 (1H, m), 4.13 (2H, s), 2.97 (6H, s), 2.95–2.62 (2H, m), 2.31 (6H, s).

Example 15(39)

N-(benzylthio)carbonyl-3-amino-4-oxo-5-(5-(2,6-dimethyl-4-t-butylphenylthio)tetrazol-2-yl)pentanoic acid

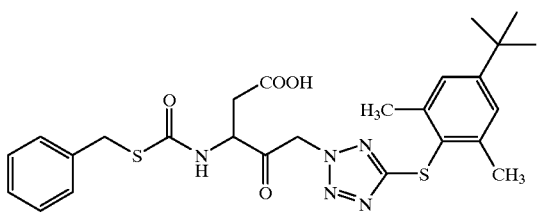

HPTLC: Rf 0.41 (chloroform:methanol:acetic acid=48:1:1); NMR (DMSO-d$_6$): δ 12.50 (1H, brs), 8.88 (1H, d, J=7.6 Hz), 7.35–7.12 (7H, m), 5.92 (1H, d, J=17.8 Hz), 5.71 (1H, d, J=17.8 Hz), 4.87–4.70 (1H, m), 4.09 (2H, s), 2.81 (1H, dd, J=17.3, 5.6 Hz), 2.63 (1H, dd, J=17.3, 7.1 Hz), 2.41 (6H, s), 1.28 (9H, s).

Example 15(40)

N-(benzylthio)carbonyl-3-amino-4-oxo-5-(5-(2,6-dimethyl-4-t-butylphenylthio)tetrazol-1-yl)pentanoic acid

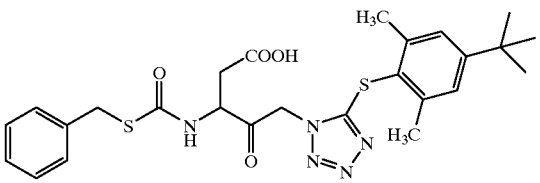

TLC: Rf 0.31 (chloroform:methanol:acetic:acid=47:2:1); NMR (DMSO-d$_6$): δ 12.57 (1H, brs), 8.98 (1H, d, J=7.0 Hz), 7.40–7.00 (1H, m), (7H, m), 5.69 (2H, s), 4.90–4.72 (1H, m), 4.12 (2H, s), 2.90–2.60 (2H, m), 2.35 (6H, s), 1.29 (9H, s).

Example 15(41)

N-(2-(pyridin-2-yl)ethyloxy)carbonyl-3-amino-4-oxo-5-(5-(2,6-dichlorophenylmethyl)tetrazol-2-yl)pentanoic acid

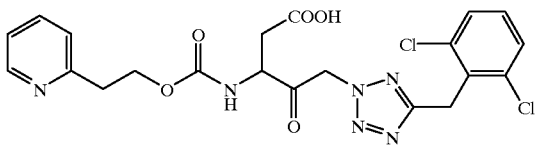

TLC: Rf 0.23 (chloroform:methanol:acetic acid=18:1:1); NMR (DMSO-d$_6$): δ 8.46 (1H, d, J=5.2 Hz), 7.71–7.62 (1H, m), 7.51–7.14 (6H, m), 5.97–5.75 (2H, m), 4.51 (2H, s), 4.51–4.34 (3H, m), 3.05 (2H, t, J=6.6 Hz), 2.61–2.52 (2H, m).

Example 15(42)

N-(2-(pyridin-2-yl)ethyloxy)carbonyl-3-amino-4-oxo-5-(5-(2,6-dichlorophenylmethyl)tetrazol-1-yl)pentanoic acid

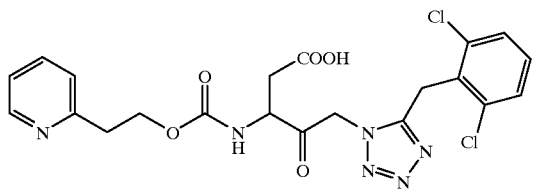

TLC: Rf 0.14 (chloroform:methanol:acetic acid=18:1:1); NMR (DMSO-d$_6$): δ 8.48 (1H, d, J=5.4 Hz), 7.74–7.64 (2H, m), 7.54–7.17 (5H, m), 5.88 (2H, br s), 4.58–4.54 (1H, m), 4.44–4.36 (4H, m), 3.07 (2H, t, J=6.6 Hz), 2.71–2.68 (2H, m).

Example 15(43)

N-(2-phenylethylthio)carbonyl-3-amino-4-oxo-5-(5-(2,6-dichloro-4-dimethylaminophenylthio)tetrazol-2-yl)pentanoic acid

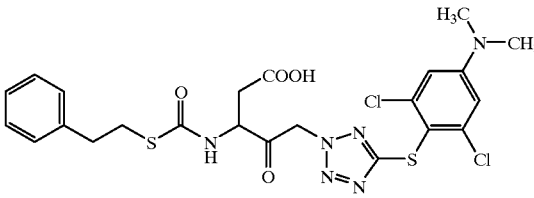

TLC: Rf 0.27 (chloroform:methanol:acetic acid=50:1:1); NMR (DMSO-d$_6$): δ 13.76–11.14 (1H, br), 8.82 (1H, d, J=6.4 Hz), 7.40–7.07 (5H, m), 6.88 (2H, s), 6.02–5.61 (2H, br), 4.90–4.65 (1H, m), 3.20–2.54 (6H, m), 2.99 (6H, s).

Example 15(44)

N-(2-phenylethylthio)carbonyl-3-amino-4-oxo-5-(5-(2,6-dichloro-4-dimethylaminophenylthio)tetrazol-1-yl)pentanoic acid

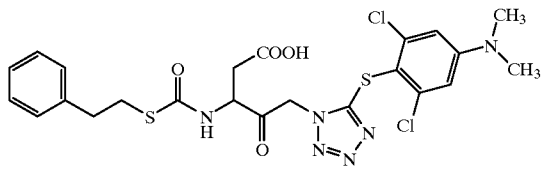

TLC: Rf 0.16 (chloroform:methanol:acetic acid=50:1:1); NMR (DMSO-d$_6$): δ 13.80–11.30 (1H, br), 8.95 (1H, d, J=6.3 Hz), 7.35–7.07 (5H, m), 6.86 (2H, s), 5.87–5.45 (2H, br), 4.91–4.72 (1H, m), 3.20–2.53 (6H, m), 2.99 (6H, s).

Example 15(45)

N-(2-(4-methoxyphenyl)ethyloxy)carbonyl-3-amino-4-oxo-5-(5-(2,3,6-trichlorophenylthio)tetrazol-2-yl)pentanoic acid

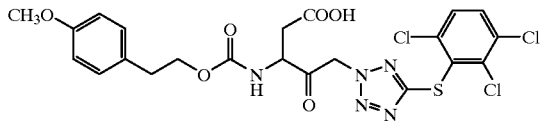

TLC: Rf 0.46 (chloroform:methanol:water=40:10:1); NMR (DMSO-d$_6$): δ 7.85 (1H, d, J=8.8 Hz), 7.72 (1H, d, J=8.8 Hz), 7.63 (1H, d, J=9 Hz), 7.16 (2H, d, J=8.4 Hz), 6.83 (2H, d, J=8.4 Hz), 5.88 (2H, s), 4.50 (1H, m), 4.16 (2H, m), 3.69 (3H, s), 2.81 (2H, m), 2.62 (2H, m).

Example 15(46)

N-(2-(4-methoxyphenyl)ethyloxy)carbonyl-3-amino-4-oxo-5-(5-(2,3,6-trichlorophenylthio)tetrazol-1-yl)pentanoic acid

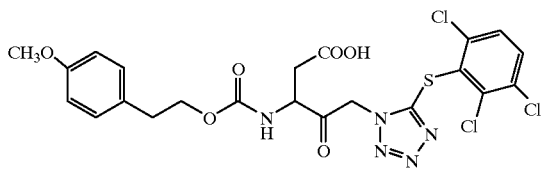

TLC: Rf 0.39 (chloroform:methanol:water=40:10:1); NMR (DMSO-d$_6$): δ 7.86 (1H, d, J=8.8 Hz), 7.71 (1H, d, J=8.8 Hz), 7.67 (1H, m), 7.15 (2H, d, J=8.4 Hz), 6.81 (2H, d, J=8.4 Hz), 5.78 (2H, m), 4.52 (1H, m), 4.17 (2H, m), 3.68 (3H, s), 2.82 (2H, m), 2.62 (2H, m).

Example 15(47)

N-(2-(4-methoxyphenyl)ethyloxy)carbonyl-3-amino-4-oxo-5-(5-(2,6-dichloro-4-methylphenylthio)tetrazol-2-yl)pentanoic acid

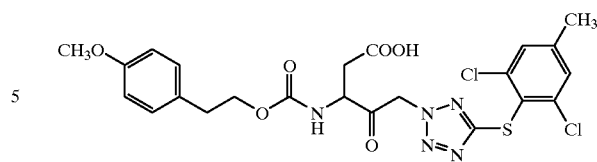

TLC: Rf 0.47 (chloroform:methanol:water=40:10:1); NMR (DMSO-d$_6$): δ 12.49 (1H, brs), 7.82 (1H, d, J=8.0 Hz), 7.53 (2H, s), 7.17 (2H, d, J=8.4 Hz), 6.83 (2H, d, J=8.4 Hz), 5.88 (2H, m), 4.56 (1H, m), 4.18 (2H, t, J=6.6 Hz), 3.69 (3H, s), 2.82 (2H, t, J=6.6 Hz), 2.74–2.51 (2H, m), 2.36 (3H, s).

Example 15(48)

N-(2-(4-methoxyphenyl)ethyloxy)carbonyl-3-amino-4-oxo-5-(5-(2,6-dichloro-4-methylphenylthio)tetrazol-1-yl)pentanoic acid

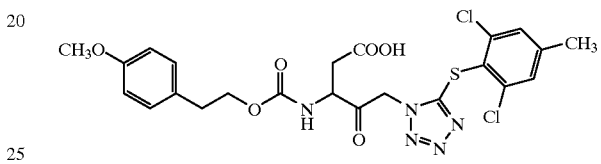

TLC: Rf 0.43 (chloroform:methanol:water=40:10:1); NMR (DMSO-d$_6$): δ 7.67 (1H, d, J=8 Hz), 7.53 (2H, s), 7.15 (2H, d, J=8.6 Hz), 6.81 (2H, d, J=8.6 Hz), 5.74 (2H, m), 4.52 (1H, m), 4.16 (2H, m), 3.68 (3H, m), 2.81 (2H, m), 2.63 (2H, m), 2.35 (3H, s).

Example 15(49)

N-(2-(4-methoxyphenyl)ethyloxy)carbonyl-3-amino-4-oxo-5-(5-(2,6-dichloro-4-dimethylaminophenylthio)tetrazol-2-yl)pentanoic acid

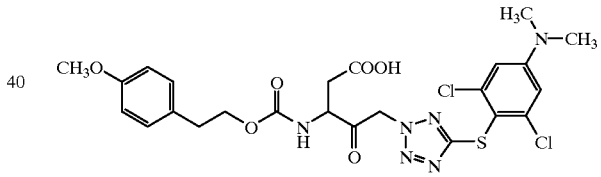

TLC: Rf 0.50 (chloroform:methanol:water=40:10:1); NMR (DMSO-d$_6$): δ 7.64 (1H, m), 7.14 (2H, d, J=8.2 Hz), 6.85 (2H, s), 6.80 (2H, d, J=8.2 Hz), 5.81 (2H, s), 4.49 (1H, m), 4.15 (2H, m), 3.66 (3H, s), 2.97 (6H, s), 2.76 (2H, m), 2.60 (2H, m).

Example 15(50)

N-(2-(4-methoxyphenyl)ethyloxy)carbonyl-3-amino-4-oxo-5-(5-(2,6-dichloro-4-dimethylaminophenylthio)tetrazol-1-yl)pentanoic acid

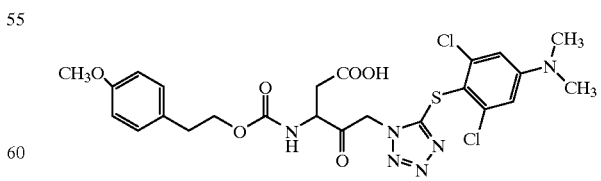

TLC: Rf 0.48 (chloroform:methanol:water=40:10:1); NMR (DMSO-d$_6$): δ 7.65 (1H, m), 7.12 (2H, d, J=8.4 Hz), 6.84 (2H, s), 6.79 (2H, d, J=8.4 Hz), 5.68 (2H, s), 4.49 (1H, m), 4.15 (2H, m), 3.66 (3H, s), 2.96 (6H, s), 2.79 (2H, m), 2.61 (2H, m).

Example 15(51)

N-(2-(4-methoxyphenyl)ethyloxy)carbonyl-3-amino-4-oxo-5-(5-(2,6-dimethyl-4-dimethylaminophenylthio)tetrazol-2-yl)pentanoic acid•hydrochloric salt

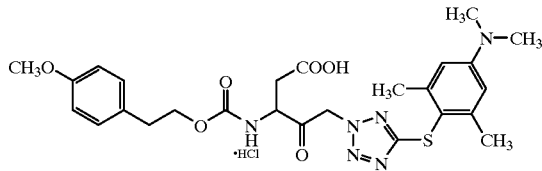

TLC: Rf 0.33 (chloroform:methanol:acetic acid=48:1:1);
NMR (DMSO-$d_6$): δ 7.78 (1H, d, J=8.0 Hz), 7.16 (2H, d, J=8.5 Hz), 6.81 (2H, d, J=8.5 Hz), 6.72 (2H, s), 5.79 (2H, s), 4.60–4.40 (1H, m), 4.17 (2H, t, J=6.5 Hz), 3.68 (3H, s), 3.00–2.50 (2H, m), 2.96 (6H, s), 2.81 (2H, t, J=6.5 Hz), 2.35 (6H, s).

Example 15(52)

N-(2-(4-methoxyphenyl)ethyloxy)carbonyl-3-amino-4-oxo-5-(5-(2,6-dimethyl-4-dimethylaminophenylthio)tetrazol-1-yl)pentanoic acid•hydrochloric acid salt

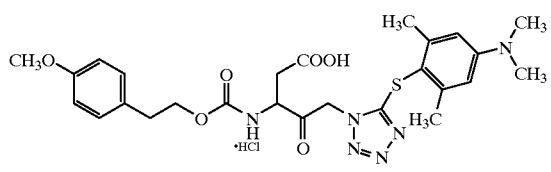

TLC: Rf 0.25 (chloroform:methanol:acetic acid=48:1:1);
NMR (DMSO-$d_6$): δ 7.88 (1H, d, J=8.0 Hz), 7.16 (2H, d, J=8.5 Hz), 6.81 (2H, d, J=8.5 Hz), 6.64 (2H, s), 5.57 (2H, s), 4.62–4.43 (1H, m), 4.28–4.10 (2H, m), 3.68 (3H, s), 3.00–2.60 (2H, m), 2.96 (6H, s), 2.84 (2H, t, J=7.0 Hz), 2.31 (6H, s).

Example 15(53)

N-(4-(4-methoxyphenyl)butyloxy)carbonyl-3-amino-4-oxo-5-(5-(2,3,6-trichlorophenylthio)tetrazol-2-yl)pentanoic acid

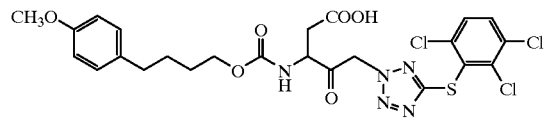

TLC: Rf 0.67 (chloroform:methanol:water=40:10:1);
NMR (DMSO-$d_6$): δ 7.82 (1H, d, J=8.8 Hz), 7.69 (1H, d, J=8.8 Hz), 7.49 (1H, m), 7.06 (2H, d, J=8.6 Hz), 6.78 (2H, d, J=8.6 Hz), 5.93 (2H, m), 4.46 (1H, m), 3.97 (2H, m), 3.68 (3H, s), 2.57 (2H, m), 2.49 (2H, m), 1.53 (4H, m).

Example 15(54)

N-(4-(4-methoxyphenyl)butyloxy)carbonyl-3-amino-4-oxo-5-(5-(2,3,6-trichlorophenylthio)tetrazol-2-yl)pentanoic acid

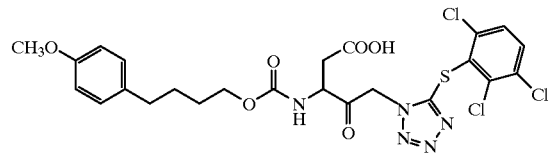

TLC: Rf0.56 (chloroform:methanol:water=40:10:1);
NMR (DMSO-$d_6$): δ 7.87 (1H, d, J=8.8 Hz), 7.71 (1H, d, J=8.8 Hz), 7.63 (1H, m), 7.06 (2H, d, J=8.6 Hz), 6.80 (2H, d, J=8.6 Hz), 5.80 (2H, m), 4.57 (1H, m), 4.05 (2H, m), 3.70 (3H, s), 2.67 (2H, m), 2.50 (2H, m), 1.57 (4H, m).

Example 15(55)

N-(4-(4-methoxyphenyl)butyloxy)carbonyl-3-amino-4-oxo-5-(5-(2,6-dichloro-4-dimethylaminophenylthio)tetrazol-2-yl)pentanoic acid

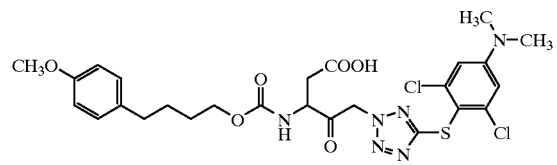

TLC: Rf 0.61 (chloroform:methanol:water=40:10:1);
NMR (DMSO-$d_6$): δ 7.68 (1H, d, J=8 Hz), 7.08 (2H, d, J=8.4 Hz), 6.86 (2H, s), 6.80 (2H, d, J=8.4 Hz), 5.86 (2H, s), 4.54 (1H, m), 4.01 (2H, m), 3.70 (3H, s), 2.99 (6H, s), 2.80–2.48 (4H, m), 1.57 (4H, m).

Example 15(56)

N-(4-(4-methoxyphenyl)butyloxy)carbonyl-3-amino-4-oxo-5-(5-(2,6-dichloro-4-dimethylaminophenylthio)tetrazol-1-yl)pentanoic acid

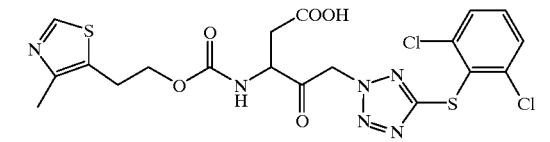

TLC: Rf 0.53 (chloroform:methanol:water=40:10:1);
NMR (DMSO-$d_6$): δ 7.61 (1H, d, J=8 Hz), 7.04 (2H, d, J=8.4 Hz), 6.84 (2H, s), 6.78 (2H, d, J=8.4 Hz), 5.71 (2H, s), 4.52 (1H, m), 4.02 (2H, m), 3.69 (3H, s), 2.98 (6H, s), 2.63 (2H, m), 2.49 (2H, m), 1.56 (4H, m).

Example 15(57)

N-(2-(4-methylthiazol-5-yl)ethyloxy)carbonyl-3-amino-4-oxo-5-(5-(2,6-dichlorophenylthio)tetrazol-2-yl)pentanoic acid TLC: Rf 0.42 (chloroform:methanol:water=40:10:1);
NMR (DMSO-$d_6$): δ 12.40 (1H, brs), 8.81 (1H, s), 7.88 (1H, d, J=7.6 Hz), 7.70–7.51 (3H, m), 5.94 (2H, s), 4.59 (1H, m), 4.18 (2H, t, J=6.2 Hz), 3.08 (2H, t, J=6.2 Hz), 2.79 (1H, dd, J=17 Hz, 5.8 Hz), 2.58 (1H, dd, J=17 Hz, 7.2 Hz), 2.33 (3H, s).

Example 15(58)

N-(2-(4-methylthiazol-5-yl)ethyloxy)carbonyl-3-amino-4-oxo-5-(5-(2,6-dichlorophenylthio)tetrazol-1-yl)pentanoic acid

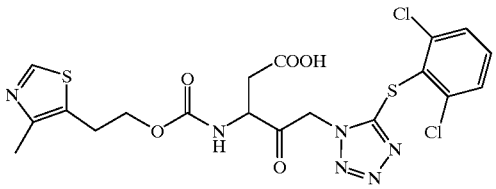

TLC: Rf 0.35 (chloroform:methanol:water=40:10:1); NMR (DMSO-d$_6$): δ 8.79 (1H, s), 7.83 (1H, d, J=8 Hz), 7.70–7.52 (3H, m), 5.75 (2H, m), 4.60 (1H, m), 4.19 (2H, m), 3.10 (2H, t, J=6.4 Hz), 2.71 (2H, m), 2.32 (3H, s).

Example 15(59)

N-(2-phenylethylthio)carbonyl-3-amino-4-oxo-5-(5-(2,6-dichlorophenylthio)tetrazol-2-yl)pentanoic acid

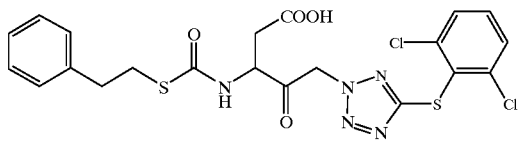

TLC: Rf 0.63 (chloroform:methanol:water=40:10:1); NMR (DMSO-d$_6$): δ 8.69 (1H, m), 7.70–7.53 (3H, m), 7.32–7.16 (5H, m), 5.91 (2H, s), 4.73 (1H, m), 3.09 (2H, m), 2.84 (2H, m), 2.55 (2H, m).

Example 15(60)

N-(2-phenylethylthio)carbonyl-3-amino-4-oxo-5-(5-(2,6-dichlorophenylthio)tetrazol-1-yl)pentanoic acid

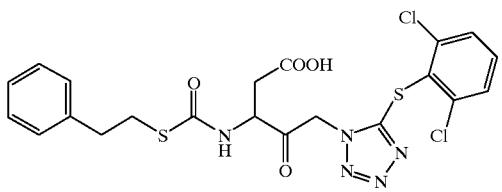

TLC: Rf 0.51 (chloroform:methanol:water=40:10:1); NMR (DMSO-d$_6$): δ 8.85 (1H, m), 7.68–7.50 (3H, m), 7.23–7.14 (5H, m), 5.84 (2H, s), 4.76 (1H, m), 3.04 (2H, m), 2.82 (2H, m), 2.65 (2H, m).

Example 15(61)

N-(2-phenylethylthio)carbonyl-3-amino-4-oxo-5-(5-(4-(pyrrolidin-1-ylmethyl)phenylthio)tetrazol-2-yl)pentanoic acid•hydrochloric acid salt

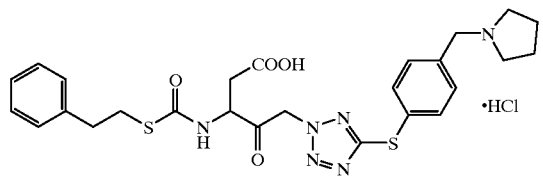

TLC: Rf 0.39 (chloroform:methanol:water=40:10:1); NMR (DMSO-d$_6$): δ 9.02–8.80 (1H, m), 7.66 (2H, d, J=8.5 Hz), 7.50 (2H, d, J=8.5 Hz), 7.40–7.10 (5H, m), 5.98 (2H, s), 4.90–4.75 (1H, m), 4.32 (2H, s), 3.60–2.93 (6H, m), 2.93–2.55 (4H, m), 2.00–1.80 (4H, m).

Example 15(62)

N-(2-phenylethylthio)carbonyl-3-amino-4-oxo-5-(5-(4-(pyrrolidin-1-ylmethyl)phenylthio)tetrazol-1-yl)pentanoic acid•hydrochloric acid salt

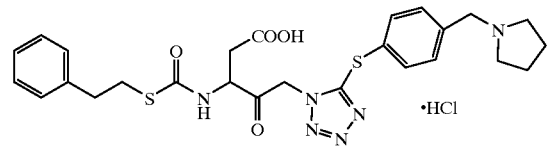

TLC: Rf 0.36 (chloroform:methanol:water=40:10:1); NMR (DMSO-d$_6$): δ 9.04–8.95 (1H, m), 7.65 (2H, d, J=8.2H), 7.57 (2H, d, J=8.2 Hz), 7.33–7.10 (5H, m), 5.76 (2H, s), 4.90–4.70 (1H, m), 4.32 (2H, s), 3.60–2.95 (6H, m), 2.95–2.54 (4H, m), 2.05–1.90 (4H, m).

Example 15(63)

N-(2-(4-methylthiazol-5-yl)ethylthio)carbonyl-3-amino-4-oxo-5-(5-(2,6-dichlorophenylthio)tetrazol-2-yl)pentanoic acid

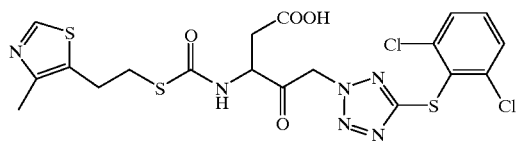

TLC: Rf 0.38 (chloroform:methanol:water=40:10:1); NMR (DMSO-d$_6$): δ 12.53 (1H, brs), 8.95 (1H, d, J=7.4 Hz), 8.79 (1H, s), 7.70–7.50 (3H, m), 5.99 (1H, d, J=18.0 Hz), 5.88 (1H, d, J=18.0 Hz), 4.82 (1H, m), 3.04 (4H, s), 2.83 (1H, dd, J=17.0 Hz, 5.6 Hz), 2.65 (1H, dd, J=17.0 Hz, 7.0 Hz), 2.32 (3H, s).

Example 15(64)

N-(2-(4-methylthiazol-5-yl)ethylthio)carbonyl-3-amino-4-oxo-5-(5-(2,6-dichlorophenylthio)tetrazol-1-yl)pentanoic acid

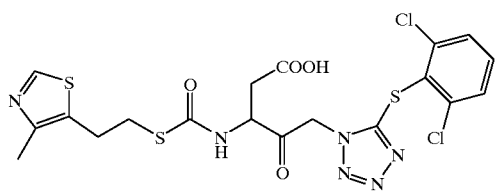

TLC: Rf 0.31 (chloroform:methanol:water=40:10:1); NMR (DMSO-d$_6$): δ 9.07 (1H, d, J=7 Hz), 8.79 (1H, s), 7.69–7.52 (3H, m), 5.87 (1H, d, J=17 Hz), 5.74 (1H, d, J=17 Hz), 4.86 (1H, m), 3.06 (4H, s), (1H, dd, J=17 Hz, 5.8 Hz), 2.75 (1H, dd, J=17 Hz, 7 Hz), 2.28 (3H, s).

Example 15(65)

N-(butylthio)carbonyl-3-amino-4-oxo-5-(5-(2,6-dichlorophenylthio) tetrazol-2-yl)pentanoic acid

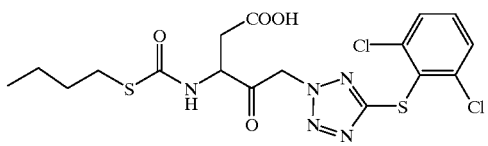

TLC: Rf 0.58 (chloroform:methanol:water=40:10:1); NMR (DMSO-d$_6$): δ 8.74 (1H, d, J=6.8 Hz), 7.70–7.51 (3H, m), 5.90 (2H, s), 4.75 (1H, m), 2.82 (2H, t, J=7.2 Hz), 2.67 (2H, m), 1.51 (2H, m), 1.33 (2H, m), 0.87 (3H, t, J=7.2 Hz).

Example 15(66)

N-(butylthio)carbonyl-3-amino-4-oxo-5-(5-(2,6-dichlorophenylthio)tetrazol-1-yl)pentanoic acid

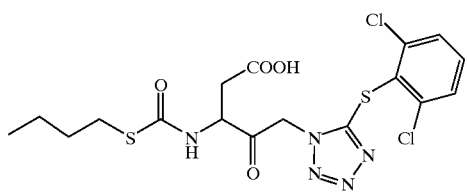

TLC: Rf 0.43 (chloroform:methanol:water=40:10:1); NMR (DMSO-d$_6$): δ 8.80 (1H, d, J=6.6 Hz), 7.69–7.51 (3H, m), 5.82 (2H, m), 4.76 (1H, m), 2.82 (2H, m), 2.67 (2H, m), 1.49 (2H, m), 1.31 (2H, m), 0.80 (3H, t, J=7.2 Hz).

Example 15(67)

N-(2-(4-methoxyphenyl)ethylthio)carbonyl-3-amino-4-oxo-5-(5-(2,6-dichlorophenylthio)tetrazol-2-yl)pentanoic acid

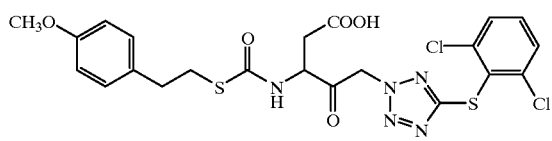

TLC: Rf 0.52 (chloroform:methanol:water=40:10:1); NMR (DMSO-d$_6$): δ 12.05 (1H, brs), 8.82 (1H, m), 7.70–7.66 (3H, m), 7.59–7.54 (1H, m), 7.14 (2H, d, J=8.4 Hz), 6.83 (2H, d, J=8.4 Hz), 5.81 (2H, m), 4.78 (1H, m), 3.70 (3H, s), 3.05 (2H, m), 2.86–2.75 (3H, m), 2.62 (1H, dd, J=17 Hz, 8 Hz).

Example 15(68)

N-(2-(4-methoxyphenyl)ethylthio)carbonyl-3-amino-4-oxo-5-(5-(2,6-dichlorophenylthio)tetrazol-1-yl)pentanoic acid

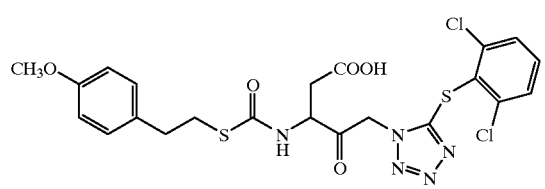

TLC: Rf 0.40 (chloroform:methanol:water=40:10:1); NMR (DMSO-d$_6$): δ 12.36 (1H, brs), 8.99 (1H, d, J=7.4 Hz), 7.70–7.65 (2H, m), 7.59–7.51 (1H, m), 7.11 (2H, d, J=8.6 Hz), 6.79 (2H, d, J=8.6 Hz), 5.89–5.69 (2H, m), 4.84 (1H, m), 3.69 (3H, s), 3.09–3.02 (2H, m), 2.94–2.61 (4H, m).

Example 15(69)

N-(3-(pyrimidin-2-yl)propyloxy)carbonyl-3-amino-4-oxo-5-(5-(2,6-dichlorophenylthio)tetrazol-2-yl)pentanoic acid

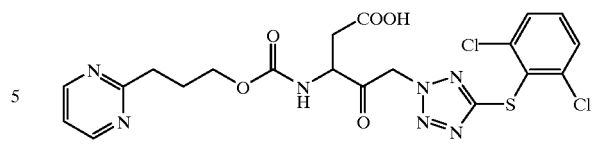

TLC: Rf 0.40 (chloroform:methanol:acetic acid=18:1:1); NMR (DMSO-d$_6$): δ 8.71 (2H, d, J=5.0 Hz), 7.75–7.48 (3H, m), 7.40 (1H, m), 7.32 (1H, t, J=5.0 Hz), 5.99 (2H, br), 4.48 (1H, m), 4.07 (2H, m), 2.94 (2H, m), 2.59 (2H, br), 2.06 (2H, m).

Example 15(70)

N-(3-(pyrimidin-2-yl)propyloxy)carbonyl-3-amino-4-oxo-5-(5-(2,6-dichlorophenylthio)tetrazol-1-yl)pentanoic acid

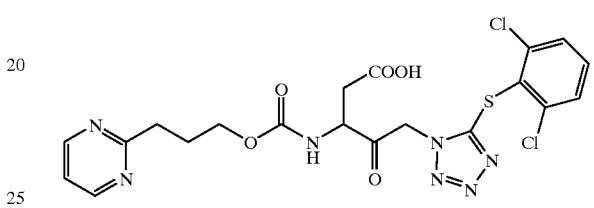

TLC: Rf 0.36 (chloroform:methanol:acetic acid=18:1:1); NMR (DMSO-d$_6$): δ 8.66 (2H, m), 7.74–7.46 (4H, m), 7.29 (1H, m), 5.83 (2H, br), 4.50 (1H, m), 4.09 (2H, m), 2.94 (2H, m), 2.63 (2H, m), 2.06 (2H, m).

Example 15(71)

N-(2-(4-acetylaminophenyl)ethylthio)carbonyl-3-amino-4-oxo-5-(5-(2,6-dichlorophenylthio)tetrazol-2-yl)pentanoic acid

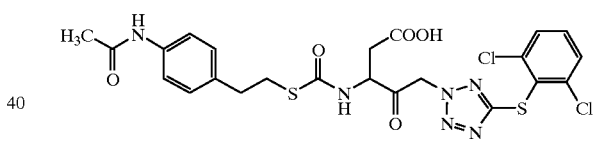

TLC: Rf 0.30 (chloroform:methanol:acetic acid=18:1:1); NMR (DMSO-d$_6$): δ 9.86 (1H, s), 8.77 (1H, d, J=7.4 Hz), 7.75–7.40 (5H, m), 7.13 (2H, d, J=8.2 Hz), 5.90 (2H, brs), 4.83–4.63 (1H, m), 3.04 (2H, t, J=7.3 Hz), 2.77 (2H, t, J=7.3 Hz), 2.70–2.50 (2H, m), 2.01 (3H, s).

Example 15(72)

N-(2-(4-acetylaminophenyl)ethylthio)carbonyl-3-amino-4-oxo-5-(5-(2,6-dichlorophenylthio)tetrazol-1-yl)pentanoic acid

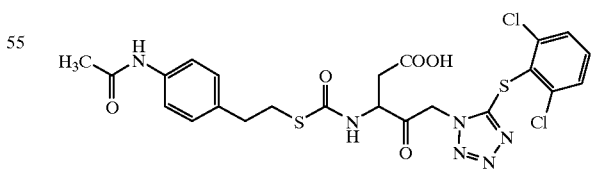

TLC: Rf 0.24 (chloroform:methanol:acetic acid=18:1:1); NMR (DMSO-d$_6$): δ 9.85 (1H, s), 8.88–8.76 (1H, m), 7.70–7.50 (3H, m), 7.44 (2H, d, J=8.2 Hz), 7.09 (2H, d, J=8.2 Hz), 5.82 (2H, brs), 4.82–4.64 (1H, m), 3.13–2.90 (2H, m), 2.90–2.68 (2H, m), 2.68–2.54 (2H, m), 2.01 (3H, s).

Example 15(73)
N-butyloxycarbonyl-3-amino-4-oxo-5-(5-(2,6-dichlorophenylthio) tetrazol-2-yl)pentanoic acid

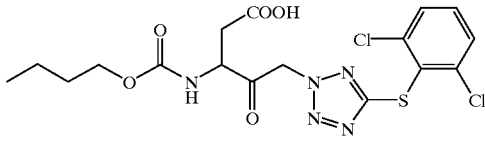

TLC: Rf 0.55 (chloroform:methanol:water=40:10:1); NMR (DMSO-d$_6$): δ 7.70–7.51 (3H, m), 5.93 (2H, s), 4.54 (1H, m), 4.00 (2H, t, J=6.6 Hz), 2.77–2.55 (2H, m), 1.55 (2H, m), 1.29 (2H, m), 0.89 (3H, t, J=7.4 Hz).

Example 15(74)
N-butyloxycarbonyl-3-amino-4-oxo-5-(5-(2,6-dichlorophenylthio) tetrazol-1-yl)pentanoic acid

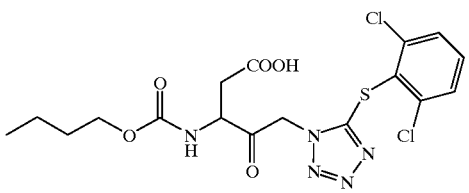

TLC: Rf 0.48 (chloroform:methanol:water=40:10:1); NMR (DMSO-d$_6$): δ 7.70–7.52 (3H, m), 5.80 (2H, s), 4.56 (1H, m), 4.01 (2H, m), 2.67 (2H, m), 1.55 (2H, m), 1.30 (2H, m), 0.86 (3H, t, J=7.4 Hz).

Example 15(75)
N-(propylthio)carbonyl-3-amino-4-oxo-5-(5-(2,6-dichlorophenylthio) tetrazol-2-yl)pentanoic acid

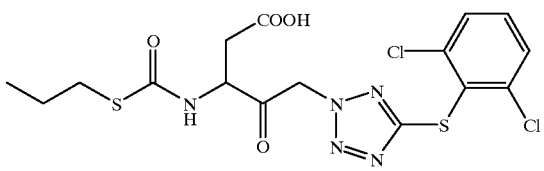

TLC: Rf 0.39 (chloroform:methanol:acetic acid=94:3:3); NMR (DMSO-d$_6$): δ 8.61 (1H, d, J=7.0 Hz), 7.70–7.49 (3H, m), 5.95 (2H, brs), 4.75–4.58 (1H, m), 2.78 (2H, t, J=7.2 Hz), 2.57 (2H, brs), 1.63–1.40 (2H, m), 0.90 (3H, t, J=7.4 Hz).

Example 15(76)
N-(propylthio)carbonyl-3-amino-4-oxo-5-(5-(2,6-dichlorophenylthio) tetrazol-1-yl)pentanoic acid

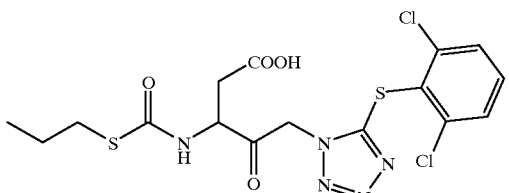

TLC: Rf 0.30 (chloroform:methanol:acetic acid=94:3:3); NMR (DMSO-d$_6$): δ 8.85–8.68 (1H, m), 7.70–7.50 (3H, m), 5.83 (2H, brs), 4.80–4.58 (1H, m), 2.90–2.68 (2H, m), 2.63–2.54 (2H, m), 1.65–1.40 (2H, m), 0.86 (3H, t, J=7.2 Hz).

Example 15(77)
N-(isopropylthio)carbonyl-3-amino-4-oxo-5-(5-(2,6-dichlorophenylthio) tetrazol-2-yl)pentanoic acid

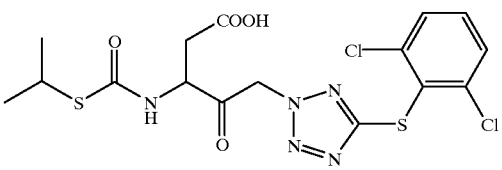

TLC: Rf 0.36 (chloroform:methanol:acetic acid=94:3:3); NMR (DMSO-d$_6$): δ 8.75 (1H, d, J=7.0 Hz), 7.80–7.50 (3H, m), 6.05–5.80 (2H, m), 4.90–4.71 (1H, m), 3.49 (1H, sep, J=6.8 Hz), 2.92–2.53 (2H, m), 1.27 (6H, d, J=6.8 Hz).

Example 15(78)
N-(isopropylthio)carbonyl-3-amino-4-oxo-5-(5-(2,6-dichlorophenylthio) tetrazol-1-yl)pentanoic acid

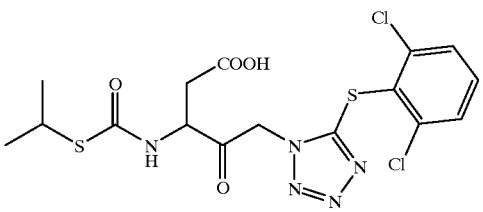

TLC: Rf 0.30 (chloroform:methanol:acetic acid=94:3:3); NMR (DMSO-d$_6$): δ 9.03–8.75 (1H, m), 7.80–7.50 (3H, m), 5.76 (2H, brs), 4.90–4.70 (1H, m), 3.52 (1H, sep, J=6.6 Hz), 2.95–2.63 (2H, m), 1.28 (6H, d, J=6.6 Hz).

Example 15(79)
N-(2-methoxyethyloxy)carbonyl-3-amino-4-oxo-5-(5-(2,6-dichlorophenylthio)tetrazol-2-yl)pentanoic acid

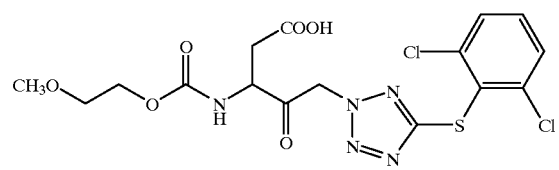

TLC: Rf 0.43 (chloroform:methanol:water=40:10:1); NMR (DMSO-d$_6$): δ 12.50 (1H, s), 7.93 (1H, d, J=7.8 Hz), 7.71–7.66 (2H, m), 7.59–7.51 (1H, m), 5.97 (2H, s), 4.58 (1H, m), 4.13 (2H, m), 3.51 (2H, t, J=4.4 Hz), 3.22 (3H, s), 2.80 (1H, dd, J=16.8 Hz, 5.8 Hz), 2.58 (1H, dd, J=16.8 Hz, 4.8 Hz).

Example 15(80)
N-(2-methoxyethyloxy)carbonyl-3-amino-4-oxo-5-(5-(2,6-dichlorophenylthio)tetrazol-1-yl)pentanoic acid

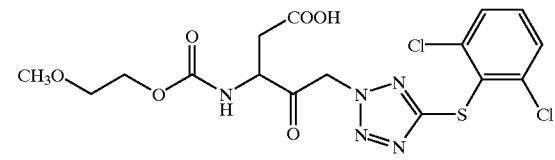

TLC: Rf 0.34 (chloroform:methanol:water=40:10:1); NMR (DMSO-d$_6$): δ 12.00 (1H, s), 7.92 (1H, d, J=7 Hz), 7.70–7.66 (2H, m), 7.60–7.53 (1H, m), 5.77 (2H, m), 4.60 (1H, m), 4.15 (2H, m), 3.53 (2H, m), 3.25 (3H, s), 2.74 (2H, m).

Example 15(81)

N-(2-cyclohexylethyloxy)carbonyl-3-amino-4-oxo-5-(5-(2,6-dichlorophenylthio)tetrazol-2-yl)pentanoic acid

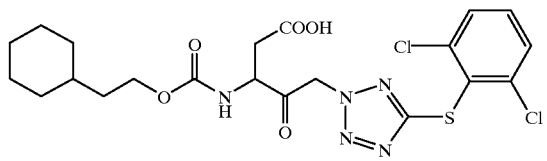

TLC: Rf 0.35 (chloroform:methanol:acetic acid=95:3:2); NMR (DMSO-d$_6$): δ 12.46 (1H, s), 7.78 (1H, d, J=7.6 Hz), 7.73–7.50 (3H, m), 5.96 (2H, s), 4.65–4.46 (1H, m), 4.04 (2H, t, J=6.4 Hz), 2.88–2.50 (2H, m), 1.80–0.78 (13H, m).

Example 15(82)

N-(2-cyclohexylethyloxy)carbonyl-3-amino-4-oxo-5-(5-(2,6-dichlorophenylthio)tetrazol-1-yl)pentanoic acid

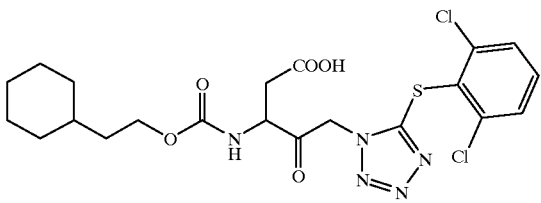

TLC: Rf 0.25 (chloroform:methanol:acetic acid=95:3:2); NMR (DMSO-d$_6$): δ 12.53 (1H, s), 7.92 (1H, d, J=7.6 Hz), 7.77–7.50 (3H, m), 5.80 (2H, s), 4.73–4.50 (1H, m), 4.13–3.92 (2H, m), 2.85 (1H, dd, J=17.0, 5.4 Hz), 2.29 (1H, dd, J=17.0, 6.6 Hz), 1.80–0.70 (13H, m).

Example 15(83)

N-cyclohexylmethyloxycarbonyl-3-amino-4-oxo-5-(5-(2,6-dichlorophenylthio)tetrazol-2-yl)pentanoic acid

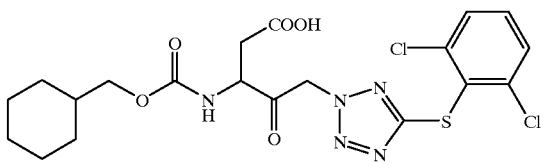

TLC: Rf 0.31 (chloroform:methanol:acetic acid=95:3:2); NMR (DMSO-d$_6$): δ 12.40 (1H, brs), 7.77 (1H, d, J=7.6 Hz), 7.75–7.50 (3H, m), 5.95 (2H, s), 4.65–4.45 (1H, m), 3.82 (2H, d, J=5.8 Hz), 2.90–2.50 (2H, m), 1.80–0.80 (11H, m).

Example 15(84)

N-cyclohexylmethyloxycarbonyl-3-amino-4-oxo-5-(5-(2,6-dichlorophenylthio)tetrazol-1-yl)pentanoic acid

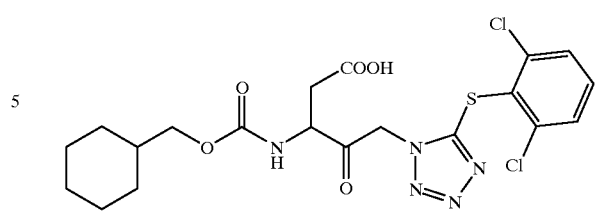

TLC: Rf 0.24 (chloroform:methanol:acetic acid=95:3:2); NMR (DMSO-d$_6$): δ 12.53 (1H, brs), 7.92 (1H, d, J=7.6 Hz), 7.74–7.52 (3H, m), 5.80 (2H, s), 4.70–4.56 (1H, m), 3.96–3.73 (2H, m), 2.85 (1H, dd, J=17.0, 6.2 Hz), 2.70 (1H, dd, J=17.0, 6.5 Hz), 1.80–0.80 (11H, m).

Example 15(85)

N-(2-phenylethyloxy)carbonyl-3-amino-4-oxo-5-(5-(2,6-dichlorophenylthio)tetrazol-2-yl)pentanoic acid

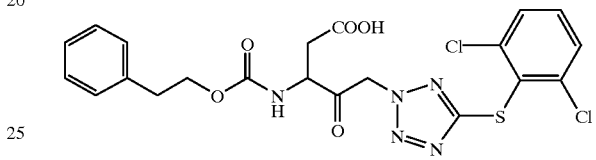

TLC: Rf 0.49 (chloroform:methanol:water=40:10:1); NMR (DMSO-d$_6$): δ 7.69–7.50 (4H, m), 7.32–7.13 (5H, m), 5.85 (2H, s), 4.52 (1H, m), 4.22 (2H, m), 2.88 (2H, t, J=7.0 Hz), 2.64 (2H, m).

Example 15(86)

N-(2-phenylethyloxy)carbonyl-3-amino-4-oxo-5-(5-(2,6-dichlorophenylthio)tetrazol-1-yl)pentanoic acid

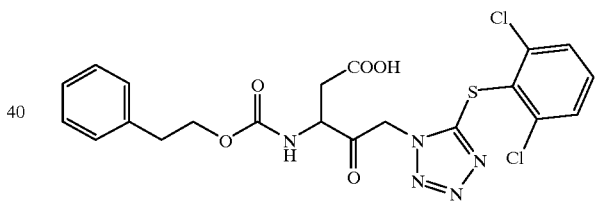

TLC: Rf 0.29 (chloroform:methanol:water=40:10:1); NMR (DMSO-d$_6$): δ 7.83 (1H, d, J=7.0 Hz), 7.70–7.66 (2H, m), 7.60–7.52 (1H, m), 7.27–7.16 (5H, m), 5.71 (2H, s), 4.59 (1H, m), 4.27 (2H, m), 2.91 (2H, t, J=6.8 Hz), 2.70 (2H, m).

Example 15(87)

N-butyloxycarbonyl-3-amino-4-oxo-5-(5-(2,6-dichloro-4-acetylaminophenylthio)tetrazol-2-yl)pentanoic acid

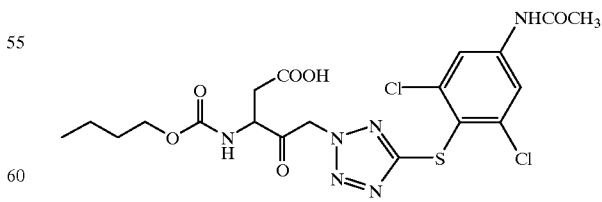

TLC: Rf 0.25 (chloroform:methanol:acetic acid=18:1:1); NMR (DMSO-d$_6$): δ 10.49 (1H, s), 7.87 (2H, s), 7.68 (1H, d, J=7.4 Hz), 5.91 (2H, s), 4.62–4.45 (1H, m), 3.99 (2H, t, J=6.4 Hz), 2.80–2.50 (2H, m), 2.10 (3H, s), 1.64–1.20 (4H, m), 0.88 (3H, t, J=7.2 Hz).

Example 15(88)

N-butyloxycarbonyl-3-amino-4-oxo-5-(5-(2,6-dichloro-4-acetylaminophenylthio)tetrazol-1-yl)pentanoic acid

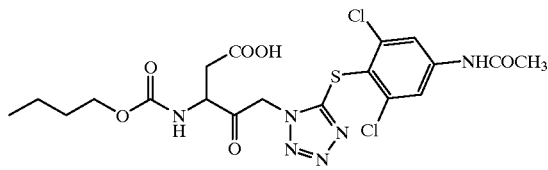

TLC: Rf 0.15 (chloroform:methanol:acetic acid=18:1:1); NMR (DMSO-$d_6$): δ 10.60 (1H, s), 7.87 (2H, s), 7.69 (1H, d, J=8.4 Hz), 5.76 (2H, s), 4.60–4.45 (1H, m), 4.07–3.92 (2H, m), 2.73–2.53 (2H, m), 2.10 (3H, s), 1.65–1.20 (4H, m), 0.86 (3H, t, J=7.2 Hz).

Example 15(89)

N-(2-(4-cyanophenyl)ethyloxy)carbonyl-3-amino-4-oxo-5-(5-(2,6-dichlorophenylthio)tetrazol-2-yl)pentanoic acid

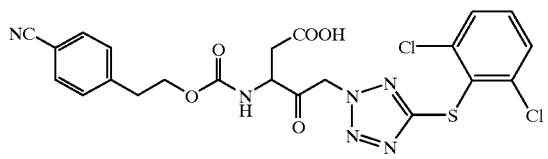

TLC: Rf 0.44 (chloroform:methanol:acetic acid=18:1:1); NMR (DMSO-$d_6$): δ 12.47 (1H, br), 7.84 (1H, d, J=7.0 Hz), 7.79–7.37 and 7.17 (total 7H, m), 5.94 and 5.87 (each 1H, each d, J=1 6.0 Hz), 4.55 (1H, m), 4.25 (2H, t, J=7.0 Hz), 3.00 (2H, t, J=7.0 Hz), 2.76 and 2.60 (each 1H, each dd, J=16.5, 6.0 Hz).

Example 15(90)

N-(2-(4-cyanophenyl)ethyloxy)carbonyl-3-amino-4-oxo-5-(5-(2,6-dichlorophenylthio)tetrazol-1-yl)pentanoic acid

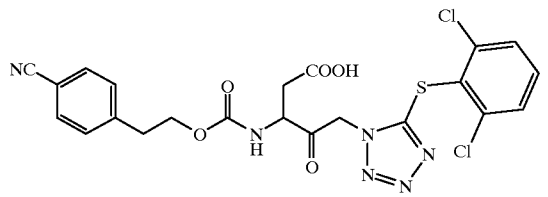

TLC: Rf 0.40 (chloroform:methanol:acetic acid=18:1:1); NMR (DMSO-$d_6$): δ 7.91 (1H, d, J=7.5 Hz), 7.79–7.41 and 7.30–7.08 (total 7H, m) 5.71 (2H, brs), 4.59 (1H, m), 4.28 (2H, t, J=6.5 Hz), 3.01 (2H, t, J=6.5 Hz), 2.73 (2H, m).

Example 15(91)

N-(2-(4-cyanophenyl)ethyloxy)carbonyl-3-amino-4-oxo-5-(5-(2,6-dichloro-4-methylphenylthio)tetrazol-2-yl)pentanoic acid

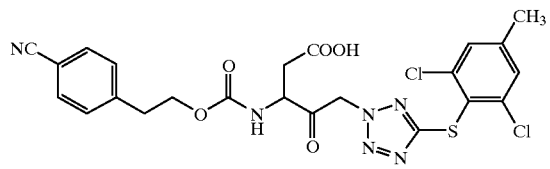

TLC: Rf 0.56 (chloroform:methanol:acetic acid=18:1:1); NMR (DMSO-$d_6$): δ 12.6–12.3 (1H, br), 7.82 (1H, m), 7.74 (2H, d, J=8.0 Hz), 7.53 (2H, s), 7.48 (2H, d, J=8.0 Hz), 5.90 (2H, brs), 4.53 (1H, m), 4.26 (2H, t, J=6.5 Hz), 2.99 (2H, t, J=6.5 Hz), 2.65 (2H, m), 2.35 (3H, s).

Example 15(92)

N-(2-(4-cyanophenyl)ethyloxy)carbonyl-3-amino-4-oxo-5-(5-(2,6-dichloro-4-methylphenylthio)tetrazol-1-yl) pentanoic acid

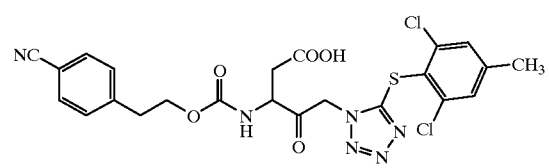

TLC: Rf 0.49 (chloroform:methanol:acetic acid=18:1:1); NMR (DMSO-$d_6$): δ 7.86 (1H, m), 7.72 (2H, d, J=8.0 Hz), 7.52 (2H, s), 7.47 (2H, d, J=8.0 Hz), 5.71 (2H, br), 4.58 (1H, m), 4.28 (2H, t, J=6.5 Hz), 3.00 (2H, t, J=6.5 Hz), 2.72 (2H, m), 2.36 (3H, s).

Example 15(93)

N-(2-methoxyethylthio)carbonyl-3-amino-4-oxo-5-(5-(2,6-dichlorophenylthio)tetrazol-2-yl)pentanoic acid

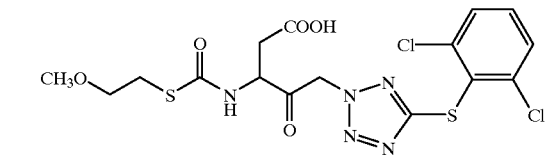

TLC: Rf 0.53 (chloroform:methanol:water=40:10:1); NMR (DMSO-$d_6$): δ 12.50 (1H, brs), 8.89 (1H, d, J=7.0 Hz), 7.70–7.66 (2H, m), 7.55 (1H, dd, J=9.2 Hz, 6.6 Hz), 6.00 (1H, d, J=18.0 Hz), 5.89 (1H, d, J=18.0 Hz), 4.79 (1H, m), 3.45 (2H, t, J=6.6 Hz), 3.24 (3H, s), 2.98 (2H, t, J=6.6 Hz), 2.82 (1H, dd, J=17.2 Hz, 5.6 Hz), 2.64 (1H, dd, J=17.2 Hz, 7.0 Hz).

Example 15(94)

N-(2-methoxyethylthio)carbonyl-3-amino-4-oxo-5-(5-(2,6-dichlorophenylthio)tetrazol-1-yl)pentanoic acid

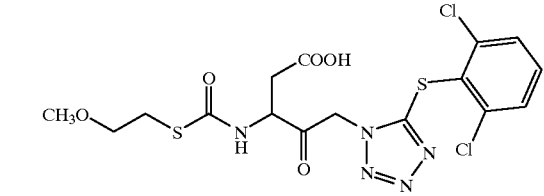

TLC: Rf 0.34 (chloroform:methanol:water=40:10:1); NMR (DMSO-$d_6$): δ 8.88 (1H, d, J=6.2 Hz), 7.70–7.51 (3H, m), 5.80 (2H, s), 4.79 (1H, m), 3.43 (2H, t, J=6.8 Hz), 3.20 (3H, s), 3.00 (2H, t, J=6.8 Hz), 2.70 (2H, d, J=5.8 Hz).

Example 15(95)

N-(2-(2-methoxyethyloxy)ethyloxy)carbonyl-3-amino-4-oxo-5-(5-(2,6-dichlorophenylthio)tetrazol-2-yl)pentanoic acid

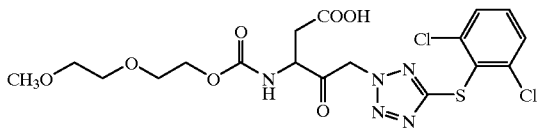

TLC: Rf 0.40 (chloroform:methanol:water=40:10:1); NMR (DMSO-d$_6$): δ 7.85 (1H, m), 7.71–7.67 (2H, m), 7.60–7.52 (1H, m), 5.94 (2H, s), 4.55 (1H, m), 4.12 (2H, m), 3.58 (2H, m), 3.50 (2H, m), 3.43 (2H, m), 3.22 (3H, s), 2.82–2.55 (2H, m).

Example 15(96)

N-(2-(2-methoxyethyloxy)ethyloxy)carbonyl-3-amino-4-oxo-5-(5-(2,6-dichlorophenylthio)tetrazol-1-yl)pentanoic acid

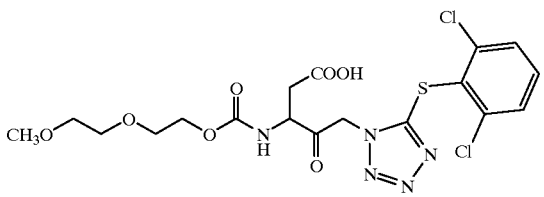

TLC: Rf 0.31 (chloroform:methanol:water=40:10:1); NMR (DMSO-d$_6$): δ 7.76–7.55 (4H, m), 5.81 (2H, s), 4.55 (1H, m), 4.13 (2H, m), 3.59 (2H, m), 3.56 (2H, m), 3.40 (2H, m), 3.21 (3H, s), 2.66 (2H, m).

Example 15(97)

N-(2-phenylethylthio)carbonyl-3-amino-4-oxo-5-(5-(2-chlorophenylthio)tetrazol-2-yl)pentanoic acid

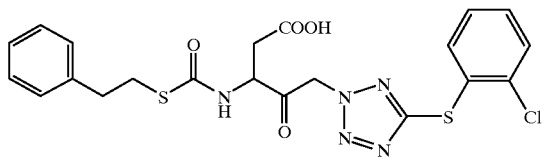

TLC: Rf 0.49 (chloroform:methanol:water=40:10:1); NMR (DMSO-d$_6$): δ 12.58 (1H, m), 8.91 (1H, d, J=7.0 Hz), 7.63–7.59 (1H, m), 7.43–7.17 (8H, m), 6.05 (1H, d, J=8.0 Hz),5.94 (1H, d, J=18.0 Hz), 4.83 (1H, m), 3.10 (2H, m),2.89–2.79 (3H, m), 2.67 (1H, dd, J=17.0 Hz, 7.0 Hz).

Example 15(98)

N-(2-phenylethylthio)carbonyl-3-amino-4-oxo-5-(5-(2-chlorophenylthio)tetrazol-1-yl)pentanoic acid

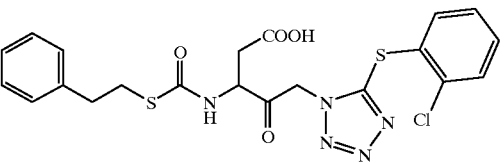

TLC: Rf 0.40 (chloroform:methanol:water=40:10:1); NMR (DMSO-d$_6$): δ 8.81 (1H, m), 7.58 (1H, d, J=7.0 Hz), 7.53–7.37 (3H, m), 7.24–7.20 (5H, m), 5.80 (2H, s), 4.76 (1H, m), 3.05 (2H, m), 2.81 (2H, m), 2.62 (2H, m).

Example 15(99)

N-(2-acetylaminoethylthio)carbonyl-3-amino-4-oxo-5-(5-(2,6-dichlorophenylthio)tetrazol-2-yl)pentanoic acid

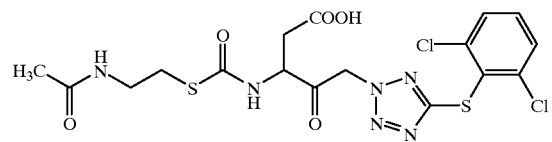

TLC: Rf 0.41 (chloroform:methanol:acetic acid=8:1:1); NMR (DMSO-d$_6$): δ 8.67 (1H, d, J=6.4 Hz), 8.06 (1H, d, J=5.8 Hz), 7.74–7.50 (3H, m), 5.98 (2H, brs), 4.80–4.55 (1H, m), 3.18 (2H, dt, J=6.4, 5.8 Hz), 2.86 (2H, t, J=5.8 Hz), 2.65–2.50 (2H, m), 1.78 (3H, s).

Example 15(100)

N-(2-acetylaminoethylthio)carbonyl-3-amino-4-oxo-5-(5-(2,6-dichlorophenylthio)tetrazol-1-yl)pentanoic acid

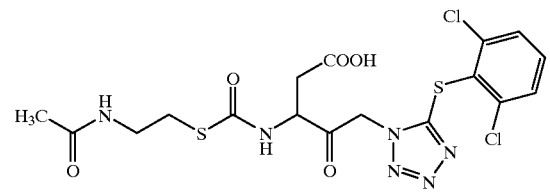

TLC: Rf 0.33 (chloroform:methanol:acetic acid=8:1:1); NMR (DMSO-d$_6$): δ 8.90–8.73 (1H, m), 8.10–8.00 (1H, m), 7.75–7.48 (3H, m), 5.84 (2H, brs), 4.80–4.60 (1H, m), 3.24–3.10 (2H, m), 3.00–2.75 (2H, m), 2.65–2.50 (2H, m), 1.77 (3H, s).

Example 15(101)

N-(2-acetylaminoethyloxy)carbonyl-3-amino-4-oxo-5-(5-(2,6-dichlorophenylthio)tetrazol-2-yl)pentanoic acid

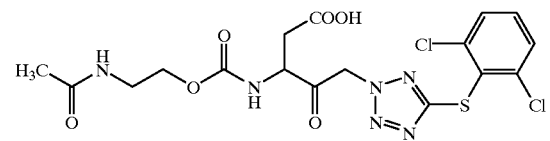

TLC: Rf 0.49 (chloroform:methanol:water=6:4:1); NMR (DMSO-d$_6$): δ 12.40 (1H, m), 7.96 (1H, m), 7.78–7.50 (4H, m), 5.96 (2H, m), 4.57 (1H, m), 4.00 (2H, m), 3.26 (2H, m), 2.70 (2H, m), 1.80 (3H, s).

Example 15(102)

N-(2-acetylaminoethyloxy)carbonyl-3-amino-4-oxo-5-(5-(2,6-dichlorophenylthio)tetrazol-1-yl)pentanoic acid

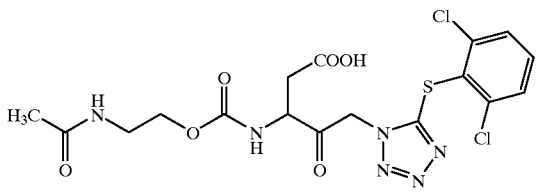

TLC: Rf 0.45 (chloroform:methanol:water=6:4:1); NMR (DMSO-d$_6$): δ 8.00 (1H, m), 7.70–7.52 (4H, m), 5.81 (2H, m), 4.57 (1H, m), 4.03 (2H, m), 3.29 (2H, m), 2.70 (2H, m), 1.81 (3H, s).

Example 15(103)
N-(2-(2-methoxyethyloxy)ethylthio)carbonyl-3-amino-4-oxo-5-(5-(2,6-dichlorophenylthio)tetrazol-2-yl)pentanoic acid

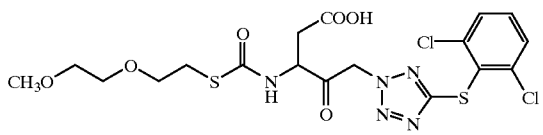

TLC: Rf 0.41 (chloroform:methanol:water=40:10:1); NMR (CDCl$_3$): δ 7.60–7.20 (4H, m), 6.20–5.40 (2H, m), 5.00–4.60 (1H, m), 3.80–3.40 (6H, m), 3.29 (3H, s), 3.20–3.00 (2H, m), 2.60–2.20 (2H, m).

Example 15(104)
N-(2-(2-methoxyethyloxy)ethylthio)carbonyl-3-amino-4-oxo-5-(5-(2,6-dichlorophenylthio)tetrazol-1-yl)pentanoic acid

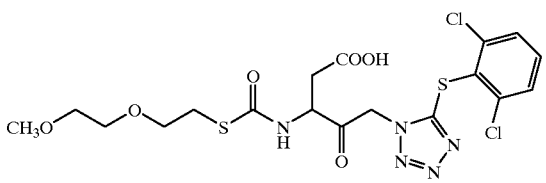

TLC: Rf 0.34 (chloroform:methanol:water=40:10:1); NMR (CDCl$_3$): δ 8.00–7.50 (1H, m), 7.50–7.20 (3H, m), 6.20–5.20 (2H, m), 5.00–4.60 (1H, m), 3.80–3.40 (6H, m), 3.32 (3H, s), 3.20–3.00 (2H, m), 2.80 (2H, brs).

Example 15(105)
N-(2-phenylethylthio)carbonyl-3-amino-4-oxo-5-(5-(phenylthio) tetrazol-2-yl)pentanoic acid

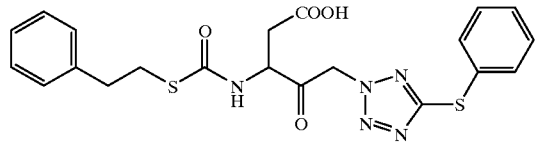

TLC: Rf 0.61 (chloroform:methanol:water=40:10:1); NMR (Acetone-$_{d6}$): δ 7.56–7.51 (2H, m), 7.42–7.38 (3H, m), 7.27 (5H, s), 7.18 (1H, m), 6.05–5.83 (2H, m), 5.01 (1H, m), 3.18 (2H, m), 2.96–2.89 (4H, m).

Example 15(106)
N-(2-phenylethylthio)carbonyl-3-amino-4-oxo-5-(5-(phenylthio) tetrazol-1-yl)pentanoic acid

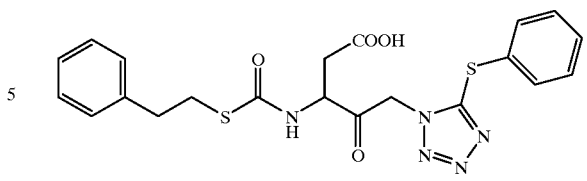

TLC: Rf 0.45 (chloroform:methanol:water=40:10:1); NMR (Acetone-$_{d6}$): δ 7.60–7.55 (2H, m), 7.42–7.39 (3H, m), 7.25 (5H, s), 7.17 (1H, m), 5.89–5.63 (2H, m), 5.02 (1H, m), 3.20 (2H, m), 2.96–2.88 (4H, m).

EXAMPLES 16(1)–16(4)

By the same procedure as provided in example 1, using the corresponding tetrazole compounds and the corresponding bromo compounds instead of N-((N-(3-phenylpropionyl)-L-valyl)-L-alanyl)-3-amino-4-oxo-5-bromopentanoic acid•t-butylester, compounds of the present invention having the following physical data were obtained.

Example 16(1)
N-(2-(4-methoxymethyloxyphenyl)ethyloxy)carbonyl-3-amino-4-oxo-5-(5-(2,6-dichlorophenylthio)tetrazol-2-yl) pentanoic acid•t-butylester

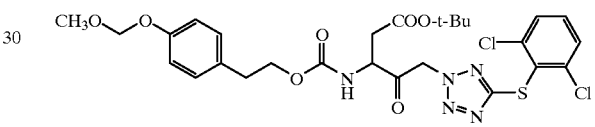

TLC: Rf 0.60 (hexane:ethyl acetate=1:1); NMR (CDCl$_3$): δ 7.44 (2H, d, J=7.4 Hz), 7.29 (1H, m), 7.14 (2H, d, J=8.4 Hz), 6.96 (2H, d, J=8.4 Hz), 5.83 (1H, m), 5.70 (1H, d, J=17.4 Hz), 5.51 (1H, d, J=17.4 Hz), 5.12 (2H, s), 4.59 (1H, m), 4.35 (2H, m), 3.45 (3H, s), 3.02–2 (3H, m), 2.66 (1H, dd, J=1 7 Hz, 5.0 Hz), 1.42 (9H, s).

Example 16(2)
N-(2-(4-methoxymethyloxyphenyl)ethyloxy)carbonyl-3-amino-4-oxo-5-(5-(2,6-dichlorophenylthio)tetrazol-1-yl) pentanoic acid•t-butylester

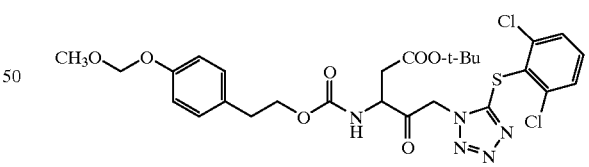

TLC: Rf 0.52 (hexane:ethyl acetate=1:1); NMR (CDCl$_3$): δ 7.45 (2H, d, J=7.4 Hz), 7.31 (1H, m), 7.16 (2H, d, J=8.6 Hz), 6.98 (2H, d, J=8.6 Hz), 5.91 (1H, m), 5.65 (1H, d, J=18.2 Hz), 5.46 d, J=18.2 Hz), 5.13 (2H, s), 4.64 (1H, m), 4.39 (2H, m), 3.46 (3H, s), 3.06 (1H, dd, J=17 Hz, 4 Hz), 2.94 (2H, t, J=6.8 Hz), 2.73 (1H, dd, J=17 Hz, 5 Hz), 1.44 (9H, s).

Example 16(3)
N-(2-(4-methoxymethyloxyphenyl)ethylthio)carbonyl-3-amino-4-oxo-5-(5-(2,6-dichlorophenylthio)tetrazol-2-yl) pentanoic acid•t-butylester

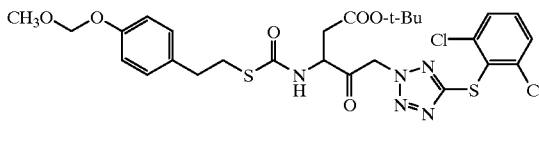

TLC: Rf 0.55 (hexane:ethyl acetate=11); NMR (CDCl$_3$): δ 7.47–7.26 (3H, m), 7.07 (2H, d, J=8.6 Hz), 6.73 (2H, d, J=8.6 Hz), 6.60 (1H, d, J=8.6 Hz), 5.66 (1H, d, J=17.8 Hz), 5.47 (1H, d, J=17.8 Hz), 4.82 (1H, m), 3.19 (2H, m), 3.02–2.80 (3H, m), 2.66 (1H, dd, J=18 Hz, 4.8 Hz), 1.42 (9H, s).

Example 16(4)

N-(2-(4-meythoxymethyoxyphenyl)ethythio)carbonyl-3-amino-4-oxo-5-(5-(2,6-dichlorophenylthio)tetrazol-1-yl)pentanoic acid•t-butylester

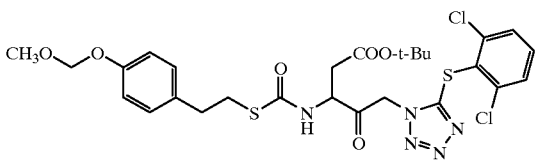

TLC: Rf 0.43 (hexane:ethyl acetate=1:1); NMR (CDCl$_3$): δ 7.47–7.31 (3H, m), 7.08 (2H, d, J=8.6 Hz), 6.76 (2H, d, J=8.6 Hz), 6.66 (1H, d, J=8.8 Hz), 5.99 (1H, d, J=18 Hz), 5.81 (1H, d, J=18 Hz), 4.88 (1H, m), 3.23 (2H, m), 3.05 (1H, dd, J=17 Hz, 4.4 Hz), 2.89 (2H, m), 2.71 (1H, dd, J=17 Hz, 4.8 Hz), 1.45 (9H, s).

EXAMPLES 17(1)–17(4)

By the same procedure as provided in example 6(1), using the compound prepared in examples 16(1)–16(4), compounds of the present invention having the following physical data were obtained.

Example 17(1)

N-(2-(4-hydroxyphenyl)ethyloxy)carbonyl-3-amino-4-oxo-5-(5-(2,6-dichlorophenylthio)tetrazol-2-yl)pentanoic acid

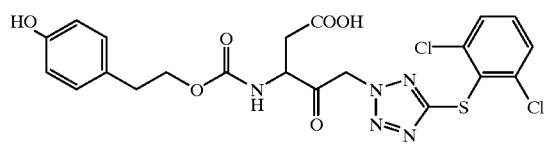

TLC: Rf 0.37 (chloroform:methanol:water=40:10:1); NMR (DMSO-d$_6$): δ 9.26 (1H, brs), 7.70–7.44 (4H, m), 7.03 (2H, d, J=8.2 Hz), 6.67 (2H, d, J=8.2 Hz), 5.94 (2H, m), 4.51 (1H, m), 4.13 (2H, t, J=6.8 Hz), 2.76 (2H, t, J=6.8 Hz), 2.59 (2H, m).

Example 17(2)

N-(2-(4-hydroxyphenyl)ethyloxy)carbonyl-3-amino-4-oxo-5-(5-(2,6-dichlorophenylthio)tetrazol-1-yl)pentanoic acid

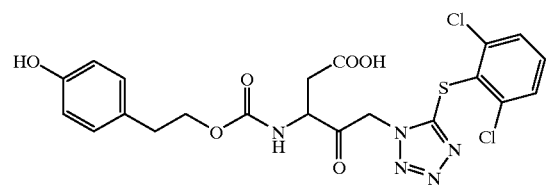

TLC: Rf 0.31 (chloroform:methanol:water=40:10:1); NMR (DMSO-d$_6$): δ 9.28 (1H, brs), 7.70–7.55 (4H, m), 7.02 (2H, d, J=8.4 Hz), 6.60 (2H, d, J=8.4 Hz), 5.80 (2H, m), 4.54 (1H, m), 4.17 (2H, m), 2.77 (2H, m), (2H, m), 2.64 (2H, m).

Example 17(3)

N-(2-(4-hydroxyphenyl)ethylthio)carbonyl-3-amino-4-oxo-5-(5-(2,6-dichlorophenylthio)tetrazol-2-yl)pentanoic acid

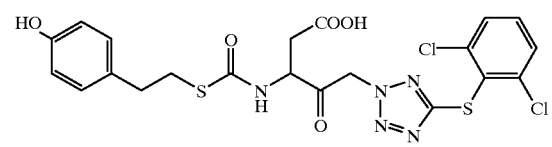

TLC: Rf 0.30 (chloroform:methanol:water=40:10:1); NMR (DMSO-d$_6$): δ 9.27 (1H, brs), 8.54 (1H, m), 7.69–7.49 (3H, m), 7.00 (2H, d, J=8.4 Hz), 6.67 (2H, d, J=8.4 Hz), 5.96 (2H, m), 4.75 (1H, m), 3.00 (2H, m), 2.71 (2H, m), 2.59 (2H, m).

Example 17(4)

N-(2-(4-hydroxyphenyl)ethylthio)carbonyl-3-amino-4-oxo-5-(5-(2,6-dichlorophenylthio)tetrazol-1-yl)pentanoic acid

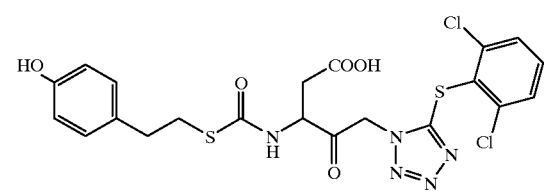

TLC: Rf 0.24 (chloroform:methanol:water=40:10:1); NMR (DMSO-d$_6$): δ 9.24 (1H, brs), 8.73 (1H, d, J=7 Hz), 7.68–7.51 (3H, m), 6.95 (2H, d, J=8.2 Hz), 6.62 (2H, d, J=8.2 Hz), 5.85 (2H, m), 4.77 (1H, m), 2.98 (2H, m), 2.70–2.61 (4H, m).

Reference Example 9(1)

3-amino-4-oxo-5-(5-(2,6-dichlorophenylmethyl)tetrazol-1-yl)pentanoic acid•t-butylester•hydrochloric acid salt

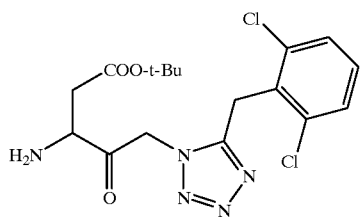

The mixture of the compound prepared in example 5(1) (8.74 g), ethanol (600 ml), 10% palladium on activated carbon (773 mg) and a 6N aqueous solution of hydrochloric acid (5.37 ml) was stirred for 20 min at room temperature under an atmosphere of hydrogen gas. The reaction mixture was filtered through Celite (trade mark) and the filtrate was concentrated to give the title compound having the following physical data.

TLC: Rf 0.36 (chloroform:methanol=19:1); NMR (DMSO-$d_6$): δ 9.10–8.40 (3H, br), 7.55 (1H, d, J=9.0 Hz), 7.55 (1H, d, J=7.2 Hz), 7.40 (1H, dd, J=9.0 Hz, 7.2 Hz), 6.11 (2H, br), 4.75–4.55 (1H, m), 4.41 (2H, s), 3.50–3.05 (2H, m), 1.44 (9H, s).

Reference Example 9(2) and Reference Example 9(3)

By the same procedure as provided in reference example 9(1), using the compound prepared in example 5(2) or example 5(3), the title compounds having the following physical data were obtained.

Reference Example 9(2)

3-amino-4-oxo-5-(5-(2,6-dichlorophenylmethyl)tetrazol-2-yl)pentanoic acid•t-butylester•hydrochloric acid salt

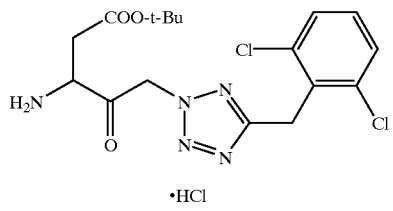

TLC: Rf 0.32 (chloroform:methanol=19:1); NMR (DMSO-$d_6$): δ 8.60–8.35 (3H, br), 7.52 (2H, each d, J=9.0, 6.8 Hz), 7.37 (1H, dd, J=9.0, 6.8 Hz), 6.14 and 6.03 (each 1H, d, J=17.5 Hz), 4.60–4.46 (1H, m), 4.54 (2H, s), 3.28–2.99 (2H, m), 1.41 (9H, s).

Reference Example 9(3)

3-amino-4-oxo-5-(5-phenylmethyltetrazol-1-yl)pentanoic acid•t-butylester•hydrochloric acid salt

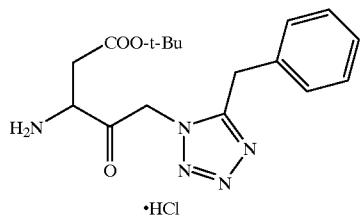

TLC: Rf 0.54 (chloroform:methanol=9:1); NMR (DMSO-$d_6$): δ 8.66 (2H, brs), 7.31 (5H, s), 5.96 (2H, s), 4.63 (1H, brs), 4.20 (2H, s), 3.17 (2H, m), 1.44 (9H, s).

Example 18(1)

3-(N-(2-(hexahydro-2-oxo-3S-(thiazol-4-ylcarbonylamino) azepin-1-yl)) propionyl)amino-4-oxo-5-(5-(2,6-dichlorophenylmethyl)tetrazol-1-yl)pentanoic acid•t-butylester

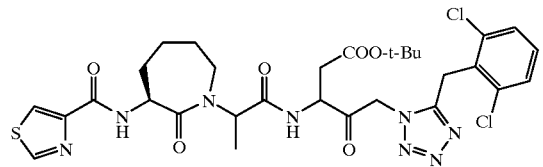

To a solution of 2-(hexahydro-2-oxo-3S-(thiazol-4-ylcarbonylamino)azepin-1-yl)propionic acid (414 mg) in dichloromethane (4 ml) and dimethylformamide (1 ml) was added 1-hydroxybenzotriazole (306 mg) and 1-ethyl-3-(3-dimethylaminopropyl)carbodiimide (383 mg) at 0° C. The mixture was stirred for 15 min at room temperature. To the mixture was added the compound prepared in reference example 9 (1) (600 mg) in dimethylformamide (3 ml) and triethylamine (0.204 ml) at 0° C. The reaction mixture was stirred for 1 h at room temperature. The reaction mixture was quenched by addition of water, and extracted with ethyl acetate. The extract was washed with a saturated aqueous solution of sodium chloride, dried over anhydrous magnesium sulfate and concentrated. The residue was purified by column chromatography on silica gel (chloroform:methanol=100:1→29:1) to give the compound of the present invention (682 mg) having the following physical data.

TLC: Rf 0.55 (chloroform:methanol=9:1); NMR (DMSO-$d_6$): δ 9.17 (1H, m), 8.94–8.51 (2H, m), 8.30 (1H, m), 7.52–7.25 (3H, m), 5.82 (2H, m), 5.27–4.68 (3H, m), 4.34 (2H, m), 3.65–3.42 (2H, m), 2.91–2.56 (2H, m), 2.08–1.52 (6H, m), 1.39 (9H, s), 1.33 (3H, m).

EXAMPLES 18(2)–18(28)

By the same procedure as provided in example 18(1), using the corresponding carboxylic acid compounds and the compound prepared in reference example 9(1), reference example 9(2) or reference example 9(3), the compounds of the present invention having the following physical data were obtained.

Example 18(2)

3-(N-(2-(hexahydro-2-oxo-3S-(thiazol-4-ylcarbonylamino) azepin-1-yl)) propionyl)amino-4-oxo-5-(5-phenylmethyltetrazol-1-yl)pentanoic acid•t-butylester

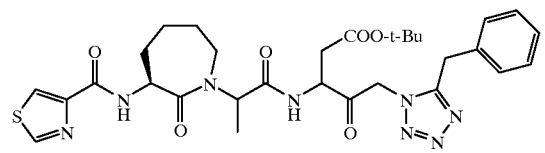

TLC: Rf 0.65 (chloroform:methanol=9:1); NMR (CDCl$_3$): δ 9.19–9.08 (1H, m), 8.85–8.50 (2H, m), 8.35–8.29 (1H, m), 7.27 (5H, m), 5.67 (2H, m), 5.26–4.69 (3H, m), 4.13 (2H, m), 3.58–3.20 (2H, m), 2.86–2.56 (2H, m), 2.07–1.43 (6H, m), 1.38–1.29 (12H, m).

Example 18(3)

3-(N-(2-(hexahydro-2-oxo-3S-(pyridin-3-ylcarbonylamino) azepin-1-yl))propionyl)amino-4-oxo-5-(5-phenylmethyltetrazol-1-yl)pentanoic acid•t-butylester

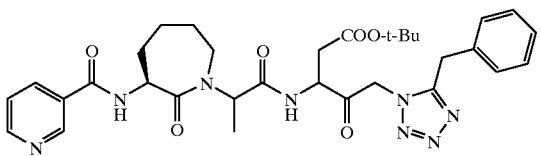

TLC: Rf 0.34 (chloroform:methanol=19:1); NMR (DMSO-d$_6$): δ 8.92 (1H, m), 8.64 (1H, m), 8.51 (2H, m), 8.08 (1H, m), 7.42 (1H, m), 7.21 (5H, s), 5.59 (2H, s), 5.13–4.57 (3H, m), 4.05 (2H, m), 3.40 (2H, m), 2.71–2.50 (2H, m), 1.82 (6H, m), 1.33 (9H, s), 1.28 (3H, m).

Example 18(4)

3-(N-(2-(hexahydro-2-oxo-3S-(quinolin-2-ylcarbonylamino)azepin-1-yl))propionyl)amino-4-oxo-5-(5-phenylmethyltetrazol-1-yl)pentanoic acid•t-butylester

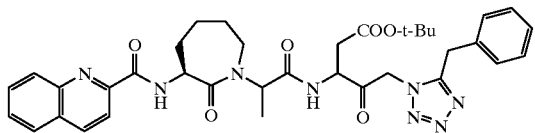

TLC: Rf 0.69 (chloroform:methanol=19:1); NMR (DMSO-d$_6$): δ 9.30 (1H, m), 8.86–8.54 (2H, m), 8.19–8.05 (2H, m), 7.99–7.68 (3H, m), 7.24 (5H, m), 5.70 (2H, m), 5.28–4.66 (2H, m), 4.14 (2H, m), 3.62–3.23 (2H, m), 2.82–2.38 (2H, m), 2.21–1.48 (6H, m), 1.37 (12H, m).

Example 18(5)

3-(N-(2-(hexahydro-2-oxo-3S-(pyridin-2-ylcarbonylamino)azepin-1-yl))propionyl)amino-4-oxo-5-(5-phenylmethyltetrazol-1-yl)pentanoic acid•t-butylester

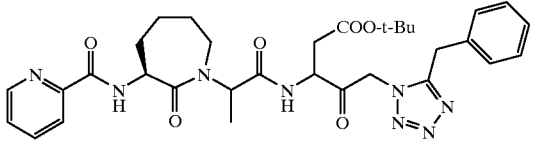

TLC: Rf 0.61 (chloroform:methanol=19:1); NMR (DMSO-d$_6$): δ 9.11 (1H, m), 8.86–8.51 (2H, m), 8.04 (2H, m), 7.62 (1H, m), 7.27 (5H, m), 5.67 (2H, m), 5.24–4.65 (2H, m), 4.11 (2H, m), 3.52 (1H, m), 3.24 (1H, m), 2.80 (1H, m), 2.56 (1H, m), 2.06–1.45 (6H, m), 1.38 (9H, s), 1.34 (3H, s).

EXAMPLES 18(6) AND 18(7)

3-(N-(2-(hexahydro-2-oxo-3S-(morpholin-1-ylcarbonylamino)azepin-1-yl))propionyl)amino-4-oxo-5-(5-phenylmethyltetrazol-1-yl)pentanoic acid•t-butylester

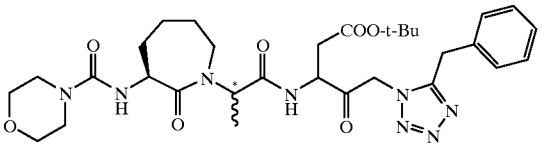

(wherein represents mixture of R and S stereochemistry. The compounds were separated to the compound of example 19(6) and example 19(7) by hydrolysis of t-butylester)

NMR (DMSO-d$_6$): δ 8.63–8.39 (1H, m), 7.25 (5H, m), 6.35 (1H, t-like), 5.58 (2H, m), 5.11–4.28 (2H, m), 4.08 (2H, s), 3.45 (6H, m), 3.15 (2H, m), 2.76 (1H, m), 2.50 (1H, m), 1.75–1.40 (6H, m), 1.34 (9H, s), 1.26 (3H, m).

Example 18(8)

3-(N-(2-(hexahydro-2-oxo-3S-(pyridin-4-ylcarbonylamino)azepin-1-yl))propionyl)amino-4-oxo-5-(5-phenylmethyltetrazol-1-yl)pentanoic acid•t-butylester

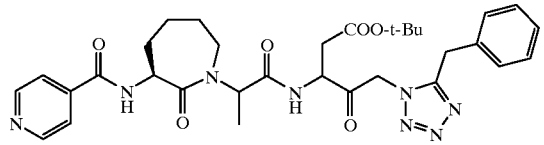

TLC: Rf 0.57 (chloroform:methanol=9:1); NMR (DMSO-d$_6$): δ 8.66 (4H, m), 7.72 (2H, m), 7.27 (5H, m), 5.65 (2H, m), 5.18–4.63 (2H, m), 3.60–3.34 (2H, m), 2.80 (1H, m), 2.54 (2H, m), 1.93–1.58 (6H, m), 1.39 (9H, m), 1.33 (3H, m).

Example 18(9)

3-(N-(2-(hexahydro-2-oxo-3S-(4-methoxyphenylcarbonylamino)azepin-1-yl))propionyl)amino-4-oxo-5-(5-phenylmethyltetrazol-1-yl)pentanoic acid•t-butylester

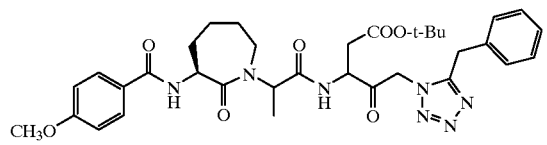

NMR (DMSO-d$_6$): δ 8.55 (1H, d, J=6.5 Hz), 8.02 (1H, d, J=6.5 Hz), 7.80 (2H, dd, J=8.0, 2.0 Hz), 7.40–7.18 (5H, m), 6.98 (2H, d, J=8.0 Hz), 5.66 (2H, s), 5.10 (1H, q, J=6.0 Hz), 4.90–4.60 (2H, m), 4.20–4.10 (2H, m), 3.80 (3H, s), 2.88–2.50 (4H, m), 2.35–1.20 (9H, m), 1.14 (9H, s).

Example 18(10)

3-(N-(2-(hexahydro-2-oxo-3S-(3-methoxyphenylcarbonylamino)azepin-1-yl))propionyl)amino-4-oxo-5-(5-phenylmethyltetrazol-1-yl)pentanoic acid•t-butylester

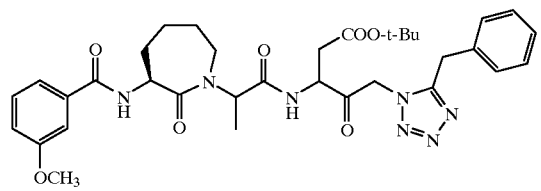

NMR (DMSO-d$_6$): δ 8.58 (1H, d, J=7.0 Hz), 8.20 (1H, d, J=7.0 Hz), 7.40–7.40 (8H, m), 7.15–7.00 (1H, m), 5.65 (2H, s), 5.34–5.05 (1H, q, J=6.5 Hz), 4.92–4.65 (2H, m), 4.12 (2H, s), 3.80 (3H, s), 2.95–2.50 (4H, m), 2.05–1.20 (9H, m), 1.15 (9H, s).

Example 18(11)

3-(N-(2-(hexahydro-2-oxo-3S-(4-(morpholin-1-ylcarbonyl)phenylcarbonylamino)azepin-1-yl))propionyl)amino-4-oxo-5-(5-phenylmethyltetrazol-1-yl)pentanoic acid•t-butylester

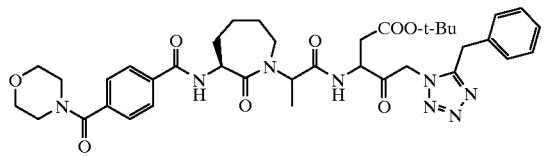

NMR (DMSO-d$_6$): δ 8.60–8.58 (2H, m), 7.92 (2H, t, J=8.0 Hz), 7.52–7.40 (2H, m), 7.32–7.15 (5H, m), 5.82–5.58 (2H, m), 5.20–5.10 (1H, m), 5.00–4.80 (1H, m), 4.70–4.50 (1H, m), 4.15 (2H, brs), 3.80–3.20 (8H, m), 2.78–2.42 (4H, m), 2.00–1.50 (7H, m), 1.45–1.20 (3H, m), 1.20 (9H, s).

EXAMPLES 18(12) AND (13)

3-(N-(2-(hexahydro-2-oxo-3S-(quinolin-3-ylcarbonylamino)azepin-1-yl))propionyl)amino-4-oxo-5-(5-phenylmethyltetrazol-1-yl)pentanoic acid•t-butylester

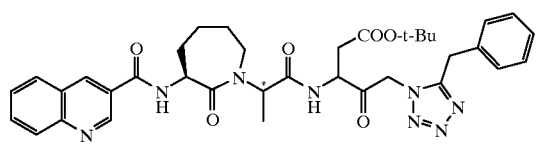

(wherein * represents mixture of R and S stereochemistry. The compounds were separated to the compound of example 19(12) and example 19(13) by hydrolysis of t-butylester)

TLC: Rf 0.71 (chloroform:methanol=9:1); NMR (DMSO-d$_6$): δ 9.37–9.24 (2H, m), 8.88–8.51 (2H, m), 8.23 (2H, m), 7.96–7.81 (2H, m), 7.26 (5H, m), 5.68 (2H, m), 5.30–4.67 (2H, m), 4.14 (2H, m), 3.56 (1H, m), 3.29 (1H, m), 2.81 (1H, m), 2.58 (1H, m), 2.13–1.49 (6H, m), 1.38 (12H, s).

Example 18(14)

3-(N-(2-(hexahydro-2-oxo-3S-(pyridin-3-ylcarbonylamino)azepin-1-yl))propionyl)amino-4-oxo-5-(5-(2,6-dichlorophenylmethyl)tetrazol-1-yl) pentanoic acid•t-butylester

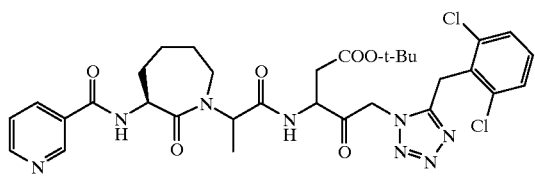

TLC: Rf 0.46 (chloroform:methanol=9:1); NMR (DMSO-d$_6$): δ 8.99 (1H, m), 8.81–8.53 (3H, m), 8.14 (1H, m), 7.48 (4H, m), 5.79 (2H, m), 5.22–4.69 (3H, m), 4.35 (2H, m), 3.63–3.40 (2H, m), 2.86 (1H, m), 2.56 (1H, m), 1.95–1.48 (6H, m), 1.39 (9H, s), 1.33 (3H, m).

Example 18(15)

3-(N-(2-(hexahydro-2-oxo-3S-(4-dimethylaminophenylcarbonylamino)azepin-1-yl))propionyl)amino-4-oxo-5-(5-phenylmethyltetrazol-1-yl)pentanoic acid•t-butylester

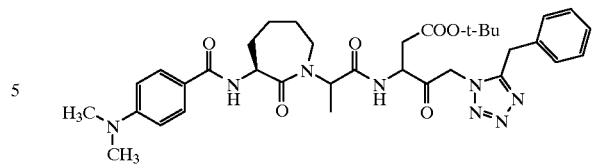

NMR (CDCl$_3$): δ 8.75 (1H, m), 7.90–7.50 (4H, m), 7.40–7.10 (8H, m), 6.70 (2H, d, J=10 Hz), 6.54 (1H, d, J=8.5 Hz), 5.60 (2H, m), 5.25–5.10 (1H, m), 4.90–4.60 (5H, m), 3.20–2.50 (3H, m), 2.65 (6H, s), 2.15–1.60 (8H, m), 1.45 (3H, d, J=7.5 Hz), 1.15 (9H, s).

Example 18(16)

3-(N-(2S-(2-phenyl-4R-methyl-4,5-dihydrothiazol-4-ylcarbonylamino) propionyl)amino-4-oxo-5-(5-(2,6-dichlorophenylmethyl)tetrazol-1-yl)pentanoic acid•t-butylester

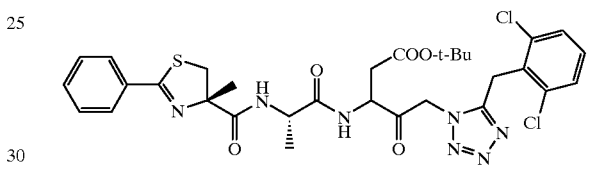

TLC: Rf 0.58 and 0.60 (hexane:ethyl acetate=1:3); NMR (CDCl$_3$): δ 7.90–7.75 (1H, m), 7.60–7.10 (7H, m), 6.90–5.35 (2H, m), 4.90–4.70 (1H, m), 4.60–4.30 (2H, m), 3.90–3.70 (2H, m), 3.40–3.30 (1H, m), 3.10–2.90 (1H, m), 2.80–2.50 (1H, m), 1.60 (9H, s), 1.60–1.35 (6H, m).

Example 18(17)

3-(N-(2S-(2-phenyl-4,5-dihydrothiazol-4-ylcarbonylamino) propionyl) amino-4-oxo-5-(5-(2,6-dichlorophenylmethyl) tetrazol-1-yl)pentanoic acid•t-butylester

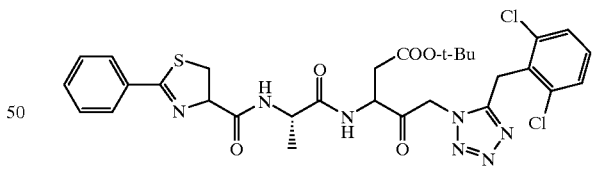

TLC: Rf 0.62 (chloroform:methanol=9:1); NMR (CDCl$_3$): δ 7.90–7.70 (1H, m), 7.60–6.90 (7H, m), 5.90–5.75 (1H, m), 5.65–5.40 (1H, m), 5.30–5.10 (1H, m), 4.95–4.70 (1H, m), 4.65–4.10 (2H, m), 4.00–3.55 (2H, m), 3.40–3.15 (1H, m), 3.15–2.95 (1H, m), 2.85–2.65 (1H, m), 1.60–1.05 (12H, m).

Example 18(18)

N-(thiazol-4-ylcarbonyl)-3-amino-4-oxo-5-(5-(2,6-dichlorophenylmethyl)tetrazol-2-yl)pentanoic acid•t-butylester

413

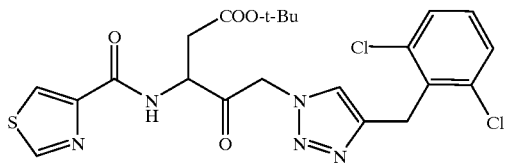

TLC: Rf 0.37 (hexane:ethyl acetate=1:1); NMR (CDCl$_3$): δ 8.81 (1H, d, J=2.0 Hz), 8.26 (1H, d, J=2.0 Hz), 7.33 (1H, d, J=8.6 Hz), 7.33 (1H, d, J=7.4 Hz), 7.16 (1H, dd, J=8.6 Hz, 7.4 Hz), 5.85 and 5.63 (each 1H, d, J=18.0 Hz), 5.17–5.02 (1H, m), 4.59 (2H, s), 3.19 (1H, dd, J=17.5 Hz, 4.6 Hz), 2.76 (1H, dd, J=17.5 Hz, 5.0 Hz), 1.45 (9H, s).

Example 18(19)

N-phenylthiomethylcarbonyl-3-amino-4-oxo-5-(5-(2,6-dichlorophenylmethyl)tetrazol-2-yl)pentanoic acid•t-butylester

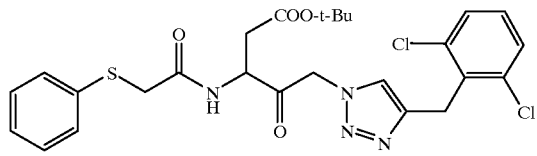

TLC: Rf 0.58 (hexane:ethyl acetate=1:1); NMR (CDCl$_3$): δ 7.94 (1H, d, J=9.0 Hz), 7.39–7.22 (8H, m), 5.16 (2H, s), 4.81 (1H, dt, J=9.0, 4.6 Hz), 4.58 (2H, s), 3.83 (1h, d, J=17.0 Hz), 3.68 (1h, d, J=17.0 Hz), 2.95 (1H, dd, J=17.5, 4.7 Hz), 2.46 (1H, dd, J=17.5, 4.7 Hz), 1.40 (9H, s).

Example 18(20)

N-(perhydrobenzo-1,4-diazepin-2,5-dion-3-ylcarbonyl)-3-amino-4-oxo-5-(5-(2,6-dichlorophenylmethyl)tetrazol-2-yl)pentanoic acid•t-butylester

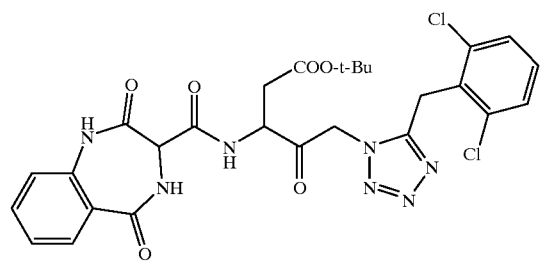

TLC: Rf 0.30 (chloroform:methanol=8:1); NMR (CDCl$_3$): δ 9.50–8.90 (1H, m), 8.50–8.10 (1H, m), 7.90–7.80 (1H, m), 7.60–7.10 (6H, m), 7.10–6.80 (1H, m), 5.80–5.30 (1H, m), 4.90–4.60 (1H, m), 4.50–4.00 (2H, m), 3.20–2.50 (2H, m), 1.50–1.20 (9H, m).

Example 18(21)

3-(N-(2-(hexahydro-2-oxo-3S-(3-t-butoxycarbonylphenylcarbonylamino)azepin-1-yl))propionyl)amino-4-oxo-5-(5-phenylmethyltetrazol-1-yl)pentanoic acid•t-butylester

414

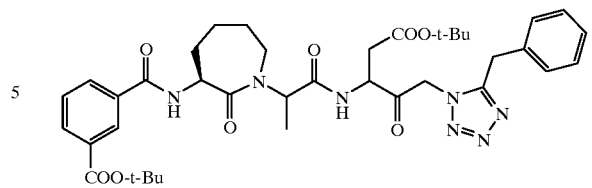

TLC: Rf 0.43 (chloroform:methanol=19:1); NMR (DMSO-d$_6$): δ 8.78–8.48 (2H, m), 8.34 (1H, m), 8.06 (2H, m), 7.58 (1H, m), 7.25 (5H, m), 5.65 (2H, s), 5.23–4.65 (3H, m), 4.12 (2H, m), 3.61–3.35 (2H, m), 2.80 (1H, m), 2.54 (1H, m), 1.94–1.61 (6H, m), 1.57 (9H, s), 1.38 (9H, s), 1.34 (3H, m).

Example 18(22)

3-(N-(2-(hexahydro-2-oxo-3S-(4-t-butoxycarbonylphenylcarbonylamino)azepin-1-yl))propionyl)amino-4-oxo-5-(5-phenylmethyltetrazol-1-yl)pentanoic acid•t-butylester

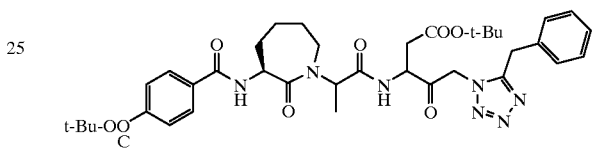

TLC: Rf 0.58 (chloroform:methanol=9:1); NMR (DMSO-d$_6$): δ 8.81–8.45 (2H, m), 7.93 (4H, m), 7.26 (5H, m), 5.66 (2H, m), 5.23–4.64 (3H, m), 4.13 (2H, m), 3.61–3.28 (2H, m), 2.81 (1H, m), 2.55 (1H, m), 1.97–1.47 (6H, m), 1.57 (9H, s), 1.38 (9H, s), 1.34 (3H, m).

Example 18(23)

N-(1-benzyloxycarbonylpiperidin-2S-ylcarbonyl)-3-amino-4-oxo-5-(5-(2,6-dichlorophenylmethyl)tetrazol-1-yl)pentanoic acid•t-butylester

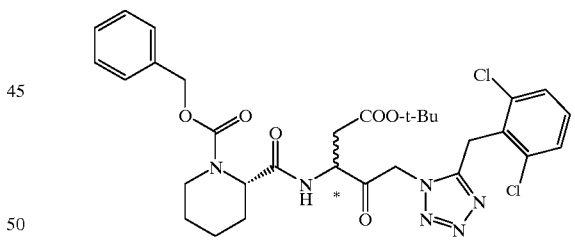

(wherein * represent R or S stereochemistry. The stereostructure has not been identified yet. However, the above compound has the opposite stereoconfiguration as the compound of example 18(24))

TLC: Rf 0.52 (hexane:ethyl acetate=1:1); NMR (DMSO-d$_6$): δ 8.80–8.65 (1H, m), 7.60–7.15 (8H, m), 5.90–5.67 (2H, m), 5.06 (2H, brs), 4.99–4.81 and 4.81–4.65 (each 1H, m), 4.51–4.15 (2H, m), 4.02–3.80 (1H, m), 3.45–2.95 (1H, m), 2.95–2.55 (2H, m), 2.20–2.00 (1H, m), 1.80–1.10 (5H, m), 1.39 (9H, s).

Example 18(24)

N-(1-benzyloxycarbonylpiperidin-2S-ylcarbonyl)-3-amino-4-oxo-5-(5-(2,6-dichlorophenylmethyl)tetrazol-1-yl)pentanoic acid•t-butylester

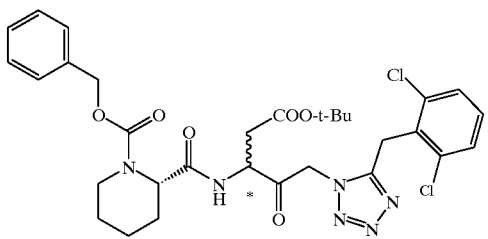

(wherein * represents R or S stereochemistry. The stereostructure has not been identified yet. However, the above compound has the opposite stereoconfiguration as the compound of example 18(23))

TLC: Rf 0.44 (hexane:ethyl acetate=1:1); NMR (DMSO-$d_6$): δ 9.00–8.75 (1H, m), 7.57–7.15 (8H, m), 5.98–5.50 (2H, m), 5.14–4.90 (2H, m), 4.90–4.65 (2H, m), 4.44–4.14 (2H, m), 4.05–3.98 (1H, m), 3.45–2.95 (1H, m), 2.95–2.45 (2H, m), 2.21–2.05 (1H, m), 1.80–1.10 (5H, m), 1.40 (9H, s).

Example 18(25)

N-(1-acetylpiperidin-2S-ylcarbonyl)-3-amino-4-oxo-5-(5-(2,6-dichlorophenylmethyl)tetrazol-1-yl)pentanoic acid•t-butylester

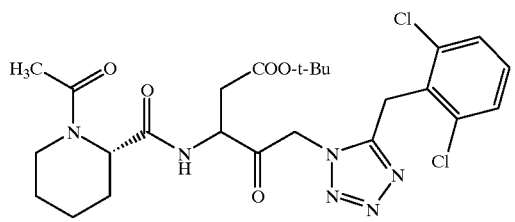

TLC: Rf 0.40 (chloroform:methanol=19:1); NMR (DMSO-$d_6$): δ 8.87–8.51 (1H, m), 7.58–7.20 (3H, m), 5.93–5.60 (2H, m), 5.11–4.47 (2H, m), 4.47–4.07 and 3.80–3.60 (3H, m), 3.40–3.13 (1H, m), 2.98–2.56 (2H, m), 2.22–1.90 (1H, m), 2:04 and 1.99 (total 3H, each s), 1.75–1.10 (5H, m), 1.40 (9H, s).

Example 18(26)

N-(1-benzyloxycarbonylpyrrolidin-2S-ylcarbonyl)-3-amino-4-oxo-5-(5-(2,6-dichlorophenylmethyl)tetrazol-1-yl) pentanoic acid•t-butylester

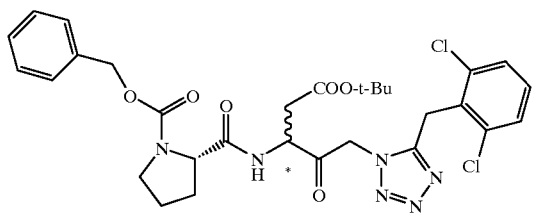

(wherein * represents R or S stereochemistry. The stereostructure has not been identified yet. However, the above compound has the opposite stereoconfiguration as the compound of example 18(27))

TLC: Rf 0.30 (hexane:ethyl acetate=1:1); NMR (CDCl$_3$): δ 7.76–7.55 (1H, br), 7.42–7.14 (8H, m), 5.90–5.33 (2H, m), 5.12 (2H, s), 4.96–4.62 (1H, m), 4.31 (3H, brs), 3.81–3.34 (2H, m), 3.17–2.50 (2H, m), 2.45–1.78 (4H, m), 1.44 (9H, s).

Example 18(27)

N-(1-benzyloxycarbonylpyrrolidin-2S-ylcarbonyl)-3-amino-4-oxo-5-(5-(2,6-dichlorophenylmethyl)tetrazol-1-yl) pentanoic acid•t-butylester

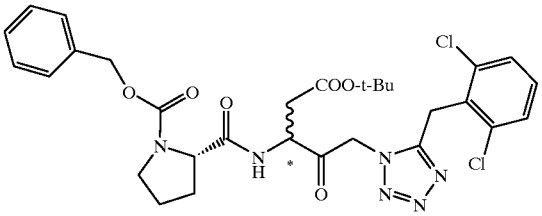

(wherein * represents R or S stereochemistry. The stereostructure has not been identified yet. However, the above compound has the opposite stereoconfiguration as the compound of example 18(26))

TLC: Rf 0.24 (hexane:ethyl acetate=1:1); NMR (CDCl$_3$): δ 7.86–7.64 (1H, m), 7.45–7.10 (8H, m), 5.95–5.35 (2H, m), 5.31–5.00 (2H, m), 4.95–4.60 (1H, m), 4.52–4.34 (1H, m), 4.27 (2H, s), 3.77–3.33 (2H, br), 3.15–2.50 (2H, m), 2.44–1.73 (4H, m), 1.43 (9H, s).

Example 18(28)

N-(1-acetylpyrrolidin-2S-ylcarbonyl)-3-amino-4-oxo-5-(5-(2,6-dichlorophenylmethyl)tetrazol-1-yl)pentanoic acid•t-butylester

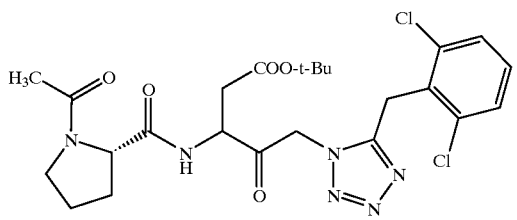

TLC: Rf 0.19 (ethyl acetate); NMR (CDCl$_3$): δ 9.05 and 8.86 (total 1H, each d, J=7.0 and 7.4 Hz), 7.64–7.30 (3H, m), 6.01–5.64 (2H, m), 4.99–4.54 (1H, m), 4.54–3.98 (1H, m), 4.34 and 4.26 (total 2H, each s), 3.80–3.23 (2H, m), 3.00–2.38 (2H, m), 2.34–1.57 (4H, m), 1.99 and 1.95 (total 3H, each s), 1.41 (9H, s).

EXAMPLES 19(1)–19(26)

By the same procedure as provided in example 6(1), using the compound prepared in examples 18(1)–18(20) or examples 18(23)–18(28), the compounds of the present invention having the following physical data were obtained.

Example 19(1)

3-(N-(2-(hexahydro-2-oxo-3S-(thiazol-4-ylcarbonylamino) azepin-1-yl)) propionyl)amino-4-oxo-5-(5-(2,6-dichlorophenylmethyl)tetrazol-1-yl)pentanoic acid

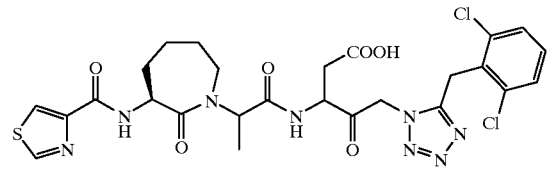

TLC: Rf 0.57 (chloroform:methanol:water=6:4:1); NMR (DMSO-$d_6$): δ 9.18–9.08 (1H, m), 8.75–8.50 (2H, m), 8.34–8.29 (1H, m), 7.52–7.26 (3H, m), 6.02–5.69 (2H, m), 5.24–4.63 (3H, m), 4.35 (2H, m), 3.62–3.30 (2H, m), 2.70 (2H, m), 2.07–1.44 (6H, m), 1.39–1.27 (3H, m).

Example 19(2)

3-(N-(2-(hexahydro-2-oxo-3S-(thiazol-4-ylcarbonylamino) azepin-1-yl)) propionyl)amino-4-oxo-5-(5-phenylmethyltetrazol-1-yl)pentanoic acid

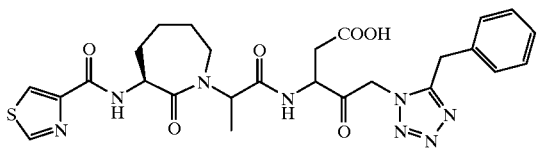

TLC: Rf 0.57 (chloroform:methanol:water=6:4:1); NMR (CDCl$_3$): δ 12.72 (1H, brs), 9.13 (1H, m), 8.90–8.49 (2H, m), 8.30 (1H, m), 7.27 (5H, m), 5.69 (2H, m), 5.23–4.65 (3H, m), 4.14 (2H, m), 3.48 (2H, m), 2.90–2.54 (2H, m), 2.05–1.41 (6H, m), 1.32 (3H, m).

Example 19(3)

3-(N-(2-(hexahydro-2-oxo-3S-(pyridin-3-ylcarbonylamino) azepin-1-yl))propionyl)amino-4-oxo-5-(5-phenylmethyltetrazol-1-yl)pentanoic acid

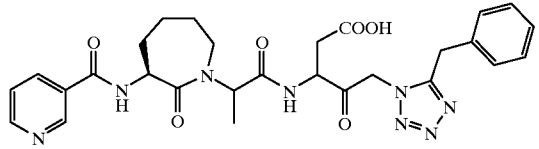

TLC: Rf 0.54 (chloroform:methanol:water=6:4:1); NMR (DMSO-d$_6$): δ 12.60 (1H, brs), 8.98 (1H, m), 8.69–8.58 (3H, m), 8.13 (1H, m), 7.47 (1H, m), 7.27 (5H, m), 5.66 (2H, m), 5.20–4.61 (3H, m), 4.11 (2H, m), 3.42 (2H, m), 2.72 (2H, m), 1.87 (6H, m), 1.32 (3H, m).

Example 19(4)

3-(N-(2-(hexahydro-2-oxo-3S-(quinolin-2-ylcarbonylamino)azepin-1-yl))propionyl)amino-4-oxo-5-(5-phenylmethyltetrazol-1-yl)pentanoic acid

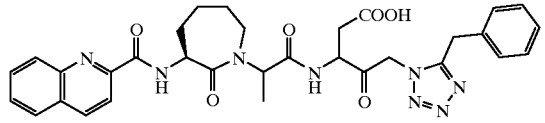

TLC: Rf 0.40 (chloroform:methanol:water=40:10:1); NMR (DMSO-d$_6$): δ 12.51 (1H, m), 9.34 (1H, dd, J=6.4 Hz, 0.8 Hz), 8.66 (1H, m), 8.60 (1H, d, J=8.4 Hz), 8.19 (1H, d, J=8.4 Hz), 8.08 (2H, m),7.88 (1H, m), 7.77 (1H, m), 7.22 (5H, m), 5.70 (2H, s), 5.24 (1H, m), 4.80 (2H, m), 4.13 (2H, m), 3.62–3.22 (2H, m), 2.84 (1H, m), 2.56 (1H, m), 2.14–1.23 (6H, m), 1.37 (3H, d, J=7.0 Hz).

Example 19(5)

3-(N-(2-(hexahydro-2-oxo-3S-(pyridin-2-ylcarbonylamino) azepin-1-yl))propionyl)amino-4-oxo-5-(5-phenylmethyltetrazol-1-yl)pentanoic acid

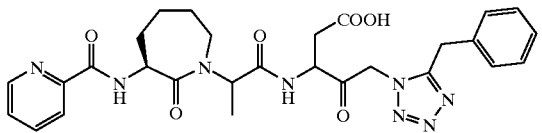

TLC: Rf 0.70 (chloroform:methanol:water=6:4:1); NMR (DMSO-d$_6$): δ 9.12 (1H, m), 8.64 (2H, m), 8.02 (2H, m), 7.62 (1H, m), 7.27 (5H, m), 5.67 (2H, m), 5.26–4.74 (3H, m), 4.14 (2H, m), 3.40 (2H, m), 2.90–2.59 (2H, m), 2.08–1.43 (6H, m), 1.32 (3H, m).

Example 19(6)

3-(N-(2-(hexahydro-2-oxo-3S-(morpholin-1-ylcarbonylamino)azepin-1-yl))propionyl)amino-4-oxo-5-(5-phenylmethyltetrazol-1-yl)pentanoic acid

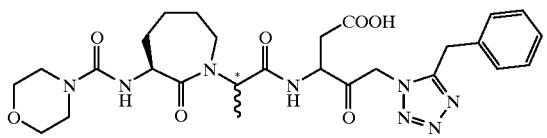

(wherein * represents R or S stereochemistry. The stereo-structure has not been identified yet. However, the above compound has the opposite stereoconfiguration as the compound of example 18(7))

TLC: Rf 0.62 (chloroform:methanol:water=6:4:1); NMR (DMSO-d$_6$): δ 12.53 (1H, brs), 8.52 (1H, m), 7.27 (5H, m), 6.43 (1H, m), 5.66 (2H, s), 5.12 (1H, m), 4.74 (1H, m), 4.52 (1H, m), 4.13 (2H, m), 3.52 (4H, m), 3.44 (2H, m), 3.24 (4H, m), 2.81 (1H, m), 2.60 (1H, m), 1.85–1.37 (6H, m), 1.30 (3H, m).

Example 19(7)

3-(N-(2-(hexahydro-2-oxo-3S-(morpholin-1-ylcarbonylamino)azepin-1-yl))propionyl)amino-4-oxo-5-(5-phenylmethyltetrazol-1-yl)pentanoic acid

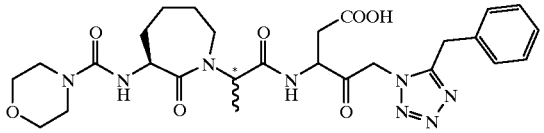

(wherein * represents R or S stereochemistry. The stereo-structure has not been identified yet. However, the above compound has the opposite stereoconfiguration as the compound of example 18(6))

TLC: Rf 0.59 (chloroform:methanol:water=6:4:1); NMR (DMSO-d$_6$): δ 12.56 (1H, brs), 8.68–8.48 (1H, m), 7.30 (3H, m), 6.42 (1H, m), 5.66 (2H, m), 4.66 (2H, m), 4.41 (1H, m), 4.13 (2H, m), 3.48 (4H, m), 3.42 (2H, m), 3.17 (4H, m), 2.82 (1H, m), 2.61 (1H, m), 1.80–1.42 (6H, m), 1.30 (3H, m).

Example 19(8)

3-(N-(2-(hexahydro-2-oxo-3S-(pyridin-4-ylcarbonylamino) azepin-1-yl))propionyl)amino-4-oxo-5-(5-phenylmethyltetrazol-1-yl)pentanoic acid

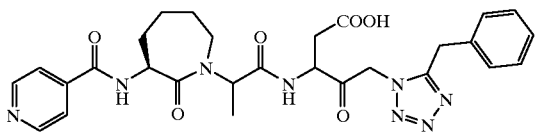

TLC: Rf 0.59 (chloroform:methanol:water=6:4:1); NMR (DMSO-d$_6$): δ 8.70 (4H, m), 7.73 (2H, m), 7.26 (5H, m), 5.67 (2H, m), 5.19–4.65 (3H, m), 4.13 (2H, m), 3.55 (2H, m), 2.83 (1H, m), 2.60 (1H, m), 1.94–1.60 (6H, m), 1.32 (3H, m).

Example 19(9)
3-(N-(2-(hexahydro-2-oxo-3S-(4-methoxyphenylcarbonylamino)azepin-1-y))propionyl)amino-4-oxo-5-(5-phenylmethyltetrazol-1-yl)pentanoic acid

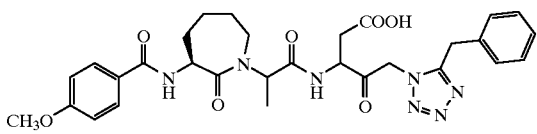

TLC: Rf 0.50 (chloroform:methanol:water=50:10:1); NMR (DMSO-d$_6$): δ 8.58 (1H, d, J=6.5 Hz), 8.05 (1H, d, J=6.5 Hz), 7.80 (2H, dd, J=8.0, 2.0 Hz), 7.40–7.18 (5H, m), 6.98 (2H, d, J=8.0 Hz), 5.62 (2H, s), 5.08 (1H, q, J=6.0 Hz), 4.90–4.60 (2H, m), 4.20–4.00 (2H, m) 3.80 (3H, s), 2.88–2.50 (4H, m), 2.05–1.20 (9H, m).

Example 19(10)
3-(N-(2-(hexahydro-2-oxo-3S-(3-methoxyphenylcarbonylamino)azepin-1-yl))propionyl)amino-4-oxo-5-(5-phenylmethyltetrazol-1-yl)pentanoic acid

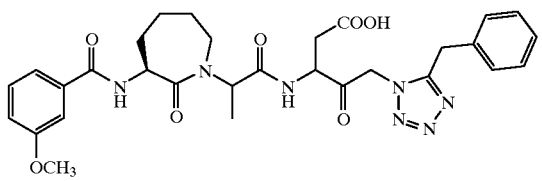

TLC: Rf 0.48 (chloroform:methanol:water=50:10:1); NMR (DMSO-d$_6$): δ 8.58 (1H, d, J=7.0 Hz), 8.20 (1H, d, J=7.0 Hz), 7.40–7.20 (8H, m),7.15–7.00 (1H, m), 5.65 (2H, s), 5.30–5.10 (1H, q, J=6.5 Hz), 4.92–4.65 (2H, m), 4.12 (2H, s), 3.80 (3H, s), 2.95–2.50 (4H, m), 2.05–1.20 (9H, m).

Example 19(11)
3-(N-(2-(hexahydro-2-oxo-3S-(4-(morpholin-1-ylcarbonyl)phenylcarbonylamino)azepin-1-yl))propionyl)amino-4-oxo-5-(5-phenylmethyltetrazol-1-yl)pentanoic acid

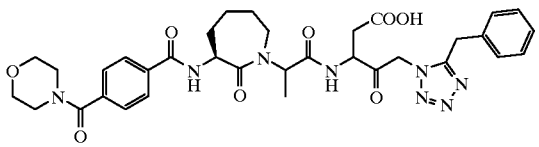

TLC: Rf 0.45 (chloroform:methanol:water=70:30:1); NMR (DMSO-d$_6$): δ 8.60–8.58 (2H, m), 7.92 (2H, t, J=8.0 Hz), 7.52–7.40 (2H, m), 7.32–7.15 (5H, m), 5.82–5.58 (2H, m), 5.20–5.10 (1H, m), 5.00–4.80 (1H, m), 4.70–4.50 (1H, m), 4.15 (2H, brs), 3.80–3.20 (8H, m), 2.78–2.42 (4H, m), 2.00–1.50 (7H, m), 1.45–1.20 (3H, m).

Example 19(12)
3-(N-(2-(hexahydro-2-oxo-3S-(quinolin-3-ylcarbonylamino)azepin-1-yl))propionyl)amino-4-oxo-5-(5-phenylmethyltetrazol-1-yl)pentanoic acid

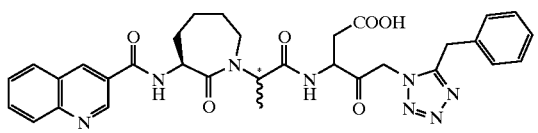

(wherein * represents R or S stereochemistry. The stereo-structure has not been identified yet.)

TLC: Rf 0.30 (chloroform:methanol:water=40:10:1); NMR (DMSO-d$_6$): δ 12.40 (1H, brs), 9.38 (1H, s), 9.35 (1H, m), 8.81 (1H, m), 8.57 (1H, s), 8.27 (2H, m), 7.89 (2H, m), 7.26 (5H, m), 5.68 (2H, m), 5.24 (1H, m), 4.82 (2H, m), 4.14 (2H, m), 3.55–3.27 (2H, m), 2.84 (1H, m), 2.58 (1H, m), 2.15–1.46 (6H, m), 1.37 (3H, m).

Example 19(13)
3-(N-(2-(hexahydro-2-oxo-3S-(quinolin-3-ylcarbonylamino)azepin-1-yl))propionyl)amino-4-oxo-5-(5-phenylmethyltetrazol-1-yl)pentanoic acid

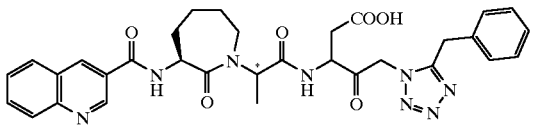

TLC: Rf 0.30 and 0.25 (chloroform:methanol:water=40:10:1); NMR (DMSO-d$_6$): δ 12.50 (1H, brs), 9.25 (2H, m), 8.86–8.67 (1H, m), 8.54 (1H, s), 8.21 (2H, m), 7.85 (2H, m), 7.27 (5H, m), 5.72 (2H, m), 4.81 (3H, m), 4.12 (2H, m), 3.52 (2H, m), 2.87 (1H, m), 2.67 (1H, m), 2.07–1.52 (6H, m), 1.34 (3H, m).

Example 19(14)
3-(N-(2-(hexahydro-2-oxo-3S-(pyridin-3-ylcarbonylamino)azepin-1-yl))propionyl)amino-4-oxo-5-(5-(2,6-dichlorophenylmethyl)tetrazol-1-yl) pentanoic acid

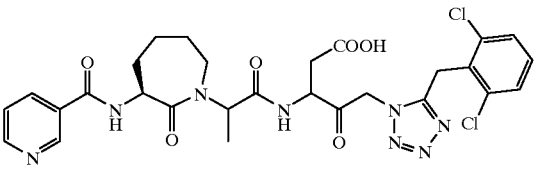

TLC: Rf 0.55 (chloroform:methanol:water=6:4:1); NMR (DMSO-d$_6$): δ 12.50 (1H, brs), 8.99 (1H, m), 8.81–8.52 (3H, m), 8.19–8.08 (1H, m), 7.55–7.26 (4H, m), 5.98–5.67 (2H, m), 5.24–4.70 (3H, m), 4.32 (2H, m), 3.80–3.37 (2H, m), 2.96–2.61 (2H, m), 1.95–1.57 (6H, m), 1.35 (3H, m).

Example 19(15)
3-(N-(2-(hexahydro-2-oxo-3S-(4-dimethylaminophenylcarbonylamino)azepin-1-yl))propionyl)amino-4-oxo-5-(5-phenylmethyltetrazol-1-yl) pentanoic acid

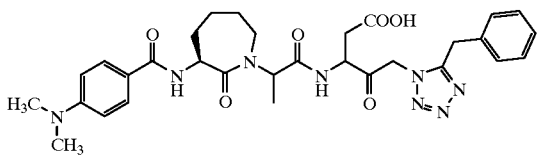

TLC: Rf 0.24 (chloroform:methanol:water=70:30:1); NMR (CDCl₃): δ 8.75 (1H, m), 7.90–7.50 (4H, m), 7.40–7.10 (8H, m), 6.65 (2H, d, J=10 Hz), 6.54 (1H, d, J=8.5 Hz), 5.60 (2H, m), 5.25–5.10 (1H, m), 4.90–4.60 (5H, m), 3.20–2.50 (3H, m), 2.65 (6H, s), 2.15–1.60 (8H, m), 1.35 (3H, d, J=7.5 Hz).

Example 19(16)
3-(N-(2S-(2-phenyl-4R-methyl-4,5-dihydrothiazol-4-ylcarbonylamino) propionyl)amino-4-oxo-5-(5-(2,6-dichlorophenylmethyl)tetrazol-1-yl)pentanoic acid

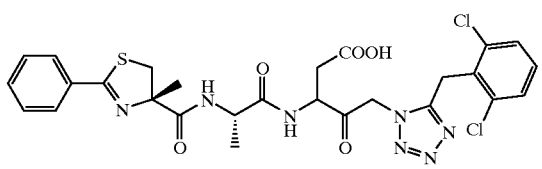

TLC: Rf 0.18 (chloroform:methanol:water=100:20:1); NMR (DMSO-d₆): δ 8.93 (d, J=8 Hz) and 8.80 (d, J=8 Hz) total 1H, 7.90–7.70 (3H, m), 7.60–7.20 (6H, m), 5.90–5.60 (2H, m), 4.80–4.60 (1H, m), 4.50–4.10 (3H, m), 2.90–2.70 (2H, brd), 1.45 (3H, s), 1.30 (3H, d, J=8 Hz).

Example 19(17)
3-(N-(2S-(2-phenyl-4,5-dihydrothiazol-4-ylcarbonylamino)propionyl)amino-4-oxo-5-(5-(2,6-dichlorophenylmethyl)tetrazol-1-yl)pentanoic acid

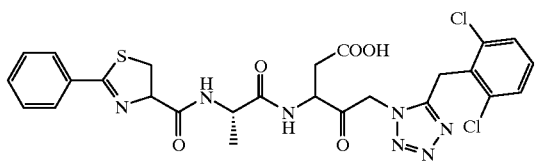

TLC: Rf 0.48 (chloroform:methanol:acetic acid=10:1:1); NMR (DMSO-d₆): δ 8.90–8.70 (1H, m), 8.50–8.20 (1H, m), 7.85–7.75 (2H, m), 7.60–7.20 (6H, m), 6.10–5.50 (2H, m), 5.30–5.15 (1H, m), 4.60–4.15 (4H, m), 3.80–3.10 (2H, m), 2.80–2.40 (2H, m), 1.40–1.20 (3H, m).

Example 19(18)
N-(thiazol-4-ylcarbonyl)-3-amino-4-oxo-5-(5-(2,6-dichlorophenylmethyl)tetrazol-2-yl)pentanoic acid

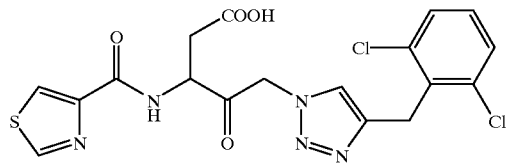

TLC: Rf 0.47 (chloroform:methanol:acetic acid=18:1:1); NMR (DMSO-d₆): δ 12.70–12.20 (1H, br), 9.10–8.90 (1H, m), 8.45 and 8.44 (1H, each s), 8.31 (1H, s), 7.56–7.45 and 7.45–7.27 (total 3H, m), 6.04–5.75 (2H, m), 5.13–4.96 (1H, m), 4.50 (2H, s), 3.05–2.67 (2H, m).

Example 19(19)
N-phenylthiomethylcarbonyl-3-amino-4-oxo-5-(5-(2,6-dichlorophenylmethyl)tetrazol-2-yl)pentanoic acid

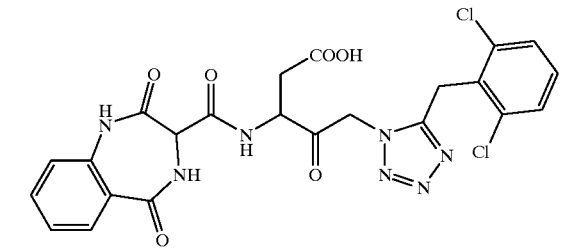

TLC: Rf 0.54 (chloroform:methanol:acetic acid=25:1:1); NMR (DMSO-d₆): δ 12.72–12.20 (1H, br), 8.83 (1H, d), 7.54–7.18 (8H, m), 5.69 (2H, s), 4.79–4.70 (1H, m), 4.51 (2H, s), 3.77 (2H, s), 2.80–2.72 (2H, m).

Example 19(20)
N-(perhydrobenzo-1,4-diazepin-2,5-dion-3-ylcarbonyl)-3-amino-4-oxo-5-(5-(2,6-dichlorophenylmethyl)tetrazol-2-yl)pentanoic acid

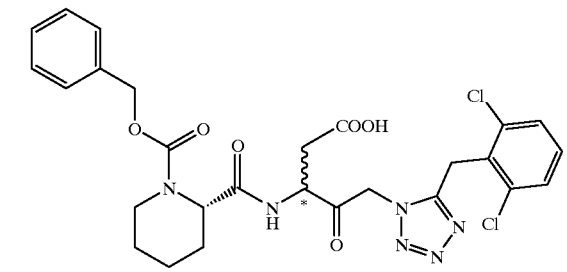

TLC: Rf 0.25 (chloroform:methanol:acetic acid=10:1:1); NMR (DMSO-d₆): δ 10.7–10.5 (1H, m), 9.10–8.70 (1H, m), 8.10–7.85 (1H, m), 7.80–7.70 (1H, m), 7.60–7.10 (6H, m), 6.10–5.70 (2H, m), 4.85–4.75 (1H, m), 4.60–4.40 (1H, m), 4.40–4.10 (2H, m), 2.90–2.60 (2H, m).

Example 19(21)
N-(1-benzyloxycarbonylpiperidin-2S-ylcarbonyl)-3-amino-4-oxo-5-(5-(2,6-dichlorophenylmethyl)tetrazol-1-yl)pentanoic acid (wherein * represents R or S stereochemistry. The above compound has the opposite stereocondiguration as the compound of example 19(22))

TLC: Rf 0.39 (chloroform:methanol:acetic acid=18:1:11); NMR (DMSO-d₆): δ 13.40–11.80 (1H, br), 8.94–8.65 (1H, m), 7.58–7.13 (8H, m), 5.92–5.62 (2H, m), 5.06 (2H, brs), 4.90–4.65 (2H, m), 4.42–4.19 (2H, m), 4.01–3.77 (1H, m), 3.47–2.99 (1H, m), 2.99–2.60 (2H, m), 2.21–2.00 (1H, m), 1.75–1.47 and 1.47–1.15 (5H, m).

Example 19(22)
N-(1-benzyloxycarbonylpiperidin-2S-ylcarbonyl)-3-amino-4-oxo-5-(5-(2,6-dichlorophenylmethyl)tetrazol-1-yl)pentanoic acid

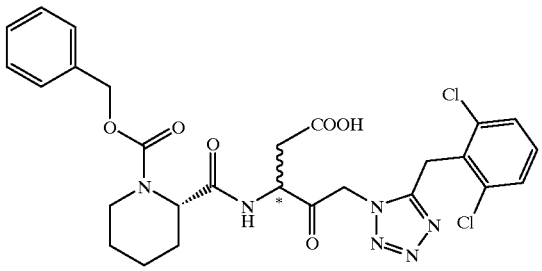

(wherein * represents R or S stereochemistry. The above compound has the opposite stereocondiguration as the compound of example 19(21))

TLC: Rf 0.39 (chloroform:methanol:acetic acid=18:1:1); NMR (DMSO-d$_6$): δ 13.60–11.90 (1H, br), 8.93–8.65 (1H, m), 7.58–7.07 (8H, m), 5.92–5.60 (2H, m), 5.06 (2H, brs), 4.90–4.65 (2H, m), 4.42–4.19 (2H, m), 4.01–3.77 (1H, m), 3.47–2.99 (1H, m), 2.99–2.60 (2H, m), 2.21–2.00 (1H, m), 1.75–1.47 and 1.47–1.15 (5H, m).

Example 19(23)
N-(1-acetylpiperidin-2S-ylcarbonyl)-3-amino-4-oxo-5-(5-(2,6-dichlorophenylmethyl)tetrazol-1-yl)pentanoic acid

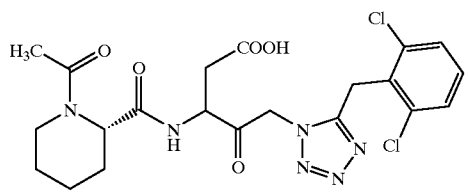

TLC: Rf 0.58 (chloroform:methanol:acetic acid=8:1:1); NMR (DMSO-d$_6$): δ 8.82–8.52 (1H, m), 7.60–7.20 (3H, m), 5.95–5.60 (2H, m), 5.10–4.95, 4.95–4.55 and 4.40–4.10 (5H, m), 3.75–3.60 (1H, m), 3.00–253 (2H, m), 2.33–1.95 (1H, m), 2.03 and 2.00 (total 3H, each s), 1.75–1.10 (5H, m).

Example 19(24)
N-(1-benzyloxycarbonylpyrrolidin-2S-ylcarbonyl)-3-amino-4-oxo-5-(5-(2,6-dichlorophenylmethyl)tetrazol-1-yl)pentanoic acid

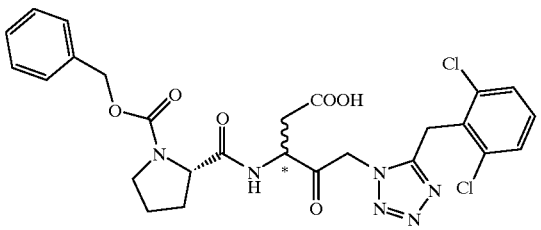

(wherein * represents R or S stereochemistry. The stereostructure has not been identified yet. However, the above compound has the opposite stereoconfiguration as the compound of example 19(25))

TLC: Rf 0.40 (chloroform:methanol:acetic acid=18:1:1); NMR (DMSO-d$_6$): δ 9.16–8.73 (1H, m), 7.72–7.01 (8H, m), 6.00–5.40 (2H, m), 5.22–4.84 (2H, m), 4.84–4.80 (1H, m), 4.80–4.04 (3H, m), 3.70–3.23 (2H, m), 2.98–2.40 (2H, m), 2.40–1.–57 (4H, m).

Example 19(25)
N-(1-benzyloxycarbonylpyrrolidin-2S-ylcarbonyl)-3-amino-4-oxo-5-(5-(2,6-dichlorophenylmethyl)tetrazol-1-yl)pentanoic acid

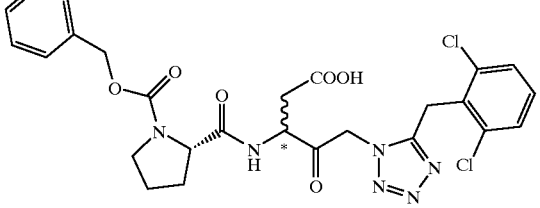

(wherein * represents R or S stereochemistry. The stereostructure has not been identified yet. However, the above compound has the opposite stereoconfiguration as the compound of example 19(24))

TLC: Rf 0.40 (chloroform:methanol:acetic acid=18:1:1); NMR (DMSO-d$_6$): δ 9.22–8.66 (1H, m), 7.75–7.10 (8H, m), 6.06–5.40 (2H, m), 5.21–4.84 (2H, m), 4.84–4.56 (1H, m), 4.56–4.00 (3H, m), 3.70–3.23 (2H, m), 3.00–2.40 (2H, m), 2.40–1.40 (4H, m).

Example 19(26)
N-(1-acetylpyrrolidin-2S-ylcarbonyl)-3-amino-4-oxo-5-(5-(2,6-dichlorophenylmethyl)tetrazol-1-yl)pentanoic acid

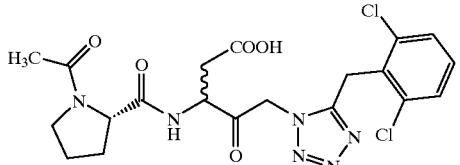

TLC: Rf 0.13 (chloroform:methanol:acetic acid=18:1:1); NMR (DMSO-d$_6$): δ 9.07–8.54 (1H, m), 7.67–7.23 (3H, m), 6.18–5.59 (2H, m), 4.92–4.02 (4H, m), 3.71–3.20 (2H, m), 2.92–2.39 (2H, m), 2.39–1.50 (4H, m), 1.96 and 1.89 (total 3H, each s).

EXAMPLES 20(1)–20(2)

By the same procedure as provided in example 6(1), using the compound prepared in example 18(21) or 18(22), the compounds of the present invention having the following physical data were obtained.

Example 20(1)
3-(N-(2-(hexahydro-2-oxo-3S-(3-carboxyphenylcarbonylamino)azepin-1-yl))propionyl)amino-4-oxo-5-(5-phenylmethyltetrazol-1-yl)pentanoic acid

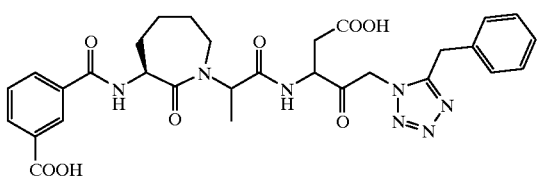

TLC: Rf 0.38 (chloroform:methanol:water=6:4:1); NMR (DMSO-d$_6$): δ 12.84 (2H, brs), 8.54 (2H, m), 8.41 (1H, s) 8.07 (2H, m), 7.59 (1H, m), 7.26 (5H, m), 5.66 (2H, m), 5.24–4.62 (3H, m), 4.13 (2H, m), 3.39 (2H, m), 2.83 (1H, m), 2.60 (1H, m) 1.97–1.55 (6H, m), 1.33 (3H, m).

Example 20(2)

3-(N-(2-(hexahydro-2-oxo-3S-(4-carboxyphenylcarbonylamino)azepin-1-yl))propionyl)amino-4-oxo-5-(5-phenylmethyltetrazol-1-yl)pentanoic acid

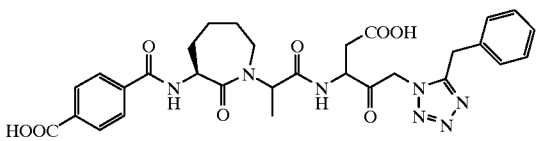

TLC: Rf 0.39 (chloroform:methanol:water=6:4:1); NMR (DMSO-d$_6$): δ 8.57 (1H, m), 8.44 (1H, m), 8.04–7.89 (4H, m), 7.27 (5H, m), 5.66 (2H, m), 5.22–4.67 (3H, m), 4.13 (2H, m), 3.53 (2H, m), 2.83 (1H, m), 2.65 (1H, m), 1.99–1.53 (6H, m), 1.34 (3H, m).

Reference Example 10

3-(N-(2-(hexahydro-2-oxo-3S-(1-((2-trimethylsilyl)ethoxymethyl)imizazol-5-ylcarbonylamino)azepin-1-yl))propionyl)amino-4-oxo-5-(5-phenylmethyltetrazol-1-yl)pentanoic acid•t-butylester

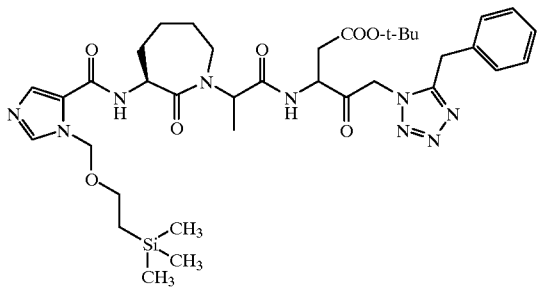

By the same procedure as provided in example 18(1) using the compound prepared in reference example 9(3) and 2-(hexahydro-2-oxo-3S-(1-((2-trimethylsilyl)ethoxymethyl)imizazol-5-ylcarbonylamino)azepin-1-yl)propionic acid instead of 2-(hexahydro-2-oxo-3S-(thiazol-4-ylcarbonylamino)azepin-1-yl)propionic acid, the compound of the present invention having the following physical data was obtained.

TLC: Rf 0.63 (chloroform:methanol=9:1); NMR (DMSO-d$_6$): δ 8.87–8.53 (2H, m), 8.29–8.17 (1H, m), 7.87–7.75 (2H, m), 7.27 (5H, m), 5.67 (2H, m), 5.37 (2H, m), 5.26–4.62 (3H, m), 4.13 (2H, m), 3.48 (2H, t, J=7.7 Hz), 3.28 (2H, m), 2.80 (1H, m), 2.57 (1H, m), 2.02–1.45 (6H, m), 1.38 (9H, s), 1.32 (3H, m), 0.84 (2H, t, J=7.7 Hz), −0.04 (9H, s).

Example 21 (1)

3-(N-(2-(hexahydro-2-oxo-3S-(imizazol-5-ylcarbonylamino)azepin-1-yl))propionyl)amino-4-oxo-5-(5-phenylmethyltetrazol-1-yl)pentanoic acid

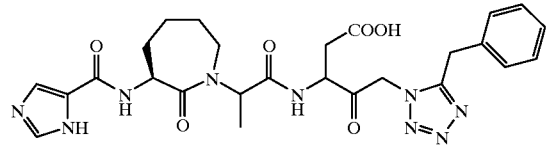

By the same procedure as provided in example 6(1), using the compound prepared in reference example 10, the compound of the present invention having the following physical data was obtained.

TLC: Rf 0.69 (chloroform:methanol:water=6:4:1); NMR (DMSO-d$_6$): δ 12.53 (1H, brs), 8.78–8.53 (1H, m), 8.30–8.16 (1H, m), 7.71–7.60 (2H, m), 7.28 (5H, m), 5.67 (2H, m), 5.25–4.60 (3H, m), 4.14 (2H, m), 3.35 (2H, m), 2.85–2.60 (2H, m), 2.04–1.40 (6H, m), 1.32 (3H, m).

Example 22(1) and Example 22(2)

By the same procedure as provided in example 1, using 5-(2,6-dichlorophenylmethyl)tetrazole and N-t-butoxycarbonyl-3-amino-4-oxo-5-bromopentanoic acid•ethylester instead of N-((N-(3-phenylpropionyl)-L-valyl)-L-alanyl)-3-amino-4-oxo-5-bromopentanoic acid•t-butylester, the compounds of the present invention having the following physical data were obtained.

Example 22(1)

N-t-butoxycarbonyl-3-amino-4-oxo-5-(5-(2,6-dichlorophenylmethyl)tetrazol-2-yl)pentanoic acid•ethylester

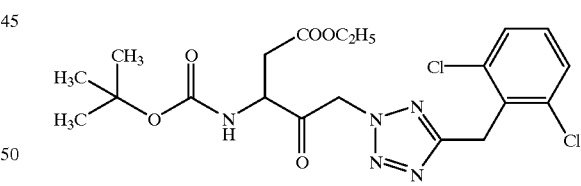

TLC: Rf 0.41 (hexane:ethyl acetate=2:1); NMR (CDCl$_3$): δ 7.35 (1H, d, J=8.8 Hz), 7.34 (1H, d, J=7.6 Hz), 7.16 (1H, dd, J=8.8 Hz, 7.6 Hz), 5.82 and 5.61 (each 1H, d, J=17.8 Hz), 5.72–5.59 (1H, m), 4.68–4.53 (1H, m), 4.61 (2H, s), 4.15 (2H, q, J=7.2 Hz), 3.06 (1H, dd, J=17.5 Hz, 5.0 Hz), 2.76 (1H, dd, J=17.5 Hz, 5.0 Hz), 1.47 (9H, s), 1.25 (3H, t, J=7.2 Hz).

Example 22(2)

N-t-butoxycarbonyl-3-amino-4-oxo-5-(5-(2,6-dichlorophenylmethyl)tetrazol-1-yl)pentanoic acid•ethylester

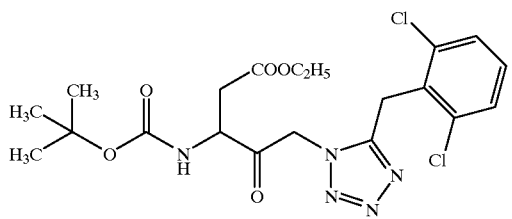

TLC: Rf 0.23 (hexane:ethyl acetate=2:1); NMR (CDCl$_3$): δ 7.37 (1H, d, J=8.8 Hz), 7.37 (1H, d, J=7.2 Hz), 7.21 (1H, dd, J=8.8 Hz, 7.2 Hz), 5.74 and 5.57 (each 1H, d, J=18.6 Hz), 5.66–5.52 (1H, m), 4.65–4.50 (1H, m), 4.39 and 4.29 (each 1H, d, J=17.5 Hz), 4.17 (2H, q, J=7.0 Hz), 3.13 (1H, dd, J=17.5 Hz, 5.0 Hz), 2.83 (1H, dd, J=17.5 Hz, 5.0 Hz), 1.50 (9H, s), 1.27 (3H, t, J=7.0 Hz).

Example 23(1)
N-t-butoxycarbonyl-3-amino-4-oxo-5-(5-(2,6-dichlorophenylmethyl)tetrazol-2-yl)pentanoic acid

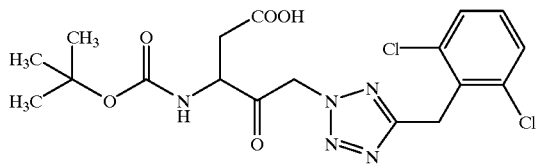

To a solution of the compound prepared in example 22(1) (72 mg) in 1,2-dimethoxyethane (0.5 ml) was added 1N aqueous solution of sodium hydroxide (0.15 ml) at 0° C. The reaction mixture was stirred for 30 min at 0° C. The mixture was quenched by addition of 1N aqueous solution oh hydrochloric acid, extracted with ethyl acetate. The extract was washed with a saturated aqueous solution of sodium chloride, dried over anhydrous sodium sulfate, concentrated to give the compound of the present invention (62 mg) having the following physical data.

TLC: Rf 0.49 (chloroform:methanol:acetic acid=18:1:1); NMR (DMSO-d$_6$): δ 7.57–7.30 (4H, m), 5.95–5.74 (2H, m), 4.51 (2H, s), 4.58–4.40 (1H, m), 2.82–2.39 (2H, m), 1.40 (9H, s).

Example 23(2)
N-t-butoxycarbonyl-3-amino-4-oxo-5-(5-(2,6-dichlorophenylmethyl)tetrazol-1-yl)pentanoic acid

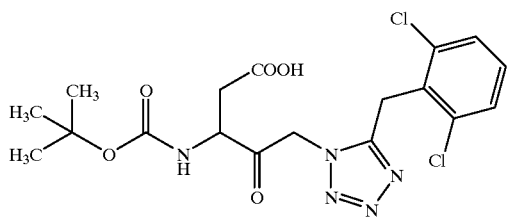

By the same procedure as provided in example 23(1), using the compound prepared in example 22(2), the compound of the present invention having the following physical data was obtained.

TLC: Rf 0.37 (chloroform:methanol:acetic acid=18:1:1); NMR (DMSO-d$_6$): δ 7.68–7.33 (4H, m), 5.92–5.77 (2H, m), 4.60–4.43 (1H, m), 4.34 (2H, s), 2.86–2.58 (2H, m), 1.41 (9H, s).

Reference Example 11 (1)
3-amino-4-oxo-5-(5-(2,6-dichlorophenylmethyl)tetrazol-2-yl)pentanoic acid•ethylester•hydrochloric acid salt

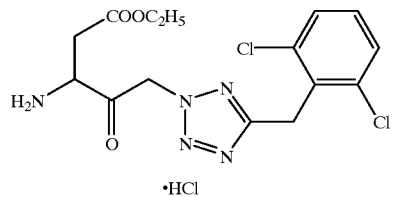

•HCl

To the compound prepared in example 22(1) (201 mg) was added 4N hydrochloric acid in dioxane (4 ml). The reaction mixture was stirred for 30 min at room temperature. The mixture was concentrated. The residue was removed as toluene azeotrope. The obtained residue was washed with ether, to give the title compound (150 mg) having the following physical data.

TLC: Rf 0.28 (chloroform:methanol=19:1); NMR (DMSO-d$_6$): δ 8.60–8.20 (3H, br), 7.62 (1H, d, J=9.0 Hz), 7.62 (1H, d, J=6.8 Hz), 7.37 (1H, dd, J=9.0 Hz, 6.8 Hz), 6.21 and 6.02 (each 1H, d, J=18.0 Hz), 4.65–4.55 (1H, m), 4.54 (2H, s), 4.12 (2H, q, J=7.0 Hz), 3.35–3.03 (2H, m), 1.20 (3H, t, J=7.0 Hz).

Reference Example 11(2)
3-amino-4-oxo-5-(5-(2,6-dichlorophenylmethyl)tetrazol-1-yl)pentanoic acid•ethylester•hydrochloric acid salt

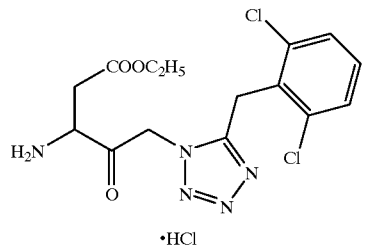

•HCl

By the same procedure as provided in reference example 11(1), using the compound prepared in example 22(2), the title compound having the following physical data was obtained.

TLC: Rf 0.33 (chloroform:methanol=19:1).

Reference Example 11(3)
3-amino-4-oxo-5-(5-phenylmethyltetrazol-1-yl)pentanoic acid•ethylester•hydrochloric acid salt

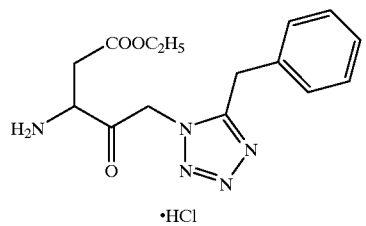

•HCl

By the same procedure as provided in example 1→reference example 11(1), using 5-phenylmethyltetrazole and N-t-butoxycarbonyl-3-amino-4-oxo-5-bromopentanoic acid•ethylester instead of N-((N-(3-phenylpropionyl)-L-valyl)-L-alanyl)-3-amino-4-oxo-5-bromopentanoic acid•t- butylester, the title compound having the following physical data was obtained.

TLC: Rf 0.50 (chloroform:methanol=19:1).

EXAMPLES 24(1)–24(12)

By the same procedure as provided in example 18(1), using the corresponding carboxylic acid compounds and the compound prepared in reference example 11(1), reference example 11(2) or reference example 11(3) instead of the compound prepared in reference example 9(1), the compounds of the present invention having the following physical data were obtained.

Example 24(1)

N-(N-benzyloxycarbonyl-L-alanyl)-3-amino-4-oxo-5-(5-(2,6-dichlorophenylmethyl)tetrazol-2-yl)pentanoic acid•ethylester

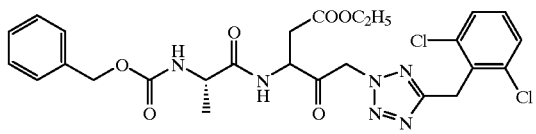

TLC: Rf 0.43 (chloroform:methanol 19:1); NMR (CDCl$_3$): δ 7.50–7.07 (9H, m), 5.82–5.61 and 5.61–5.39 (2H, m), 5.36 and 5.25 (total 1H, each d, J=5.5 Hz), 5.10 and 5.08 (total 2H, each s), 4.98–4.82 (1H, m), 4.59 (2H, s), 4.33–4.13 (1H, m),4.12 (2H, q, J=7.0 Hz), 3.10–285 and 2.81–2.59 (total 2H, m), 1.41 and 1.40 (total 3H, each d, J=7.0 Hz), 1.23 (3H, t, J=7.0 Hz).

Example 24(2)

N-(N-benzyloxycarbonyl-L-alanyl)-3-amino-4-oxo-5-(5-(2,6-dichlorophenylmethyl)tetrazol-1-yl)pentanoic acid•ethylester

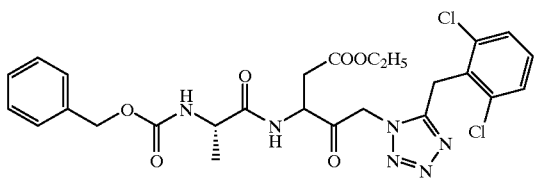

NMR (CDCl$_3$): δ 7.50–7.10 (8H, m), 5.85–5.60 and 5.60–5.28 (2H, m), 5.25–5.00 (2H, m), 4.90–4.77 (1H, m), 4.35–4.07 (5H, m), 3.19–2.99 and 2.87–2.79 (2H, m), 1.52–1.38 (3H, m), 1.27 (3H, t, J=7.0 Hz).

Example 24(3)

N-(N-benzyloxycarbonyl-L-valyl)-3-amino-4-oxo-5-(5-(2,6-dichlorophenylmethyl)tetrazol-2-yl)pentanoic acid•ethylester

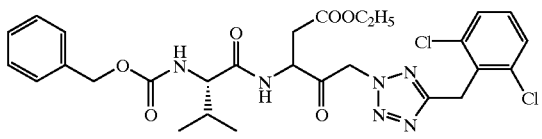

TLC: Rf 0.20 (chloroform:methanol=19:1); NMR (DMSO-d$_6$): δ 8.92–8.79 and 8.72–8.60 (2H, m), 7.61–7.44 and 7.44–7.15 (8H, m), 5.84 (2H, m), 4.80–4.62 (1H, m)4.51 (2H, s), 4.04 (2H, q, J=7.0 Hz), 3.93 (1H, m), 3.00–2.55 (2H, m), 2.08–1.92 (1H, m), 1.16 (3H, t, J=7.0 Hz), 0.96–0.75 (6H, m).

Example 24(4)

N-(N-benzyloxycarbonyl-N'-t-butyloxycarbonyl-L-lysinyl)-3-amino-4-oxo-5-(5-(2,6-dichlorophenylmethyl)tetrazol-2-yl)pentanoic acid•ethylester

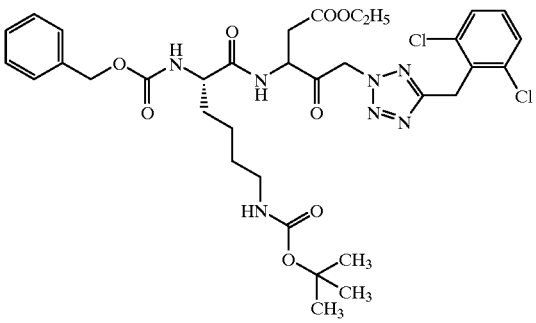

TLC: Rf 0.47 (chloroform:methanol=19:1); NMR (DMSO-d$_6$): δ 8.88–8.75 and 8.72–8.60 (total 1H, m), 7.63–7.45 and 7.45–7.10 (9H, m), 6.82–6.68 (total 1H, m), 5.96–5.72 (2H, m), 4.99 (2H, s), 4.93–4.60 (1H, m), 4.51 (2H, s), 4.15–3.85 (1H, m), 4.05 (2H, q, J=6.8 Hz), 2.96–2.55 (2H, m), 1.68–1.05 (6H, m), 1.36 (9H, s), 1.16 (3H, t, J=6.8 Hz).

Example 24(5)

N-phenylcarbonyl-3-amino-4-oxo-5-(5-(2,6-dichlorophenylmethyl)tetrazol-2-yl)pentanoic acid•ethylester

TLC: Rf 0.54 (chloroform:methanol=19:1); NMR (DMSO-d$_6$): δ 9.07 (1H, d, J=9.5 Hz), 7.95–7.84 and 7.63–7.25 (8H, m), 5.94 (2H, s), 5.08–4.94 (1H, m), 4.50 (2H, s), 4.06 (2H, q, J=7.2 Hz), 2.96 (1H, dd, J=16.0 Hz, 5.5 Hz), 2.74 (1H, dd, J=16.0 Hz, 7.5 Hz), 1.15 (3H, t, J=7.0 Hz).

Example 24(6)

N-(2-phenylethylcarbonyl)-3-amino-4-oxo-5-(5-(2,6-dichlorophenylmethyl)tetrazol-2-yl)pentanoic acid•ethylester

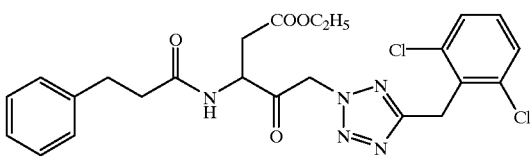

TLC: Rf 0.24 (chloroform:methanol=19:1); NMR (CDCl$_3$): δ 7.43–6.97 (8H, m), 6.57 (1H, d, J=9.5 Hz), 5.21 and 5.09 (each 1H, d, J=18.0 Hz), 4.94–4.76 (1H, m), 4.59 (2H, s), 4.10 (2H, q, J=7.0 Hz), 3.10–2.85 and 2.79–2.45 (6H, m), 1.23 (3H, t, J=7.0 Hz).

Example 24(7)

N-phenyloxymethylcarbonyl-3-amino-4-oxo-5-(5-(2,6-dichlorophenylmethyl)tetrazol-2-yl)pentanoic acid•ethylester

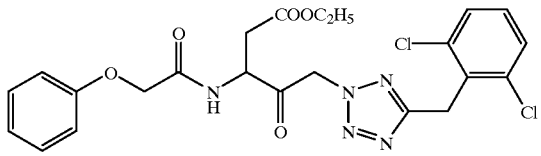

TLC: Rf 0.52 (chloroform:methanol=19:1); NMR (CDCl$_3$): δ 7.80–7.66 (1H, m), 7.42–6.87 (8H, m), 5.63 and 5.52 (each 1H, d, J=18.0 Hz), 5.07–4.92 (1H, m), 4.60 (4H, s), 4.13 (2H, q, J=7.0 Hz), 3.07 (1H, dd, J=17.5 Hz, 4.5 Hz), 2.74 (1H, dd, J=17.5 Hz, 5.0 Hz), 1.24 (3H, t, J=7.0 Hz).

Example 24(8)

N-(2-(hexahydro-2-oxo-azepin-1-yl)propionyl)-3-amino-4-oxo-5-(5-(2,6-dichlorophenylmethyl)tetrazol-1-yl)pentanoic acid•ethylester

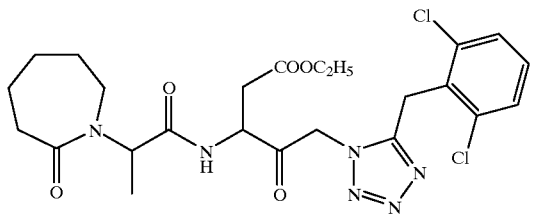

TLC: Rf 0.47 (ethyl acetate); NMR (CDCl$_3$): δ 7.50–7.15 (3H, m), 5.80–5.42 (2H, m), 5.08–4.91 (1H, m), 4.91–4.74 (1H, m), 4.36 and 4.35 (total 2H, each s), 4.22–4.11 (2H, m), 3.46–3.22 (2H, m), 3.11–2.68 (2H, m), 2.69–2.44 (2H, m), 1.98–1.39 (6H, m), 1.63 (9H, s), 1.48–1.34 (3H, m), 1.27 (3H, t, J=7.2 Hz).

Example 24(9)

N-(2S-(tetrahydro-5-oxo-1,4-benzooxsazepin-4-yl)propionyl)-3-amino-4-oxo-5-(5-(2,6-dichlorophenylmethyl)tetrazol-1-yl)pentanoic acid•ethylester

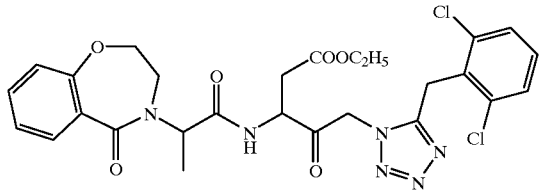

TLC: Rf 0.12 (hexane:ethyl acetate=1:1); NMR (CDCl$_3$): δ 7.85–6.93 (8H, m), 5.84–5.40 (2H, m), 5.35–5.11 (1H, m), 4.98–4.75 (1H, m), 4.51–3.96 (6H, m), 3.72–3.42 (2H, m), 3.25–2.69 (2H, m), 1.71–1.40 (2H, m), 1.40–1.02 (3H, m).

Example 24(10)

N-(2S-(2,3-indol-3,4-tetrahydro-2-oxo-azepin-1-yl)propionyl)-3-amino-4-oxo-5-(5-(2,6-dichlorophenylmethyl)tetrazol-1-yl)pentanoic acid•ethylester

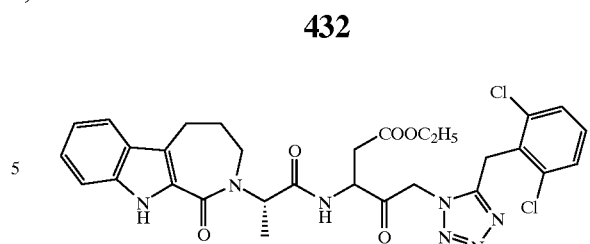

TLC: Rf 0.16 (hexane:ethyl acetate=3:1); NMR (CDCl$_3$): δ 11.18 (1H, s), 8.90–8.69 (1H, m), 7.62–6.89 (1H, m), 5.87 (2H, m), 5.38–5.16 (1H, m), 4.98–4.79 (1H, m) 4.46–4.17 (2H, m), 4.17–3.95 (2H, m), 3.65–2.63 (6H, m), 2.42–1.85 (2H, m), 1.50–1.30 (3H, m), 1.30–0.98 (3H, m).

Example 24(11)

N-(2-(4-fluorophenyl)-4-oxo-5-benzyloxocarbonylaminopyrimidin-3-yl)methylcarbonyl-3-amino-4-oxo-5-(5-(2,6-dichlorophenylmethyl)tetrazol-1-yl)pentanoic acid•ethylester

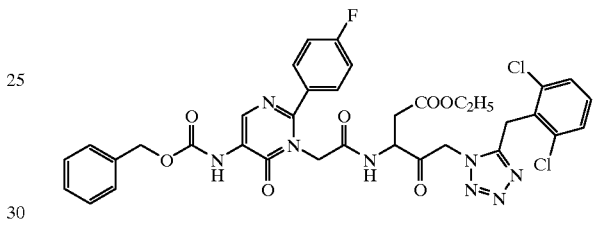

TLC: Rf 0.56 (chloroform:methanol=10:1); NMR (CDCl$_3$): δ 8.77 (1H, brs), 7.70–7.07 (14H, m), 5.90 and 5.52 (each 1H, each d, J=18.5 Hz), 5.18 (2H, s), 4.91 (1H, m), 4.60 and 4.52 (each 1H, each d, J=15.0 Hz), 4.31 (2H, s), 4.11 (2H, q, J=7.0 Hz), 3.06 and 2.82 (each 1H, each dd, J=16.0, 5.0 Hz), 1.22 (3H, t, J=7.0 Hz).

Example 24(12)

3-(N-(2-(hexahydro-2-oxo-3S-(quinolin-3-ylcarbonylamino)azepin-1-yl))propionyl)amino-4-oxo-5-(5-phenylmethyltetrazol-1-yl)pentanoic acid•ethylester

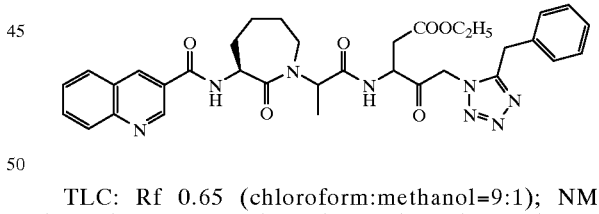

TLC: Rf 0.65 (chloroform:methanol=9:1); NMR (CDCl$_3$): δ 9.31–9.22 (1H, m), 9.13 (1H, m), 8.54 (1H, m), 8.02 (2H, m), 7.73 (2H, m), 7.48 (1H, m), 7.32–7.21 (5H, m), 5.60–5.25 (2H, m), 4.97–4.73 (3H, m), 4.24–4.06 (4H, m), 3.55 (2H, m), 3.05–2.72 (2H, m), 2.27–1.84 (6H, m), 1.44 (3H, d, J=7.0 Hz), 1.30–1.18 (3H, m).

EXAMPLES 25(1)–25(11)

By the same procedure as provided in example 23(1), using the compound prepared in examples 24(1)–24(11), the compounds of the present invention having the following physical data were obtained.

Example 25(1)

N-(N-benzyloxycarbonyl-L-alanyl)-3-amino-4-oxo-5-(5-(2,6-dichlorophenylmethyl)tetrazol-2-yl)pentanoic acid

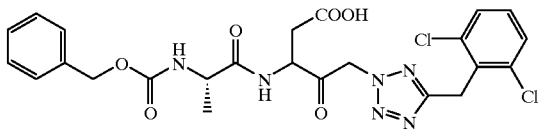

TLC: Rf 0.29 (chloroform:methanol:acetic acid=18:1:1); NMR (DMSO-d$_6$): δ 12.64–12.25 (1H, m), 8.79–8.56 (1H, m), 7.66–7.55 (1H, m), 7.55–7.45 and 7.45–7.12 (8H, m), 6.00–5.55 (2H, m), 5.00 (2H, s), 4.81–4.57 (1H, m), 4.51 (2H, s), 4.14–4.00 (1H, m), 2.86–2.35 (2H, m), 1.23 and 1.21 (total 3H, each d, J=7.4 Hz).

Example 25(2)

N-(N-benzyloxycarbonyl-L-alanyl)-3-amino-4-oxo-5-(5-(2,6-dichlorophenylmethyl)tetrazol-1-yl)pentanoic acid

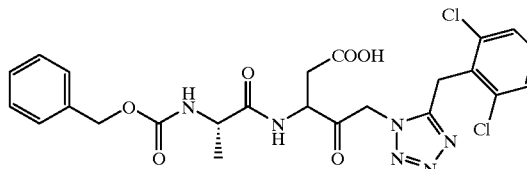

TLC: Rf 0.24 (chloroform:methanol:acetic acid=18:1:1); NMR (DMSO-d$_6$): δ 12.63–12.35 (1H, m), 9.00–8.72 (1H, m), 7.70–7.20 (9H, m), 5.87–5.73 (2H, m), 5.06–4.87 (2H, s), 4.87–4.60 (1H, m), 4.36–4.22 (2H, s), 4.22–3.95 (1H, m), 2.90–2.55 (2H, m), 1.30–1.05 (3H, m).

Example 25(3)

N-(N-benzyloxycarbonyl-L-valyl)-3-amino-4-oxo-5-(5-(2,6-dichlorophenylmethyl)tetrazol-2-yl)pentanoic acid

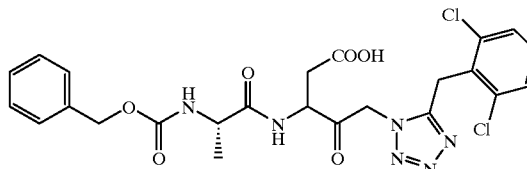

TLC: Rf 0.61 (chloroform:methanol:acetic acid=18:1:1); NMR (DMSO-d$_6$): δ 12.65–12.25 (1H, br), 8.86–8.55 (1H, m), 7.59–7.15 (9H, m), 6.02–5.50 (2H, m), 5.00 (2H, s), 4.88–4.58 (1H, m), 4.51 (2H, s), 3.93–3.77 (1H, m), 2.92–2.22 (2H, m), 2.06–1.93 (1H, m), 0.95–0.76 (6H, m).

Example 25(4)

N-(N-benzyloxycarbonyl-N'-t-butyloxycarbonyl-L-lysinyl)-3-amino-4-oxo-5-(5-(2,6-dichlorophenylmethyl)tetrazol-2-yl)pentanoic acid

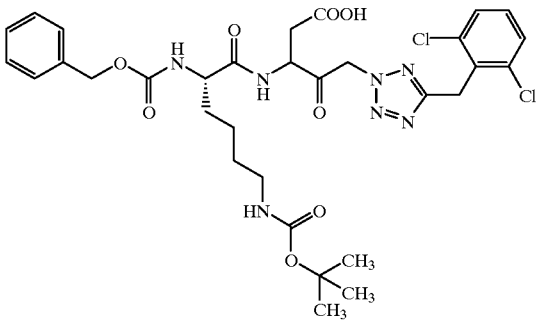

TLC: Rf 0.38 (chloroform:methanol:acetic acid=18:1:1); NMR (DMSO-d$_6$): δ 8.72–8.55 (1H, m), 7.61–7.43 (3H, m), 7.43–7.05 (6H, m), 6.81–6.70 (1H, m), 5.92–5.53 (2H, m), 4.99 (2H, s), 4.72–4.55 (1H, m), 4.50 (2H, s), 4.04–3.87 (1H, m), 2.96–2.79 (4H, m), 2.72–2.56 (2H, m), 1.71–1,12 (15H, m).

Example 25(5)

N-phenylcarbonyl-3-amino-4-oxo-5-(5-(2,6-dichlorophenyl methyl) tetrazol-2-yl)pentanoic acid

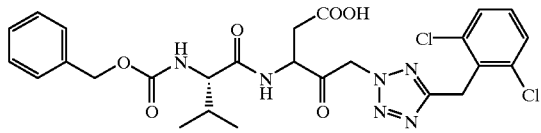

TLC: Rf 0.48 (chloroform:methanol:acetic acid=18:1:1); NMR (CDCl$_3$): δ 12.60–12.25 (1H, br), 9.12–9.00 (1H, m), 7.95–7.86 (2H, m), 7.65–7.10 (6H, m), 6.00–5.87 (2H, m), 5.02–4.89 (1H, m), 4.50 (2H, s), 3.00–2.80 and 2.80–2.58 (2H, m).

Example 25(6)

N-(2-phenylethylcarbonyl)-3-amino-4-oxo-5-(5-(2,6-dichlorophenylmethyl)tetrazol-2-yl)pentanoic acid

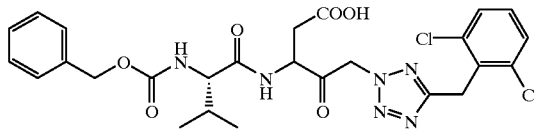

TLC: Rf 0.50 (chloroform:methanol:acetic acid=18:1:1); NMR (DMSO-d$_6$): δ 12.65–12.30 (1H, br), 8.65–8.52 (1H, m), 7.53 (2H, dd, J=9.0, 7.4 Hz), 7.34 (1H, dd, J=9.0, 7.4 Hz), 7.29–7.00 (6H, m), 5.68–5.52 (2H, m), 4.74–4.58 (1H, m), 4.51 (2H, s), 2.93–2.40 (6H, m).

Example 25(7)

N-phenyloxymethylcarbonyl-3-amino-4-oxo-5-(5-(2,6-dichlorophenylmethyl)tetrazol-2-yl)pentanoic acid

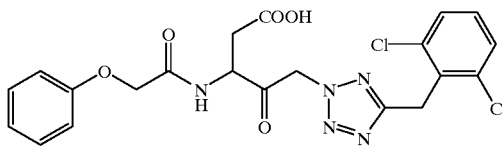

TLC: Rf 0.61 (chloroform:methanol:acetic acid=50:1:1); NMR (DMSO-d$_6$): δ 12.62–12.30 (1H, br), 8.77–7.66 (1H, m), 7.52 (2H, d, J=7.5 Hz), 7.44–7.22 (4H, m), 7.02–6.88 (3H, m), 5.91–5.75 (2H, m), 5.00–4.81 (1H, m), 4.61 (2H, s), 4.51 (2H, s), 2.92–2.56 (2H, m).

Example 25(8)

N-(2-(hexahydro-2-oxo-azepin-1-yl)propionyl)-3-amino-4-oxo-5-(5-(2,6-dichlorophenylmethyl)tetrazol-1-yl)pentanoic acid

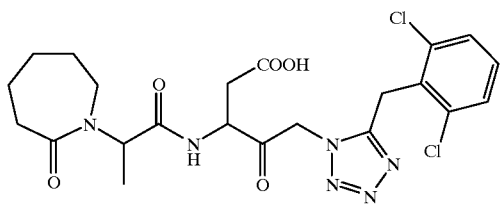

TLC: Rf 0.40 (chloroform:methanol:acetic acid=18:11); NMR (DMSO-d$_6$): δ 13.09–11.98 (1H, br), 8.74–8.43 (1H, m), 7.60–7.29 (3H, m), 5.83 (2H, brs), 5.06–4.86 (1H, m), 4.85–4.62 (1H, m), 4.34 (2H, s), 3.35 (2H, brs), 2.97–2.56 (2H, m), 2.47 (2H, brs), 1.95–1.30 (6H, m), 1.27 (3H, d, J=7.2 Hz).

Example 25(9)

N-(2S-(tetrahydro-5-oxo-1,4-benzooxsazepin-4-yl)propionyl)-3-amino-4-oxo-5-(5-(2,6-dichlorophenylmethyl)tetrazol-1-yl)pentanoic acid

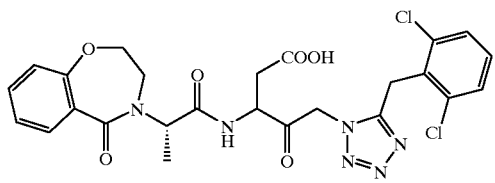

TLC: Rf 0.42 (chloroform:methanol:acetic acid=18:1:1); NMR (DMSO-d$_6$): δ 12.98–12.14 (1H, br), 9.12–8.70 (1H, m), 7.75–7.26 (5H, m), 7.10–6.86 (2H, m), 6.07–5.63 (2H, brs), 5.28–4.96 (1H, m), 4.96–4.60 (1H, m), 4.52–4.12 (4H, m), 3.76–3.42 (2H, m), 3.03–2.55 (2H, m), 1.44 (3H, d, J=7.2 Hz).

Example 25(10)

N-(2S-(2,3-indol-3,4-tetrahydro-2-oxo-azepin-1-yl)propionyl)-3-amino-4-oxo-5-(5-(2,6-dichlorophenylmethyl)tetrazol-1-yl)pentanoic acid

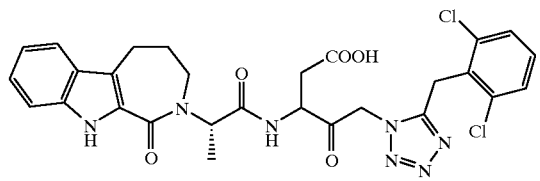

TLC: Rf 0.30 (chloroform:methanol:acetic acid=18:1:1); NMR (DMSO-d$_6$): δ 12.90–12.16 (1H, br), 11.18 (1H, s), 8.97–8.64 (1H, m), 7.68–6.86 (7H, m), 5.88 (1H, brs), 5.43–5.10 (1H, m), 4.98–4.62 (1H, m), 4.49–4.12 (1H, m), 3.70–3.35 (2H, m), 3.15–2.53 (4H, m), 2.36–1.82 (2H, m), 1.55–1.20 (3H, m).

Example 25(11)

N-(2-(4-fluorophenyl)-4-oxo-5-benzyloxocarbonylaminopyrimidin-3-yl)methylcarbonyl-3-amino-4-oxo-5-(5-(2,6-dichlorophenylmethyl)tetrazol-1-yl)pentanoic acid

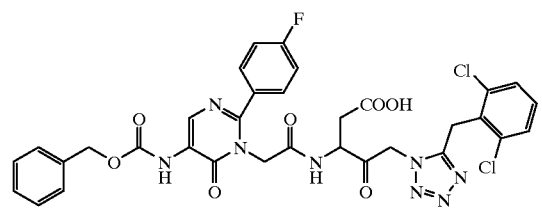

TLC: Rf 0.31 (chloroform:methanol=4:1); NMR (DMSO-d$_6$): δ 9.21 (1H, m), 8.86 (1H, brs), 8.48 (1H, s), 7.70 14 7.20 (12H, m), 5.82 (2H, br), 5.12 (2H, s), 4.78 (1H, m), 4,.58 (2H, brs), 4.27 (2H, brs), 2.80 (2H, m).

EXAMPLE 26(1) and EXAMPLE 26(2)

By the same procedure as provided in reference example 11(1) and if necessary, by known methods converted to accommodate the corresponding salts, using the compounds prepared in example 24(4) or example 25(4), the compounds of the present invention having the following physical data were obtained.

Example 26(1)

N-(N-benzyloxycarbonyl-L-lysinyl)-3-amino-4-oxo-5-(5-(2,6-dichlorophenylmethyl)tetrazol-2-yl)pentanoic acid•ethylester•hydrochloric acid salt

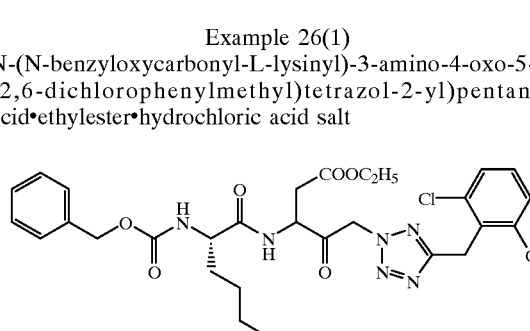

TLC: Rf 0.38 (chloroform:methanol:acetic acid=8:1:1); NMR (DMSO-d$_6$): δ 8.90–8.79 and 8.79–8.66 (1H, m), 7.92–7.65 (3H, br), 7.65–7.55 (1H, m), 7.50 (2H, d, J=7.5 Hz), 7.43–7.10 (6H, m), 5.95–5.53 (2H, m), 5.00 (2H, s), 4.91–4.65 (1H, m), 4.51 (2H, s), 4.13–3.83 (3H, m), 2.93–2.55 (4H, m), 1.75–1.22 (6H, m), 1.16 (3H, t, J=7.2 Hz).

Example 26(2)
N-(N-benzyloxycarbonyl-L-lysinyl)-3-amino-4-oxo-5-(5-(2,6-dichlorophenylmethyl)tetrazol-2-yl)pentanoic acid•hydrochloric acid salt

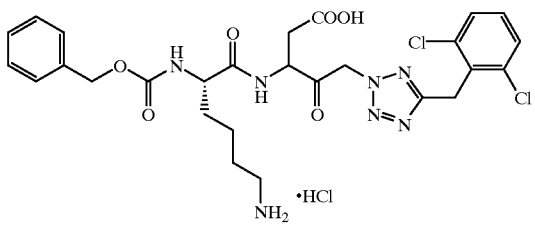

TLC: Rf 0.11 (chloroform:methanol:water=70:30:3); NMR (DMSO-d$_6$): δ 12.80–12.18 (1H, br), 8.87–8.65 (1H, m), 8.10–7.70 (3H, m), 7.70–7.45 (3H, m), 7.45–7.12 (6H, m), 5.99–5.50 (2H, m), 5.00 (2H, s), 4.84–4.59 (1H, m), 4.51 (2H, s), 4.07–3.87 (1H, m), 2.90–2.55 (4H, m), 1.72–1.19 (6H, m).

EXAMPLES 27(1)–27(9)

By the same procedure as provided in example 1, using the corresponding tetrazole compounds and the corresponding bromo compounds instead of N-((N-(3-phenylpropionyl)-L-valyl)-L-alanyl)-3-amino-4-oxo-5-bromopentanoic acid•t-butylester, compounds of the present invention having the following physical data were obtained.

Example 27(1)
N-(2-methylbenzyloxy)carbonyl-3-amino-4-oxo-5-(5-(2,6-dichlorophenylmethyl)tetrazol-2-yl)pentanoic acid•ethylester

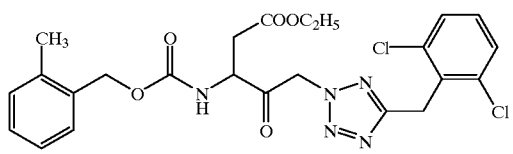

TLC: Rf 0.43 (hexane:ethyl acetate=2:1); NMR (CDCl$_3$): δ 7.40–7.09 (7H, m), 6.02–5.86 (1H, m), 5.78 and 5.60 (each 1H, d, J=18.0 Hz), 5.18 (2H, s), 4.76–4.62 (1H, m), 4.59 (2H, s), 4.12 (2H, q, J=7.0 Hz), 3.06 (1H, dd, J=17.5 Hz, 5.0 Hz), 2.77 (1H, dd, J=17.5 Hz, 5.0 Hz), 2.35 (3H, s), 1.23 (3H, t, J=7.0 Hz).

Example 27(2)
N-(pyridin-4-ylmethyloxy)carbonyl-3-amino-4-oxo-5-(5-(2,6-dichlorophenylmethyl)tetrazol-2-yl)pentanoic acid•ethylester

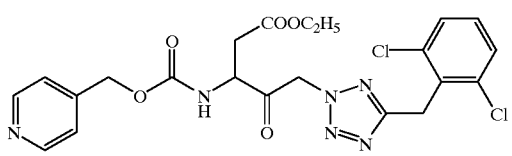

TLC: Rf 0.40 (chloroform:methanol=19:1); NMR (DMSO-d$_6$): δ 8.55 (2H, d, J=5.8 Hz), 8.12 (1H, d, J=9.5 Hz), 7.57–7.28 (3H, m), 7.34 (2H, d, J=5.8 Hz), 5.96 (each 1H, s), 5.14 (2H, s), 4.76–4.60 (1H, m), 4.52 (2H, s), 4.06 (2H, q, J=7.2 Hz), 2.86 (1H, dd, J=17.5 Hz, 5.0 Hz), 2.70 (1H, dd, J=17.5 Hz, 6.0 Hz), 2.35 (3H, s), 1.16 (3H, t, J=7.2 Hz).

Example 27(3)
N-(tetrahydrofuran-3-yloxy)carbonyl-3-amino-4-oxo-5-(5-(2,6-dichlorophenylmethyl)tetrazol-2-yl)pentanoic acid•ethylester

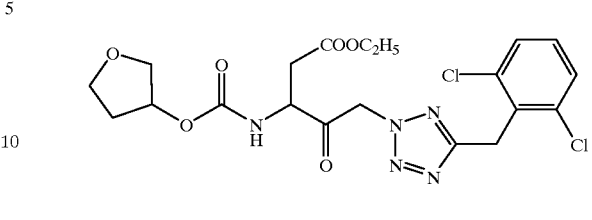

TLC: Rf 0.33 (chloroform:methanol=19:1); NMR (CDCl$_3$): δ 7.34 (1H, d, J=8.8 Hz), 7.34 (1H, d, J=7.6 Hz), 7.18 (1H, dd, J=8.8 Hz, 7.6 Hz), 5.95 (1H, d, J=9.5 Hz), 5.80 and 5.62 (each 1H, d, J=18.0 Hz), 5.41–5.19 (1H, m), 4.73–4.52 (1H, m), 4.60 (2H, s), 4.15 (2H, q, J=7.0 Hz), 4.02–3.75 (4H, m), 3.15–2.98 and 2.78–2.69 (2H, m), 2.32–1.92 (2H, s), 1.25 (3H, t, J=7.0 Hz).

Example 27(4)
N-(3-chlorobenzyloxy)carbonyl-3-amino-4-oxo-5-(5-(2,6-dichlorophenylmethyl)tetrazol-2-yl)pentanoic acid•ethylester

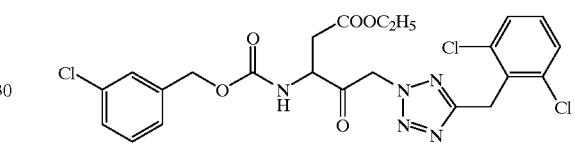

TLC: Rf 0.71 (hexane:ethyl acetate=1:1); NMR (CDCl$_3$): δ 7.45–7.10 (7H, m), 6.01–5.86 (1H, m), 5.78 and 5.61 (each 1H, d, J=18.0 Hz), 5.12 (2H, s), 4.74–4.55 (1H, m), 4.60 (2H, s), 4.15 (2H, q, J=7.2 Hz), 3.08 (1H, dd, J=17.5 Hz, 4.5 Hz), 2.76 (1H, dd, J=17.5 Hz, 5.0 Hz), 1.24 (3H, t, J=7.2 Hz).

Example 27(5)
N-(2-propenoxy)carbonyl-3-amino-4-oxo-5-(5-(2,6-dichlorophenylmethyl)tetrazol-2-yl)pentanoic acid•ethylester

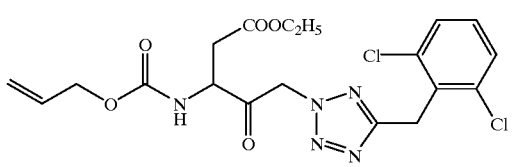

TLC: Rf 0.33 (hexane:ethyl acetate=2:1); NMR (CDCl$_3$): δ 7.26 (1H, d, J=8.6 Hz), 7.26 (1H, d, J=7.4 Hz), 7.09 (1H, dd, J=8.6 Hz, 7.4 Hz), 6.00–5.73 (2H, m), 5.75 and 5.56 (each 1H, d, J=18.0 Hz), 5.25 (1H, dd, J=17.2 Hz, 1.0 Hz), 5.18 (1H, dd, J=1 1.2 Hz, 1.0 Hz), 4.68–4.45 m), 4.54 (2H, s), 4.52 (2H, s), 4.06 (2H, q, J=7.0 Hz), 2.98 (1H, dd, J=17.5 Hz, 4.5 Hz), 2.72 (1H, dd, J=17.5 Hz, 5.0 Hz), 1.16 (3H, t, J=7.0 Hz).

Example 27(6)
N-(naphthalen-2-ylmethyloxy)carbonyl-3-amino-4-oxo-5-(5-(2,6-dichlorophenylmethyl)tetrazol-2-yl)pentanoic acid•ethylester

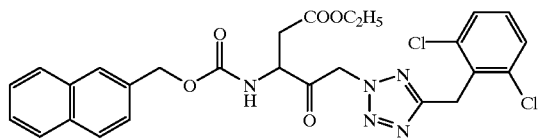

TLC: Rf 0.41 (hexane:ethyl acetate=2:1); NMR (CDCl$_3$): δ 7.92–7.75 and 7.56–7.41 (7H, m), 7.34 (1H, d, J=8.8 Hz), 7.33 (1H, d, J=7.6 Hz), 7.18 (1H, dd, J=8.8 Hz, 7.6 Hz), 6.02–5.87 (1H, m), 5.78 and 5.59 (each 1H, d, J=18.0 Hz), 5.32 (2H, s), 4.72–4.50 (1H, m), 4.60 (2H, s), 2.99 (1H, dd, J=17.5 Hz, 4.5 Hz), 2.72 (1H, dd, J=17.5 Hz, 5.0 Hz), 1.40 (9H, s).

Example 27(7)

N-(naphthalen-1-ylmethyloxy)carbonyl-3-amino-4-oxo-5-(5-(2,6-dichlorophenylmethyl)tetrazol-2-yl)pentanoic acid•ethylester

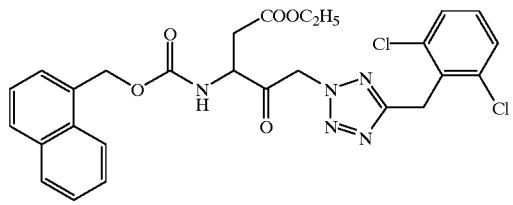

TLC: Rf 0.44 (hexane:ethyl acetate=2:1); NMR (CDCl$_3$): δ 8.11–7.98, 7.95–7.81 and 7.63–7.40 (7H, m), 7.34 (1H, d, J=9.0 Hz), 7.34 (1H, d, J=7.0 Hz), 7.18 (1H, dd, J=9.0 Hz, 7.0 Hz), 5.96–5.85 (1H, m), 5.76 (1H, d, J=18.0 Hz), 5.64 (2H, s), 5.58 (1H, d, J=18.0 Hz), 4.72–4.50 (1H, m), 4.60 (2H, s), 2.99 (1H, dd, J=17.5 Hz, 4.0 Hz), 2.68 (1H, dd, J=17.5 Hz, 4.5 Hz), 1.38 (9H, s).

Example 27(8)

N-(2-phenylethylthio)carbonyl-3-amino-4-oxo-5-(5-(2,6-dichlorophenylmethyl)tetrazol-2-yl)pentanoic acid•ethylester

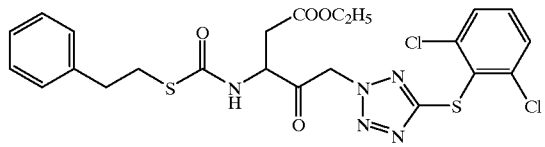

TLC: Rf 0.63 (hexane:ethyl acetate=1:1); NMR (CDCl$_3$): δ 7.48–7.42 (2H, m), 7.34–7.14 (6H, m), 6.56 (1H, d, J=8.4 Hz), 5.67 (1H, d, J=17.8 Hz), 5.46 (1H, d, J=17.8 Hz), 4.87 (1H, m), 4.15 (2H, q, J=7.2 Hz), 3.23 (2H, m), 3.08 (1H, dd, J=17.4 Hz, 4.4 Hz), 2.93 (2H, m), 2.74 (1H, dd, J=7.4 Hz, 4.8 Hz), 1.25 (3H, t, J=7.2 Hz).

Example 27(9)

N-(2-phenylethylthio)carbonyl-3-amino-4-oxo-5-(5-(2,6-dichlorophenylmethyl)tetrazol-1-yl)pentanoic acid•ethylester

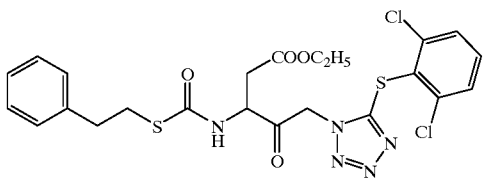

TLC: Rf 0.54 (hexane:ethyl acetate=1:1); NMR (CDCl$_3$): δ 7.48–7.43 (2H, m), 7.37–7.17 (6H, m), 6.62 (1H, d, J=8.8 Hz), 5.61 (1H, d, J=18.6 Hz), 5.40 (1H, d, J=18.6 Hz), 4.93 (1H, m), 4.18 (2H, q, J=7.2 Hz), 3.28 (2H, m), 3.16 (1H, dd, J=17.6 Hz, 4.4 Hz), 2.96 (2H, m), 2.79 (1H, dd, J=17.4 Hz, 5.0 Hz), 1.28 (3H, t, J=7.2 Hz).

EXAMPLES 28(1)–28(7)

By the same procedure as provided in example 23(1), using the compounds prepared in examples 27(1)–27(7), the compounds of the present invention having the following physical data were obtained.

Example 28(1)

N-(2-methylbenzyloxy)carbonyl-3-amino-4-oxo-5-(5-(2,6-dichlorophenylmethyl)tetrazol-2-yl)pentanoic acid

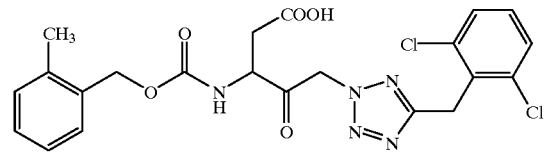

TLC: Rf 0.25 (chloroform:methanol=50:1); NMR (DMSO-d$_6$): δ 12.65–12.30 (1H, br), 8.02–7.86 (1H, m), 7.51 (2H, d, J=7.5 Hz), 7.42–7.25 (2H, m), 7.25–7.10 (3H, m), 5.98–5.83 (2H, m), 5.07 (2H, s), 4.67–4.53 (1H, m), 4.50 (2H, s), 2.88–2.40 (2H, m), 2.28 (3H, s).

Example 28(2)

N-(pyridin-4-ylmethyloxy)carbonyl-3-amino-4-oxo-5-(5-(2,6-dichlorophenylmethyl)tetrazol-2-yl)pentanoic acid

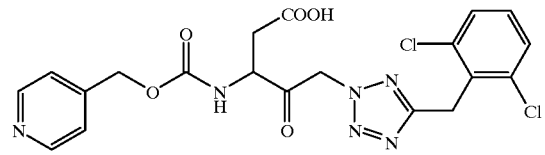

TLC: Rf 0.46 (chloroform:methanol:acetic acid=8:1:1); NMR (DMSO-d$_6$): δ 12.80–12.25 (1H, br), 8.70–8.45 (2H, m), 8.18–8.01 (1H, m), 7.53 (2H, d, J=7.0 Hz), 7.46–7.28 (3H, m), 6.10–5.80 (2H, m), 5.13 (2H, s), 4.70–4.56 (1H, m), 4.51 (2H, s), 2.91–2.56 (2H, m).

Example 28(3)

N-(tetrahydrofuran-3-yloxy)carbonyl-3-amino-4-oxo-5-(5-(2,6-dichlorophenylmethyl)tetrazol-2-yl)pentanoic acid

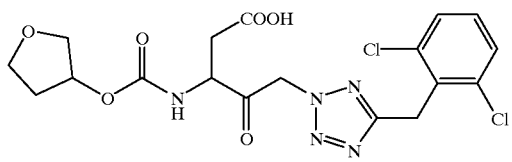

TLC: Rf 0.46 (chloroform:methanol:acetic acid=18:1:1); NMR (DMSO-d$_6$): δ 7.88–7.76 (1H, m), 7.52 (1H, d, J=8.8 Hz), 7.51 (1H, d, J=6.8 Hz), 7.37 (1H, dd, J=8.8 Hz, 6.8 Hz), 5.95–5.78 (2H, m), 5.20–5.07 (1H, m), 4.61–4.43 (1H, m), 4.50 (2H, s), 3.83–3.60 (4H, m), 2.87–2.20 (2H, m), 2.23–2.00 and 2.00–1.80 (each 1H, m).

Example 28(4)
N-(3-chlorobenzyloxy)carbonyl-3-amino-4-oxo-5-(5-(2,6-dichlorophenylmethyl)tetrazol-2-yl)pentanoic acid

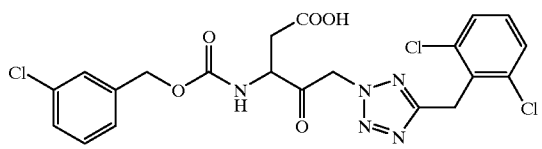

TLC: Rf 0.20 (chloroform:methanol:acetic acid=50:11); NMR (DMSO-d$_6$): δ 8.00–7.87 (1H, m), 7.60–7.27 (7H, m), 6.00–5.80 (2H, m), 5.07 (2H, s), 4.67–4.42 (1H, m), 4.50 (2H, s), 2.86–2.54 (2H, m).

Example 28(5)
N-(2-propenoxy)carbonyl-3-amino-4-oxo-5-(5-(2,6-dichlorophenylmethyl)tetrazol-2-yl)pentanoic acid

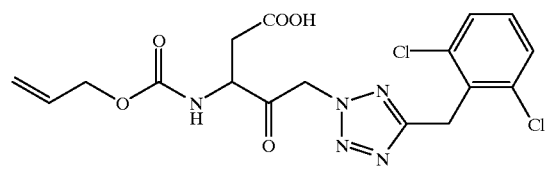

TLC: Rf 0.22 (chloroform:methanol:acetic acid=50:1:1); NMR (DMSO-d$_6$): δ 12.53–12.30 (1H, m), 7.58 and 7.57 (total 2H, each d, J=8.4 Hz and 7.0 Hz), 7.43 (1H, dd, J=8.4 Hz and 7.0 Hz), 6.10–5.84 (3H, m), 5.36 (1H, dd, J=17.4 Hz, 1.4 Hz), 5.25 (1H, dd, J=10.6 Hz, 1.4 Hz), 4.74–4.5 (1H, m), 4.58 (2H, d, J=5.2 Hz), 4.57 (2H, s), 2.93–2.52 (2H, m).

Example 28(6)
N-(naphthalen-2-ylmethyloxy)carbonyl-3-amino-4-oxo-5-(5-(2,6-dichlorophenylmethyl)tetrazol-2-yl)pentanoic acid

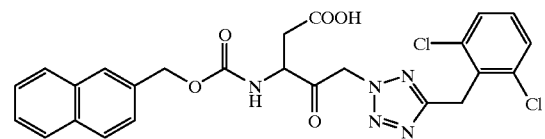

TLC: Rf 0.26 (chloroform:methanol:acetic acid=50:1:1); NMR (DMSO-d$_6$): δ 8.08–7.81 (5H, m), 7.58–7.42 (5H, m), 7.36 (2H, d, J=9.0 Hz, 7.5 Hz), 6.03–5.80 (2H, m), 5.25 (2H, s), 4.70–4.55 (1H, m), 4.52 (2H, s), 2.91–2.53 (2H, m).

Example 28(7)
N-(naphthalen-1-ylmethyloxy)carbonyl-3-amino-4-oxo-5-(5-(2,6-dichlorophenylmethyl)tetrazol-2-yl)pentanoic acid

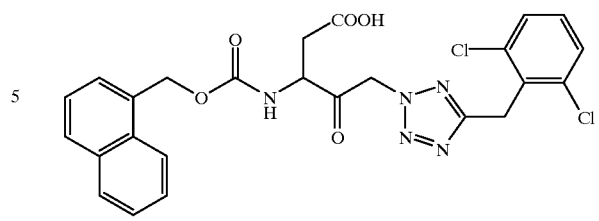

TLC: Rf 0.63 (chloroform:methanol:acetic acid=18:1:1); NMR (DMSO-d$_6$): δ 8.12–7.84 and 7.65–7.26 (total 11H, m), 6.07–5.78 (2H, m), 5.56 (2H, s), 4.70–4.55 (1H, m), 4.52 (2H, s), 2.9,0–2.55 (2H, m).

Example 29(1)
N-(4-t-butylphenyl)sulfonyl-3-amino-4-oxo-5-(5-(2,6-dichlorophenylmethyl)tetrazol-1-yl)pentanoic acid•t-butylester

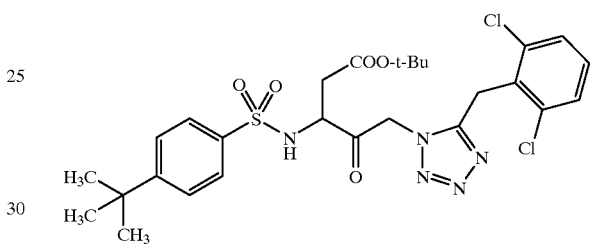

To a solution of the compound prepared in reference example (725 mg) in dichloromethane (5 ml) was added 4-t-butylbenzenesulfonyl chloride (524 mg), triethylamine (0.2 ml) and dimethylaminopyridine (185 mg) at 0° C., successively. The reaction mixture was stirred for 6 h for room temperature. The reaction mixture was quenched by addition of 1N aqueous solution of hydrochloric acid, extracted with ethyl acetate. The extract was washed with water and a saturated aqueous solution of sodium chloride, successively, dried over anhydrous magnesium sulfate and concentrated. The residue was purified by column chromatography on silica gel (hexane:ethyl acetate=3:1) to give the compound of the present invention (526 mg) having the following physical data.

TLC: Rf 0.46 (hexane:ethyl acetate=2:1); NMR (DMSO-d$_6$): δ 7.91–7.72 (2H, m), 7.68–7.50 (2H, m), 7.46–7.16 (3H, m), 6.01 (1H, d, J=9.2 Hz), 5.76 (1H, d, J=18.8 Hz), 5.63 (1H, d, J=18.8 Hz), 4.29 (2H, s), 4.21–4.02 (1H, m), 2.96 (1H, dd, J=17.6 and 4.2 Hz), 2.40 (1H, dd, J=17.6 and 4.4 Hz), 1.37 (9H, s), 1.36 (9H, s).

EXAMPLES 29(2)–29(74)

By the same procedure as provided in example 29(1), using the compounds prepared in reference example 9(1) or reference example 9(2) and the corresponding sulfonyl chloride compounds, the compounds of the present invention having the following physical data were obtained.

Example 29(2)
N-phenylmethylsulfonyl-3-amino-4-oxo-5-(5-(2,6-dichlorophenylmethyl)tetrazol-2-yl)pentanoic acid•t-butylester

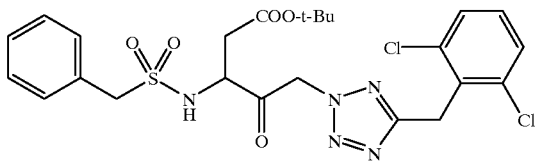

TLC: Rf 0.77 (chloroform:methanol=19:1); NMR (DMSO-d$_6$): δ 7.90 (1H, d, J=9.0 Hz), 7.58–7.29 (8H, m), 5.98 (2H, m), 4.52 (4H, m), 2.77–2.64 (2H, m), 1.38 (9H, s).

Example 29(3)

N-phenylsulfonyl-3-amino-4-oxo-5-(5-(2,6-dichlorophenylmethyl)tetrazol-2-yl)pentanoic acid•t-butylester

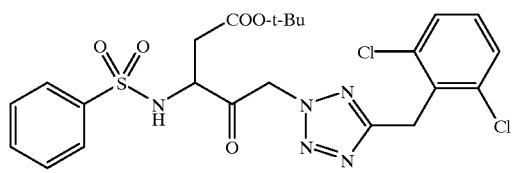

TLC: Rf 0.57 (chloroform:methanol=19:1); NMR (CDCl$_3$): δ 7.93–7.83 and 7.71–7.48 (5H, m), 7.35 (1H, d, J=9.0 Hz), 7.35 (1H, d, J=7.0 Hz), 7.18 (1H, dd, J=9.0 Hz, 7.0 Hz), 6.07 (1H, J=9.5 Hz), 5.83 and 5.62 (each 1H, d, J=18.0 Hz), 4.59 (2H, s), 4.20–4.05 (1H, m), 2.82 (1H, dd, J=17.5 Hz, 4.0 Hz), 2.24 (1H, dd, J=17.5 Hz, 4.5 Hz), 1.37 (9H, s).

Example 29(4)

N-(2-(naphthalen-1-yl)ethyl)sulfonyl-3-amino-4-oxo-5-(5-(2,6-dichlorophenylmethyl)tetrazol-2-yl)pentanoic acid•t-butylester

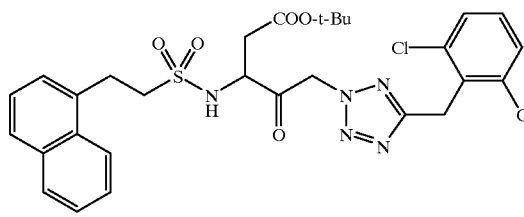

TLC: Rf 0.43 (hexane:ethyl acetate=2:1); NMR (CDCl$_3$): δ 8.11–7.73 and 7.63–7.08 (10H, m), 5.72 and 5.58 (each 1H, d, J=18.0 Hz), 4.58 (2H, s), 4.32–4.19 (1H, m), 3.74–3.55 and 3.53–3.37 (total 4H, m), 2.91 (1H, dd, J=17.5 Hz, 4.5 Hz), 2.52 (1H, dd, J=17.5 Hz, 5.0 Hz), 1.38 (9H, s).

Example 29(5)

N-(naphthalen-2-yl)sulfonyl-3-amino-4-oxo-5-(5-(2,6-dichlorophenylmethyl)tetrazol-2-yl)pentanoic acid•t-butylester

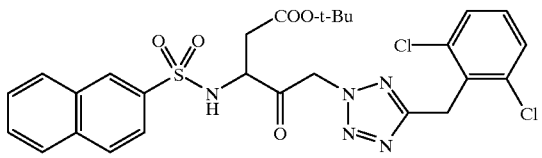

TLC: Rf 0.24 (hexane:ethyl acetate=3:1); NMR (CDCl$_3$): δ 8.45 (1H, m), 8.07–7.59 (6H, m), 7.34 (1H, d, J=9.0 Hz), 7.34 (1H, d, J=7.0 Hz), 7.17 (1H, dd, J=9.0 Hz, 7.0 Hz), 6.20 (1H, d, J=9.5 Hz), 5.88 and 5.67 (each 1H, d, J=18.0 Hz), 4.58 (2H, s), 4.26 (1H, m), 2.79 (1H, dd, J=17.5 Hz, 4.0 Hz), 2.20 (1H, dd, J=17.5 Hz, 4.5 Hz), 1.33 (9H, s).

Example 29(6)

N-(naphthalen-1-yl)sulfonyl-3-amino-4-oxo-5-(5-(2,6-dichlorophenylmethyl)tetrazol-2-yl)pentanoic acid•t-butylester

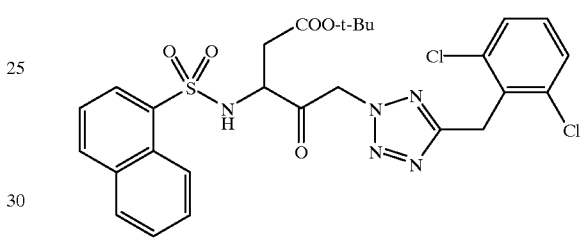

TLC: Rf 0.21 (hexane:ethyl acetate=3:1); NMR (CDCl$_3$): δ 8.62–8.50, 8.35–8.26, 8.18–8.07, 8.05–7.94 and 7.76–7.46 (7H, m), 7.33 (1H, d, J=9.0 Hz), 7.33 (1H, d, J=7.0 Hz), 7.16 (1H, dd, J=9.0 Hz, 7.0 Hz), 6.50–6.39 (1H, m), 5.84 and 5.56 (each 1H, d, J=18.0 Hz), 4.57 (2H, s), 4.12–3.95 (1H, m), 2.65 (1H, dd, J=17.5 Hz, 4.0 Hz), 1.78 (1H, dd, J=17.5 Hz, 5.0 Hz), 1.24 (9H, s).

Example 29(7)

N-(2-phenylethenyl)sulfonyl-3-amino-4-oxo-5-(5-(2,6-dichlorophenylmethyl)tetrazol-2-yl)pentanoic acid•t-butylester

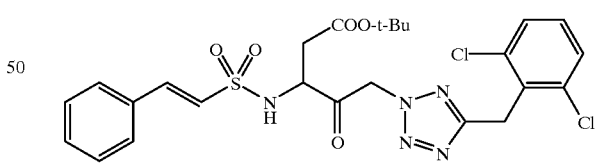

TLC: Rf 0.53 (hexane:ethyl acetate=3:1); NMR (DMSO-d$_6$): δ 7.55 (1H, d, J=15.6 Hz), 7.52–7.40 (5H, m), 7.36–7.17 (3H, m), 6.77 (1H, d, J=15.6 Hz), 5.92 (1H, d, J=18.2 Hz), 5.73 (1H, d, J=18.2 Hz), 4.59 (2H, s), 4.20 (1H, m), 2.98 (1H, dd, J=17.4, 4.2 Hz), 2.70 (1H, dd, J=17.4, 4.2 Hz), 1.39 (9H, s).

Example 29(8)

N-(4-bromophenyl)sulfonyl-3-amino-4-oxo-5-(5-(2,6-dichlorophenylmethyl)tetrazol-2-yl)pentanoic acid•t-butylester

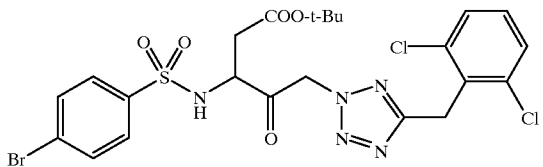

TLC: Rf 0.44 (hexane:ethyl acetate=2:1); NMR (DMSO-$d_6$): δ 7.76 and 7.66 (each 2H, d, J=8.5 Hz), 7.34 (1H, d, J=9.0 Hz), 7.34 (1H, d, J=7.0 Hz), 7.16 (1H, dd, J=9.0 Hz, 7.0 Hz), 6.12 (1H, d, J=9.6 Hz), 5.84 and 5.64 (each 1H, d, J=18.0 Hz), 4.60 (2H, s), 4.19–4.03 (1H, m), 2.82 (1H, dd, J=17.8 Hz, 3.8 Hz), 2.31 (1H, dd, J=17.8 Hz, 4.6 Hz), 1.38 (9H, s).

Example 29(9)

N-butylsulfonyl-3-amino-4-oxo-5-(5-(2,6-dichlorophenylmethyl)tetrazol-2-yl)pentanoic acid•t-butylester

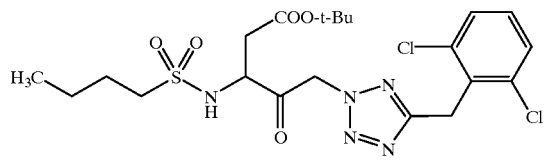

TLC: Rf 0.60 (hexane:ethyl acetate=2:1); NMR (CDCl$_3$): δ 7.37–7.24 (3H, m), 5.89 (2H, d, J=7.2 Hz), 5.74 (1H, d, J=17.2 Hz), 4.61 (1H, s), 4.38–4.28 (1H, m), 3.12–3.02 (2H, m), 2.98 (1H, dd, J=17.0, 4.6 Hz), 2.74 (1H, dd, J=17.0, 4.6 Hz), 1.91–1.79 (2H, m), 1.63–1.61 (2H, m), 1.43 (9H, s), 0.96 (3H, t, J=7.2 Hz).

Example 29(10)

N-(quinolin-8-yl)sulfonyl-3-amino-4-oxo-5-(5-(2,6-dichlorophenylmethyl)tetrazol-2-yl)pentanoic acid•t-butylester

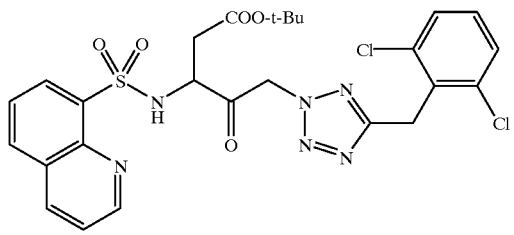

TLC: Rf 0.46 (hexane:ethyl acetate=1:1); NMR (CDCl$_3$): δ 9.02 (1H, dd, J=4.3, 1.7 Hz), 8.47–8.10 (3H, m), 7.73–7.55 (2H, m), 7.44 (1H, d, J=7.5 Hz), 7.37–7.13 (4H, m), 6.02 (1H, d, J=16.6 Hz), 5.87 (1H, d, J=16.6 Hz), 4.60 (2H, s), 4.48–4.41 (1H, m), 2.66 (1H, dd, J=17.0, 4.5 Hz), 2.96 (1H, dd, J=17.0, 4.5 Hz), 1.27 (9H, s).

Example 29(11)

N-(5-dimethylaminonaphthalen-1-yl)sulfonyl-3-amino-4-oxo-5-(5-(2,6-dichlorophenylmethyl)tetrazol-2-yl) pentanoic acid•t-butylester

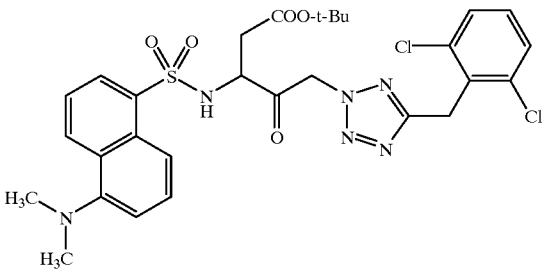

TLC: Rf 0.58 (hexane:ethyl acetate=2:1); NMR (CDCl$_3$): δ 8.60 (1H, d, J=8.5 Hz), 8.31–8.19 (2H, m), 7.63–7.52 (2H, m), 7.36–7.13 (5H, m), 6.39 (1H, d, J=9.9 Hz), 5.84 (1H, d, J=18.2 Hz), 5.55 (1H, d, J=18.2 Hz), 4.58 (2H, s), 4.05–3.96 (1H, m), 2.89 (6H, s), 2.66 (1H, dd, J=17.2, 4.5 Hz), 1.79 (1H, dd, J=17.2, 4.5 Hz), 1.25 (9H, s).

Example 29(12)

N-(4-nitrophenyl)sulfonyl-3-amino-4-oxo-5-(5-(2,6-dichlorophenylmethyl)tetrazol-2-yl)pentanoic acid•t-butylester

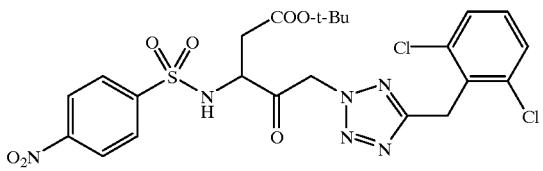

TLC: Rf 0.60 (chloroform:methanol=19:1); NMR (CDCl$_3$): δ 8.38 and 8.05 (each 2H, d, J=9.2 Hz), 7.36 (1H, d, J=8.8 Hz), 7.36 (1H, d, J=7.2 Hz), 7.20 (1H, dd, J=8.8 Hz, 7.2 Hz), 6.25 (1H, d, J=9.6 Hz), 5.71 and 5.56 (each 1H, d, J=18.0 Hz), 4.61 (2H, s), 4.27–4.10 (1H, m), 2.92 (1H, dd, J=17.8 Hz, 4.0 Hz), 2.38 (1H, dd, J=17.8 Hz, 5.0 Hz), 1.38 (9H, s).

Example 29(13)

N-phenylsulfonyl-3-amino-4-oxo-5-(5-(2,6-dichlorophenylmethyl)tetrazol-1-yl)pentanoic acid•t-butylester

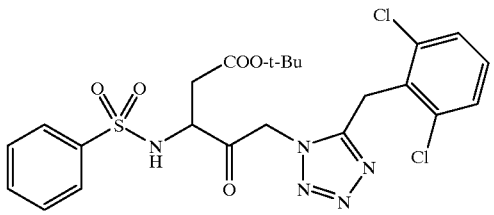

TLC: Rf 0.46 (hexane:ethyl acetate=1:1); NMR (DMSO-$d_6$): δ 8.66 (1H, d, J=10.0 Hz), 7.94–7.89 (2H, m), 7.65–7.33 (6H, m), 6.04–5.79 (2H, m), 4.53–4.42 (1H, m), 4.28 (2H, s), 2.65–2.61 (2H, m), 1.33 (9H, s).

Example 29(14)

N-(2-fluorophenyl)sulfonyl-3-amino-4-oxo-5-(5-(2,6-dichlorophenylmethyl)tetrazol-2-yl)pentanoic acid•t-butylester

447

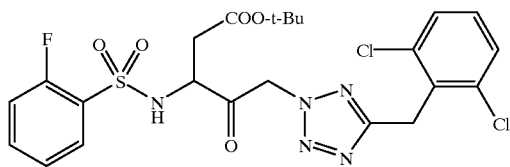

TLC: Rf 0.43 (hexane:ethyl acetate=2:1); NMR (CDCl₃): δ 7.92 (1H, dt, J=1.8, 7.8 Hz), 7.70–7.59 (1H, m), 7.37–7.14 (5H, m), 6.28 (1H, d, J=9.4 Hz), 5.92 (1H, d, J=18.0 Hz), 5.74 (1H, d, J=18.0 Hz), 4.60 (2H, s), 4.30–4.21 (1H, m), 2.92 (2H, dd, J=17.6, 3.7 Hz), 2.34 (2H, dd, J=17.6, 3.7 Hz), 1.40 (9H, s).

Example 29(15)

N-(4-fluorophenyl)sulfonyl-3-amino-4-oxo-5-(5-(2,6-dichlorophenylmethyl)tetrazol-2-yl)pentanoic acid•t-butylester

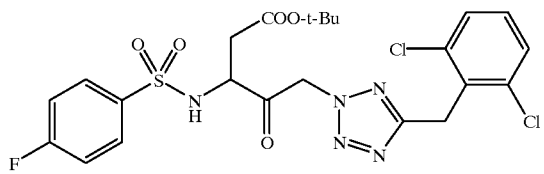

TLC: Rf 0.46 (hexane:ethyl acetate=2:1); NMR (CDCl₃): δ 7.93–7.86 (2H, m), 7.38–7.15 (5H, m), 6.08 (1H, d, J=8.5 Hz), 5.83 (1H, d, J=18.0 Hz), 5.63 (1H, d, J=18.0 Hz), 4.60 (2H, s), 4.18–4.08 (1H, m), 2.82 (2H, dd, J=17.4, 3.9 Hz), 2.30 (2H, dd, J=17.4, 3.9 Hz), 1.38 (9H, s).

Example 29(16)

N-(3-fluorophenyl)sulfonyl-3-amino-4-oxo-5-(5-(2,6-dichlorophenylmethyl)tetrazol-2-yl)pentanoic acid•t-butylester

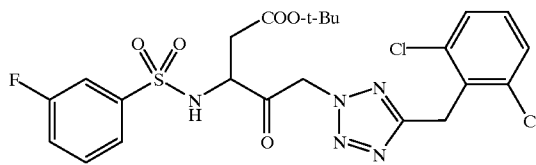

TLC: Rf 0.62 (chloroform:methanol=19:1); NMR (CDCl₃): δ 7.72–7.46 and 7.42–7.12 (7H, m), 6.23–6.10 (1H, m), 5.84 and 5.64 (each 1H, d, J=18.0 Hz), 4.60 (2H, s), 4.22–4.07 (1H, m), 2.84 (1H, dd, J=17.5 Hz, 4.0 Hz), 2.38 (1H, dd, J=17.5 Hz, 5.0 Hz), 1.37 (9H, s).

Example 29(17)

N-(2-bromophenyl)sulfonyl-3-amino-4-oxo-5-(5-(2,6-dichlorophenylmethyl)tetrazol-2-yl)pentanoic acid•t-butylester

448

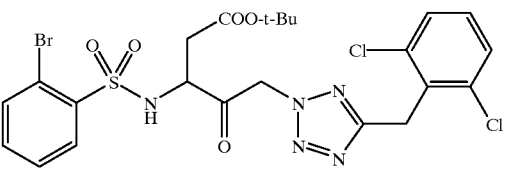

TLC: Rf 0.24 (hexane:ethyl acetate=3:1); NMR (CDCl₃): δ 8.20–8.08 (1H, m), 7.92–7.72 (1H, m), 7.60–7.40 (2H, m), 7.34 (1H, d, J=9.0 Hz), 7.34 (1H, d, J=7.0 Hz), 7.18 (1H, dd, J=9.0 Hz, 7.0 Hz), 6.68 (1H, d, J=9.6 Hz), 5.98 and 5.80 (each 1H, d, J=18.0 Hz), 4.60 (2H, s), 4.17–4.00 (1H, m), 2.88 (1H, dd, J=17.5 Hz, 4.0 Hz), 2.19 (1H, dd, J=17.5 Hz, 5.0 Hz), 1.40 (9H, s).

Example 29(18)

N-(4-methoxyphenyl)sulfonyl-3-amino-4-oxo-5-(5-(2,6-dichlorophenylmethyl)tetrazol-2-yl)pentanoic acid•t-butylester

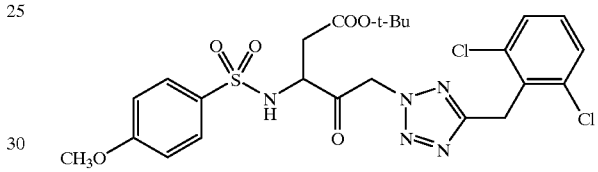

TLC: Rf 0.38 (hexane:ethyl acetate=2:1); NMR (CDCl₃): δ 7.81 (2H, d, J=9.0 Hz), 7.36–7.14 (3H, m), 7.01 (2H, d, J=9.0 Hz), 5.99 (1H, d, J=9.8 Hz), 5.85 (1H, d, J=16.9 Hz), 5.63 (1H, d, J=16.9 Hz), 4.60 (2H, s), 4.14–4.03 (1H, m), 2.81 (2H, dd, J=12.6, 3.7 Hz), 2.26 (2H, dd, J=12.6, 3.7 Hz), 1.37 (9H, s).

Example 29(19)

N-(4-trifluoromethylphenyl)sulfonyl-3-amino-4-oxo-5-(5-(2,6-dichlorophenylmethyl)tetrazol-2-yl)pentanoic acid•t-butylester

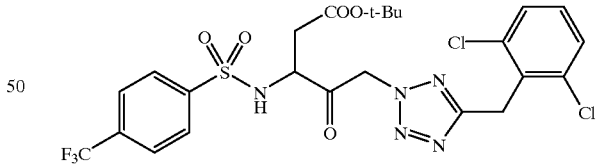

TLC: Rf 0.43 (hexane:ethyl acetate=2:1); NMR (DMSO-d₆): δ 8.01 (2H, d, J=8.8 Hz), 7.82 (2H, d, J=8.8 Hz), 7.37–7.15 (3H, m), 6.21 (1H, d, J=9.2 Hz), 5.84 (1H, d, J=17.9 Hz), 5.65 (1H, d, J=17.9 Hz), 4.61 (2H, s), 4.23–4.12 (1H, m), 2.81 (2H, dd, J=16.6, 4.0 Hz), 2.26 (2H, dd, J=16.6, 4.0 Hz), 1.36 (9H, s).

Example 29(20)

N-(thiophen-2-yl)sulfonyl-3-amino-4-oxo-5-(5-(2,6-dichlorophenylmethyl)tetrazol-2-yl)pentanoic acid•t-butylester

449

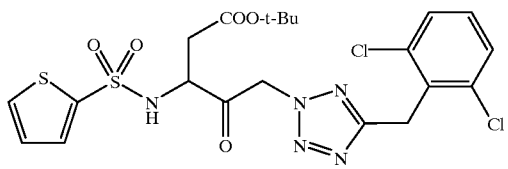

TLC: Rf 0.43 (hexane:ethyl acetate=2:1); NMR (DMSO-$d_6$): δ 7.68–7.65 (2H, m), 7.37–7.14 (3H, m), 7.13 (1H, t, J=4.4 Hz), 6.17 (1H, d, J=9.4 Hz), 5.86 (1H, d, J=18.1 Hz), 5.66 (1H, d, J=18.1 Hz), 4.60 (2H, s), 4.24–4.13 (1H, m), 2.89 (2H, dd, J=17.5, 3.7 Hz), 2.26 (2H, dd, J=17.5, 3.7 Hz), 1.38 (9H, s).

Example 29(21)

N-(3-phenylpropyl)sulfonyl-3-amino-4-oxo-5-(5-(2,6-dichlorophenylmethyl)tetrazol-2-yl)pentanoic acid•t-butylester

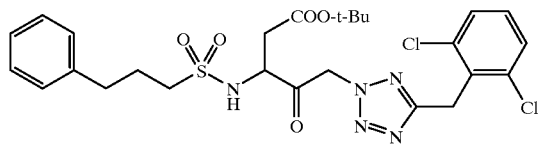

TLC: Rf 0.41 (hexane:ethyl acetate=2:1); NMR (CDCl$_3$): δ 7.40–7.10 (8H, m), 5.82 and 5.66 (each 1H, d, J=18.0 Hz), 4.61 (2H, s), 4.32–4.16 (1H, m), 3.12–2.52 (6H, m), 2.30–2.50 (2H, m), 1.42 (9H, s).

Example 29(22)

N-(2-fluorophenyl)sulfonyl-3-amino-4-oxo-5-(5-(2,6-dichlorophenylmethyl)tetrazol-1-yl)pentanoic acid•t-butylester

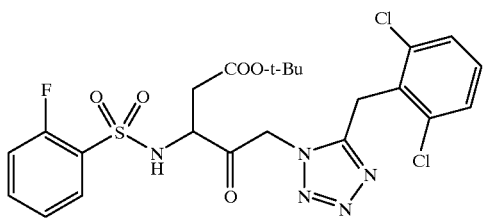

HPTLC: Rf 0.34 (hexane:ethyl acetate=2:1); NMR (CDCl$_3$): δ 7.96 (1H, m), 7.68 (1H, m), 7.46–7.10 (5H, m), 6.24 (1H, m), 5.84 and 5.75 (each 1H, each d, J=18.0 Hz), 4.30 (2H, s), 4.28 (1H, m), 3.05 and 2.45 (each 1H, each dd, J=17.5, 5.0 Hz), 1.40 (9H, s).

Example 29(23)

N-(4-chlorophenyl)sulfonyl-3-amino-4-oxo-5-(5-(2,6-dichlorophenylmethyl)tetrazol-2-yl)pentanoic acid•t-butylester

450

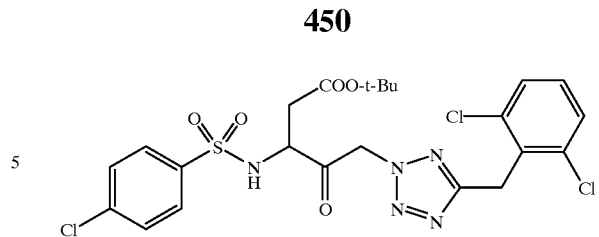

TLC: Rf 0.61 (chloroform:methanol=19:1); NMR (CDCl$_3$): δ 7.81 and 7.52 (each 2H, d, J=8.0 Hz), 7.35 (1H, d, J=8.0 Hz), 7.35 (1H, d, J=8.2 Hz), 7.19 (1H, dd, J=8.2 Hz, 7.0 Hz), 6.13 (1H, d, J=9.5 Hz), 5.84 and 5.64 (each 1H, d, J=18.0 Hz), 4.60 (2H, s), 4.21–4.05 (1H, m), 2.83 (1H, dd, J=17.5 Hz, 4.5 Hz), 2.33 (1H, dd, J=17.5 Hz, 5.0 Hz), 1.37 (9H, s).

Example 29(24)

N-(3-chlorophenyl)sulfonyl-3-amino-4-oxo-5-(5-(2,6-dichlorophenylmethyl)tetrazol-2-yl)pentanoic acid•t-butylester

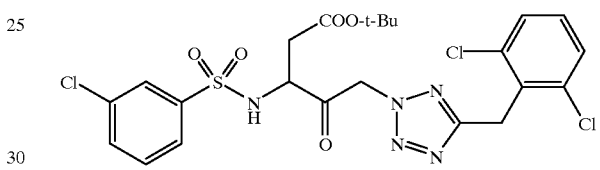

TLC: Rf 0.66 (chloroform:methanol=19:1); NMR (CDCl$_3$): δ 7.95–7.41 (4H, m), 7.34 (1H, d, J=9.0 Hz), 7.34 (1H, d, J=8.0 Hz), 7.18 (1H, dd, J=9.0 Hz, 7.0 Hz), 6.17 (1H, d, J=9.6 Hz), 5.84 and 5.65 (each 1H, d, J=18.0 Hz), 4.60 (2H, s), 4.23–4.08 (1H, m), 2.84 (1H, dd, J=17.6 Hz, 4.0 Hz), 2.29 (1H, dd, J=17.6 Hz, 4.6 Hz), 1.38 (9H, s).

Example 29(25)

N-(2-chlorophenyl)sulfonyl-3-amino-4-oxo-5-(5-(2,6-dichlorophenylmethyl)tetrazol-2-yl)pentanoic acid•t-butylester

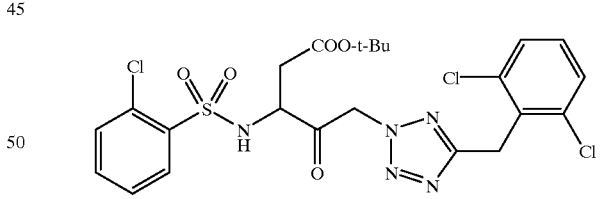

TLC: Rf 0.64 (chloroform:methanol=19:1); NMR (CDCl$_3$): δ 8.15–8.07 (1H, m), 7.61–7.40 (3H, m), 7.34 (1H, d, J=9.0 Hz), 7.34 (1H, d, J=7.0 Hz), 7.17 (1H, dd, J=9.0 Hz, 7.0 Hz), 6.58 (1H, d, J=9.6 Hz), 5.97 and 5.79 (each 1H, d, J=18.2 Hz), 4.60 (2H, s), 4.18–4.04 (1H, m), 2.88 (1H, dd, J=17.6 Hz, 3.6 Hz), 2.19 (1H, dd, J=17.6 Hz, 4.4 Hz), 1.40 (9H, s).

Example 29(26)

N-(2-phenyloxyphenyl)sulfonyl-3-amino-4-oxo-5-(5-(2,6-dichlorophenylmethyl)tetrazol-2-yl)pentanoic acid•t-butylester

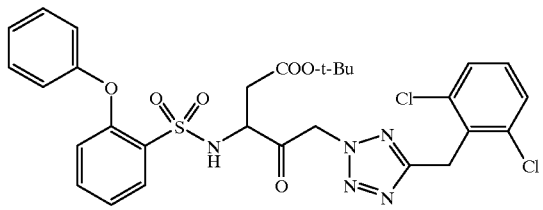

TLC: Rf 0.33 (hexane:ethyl acetate=3:1); NMR (CDCl₃): δ 8.03–7.93, 7.58–6.97 and 6.95–6.85 (1H, m), 6.38 (1H, d, J=9.6 Hz), 5.93 and 5.82 (each 1H, d, J=18.0 Hz), 4.60 (2H, s), 4.38–4.22 (1H, m), 2.94 (1H, dd, J=17.5 Hz, 4.0 Hz), 2.46 (1H, dd, J=17.5 Hz, 5.0 Hz), 1.38 (9H, s).

Example 29(27)

N-(2-phenylphenyl)sulfonyl-3-amino-4-oxo-5-(5-(2,6-dichlorophenylmethyl)tetrazol-2-yl)pentanoic acid•t-butylester

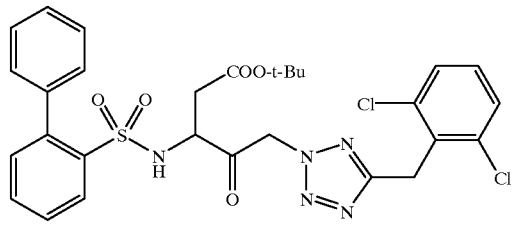

TLC: Rf 0.45 (hexane:ethyl acetate=2:1); NMR (CDCl₃): δ 8.14 (1H, dd, J=1.4, 7.8 Hz), 7.70–7.12 (11H, m), 5.67 (2H, s), 5.18 (1H, d, J=9.4 Hz), 4.58 (2H, s), 3.96 (1H, m), 2.74 (1H, dd, J=4.0, 17 Hz), 2.25 (1H, d, J=4.8, 17 Hz), 1.36 (9H, s).

Example 29(28)

N-(3-phenylpropyl)sulfonyl-3-amino-4-oxo-5-(5-(2,6-dichlorophenylmethyl)tetrazol-1-yl)pentanoic acid•t-butylester

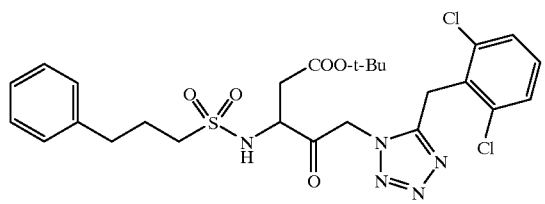

TLC: Rf 0.28 (dichloromethane:ethyl acetate=20:1); NMR (CDCl₃): δ 7.41–7.14 (8H, m), 5.78 and 5.68 (each 1H, d, J=19.0 Hz), 5.70 (1H, d, J=9.4 Hz), 4.35–4.19 (1H, m), 4.31 (2H, s), 3.19–2.95 and 2.87–2.60 (6H, m), 2.35–2.07 (2H, m), 1.43 (9H, s).

Example 29(29)

N-(2-methoxyphenyl)sulfonyl-3-amino-4-oxo-5-(5-(2,6-dichlorophenylmethyl)tetrazol-2-yl)pentanoic acid•t-butylester

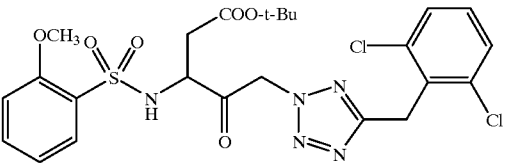

TLC: Rf 0.40 (hexane:ethyl acetate=2:1); NMR (CDCl₃): δ 7.95–7.86 (1H, m), 7.63–7.46 (1H, m), 7.38–6.93 (5H, m), 6.38 (1H, d, J=8.5 Hz), 5.78 (2H, s), 4.60 (2H, s), 4.30–4.12 (1H, m), 3.93 (3H, s), 2.85 (1H, dd, J=17.6 Hz, 4.0 Hz), 2.26 (1H, dd, J=17.6 Hz, 5.0 Hz), 1.40 (9H, s).

Example 29(30)

N-(2,6-difluorophenyl)sulfonyl-3-amino-4-oxo-5-(5-(2,6-dichlorophenylmethyl)tetrazol-2-yl)pentanoic acid•t-butylester

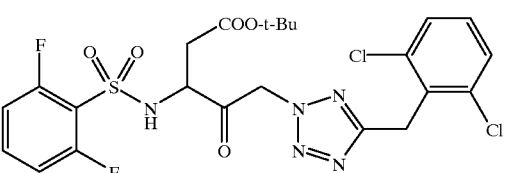

TLC: Rf 0.33 (hexane:ethyl acetate=2:1); NMR (CDCl₃): δ 7.65–7.46 (1H, m), 7.34 (1H, d, J=8.8 Hz), 7.34 (1H, d, J=7.2 Hz), 7.18 (1H, dd, J=8.8 Hz, 7.2 Hz), 7.09 and 7.05 (each 1H, d, J=8.6 Hz), 6.56–6.45 (1H, m), 5.91 and 5.75 (each 1H, d, J=18.0 Hz), 4.60 (2H, s), 4.45–4.53 (1H, m), 2.98 (1H, dd, J=17.8 Hz, 3.6 Hz), 2.45 (1H, dd, J=17.8 Hz, 4.6 Hz), 1.41 (9H, s).

Example 29(31)

N-(4-cyanophenyl)sulfonyl-3-amino-4-oxo-5-(5-(2,6-dichlorophenylmethyl)tetrazol-2-yl)pentanoic acid•t-butylester

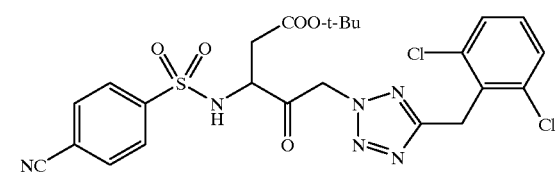

TLC: Rf 0.63 (hexane:ethyl acetate=2:1); NMR (CDCl₃): δ 7.97 (2H, d, J=8.5 Hz), 7.83 (2H, d, J=8.5 Hz), 7.36 (2H, d, J=8.0 Hz), 7.19 (1H, t, J=8.0 Hz), 6.33–6.19 (1H, m), 5.81 and 5.61 (each 1H, d, J=18.0 Hz), 4.61 (2H, s), 4.25–4.13 (1H, m), 2.80 (1H, dd, J=17.5 Hz, 4.0 Hz), 2.38 (1H, dd, J=17.5 Hz, 4.6 Hz), 1.37 (9H, s).

Example 29(32)

N-(2-methylphenyl)sulfonyl-3-amino-4-oxo-5-(5-(2,6-dichlorophenylmethyl)tetrazol-2-yl)pentanoic acid•t-butylester

453

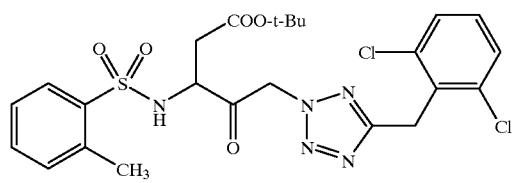

TLC: Rf 0.42 (hexane:ethyl acetate=2:1); NMR (CDCl$_3$): δ 8.04–7.90 (1H, m), 7.58–7.19 (6H, m), 6.33–6.09 (1H, br), 5.81 (1H, dd, J=18.0 Hz), 5.63 (1H, dd, J=18.0 Hz), 4.59 (2H, s), 4.14–3.97 (1H, m), 2.79 (1H, dd, J=17.6 and 3.6 Hz), 2.64 (3H, s), 2.18 (1H, dd, J=17.6 and 4.6 Hz), 1.38 (9H, s).

Example 29(33)

N-(4-methylphenyl)sulfonyl-3-amino-4-oxo-5-(5-(2,6-dichlorophenylmethyl)tetrazol-2-yl)pentanoic acid•t-butylester

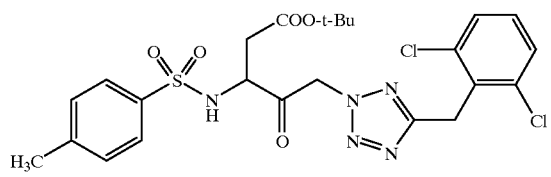

TLC: Rf 0.35 (hexane:ethyl acetate=2:1); NMR (CDCl$_3$): δ 7.82–7.68 (2H, m), 7.44–7.10 (5H, m), 6.05 (1H, d, J=9.0 Hz), 5.86 (1H, dd, J=18.2 Hz), 5.62 (1H, dd, J=18.2 Hz), 4.60 (2H, s), 4.22–4.02 (1H, m), 2.82 (1H, dd, J=17.6 and 3.8 Hz), 2.48 (3H, s), 2.26 (1H, dd, J=17.6 and 4.6 Hz), 1.37 (9H, s).

Example 29(34)

N-(4-phenylphenyl)sulfonyl-3-amino-4-oxo-5-(5-(2,6-dichlorophenylmethyl)tetrazol-2-yl)pentanoic acid•t-butylester

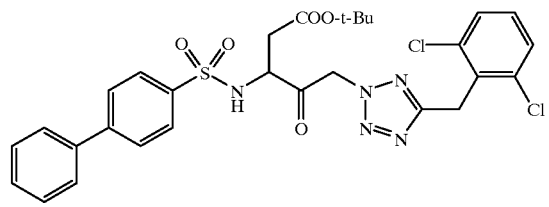

TLC: Rf 0.26 (hexane:ethyl acetate=3:1); NMR (CDCl$_3$): δ 8.00–7.86 (2H, m), 7.84–7.69 (2H, m), 7.67–7.38 (5H, m), 7.38–7.11 (3H, m, 6.14 (1H, brs), 5.87 (1H, d, J=18.2 Hz), 5.67 (1H, d, J=18.2 Hz), 4.59 (2H, s), 4.27–4.06 (1H, m), 2.85 (1H, dd, J=17.4 and 4.0 Hz), 2.33 (1H, dd, J=17.4 and 4.6 Hz), 1.37 (9H, s).

Example 29(35)

N-(5-dibutylaminonaphthalen-1-yl)sulfonyl-3-amino-4-oxo-5-(5-(2,6-dichlorophenylmethyl)tetrazol-2-yl)pentanoic acid•t-butylester

454

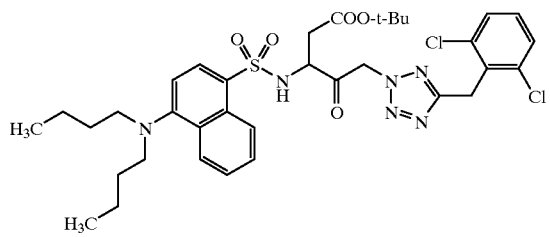

TLC: Rf 0.50 (hexane:ethyl acetate=3:1); NMR (CDCl$_3$): δ 8.69 (1H, d, J=8.8 Hz), 8.37–8.14 (2H, m), 7.59–7.43 (2H, m), 7.43–7.06 (4H, m), 6.43 (1H, d, J=10.0 Hz), 5.87 (1H, d, J=18.4 Hz), 5.57 (1H, d, J=18.4 Hz), 4.58 (2H, s), 4.10–3.93 (1H, m), 3.11 (4H, t, J=7.2 Hz), 2.65 (1H, dd, J=17.8 and 3.4 Hz), 1.75 (1H, dd, J=17.8 and 4.6 Hz), 1.55–1.05 (8H, m), 1.24 (9H, s), 0.83 (6H, t, J=7.0 Hz).

Example 29(36)

N-(3-phenylphenyl)sulfonyl-3-amino-4-oxo-5-(5-(2,6-dichlorophenylmethyl)tetrazol-2-yl)pentanoic acid•t-butylester

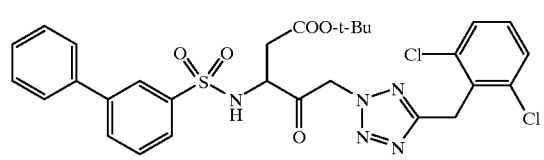

TLC: Rf 0.67 (chloroform:methanol=19:1); NMR (CDCl$_3$): δ 8.10 (1H, m), 7.90–7.80 (2H, m), 7.67–7.39 (6H, m), 7.34 (1H, d, J=8.8 Hz), 7.34 (1H, d, J=7.0 Hz), 7.17 (1H, dd, J=8.8 Hz, 7.0 Hz), 6.24–6.11 (1H, m), 5.86 and 5.67 (each 1H, d, J=18.0 Hz), 4.58 (2H, s), 4.25–4.12 (1H, m), 2.82 (1H, dd, J=17.6 Hz, 4.0 Hz), 2.26 (1H, dd, J=17.6 Hz, 4.6 Hz), 1.33 (9H, s).

Example 29(37)

N-(4-acetylaminophenyl)sulfonyl-3-amino-4-oxo-5-(5-(2,6-dichlorophenylmethyl)tetrazol-2-yl)pentanoic acid•t-butylester

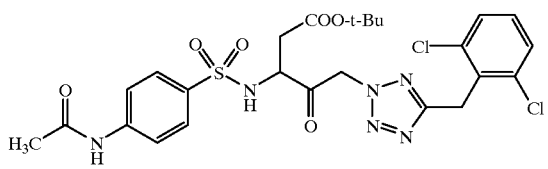

TLC: Rf 0.47 (chloroform:methanol=19:1); NMR (CDCl$_3$): δ 7.80 (2H, d, J=9.2 Hz), 7.74–7.60 (1H, m), 7.69 (2H, d, J=9.2 Hz), 7.33 (1H, d, J=9.2 Hz), 7.33 (1H, d, J=7.0 Hz), 7.17 (1H, dd, J=9.2 Hz, 7.0 Hz), 6.20–6.00 (1H, m), 5.85 and 5.65 (each 1H, d, J=18.0 Hz), 4.59 (2H, s), 4.17–4.04 (1H, m), 2.81 (1H, dd, J=17.4 Hz, 4.0 Hz), 2.21 (1H, dd, J=17.4 Hz, 4.8 Hz), 1.35 (9H, s).

Example 29(38)

N-(4-t-butylphenyl)sulfonyl-3-amino-4-oxo-5-(5-(2,6-dichlorophenylmethyl)tetrazol-2-yl)pentanoic acid•t-butylester

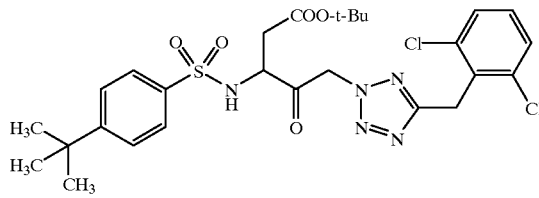

TLC: Rf 0.23 (hexane:ethyl acetate=3:1); NMR (CDCl₃): δ 7.86–7.72 (2H, m), 7.63–7.48 (2H, m), 7.42–7.10 (3H, m), 6.13–5.95 (1H, m, 5.84 (1H, d, J=18.0 Hz), 4.59 (2H, s), 4.22–4.01 (1H, m), 2.84 (1H, dd, J=17.6 and 4.0 Hz), 2.27 (1H, dd, J=17.6 and 4.6 Hz), 1.36 (9H, s), 1.34 (9H, s).

Example 29(39)

N-(5-dimethylaminonaphthalen-1-yl)sulfonyl-3-amino-4-oxo-5-(5-(2,6-dichlorophenylmethyl)tetrazol-1-yl)pentanoic acid•t-butylester

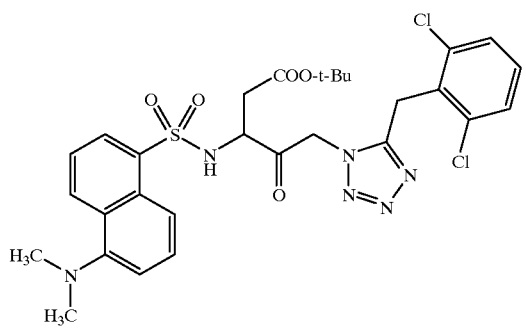

TLC: Rf 0.29 (hexane:ethyl acetate=2:1); NMR (DMSO-d₆): δ 8.63 (1H, d, J=8.6 Hz), 8.30–8.12 (2H, m), 7.72–7.48 (2H, m), 7.48–7.10 (4H, m), 6.42–6.20 (1H, br), 5.67 (1H, d, J=18.8 Hz), 5.46 (1H, d, J=18.8 Hz), 4.32–3.87 (3H, m), 2.90 (6H, s), 2.81 (1H, dd, J=18.0 and 4.0 Hz), 2.01 (1H, dd, J=18.0 and 4.0 Hz), 1.27 (9H, s).

Example 29(40)

N-(5-(pyridin-2-yl)thiophen-2-yl)sulfonyl-3-amino-4-oxo-5-(5-(2,6-dichlorophenylmethyl)tetrazol-2-yl)pentanoic acid•t-butylester

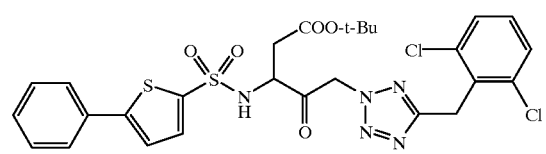

TLC: Rf 0.28 (hexane:ethyl acetate=2:1); NMR (CDCl₃): δ 8.66–8.48 (1H, m), 7.88–7.66 (2H, m), 7.64 (1H, d, J=4.0 Hz), 7.51 (1H, d, J=4.0 Hz), 7.43–7.06 (4H, m), 6.35–6.12 (1H, br), 5.92 (1H, d, J=18.2 Hz), 5.73 (1H, d, J=18.2 Hz), 4.59 (2H, s), 4.31–4.15 (1H, m), 2.92 (1H, dd, J=17.2 and 3.4 Hz), 2.41 (1H, dd, J=17.2 and 4.4 Hz), 1.37 (9H, s).

Example 29(41)

N-(1-(3-chloro-5-trifluoromethylpyridin-2-yl)pyrrol-2-yl)sulfonyl-3-amino-4-oxo-5-(5-(2,6-dichlorophenylmethyl)tetrazol-2-yl)pentanoic acid•t-butylester

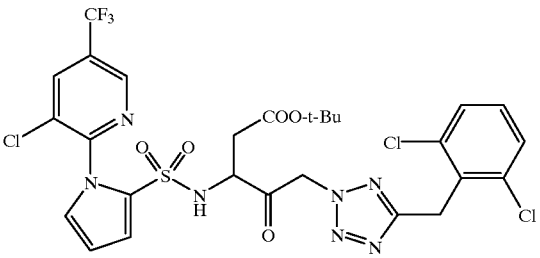

TLC: Rf 0.26 (hexane:ethyl acetate=1:1); NMR (CDCl₃): δ 8.74–8.64 (1H, m), 8.21–8.11 (1H, m), 8.06 (1H, t, J=2.6 Hz), 7.56 (1H, t, J=2.2 Hz), 7.44–7.04 (3H, m), 6.70–6.59 (1H, m), 607 (1H, d, J=9.4 Hz), 5.90 (1H, d, J=18.4 Hz), 5.71 (1H, d, J=18.4 Hz), 5.10 (2H, s), 4.28–4.04 (1H, m), 2.92 (1H, dd, J=17.2 and 3.8 Hz), 2.50 (1H, dd, J=17.2 and 4.6 Hz), 1.39 (9H, s).

Example 29(42)

N-(4-phenyloxyphenyl)sulfonyl-3-amino-4-oxo-5-(5-(2,6-dichlorophenylmethyl)tetrazol-2-yl)pentanoic acid•t-butylester

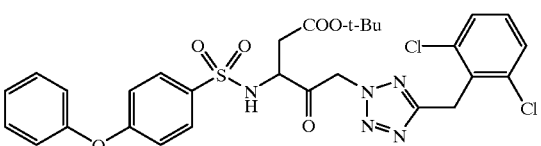

TLC: Rf 0.42 (hexane:ethyl acetate=2:1); NMR (CDCl₃): δ 7.85–7.75 and 7.50–7.00 (12H, m), 6.03 (1H, d, J=9.6 Hz), 5.85 and 5.64 (each 1H, d, J=18.0 Hz), 4.60 (2H, s), 4.19–4.03 (1H, m), 2.85 (1H, dd, J=17.4 Hz, 4.0 Hz), 2.33 (1H, dd, J=17.4 Hz, 4.6 Hz), 1.38 (9H, s).

Example 29(43)

N-(4-phenylthiophenyl)sulfonyl-3-amino-4-oxo-5-(5-(2,6-dichlorophenylmethyl)tetrazol-2-yl)pentanoic acid•t-butylester

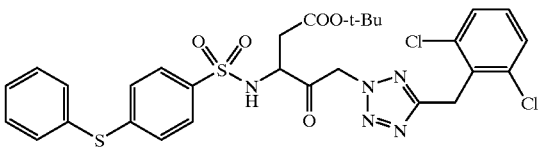

TLC: Rf 0.48 (hexane:ethyl acetate=2:1); NMR (CDCl₃): δ 7.75–7.60 and 7.60–7.12 (12H, m), 6.15–5.95 (1H, m), 5.84 and 5.62 (each 1H, d, J=18.0 Hz), 4.60 (2H, s), 4.15–4.00 (1H, m), 2.82 (1H, dd, J=17.6 Hz, 4.0 Hz), 2.30 (1H, dd, J=17.6 Hz, 4.6 Hz), 1.37 (9H, s).

Example 29(44)

N-octanylsulfonyl-3-amino-4-oxo-5-(5-(2,6-dichlorophenylmethyl)tetrazol-2-yl)pentanoic acid•t-butylester

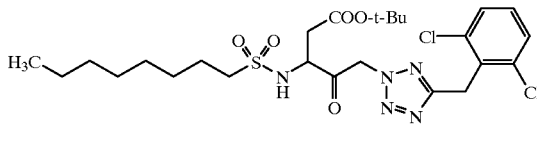

TLC: Rf 0.32 (hexane:ethyl acetate=3:1); NMR (CDCl$_3$): δ 7.40–7.10 (3H, m), 5.89 (1H, d, J=17.8 Hz), 5.74 (1H, d, J=17.8 Hz), 4.61 (2H, s), 4.44–4.24 (1H, m), 3.17–2.86 (3H, m), 2.74 (1H, dd, J=17.6 and 4.8 Hz), 1.95–1.70 (2H, m), 1.58–1.14 (10H, m), 1.43 (9H, s), 0.88 (3H, t, J=7.5 Hz).

Example 29(45)

N-(4-phenylphenyl)sulfonyl-3-amino-4-oxo-5-(5-(2,6-dichlorophenylmethyl)tetrazol-2-yl)pentanoic acid•t-butylester

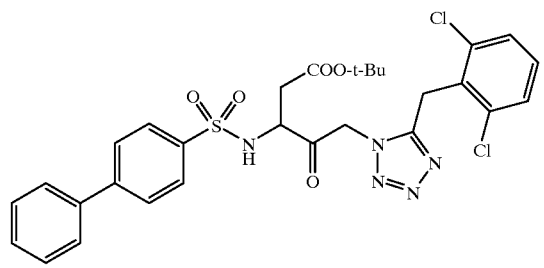

TLC: Rf 0.17 (hexane:ethyl acetate=3:1); NMR (CDCl$_3$): δ 8.06–7.89 (2H, m), 7.89–7.70 (2H, m), 7.70–7.16 (8H, m), 6.10 (1H, d, J=9.2 Hz), 5.80 (1H, d, J=18.8 Hz), 5.68 (1H, d, J=18.8 Hz), 4.29 (2H, s), 4.27–4.09 (1H, m), 2.98 (1H, dd, J=17.8 and 4.2 Hz), 2.44 (1H, dd, J=17.8 and 4.8 Hz), 1.38 (9H, s).

Example 29(46)

N-(4-phenylcarbonylmethylphenyl)sulfonyl-3-amino-4-oxo-5-(5-(2,6-dichlorophenylmethyl)tetrazol-2-yl)pentanoic acid•t-butylester

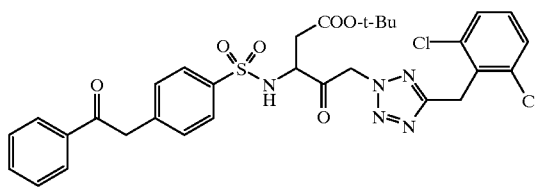

TLC: Rf 0.79 (chloroform:methanol=19:1); NMR (CDCl$_3$): δ 8.06–7.93, 7.90–7.75 and 7.70–7.10 (12H, m), 6.09 (1H, d, J=8.6 Hz), 5.83 and 5.69 (each 1H, d, J=18.0 Hz), 4.60 (2H, s), 4.39 (2H, s), 4.20–4.05 (1H, m), 2.82 (1H, dd, J=17.6 Hz, 3.6 Hz), 2.27 (1H, dd, J=17.6 Hz, 4.6 Hz), 1.37 (9H, s).

Example 29(47)

N-(2-acetylamino-4-methylthiazol-5-yl)sulfonyl-3-amino-4-oxo-5-(5-(2,6-dichlorophenylmethyl)tetrazol-2-yl)pentanoic acid•t-butylester

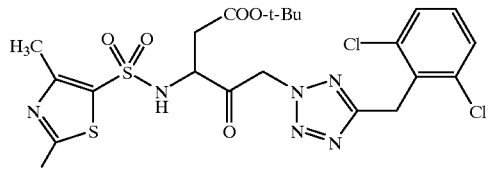

TLC: Rf 0.26 (chloroform:methanol=19:1); NMR (CDCl$_3$): δ 9.55–9.35 (1H, m), 7.34 (1H, d, J=9.0 Hz), 7.34 (1H, d, J=7.0 Hz), 7.17 (1H, dd, J=9.0 Hz, 7.0 Hz), 6.40–6.26 (1H, m), 5.87 and 5.69 (each 1H, d, J=18.0 Hz), 4.60 (2H, s), 4.31–4.15 (1H, m), 2.91 (1H, dd, J=17.6 Hz, 4.0 Hz), 2.52 (3H, s), 2.35 (1H, dd, J=17.6 Hz, 4.4 Hz), 2.30 (3H, s), 1.39 (9H, s).

Example 29(48)

N-(2,2,2-trifluoroethylsulfonyl-3-amino-4-oxo-5-(5-(2,6-dichlorophenylmethyl)tetrazol-2-yl)pentanoic acid•t-butylester

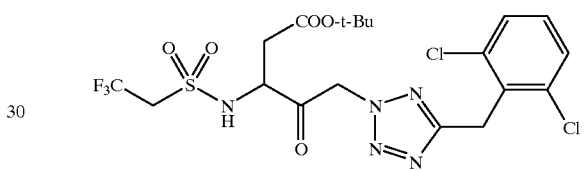

TLC: Rf 0.41 (chloroform:methanol=19:1); NMR (CDCl$_3$): δ 7.51 (1H, d, J=9.0 Hz), 7.51 (1H, d, J=7.0 Hz), 7.17 (1H, dd, J=9.0 Hz, 7.0 Hz), 6.27 (1H, d, J=9.2 Hz), 5.91 and 5.72 (each 1H, d, J=18.0 Hz), 4.61 (2H, s), 4.49–4.35 (1H, m), 4.19–4.82 (2H, m), 2.90–2.73 (2H, m), 1.43 (9H, s).

Example 29(49)

N-(2-trifluoromethylphenyl)sulfonyl-3-amino-4-oxo-5-(5-(2,6-dichlorophenylmethyl)tetrazol-2-yl)pentanoic acid•t-butylester

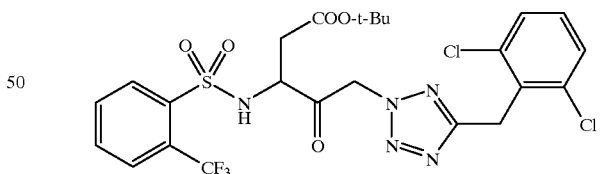

TLC: Rf 0.33 (hexane:ethyl acetate=2:1); NMR (CDCl$_3$): δ 8.29–8.13 (1H, m), 8.00–7.84 (1H, m), 7.84–7.66 (2H, m), 7.41–7.10 (3H, m), 6.28 (1H, d, J=9.4 Hz), 5.91 (1H, d, J=18.0 Hz), 5.73 (1H, d, J=18.0 Hz), 4.60 (2H, s), 4.25–4.08 (1H, m), 2.86 (1H, dd, J=17.6 and 3.6 Hz), 2.13 (1H, dd, J=17.6 and 4.8 Hz), 1.36 (9H, s).

Example 29(50)

N-(benzofurazan-4-yl)sulfonyl-3-amino-4-oxo-5-(5-(2,6-dichlorophenylmethyl)tetrazol-2-yl)pentanoic acid•t-butylester

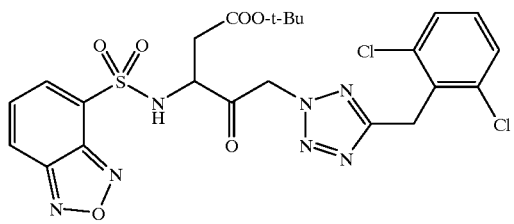

TLC: Rf 0.21 (hexane:ethyl acetate=2:1); NMR (CDCl$_3$): δ 8.22–8.00 (2H, m), 7.67–7.47 (1H, d, J=9.0 and 7.0 Hz), 7.47–7.10 (3H, m), 6.52 (1H, d, J=9.0 Hz), 5.94 (1H, d, J=18.0 Hz), 5.78 (1H, d, J=18.0 Hz), 4.70–4.49 (1H, m), 4.60 (2H, s), 2.93 (1H, dd, J=17.8 and 4.2 Hz), 2.35 (1H, dd, J=17.8 and 4.8 Hz), 1.35 (9H, s).

Example 29(51)

N-(3,5-dimethylisooxazol-4-yl)sulfonyl-3-amino-4-oxo-5-(5-(2,6-dichlorophenylmethyl)tetrazol-2-yl)pentanoic acid•t-butylester

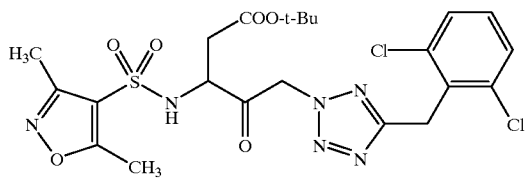

TLC: Rf 0.64 (chloroform:methanol=19:1); NMR (CDCl$_3$): δ 7.35 (1H, d, J=9.0 Hz), 7.35 (1H, d, J=7.2 Hz), 7.19 (1H, dd, J=9.0 Hz, J=7.2 Hz), 6.28 (1H, d, J=8.8 Hz), 5.85 and 5.68 (each 1H, d, J=18.0 Hz), 4.61 (2H, s), 4.16–4.00 (1H, m), 2.82 (1H, dd, J=17.4 Hz, J=4.4 Hz), 2.64 (3H, s), 2.46 (1H, dd, J=17.4 Hz, J=4.6 Hz), 2.40 (3H, s), 1.40 (9H, s).

Example 29(52)

N-(2-benzyloxycarbonylaminoethyl)sulfonyl-3-amino-4-oxo-5-(5-(2,6-dichlorophenylmethyl)tetrazol-2-yl)pentanoic acid•t-butylester

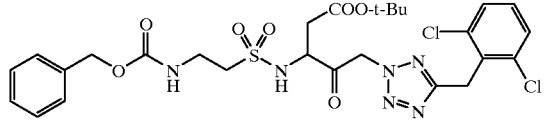

TLC: Rf 0.52 (chloroform:methanol=19:1); NMR (CDCl$_3$): δ 7.38–7.08 (8H, m), 6.10–5.93 (1H, m), 5.93–5.64 (2H, m), 5.48–5.25 (1H, m), 5.10 (2H, s), 4.60 (2H, s), 4.41–4.21 (1H, m), 3.80–3.55 and 3.55–3.18 (4H, m), 3.03–2.62 (2H, m), 1.42 (9H, s).

Example 29(53)

N-(1,1-dioxotetrahydrothiophen-3-yl)sulfonyl-3-amino-4-oxo-5-(5-(2,6-dichlorophenylmethyl)tetrazol-2-yl)pentanoic acid•t-butylester

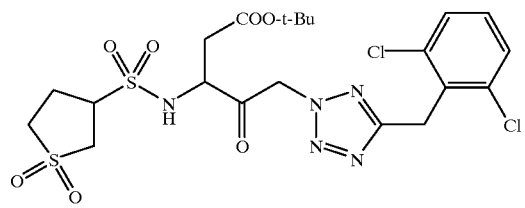

TLC: Rf 0.32 (hexane:ethyl acetate=1:1); NMR (CDCl$_3$): δ 7.44–7.08 (3H, m), 6.12–5.87 (1H, m), 5.87–5.57 (2H, m), 4.62 (2H, s), 4.67–4.25 (1H, m), 4.25–3.80 (1H, m), 3.66–2.93 (4H, m), 2.93–2.30 (4H, m), 1.44 (9H, s).

Example 29(54)

N-(5-phenylcarbonylaminomethylthiophen-2-yl)sulfonyl-3-amino-4-oxo-5-(5-(2,6-dichlorophenylmethyl)tetrazol-2-yl)pentanoic acid•t-butylester

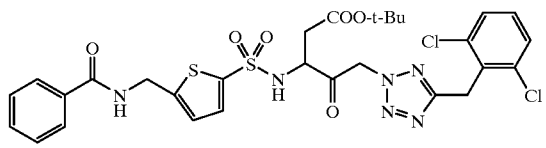

TLC: Rf 0.38 (hexane:ethyl acetate=1:1); NMR (CDCl$_3$): δ 7.86–7.70 (2H, m), 7.64–7.06 (7H, m), 7.02 (1H, d, J=3.8 Hz), 6.93–6.76 (1H, m), 6.15 (1H, d, J=9.0 Hz), 5.78 (1H, d, J=18.0 Hz), 5.59 (1H, d, J=18.0 Hz), 4.81 (2H, d, J=6.2 Hz), 4.58 (2H, s), 4.27–4.07 (1H, m), 2.90 (1H, dd, J=17.6 and 4.0 Hz), 2.47 (1H, dd, J=17.6 and 5.0 Hz), 1.38 (9H, s).

Example 29(55)

N-(2,1,3-benzothiadiazol-4-yl)sulfonyl-3-amino-4-oxo-5-(5-(2,6-dichlorophenylmethyl)tetrazol-2-yl)pentanoic acid•t-butylester

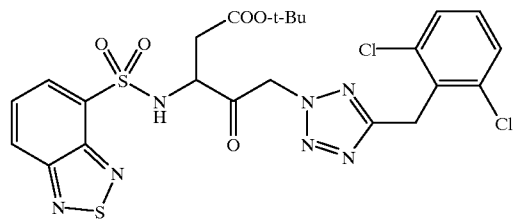

TLC: Rf 0.30 (hexane:ethyl acetate=2:1); NMR (CDCl$_3$): δ 8.36–8.21 (2H, m), 7.75 (1H, dd, J=8.8 and 7.2 Hz), 7.42–7.11 (3H, m), 6.59 (1H, d, J=9.4 Hz), 5.90 (1H, d, J=18.0 Hz), 5.73 (1H, d, J=18.0 Hz), 4.72–4.47 (1H, m), 4.59 (2H, s), 2.88 (1H, dd, J=17.6 and 3.6 Hz), 2.19 (1H, dd, J=17.6 and 4.8 Hz), 1.35 (9H, s).

Example 29(56)

N-(4-acetylaminophenyl)sulfonyl-3-amino-4-oxo-5-(5-(2,6-dichlorophenylmethyl)tetrazol-1-yl)pentanoic acid•t-butylester

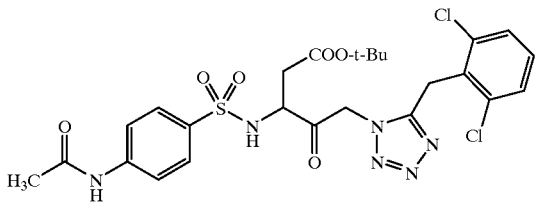

TLC: Rf 0.26 (chloroform:methanol=19:1); NMR (CDCl₃): δ 7.9 7 (1H, s), 7.83 and 7.73 (each 2H, d, J=8.5 Hz), 7.34 (1H, d, J=9.0 Hz), 7.34 (1H, d, J=7.0 Hz), 7.20 (1H, dd, J=9.0 Hz, J=7.0 Hz), 6.10 (1H, d, J=9.2 Hz), 5.77 and 5.65 (each 1H, d, J=19.0 Hz), 4.28 (2H, s), 4.23–4.04 (1H, m), 2.96 (1H, dd, J=17.6 Hz, J=3.8 Hz), 2.46 (1H, dd, J=17.6 Hz, J=5.2 Hz), 1.38 (9H, s).

Example 29(57)

N-(4-phenylthiophenyl)sulfonyl-3-amino-4-oxo-5-(5-(2,6-dichlorophenylmethyl)tetrazol-1-yl)pentanoic acid•t-butylester

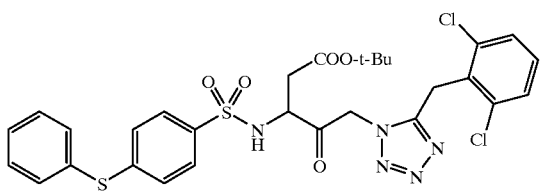

TLC: Rf 0.52 (chloroform:methanol=19:1); NMR (CDCl₃): δ 7.72 (2H, d, J=8.8 Hz), 7.59–7.13 (8H, m), 7.23 (2H, d, J=8.8 Hz), 6.20 (1H, d, J=9.0 Hz), 5.88 and 5.66 (each 1H, d, J=18.8 Hz), 4.28 (2H, s), 4.19–4.05 (1H, m), 2.93 (1H, dd, J=17.6 Hz, J=3.8 Hz), 2.44 (1H, dd, J=17.6 Hz, J=4.6 Hz), 1.36 (9H, s).

Example 29(58)

N-(2-nitrophenyl)sulfonyl-3-amino-4-oxo-5-(5-(2,6-dichlorophenylmethyl)tetrazol-2-yl)pentanoic acid•t-butylester

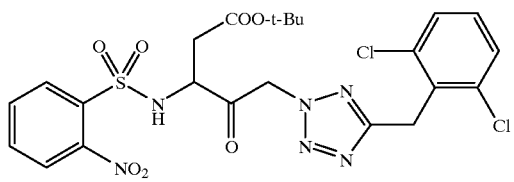

TLC: Rf 0.61 (chloroform:methanol=19:1); NMR (CDCl₃): δ 8.20–8.06 and 8.05–7.70 (4H, m), 7.34 (1H, d, J=9.0 Hz), 7.34 (1H, d, J=7.0 Hz), 7.18 (1H, dd, J=9.0 Hz, J=7.0 Hz), 6.74 (1H, d, J=9.2 Hz,), 5.93 and 5.75 (each 1H, d, J=18.0 Hz), 4.61 (2H, s), 4.42–4.25 (1H, m), 2.95 (1H, dd, J=17.6 Hz, J=4.2 Hz), 2.40 (1H, dd, J=17.6 Hz, J=4.4 Hz), 1.38 (9H, s).

Example 29(59)

N-(camphor-10-yl)sulfonyl-3-amino-4-oxo-5-(5-(2,6-dichlorophenylmethyl)tetrazol-2-yl)pentanoic acid•t-butylester

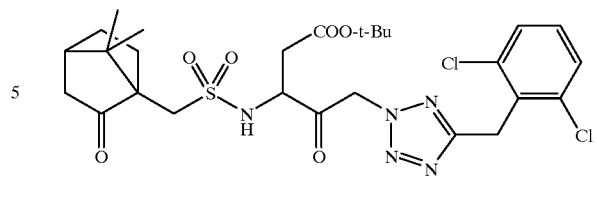

TLC: Rf 0.63 (chloroform:methanol=19:1); NMR (CDCl₃): δ 7.35 (1H, d, J=9.0 Hz), 7.35 (1H, d, J=6.8 Hz), 7.18 (1H, dd, J=9.0 Hz, J=6.8 Hz), 6.61 (1H, d, J=8.0 Hz), 6.01 and 5.85 (each 1H, d, J=18.5 Hz), 4.64–4.33 (1H, m), 4.61 (2H, s), 3.56–3.40 and 3.15–2.70 (4H, m), 2.53–2.27 and 2.27–1.82 (7H, m), 1.43 (9H, s), 1.02 (3H, s), 0.94 (3H, s).

Example 29(60)

N-(6-chloroimizazo[2,1-B]thiazol-5-yl)sulfonyl-3-amino-4-oxo-5-(5-(2,6-dichlorophenylmethyl)tetrazol-2-yl)pentanoic acid•t-butylester

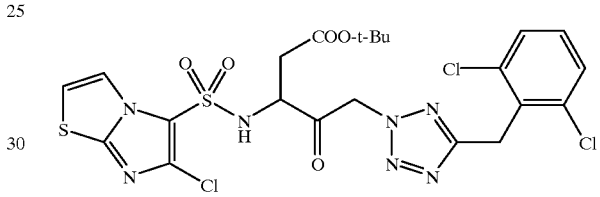

TLC: Rf 0.19 (hexane:ethyl acetate=2:1); NMR (CDCl₃): δ 7.93 (1H, d, J=4.4 Hz), 7.44–7.07 (4H, m), 6.76–6.53 (1H, m), 5.94 (1H, d, J=18.0 Hz), 5.78 (1H, d, J=18.0 Hz), 4.61 (2H, s), 4.36 (1H, m), 2.91 (1H, dd, J17.6 and 4.0 Hz), 2.48 (1H, dd, J=17.6 and 4.6 Hz), 1.39 (9H, s).

Example 29(61)

N-(5-(2-methylthiopyrimidin-4-yl)thiophen-2-yl)sulfonyl-3-amino-4-oxo-5-(5-(2,6-dichlorophenylmethyl)tetrazol-2-yl)pentanoic acid•t-butylester

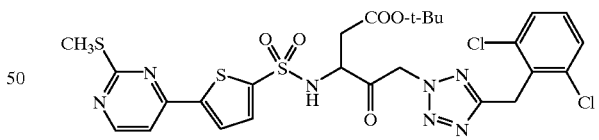

TLC: Rf 0.19 (hexane:ethyl acetate=2:1); NMR (CDCl₃): δ 8.58 (1H, d, J=5.2 Hz), 7.72–7.58 (2H, m), 7.41–7.10 (4H, m), 6.32 (1H, d, J=8.8 Hz), 5.89 (1H, d, J=18.2 Hz), 5.70 (1H, d, J=18.2 Hz), 4.60 (2H, s), 4.35–4.15 (1H, m), 2.92 (1H, dd, J=17.6 and 3.6 Hz), 2.61 (3H, s), 2.41 (1H, dd, J=17.6 and 4.8 Hz), 1.38 (9H, s).

Example 29(62)

N-(4-butylphenyl)sulfonyl-3-amino-4-oxo-5-(5-(2,6-dichlorophenylmethyl)tetrazol-2-yl)pentanoic acid•t-butylester

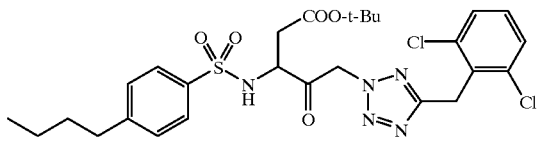

TLC: Rf 0.67 (chloroform:methanol=19:1); NMR (CDCl₃): δ 7.77 (2H, d, J=8.8 Hz), 7.35 (2H, d, J=8.8 Hz), 7.40–7.12 (3H, m), 6.02 (1H, d, J=9.6 Hz), 5.84 and 5.62 (each 1H, d, J=18.0 Hz), 4.59 (2H, s), 4.18–4.05 (1H, m), 2.82 (1H, dd, J=17.6 Hz, J=3.6 Hz), 2.70 (2H, t, J=7.5 Hz), 2.32 (1H, dd, J=17.6 Hz, J=5.0 Hz), 1.72–1.18 (4H, m), 1.37 (9H, s), 0.93 (3H, s).

Example 29(63)

N-(4-butylphenyl)sulfonyl-3-amino-4-oxo-5-(5-(2,6-dichlorophenylmethyl)tetrazol-1-yl)pentanoic acid•t-butylester

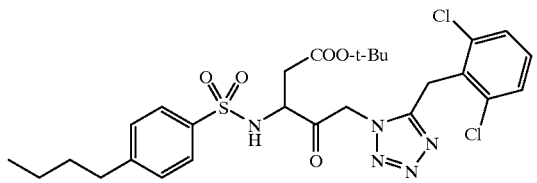

TLC: Rf 0.57 (chloroform:methanol=19:1); NMR (CDCl₃): δ 7.81 (2H, d, J=8.5 Hz), 7.45–7.15 (3H, m), 7.38 (2H, d, J=8.5 Hz), 5.98 (1H, d, J=9.0 Hz), 5.76 and 5.63 (each 1H, d, J=18.6 Hz), 4.28 (2H, s), 4.20–4.03 (1H, m), 2.95 (1H, dd, J=17.6 Hz, J=3.6 Hz), 2.71 (2H, t, J=7.6 Hz), 2.36 (1H, dd, J=17.6 Hz, J=5.0 Hz), 1.74–1.18 (4H, m), 1.37 (9H, s), 0.93 (3H, s).

Example 29(64)

N-(5-(isooxazol-3-yl)thiophen-2-yl)sulfonyl-3-amino-4-oxo-5-(5-(2,6-dichlorophenylmethyl)tetrazol-2-yl)pentanoic acid•t-butylester

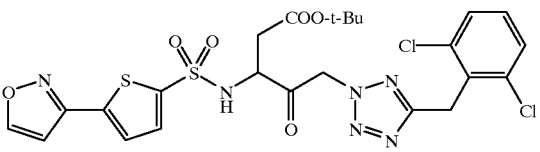

TLC: Rf 0.21 (hexane:ethyl acetate=2:1); NMR (CDCl₃): δ 8.33 (1H, d, J=2.0 Hz), 7.63 (1H, d, J=3.8 Hz), 7.47 (1H, d, J=3.8 Hz), 7.40–7.11 (3H, m), 6.56 (1H, d, J=2.0 Hz), 6.37 (1H, d, J=8.0 Hz), 5.88 (1H, d, J=17.8 Hz), 5.69 (1H, d, J=17.8 Hz), 4.60 (2H, s), 4.34–4.12 (1H, m), 2.90 (1H, dd, J=17.2 and 3.8 Hz), 2.44 (1H, dd, J=17.2 and 4.8 Hz), 1.38 (9H, s).

Example 29(65)

N-(5-(4-chlorophenylcarbonylaminomethyl)thiophen-2-yl)sulfonyl-3-amino-4-oxo-5-(5-(2,6-dichlorophenylmethyl)tetrazol-2-yl)pentanoic acid•t-butylester

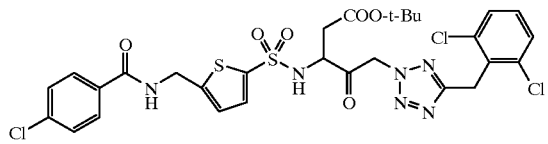

TLC: Rf 0.31 (hexane:ethyl acetate=1:1); NMR (CDCl₃): δ 7.82–7.65 (2H, m), 7.55–6.90 (8H, m), 6.18 (1H, d, J=9.0 Hz), 5.75 (1H, d, J=17.8 Hz), 5.56 (1H, d, J=17.8 Hz), 4.78 (2H, d, J=6.0 Hz), 4.57 (2H, s), 4.28–4.10 (1H, m), 2.90 (1H, dd, J=17.4 and 4.0 Hz), 2.51 (1H, dd, J=17.4 and 5.0 Hz), 1.38 (9H, s).

Example 29(66)

N-(4-(pyrrolidin-1-yl)phenyl)sulfonyl-3-amino-4-oxo-5-(5-(2,6-dichlorophenylmethyl)tetrazol-1-yl)pentanoic acid•t-butylester

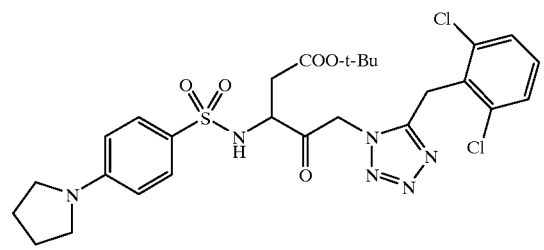

TLC: Rf 0.43 (hexane:ethyl acetate=1:1); NMR (DMSO-d₆): δ 8.27–8.06 (1H, brs), 7.80–7.19 (5H, m), 6.71–6.46 (2H, m), 6.04–5.70 (2H, m), 4.44–3.90 (3H, m), 3.35–3.05 (4H, m), 2.74–2.49 (2H, m), 2.03–1.76 (4H, m), 1.34 (9H, s).

Example 29(67)

N-(4-(morpholin-4-yl)phenyl)sulfonyl-3-amino-4-oxo-5-(5-(2,6-dichlorophenylmethyl)tetrazol-1-yl)pentanoic acid•t-butylester

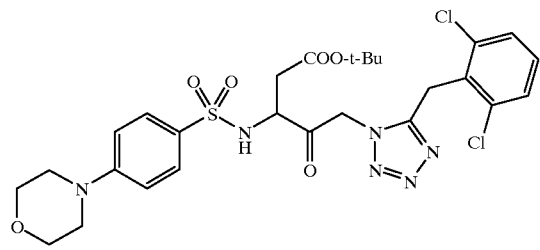

TLC: Rf 0.19 (hexane:ethyl acetate=1:1); NMR (CDCl₃): δ 7.85–7.66 (2H, m), 7.47–7.10 (3H, m), 7.02–6.85 (2H, m), 5.83 (1H, d, J=9.4 Hz), 5.73 (1H, d, J-18.8 Hz), 5.61 (1H, d, J=18.8 Hz), 4.25 (2H, s), 4.15–4.00 (1H, m), 3.94–3.76 (4H, m), 3.40–3.22 (4H, m), 2.98 (1H, dd, J=17.6 and 4.2 Hz), 2.47 (1H, dd, J=17.6 and 4.6 Hz), 1.39 (9H, s).

Example 29(68)

N-(2-diethylaminoethyl)sulfonyl-3-amino-4-oxo-5-(5-(2,6-dichlorophenylmethyl)tetrazol-2-yl)pentanoic acid•t-butylester

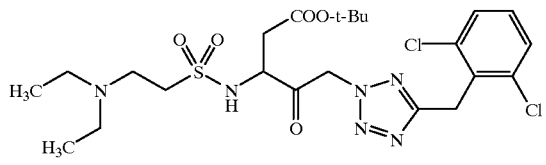

TLC: Rf 0.67 (chloroform:methanol=9:1); NMR (CDCl₃): δ 7.34 (1H, d, J=8.8 Hz), 7.34 (1H, d, J=7.0 Hz), 7.17 (1H, dd, J=8.8 Hz, 7.0 Hz), 5.87 and 5.78 (each 1H, d, J=18.0 Hz), 4.61 (2H, s), 4.53–4.43 (1H, m), 3.47–2.41 (10H, m), 1.42 (9H, s), 1.05 (3H, t, J=7.0 Hz).

Example 29(69)

N-(3-methylphenyl)sulfonyl-3-amino-4-oxo-5-(5-( 2,6-dichlorophenylmethyl)tetrazol-2-yl)pentanoic acid•t-butylester

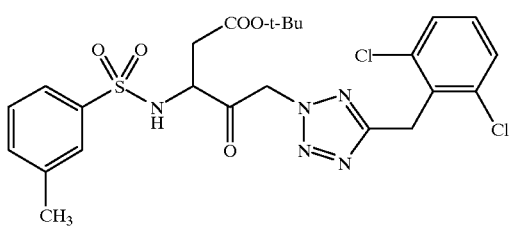

TLC: Rf 0.23 (hexane:ethyl acetate=3:1); NMR (CDCl₃): δ 7.74–7.59 (2H, m), 7.51–7.10 (5H, m), 6.06 (1H, d, J=9.6 Hz), 5.83 (1H, d, J=18.2 Hz), 5.62 (1H, d, J=18.2 Hz), 4.59 (2H, s), 4.21–4.05 (1H, m), 2.82 (1H, dd, J=17.4 and 3.8 Hz), 2.44 (3H, s), 2.24 (1H, dd, J=17.4 and 5.0 Hz), 1.37 (9H, s).

Example 29(70)

N-(4-isopropylphenyl)sulfonyl-3-amino-4-oxo-5-(5-(2,6-dichlorophenylmethyl)tetrazol-2-yl)pentanoic acid•t-butylester

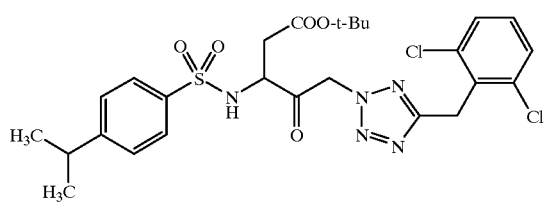

TLC: Rf 0.31 (hexane:ethyl acetate=3:1); NMR (CDCl₃): δ 7.86–7.71 (2H, m), 7.46–7.10 (5H, m), 6.04 (1H, d, J=9.6 Hz), 5.84 (1H, d, J=18.0 Hz), 5.61 (1H, d, J=18.0 Hz), 4.59 (2H, s), 4.20–4.01 (1H, m, 3.10–2.87 (1H, m), 2.83 (1H, dd, J=17.6 and 3.6 Hz), 2.27 (1H, dd, J=17.6 and 5.0 Hz), 1.36 (9H, s), 1.27 (6H, d, J=7.0 Hz).

Example 29(71)

N-(4-isopropylphenyl)sulfonyl-3-amino-4-oxo-5-(5-(2,6-dichlorophenylmethyl)tetrazol-1-yl)pentanoic acid•t-butylester

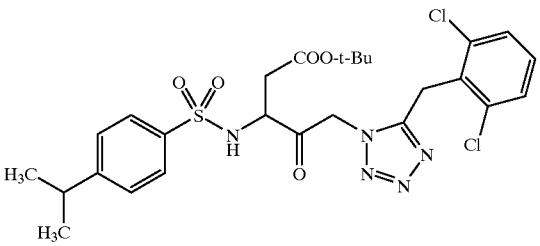

TLC: Rf 0.26 (hexane:ethyl acetate=2:1); NMR (CDCl₃): δ 7.90–7.73 (2H, m), 7.51–7.15 (5H, m), 5.98 (1H, d, J=9.6 Hz), 5.76 (1H, d, J=18.8 Hz), 5.63 (1H, d, J=18.8 Hz), 4.29 (2H, s), 4.22–4.02 (1H, m), 3.13–2.83 (2H, m), 2.39 (1H, dd, J=17.8 and 4.4 Hz), 1.37 (9H, s), 1.29 (6H, d, J=6.8 Hz).

Example 29(72)

N-(2-diethylaminoethyl)sulfonyl-3-amino-4-oxo-5-(5-(2,6-dichlorophenylmethyl)tetrazol-1-yl)pentanoic acid•t-butylester

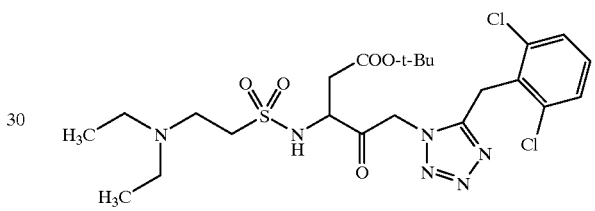

TLC: Rf 0.37 (chloroform:methanol=9:1); NMR (CDCl₃): δ 7.43–7.15 (3H, m), 5.81 (2H, s), 4.60–4.47 (1H, m), 4.39–4.26 (2H, m), 3.41–2.45 (10H, m), 1.42 (9H, s), 1.08 (3H, t, J=7.0 Hz).

Example 29(73)

N-(4-butyloxyphenyl)sulfonyl-3-amino-4-oxo-5-(5-(2,6-dichlorophenylmethyl)tetrazol-2-yl)pentanoic acid•t-butylester

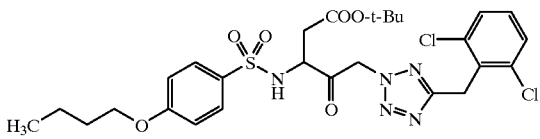

TLC: Rf 0.51 (hexane:ethyl acetate=2:1); NMR (CDCl₃): δ 7.92–7.69 (2H, m), 7.28–7.10 (3H, m), 7.10–6.89 (2H, m), 6.00 (1H, d, J=8.6 Hz), 5.86 (1H, d, J=18.2 Hz), 5.65 (1H, d, J=18.2 Hz), 4.60 (2H, s), 4.22–3.89 (3H, m), 2.83 (1H, dd, J=17.2 and 3.4 Hz), 2.27 (1H, dd, J=17.2 and 4.8 Hz), 1.94–1.69 (2H, m), 1.64–1.24 (2H, m), 1.37 (9H, s), 0.99 (3H, t, J=7.4 Hz).

Example 29(74)

N-(4-butyloxyphenyl)sulfonyl-3-amino-4-oxo-5-(5-(2,6-dichlorophenylmethyl)tetrazol-1-yl)pentanoic acid•t-butylester

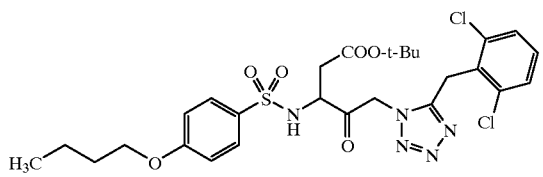

TLC: Rf 0.28 (hexane:ethyl acetate=2:1); NMR (CDCl₃): δ 7.91–7.74 (2H, m), 7.46–7.14 (3H, m), 7.10–6.93 (2H, m), 6.03–5.82 (1H, brs), 5.76 (1H, d, J=19.2 Hz), 5.64 (1H, d, J=19.2 Hz), 4.27 (2H, s), 4.18–3.97 (1H, m), 4.04 (2H, t, J=6.4 Hz), 2.96 (1H, dd, J=17.4 and 4.0 Hz), 2.39 (1H, dd, J=17.4 and 4.6 Hz), 1.92–1.67 (2H, m), 1.67–1.35 (2H, m), 1.38 (9H, s), 0.99 (3H, t, J=7.4 Hz).

EXAMPLES 30(1)–30(74)

By the same procedure as provided in example 6(1), and if necessary, by known methods converted to accommodate the corresponding salts, using the compound prepared in examples 29(1)–29(74), the compounds of the present invention having the following physical data were obtained.

Example 30(1)

N-(4-t-butylphenyl)sulfonyl-3-amino-4-oxo-5-(5-(2,6-dichlorophenylmethyl)tetrazol-1-yl)pentanoic acid

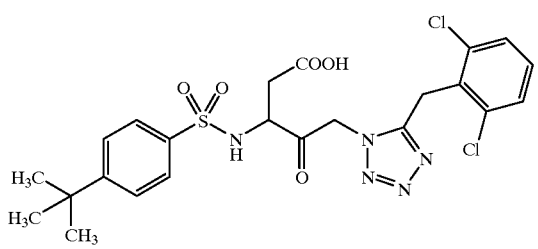

TLC: Rf 0.19 (chloroform:methanol:acetic acid=50:1:1); NMR (DMSO-d₆): δ 8.83–8.34 (1H, br), 7.92–7.75 (2H, m), 7.72–7.31 (5H, m), 6.10–5.54 (2H, br), 4.43–4.26 (1H, m), 4.30 (2H, s), 2.82–2.50 (2H, m), 1.30 (9H, s).

Example 30(2)

N-phenylmethylsulfonyl-3-amino-4-oxo-5-(5-(2,6-dichlorophenylmethyl)tetrazol-2-yl)pentanoic acid

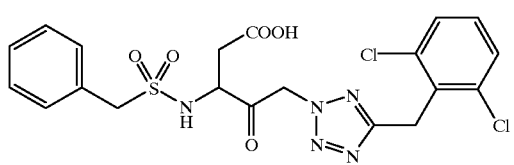

TLC: Rf 0.14 (chloroform:methanol:acetic acid=50:1:1); NMR (DMSO-d₆): δ 7.99–7.70 (1H, br), 7.52 (2H, d, J=7.5 Hz), 7.45–7.27 (6H, m), 6.01–5.80 (2H, m), 4.52 (total 4H, s), 4.58–4.38 (1H, m), 2.77–2.66 (2H, m).

Example 30(3)

N-phenylsulfonyl-3-amino-4-oxo-5-(5-(2,6-dichlorophenylmethyl)tetrazol-2-yl)pentanoic acid

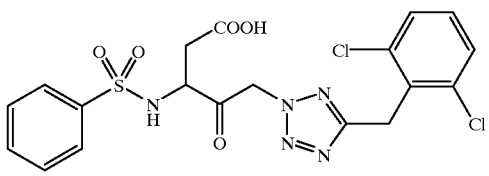

TLC: Rf 0.49 (chloroform:methanol:acetic acid=18:1:1); NMR (CDCl₃+DMSO-d₆): δ 7.98–7.80 and 7.68–7.10 (total 9H, m), 6.10–5.30 (2H, br), 4.58 (2H, s), 4.30–4.10 (1H, m), 2.76–2.33 (2H, m).

Example 30(4)

N-(2-(naphthalen-1-yl)ethyl)sulfonyl-3-amino-4-oxo-5-(5-(2,6-dichlorophenylmethyl)tetrazol-2-yl)pentanoic acid

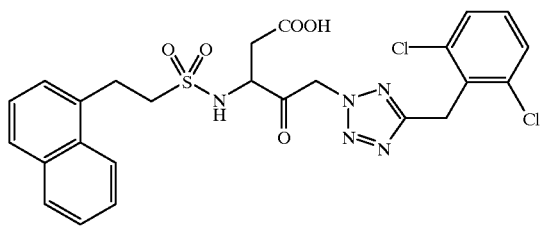

TLC: Rf 0.59 (chloroform:methanol:acetic acid=18:1:1); NMR (DMSO-d₆): δ 8.10–7.75 and 7.65–7.13 (total 11H, m), 6.10–5.87 (2H, m), 4.89 (2H, s), 4.55–4.38 (1H, m), 3.60–3.46 (4H, m), 2.75–2.62 (2H,m).

Example 30(5)

N-(naphthalen-2-yl)sulfonyl-3-amino-4-oxo-5-(5-(2,6-dichlorophenylmethyl)tetrazol-2-yl)pentanoic acid

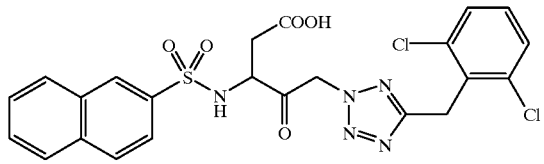

TLC: Rf 0.49 (chloroform:methanol:acetic acid=18:1:1); NMR (DMSO-d₆): δ 12.80–12.10 (1H, br), 8.72–8.47 (2H, m), 8.23–8.00 (3H, m), 7.94–7.83 (1H, m), 7.79–7.60 (2H, m), 7.57–7.45 (2H, m), 7.43–7.29 (1H, m), 6.15–5.77 (2H, m), 4.49 (2H, s), 4.43–4.29 (1H, m), 2.64–2.37 (2H, m).

Example 30(6)

N-(naphthalen-1-yl)sulfonyl-3-amino-4-oxo-5-(5-(2,6-dichlorophenylmethyl)tetrazol-2-yl)pentanoic acid

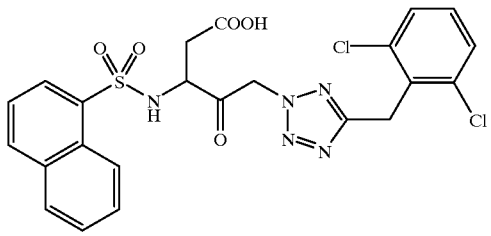

TLC: Rf 0.54 (chloroform:methanol:acetic acid=18:1:1); NMR (DMSO-d₆): δ 12.70–12.20 (1H, br), 8.99–8.75 (1H, m), 8.70–8.57 (1H, m), 8.32–8.15 and 8.15–8.02 (total 3H, m), 7.78–7.56 (3H, m), 7.56–7.46 (2H, m), 7.42–7.30 (1H, m), 6.00–5.70 (2H, m), 4.49 (2H, s), 4.42–4.25 (1H, m), 2.42–2.21 (2H, m).

Example 30(7)

N-(2-phenylethenyl)sulfonyl-3-amino-4-oxo-5-(5-(2,6-dichlorophenylmethyl)tetrazol-2-yl)pentanoic acid

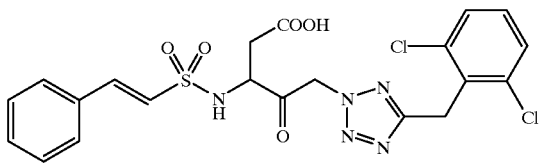

TLC: Rf 0.57 (chloroform:methanol:acetic acid=25:1:1); NMR (DMSO-$d_6$): δ 8.90–8.40 (1H, br), 7.72–7.68 (2H, m), 7.55–7.15 (8H, m), 6.10–5.90 (2H, m), 4.51 (2H, s), 4.45–4.35 (1H, m), 2.80–2.72 (2H, m).

Example 30(8)

N-(4-bromophenyl)sulfonyl-3-amino-4-oxo-5-(5-(2,6-dichlorophenylmethyl)tetrazol-2-yl)pentanoic acid

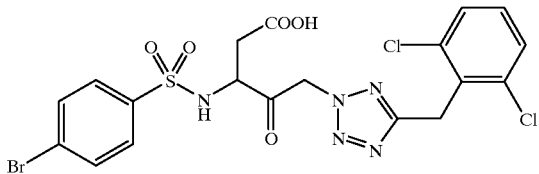

TLC: Rf 0.50 (chloroform:methanol:acetic acid=18:1:1); NMR (DMSO-$d_6$): δ 8.85–8.25 (1H, br), 7.86–7.70 (4H, m), 7.56–7.30 (3H, m), 6.07–5.72 (2H, m), 4.51 (2H, s), 4.43–4.27 (1H, m), 2.69–2.52 (2H, m).

Example 30(9)

N-butylsulfonyl-3-amino-4-oxo-5-(5-(2,6-dichlorophenylmethyl)tetrazol-2-yl)pentanoic acid

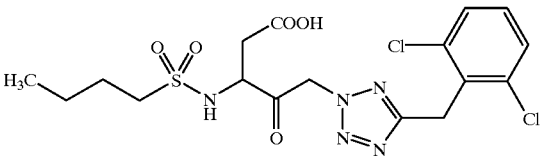

TLC: Rf 0.30 (chloroform:methanol:acetic acid=25:1:1); NMR (DMSO-$d_6$): δ 7.94–7.72 (1H, d), 7.53–7.33 (3H, m), 6.16–5.85 (2H, m), 4.52 (2H, s), 4.50–4.40 (1H, m), 3.18–3.10 (2H, m), 2.77–2.73 (2H, m), 1.75–1.55 (2H, m), 1.48–1.28 (2H, m), 0.90 (3H, t).

Example 30(10)

N-(quinolin-8-yl)sulfonyl-3-amino-4-oxo-5-(5-(2,6-dichlorophenylmethyl)tetrazol-2-yl)pentanoic acid

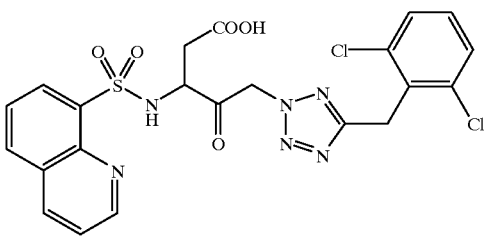

TLC: Rf 0.42 (chloroform:methanol:acetic acid=25:1:1); NMR (DMSO-$d_6$): δ 9.05–9.01 (1H, m), 8.58–8.53 (1H, m), 8.39–8.29 (2H, m), 8.17–8.00 (1H, m), 7.80–7.67 (2H, m), 7.53–7.33 (3H, m), 6.16–5.63 (2H, m), 4.91–4.73 (1H, m), 4.49 (2H, s).

Example 30(11)

N-(5-dimethylaminonaphthalen-1-yl)sulfonyl-3-amino-4-oxo-5-(5-(2,6-dichlorophenylmethyl)tetrazol-2-yl) pentanoic acid

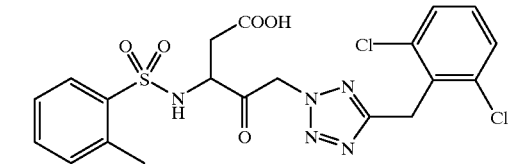

TLC: Rf 0.43 (chloroform:methanol:acetic acid=30:1:1); NMR (DMSO-$d_6$): δ 12.84–11.80 (1H, br), 8.94–8.64 (1H, m), 8.52–8.47 (1H, m), 8.30–8.19 (2H, m), 7.66–7.23 (6H, m), 5.93–5.68 (2H, m), 4.49 (2H, s), 4.42–4.26 (1H, m), 2.83 (6H, s), 2.60–2.25 (2H, m).

Example 30(12)

N-(4-nitrophenyl)sulfonyl-3-amino-4-oxo-5-(5-(2,6-dichlorophenylmethyl)tetrazol-2-yl)pentanoic acid

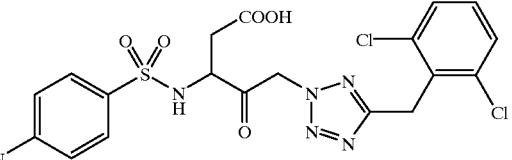

TLC: Rf 0.53 (chloroform:methanol:acetic acid=18:1:1); NMR (DMSO-$d_6$): δ 8.40 (2H, d, J=9.0 Hz), 8.10 (2H, d, J=9.0 Hz), 7.51 (1H, d, J=9.0 Hz), 7.50 (1H, d, J=6.8 Hz), 6.10–5.75 (2H, br), 4.50 (2H, s), 4.55–4.37 (1H, m), 2.68–2.55 (2H, m).

Example 30(13)

N-phenylsulfonyl-3-amino-4-oxo-5-(5-(2,6-dichlorophenylmethyl)tetrazol-1-yl)pentanoic acid

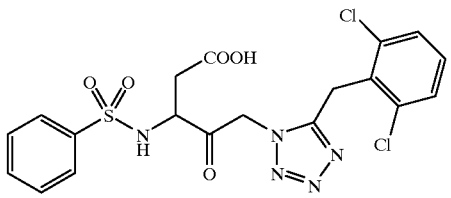

TLC: Rf 0.33 (chloroform:methanol:acetic acid=20:1:1); NMR (DMSO-d$_6$): δ 13.04–12.28 (1H, br), 8.68–8.50 (1H, m), 7.94–7.89 (2H, m), 7.68–7.34 (6H, m), 6.04–5.79 (2H, m), 4.46–4.36 (1H, m), 4.29 (2H, m), 2.79–2.56 (2H, m).

Example 30(14)
N-(2-fluorophenyl)sulfonyl-3-amino-4-oxo-5-(5-(2,6-dichlorophenylmethyl)tetrazol-2-yl)pentanoic acid

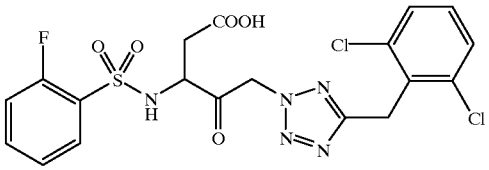

TLC: Rf 0.36 (chloroform:methanol:acetic acid=25:1:1); NMR (DMSO-d$_6$): δ 12.94–12.36 (1H, br), 8.86–8.70 (1H, m), 7.88–7.33 (7H, m), 5.97 (2H, brs), 4.52 (2H, s), 4.46 (1H, m), 2.78–2.47 (2H, m).

Example 30(15)
N-(4-fluorophenyl)sulfonyl-3-amino-4-oxo-5-(5-(2,6-dichlorophenylmethyl)tetrazol-2-yl)pentanoic acid

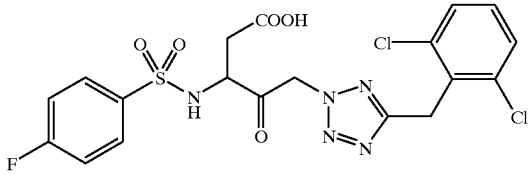

TLC: Rf 0.31 (chloroform:methanol:acetic acid=25:1:1); NMR (DMSO-d$_6$): δ 13.09–12.00 (1H, br), 8.62–8.46 (1H, m), 7.96–7.89 (2H, m), 7.53–7.32 (5H, m), 6.07–5.83 (2H, m), 4.51 (2H, s), 4.35 (1H, m), 2.56 (2H, m).

Example 30(16)
N-(3-fluorophenyl)sulfonyl-3-amino-4-oxo-5-(5-(2,6-dichlorophenylmethyl)tetrazol-2-yl)pentanoic acid

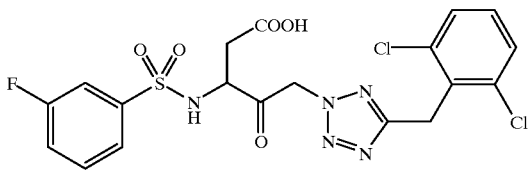

TLC: Rf 0.17 (chloroform:methanol:acetic acid=50:1:1); NMR (DMSO-d$_6$): δ 8.60 (1H, br), 7.75–7.32 (7H, m), 6.20–5.70 (2H, m), 4.51 (2H, s), 4.46–4.32 (1H, m), 2.62–2.53 (2H, m).

Example 30(17)
N-(2-bromophenyl)sulfonyl-3-amino-4-oxo-5-(5-(2,6-dichlorophenylmethyl)tetrazol-2-yl)pentanoic acid

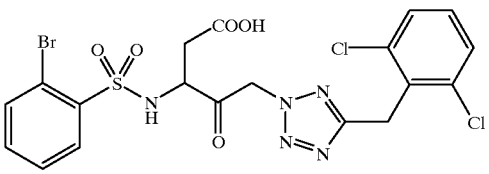

TLC: Rf 0.27 (chloroform:methanol:acetic acid=8:1:1); NMR (DMSO-d$_6$): δ 12.80–12.20 (1H, brs), 8.80–8.40 (1H, m), 8.12–8.00 and 7.90–7.79 (each 1H, m), 7.65–7.46 and 7.46–7.32 (total 5H, m), 6.15–5.75 (2H, m), 4.51 (2H, s), 4.60–4.30 (1H, m), 2.80–2.42 (2H, m).

Example 30(18)
N-(4-methoxyphenyl)sulfonyl-3-amino-4-oxo-5-(5-(2,6-dichlorophenylmethyl)tetrazol-2-yl)pentanoic acid

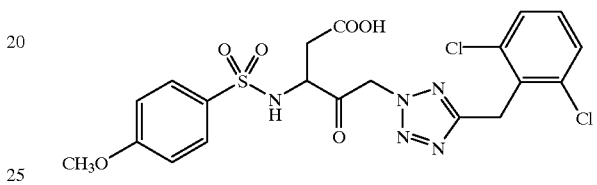

TLC: Rf 0.33 (chloroform:methanol:acetic acid=25:1:1); NMR (DMSO-d$_6$): δ 8.48–8.16 (1H, m), 7.82–7.78 (2H, m), 7.53–7.08 (5H, m), 6.15–5.63 (2H, m), 4.51 (2H, s), 4.33–4.15 (1H, m), 3.85 (3H, s).

Example 30(19)
N-(4-trifluoromethylphenyl)sulfonyl-3-amino-4-oxo-5-(5-(2,6-dichlorophenylmethyl)tetrazol-2-yl)pentanoic acid

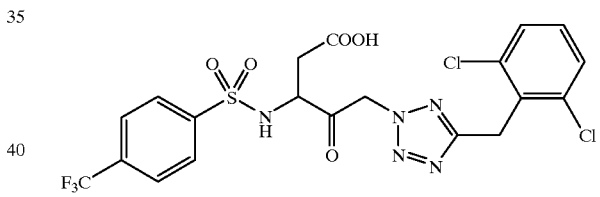

TLC: Rf 0.35 (chloroform:methanol:acetic acid=25:1:1); NMR (DMSO-d$_6$): δ 8.07 (2H, d, J=8.5 Hz), 7.96 (2H, t, J=8.5 Hz), 7.53–7.33 (3H, m), 6.08–5.65 (2H, m), 4.51 (2H, s), 4.46–4.55 (1H, m), 2.61–2.58 (2H, m).

Example 30(20)
N-(thiophen-2-yl)sulfonyl-3-amino-4-oxo-5-(5-(2,6-dichlorophenylmethyl)tetrazol-2-yl)pentanoic acid

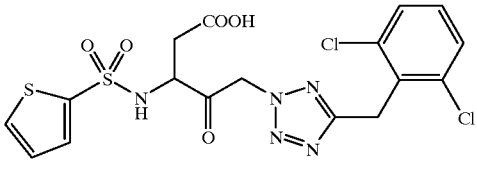

TLC: Rf 0.38 (chloroform:methanol:acetic acid=25:1:1); NMR (DMSO-d$_6$): δ 13.13–11.94 (1H, br), 8.92–8.46 (1H, m), 7.95 (1H, dd, J=5.0, 1.4 Hz), 7.70 (1H, m), 7.53–7.49 (2H, m,), 7.40–7.32 (1H, m), 7.18 (1H, dd, J=5.0, 4.0 Hz), 6.08–5.78 (2H, m), 4.52 (2H, s), 4.39 (1H, m), 2.57 (2H, m).

Example 30(21)
N-(3-phenylpropyl)sulfonyl-3-amino-4-oxo-5-(5-(2,6-dichlorophenylmethyl)tetrazol-2-yl)pentanoic acid

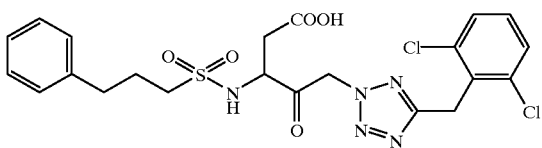

TLC: Rf 0.57 (chloroform:methanol:acetic acid=18:1:1); NMR (DMSO-d$_6$): δ 8.00–7.80 (1H, m), 7.56–7.47 and 7.43–7.13 (8H, m), 6.12–5.82 (2H, m), 4.52 (2H, s), 4.56–4.40 (1H, m), 3.22–3.07 (2H, m), 2.80–2.60 (4H, m), 2.06–1.87 (2H, m).

Example 30(22)

N-(2-fluorophenyl)sulfonyl-3-amino-4-oxo-5-(5-(2,6-dichlorophenylmethyl)tetrazol-1-yl)pentanoic acid

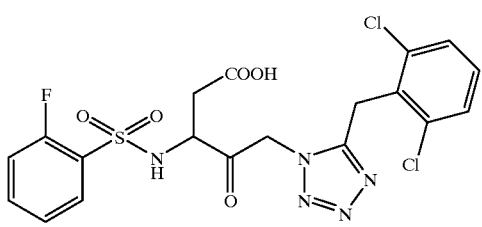

TLC: Rf 0.35 (chloroform:ethanol:acetic acid=18:1:1); NMR (DMSO-d$_6$): δ 8.9 (1H, br), 7.95–7.30 (7H, m), 5.94 (2H, br), 4.54 (1H, m), 4.30 (2H, brs), 2.74 (2H, m).

Example 30(23)

N-(4-chlorophenyl)sulfonyl-3-amino-4-oxo-5-(5-(2,6-dichlorophenylmethyl)tetrazol-2-yl)pentanoic acid

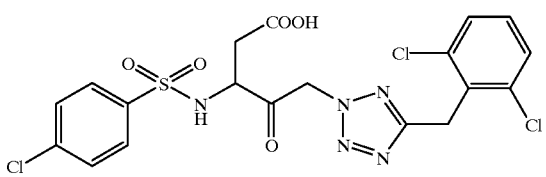

TLC: Rf 0.15 (chloroform:methanol:acetic acid=50:1:1); NMR (DMSO-d$_6$): δ 13.00–12.20 (1H, br), 8.78–8.40 (1H, br), 7.87 and 7.65 (each 2H, d, J=8.6 Hz), 7.52 (1H, d, J=8.6 Hz), 7.51 (1H, d, J=7.4 Hz), 7.41 (1H, dd, J=8.6 Hz, 7.4 Hz), 6.15–5.76 (2H, br), 4.51 (2H, s), 4.45–4.27 (1H, m), 2.67–2.53 (2H, m).

Example 30(24)

N-(3-chlorophenyl)sulfonyl-3-amino-4-oxo-5-(5-(2,6-dichlorophenylmethyl)tetrazol-2-yl)pentanoic acid

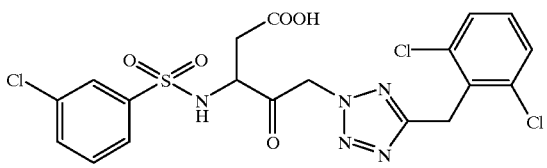

TLC: Rf 0.15 (chloroform:methanol:acetic acid=50:1:1); NMR (DMSO-d$_6$): δ 12.80–12.40 (1H, brs), 8.64 (1H, d, J=7.4 Hz), 7.90–7.70 and 7.42–7.32 (7H, m), 6.02 and 5.89 (each 1H, d, J=18.4 Hz), 4.51 (2H, s), 4.57–4.38 (1H, m), 2.66–2.55 (2H, m).

Example 30(25)

N-(2-chlorophenyl)sulfonyl-3-amino-4-oxo-5-(5-(2,6-dichlorophenylmethyl)tetrazol-2-yl)pentanoic acid

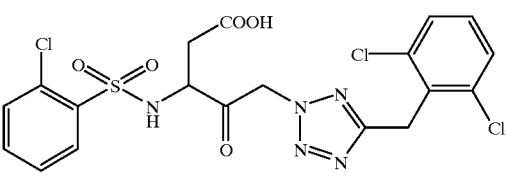

TLC: Rf 0.21 (chloroform:methanol:acetic acid=50:1:1); NMR (DMSO-d$_6$): δ 12.80–11.80 (1H, brs), 8.80–8.50 (1H, m), 8.02 (1H, d, J=7.4 Hz), 7.73–7.45 and 7.45–7.30 (6H, m), 6.10–5.80 (2H, m), 4.51 (2H, s), 4.57–4.32 (1H, m), 2.77–2.40 (2H, m).

Example 30(26)

N-(2-phenyloxyphenyl)sulfonyl-3-amino-4-oxo-5-(5-(2,6-dichlorophenylmethyl)tetrazol-2-yl)pentanoic acid

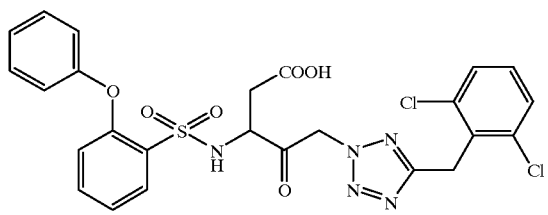

TLC: Rf 0.26 (chloroform:methanol:acetic acid=50:1:1); NMR (DMSO-d$_6$): δ 12.80–12.20 (1H, brs), 8.39–8.27 (1H, m), 7.95–7.85 (1H, m), 7.65–7.05 and 6.99–6.82 (11H, m), 6.03 and 5.91 (each 1H, d, J=18.4 Hz), 4.52 (2H, s), 4.60–4.40 (1H, m), 2.80–2.47 (2H, m).

Example 30(27)

N-(2-phenylphenyl)sulfonyl-3-amino-4-oxo-5-(5-(2,6-dichlorophenylmethyl)tetrazol-2-yl)pentanoic acid

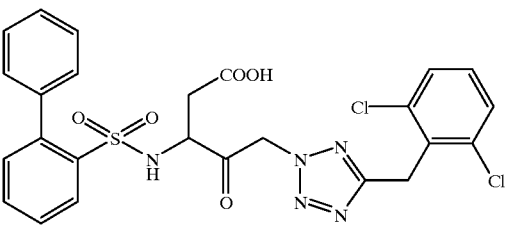

TLC: Rf 0.38 (chloroform:methanol:water=50:10:1); NMR (DMSO-d$_6$): δ 8.05 (1H, dd, J=1.0, 7.6 Hz), 7.68–7.30 (12H, m), 5.79 (2H, brs), 4.49 (2H, s), 3.96 (1H, m), 2.48–2.28 (2H, m).

Example 30(28)

N-(3-phenylpropyl)sulfonyl-3-amino-4-oxo-5-(5-(2,6-dichlorophenylmethyl)tetrazol-1-yl)pentanoic acid

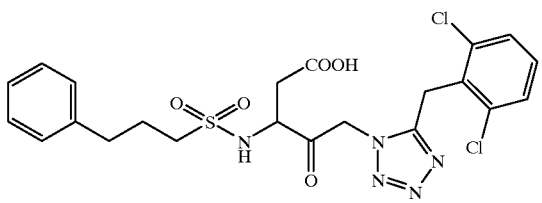

TLC: Rf 0.43 (chloroform:methanol:acetic acid=18:1:1); NMR (DMSO-d$_6$): δ 13.10–12.20 (1H, brs), 8.10–7.90 (1H, m), 7.61–7.13 (8H, m), 6.13–5.75 (2H, br), 4.65–4.47 (1H, m), 4.35 (2H, s), 3.25–3.10 (2H, m), 2.91–2.79 (2H, m) 2.79–2.64 (2H, m), 2.11–1.87 (2H, m).

Example 30(29)
N-(2-methoxyphenyl)sulfonyl-3-amino-4-oxo-5-(5-(2,6-dichlorophenylmethyl)tetrazol-2-yl)pentanoic acid

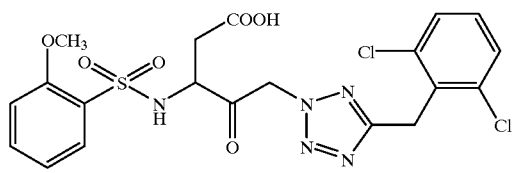

TLC: Rf 0.51 (chloroform:methanol:acetic acid=18:1:1); NMR (DMSO-d$_6$): δ 12.90–12.10 (1H, brs), 8.10–7.90 (1H, m), 7.80–7.01 (7H, m), 6.10–5.70 (2H, br), 4.50 (2H, s), 4.53–4.33 (1H, m), 3.85 (3H, s), 2.67–2.39 (2H, m).

Example 30(30)
N-(2,6-difluorophenyl)sulfonyl-3-amino-4-oxo-5-(5-(2,6-dichlorophenylmethyl)tetrazol-2-yl)pentanoic acid

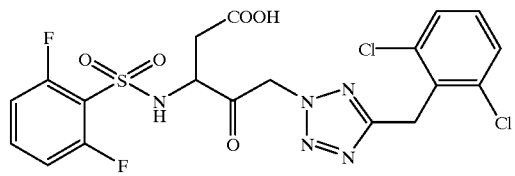

TLC: Rf 0.48 (chloroform:methanol:acetic acid=18:1:1); NMR (DMSO-d$_6$): δ 7.80–7.60, 7.60–7.47 and 7.47–7.17 (6H, m), 6.10–5.80 (2H, br), 4.63–4.52 (1H, m), 4.51 (2H, m), 2.85–2.43 (2H, m).

Example 30(31)
N-(4-cyanophenyl)sulfonyl-3-amino-4-oxo-5-(5-(2,6-dichlorophenylmethyl)tetrazol-2-yl)pentanoic acid

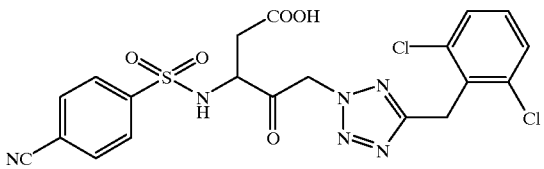

TLC: Rf 0.49 (chloroform:methanol:acetic acid=18:1:1); NMR (DMSO-d$_6$): δ 8.08 (2H, d, J=8.6 Hz), 8.00 (2H, d, J=8.6 Hz), 7.52 (1H, d, J=9.0 Hz), 7.51 (1H, d, J=6.8 Hz), 7.37 (1H, dd, J=9.0 Hz, 6.8 Hz), 6.10–5.75 (2H, br), 4.51 (2H, s), 4.48 (1H, m), 2.68–2.55 (2H, m).

Example 30(32)
N-(2-methylphenyl)sulfonyl-3-amino-4-oxo-5-(5-(2,6-dichlorophenylmethyl)tetrazol-2-yl)pentanoic acid

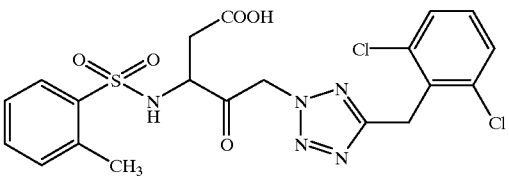

TLC: Rf 0.50 (chloroform:methanol:acetic acid=18:1:1); NMR (DMSO-d$_6$): δ 8.95–8.20 (1H, br), 7.90 (1H, d, J=7.6 Hz), 7.70–7.08 (6H, m), 6.30–5.42 (2H, br), 4.52 (2H, s), 4.30 (1H, brs), 2.58 (3H, s), 2.84–2.12 (2H, m).

Example 30(33)
N-(4-methylphenyl)sulfonyl-3-amino-4-oxo-5-(5-(2,6-dichlorophenylmethyl)tetrazol-2-yl)pentanoic acid

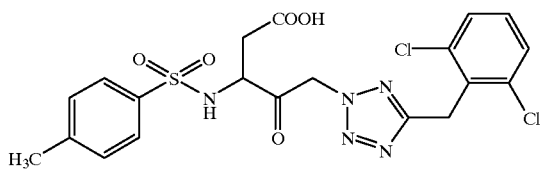

TLC: Rf 0.44 (chloroform:methanol:acetic acid=18:1:1); NMR (DMSO-d$_6$): δ 8.79–8.03 (1H, br), 7.76 (2H, d, J=8.0 Hz), 7.61–7.20 (5H, m), 6.32–5.42 (2H, br), 4.51 (2H, s), 4.43–4.14 (1H, m), 2.71–2.12 (2H, m), 2.39 (3H, s).

Example 30(34)
N-(4-phenylphenyl)sulfonyl-3-amino-4-oxo-5-(5-(2,6-dichlorophenylmethyl)tetrazol-2-yl)pentanoic acid

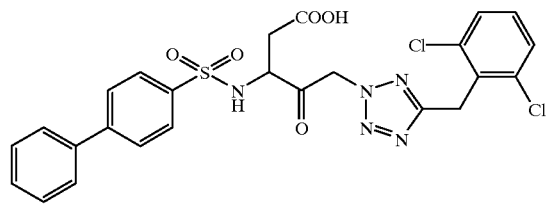

TLC: Rf 0.25 (chloroform:methanol:acetic acid=50:1:1); NMR (DMSO-d$_6$): δ 13.45–11.25 (1H, br), 8.87–8.27 (1H, br), 8.13–7.80 (4H, m), 7.76 (2H, d, J=6.6 Hz), 7.65–7.23 (6H, m), 6.33–5.55 (2H, br), 4.51 (2H, s), 4.58–4.20 (1H, m), 2.82–2.35 (2H, m).

Example 30(35)
N-(5-dibutylaminonaphthalen-1-yl)sulfonyl-3-amino-4-oxo-5-(5-(2,6-dichlorophenylmethyl)tetrazol-2-yl)pentanoic acid

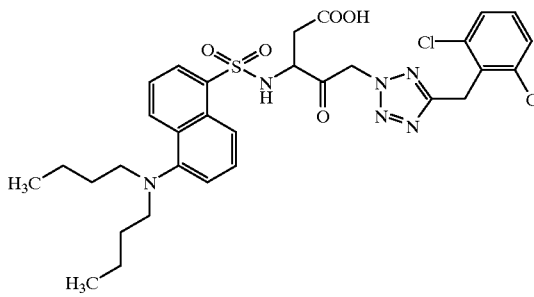

TLC: Rf 0.33 (chloroform:methanol:acetic acid=50:1:1); NMR (DMSO-d₆): δ 13.20–11.60 (1H, br), 9.10–8.49 (1H, br), 8.57 (1H, d, J=8.4 Hz), 8.33 (1H, d, J=8.2 Hz), 8.20 (1H, d, J=7.0 Hz), 7.75–7.22 (6H, m), 6.09–5.18 (2H, br), 4.47 (2H, s), 4.46–4.18 (1H, m), 3.08 (4H, t, J=7.4 Hz), 2.68–2.20 (2H, m), 1.54–0.97 (8H, m), 0.76 (6H, t, J=6.8 Hz).

Example 30(36)

N-(3-phenylphenyl)sulfonyl-3-amino-4-oxo-5-(5-(2,6-dichlorophenylmethyl)tetrazol-2-yl)pentanoic acid

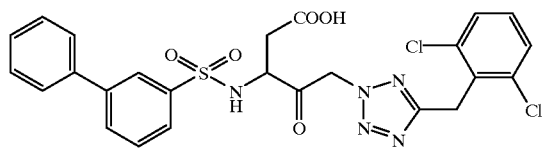

TLC: Rf 0.65 (chloroform:methanol:acetic acid=18:1:1); NMR (DMSO-d₆): δ 13.00–12.10 (1H, br), 8.71–8.40 (1H, br), 8.17–8.10, 8.00–7.79, 7.79–7.60 and 7.60–7.30 (12H, m), 6.15–5.73 (2H, br), 4.49 (2H, s), 4.55–4.35 (1H, m), 2.64–2.40 (2H, m).

Example 30(37)

N-(4-acetylaminophenyl)sulfonyl-3-amino-4-oxo-5-(5-(2,6-dichlorophenylmethyl)tetrazol-2-yl)pentanoic acid

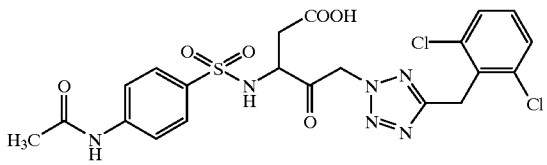

TLC: Rf 0.32 (chloroform:methanol:acetic acid=18:1:1); NMR (DMSO-d₆): δ 12.90–12.10 (1H, br), 10.34 (1H, s), 8.43–8.25 (1H, br), 7.83–7.70 (4H, m), 7.53 (1H, d, J=9.0 Hz), 7.52 (1H, d, J=6.8 Hz), 7.37 (1H, dd, J=9.0 Hz, 6.8 Hz), 6.10–5.77 (2H, br), 4.51 (2H, s), 4.39–4.20 (1H, m), 2.62–2.37 (2H, m) 2.09 (3H, s).

Example 30(38)

N-(4-t-butylphenyl)sulfonyl-3-amino-4-oxo-5-(5-(2,6-dichlorophenylmethyl)tetrazol-2-yl)pentanoic acid

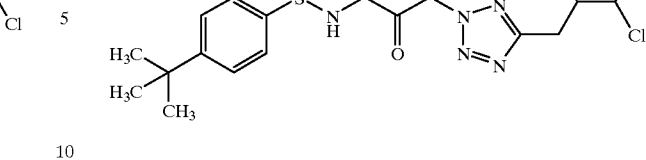

TLC: Rf 0.31 (chloroform:methanol:acetic acid=35:1:1); NMR (DMSO-d₆): δ 13.15–11.35 (1H, br), 8.86–8.03 (1H, br), 7.79 (2H, d, J=8.6 Hz), 7.61 (2H, d, J=8.6 Hz), 7.56–7.26 (3H, m), 6.24–5.42 (2H, br), 4.50 (2H, s), 4.40–4.20 (1H, m), 2.63–2.37 (2H, m), 1.29 (9H, s).

Example 30(39)

N-(5-dimethylaminonaphthalen-1-yl)sulfonyl-3-amino-4-oxo-5-(5-(2,6-dichlorophenylmethyl)tetrazol-1-yl)pentanoic acid

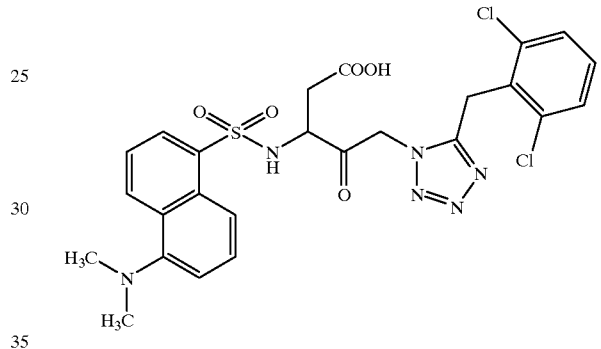

TLC: Rf 0.12 (chloroform:methanol:acetic acid=50:1:1); NMR (DMSO-d₆): δ 9.46–8.63 (1H, br), 8.49 (1H, d, J=8.4 Hz), 8.40–8.16 (2H, m), 7.74–7.15 (6H, m), 5.70 (2H, br), 4.48–4.32 (1H, m), 4.16 (2H, s), 2.81 (6H, s), 2.70–2.40 (2H, m).

Example 30(40)

N-(5-(pyridin-2-yl)thiophen-2-yl)sulfonyl-3-amino-4-oxo-5-(5-(2,6-dichlorophenylmethyl)tetrazol-2-yl)pentanoic acid•hydrochloric acid salt

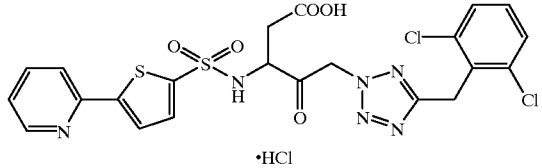

TLC: Rf 0.22 (chloroform:methanol:acetic acid=35:1:1); NMR (DMSO-d₆) δ 8.84 (1H, d, J=7.8 Hz), 8.59 (1H, d, J=4.4 Hz), 8.06 (1H, d, J=7.8 Hz), 8.00–7.80 (2H, m), 7.71 (1H, d, J=4.2 Hz), 7.58–7.27 (4H, m), 6.05 (2H, d, J=18.1 Hz), 5.91 (1H, d, J=18.1 Hz), 4.61–4.30 (1H, m), 4.49 (2H, s), 2.77–2.46 (2H, m).

Example 30(41)

N-(1-(3-chloro-5-trifluoromethylpyridin-2-yl)pyrrol-2-yl) sulfonyl-3-amino-4-oxo-5-(5-(2,6-dichlorophenylmethyl) tetrazol-2-yl)pentanoic acid hydrochloric acid salt

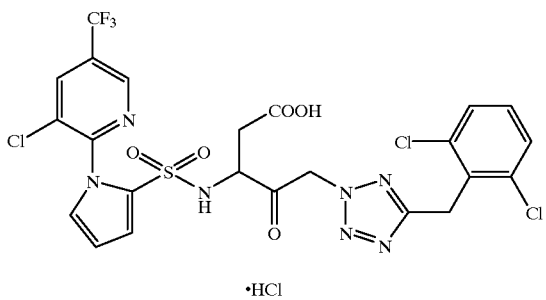

TLC: Rf 0.16 (chloroform:methanol:acetic acid=50:1:1); NMR (DMSO-d$_6$): δ 13.50–11.80 (1H, br), 8.95 (1H, brs), 8.77 (1H, brs), 8.41–8.17 (1H, m), 8.00 (1H, brs), 7.64–7.00 (4H, m), 6.66 (1H, brs), 6.23–5.68 (2H, m), 4.55–4.14 (1H, m), 4.50 (2H, s), 2.75–2.28 (2H, m).

Example 30(42)
N-(4-phenyloxyphenyl)sulfonyl-3-amino-4-oxo-5-(5-(2,6-dichlorophenylmethyl)tetrazol-2-yl)pentanoic acid

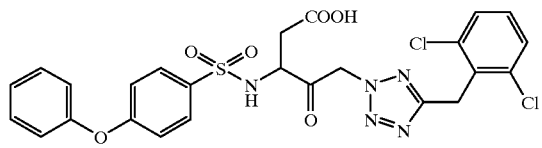

TLC: Rf 0.24 (chloroform:methanol:acetic acid=50:1:1); NMR (DMSO-d$_6$): δ 8.60–8.25 (1H, br), 7.93–7.79 (2H, m), 7.60–7.05 (10H, m), 6.10–5.70 (2H, br), 4.51 (2H, s), 4.40–4.23 (1H, m), 2.65–2.35 (2H, m).

Example 30(43)
N-(4-phenylthiophenyl)sulfonyl-3-amino-4-oxo-5-(5-(2,6-dichlorophenylmethyl)tetrazol-2-yl)pentanoic acid

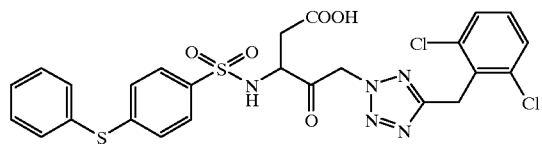

TLC: Rf 0.24 (chloroform:methanol:acetic acid=50:1:1); NMR (DMSO-d$_6$): δ 8.67–8.25 (1H, br), 7.83–7.72 (2H, m), 7.60–7.25 (10H, m), 6.12–5.65 (2H, br), 4.51 (2H, s), 4.40–4.23 (1H, m), 2.65–2.33 (2H, m).

Example 30(44)
N-octanylsulfonyl-3-amino-4-oxo-5-(5-(2,6-dichlorophenylmethyl) tetrazol-2-yl)pentanoic acid

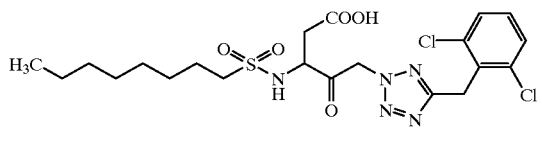

TLC: Rf 0.17 (chloroform:methanol:acetic acid=50:1:1); NMR (DMSO-d$_6$): δ 8.00–7.64 (1H, br), 7.60–7.30 (3H, m), 6.20–5.63 (2H, br), 4.61–4.33 (1H, m), 4.52 (2H, s), 3.25–3.00 (2H, m), 2.88–2.60 (2H, m), 1.82–1.48 (2H, m), 1.48–1.06 (10H, m), 0.97–0.70 (3H, m).

Example 30(45)
N-(4-phenylphenyl)sulfonyl-3-amino-4-oxo-5-(5-(2,6-dichlorophenylmethyl)tetrazol-2-yl)pentanoic acid

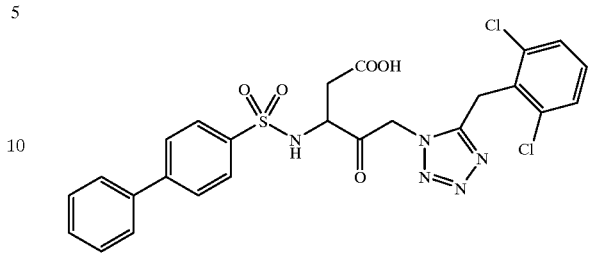

TLC: Rf 0.10 (chloroform:methanol:acetic acid=50:1:1); NMR (DMSO-d$_6$): δ 9.23–8.40 (1H, br), 8.06–7.82 (4H, m), 7.82–7.64 (2H, m), 7.64–7.24 (6H, m), 6.26–5.45 (2H, br), 4.56–4.30 (1H, m), 4.33 (1H, d, J=18.0 Hz), 4.22 (1H, d, J=18.0 Hz), 2.90–2.50 (2H, m).

Example 30(46)
N-(4-phenylcarbonylmethylphenyl)sulfonyl-3-amino-4-oxo-5-(5-(2,6-dichlorophenylmethyl)tetrazol-2-yl)pentanoic acid

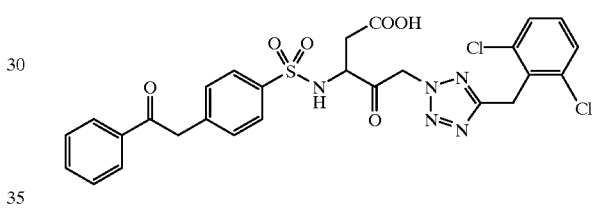

TLC: Rf 0.61 (chloroform:methanol:acetic acid=18:1:1); NMR (DMSO-d$_6$): δ 8.70–8.20 (1H, br), 8.10–7.99, 7.88–7.78 and 7.78–7.33 (total 12H, m), 6.10–5.64 (2H, br), 4.56 (2H, s), 4.51 (2H, s), 4.40–4.27 (1H, m), 2.60–2.38 (2H, m).

Example 30(47)
N-(2-acetylamino-4-methylthiazol-5-yl)sulfonyl-3-amino-4-oxo-5-(5-(2,6-dichlorophenylmethyl)tetrazol-2-yl)pentanoic acid

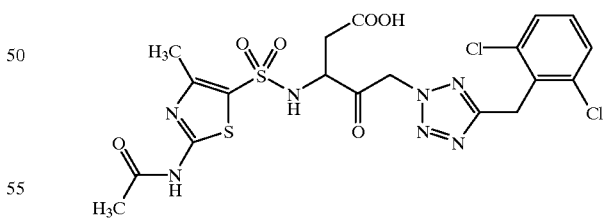

TLC: Rf 0.35 (chloroform:methanol:acetic acid=18:1:1); NMR (DMSO-d$_6$): δ 12.70–12.35 (1H, br), 7.52 (1H, d, J=9.0 Hz), 7.52 (1H, d, J=7.0 Hz), 7.37 (1H, dd, J=9.0 Hz, 7.0 Hz), 6.12–5.71 (2H, br), 4.51 (2H, s), 4.39–4.23 (1H, m), 2.64–2.38 (2H, m) 2.50 (3H, s), 2.17 (3H, s).

Example 30(48)
N-(2,2,2-trifluoroethylsulfonyl-3-amino-4-oxo-5-(5-(2,6-dichlorophenylmethyl)tetrazol-2-yl)pentanoic acid

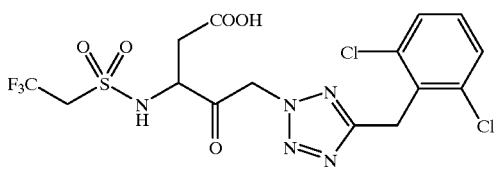

TLC: Rf 0.32 (chloroform:methanol:acetic acid=18:1:1); NMR (DMSO-d$_6$): δ 7.52 (1H, d, J=9.4 Hz), 7.52 (1H, d, J=6.8 Hz), 7.37 (1H, dd, J=9.4 Hz, 6.8 Hz), 6.20–5.80 (2H, br), 4.72–4.45 (3H, m), 4.52 (2H, s), 2.89–2.65 (2H, m).

Example 30(49)

N-(2-trifluoromethylphenyl)sulfonyl-3-amino-4-oxo-5-(5-(2,6-dichlorophenylmethyl)tetrazol-2-yl)pentanoic acid

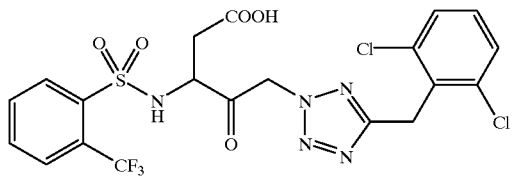

TLC: Rf 0.24 (chloroform:methanol:acetic acid=35:1:1); NMR (DMSO-d$_6$): δ 13.10–11.85 (1H, br), 9.22–8.18 (1H, br), 8.26–8.12 (1H, m), 8.22–7.76 (2H, m), 7.52 (1H, d, J=9.0 Hz), 7.52 (1H, d, J=7.0 Hz), 7.37 (1H, dd, J=9.0 and 7.0 Hz), 6.25–5.60 (2H, br), 4.63–4.34 (1H, m), 4.51 (2H, s), 2.83–2.49 (2H, m).

Example 30(50)

N-(benzofurazan-4-yl)sulfonyl-3-amino-4-oxo-5-(5-(2,6-dichlorophenylmethyl)tetrazol-2-yl)pentanoic acid

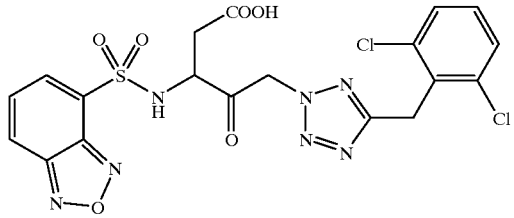

TLC: Rf 0.18 (chloroform:methanol:acetic acid=35:1:1); NMR (DMSO-d$_6$): δ 12.80–11.80 (1H, br), 9.50–8.82 (1H, br), 8.36 (1H, d, J=9.0 Hz), 8.12 (1H, d, J=6.8 Hz), 7.74 (1H, dd, J=9.0 and 6.8 Hz), 7.52 (1H, d, J=9.1 Hz), 7.52 (1H, d, J=7.1 Hz), 7.37 (1H, dd, J=9.1 and 7.1 Hz), 5.98 (2H, s), 4.75–4.41 (1H, m), 4.50 (2H, s), 2.85–2.42 (2H, m).

Example 30(51)

N-(3,5-dimethylisooxazol-4-yl)sulfonyl-3-amino-4-oxo-5-(5-(2,6-dichlorophenylmethyl)tetrazol-2-yl)pentanoic acid

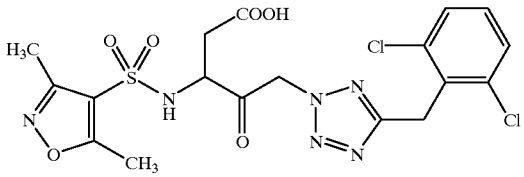

TLC: Rf 0.50 (chloroform:methanol:acetic acid=18:1:1); NMR (DMSO-d$_6$): δ 13.10–11.90 (1H, br), 9.20–8.40 (1H, br), 7.52 (1H, d, J=8.8 Hz), 7.52 (1H, d, J=7.0 Hz), 7.37 (1H, dd, J=8.8 Hz, 7.0 Hz), 6.15–5.80 (2H, br), 4.52 (2H, s), 4.42–4.30 (1H, m), 2.82–2.35 (2H, m), 2.57 (3H, s), 2.32 (3H, s).

Example 30(52)

N-(2-benzyloxycarbonylaminoethyl)sulfonyl-3-amino-4-oxo-5-(5-(2,6-dichlorophenylmethyl)tetrazol-2-yl)pentanoic acid

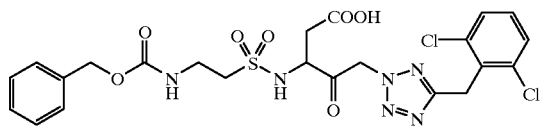

TLC: Rf 0.42 (chloroform:methanol:acetic acid=18:1:1); NMR (DMSO-d$_6$): δ 8.10–7.65 (1H, br), 7.58–7.20 (8H, m), 6.15–5.80 (2H, br), 5.01 (2H, s), 4.57–4.40 (1H, m), 4.52 (2H, s), 3.80–2.90 (4H, m), 2.90–2.60 (2H, m).

Example 30(53)

N-(1,1-dioxotetrahydrothiophen-3-yl)sulfonyl-3-amino-4-oxo-5-(5-(2,6-dichlorophenylmethyl)tetrazol-2-yl)pentanoic acid

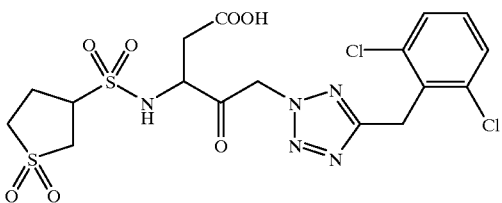

TLC: Rf 0.14 (chloroform:methanol:acetic acid=20:1:1); NMR (DMSO-d$_6$): δ 7.64–7.22 (3H, m), 5.97 (2H, brs), 4.68–4.14 (2H, m), 4.52 (2H, s), 3.85–3.00 (4H, m), 2.90–2.20 (4H, m).

Example 30(54)

N-(5-phenylcarbonylaminomethylthiophen-2-yl)sulfonyl-3-amino-4-oxo-5-(5-(2,6-dichlorophenylmethyl)tetrazol-2-yl)pentanoic acid

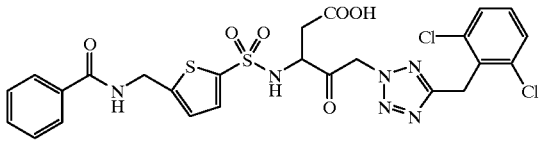

TLC: Rf 0.16 (chloroform:methanol:acetic acid=20:1:1); NMR (DMSO-d$_6$): δ 9.30 (1H, t, J=5.8 Hz), 7.88 (2H, d, J=6.6 Hz), 7.66–6.99 (8H, m), 6.06–5.70 (2H, m), 4.66 (2H, d, J=5.8 Hz), 4.50 (2H, s), 4.17 (1H, t, J=6.2 Hz), 2.64–2.23 (2H, m).

Example 30(55)

N-(2,1,3-benzothiadiazol-4-yl)sulfonyl-3-amino-4-oxo-5-(5-(2,6-dichlorophenylmethyl)tetrazol-2-yl)pentanoic acid

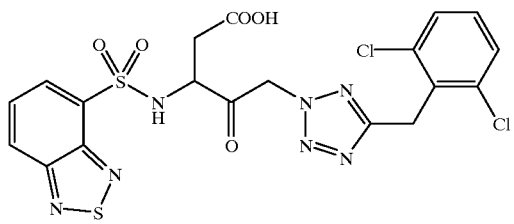

TLC: Rf 0.24 (chloroform:methanol:acetic acid=40:1:1); NMR (DMSO-d₆): δ 13.30–11.70 (1H, br), 9.20–8.00 (1H, br), 8.38 (1H, d, J=9.0 Hz), 8.25 (1H, d, J=6.0 Hz), 7.85 (1H, dd, J=9.0 and 6.0 Hz), 7.52 (2H, m), 7.38 (1H, dd, J=9.0 and 6.8 Hz), 6.25–5.52 (2H, m), 5.00–4.64 (1H, m), 4.49 (2H, s), 2.89–2.35 (2H, m).

Example 30(56)

N-(4-acetylaminophenyl)sulfonyl-3-amino-4-oxo-5-(5-(2,6-dichlorophenylmethyl)tetrazol-1-yl)pentanoic acid

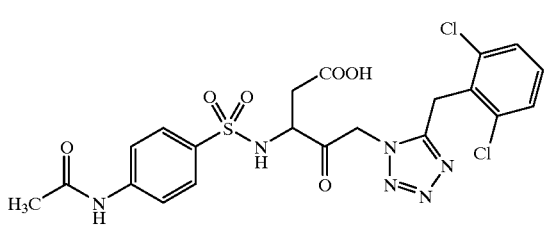

TLC: Rf 0.39 (chloroform:methanol:acetic acid=8:1:1); NMR (DMSO-d₆): δ 10.39 (1H, s), 7.88–7.70 (4H, m), 7.56–7.34 (3H, m), 6.03–5.70 (2H, br), 4.33 and 4.22 (each 1H, d, J=15.0 Hz), 4.12–4.00 (1H, m), 2.55–2.22 (2H, m), 2.07 (3H, s).

Example 30(57)

N-(4-phenylthiophenyl)sulfonyl-3-amino-4-oxo-5-(5-(2,6-dichlorophenylmethyl)tetrazol-1-yl)pentanoic acid

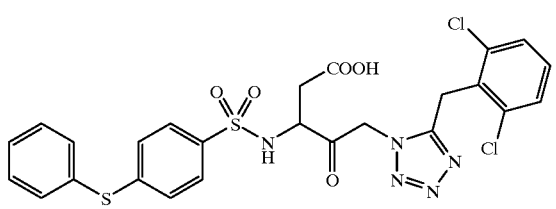

TLC: Rf 0.47 (chloroform:methanol:acetic acid=18:1:1); NMR (DMSO-d₆): δ 13.00–11.90 (1H, br), 9.00–8.40 (1H, br), 7.81 (2H, d, J=8.2 Hz), 7.60–7.38 (8H, m), 7.32 (2H, d, J=8.2 Hz), 6.02–5.65 (2H, br), 4.45–4.31 (1H, m), 4.29 (2H, s), 2.81–2.52 (2H, m).

Example 30(58)

N-(2-nitrophenyl)sulfonyl-3-amino-4-oxo-5-(5-(2,6-dichlorophenylmethyl)tetrazol-2-yl)pentanoic acid

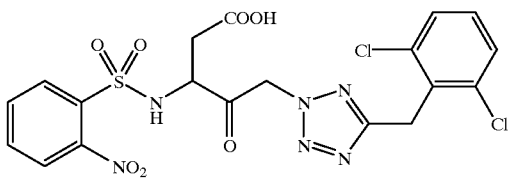

TLC: Rf 0.52 (chloroform:methanol:acetic acid=18:1:1); NMR (DMSO-d₆): δ 12.90–12.00 (1H, br), 9.20–8.35 (1H, br), 8.15–7.80 (4H, m), 7.52 (1H, d, J=9.0 Hz), 7.52 (1H, d, J=7.0 Hz), 7.37 (1H, dd, J=9.0 Hz, J=7.0 Hz), 6.10–5.70 (2H, br), 4.65–4.45 (1H, m), 4.51 (2H, s), 2.85–2.55 (2H, m).

Example 30(59)

N-(camphor-10-yl)sulfonyl-3-amino-4-oxo-5-(5-(2,6-dichlorophenylmethyl)tetrazol-2-yl)pentanoic acid

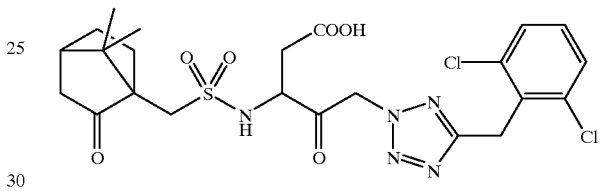

TLC: Rf 0.57 and 0.49 (chloroform:methanol:acetic acid= 18:1:1); NMR (DMSO-d₆): δ 13.10–11.90 (1H, br), 8.00–7.74 (1H, br), 7.52 (1H, d, J=9.0 Hz), 7.52 (1H, d, J=6.8 Hz), 7.37 (1H, dd, J=9.0 Hz, J=6.8 Hz), 6.18–5.79 (2H, br), 4.65–4.45 (1H, m), 4.52 (2H, s), 3.54, 3.45, 3.20 and 3.13 (total 2H, each d, J=14.0 Hz), 2.87–2.68 (2H, m), 2.46–2.36, 2.10–1.81 and 1.62–1.30 (total 7H, m), 1.03 (3H, s), 0.82 and 0.81 (total 3H, each s).

Example 30(60)

N-(6-chloroimizazo[2,1-B]thiazol-5-yl)sulfonyl-3-amino-4-oxo-5-(5-(2,6-dichlorophenylmethyl)tetrazol-2-yl)pentanoic acid

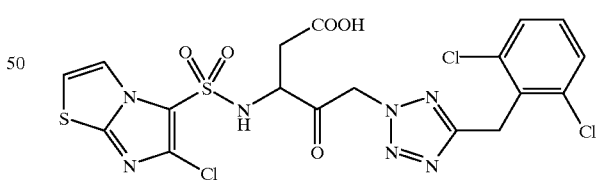

TLC: Rf 0.40 (chloroform:methanol:acetic acid=20:1:1); NMR (DMSO-d₆): δ 8.01 (1H, d, J=4.6 Hz), 7.59 (1H, d, J=4.6 Hz), 7.56–7.25 (3H, m), 6.12–5.74 (2H, br), 4.51 (2H, s), 4.40 (1H, t, J=6.0 Hz), 2.85–2.46 (2H, m).

Example 30(61)

N-(5-(2-methylthiopyrimidin-4-yl)thiophen-2-yl)sulfonyl-3-amino-4-oxo-5-(5-(2,6-dichlorophenylmethyl)tetrazol-2-yl)pentanoic acid

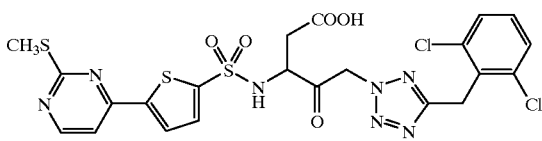

TLC: Rf 0.34 (chloroform:methanol:acetic acid=18:1:1); NMR (DMSO-d$_6$): δ 13.10–12.20 (1H, br), 9.44–8.40 (1H, br), 8.72 (1H, d, J=5.2 Hz), 8.10 (1H, d, J=4.1 Hz), 7.81 (1H, d, J=5.2 Hz), 7.76 (1H, d, J=4.1 Hz), 7.60–7.23 (3H, m), 6.25–5.70 (2H, br), 4.49 (3H, brs), 2.96–2.33 (2H, m), 2.57 (3H, s).

Example 30(62)
N-(4-butylphenyl)sulfonyl-3-amino-4-oxo-5-(5-(2,6-dichlorophenylmethyl)tetrazol-2-yl)pentanoic acid

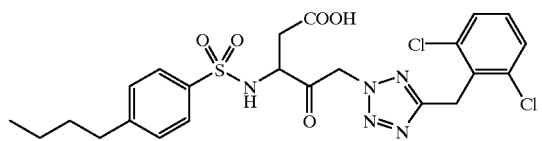

TLC: Rf 0.35 (chloroform:methanol:acetic acid=50:1:1); NMR (DMSO-d$_6$): δ 13.10–11.90 (1H, br), 8.55–8.20 (1H, br), 7.77 (2H, d, J=8.0 Hz), 7.52 (1H, d, J=9.0 Hz), 7.52 (1H, d, J=7.2 Hz), 7.41 (2H, d, J=8.0 Hz), 7.37 (1H, dd, J=9.0 Hz, J=7.2 Hz), 6.10–5.58 (2H, br), 4.51 (2H, s), 4.39–4.20 (1H, m), 2.66 (2H, t, J=7.6 Hz), 2.56–2.32 (2H, m), 1.66–1.45 and 1.37–1.14 (each 2H, m), 0.87 (3H, t, J=7.4 Hz).

Example 30(63)
N-(4-butylphenyl)sulfonyl-3-amino-4-oxo-5-(5-( 2,6-dichlorophenylmethyl)tetrazol-1-yl)pentanoic acid

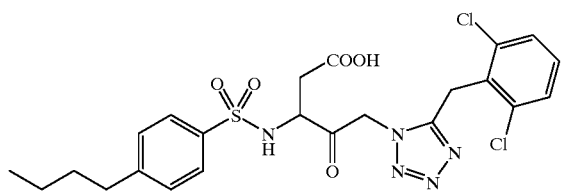

TLC: Rf 0.17 (chloroform:methanol:acetic acid=50:1:1); NMR (DMSO-d$_6$): δ 12.90–11.50 (1H, br), 8.80–8.10 (1H, br), 7.81 (2H, d, J=8.4 Hz), 7.60–7.32 (3H, m), 7.42 (2H, d, J=8.4 Hz), 6.03–5.60 (2H, br), 4.42–4.12 (3H, m), 2.80–2.58 (4H, m), 1.65–1.43 and 1.40–1.15 (each 2H, m), 0.87 (3H, t, J=7.4 Hz).

Example 30(64)
N-(5-(isooxazol-3-yl)thiophen-2-yl)sulfonyl-3-amino-4-oxo-5-(5-(2,6-dichlorophenylmethyl)tetrazol-2-yl)pentanoic acid

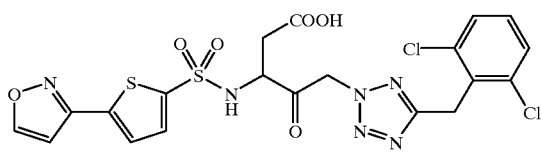

TLC: Rf 0.38 (chloroform:methanol:acetic acid=20:1:1); NMR (DMSO-d$_6$): δ 8.73 (1H, d, J=1.8 Hz), 7.89–7.64 (2H, m), 7.64–7.23 (3H, m), 7.10 (1H, d, J=1.8 Hz), 6.27–5.55 (2H, br), 4.63–4.30 (3H, m), 2.92–2.47 (2H, m).

Example 30(65)
N-(5-(4-chlorophenylcarbonylaminomethyl)thiophen-2-yl)sulfonyl- 3-amino-4-oxo-5-(5-(2,6-dichlorophenylmethyl)tetrazol-2-yl)pentanoic acid

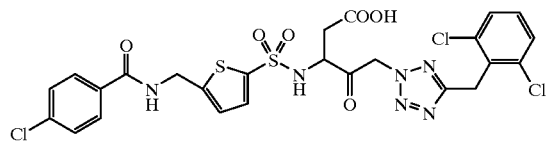

TLC: Rf 0.18 (chloroform:methanol:acetic acid=20:1:1); NMR (DMSO-d$_6$): δ 9.36 (1H, t, J=5.8 Hz), 8.03–7.76 (2H, m), 7.76–7.27 (5H, m), 7.09 (1H, d, J=4.0 Hz), 6.06–5.61 (2H, m), 4.66 (2H, d, J=5.8 Hz), 4.50 (2H, s), 4.30 (1H, t, J=6.0 Hz), 2.69–2.37 (2H, m).

Example 30(66) ps N-(4-(pyrrolidin-1-yl)phenyl)sulfonyl-3-amino-4-oxo-5-(5-(2,6-dichlorophenylmethyl)tetrazol-1-yl)pentanoic acid

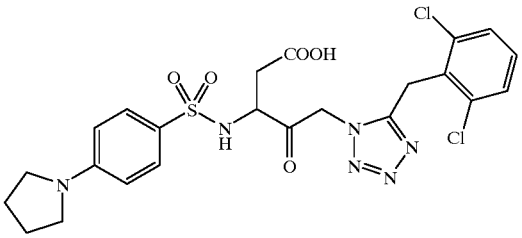

TLC: Rf 0.49 (chloroform:methanol:acetic acid=20:1:1); NMR (DMSO-d$_6$): δ 8.33–7.94 (1H, br), 7.83–7.18 (5H, m), 6.74–6.45 (2H, m), 6.07–5.51 (2H, br), 4.39–4.00 (3H, m), 3.45–3.00 (4H, m), 2.92–2.58 (2H, m), 2.10–1.70 (4H, m).

Example 30(67)
N-(4-(morpholin-4-yl)phenyl)sulfonyl-3-amino-4-oxo-5-(5-( 2,6-dichlorophenylmethyl)tetrazol-1-yl)pentanoic acid

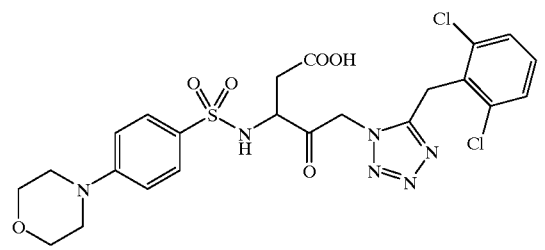

TLC: Rf 0.24 (chloroform:methanol:acetic acid=20:1:1); NMR (DMSO-d$_6$): δ 8.62–7.90 (1H, br), 7.81–7.61 (2H, m), 7.61–7.17 (3H, m), 7.17–6.97 (2H, m), 6.02–5.57 (2H, m), 4.44–4.02 (3H, m), 3.95–3.55 (4H, m), 3.30–3.00 (4H, m), 2.78–2.40 (2H, m).

Example 30(68)
N-(2-diethylaminoethyl)sulfonyl-3-amino-4-oxo-5-(5-(2,6-dichlorophenylmethyl)tetrazol-2-yl)pentanoic acid•hydrochloric acid salt

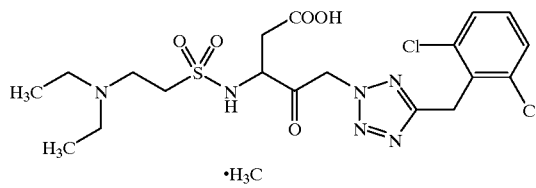

TLC: Rf 0.40 (chloroform:methanol:acetic acid=6:2:2); NMR (DMSO-d$_6$): δ 8.50–8.10 (1H, br), 7.53 (2H, d, J=8.8 Hz), 7.52 (2H, d, J=7.4 Hz), 7.34 (2H, d, J=8.8 Hz, 7.4 Hz), 6.06 (2H, br), 4.65–4.40 (1H, m), 4.52 (2H, s), 3.84–3.00 (8H, m), 3.00–2.83 (2H, m), 1.22 (6H, t, J=7.0 Hz).

Example 30(69)

N-(3-methylphenyl)sulfonyl-3-amino-4-oxo-5-(5-(2,6-dichlorophenylmethyl)tetrazol-2-yl)pentanoic acid

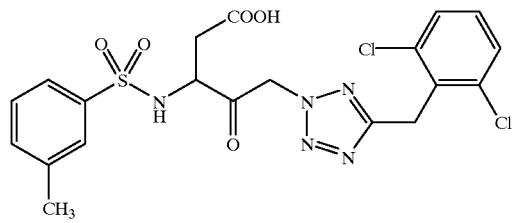

TLC: Rf 0.22 (chloroform:methanol:acetic acid=40:1:1); NMR (DMSO-d$_6$): δ 13.45–11.42 (1H, br), 8.79–8.10 (1H, br), 7.83–7.10 (7H, m), 6.20–5.54 (2H, br), 4.51 (2H, s), 4.43–4.20 (1H, m), 2.69–2.22 (2H, m), 2.39 (3H, s).

Example 30(70)

N-(4-isopropylphenyl)sulfonyl-3-amino-4-oxo-5-(5-(2,6-dichlorophenylmethyl)tetrazol-2-yl)pentanoic acid

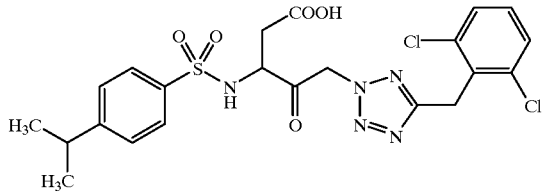

TLC: Rf 0.31 (chloroform:methanol:acetic acid=40:1:1); NMR (DMSO-d$_6$): δ 13.60–11.40 (1H, br), 8.82–8.03 (1H, br), 7.93–7.65 (2H, m), 7.65–7.10 (5H, m), 6.28–5.39 (2H, br), 4.51 (2H, s), 4.43–4.17 (1H, m), 3.10–2.81 (1H, m), 2.78–2.29 (2H, m), 1.21 (6H, d, J=6.8 Hz).

Example 30(71)

N-(4-isopropylphenyl)sulfonyl-3-amino-4-oxo-5-(5-(2,6-dichlorophenylmethyl)tetrazol-1-yl)pentanoic acid

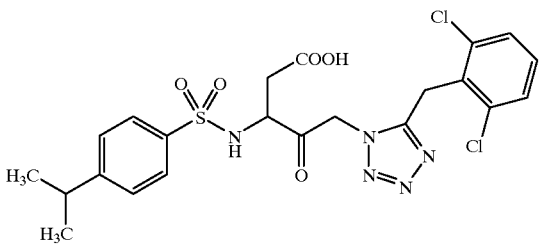

TLC: Rf 0.41 (chloroform:methanol:acetic acid=18:1:1); NMR (DMSO-d$_6$): δ 13.40–11.70 (1H, br), 8.89–8.20 (1H, br), 7.95–7.69 (2H, m), 7.69–7.05 (5H, m), 6.18–5.50 (2H, br), 4.52–4.14 (1H, m), 4.30 (2H, s), 3.07–2.85 (1H, m), 2.85–2.43 (2H, m), 1.21 (6H, d, J=6.8 Hz).

Example 30(72)

N-(2-diethylaminoethyl)sulfonyl-3-amino-4-oxo-5-(5-(2,6-dichlorophenylmethyl)tetrazol-1-yl)pentanoic acid•hydrochloric acid salt

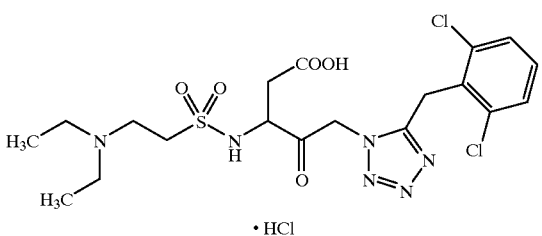

TLC: Rf 0.32 (chloroform:methanol:acetic acid=6:2:2); NMR (DMSO-d$_6$): δ 7.55 (1H, d, J=9.2 Hz), 7.55 (1H, d, J=6.8 Hz), 7.55 (1H, dd, J=9.2 Hz, 6.8 Hz), 6.05–5.87 (2H, br), 4.95–4.54 (1H, m), 4.38 (2H, m), 3.78–2.75 (10H, m), 1.16 (6H, t, J=7.0 Hz).

Example 30(73)

N-(4-butyloxyphenyl)sulfonyl-3-amino-4-oxo-5-(5-(2,6-dichlorophenylmethyl)tetrazol-2-yl)pentanoic acid

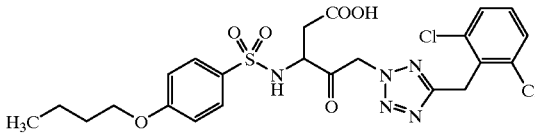

TLC: Rf 0.32 (chloroform:methanol:acetic acid=40:1:1l); NMR (DMSO-d$_6$): δ 13.25–11.90 (1H, br), 8.54–8.10 (1H, br), 7.89–7.65 (2H, m), 7.60–7.26 (3H, m), 7.20–6.97 (2H, m), 6.28–5.49 (2H, br), 4.51 (2H, s), 4.40–4.09 (1H, m), 4.06 (2H, t, J=6.2 Hz), 2.74–2.26 (2H, m), 1.87–1.58 (2H, m), 1.58–1.26 (2H, m), 0.93 (3H, t, J=7.2 Hz).

Example 30(74)

N-(4-butyloxyphenyl)sulfonyl-3-amino-4-oxo-5-(5-(2,6-dichlorophenylmethyl)tetrazol-1-yl)pentanoic acid

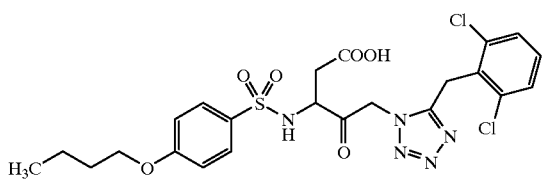

TLC: Rf 0.10 (chloroform:methanol:acetic acid=40:1:1); NMR (DMSO-d$_6$): δ 13.52–11.75 (1H, br), 8.74–8.12 (1H, br), 8.00–7.67 (2H, m), 7.67–7.25 (3H, m), 7.25–6.98 (2H, m), 6.15–5.48 (2H, br), 4.48–4.11 (1H, m), 4.26 (2H, s), 4.02 (2H, t, J=6.4 Hz), 2.83–2.37 (2H, m), 1.84–1.55 (2H, m), 1.55–1.24 (2H, m), 0.93 (3H, t, J=7.2 Hz).

Example 31 (1)
N-(4-phenylsulfinylphenyl)sulfonyl-3-amino-4-oxo-5-(5-(2,6-dichlorophenylmethyl)tetrazol-2-yl)pentanoic acid•t-butylester

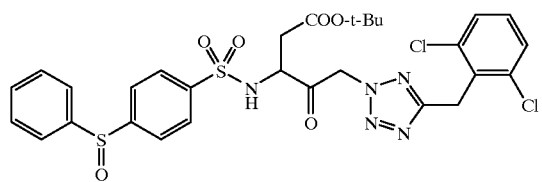

By the same procedure as provided in example 8(1), using the compound prepared in example 29(43), the compound of the present invention having the following physical data was obtained.

TLC: Rf 0.12 (hexane:ethyl acetate=2:1); NMR (CDCl$_3$): δ 8.00–7.88 and 7.88–7.75 (4H, m), 7.70–7.56 and 7.53–7.43 (5H, m), 7.40–7.12 (3H, m), 6.30–6.15 (1H, m), 5.80 (1H, d, J=17.8 Hz), 5.59 and 5.58 (total 1H, d, J=17.8 Hz), 4.60 (2H, s), 4.21–4.05 (1H, m), 2.78 (1H, dd, J=17.4 Hz, 4.0 Hz), 2.28 and 2.27 (1H, dd, J=17.4 Hz, 4.6 Hz), 1.36 (9H, s).

Example 32(1)
N-(4-phenylsulfonylphenyl)sulfonyl-3-amino-4-oxo-5-(5-(2,6-dichlorophenylmethyl)tetrazol-2-yl)pentanoic acid•t-butylester

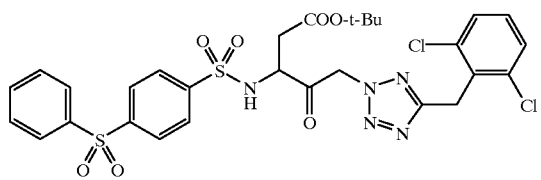

By the same procedure as provided in example 9(1), using the compound prepared in example 29(43), the compound of the present invention having the following physical data was obtained.

TLC: Rf 0.21 (hexane:ethyl acetate=2:1); NMR (CDCl$_3$): δ 8.10 (2H, d, J=8.0 Hz), 7.97 (2H, d, J=8.0 Hz), 7.98–7.90 (2H, m), 7.70–7.47 (3H, m), 7.36 (1H, d, J=9.0 Hz), 7.36 (1H, d, J=7.0 Hz), 7.18 (1H, dd, J=9.0 Hz, 7.0 Hz), 6.15 (1H, d, J=9.0 Hz), 5.82 and 5.62 (each 1H, d, J=17.8 Hz), 4.60 (2H, s), 4.22–4.08 (1H, m), 2.78 (1H, dd, J=17.6 Hz, 4.0 Hz), 2.29 (1H, dd, J=17.6 Hz, 4.6 Hz), 1.35 (9H, s).

EXAMPLE 33(1) AND EXAMPLE 33(2)

By the same procedure as provided in example 6(1), using the compound prepared in example 31(1) or example 32(1), the compounds of the present invention having the following physical data were obtained.

Example 33(1)
N-(4-phenylsulfinylphenyl)sulfonyl-3-amino-4-oxo-5-(5-(2,6-dichlorophenylmethyl)tetrazol-2-yl)pentanoic acid

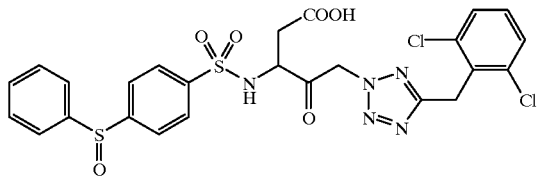

TLC: Rf 0.10 (chloroform:methanol:acetic acid=50:1:1); NMR (DMSO-d$_6$): δ 8.00 (2H, d, J=8.4 Hz), 7.96 (2H, d, J=8.4 Hz), 7.80–7.67 (2H, m), 7.61–7.46 and 7.42–7.32 (6H, m), 6.00–5.62 (2H, br), 4.50 (2H, s), 4.33–4.22 (1H, m), 2.57–2.37 (2H, m).

Example 33(2)
N-(4-phenylsulfonylphenyl)sulfonyl-3-amino-4-oxo-5-(5-(2,6-dichlorophenylmethyl)tetrazol-2-yl)pentanoic acid

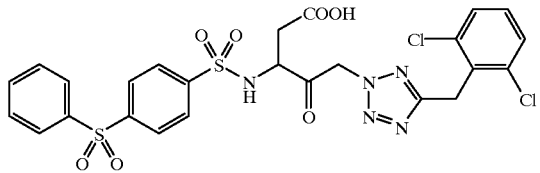

TLC: Rf 0.14 (chloroform:methanol:acetic acid=50:1:1); NMR (CDCl$_3$): δ 8.17 (2H, d, J=8.4 Hz), 8.06 (2H, d, J=8.4 Hz), 8.01–7.93 (2H, m), 7.78–7.45 and 7.45–7.31 (6H, m), 6.03–5.68 (2H, br), 4.51 (2H, s), 4.45–4.33 (1H, m), 2.65–2.52 (2H, m).

Example 34(1)
N-(4-aminophenyl)sulfonyl-3-amino-4-oxo-5-(5-(2,6-dichlorophenylmethyl)tetrazol-2-yl)pentanoic acid

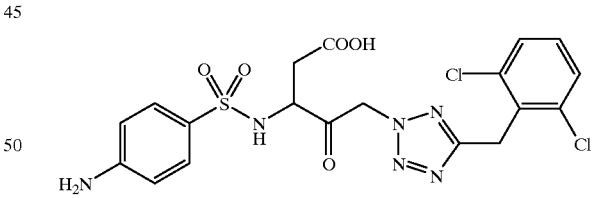

By the same procedure as provided in reference example 9(1), using the compound prepared in example 30(12), the compound of the present invention having the following physical data was obtained.

TLC: Rf 0.29 (chloroform:methanol:acetic acid=18:1:1); NMR (DMSO-d$_6$): δ 8.50–7.80 (1H, br), 7.80–7.25 (5H, m), 6.61 (2H, d, J=8.8 Hz), 6.15–5.72 (2H, m), 4.50 (2H, s), 3.97–3.81 (1H, m), 2.38–2.05 (2H, m).

Example 35(1)
N-(N,N-dibenzylamino)carbonyl-3-amino-4-oxo-5-(5-(2,6-dichlorophenylmethyl)tetrazol-1-yl)pentanoic acid•ethylester

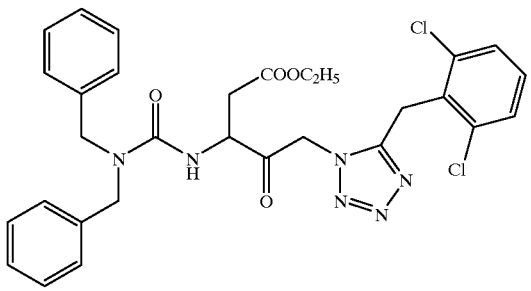

To a solution of dibenzylamine (0.06 ml) in dimethylformamide (0.5 ml) was added 1,1'-carbonylduimidazole (50 mg) at room,temperature under an atomsphere of argon. The mixture was stirred for 30 min. To the mixture was added the compound prepared in reference example 11(2) (139 mg) in dimethylformamide (0.5 ml) at 0° C. The mixture was stirred for room temperature overnight. The reaction mixture was quenched by addition of 1N aqueous solution of hydrochloric acid, extracted with ethyl acetate. The extract was washed with a saturated aqueous solution of sodium hydrocarbonate, water, a saturated aqueous solution of sodium chloride, successively, dried over anhydrous magnesium sulfate and concentrated. The residue was purified by column chromatography on silica gel (hexane: ethyl acetate=1:1) to give the compound of the present invention (79 mg) having the following physical data.

TLC: Rf 0.46 (hexane:ethyl acetate=1:1); NMR (CDCl$_3$): δ 7.50–7.10 (13H, m), 5.59 (1H, d, J=8.2 Hz), 5.41 (1H, d, J=18.6 Hz), 5.23 (1H, d, J=18.6 Hz), 4.84–4.66 (1H, m), 4.69–4.47 (2H, m), 4.29 (1H, d, J=16.6 Hz), 4.17 (1H, d, J=16.6 Hz), 4.04 (2H, q, J=7.0 Hz), 3.02 (1H, dd, J=17.8 and 5.0 Hz), 2.70 (1H, dd, J=17.8 and 4.8 Hz), 1.21 (3H, t, J=7.0 Hz).

Example 36(1)
N-(N,N-dibenzylamino)carbonyl-3-amino-4-oxo-5-(5-(2,6-dichlorophenylmethyl)tetrazol-1-yl)pentanoic acid

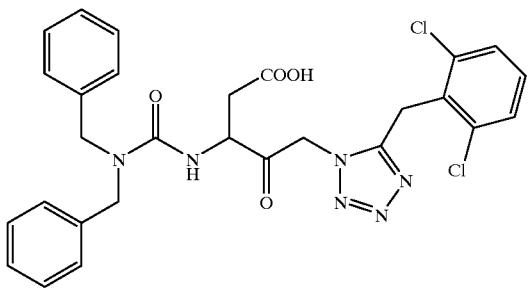

By the same procedure as provided in example 23(1), using the compound prepared in example 35(1), the compound of the present invention having the following physical data was obtained.

TLC: Rf 0.78 (chloroform:methanol:acetic acid=18:1:1); NMR (DMSO-d$_6$): δ 12.88–12.00 (1H, br), 7.65–7.06 (14H, m), 5.98–5.62 (2H, m), 4.82–4.62 (1H, m), 4.59–4.13 (6H, m), 2.91 (1H, dd, J=17 and 7 Hz), 2.66 (1H, dd, J=17 and 7 Hz).

Example 37(1)
N-(N-benzyl-N-methylamino)carbonyl-3-amino-4-oxo-5-(5-(2,6-dichlorophenylmethyl)tetrazol-1-yl)pentanoic acid•t-butylester

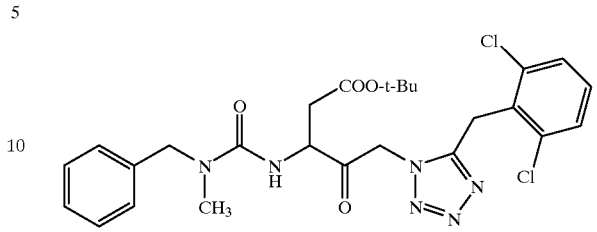

By the same procedure as provided in example 35(1), using the compound prepared in reference example 9(1) instead of the compound prepared in reference example 11(2) and N-benzyl-N-methylamine instead of dibenzylamine, compound of the present invention having the following physical data was obtained.

TLC: Rf 0.37 (hexane:ethyl acetate=1:1); NMR (CDCl$_3$): δ 7.40–7.16 (8H, m), 5.76 (1H, d, J=7.8 Hz), 5.53 (2H, s), 4.73 (1H, m), 4.53 (2H, s), 4.30 (2H, m), 3.00 (3H, s), 2.98–2.67 (2H, m), 1.41 (9H, s).

Example 38(1)
N-(N-benzyl-N-methylamino)carbonyl-3-amino-4-oxo-5-(5-(2,6-dichlorophenylmethyl)tetrazol-1-yl)pentanoic acid

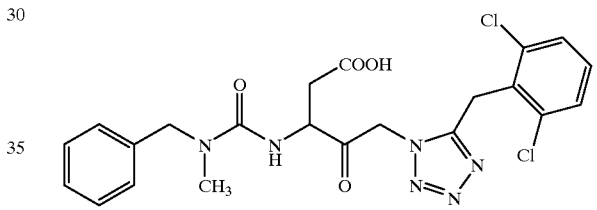

By the same procedure as provided in example 6(1), using the compound prepared in example 37(1), the compound of the present invention having the following physical data was obtained.

TLC: Rf 0.28 (chloroform:methanol:acetic acid=10:1:1); NMR (DMSO-d$_6$): δ 7.54–7.18 (9H, m), 5.81 (2H, brs), 4.60 (1H, m), 4.47 (2H, s), 4.32 (2H, m), 2.92–2.56 (5H, m).

Example 39(1)
N-benzyloxycarbonyl-3-amino-4-oxo-5-(5-(4-aminophenylthio)tetrazol-2-yl)pentanoic acid

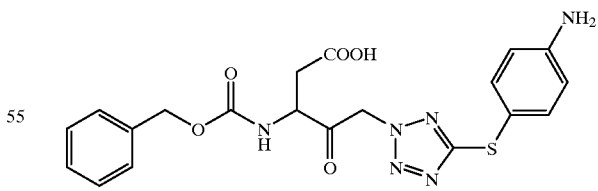

To the mixture solution of the compound prepared In example 5(157) (770 mg) in methanol (11 ml) and water (3 ml) was added potassium carbonate (350 mg). The reaction mixture was stirred for 7 h at room temperature. The reaction mixture was added 1N aqueous solution of hydrochloric acid until pH 4, extracted with ethyl acetate. The extract was washed with a saturated aqueous solution of ammonium chloride, water, a saturated aqueous solution of sodium chloride, successively, dried over anhydrous magnesium sulfate, concentrated. The residue was purified by column chromatography on silica gel (chloroform:methanol:acetic acid=18:1:1) to give the compound of the present invention (235 mg) having the following physical data.

TLC: Rf 0.31 (chloroform:methanol:acetic acid=18:1:1);
NMR (DMSO-$d_6$): δ 7.94 (1H, d, J=7.4 Hz), 7.46–7.24 (5H, m), 7.25 (2H, d, J=8.5 Hz), 6.59 (2H, d, J=8.5 Hz), 5.90 (2H, brs), 5.72–5.20 (2H, br), 5.08 (2H, s), 4.74–4.43 (1H, m), 2.90–2.50 (2H, m).

Example 39(2)

N-benzyloxycarbonyl-3-amino-4-oxo-5-(5-(4-aminophenylthio)tetrazol-1-yl)pentanoic acid

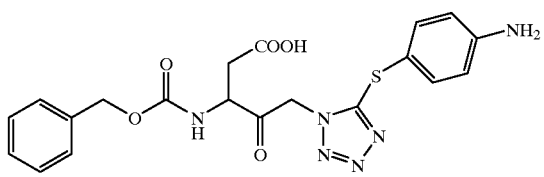

By the same procedure as provided in example 39(1), using the compound prepared in example 5(158) instead of the compound prepared in example 5(157), compound of the present invention having the following physical data was obtained.

TLC: Rf 0.22 (chloroform:methanol:acetic acid=18:1:1);
NMR (DMSO-$d_6$): δ 13.50–11.50 (1H, br), 8.03 (1H, d, J=7.8 Hz), 7.46–7.22 (5H, m), 7.22 (2H, d, J=8.6 Hz), 6.57 (2H, d, J=8.6 Hz), 5.94–5.30 (4H, br), 5.12 (2H, s), 4.73–4.50 (1H, m), 2.93–2.55 (2H, m).

Example 40(1)

N-(2-aminoethyl)sulfonyl-3-amino-4-oxo-5-(5-(2,6-dichlorophenylmethyl)tetrazol-2-yl)pentanoic acid

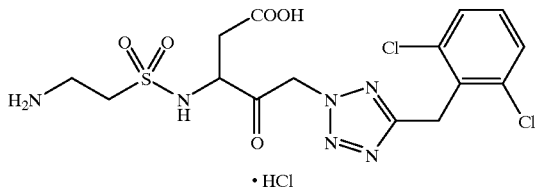

By the same procedure as provided in reference example 9(1) using the compound prepared in example 30(52), the compound of the present invention having the following physical data was obtained.

TLC: Rf 0.42 (chloroform:methanol:acetic acid=3:1:1)
NMR (DMSO-$d_6$): δ 13.00–12.40 (1H, br), 8.40–8.23 (1H, br), 8.23–8.00 (3H, br) 7.53 (1H, d, J=9.0 Hz), 7.52 (1H, d, J=7.0 Hz), 7.37 (1H, dd, J=9.0 Hz, 7.0 Hz), 6.20–5.95 (2H, br), 4.53 (2H, s), 4.65–4.40 (1H, m), 3.61–3.00 (4H, m), 3.00–2.65 (2H, m).

Reference Example 13

N-(N-t-butyloxycarbonylamino)sulfonyl-3-amino-4-oxo-5-(5-(2,6-dichlorophenylmethyl)tetrazol-2-yl)pentanoic acid•t-butylester

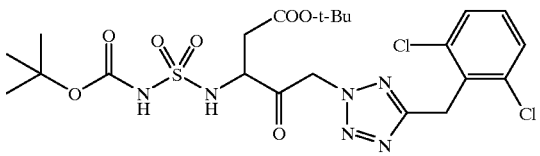

By the same procedure as provided in example 29(1), using the compound prepared in reference example 9(2) instead of the compound prepared in reference example 9(1) and (N-t-butyloxycarbonylamino)sulfonyl chloride instead of 4-t-butylbenzenesulfonyl chloride, title compound having the following physical data was obtained.

TLC: Rf 0.21 (hexane:ethyl acetate=2:1).

Reference Example 14

N-(N-t-butyloxycarbonyl-N-benzylamino)sulfonyl-3-amino-4-oxo-5-(5-(2,6-dichlorophenylmethyl)tetrazol-2-yl)pentanoic acid•t-butylester

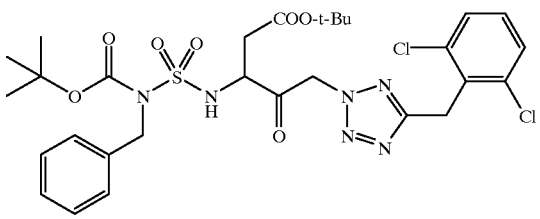

To a solution of the compound prepared in reference example 13 (548 mg) in tetrahydrofuran (7 ml) was added benzyl alcohol (0.14 ml), triphenylphosphine (361 mg) and diethylazodicarboxylate (0.55 ml) at 0° C. The reaction mixture was stirred for 2 h at room temperature. The reaction mixture was diluted with ethyl acetate, washed with water and a saturated aqueous solution of sodium chloride, successively, dried over anhydrous magnesium sulfate, concentrated. The residue was purified by column chromatography on silica gel (hexane:ethyl acetate=5:1–2:1) to give the title compound having the following physical data.

TLC: Rf 0.60 (hexane:ethyl acetate=2:1).

Example 41(1)

N-(N-benzylamino)sulfonyl-3-amino-4-oxo-5-(5-(2,6-dichlorophenylmethyl)tetrazol-2-yl)pentanoic acid

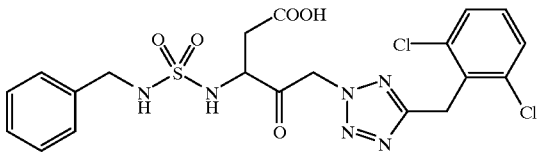

By the same procedure as provided in example 6(1), using the compound prepared in reference example 14, the compound of the present invention having the following physical data was obtained.

TLC: Rf 0.16 (chloroform:methanol:acetic acid=40:1:1).
NMR (DMSO-$d_6$): δ 13.00–11.60 (1H, br), 8.05–7.50 (1H, br), 7.70 (1H, t, J=6.1 Hz), 7.62–7.43 (2H, m), 7.43–7.07 (6H, m), 6.19–5.74 (2H, m), 4.52 (2H, s), 4.42–4.20 (1H, m), 4.10 (2H, d, J=6.1 Hz), 2.89–2.35 (2H, m).

Example 42(1)
N-benzyloxycarbonyl-3-amino-4-oxo-5-(5-(methylaminocarbonylmethyl)tetrazol-2-yl)pentanoic acid

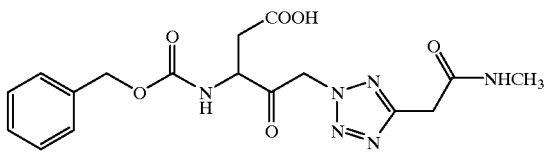

To a suspension of the compound prepared in example 5 (18) (190 mg) in methanol (0.2 ml) was added 40% aqueous solution of methylamine (0.4 ml). The reaction mixture was stirred for 5 h at room temperature. The reaction mixture was quenched by addition of 1N aqueous solution of hydrochloric acid, extracted with ethyl acetate. The extract was washed with water, a saturated aqueous solution of sodium chloride, dried over anhydrous magnesium sulfate, concentrated. The residue was purified by column chromatography on silica gel (chloroform:methanol:acetic acid=20:1:1) to give the compound of the present invention (120 mg) having the following physical data.

TLC: Rf 0.11 (chloroform:methanol:acetic acid=18:1:1).
NMR (DMSO-$d_6$): δ 8.15 (1H, d, J=5.0 Hz), 7.74 (1H, d, J=7.0 Hz), 7.53–7.13 (5H, m), 5.93 (2H, s), 5.08 (2H, s), 4.64–4.33 (1H, m), 3.74 (2H, s), 2.70–2.48 (5H, m).

Example 42(2)
N-benzyloxycarbonyl-3-amino-4-oxo-5-(5-(methylaminocarbonylmethyl)tetrazol-1-yl)pentanoic acid

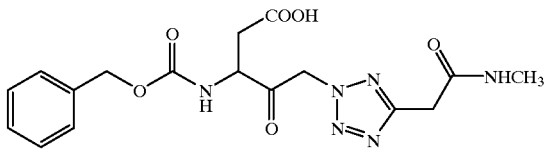

By the same procedure as provided in example 42(1), using the compound prepared in example 5(21) instead of the compound prepared in example 5(18), the compound of the present invention having the following physical data was obtained.

TLC: Rf 0.08 (chloroform:methanol:acetic acid=8:1:1).
NMR (DMSO-$d_6$): δ 8.40 (1H, d, J=4.8 Hz), 7.87 (1H, d, J=7.6 Hz), 7.52–7.12 (5H, m), 5.94–5.61 (2H, m), 5.08 (2H, s), 4.66–4.40 (1H, m), 3.80 (2H, s), 2.85–2.49 (5H, m).

FORMULATION EXAMPLE

Formulation Example 1

The following components were admixed in conventional manner and punched out to obtain 100 tablets each containing 50 mg of active ingredient.

| | |
|---|---|
| N-((N-(3-phenylpropionyl)-L-valyl)-L-alanyl)-3-amino-4-oxo-5-(5-(2,6-dichlorophenylmethyl)tetrazol-1-yl)pentanoic acid | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional manner. The solution was sterilized in conventional manner, placed 5 ml portion into ampoules and freeze-dried to obtain 100 ampoules each containing 20 mg of the active ingredient.

| | |
|---|---|
| N-((N-(3-phenylpropionyl)-L-valyl)-L-alanyl)-3-amino-4-oxo-5-(5-(2,6-dichlorophenylmethyl)tetrazol-1-yl)pentanoic acid | 2.0 g |
| mannitol | 20 g |
| Distilled water | 1000 ml |

What is claimed is:

1. A tetrazole derivative of formula (I), a non-toxic salt thereof, an acid addition salt thereof, or a hydrate thereof:

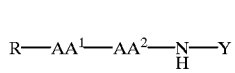

(I)

wherein R is a hydrogen atom,

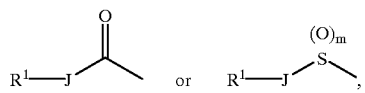

and in which J is a bond, C1–6 alkylene, C1–6 oxyalkylene, C1–6 aminoalkylene, C1–6 thioalkylene, C2–6 alkenylene, or carbocyclic ring, wherein the carbocyclic ring may be substituted by C1–4 alkyl with the proviso that when J contains an oxygen atom, a nitrogen atom or a sulfur atom, and wherein the oxygen atom, the nitrogen atom or the sulfur atom is bonded to C=O or S(O)$_m$ group in R);

$R^1$ is
1) C1–8 alkyl,
2) C1–8 alkoxy,
3) C2–8 alkenyl,
4) C2–8 alkenyloxy,
5) C1–8 alkylamino,
6) di(C1–8 alkyl)amino,
7) C1–8 alkylthio,
8) $Cyc^1$ in which $Cyc^1$ is a carbocyclic ring which may be substituted by 1 to 5 substituents selected from the group consisting of a hydrogen atom, C1–8 alkyl, phenyl, phenyloxy, C1–8 alkyl substituted by phenyl, a halogen atom, nitro, trifluoromethyl, nitrile, keto, —$OR^2$, —$NR^2R^3$, —$S(O)R^2$, —$SO_2R^2$, —$COOR^2$ or —$COR^2$, wherein $R^2$ is a hydrogen atom, C1–8 alkyl, phenyl or C1–4 alkyl substituted by phenyl, $R^3$ is a hydrogen atom, C1–8 alkyl, phenyl or C1–4 alkyl substituted by phenyl, or C2–5 acyl,
9) $Cyc^1$—O— wherein $Cyc^1$ is the same as hereinbefore defined,
10) $Cyc^1$—S— wherein $Cyc^1$ is the same as hereinbefore defined,
11) $Cyc^1$—CO— wherein $Cyc^1$ is the same as hereinbefore defined,
12) C1–8 alkyl, C1–8 alkoxy, C1–8 alkylamino, di(C1–8 alkyl)amino or C1–8 alkylthio mono or di-substituted by $Cyc^1$, $Cyc^1$—O—, $Cyc^1$—S—, or $Cyc^1$—CO— wherein $Cyc^1$ is the same as hereinbefore defined,
13) trifluoromethyl,
14) $Cyc^1$—CO—NH—CH$_2$— wherein $Cyc^1$ is the same as hereinbefore defined,
15) amino, 16) benzyloxycarbonyl,
17) C2–5 acylamino, or
18) C1–8 alkoxy substituted by C1–8 alkoxy;

m is 0 or 1–2, with the proviso that
(1) when m is 0, then —S(O)$_m$— is not directly bonded to a nitrogen atom or a sulfur atom, and
(2) when m is 1, then S(O)$_m$— is not directly bonded to a sulfur atom;

AA$^1$ is
1) a bond or
2)

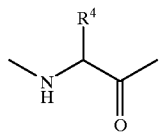

in which R$^4$ is
(1) a hydrogen atom,
(2) C1–8 alkyl,
(3) Cyc$^2$ in which Cyc$^2$ is a carbocyclic ring which may be substituted by 1 to 5 substituents selected from the group consisting of a hydrogen atom, C1–8 alkyl, phenyl, C1–4 alkyl substituted by phenyl, a halogen atom, nitro, trifluoromethyl, nitrile, tetrazole, —OR$^5$, —NR$^5$R$^6$, —SR$^5$, —COOR$^5$ or —COR$^5$, wherein R$^5$ and R$^6$ each, independently, is a hydrogen atom, C1–4 alkyl, phenyl or C1–4 alkyl substituted by phenyl or
(4) C1–8 alkyl substituted by a substituent selected from —OR$^7$, —NR$^7$R$^8$, —SR$^7$, —COOR$^7$, —COR$^7$, —CONH$_2$, —NR$^7$—CO—NR$^7$R$^8$, guanidino or Cyc$^2$ in which R$^7$ and R$^8$ each, independently, is a hydrogen atom, C1–4 alkyl, phenyl or C1–4 alkyl substituted by phenyl and Cyc$^2$ is the same as hereinbefore defined;

AA$^2$ is
1) a bond or
2)

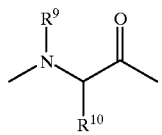

in which R$^9$ and R$^{10}$ each, independently, is
(1) a hydrogen atom,
(2) C1–8 alkyl,
(3) Cyc$^3$ in which Cyc$^3$ is a carbocyclic ring or hetero ring, and Cyc$^3$ which may be substituted by 1 to 5 substituents selected from the group consisting of a hydrogen atom, C1–8 alkyl, phenyl, C1–4 alkyl substituted by phenyl, a halogen atom, nitro, trifluoromethyl, nitrile, tetrazole, —OR$^{11}$, —NR$^{11}$R$^{12}$, —SR$^{11}$, —COOR$^{11}$ or —COR$^{11}$, wherein R$^{11}$ and R$^{12}$ each, independently, is a hydrogen atom, C1–4 alkyl, phenyl or C1–4 alkyl substituted by phenyl, or
(4) C1–8 alkyl substituted by a substituent selected from —OR$^{13}$, —NR$^{13}$R$^{14}$, —SR$^{13}$, —COOR$^{13}$, —COR$^{13}$, —CONH$_2$, —NR$^{13}$—CO—NR$^{13}$R$^{14}$, guanidino or Cyc$^3$ in which R$^{13}$ is a hydrogen atom, C1–4 alkyl, phenyl or C1–4 alkyl substituted by phenyl, R$^{14}$ is a hydrogen atom, C1–4 alkyl, phenyl, C1–4 alkyl substituted by phenyl, t-butyloxycarbonyl or benzyloxycarbonyl and Cyc$^3$ is the same as hereinbefore defined;

AA$^1$ and AA$^2$, together, may have the formula:

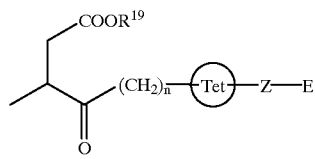

in which R$^{19}$ is a hydrogen atom, C1–8 alkyl, phenyl or C1–4 alkyl substituted by phenyl;
n is 1–4;

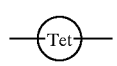

is

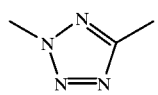

or

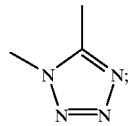

Z is
1) C1–6 alkylene,
2) C2–6 alkenylene,
3) oxygen atom,
4) sulfur atom,
5) —CO—,
6) —SO—,
7) —SO$_2$—,
8) —NR$^{26}$— in which R$^{26}$ is a hydrogen atom, C1–4 alkyl, phenyl, C1–4 alkyl substituted by phenyl, or
9) a carbon atom in C1–6 alkylene replaced by an oxygen atom, sulfur atom, —CO—, —SO—, —SO$_2$— or —NR$^{26}$— in which R$^{26}$ is the same as hereinbefore defined, with the proviso that Z is bonded directly to the carbon atom on a tetrazole ring;

E is a hydrogen atom, a halogen atom, C1–4 alkyl, —COOR$^{27}$ in which R$^{27}$ is a hydrogen atom, C1–4 alkyl, phenyl, C1–4 substituted by phenyl, —CONR$^{28}$R$^{29}$ in which R$^{28}$ and R$^{29}$ each, independently, is a hydrogen atom, C1–4 alkyl, phenyl, C1–4 substituted by phenyl or —NR$^{28}$R$^{29}$ in which R$^{28}$ and R$^{29}$ are the same as hereinbefore defined, or

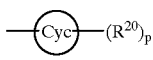

in which

is a carbocyclic ring substituted by —(R$^{20}$)$_p$ wherein R$^{20}$ is
1) a hydrogen atom,
2) C1–8 alkyl,
3) a halogen atom,
4) nitro,
5) trifluoromethyl,
6) nitrile,
7) —OR$^{22}$,
8) —NR$^{22}$R$^{23}$,
9) —SR$^{22}$,
10) —COOR$^{22}$,
11) —COR$^{22}$,
12) —CONR$^{28}$R$^{29}$ in which R$^{28}$ and R$^{29}$ are the same as hereinbefore defined,
13) Cyc$^4$ in which Cyc$^4$ is a carbocyclic ring which may be substituted by 1 to 5 substituents selected from the group consisting of a hydrogen atom, C1–8 alkyl, phenyl, C1–4 alkyl substituted by phenyl, a halogen atom, nitro, trifluoromethyl, nitrile, tetrazole, —OR$^{24}$, —NR$^{24}$R$^{25}$, —SR$^{24}$, —COOR$^{24}$ or —COR$^{24}$ in which R$^{24}$ and R$^{25}$ each, independently, is a hydrogen atom, C1–4 alkyl, phenyl or C1–4 alkyl substituted by phenyl, or
14) C1–8 alkyl substituted by Cyc$^4$ in which Cyc$^4$ is the same as hereinbefore defined, R$^{22}$ is a hydrogen atom, C1–4 alkyl, phenyl or C1–4 alkyl substituted by phenyl, R$^{23}$ is a hydrogen atom, C1–4 alkyl, phenyl, C1–4 alkyl substituted by phenyl, C2–5 acyl or trifluoromethylcarbonyl;

p is 1–5; or

—Z—E is a halogen atom, trifluoromethyl, C1–4 alkyl di-substituted by phenyl or tri(C1–4 alkyl)silyl with the proviso that
(1) when Z is C1–6 alkylene or C2–6 alkenylene, E is not a hydrogen atom or C1–4 alkyl, or
(2) when Z is —SO—, E is not a hydrogen atom.

2. The compound according to claim 1, wherein the E group in Y is a hydrogen atom, halogen atom, C1–4 alkyl, —COOR$^{27}$, —CONR$^{28}$R$^{29}$, or —NR$^{28}$R$^{29}$ in which R$^{27}$, R$^{28}$ and R$^{29}$ are defined as in claim 1.

3. The compound according to claim 1, wherein the E group in Y is

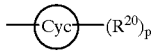

in which R$^{20}$ and p are defined as in claim 1, and

is a 3–10 membered mono-cyclic or bi-cyclic carbocyclic ring.

4. The compound according to claim 1, wherein the —Z—E group in Y is a halogen atom, trifluoromethyl, diphenylmethyl or tri(C1–4 alkyl)silyl.

5. The compound according to claim 1, wherein AA$^1$ is α-amino acid residue and AA$^2$ is α-amino acid residue.

6. The compound according to claim 1, wherein AA$^1$ is a bond and AA$^2$ is α-amino acid residue.

7. The compound according to claim 1, wherein AA$^1$ is a bond and AA$^2$ is a bond.

8. The compound according to claim 1, which is
(1) N-((N-(3-phenylpropionyl)-L-valyl)-L-alanyl)-3-amino-4-oxo-5-(5-(N,N-dimethylamino)tetrazol-2-yl)pentanoic acid,
(2) N-benzyloxycarbonyl-3-amino-4-oxo-5-(5-methoxytetrazol-1-yl)pentanoic acid,
(3) N-benzyloxycarbonyl-3-amino-4-oxo-5-(5-methoxytetrazol-2-yl)pentanoic acid,
(4) N-benzyloxycarbonyl-3-amino-4-oxo-5-(5-(ethoxycarbonylmethyl)tetrazol-2-yl)pentanoic acid,
(5) N-benzyloxycarbonyl-3-amino-4-oxo-5-(5-ethylthiotetrazol-1-yl)pentanoic acid,
(6) N-benzyloxycarbonyl-3-amino-4-oxo-5-(5-ethylthiotetrazol-2-yl)pentanoic acid,
(7) N-benzyioxycarbonyl-3-amino-4-oxo-5-(5-(ethoxycarbonylmethyl)tetrazol-1-yl)pentanoic acid,
(8) N-benzyloxycarbonyl-3-amino-4-oxo-5-(5-(2-methoxycarbonylethyl)tetrazol-2-yl)pentanoic acid,
(9) N-benzyloxycarbonyl-3-amino-4-oxo-5-(5-(2-methoxycarbonylethyl)tetrazol-1-yl)pentanoic acid,
(10) N-benzyloxycarbonyl-3-amino-4-oxo-5-(5-(2-chloroethyl)tetrazol-2-yl)pentanoic acid,
(11) N-benzyloxycarbonyl-3-amino-4-oxo-5-(5-(2-chloroethyl)tetrazol-1-yl)pentanoic acid,
(12) N-benzyloxycarbonyl-3-amino-4-oxo-5-(5-(2-dimethylaminoethyl)tetrazol-2-yl)pentanoic acid,
(13) N-benzyloxycarbonyl-3-amino-4-oxo-5-(5-(2-dimethylaminoethyl)tetrazol-1-yl)pentanoic acid,
(14) N-benzyloxycarbonyl-3-amino-4-oxo-5-(5-(carboxymethyl)tetrazol-2-yl)pentanoic acid,
(15) N-benzyloxycarbonyl-3-amino-4-oxo-5-(5-(carboxymethyl)tetrazol-1-yl)pentanoic acid,
(16) N-benzyloxycarbonyl-3-amino-4-oxo-5-(5-(2-carboxyethyl)tetrazol-2-yl)pentanoic acid,
(17) N-benzyloxycarbonyl-3-amino-4-oxo-5-(5-(2-carboxyethyl)tetrazol-1-yl)pentanoic acid,
(18) N-benzyloxycarbonyl-3-amino-4-oxo-5-(5-ethylsulfinyltetrazol-1-yl)pentanoic acid,
(19) N-benzyloxycarbonyl-3-amino-4-oxo-5-(5-ethylsulfonyltetrazol-1-yl)pentanoic acid,
(20) N-benzyioxycarbonyl-3-amino-4-oxo-5-(5-ethylsulfinyltetrazol-2-yl)pentanoic acid,
(21) N-benzyloxycarbonyl-3-amino-4-oxo-5-(5-ethylsulfonyltetrazol-2-yl)pentanoic acid,
(22) N-benzyloxycarbonyl-3-amino-4-oxo-5-(5-(methylaminocarbonylmethyl)tetrazol-2-yl)pentanoic acid, or
(23) N-benzyloxycarbonyl-3-amino-4-oxo-5-(5-(methylaminocarbonylmethyl)tetrazol-1-yl)pentanoic acid, an ester thereof, a non-toxic salt thereof, an acid addition salt thereof or a hydrate thereof.

9. A compound according to claim 1, which is
(1) N-((N-(3-phenylpropionyl)-L-valyl)-L-alanyl)-3-amino-4-oxo-5-(5-(2,6-dichlorophenylmethyl)tetrazol-1-yl)pentanoic acid, (2) N-((N-(3-phenylpropionyl)-L-valyl)-L-alanyl)-3-amino-4-oxo-5-(5-(2,6-dichlorophenylmethyl)tetrazol-2-yl)pentanoic acid, (3) N-((N-(3-phenylpropionyl)-L-valyl)-L-alanyl)-3-amino-4-oxo-5-(5-(4-methylphenoxy)tetrazol-1-yl) pentanoic acid, or (4) N-((N-(3-phenylpropionyl)-L-valyl)-L-alanyl)-3-amino-4-oxo-5-(5-(4-methylphenoxy)tetrazol-2-yl) pentanoic acid, an ester thereof, a non-toxic salt thereof, an acid addition salt thereof or a hydrate thereof.

10. A compound according to claim 1, which is (1) N-(N-benzyloxycarbonyl-L-alanyl)-3-amino-4-oxo-5-(5-(2,6-dichlorophenylmethyl)tetrazol-2-yl) pentanoic acid, (2) N-(N-benzyloxycarbonyl-L-alanyl)-3-amino-4-oxo-5-(5-(2,6-dichlorophenylmethyl)tetrazol-1-yl) pentanoic acid, (3) N-(N-benzyloxycarbonyl-L-valyl)-3-amino-4-oxo-5-(5-(2,6-dichlorophenylmethyl)tetrazol-2-yl)pentanoic acid, (4) N-(N-benzyloxycarbonyl-N'-t-butyloxycarbonyl-L-lysinyl)-3-amino-4-oxo-5-(5-(2,6-dichlorophenylmethyl)tetrazol-2-yl)pentanoic acid, (5) N-(N-benzyloxycarbonyl-L-lysinyl)-3-amino-4-oxo-5-(5-(2,6-dichlorophenylmethyl)tetrazol-2-yl) pentanoic acid, or an ester thereof, a non-toxic salt thereof, an acid addition salt thereof or a hydrate thereof.

11. A compound according to claim 1, which is (1) N-benzyloxycarbonyl-3-amino-4-oxo-5-(5-(2,6-dichlorophenylmethyl)tetrazol-1-yl)pentanoic acid, (2) N-benzyloxycarbonyl-3-amino-4-oxo-5-(5-(2,6-dichlorophenylmethyl)tetrazol-2-yl)pentanoic acid, (3) N-benzyloxycarbonyl-3-amino-4-oxo-5-(5-phenylmethyltetrazol-1-yl)pentanoic acid, (4) N-benzyloxycarbonyl-3-amino-4-oxo-5-(5-phenylmethyltetrazol-2-yl)pentanoic acid, (5) N-benzyloxycarbonyl-3-amino-4-oxo-5-(5-(4-methylphenoxy)tetrazol-1-yl)pentanoic acid, (6) N-benzyloxycarbonyl-3-amino-4-oxo-5-(5-(4-methylphenoxy)tetrazol-2-yl)pentanoic acid, (7) N-benzyloxycarbonyl-3-amino-4-oxo-5-(5-(3-t-butylphenoxy)tetrazol-1-yl)pentanoic acid, (8) N-benzyloxycarbonyl-3-amino-4-oxo-5-(5-(3-t-butylphenoxy)tetrazol-2-yl)pentanoic acid, (9) N-benzyloxycarbonyl-3-amino-4-oxo-5-(5-styryltetrazol-1-yl)pentanoic acid,

(10) N-benzyloxycarbonyl-3-amino-4-oxo-5-(5-styryltetrazol-2-yl)pentanoic acid,

(11) N-benzyloxycarbonyl-3-amino-4-oxo-5-(5-phenylethyltetrazol-1-yl)pentanoic acid,

(12) N-benzyloxycarbonyl-3-amino-4-oxo-5-(5-phenylethyltetrazol-1-yl)pentanoic acid,

(13) N-benzyloxycarbonyl-3-amino-4-oxo-5-(5-(N,N-dibenzylamino)tetrazol-2-yl)pentanoic acid,

(14) N-benzyloxycarbonyl-3-amino-4-oxo-5-(5-((4-chlorophenyl)thiomethyl)tetrazol-2-yl)pentanoic acid,

(15) N-benzyloxycarbonyl-3-amino-4-oxo-5-(5-((4-chlorophenyl)thiomethyl)tetrazol-1-yl)pentanoic acid,

(16) N-benzyloxycarbonyl-3-amino-4-oxo-5-(5-(3-phenylpropyl)tetrazol-2-yl)pentanoic acid,

(17) N-benzyloxycarbonyl-3-amino-4-oxo-5-(5-(3-phenylpropyl)tetrazol-1-yl)pentanoic acid,

(18) N-benzyloxycarbonyl-3-amino-4-oxo-5-(5-(2,6-dichlorophenyloxy)tetrazol-2-yl)pentanoic acid,

(19) N-benzyloxycarbonyl-3-amino-4-oxo-5-(5-(2,6-dichlorophenyloxy)tetrazol-1-yl)pentanoic acid,

(20) N-benzyloxycarbonyl-3-amino-4-oxo-5-(5-(2-chlorophenyloxymethyl)tetrazol-2-yl)pentanoic acid,

(21) N-benzyloxycarbonyl-3-amino-4-oxo-5-(5-(2-chlorophenyloxymethyl)tetrazol-1-yl)pentanoic acid,

(22) N-benzyloxycarbonyl-3-amino-4-oxo-5-(5-(2,6-difluorophenylmethyl)tetrazol-2-yl)pentanoic acid,

(23) N-benzyloxycarbonyl-3-amino-4-oxo-5-(5-(2,6-difluorophenylmethyl)tetrazol-1-yl)pentanoic acid,

(24) N-benzyloxycarbonyl-3-amino-4-oxo-5-(5-(phenylthio)tetrazol-2-yl)pentanoic acid,

(25) N-benzyloxycarbonyl-3-amino-4-oxo-5-(5-(phenylthio)tetrazol-1-yl)pentanoic acid,

(26) N-benzyloxycarbonyl-3-amino-4-oxo-5-(5-(2,6-dichlorophenylthio)tetrazol-2-yl)pentanoic acid,

(27) N-benzyloxycarbonyl-3-amino-4-oxo-5-(5-(2,6-dichlorophenylthio)tetrazol-1-yl)pentanoic acid,

(28) N-benzyloxycarbonyl-3-amino-4-oxo-5-(5-(2,6-dimethylphenylmethyl)tetrazol-2-yl)pentanoic acid,

(29) N-benzyloxycarbonyl-3-amino-4-oxo-5-(5-(2,6-dimethylphenylmethyl)tetrazol-1-yl)pentanoic acid,

(30) N-benzyloxycarbonyl-3-amino-4-oxo-5-(5-(cyclohexylmethyl)tetrazol-2-yl)pentanoic acid,

(31) N-benzyloxycarbonyl-3-amino-4-oxo-5-(5-(cyclohexylmethyl)tetrazol-1-yl)pentanoic acid,

(32) N-benzyloxycarbonyl-3-amino-4-oxo-5-(5-(4-methylphenylthio)tetrazol-2-yl)pentanoic acid,

(33) N-benzyloxycarbonyl-3-amino-4-oxo-5-(5-(4-methylphenylthio)tetrazol-1-yl)pentanoic acid,

(34) N-benzyloxycarbonyl-3-amino-4-oxo-5-(5-(4-chlorophenylthio)tetrazol-2-yl)pentanoic acid,

(35) N-benzyloxycarbonyl-3-amino-4-oxo-5-(5-(4-chlorophenylthio)tetrazol-1-yl)pentanoic acid,

(36) N-benzyloxycarbonyl-3-amino-4-oxo-5-(5-(3,5-dichlorophenylthio)tetrazol-2-yl)pentanoic acid,

(37) N-benzyloxycarbonyl-3-amino-4-oxo-5-(5-(3,5-dichlorophenylthio)tetrazol-1-yl)pentanoic acid,

(38) N-benzyloxycarbonyl-3-amino-4-oxo-5-(5-(phenylcarbonyl)tetrazol-2-yl)pentanoic acid,

(39) N-benzyloxycarbonyl-3-amino-4-oxo-5-(5-(phenylcarbonyl)tetrazol-1-yl)pentanoic acid,

(40) N-benzyloxycarbonyl-3-amino-4-oxo-5-(5-(2-chloro-6-fluoro-phenylmethyl)tetrazol-2-yl)pentanoic acid,

(41) N-benzyloxycarbonyl-3-amino-4-oxo-5-(5-(2-chloro-6-fluoro-phenylmethyl)tetrazol-1-yl)pentanoic acid,

(42) N-benzyloxycarbonyl-3-amino-4-oxo-5-(5-(cyclohexylthio)tetrazol-2-yl)pentanoic acid,

(43) N-benzyloxycarbonyl-3-amino-4-oxo-5-(5-(cyclohexylthio)tetrazol-1-yl)pentanoic acid,

(44) N-benzyloxycarbonyl-3-amino-4-oxo-5-(5-(4-methoxyphenylthio)tetrazol-2-yl)pentanoic acid,

(45) N-benzyloxycarbonyl-3-amino-4-oxo-5-(5-(4-methoxyphenylthio)tetrazol-1-yl)pentanoic acid,

(46) N-benzyloxycarbonyl-3-amino-4-oxo-5-(5-(2-chlorophenylthio)tetrazol-2-yl)pentanoic acid,

(47) N-benzyloxycarbonyl-3-amino-4-oxo-5-(5-(2-chlorophenylthio)tetrazol-1-yl)pentanoic acid,

(48) N-benzyloxycarbonyl-3-amino-4-oxo-5-(5-(2,4-dichlorophenylthio)tetrazol-2-yl)pentanoic acid,
(49) N-benzyloxycarbonyl-3-amino-4-oxo-5-(5-(2,4-dichlorophenylthio)tetrazol-1-yl)pentanoic acid,
(50) N-benzyloxycarbonyl-3-amino-4-oxo-5-(5-(2-chloro-6-methylphenylthio)tetrazol-2-yl)pentanoic acid,
(51) N-benzyloxycarbonyl-3-amino-4-oxo-5-(5-(2-chloro-6-methylphenylthio)tetrazol-1-yl)pentanoic acid,
(52) N-benzyloxycarbonyl-3-amino-4-oxo-5-(5-(4-trifluoromethylphenylthio)tetrazol-2-yl)pentanoic acid,
(53) N-benzyloxycarbonyl-3-amino-4-oxo-5-(5-(4-trifluoromethylphenylthio)tetrazol-1-yl)pentanoic acid,
(54) N-benzyloxycarbonyl-3-amino-4-oxo-5-(5-(naphthalen-2-ylthio)tetrazol-2-yl)pentanoic acid,
(55) N-benzyloxycarbonyl-3-amino-4-oxo-5-(5-(naphthalen-2-ylthio)tetrazol-1-yl)pentanoic acid,
(56) N-benzyloxycarbonyl-3-amino-4-oxo-5-(5-(4-t-butylphenylthio)tetrazol-2-yl)pentanoic acid,
(57) N-benzyloxycarbonyl-3-amino-4-oxo-5-(5-(4-t-butylphenylthio)tetrazol-1-yl)pentanoic acid,
(58) N-benzyloxycarbonyl-3-amino-4-oxo-5-(5-(4-trifluoromethyloxyphenylthio)tetrazol-2-yl)pentanoic acid,
(59) N-benzyloxycarbonyl-3-amino-4-oxo-5-(5-(4-trifluoromethyloxyphenylthio)tetrazol-1-yl)pentanoic acid,
(60) N-benzyloxycarbonyl-3-amino-4-oxo-5-(5-(2,3,6-trichlorophenylthio)tetrazol-2-yl)pentanoic acid,
(61) N-benzyloxycarbonyl-3-amino-4-oxo-5-(5-(2,3,6-trichlorophenylthio)tetrazol-1-yl)pentanoic acid,
(62) N-benzyloxycarbonyl-3-amino-4-oxo-5-(5-(2,4-dimethylphenylthio)tetrazol-2-yl)pentanoic acid,
(63) N-benzyloxycarbonyl-3-amino-4-oxo-5-(5-(2,4-dimethylphenylthio)tetrazol-1-yl)pentanoic acid,
(64) N-benzyloxycarbonyl-3-amino-4-oxo-5-(5-(2,5-dichlorophenylthio)tetrazol-2-yl)pentanoic acid,
(65) N-benzyloxycarbonyl-3-amino-4-oxo-5-(5-(2,5-dichlorophenylthio)tetrazol-1-yl)pentanoic acid,
(66) N-benzyloxycarbonyl-3-amino-4-oxo-5-(5-(4-bromophenylthio)tetrazol-2-yl)pentanoic acid,
(67) N-benzyloxycarbonyl-3-amino-4-oxo-5-(5-(4-bromophenylthio)tetrazol-1-yl)pentanoic acid,
(68) N-benzyloxycarbonyl-3-amino-4-oxo-5-(5-(2,6-dichloro-4-methylphenylthio)tetrazol-2-yl)pentanoic acid,
(69) N-benzyloxycarbonyl-3-amino-4-oxo-5-(5-(2,6-dichloro-4-methylphenylthio)tetrazol-1-yl)pentanoic acid,
(70) N-benzyloxycarbonyl-3-amino-4-oxo-5-(5-(3,4-dichlorophenylthio)tetrazol-2-yl)pentanoic acid,
(71) N-benzyloxycarbonyl-3-amino-4-oxo-5-(5-(3,4-dichlorophenylthio)tetrazol-1-yl)pentanoic acid,
(72) N-benzyloxycarbonyl-3-amino-4-oxo-5-(5-(4-nitrophenylthio)tetrazol-2-yl)pentanoic acid,
(73) N-benzyloxycarbonyl-3-amino-4-oxo-5-(5-(4-nitrophenylthio)tetrazol-1-yl)pentanoic acid,
(74) N-benzyloxycarbonyl-3-amino-4-oxo-5-(5-(naphthalen-1-ylthio)tetrazol-2-yl)pentanoic acid,
(75) N-benzyloxycarbonyl-3-amino-4-oxo-5-(5-(naphthalen-1-ylthio)tetrazol-1-yl)pentanoic acid,
(76) N-benzyloxycarbonyl-3-amino-4-oxo-5-(5-(2,4-di-t-butylphenylthio)tetrazol-2-yl)pentanoic acid,
(77) N-benzyloxycarbonyl-3-amino-4-oxo-5-(5-(2,4-di-t-butylphenylthio)tetrazol-1-yl)pentanoic acid,
(78) N-benzyloxycarbonyl-3-amino-4-oxo-5-(5-(2-methoxyphenylthio)tetrazol-2-yl)pentanoic acid,
(79) N-benzyloxycarbonyl-3-amino-4-oxo-5-(5-(2-methoxyphenylthio)tetrazol-1-yl)pentanoic acid,
(80) N-benzyloxycarbonyl-3-amino-4-oxo-5-(5-(2,6-dichloro-4-dimethylaminophenylthio)tetrazol-2-yl)pentanoic acid,
(81) N-benzyloxycarbonyl-3-amino-4-oxo-5-(5-(2,6-dichloro-4-dimethylaminophenylthio)tetrazol-1-yl)pentanoic acid,
(82) N-benzyloxycarbonyl-3-amino-4-oxo-5-(5-(2,3-dichlorophenylthio)tetrazol-2-yl)pentanoic acid,
(83) N-benzyloxycarbonyl-3-amino-4-oxo-5-(5-(2,3-dichlorophenylthio)tetrazol-1-yl)pentanoic acid,
(84) N-benzyloxycarbonyl-3-amino-4-oxo-5-(5-(2,6-dimethylphenylthio)tetrazol-2-yl)pentanoic acid,
(85) N-benzyloxycarbonyl-3-amino-4-oxo-5-(5-(2,6-dimethylphenylthio)tetrazol-1-yl)pentanoic acid,
(86) N-benzyloxycarbonyl-3-amino-4-oxo-5-(5-(2-chloro-4-t-butylphenylthio)tetrazol-2-yl)pentanoic acid,
(87) N-benzyloxycarbonyl-3-amino-4-oxo-5-(5-(2-chloro-4-t-butylphenylthio)tetrazol-1-yl)pentanoic acid,
(88) N-benzyloxycarbonyl-3-amino-4-oxo-5-(5-(N-phenyl-N-methylamino)tetrazol-2-yl)pentanoic acid,
(89) N-benzyloxycarbonyl-3-amino-4-oxo-5-(5-(N-phenyl-N-methylamino)tetrazol-1-yl)pentanoic acid,
(90) N-benzyloxycarbonyl-3-amino-4-oxo-5-(5-(2,6-diisopropylphenylthio)tetrazol-2-yl)pentanoic acid,
(91) N-benzyloxycarbonyl-3-amino-4-oxo-5-(5-(2,6-diisopropylphenylthio)tetrazol-1-yl)pentanoic acid,
(92) N-benzyloxycarbonyl-3-amino-4-oxo-5-(5-(2-methyl-4-t-butylphenylthio)tetrazol-2-yl)pentanoic acid,
(93) N-benzyloxycarbonyl-3-amino-4-oxo-5-(5-(2-methyl-4-t-butylphenylthio)tetrazol-1-yl)pentanoic acid,
(94) N-benzyloxycarbonyl-3-amino-4-oxo-5-(5-(2,6-dimethyl-4-t-butylphenylthio)tetrazol-2-yl)pentanoic acid,
(95) N-benzyloxycarbonyl-3-amino-4-oxo-5-(5-(2,6-dimethyl-4-t-butylphenylthio)tetrazol-1-yl)pentanoic acid,
(96) N-benzyloxycarbonyl-3-amino-4-oxo-5-(5-(2,6-dimethyl-4-dimethylaminophenylthio)tetrazol-2-yl)pentanoic acid,
(97) N-benzyloxycarbonyl-3-amino-4-oxo-5-(5-(2,6-dimethyl-4-dimethylaminophenylthio)tetrazol-1-yl)pentanoic acid,
(98) N-benzyloxycarbonyl-3-amino-4-oxo-5-(5-(4-isopropylphenylthio)tetrazol-2-yl)pentanoic acid,
(99) N-benzyloxycarbonyl-3-amino-4-oxo-5-(5-(4-isopropylphenylthio)tetrazol-1-yl)pentanoic acid,
(100) N-benzyloxycarbonyl-3-amino-4-oxo-5-(5-(2,4,6-trichlorophenylthio)tetrazol-2-yl)pentanoic acid,
(101) N-benzyloxycarbonyl-3-amino-4-oxo-5-(5-(2,4,6-trichlorophenylthio)tetrazol-1-yl)pentanoic acid, (102) N-benzyloxycarbonyl-3-amino-4-oxo-5-(5-(2,6-dichloro-4-(1,1-dimethylpropyl)phenylthio)tetrazol-2-yl)pentanoic acid,
(103) N-benzyloxycarbonyl-3-amino-4-oxo-5-(5-(2,6-dichloro-4-(1,1-dimethylpropyl)phenylthio)tetrazol-1-yl)pentanoic acid,
(104) N-benzyloxycarbonyl-3-amino-4-oxo-5-(5-(2-chloro-4-fluorophenylthio)tetrazol-2-yl)pentanoic acid,
(105) N-benzyloxycarbonyl-3-amino-4-oxo-5-(5-(2-chloro-4-fluorophenylthio)tetrazol-1-yl)pentanoic acid,
(106) N-benzyloxycarbonyl-3-amino-4-oxo-5-(5-(4-trifluoromethylcarbonylaminophenylthio)tetrazol-2-yl)pentanoic acid,
(107) N-benzyloxycarbonyl-3-amino-4-oxo-5-(5-(4-trifluoromethylcarbonylaminophenylthio)tetrazol-1-yl)pentanoic acid,
(108) N-benzyloxycarbonyl-3-amino-4-oxo-5-(5-(4-chlorophenylsulfinylmethyl)tetrazol-2-yl)pentanoic acid,
(109) N-benzyloxycarbonyl-3-amino-4-oxo-5-(5-(4-chlorophenylsulfinylmethyl)tetrazol-1-yl)pentanoic acid,
(110) N-benzyloxycarbonyl-3-amino-4-oxo-5-(5-(4-chlorophenylsulfonylmethyl)tetrazol-2-yl)pentanoic acid,
(111) N-benzyloxycarbonyl-3-amino-4-oxo-5-(5-(4-chlorophenylsulfonylmethyl)tetrazol-1-yl)pentanoic acid,
(112) N-(benzylthio)carbonyl-3-amino-4-oxo-5-(5-(2,6-dichlorophenylmethyl)tetrazol-2-yl)pentanoic acid,
(113) N-(benzylthio)carbonyl-3-amino-4-oxo-5-(5-(2,6-dichlorophenylmethyl)tetrazol-2-yl)pentanoic acid,
(114) N-(benzylthio)carbonyl-3-amino-4-oxo-5-(5-(2,6-dichlorophenylthio)tetrazol-2-yl)pentanoic acid,
(115) N-(benzylthio)carbonyl-3-amino-4-oxo-5-(5-(2,6-dichlorophenylthio)tetrazol-2-yl)pentanoic acid,
(116) N-(2-phenylethyloxy)carbonyl-3-amino-4-oxo-5-(5-(2,6-dichlorophenylmethyl)tetrazol-2-yl)pentanoic acid,
(117) N-(2-phenylethyloxy)carbonyl-3-amino-4-oxo-5-(5-(2,6-dichlorophenylmethyl)tetrazol-1-yl)pentanoic acid,
(118) N-(2-phenylethylthio)carbonyl-3-amino-4-oxo-5-(5-(2,6-dichlorophenylmethyl)tetrazol-2-yl)pentanoic acid,
(119) N-(2-phenylethylthio)carbonyl-3-amino-4-oxo-5-(5-(2,6-dichlorophenylmethyl)tetrazol-1-yl)pentanoic acid,
(120) N-(2,6-dichlorobenzyloxy)carbonyl-3-amino-4-oxo-5-(5-phenylmethyltetrazol-1-yl)pentanoic acid,
(121) N-(2,6-dichlorobenzyloxy)carbonyl-3-amino-4-oxo-5-(5-(2,6-dichlorophenylmethyl)tetrazol-2-yl)pentanoic acid,
(122) N-(3-phenylpropyloxy)carbonyl-3-amino-4-oxo-5-(5-(2,6-dichlorophenylmethyl)tetrazol-2-yl)pentanoic acid,
(123) N-(3-phenylpropyloxy)carbonyl-3-amino-4-oxo-5-(5-(2,6-dichlorophenylmethyl)tetrazol-1-yl)pentanoic acid,
(124) N-(4-phenylbutyloxy)carbonyl-3-amino-4-oxo-5-(5-(2,6-dichlorophenylmethyl)tetrazol-2-yl)pentanoic acid,
(125) N-(4-phenylbutyloxy)carbonyl-3-amino-4-oxo-5-(5-(2,6-dichlorophenylmethyl)tetrazol-1-yl)pentanoic acid,
(126) N-(2-(4-methoxyphenyl)ethyloxy)carbonyl-3-amino-4-oxo-5-(5-(2,6-dichlorophenylmethyl)tetrazol-2-yl)pentanoic acid,
(127) N-(2-(4-methoxyphenyl)ethyloxy)carbonyl-3-amino-4-oxo-5-(5-(2,6-dichlorophenylmethyl)tetrazol-1-yl)pentanoic acid,
(128) N-(2-(4-fluorophenyl)ethyloxy)carbonyl-3-amino-4-oxo-5-(5-(2,6-dichlorophenylmethyl)tetrazol-2-yl)pentanoic acid,
(129) N-(2-(4-fluorophenyl)ethyloxy)carbonyl-3-amino-4-oxo-5-(5-(2,6-dichlorophenylmethyl)tetrazol-1-yl)pentanoic acid,
(130) N-(2-(phenylmethyloxy)ethyloxy)carbonyl-3-amino-4-oxo-5-(5-(2,6-dichlorophenylmethyl)tetrazol-2-yl)pentanoic acid,
(131) N-(2-(phenylmethyloxy)ethyloxy)carbonyl-3-amino-4-oxo-5-(5-(2,6-dichlorophenylmethyl)tetrazol-1-yl)pentanoic acid,
(132) N-(2-(4-dimethylaminophenyl)ethyloxy)carbonyl-3-amino-4-oxo-5-(5-(2,6-dichlorophenylmethyl)tetrazol-2-yl)pentanoic acid,
(133) N-(2-(4-dimethylaminophenyl)ethyloxy)carbonyl-3-amino-4-oxo-5-(5-(2,6-dichlorophenylmethyl)tetrazol-1-yl)pentanoic acid,
(134) N-(benzylthio)carbonyl-3-amino-4-oxo-5-(5-(2,3,6-trichlorophenylthio)tetrazol-2-yl)pentanoic acid,
(135) N-(benzylthio)carbonyl-3-amino-4-oxo-5-(5-(2,3,6-trichlorophenylthio)tetrazol-1-yl)pentanoic acid,
(136) N-(benzylthio)carbonyl-3-amino-4-oxo-5-(5-(2,6-dichloro-4-methylphenylthio)tetrazol-2-yl)pentanoic acid,
(137) N-(benzylthio)carbonyl-3-amino-4-oxo-5-(5-(2,6-dichloro-4-methylphenylthio)tetrazol-1-yl)pentanoic acid,
(138) N-(3-phenylpropylthio)carbonyl-3-amino-4-oxo-(5-(2,6-dichlorophenylmethyl)tetrazol-2-yl)pentanoic acid,
(139) N-(3-phenylpropylthio)carbonyl-3-amino-4-oxo-5-(5-(2,6-dichlorophenylmethyl)tetrazol-1-yl)pentanoic acid,
(140) N-(benzylthio)carbonyl-3-amino-4-oxo-5-(5-(2,6-dichloro-4-dimethylaminophenylthio)tetrazol-2-yl)pentanoic acid,
(141) N-(benzylthio)carbonyl-3-amino-4-oxo-5-(5-(2,6-dichloro-4-dimethylaminophenylthio)tetrazol-1-yl)pentanoic acid,
(142) N-(2-phenylethylthio)carbonyl-3-amino-4-oxo-5-(5-(2,3,6-trichlorophenylthio)tetrazol-2-yl)pentanoic acid,
(143) N-(2-phenylethylthio)carbonyl-3-amino-4-oxo-5-(5-(2,3,6-trichlorophenylthio)tetrazol-1-yl)pentanoic acid,
(144) N-(2-phenylethylthio)carbonyl-3-amino-4-oxo-5-(5-(2,6-dichloro-4-methylphenylthio)tetrazol-2-yl)pentanoic acid,
(145) N-(2-phenylethylthio)carbonyl-3-amino-4-oxo-5-(5-(2,6-dichloro-4-methylphenylthio)tetrazol-1-yl)pentanoic acid,
(146) N-(benzylthio)carbonyl-3-amino-4-oxo-5-(5-(2,6-dimethyl-4-dimethylaminophenylthio)tetrazol-2-yl)pentanoic acid,
(147) N-(benzylthio)carbonyl-3-amino-4-oxo-5-(5-(2,6-dimethyl-4-dimethylaminophenylthio)tetrazol-1-yl)pentanoic acid, (148) N-(benzylthio)carbonyl-3-amino-4-oxo-5-(5-(2,6-dimethyl-4-t-butylphenylthio)tetrazol-2-yl)pentanoic acid,
(149) N-(benzylthio)carbonyl-3-amino-4-oxo-5-(5-(2,6-dimethyl-4-t-butylphenylthio)tetrazol-1-yl)pentanoic acid,
(150) N-(2-phenylethylthio)carbonyl-3-amino-4-oxo-5-(5-(2,6-dichloro-4-dimethylaminophenylthio)tetrazol-2-yl)pentanoic acid,
(151) N-(2-phenylethylthio)carbonyl-3-amino-4-oxo-5-(5-(2,6-dichloro-4-dimethylaminophenylthio)tetrazol-1-yl)pentanoic acid,
(152) N-(2-(4-methoxyphenyl)ethyloxy)carbonyl-3-amino-4-oxo-5-(5-(2,3,6-trichlorophenylthio)tetrazol-2-yl)pentanoic acid,
(153) N-(2-(4-methoxyphenyl)ethyloxy)carbonyl-3-amino-4-oxo-5-(5-(2,3,6-trichlorophenylthio)tetrazol-1-yl)pentanoic acid,
(154) N-(2-(4-methoxyphenyl)ethyloxy)carbonyl-3-amino-4-oxo-5-(5-(2,6-dichloro-4-methylphenylthio)tetrazol-2-yl)pentanoic acid,
(155) N-(2-(4-methoxyphenyl)ethyloxy)carbonyl-3-amino-4-oxo-5-(5-(2,6-dichloro-4-methylphenylthio)tetrazol-1-yl)pentanoic acid,
(156) N-(2-(4-methoxyphenyl)ethyloxy)carbonyl-3-amino-4-oxo-5-(5-(2,6-dichloro-4-dimethylaminophenylthio)tetrazol-2-yl)pentanoic acid,
(157) N-(2-(4-methoxyphenyl)ethyloxy)carbonyl-3-amino-4-oxo-5-(5-(2,6-dichloro-4-dimethylaminophenylthio)tetrazol-1-yl)pentanoic acid,
(158) N-(2-(4-methoxyphenyl)ethyloxy)carbonyl-3-amino-4-oxo-5-(5-(2,6-dimethyl-4-dimethylaminophenylthio)tetrazol-2-yl)pentanoic acid,
(159) N-(2-(4-methoxyphenyl)ethyloxy)carbonyl-3-amino-4-oxo-5-(5-(2,6-dimethyl-4-dimethylaminophenylthio)tetrazol-1-yl)pentanoic acid,
(160) N-(4-(4-methoxyphenyl)butyloxy)carbonyl-3-amino-4-oxo-5-(5-(2,3,6-trichlorophenylthio)tetrazol-2-yl)pentanoic acid,
(161) N-(4-(4-methoxyphenyl)butyloxy)carbonyl-3-amino-4-oxo-5-(5-(2,3,6-trichlorophenylthio)tetrazol-2-yl)pentanoic acid,
(162) N-(4-(4-methoxyphenyl)butyloxy)carbonyl-3-amino-4-oxo-5-(5-(2,6-dichloro-4-dimethylaminophenylthio)tetrazol-2-yl)pentanoic acid,
(163) N-(4-(4-methoxyphenyl)butyloxy)carbonyl-3-amino-4-oxo-5-(5-(2,6-dichloro-4-dimethylaminophenylthio)tetrazol-1-yl)pentanoic acid,
(164) N-(2-phenylethylthio)carbonyl-3-amino-4-oxo-5-(5-(2,6-dichlorophenylthio)tetrazol-2-yl)pentanoic acid,
(165) N-(2-phenylethylthio)carbonyl-3-amino-4-oxo-5-(5-(2,6-dichlorophenylthio)tetrazol-1-yl)pentanoic acid,
(166) N-(butylthio)carbonyl-3-amino-4-oxo-5-(5-(2,6-dichlorophenylthio)tetrazol-2-yl)pentanoic acid,
(167) N-(butylthio)carbonyl-3-amino-4-oxo-5-(5-(2,6-dichlorophenylthio)tetrazol-1-yl)pentanoic acid,
(168) N-(2-(4-methoxyphenyl)ethylthio)carbonyl-3-amino-4-oxo-5-(5-(2,6-dichlorophenylthio)tetrazol-2-yl)pentanoic acid,
(169) N-(2-(4-methoxyphenyl)ethylthio)carbonyl-3-amino-4-oxo-5-(5-(2,6-dichlorophenylthio)tetrazol-1-yl)pentanoic acid,
(170) N-(2-(4-acetylaminophenyl)ethylthio)carbonyl-3-amino-4-oxo-5-(5-(2,6-dichlorophenylthio)tetrazol-2-yl)pentanoic acid,
(171) N-(2-(4-acetylaminophenyl)ethylthio)carbonyl-3-amino-4-oxo-5-(5-(2,6-dichlorophenylthio)tetrazol-1-yl)pentanoic acid,
(172) N-butyloxycarbonyl-3-amino-4-oxo-5-(5-(2,6-dichlorophenylthio)tetrazol-2-yl)pentanoic acid,
(173) N-butyloxycarbonyl-3-amino-4-oxo-5-(5-(2,6-dichlorophenylthio)tetrazol-1-pentanoic acid,
(174) N-(propylthio)carbonyl-3-amino-4-oxo-5-(5-(2,6-dichlorophenylthio)tetrazol-2-yl)pentanoic acid,
(175) N-(propylthio)carbonyl-3-amino-4-oxo-5-(5-(2,6-dichlorophenylthio)tetrazol-1-yl)pentanoic acid,
(176) N-(isopropylthio)carbonyl-3-amino-4-oxo-5-(5-(2,6-dichlorophenylthio)tetrazol-2-yl)pentanoic acid,
(177) N-(isopropylthio)carbonyl-3-amino-4-oxo-5-(5-(2,6-dichlorophenylthio)tetrazol-1-yl)pentanoic acid,
(178) N-(2-methoxyethyloxy)carbonyl-3-amino-4-oxo-5-(5-(2,6-dichlorophenylthio)tetrazol-2-yl)pentanoic acid,
(179) N-(2-methoxyethyloxy)carbonyl-3-amino-4-oxo-5-(5-(2,6-dichlorophenylthio)tetrazol-1-yl)pentanoic acid,
(180) N-(2-cyclohexylethyloxy)carbonyl-3-amino-4-oxo-5-(5-(2,6-dichlorophenylthio)tetrazol-2-yl)pentanoic acid,
(181) N-(2-cyclohexylethyloxy)carbonyl-3-amino-4-oxo-5-(5-(2,6-dichlorophenylthio)tetrazol-1-yl)pentanoic acid,
(182) N-cyclohexylmethyloxycarbonyl-3-amino-4-oxo-5-(5-(2,6-dichlorophenylthio)tetrazol-2-yl)pentanoic acid,
(183) N-cyclohexylmethyloxycarbonyl-3-amino-4-oxo-5-(5-(2,6-dichlorophenylthio)tetrazol-1-yl)pentanoic acid,
(184) N-(2-phenylethyloxy)carbonyl-3-amino-4-oxo-5-(5-(2,6-dichlorophenylthio)tetrazol-2-yl)pentanoic acid,
(185) N-(2-phenylethyloxy)carbonyl-3-amino-4-oxo-5-(5-(2,6-dichlorophenylthio)tetrazol-1-yl)pentanoic acid,
(186) N-butyloxycarbonyl-3-amino-4-oxo-5-(5-(2,6-dichloro-4-acetylaminophenylthio)tetrazol-2-yl)pentanoic acid,
(187) N-butyloxycarbonyl-3-amino-4-oxo-5-(5-(2,6-dichloro-4-acetylaminophenylthio)tetrazol-1-yl)pentanoic acid,
(188) N-(2-(4-cyanophenyl)ethyloxy)carbonyl-3-amino-4-oxo-5-(5-(2,6-dichlorophenylthio)tetrazol-2-yl)pentanoic acid,
(189) N-(2-(4-cyanophenyl)ethyloxy)carbonyl-3-amino-4-oxo-5-(5-(2,6-dichlorophenylthio)tetrazol-1-yl)pentanoic acid,
(190) N-(2-(4-cyanophenyl)ethyloxy)carbonyl-3-amino-4-oxo-5-(5-(2,6-dichloro-4-methylphenylthio)tetrazol-2-yl)pentanoic acid,
(191) N-(2-(4-cyanophenyl)ethyloxy)carbonyl-3-amino-4-oxo-5-(5-(2,6-dichloro-4-methylphenylthio)tetrazol-1-yl)pentanoic acid,
(192) N-(2-methoxyethylthio)carbonyl-3-amino-4-oxo-5-(5-(2,6-dichlorophenylthio)tetrazol-2-yl)pentanoic acid, (193) N-(2-methoxyethylthio)carbonyl-3-amino-4-oxo-5-(5-(2,6-dichlorophenylthio)tetrazol-1-yl)pentanoic acid,
(194) N-(2-(4-hydroxyphenyl)ethyloxy)carbonyl-3-amino-4-oxo-5-(5-(2,6-dichlorophenylthio)tetrazol-2-yl)pentanoic acid,
(195) N-(2-(4-hydroxyphenyl)ethyloxy)carbonyl-3-amino-4-oxo-5-(5-(2,6-dichlorophenylthio)tetrazol-1-yl)pentanoic acid,
(196) N-(2-(4-hydroxyphenyl)ethylthio)carbonyl-3-amino-4-oxo-5-(5-(2,6-dichlorophenylthio)tetrazol-2-yl)pentanoic acid,
(197) N-(2-(4-hydroxyphenyl)ethylthio)carbonyl-3-amino-4-oxo-5-(5-(2,6-dichlorophenylthio)tetrazol-1-yl)pentanoic acid,
(198) N-phenylthiomethylcarbonyl-3-amino-4-oxo-5-(5-(2,6-dichlorophenylmethyl)tetrazol-2-yl)pentanoic acid,
(199) N-t-butoxycarbonyl-3-amino-4-oxo-5-(5-(2,6-dichlorophenylmethyl)tetrazol-2-yl)pentanoic acid,
(200) N-t-butoxycarbonyl-3-amino-4-oxo-5-(5-(2,6-dichlorophenylmethyl)tetrazol-1-yl)pentanoic acid,
(201) N-phenylcarbonyl-3-amino-4-oxo-5-(5-(2,6-dichlorophenylmethyl)tetrazol-2-yl)pentanoic acid,
(202) N-(2-phenylethylcarbonyl)-3-amino-4-oxo-5-(5-(2,6-dichlorophenylmethyl)tetrazol-2-yl)pentanoic acid,
(203) N-phenyloxymethylcarbonyl-3-amino-4-oxo-5-(5-(2,6-dichlorophenylmethyl)tetrazol-2-yl)pentanoic acid,
(204) N-(2-methylbenzyloxy)carbonyl-3-amino-4-oxo-5-(5-(2,6-dichlorophenylmethyl)tetrazol-2-yl)pentanoic acid,
(205) N-(3-chlorobenzyloxy)carbonyl-3-amino-4-oxo-5-(5-(2,6-dichlorophenylmethyl)tetrazol-2-yl)pentanoic acid,
(206) N-(2-propenoxy)carbonyl-3-amino-4-oxo-5-(5-(2,6-dichlorophenylmethyl)tetrazol-2-yl)pentanoic acid,
(207) N-(naphthalen-2-ylmethyloxy)carbonyl-3-amino-4-oxo-5-(5-(2,6-dichlorophenylmethyl)tetrazol-2-yl)pentanoic acid,
(208) N-(naphthalen-1-ylmethyloxy)carbonyl-3-amino-4-oxo-5-(5-(2,6-dichlorophenylmethyl)tetrazol-2-yl)pentanoic acid,
(209) N-(4-t-butylphenyl)sulfonyl-3-amino-4-oxo-5-(5-(2,6-dichlorophenylmethyl)tetrazol-1-yl)pentanoic acid,
(210) N-phenylmethylsulfonyl-3-amino-4-oxo-5-(5-(2,6-dichlorophenylmethyl)tetrazol-2-yl)pentanoic acid,
(211) N-phenylsulfonyl-3-amino-4-oxo-5-(5-(2,6-dichlorophenylmethyl)tetrazol-2-pentanoic acid,
(212) N-(2-(naphthalen-1-yl)ethyl)sulfonyl-3-amino-4-oxo-5-(5-(2,6-dichlorophenylmethyl)tetrazol-2-yl)pentanoic acid,
(213) N-(naphthalen-2-yl)sulfonyl-3-amino-4-oxo-5-(5-(2,6-dichlorophenylmethyl)tetrazol-2-yl)pentanoic acid,
(214) N-(naphthalen-1-yl)sulfonyl-3-amino-4-oxo-5-(5-(2,6-dichlorophenylmethyl)tetrazol-2-yl)pentanoic acid,
(215) N-(2-phenylethenyl)sulfonyl-3-amino-4-oxo-5-(5-(2,6-dichlorophenylmethyl)tetrazol-2-yl)pentanoic acid,
(216) N-(4-bromophenyl)sulfonyl-3-amino-4-oxo-5-(5-(2,6-dichlorophenylmethyl)tetrazol-2-yl)pentanoic acid,
(217) N-butylsulfonyl-3-amino-4-oxo-5-(5-(2,6-dichlorophenylmethyl)tetrazol-2-yl)pentanoic acid,
(218) N-(5-dimethylaminonaphthalen-1-yl)sulfonyl-3-amino-4-oxo-5-(5-(2,6-dichlorophenylmethyl)tetrazol-2-yl)pentanoic acid,
(219) N-(4-nitrophenyl)sulfonyl-3-amino-4-oxo-5-(5-(2,6-dichlorophenylmethyl)tetrazol-2-yl)pentanoic acid,
(220) N-phenylsulfonyl-3-amino-4-oxo-5-(5-(2,6-dichlorophenylmethyl)tetrazol-1-yl)pentanoic acid,
(221) N-(2-fluorophenyl)sulfonyl-3-amino-4-oxo-5-(5-(2,6-dichlorophenylmethyl)tetrazol-2-yl)pentanoic acid,
(222) N-(4-fluorophenyl)sulfonyl-3-amino-4-oxo-5-(5-(2,6-dichlorophenylmethyl)tetrazol-2-yl)pentanoic acid,
(223) N-(3-fluorophenyl)sulfonyl-3-amino-4-oxo-5-(5-(2,6-dichlorophenylmthyl)tetrazol-2-yl)pentanoic acid,
(224) N-(2-bromophenyl)sulfonyl-3-amino-4-oxo-5-(5-(2,6-dichlorophenylmethyl)tetrazol-2-yl)pentanoic acid,
(225) N-(4-methoxyphenyl)sulfonyl-3-amino-4-oxo-5-(5-(2,6-dichlorophenylmethyl)tetrazol-2-yl)pentanoic acid,
(226) N-(4-trifluoromethylphenyl)sulfonyl-3-amino-4-oxo-5-(5-(2,6-dichlorophenylmethyl)tetrazol-2-yl)pentanoic acid,
(227) N-(3-phenylpropyl)sulfonyl-3-amino-4-oxo-5-(5-(2,6-dichlorophenylmethyl)tetrazol-2-yl)pentanoic acid,
(228) N-(2-fluorophenyl)sulfonyl-3-amino-4-oxo-5-(5-(2,6-dichlorophenylmethyl)tetrazol-1-yl)pentanoic acid,
(229) N-(4-chlorophenyl)sulfonyl-3-amino-4-oxo-5-(5-(2,6-dichlorophenylmethyl)tetrazol-2-yl)pentanoic acid,
(230) N-(3-chlorophenyl)sulfonyl-3-amino-4-oxo-5-(5-(2,6-dichlorophenylmethyl)tetrazol-2-yl)pentanoic acid,
(231) N-(2-chlorophenyl)sulfonyl-3-amino-4-oxo-5-(5-(2,6-dichlorophenylmethyl)tetrazol-2-yl)pentanoic acid,
(232) N-(2-phenyloxyphenyl)sulfonyl-3-amino-4-oxo-5-(5-(2,6-dichlorophenylmethyl)tetrazol-2-yl)pentanoic acid,
(233) N-(2-phenylphenyl)sulfonyl-3-amino-4-oxo-5-(5-(2,6-dichlorophenylmethyl)tetrazol-2-yl)pentanoic acid,
(234) N-(3-phenylpropyl)sulfonyl-3-amino-4-oxo-5-(5-(2,6-dichlorophenylmethyl)tetrazol-1-yl)pentanoic acid,
(235) N-(2-methoxyphenyl)sulfonyl-3-amino-4-oxo-5-(5-(2,6-dichlorophenylmethyl)tetrazol-2-yl)pentanoic acid,
(236) N-(2,6-difluorophenyl)sulfonyl-3-amino-4-oxo-5-(5-(2,6-dichlorophenylmethyl)tetrazol-2-yl)pentanoic acid,
(237) N-(4-cyanophenyl)sulfonyl-3-amino-4-oxo-5-(5-(2,6-dichlorophenylmethyl)tetrazol-2-yl)pentanoic acid,
(238) N-(2-methylphenyl)sulfonyl-3-amino-4-oxo-5-(5-(2,6-dichlorophenylmethyl)tetrazol-2-yl)pentanoic acid,
(239) N-(4-methylphenyl)sulfonyl-3-amino-4-oxo-5-(5-(2,6-dichlorophenylmethyl)tetrazol-2-yl)pentanoic acid, (240) N-(4-phenylphenyl)sulfonyl-3-amino-4-oxo-5-(5-(2,6-dichlorophenylmethyl)tetrazol-2-yl)pentanoic acid,
(241) N-(5-dibutylaminonaphthalen-1-yl)sulfonyl-3-amino-4-oxo-5-(5-(2,6-dichlorophenylmethyl)tetrazol-2-yl)pentanoic acid,
(242) N-(3-phenylphenyl)sulfonyl-3-amino-4-oxo-5-(5-(2,6-dichlorophenylmetyl)tetrazol-2-yl)pentanoic acid,
(243) N-(4-acctylaminophenyl)sulfonyl-3-amino-4-oxo-5-(5-(2,6-dichlorophenylmethyl)tetrazol-2-yl)pentanoic acid,
(244) N-(4-t-butylphenyl)sulfonyl-3-amino-4-oxo-5-(5-(2,6-dichlorophenylmethyl)tetrazol-2-yl)pentanoic acid,
(245) N-(5-dimethylaminonaphthalen-1-yl)sulfonyl-3-amino-4-oxo-5-(5-(2,6-dichlorophenylmethyl)tetrazol-1-yl)pentanoic acid,
(246) N-(4-phenyloxyphenyl)sulfonyl-3-amino-4-oxo-5-(5-(2,6-dichlorophenylmethyl)tetrazol-2-yl)pentanoic acid,
(247) N-(4-phenylthiophenyl)sulfonyl-3-amino-4-oxo-5-(5-(2,6-dichlorophenylmethyl)tetrazol-2-yl)pentanoic acid,
(248) N-octanylsulfonyl-3-amino-4-oxo-5-(5-(2,6-dichlorophenylmethyl)tetrazol-2-yl)pentanoic acid,
(249) N-(4-phenylphenyl)sulfonyl-3-amino-4-oxo-5-(5-(2,6-dichlorophenylmethyl)tetrazol-2-yl)pentanoic acid,
(250) N-(4-phenylcarbonylmethylphenyl)sulfonyl-3-amino-4-oxo-5-(5-(2,6-dichlorophenylmethyl)tetrazol-2-yl)pentanoic acid,
(251) N-(2,2,2-trifluoroethylsulfonyl-3-amino-4-oxo-5-(5-(2,6-dichlorophenylmethyl)tetrazol-2-yl)pentanoic acid,
(252) N-(2-trifluoromethylphenyl)sulfonyl-3-amino-4-oxo-5-(5-(2,6-dichlorophenylmethyl)tetrazol-2-yl)pentanoic acid,
(253) N-(2-benzyloxycarbonylaminoethyl)sulfonyl-3-amino-4-oxo-5-(5-(2,6-dichlorophenylmethyl)tetrazol-2-yl)pentanoic acid,
(254) N-(4-acetylaminophenyl)sulfonyl-3-amino-4-oxo-5-(5-(2,6-dichlorophenylmethyl)tetrazol-1-yl)pentanoic acid,
(255) N-(4-phenylthiophenyl)sulfonyl-3-amino-4-oxo-5-(5-(2,6-dichlorophenylmethyl)tetrazol-1-yl)pentanoic acid,
(256) N-(2-nitrophenyl)sulfonyl-3-amino-4-oxo-5-(5-(2,6-dichlorophenylmethyl)tetrazol-2-yl)pentanoic acid,
(257) N-(camphor-10-yl)sulfonyl-3-amino-4-oxo-5-(5-(2,6-dichlorophenylmethyl)tetrazol-2-yl)pentanoic acid,
(258) N-(4-butylphenyl)sulfonyl-3-amino-4-oxo-5-(5-(2,6-dichlorophenylmethyl)tetrazol-2-yl)pentanoic acid,
(259) N-(4-butylphenyl)sulfonyl-3-amino-4-oxo-5-(5-(2,6-dichlorophenylmethyl)tetrazol-1-yl)pentanoic acid,
(260) N-(4-phenylsulfinylphenyl)sulfonyl-3-amino-4-oxo-5-(5-(2,6-dichlorophenylmethyl)tetrazol-2-yl)pentanoic acid,
(261) N-(4-phenylsulfonylphenyl)sulfonyl-3-amino-4-oxo-5-(5-(2,6-dichlorophenylmethyl)tetrazol-2-yl)pentanoic acid,
(262) N-(4-aminophenyl)sulfonyl-3-amino-4-oxo-5-(5-(2,6-dichlorophenylmethyl)tetrazol-2-yl)pentanoic acid,
(263) N-(N,N-dibenzylamino)carbonyl-3-amino-4-oxo-5-(5-(2,6-dichlorophenylmethyl)tetrazol-1-yl)pentanoic acid,
(264) N-(N-benzyl-N-methylamino)carbonyl-3-amino-4-oxo-5-(5-(2,6-dichlorophenylmethyl)tetrazol-1-yl)pentanoic acid,
(265) N-benzyloxycarbonyl-3-amino-4-oxo-5-(5-(4-aminophenylthio)tetrazol-2-yl)pentanoic acid,
(266) N-benzyloxycarbonyl-3-amino-4-oxo-5-(5-(4-aminophenylthio)tetrazol-1-yl)pentanoic acid,
(267) N-(2-aminoethyl)sulfonyl-3-amino-4-oxo-5-(5-(2,6-dichlorophenylmethyl)tetrazol-2-yl)pentanoic acid,
(268) N-(N-benzylamino)sulfonyl-3-amino-4-oxo-5-(5-(2,6-dichlorophenylmethyl)tetrazol-2-yl)pentanoic acid,
(269) N-(2-(2-methoxyethyloxy)ethyloxy)carbonyl-3-amino-4-oxo-5-(5-(2,6-dichlorophenylthio)tetrazol-2-yl)pentanoic acid,
(270) N-(2-(2-methoxyethyloxy)ethyloxy)carbonyl-3-amino-4-oxo-5-(5-(2,6-dichlorophenylthio)tetrazol-1-yl)pentanoic acid,
(271) N-(2-phenylethylthio)carbonyl-3-amino-4-oxo-5-(5-(2-chlorophenylthio)tetrazol-2-yl)pentanoic acid,
(272) N-(2-phenylethylthio)carbonyl-3-amino-4-oxo-5-(5-(2-chlorophenylthio)tetrazol-1-yl)pentanoic acid,
(273) N-(2-acetylaminoethylthio)carbonyl-3-amino-4-oxo-5-(5-(2,6-dichlorophenylthio)tetrazol-2-yl)pentanoic acid,
(274) N-(2-acetylaminoethylthio)carbonyl-3-amino-4-oxo-5-(5-(2,6-dichlorophenylthio)tetrazol-1-yl)pentanoic acid,
(275) N-(2-acetylaminoethyloxy)carbonyl-3-amino-4-oxo-5-(5-(2,6-dichlorophenylthio)tetrazol-2-yl)pentanoic acid,
(276) N-(2-acetylaminoethyloxy)carbonyl-3-amino-4-oxo-5-(5-(2,6-dichlorophenylthio)tetrazol-1-yl)pentanoic acid,
(277) N-(2-(2-methoxyethyloxy)ethylthio)carbonyl-3-amino-4-oxo-5-(5-(2,6-dichlorophenylthio)tetrazol-2-yl)pentanoic acid,
(278) N-(2-(2-methoxyethyloxy)ethylthio)carbonyl-3-amino-4-oxo-5-(5-(2,6-dichlorophenylthio)tetrazol-1-yl)pentanoic acid,
(279) N-(2-phenylethylthio)carbonyl-3-amino-4-oxo-5-(5-(phenylthio)tetrazol-2-yl)pentanoic acid,
(280) N-(2-phenylethylthio)carbonyl-3-amino-4-oxo-5-(5-(phenylthio)tetrazol-1-yl)pentanoic acid,
(281) N-(2-diethylaminoethyl)sulfonyl-3-amino-4-oxo-5-(5-(2,6-dichlorophenylmethyl)tetrazol-2-yl)pentanoic acid,
(282) N-(3-methylphenyl)sulfonyl-3-amino-4-oxo-5-(5-(2,6-dichlorophenylmethyl)tetrazol-2-yl)pentanoic acid,
(283) N-(4-isopropylphenyl)sulfonyl-3-amino-4-oxo-5-(5-(2,6-dichlorophenylmethyl)tetrazol-2-yl)pentanoic acid,
(284) N-(4-isopropylphenyl)sulfonyl-3-amino-4-oxo-5-(5-(2,6-dichlorophenylmethyl)tetrazol-1-yl)pentanoic acid,
(285) N-(2-diethylaminoethyl)sulfonyl-3-amino-4-oxo-5-(5-(2,6-dichlorophenylmethyl)tetrazol-1-yl)pentanoic acid,
(286) N-(4-butyloxyphenyl)sulfonyl-3-amino-4-oxo-5-(5-(2,6-dichlorophenylmethyl)tetrazol-2-yl)pentanoic acid, or (287) N-(4-butyloxyphenyl)sulfonyl-3-amino-4-oxo-5-(5-(2,6-dichlorophenylmethyl)tetrazol-1-yl)pentanoic acid, an ester thereof, a non-toxic salt thereof, an acid addition salt thereof or a hydrate thereof.

12. A compound according to claim 1, which is (1) N-((N-(3-phenylpropionyl)-L-valyl)-L-alanyl)-3-amino-4-oxo-5-(5-trifluoromethyltetrazol-2-yl)pentanoic acid, (2) N-benzyloxycarbonyl-3-amino-4-oxo-5-(5-trifluoromethyltetrazol-1-yl)pentanoic acid, (3) N-benzyloxycarbonyl-3-amino-4-oxo-5-(5-trifluoromethyltetrazol-2-yl)pentanoic acid, (4) N-benzyloxycarbonyl-3-amino-4-oxo-5-(5-bromotetrazol-2-yl)pentanoic acid, (5) N-benzyloxycarbonyl-3-amino-4-oxo-5-(5-(1,1-diphenylmethyl)tetrazol-2-yl)pentanoic acid, (6) N-benzyloxycarbonyl-3-amino-4-oxo-5-(5-(1,1-diphenylmethyl)tetrazol-1-yl)pentanoic acid, or (7) N-benzyloxycarbonyl-3-amino-4-oxo-5-(5-trimethylsilyltetrazol-2-yl)pentanoic acid, an ester thereof, a non-toxic salt thereof, an acid addition salt thereof or a hydrate thereof.

13. A pharmaceutical composition which comprises, as an active ingredient, an effective amount of a compound of formula (I) according to claim 1, a non-toxic salt thereof, an acid addition salt thereof or a hydrate thereof, and a pharmaceutically acceptable carrier or coating.

14. A method for the treatment of a disease in an animal, including a human subject, said animal having at least one of the following diseases: insulin dependent diabetes (type I), multiple sclerosis, acute or delayed type hypersensitivity, infectious diseases, infectious complications, septic shock, arthritis, colitis, glomelular nephritis, hepatitis, hepatic cirrhosis, pancreatitis, reperfusion injury, cholangeitis, encephalitis, endocarditis, myocarditis, vasculitis, Alzheimer's disease, Parkinson's disease, dementia, cerebral vascular disturbance, neuro-degenerative diseases, bone or cartilage-resorption diseases, AIDS, ARC (AIDS related complex), adult T cell leukemia, hairy cell (pilocytic) leukemia, myelosis, respiratory dysfunction, arthropathy, uveitis, neoplasm, diffuse collagen diseases such as systemic lupus erythematosis or rheumatoid arthritis, ulcerative colitis, Sjogren's syndrome, primary biliary cirrhosis, idiopathic thrombocytopnic purpura, autoimmunohaemolytic anemia, severe myasthenia, osteodisplasia syndrome, periodic thrombocytopenia, aplastic anemia, idiopathic thrombocytopenia, various diseases accompanied with thrombocytopenia such as disseminated intravascular coagulation, adult dyspnea syndrome, byperplasia of the prostatic gland, mysoma of the uterus, asthma bronchiole, arteriosclerosis, nephritis, senile cataract, chronic fatigue syndrome, myodystrophy and peripheral nervous disturbance, and wherein said treatment comprises the administration to a subject, a therapeutically effective amount of a compound of formula (I) according to claim 1, a non-toxic salt thereof, a non-toxic acid addition salt thereof or a hydrate thereof.

* * * * *